US012624024B2

(12) United States Patent
Duncton et al.

(10) Patent No.: US 12,624,024 B2
(45) Date of Patent: May 12, 2026

(54) EP2 ANTAGONIST COMPOUNDS

(71) Applicant: Reservoir Neuroscience, Inc., Emeryville, CA (US)

(72) Inventors: Matthew Alexander James Duncton, San Bruno, CA (US); Vladimir V. Senatorov, Jr., Oakland, CA (US); Aaron R. Friedman, Berkeley, CA (US); Steven Howard Olson, San Diego, CA (US)

(73) Assignee: Reservoir Neuroscience, Inc., San Francisco, CA (US)

( * ) Notice: Subject to any disclaimer, the term of this patent is extended or adjusted under 35 U.S.C. 154(b) by 110 days.

(21) Appl. No.: 18/395,334

(22) Filed: Dec. 22, 2023

(65) Prior Publication Data

US 2024/0182459 A1 Jun. 6, 2024

Related U.S. Application Data

(63) Continuation of application No. PCT/US2022/034901, filed on Jun. 24, 2022.

(60) Provisional application No. 63/214,645, filed on Jun. 24, 2021.

(51) Int. Cl.

| | |
|---|---|
| ***C07D 413/14*** | (2006.01) |
| ***C07D 413/06*** | (2006.01) |
| ***C07D 417/14*** | (2006.01) |
| ***C07D 471/04*** | (2006.01) |
| ***C07D 487/04*** | (2006.01) |

(52) U.S. Cl.
CPC ......... *C07D 413/14* (2013.01); *C07D 413/06* (2013.01); *C07D 417/14* (2013.01); *C07D 471/04* (2013.01); *C07D 487/04* (2013.01)

(58) Field of Classification Search
CPC .. C07D 413/14; C07D 413/06; C07D 417/14; C07D 471/04; C07D 487/04
See application file for complete search history.

(56) References Cited

U.S. PATENT DOCUMENTS

| | | | |
|---|---|---|---|
| 11,241,431 | B2 | 2/2022 | Fretz et al. |
| 11,325,899 | B2 | 5/2022 | Boss et al. |
| 11,446,298 | B2 | 9/2022 | Boss et al. |
| 11,712,438 | B2 | 8/2023 | Boss et al. |
| 11,839,613 | B2 | 12/2023 | Boss et al. |
| 12,011,444 | B2 | 6/2024 | Fretz et al. |
| 2020/0289517 | A1 | 9/2020 | He |
| 2022/0048987 | A1 | 2/2022 | Andreasson et al. |
| 2022/0175775 | A1 | 6/2022 | Fretz et al. |
| 2022/0388955 | A1 | 12/2022 | Watanabe et al. |

FOREIGN PATENT DOCUMENTS

| | | |
|---|---|---|
| WO | WO2008139287 | 11/2008 |
| WO | WO2010052625 | 5/2010 |
| WO | WO2020/249527 A1 | 12/2020 |

OTHER PUBLICATIONS

B. Fox in "A Selective Prostaglandin E2 Receptor Subtype 2 (EP2) Antagonist Increases the Macrophage-Mediated Clearance of Amyloid-Beta Plaques" (J. Med. Chem. 2015, 58, 13, 5256-5273) (Year: 2015).*

Af Forselles KJ, Root J, Clarke T, Davey D, Aughton K, Dack K, Pullen N. 2011. In vitro and in vivo characterization of PF-04418948, a novel, potent and selective prostaglandin $EP_2$ receptor antagonist. British Journal of Pharmacology 164:1847-1856. doi:10.1111/j.1476-5381.2011.01495.x.

Alhallak K, Nagai J, Zaleski K, et al. Mast cells control lung type 2 inflammation via prostaglandin E2-driven soluble ST2. Immunity. 2024;57(6):1274-1288.e6. doi:10.1016/j.immuni.2024.05.003.

Amaradhi R, Banik A, Mohammed S, Patro V, Rojas A, Wang W, Motati DR, Dingledine R, Ganesh T. 2020. Potent, Selective, Water Soluble, Brain-Permeable EP2 Receptor Antagonist for Use in Central Nervous System Disease Models. J Med Chem 63:1032-1050. doi:10.1021/acs.jmedchem.9b01218.

Amaradhi R, Mohammed S, Banik A, Franklin R, Dingledine R, Ganesh T. 2022. Second-Generation Prostaglandin Receptor EP2 Antagonist, TG8-260, with High Potency, Selectivity, Oral Bioavailability, and Anti-Inflammatory Properties. ACS Pharmacol Transl Sci 5:118-133. doi:10.1021/acsptsci.1c00255.

Aoki T, Frösen J, Fukuda M, Bando K, Shioi G, Tsuji K, Ollikainen E, Nozaki K, Laakkonen J, Narumiya S. 2017. Prostaglandin E2-EP2-NF-κB signaling in macrophages as a potential therapeutic target for intracranial aneurysms. Sci Signal 10:eaah6037. doi:10.1126/scisignal.aah6037.

Arosh JA, Lee J, Balasubbramanian D, Stanley JA, Long CR, Meagher MW, Osteen KG, Bruner-Tran KL, Burghardt RC, Starzinski-Powitz A, Banu SK. 2015. Molecular and preclinical basis to inhibit PGE2 receptors EP2 and EP4 as a novel nonsteroidal therapy for endometriosis. Proc Natl Acad Sci U S A 112:9716-9721. doi:10.1073/pnas.1507931112.

(Continued)

*Primary Examiner* — Clinton A Brooks
*Assistant Examiner* — Josmalen M. Ramos-Lewis
(74) *Attorney, Agent, or Firm* — Travis Young; Bozicevic, Field & Francis LLP

(57) ABSTRACT

Described herein are compounds of Formula (II):

Formula (II)

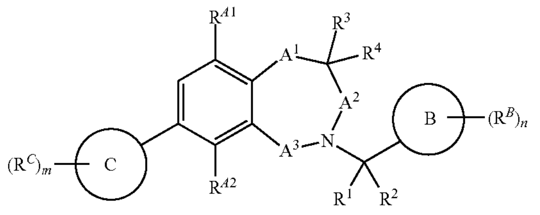

that are EP2 antagonists, methods of making such compounds, pharmaceutical compositions and medicaments comprising such compounds, and methods of using such compounds in the treatment of diseases or conditions associated with EP2 activity.

24 Claims, No Drawings

(56) References Cited

OTHER PUBLICATIONS

Banik A, Amaradhi R, Lee D, Sau M, Wang W, Dingledine R, Ganesh T. 2021. Prostaglandin EP2 receptor antagonist ameliorates neuroinflammation in a two-hit mouse model of Alzheimer's disease. J Neuroinflammation 18:273. doi:10.1186/s12974-021-02297-7.
Birrell MA, Maher SA, Buckley J, Dale N, Bonvini S, Raemdonck K, Pullen N, Giembycz MA, Belvisi MG. 2013. Selectivity profiling of the novel EP2 receptor antagonist, PF-04418948, in functional bioassay systems: atypical affinity at the guinea pig EP2 receptor. Br J Pharmacol 168:129-138. doi:10.1111/j.1476-5381.2012.02088.x.
Birrell MA, Nials AT. 2011. At last, a truly selective $EP_2$ receptor antagonist. Br J Pharmacol 164:1845-1846. doi:10.1111/j.1476-5381.2011.01494.x.
Bonfill-Teixidor E, Otxoa-de-Amezaga A, Font-Nieves M, Sans-Fons MG, Planas AM. 2017. Differential expression of E-type prostanoid receptors 2 and 4 in microglia stimulated with lipopolysaccharide. J Neuroinflammation 14:3. doi:10.1186/s12974-016-0780-7.
Chen J, Deng JC, Zemans RL, et al. Age-induced prostaglandin E2 impairs mitochondrial fitness and increases mortality to influenza infection. Nat Commun. 2022;13(1):6759. Published Nov. 9, 2022. doi: 10.1038/s41467-022-34593-y.
Fang LZ, Linehan V, Licursi M, et al. Prostaglandin E2 activates melanin-concentrating hormone neurons to drive diet-induced obesity. Proc Natl Acad Sci U S A. 2023;120(31):e2302809120. doi:10.1073/pnas.2302809120.
Fox BM, Beck HP, Roveto PM, Kayser F, Cheng Q, Dou H, Williamson T, Treanor J, Liu H, Jin L, Xu G, Ma J, Wang S, Olson SH. 2015. A selective prostaglandin E2 receptor subtype 2 (EP2) antagonist increases the macrophage-mediated clearance of amyloid-beta plaques. J Med Chem 58:5256-5273. doi:10.1021/acs.jmedchem.5b00567.
Francica BJ, Holtz A, Lopez J, Freund D, Chen A, Wang D, Powell D, Kipper F, Panigrahy D, Dubois RN, Whiting CC, Prasit P, Dubensky TW. 2023. Dual Blockade of EP2 and EP4 Signaling is Required for Optimal Immune Activation and Antitumor Activity Against Prostaglandin-Expressing Tumors. Cancer Res Commun 3:1486-1500. doi:10.1158/2767-9764.CRC-23-0249.
Ganesh T, Banik A, Dingledine R, Wang W, Amaradhi R. 2018. Peripherally Restricted, Highly Potent, Selective, Aqueous-Soluble EP2 Antagonist with Anti-Inflammatory Properties. Mol Pharm 15:5809-5817. doi:10.1021/acs.molpharmaceut.8b00764.
Ganesh T, Jiang J, Dingledine R. 2014a. Development of second generation EP2 antagonists with high selectivity. Eur J Med Chem 82:521-535, doi:10.1016/j.ejmech.2014.05.076.
Ganesh T, Jiang J, Shashidharamurthy R, Dingledine R. 2013. Discovery and characterization of carbamothioylacrylamides as EP2 selective antagonists. ACS Med Chem Lett 4:616-621. doi:10.1021/ml400112h.
Ganesh T, Jiang J, Yang M-S, Dingledine R. 2014b. Lead optimization studies of cinnamic amide EP2 antagonists. J Med Chem 57:4173-4184. doi:10.1021/jm5000672.
Ganesh T. 2014. Prostanoid receptor EP2 as a therapeutic target. J Med Chem 57:4454-4465. doi:10.1021/jm401431x.
Ganesh T. 2023. Targeting EP2 Receptor for Drug Discovery: Strengths, Weaknesses, Opportunities, and Threats (SWOT) Analysis. J Med Chem 66:9313-9324. doi:10.1021/acs.jmedchem.3c00655.
Gill SK, Yao Y, Kay LJ, Bewley MA, Marriott HM, Peachell PT. 2016. The anti-inflammatory effects of PGE2 on human lung macrophages are mediated by the EP4 receptor. Br J Pharmacol 173:3099-3109. doi:10.1111/bph.13565.
Golden J, Illingworth L, Kavarian P, et al. EP2 Receptor Blockade Attenuates COX-2 Upregulation During Intestinal Inflammation. Shock. 2020;54(3):394-401. doi:10.1097/SHK.0000000000001444.
Jiang C, Amaradhi R, Ganesh T, Dingledine R. 2020. An Agonist Dependent Allosteric Antagonist of Prostaglandin EP2 Receptors. ACS Chem Neurosci 11:1436-1446. doi:10.1021/acschemneuro.0c00078.
Jiang J, Dingledine R. 2013. Prostaglandin receptor EP2 in the crosshairs of anti-inflammation, anti-cancer, and neuroprotection. Trends Pharmacol Sci 34:413-423. doi:10.1016/j.tips.2013.05.003.
Jiang J, Ganesh T, Du Y, Quan Y, Serrano G, Qui M, Speigel I, Rojas A, Lelutiu N, Dingledine R. 2012. Small molecule antagonist reveals seizure-induced mediation of neuronal injury by prostaglandin E2 receptor subtype EP2. Proc Natl Acad Sci U S A 109:3149-3154. doi:10.1073/pnas.1120195109.
Jiang J, Quan Y, Ganesh T, Pouliot WA, Dudek FE, Dingledine R. 2013. Inhibition of the prostaglandin receptor EP2 following status epilepticus reduces delayed mortality and brain inflammation. Proc Natl Acad Sci U S A 110:3591-3596. doi:10.1073/pnas.1218498110.
Jones VC, Birrell MA, Maher SA, Griffiths M, Grace M, O'Donnell VB, Clark SR, Belvisi MG. 2016. Role of EP2 and EP4 receptors in airway microvascular leak induced by prostaglandin E2. Br J Pharmacol 173:992-1004. doi:10.1111/bph.13400.
Kameyama H, Dondapati P, Simmons R, et al. Needle biopsy accelerates pro-metastatic changes and systemic dissemination in breast cancer: Implications for mortality by surgery delay. Cell Rep Med. 2023;4(12):101330. doi:10.1016/j.xcrm.2023.101330.
Kawahara K, Hohjoh H, Inazumi T, Tsuchiya S, Sugimoto Y. 2015. Prostaglandin E2-induced inflammation: Relevance of prostaglandin E receptors. Biochim Biophys Acta 1851:414-421. doi:10.1016/j.bbalip.2014.07.008.
Kay LJ, Gilbert M, Pullen N, Skerratt S, Farrington J, Seward EP, Peachell PT. 2013. Characterization of the EP receptor subtype that mediates the inhibitory effects of prostaglandin E2 on IgE-dependent secretion from human lung mast cells. Clin Exp Allergy 43:741-751. doi:10.1111/cea. 12142.
Keery RJ, Lumley P. 1988. AH6809, a prostaglandin DP-receptor blocking drug on human platelets. Br J Pharmacol 94:745-754. doi:10.1111/j.1476-5381.1988.tb11584.x.
Li L, Yu Y, Hou R, Hao J, Jiang J. 2020. Inhibiting the PGE2 Receptor EP2 Mitigates Excitotoxicity and Ischemic Injury. ACS Pharmacol Transl Sci 3:635-643. doi:10.1021/acsptsci.0c00040.
Li P, Jiang H, Wu H, Wu D, Li H, Yu J, Lai J. 2018. AH6809 decreases production of inflammatory mediators by PGE2—EP2—CAMP signaling pathway in an experimentally induced pure cerebral concussion in rats. Brain Res 1698:11-28. doi:10.1016/j.brainres.2018.05.030.
Liu Q, Liang X, Wang Q, Wilson EN, Lam R, Wang J, Kong W, Tsai C, Pan T, Larkin PB, Shamloo M, Andreasson Kl. 2019. PGE2 signaling via the neuronal EP2 receptor increases injury in a model of cerebral ischemia. Proc Natl Acad Sci U S A 116:10019-10024. doi:10.1073/pnas.1818544116 .
Makabe T, Koga K, Nagabukuro H, et al. Use of selective PGE2 receptor antagonists on human endometriotic stromal cells and peritoneal macrophages. Mol Hum Reprod. 2021;27(1):gaaa077. doi:10.1093/molehr/gaaa077.
Markovid T, Jakopin Ž, Dolenc MS, Mlinarič-Raščan I. 2017. Structural features of subtype-selective EP receptor modulators. Drug Discov Today 22:57-71. doi:10.1016/j.drudis.2016.08.003.
Minhas PS, Latif-Hernandez A, McReynolds MR, Durairaj AS, Wang Q, Rubin A, Joshi AU, He JQ, Gauba E, Liu L, Wang C, Linde M, Sugiura Y, Moon PK, Majeti R, Suematsu M, Mochly-Rosen D, Weissman IL, Longo FM, Rabinowitz JD, Andreasson KI. 2021. Restoring metabolism of myeloid cells reverses cognitive decline in ageing. Nature. doi:10.1038/s41586-020-03160-0.
Nakamura N, Honjo M, Yamagishi R, Sakata R, Watanabe S, Aihara M. Synergic effects of EP2 and FP receptors co-activation on Blood-Retinal Barrier and Microglia. Exp Eye Res. 2023;237:109691. doi:10.1016/j.exer.2023.109691.
Morotti M, Grimm AJ, Hope HC, Arnaud M, Desbuisson M, Rayroux N, Barras D, Masid M, Murgues B, Chap BS, Ongaro M, Rota IA, Ronet C, Minasyan A, Chiffelle J, Lacher SB, Bobisse S, Murgues C, Ghisoni E, Ouchen K, Bou Mjahed R, Benedetti F, Abdellaoui N, Turrini R, Gannon PO, Zaman K, Mathevet P, Lelievre L, Crespo I, Conrad M, Verdeil G, Kandalaft LE, Dagher

(56) References Cited

OTHER PUBLICATIONS

J, Corria-Osorio J, Doucey M-A, Ho P-C, Harari A, Vannini N, Böttcher JP, Dangaj Laniti D, Coukos G. 2024. PGE2 inhibits TIL expansion by disrupting IL-2 signalling and mitochondrial function. Nature 629:426-434. doi:10.1038/s41586-024-07352-w.
Perrot CY, Herrera JL, Fournier-Goss AE, Komatsu M. 2020. Prostaglandin E2 breaks down pericyte-endothelial cell interaction via EP1 and EP4-dependent downregulation of pericyte N-cadherin, connexin-43, and R-Ras. Sci Rep 10:11186. doi:10.1038/s41598-020-68019-w.
Rawat V, Banik A, Amaradhi R, Rojas A, Taval S, Nagy T, Dingledine R, Ganesh T. 2022. Pharmacological antagonism of EP2 receptor does not modify basal cardiovascular and respiratory function, blood cell counts, and bone morphology in animal models. Biomed Pharmacother 147:112646. doi:10.1016/j.biopha.2022.112646.
Rojas A, Amaradhi R, Banik A, Jiang C, Abreu-Melon J, Wang S, Dingledine R, Ganesh T. 2021. A Novel Second-Generation EP2 Receptor Antagonist Reduces Neuroinflammation and Gliosis After Status Epilepticus in Rats. Neurotherapeutics 18:1207-1225. doi:10.1007/s13311-020-00969-5.
Rojas A, Ganesh T, Lelutiu N, Gueorguieva P, Dingledine R. 2015. Inhibition of the prostaglandin EP2 receptor is neuroprotective and accelerates functional recovery in a rat model of organophosphorus induced status epilepticus. Neuropharmacology 93:15-27. doi:10.1016/j.neuropharm.2015.01.017.
Rojas A, Ganesh T, Manji Z, O'neill T, Dingledine R. 2016. Inhibition of the prostaglandin E2 receptor EP2 prevents status epilepticus-induced deficits in the novel object recognition task in rats. Neuropharmacology 110:419-430. doi:10.1016/j.neuropharm.2016.07.028.
Rojas A, Ganesh T, Wang W, Wang J, Dingledine R. 2020. A rat model of organophosphate-induced status epilepticus and the beneficial effects of EP2 receptor inhibition. Neurobiol Dis 133:104399. doi:10.1016/j.nbd.2019.02.010.
Säfholm J, Manson ML, Bood J, et al. Prostaglandin E2 inhibits mast cell-dependent bronchoconstriction in human small airways through the E prostanoid subtype 2 receptor. J Allergy Clin Immunol. 2015;136(5):1232-9.e1. doi:10.1016/j.jaci.2015.04.002.
Sluter MN, Hou R, Li L, Yasmen N, Yu Y, Liu J, Jiang J. 2021. EP2 Antagonists (2011-2021): A Decade's Journey from Discovery to Therapeutics. J Med Chem 64:11816-11836. doi:10.1021/acs.jmedchem.1c00816.
Thumkeo D, Punyawatthananukool S, Prasongtanakij S, Matsuura R, Arima K, Nie H, Yamamoto R, Aoyama N, Hamaguchi H, Sugahara S, Takeda S, Charoensawan V, Tanaka A, Sakaguchi S, Narumiya S. 2022. PGE2-EP2/EP4 signaling elicits immunosuppression by driving the mregDC-Treg axis in inflammatory tumor microenvironment. Cell Rep 39:110914. doi:10.1016/j.celrep.2022.110914.
Varvel NH, Amaradhi R, Espinosa-Garcia C, Duddy S, Franklin R, Banik A, Alemán-Ruiz C, Blackmar-Raynolds L, Wang W, Honore T, Ganesh T, Dingledine R. 2022. Preclinical development of an EP2 antagonist for post-seizure cognitive deficits. Neuropharmacology 224:109356. doi:10.1016/j.neuropharm.2022.109356.
Wang J, Zhi Z, Ding J, et al. Suppression of PGE2/EP2 signaling alleviates Hirschsprung disease by upregulating p38 mitogen-activated protein kinase activity. J Mol Med (Berl). 2023;101(9):1125-1139. doi:10.1007/s00109-023-02353-0.
Woodward DF, Pepperl DJ, Burkey TH, Regan JW. 1995. 6-Isopropoxy-9-oxoxanthene-2-carboxylic acid (AH 6809), a human EP2 receptor antagonist. Biochem Pharmacol 50:1731-1733. doi:10.1016/0006-2952(95)02035-7.
Zasłona Z, Pålsson-McDermott EM, Menon D, et al. The Induction of Pro-IL-1β by Lipopolysaccharide Requires Endogenous Prostaglandin E2 Production. J Immunol. 2017;198(9):3558-3564. doi:10.4049/jimmunol.1602072.
PUBCHEM, Substance Record for SID 318473298, Modify Date Nov. 30, 2016.

* cited by examiner

EP2 ANTAGONIST COMPOUNDS

CROSS-REFERENCE

This application is a continuation of PCT Application No. US2022/034901, filed Jun. 24, 2022, which claims the benefit of the earlier filing date of U.S. Provisional Patent Application No. 63/214,645, filed on Jun. 24, 2021. Both prior applications are incorporated herein by reference in their entireties.

FIELD OF THE INVENTION

Described herein are compounds that are inhibitors of prostaglandin E2 receptor 2, also known as EP2, methods of making such compounds, pharmaceutical compositions and medicaments comprising such compounds, and methods of using such compounds in the treatment of diseases or conditions associated with EP2 activity.

BACKGROUND OF THE INVENTION

EP2 is a prostaglandin receptor that functions, for example, as a mediator of inflammation. EP2 signaling is implicated in, for example, inflammatory conditions, allergic diseases, ocular diseases, nervous system diseases, bone diseases, fibrotic conditions, cardiovascular diseases, and certain forms of cancer.

SUMMARY OF THE INVENTION

Compounds described herein are antagonists of EP2. In some embodiments, the compounds described herein are used in the treatment or prevention of diseases or conditions in which EP2 activity contributes to the symptomology or progression of the diseases or conditions, such as, for example, inflammatory diseases or conditions.

In an aspect, disclosed herein is a compound having the structure of Formula (II):

Formula (II)

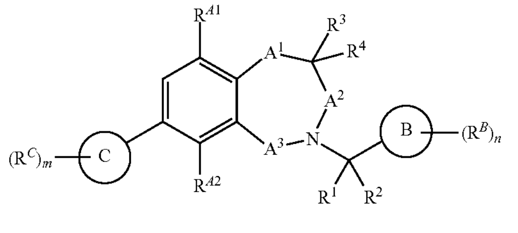

or a pharmaceutically acceptable salt thereof, wherein:

$R^1$ and $R^2$ are each independently hydrogen, deuterium, halogen, or $C_{1-4}$ alkyl;

$A^1$ is —O—, —$CR^5R^6$—, —S—, —S(═O)$_2$— or absent;

$A^2$ is —$CR^7R^8$— or —S(═O)$_2$—;

$A^3$ is —$CR^9R^{10}$— or absent;

$R^3$ and $R^4$ are each independently hydrogen, deuterium, halogen, or $C_{1-4}$ alkyl;

$R^5$ and $R^6$ are each independently hydrogen, deuterium, halogen, or $C_{1-4}$ alkyl; or $R^5$ and $R^6$ are taken together with the carbon atom to which they are attached to form an oxetane;

$R^7$ and $R^8$ are each independently hydrogen, deuterium, halogen, —CN, —$C_{1-4}$ alkyl, —$C_{1-4}$ haloalkyl, —OH, —O($C_{1-4}$ alkyl), —O($C_{1-4}$ haloalkyl), —$NH_2$, —NH($C_{1-4}$ alkyl), —N($C_{1-4}$ alkyl)$_2$, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, substituted or unsubstituted $C_{3-6}$ cycloalkyl, or substituted or unsubstituted 3- to 6-membered heterocycloalkyl; or $R^7$ and $R^8$ are taken together with the carbon atom to which they are attached to form a cyclopropane or an oxetane;

$R^9$ and $R^{10}$ are each independently hydrogen, deuterium, halogen, or $C_{1-4}$ alkyl; or $R^9$ and $R^{10}$ are taken together with the carbon atom to which they are attached to form an oxetane;

$R^{A1}$ is halogen, $C_{1-4}$ alkyl, or cyclopropyl; and $R^{A2}$ is hydrogen, deuterium, halogen, or optionally deuterated or halogenated methyl;

Ring B is $C_{3-6}$ cycloalkyl, phenyl, 5-membered heteroaryl, or 6-membered heteroaryl containing two or more nitrogen atoms; or Ring B is Ring B';

each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —NHS(O)$_2C_{1-4}$ alkyl, —OH, —O($C_{1-4}$ alkyl), —O($C_{1-4}$ haloalkyl), —SH, —S($C_{1-4}$ alkyl), —S(O)($C_{1-4}$ alkyl), —S(O)(NH)($C_{1-4}$ alkyl), —S(O)$_2$($C_{1-4}$ alkyl), —S(O)$_2NH_2$, —S($O_2$)$NHCH_3$, substituted or unsubstituted $C_{3-6}$ cycloalkyl, or substituted or unsubstituted 3- to 6-membered heterocyclyl; or two $R^B$ taken together form a carbonyl;

Ring C is bicyclic heterocycle having one or more nitrogen atoms; or Ring C is Ring C';

each $R^C$ is independently selected from the group consisting of halogen, —CN, —$C_{1-4}$ alkyl, —$C_{1-4}$ haloalkyl, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —N($C_{1-4}$ alkyl)$_2$, —OH, —O($C_{1-4}$ alkyl), —O($C_{1-4}$ haloalkyl), —S($C_{1-4}$ alkyl), —$SO_2C_{1-4}$ alkyl, —$SO_2NHC_{1-4}$ alkyl, substituted or unsubstituted $C_{3-6}$ cycloalkyl, or substituted or unsubstituted 3- to 6-membered heterocyclyl; or two $R^B$ taken together form a carbonyl;

m is 0 to 3;

n is 0 to 3; and

Ring B' is selected from the group consisting of:

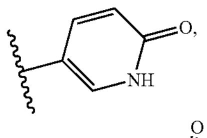

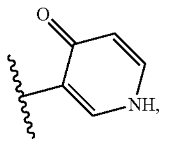

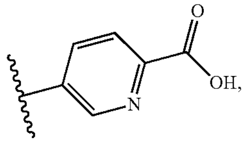

-continued
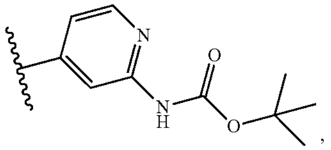, 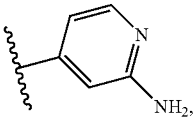,
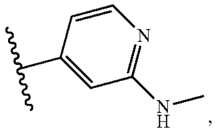, 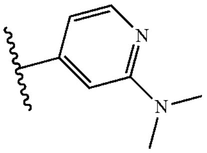,
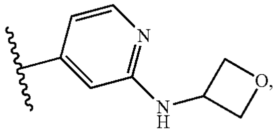, 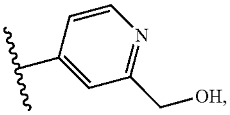,
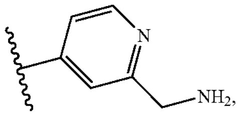, 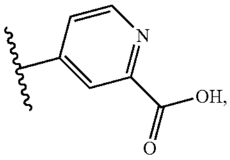,
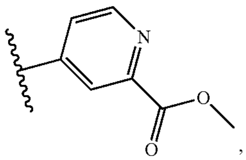, 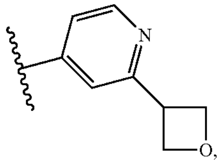,
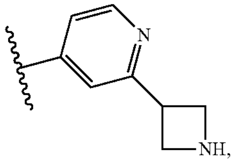, 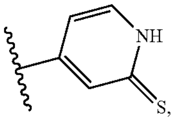,
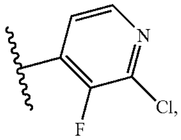, 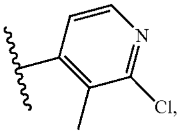,
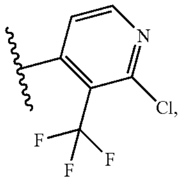, 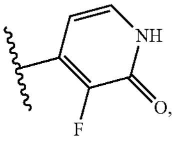,
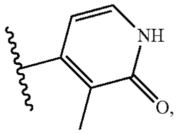, 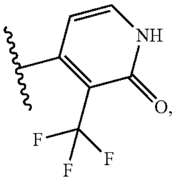,
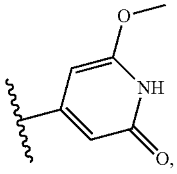, 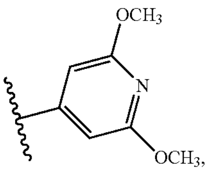,
-continued
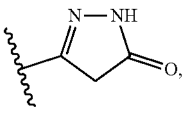, 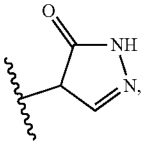, 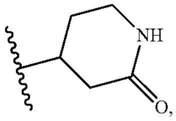,
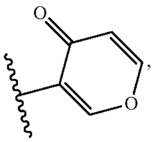, 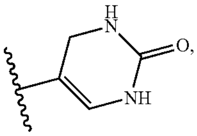,
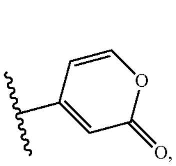, 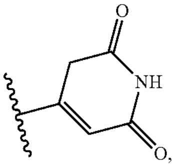,
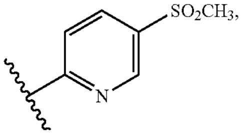, 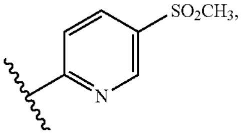,
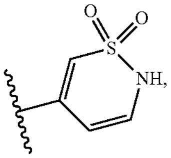, 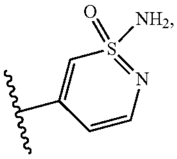,
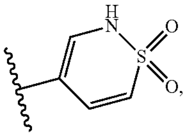, 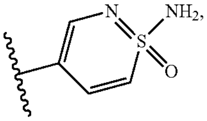,
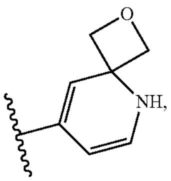, 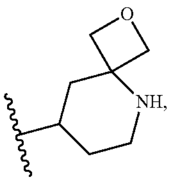,
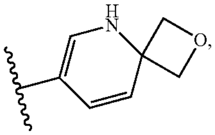, 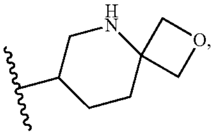, and
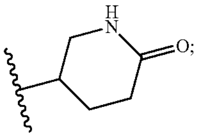;

and

Ring C' is selected from the group consisting of:

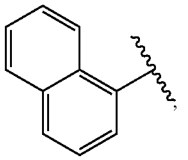,
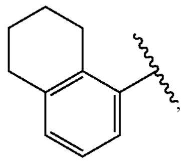,
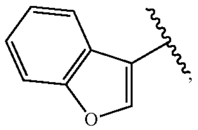, and
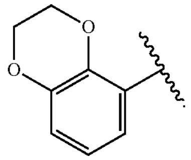.

In another embodiment is a compound having the structure of Formula III:

Formula (III)

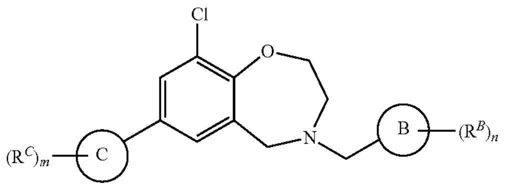

or a pharmaceutically acceptable salt thereof, wherein:

Ring B is $C_{3-6}$ cycloalkyl, phenyl, 5-membered heteroaryl, or 6-membered heteroaryl containing two or more nitrogen atoms;

each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —NHS(O)$_2C_{1-4}$ alkyl, —OH, —O($C_{1-4}$ alkyl), —O($C_{1-4}$ haloalkyl), —SH, —S($C_{1-4}$ alkyl), —SO($C_{1-4}$ alkyl), —S(O)(NH)($C_{1-4}$ alkyl), —S(O)$_2$($C_{1-4}$ alkyl), —S(O)$_2NH_2$, —S($O_2$)$NHCH_3$, substituted or unsubstituted $C_{3-6}$ cycloalkyl, or substituted or unsubstituted 3- to 6-membered heterocyclyl; or two $R^B$ taken together form a carbonyl;

Ring C is bicyclic heterocycle having one or more nitrogen atoms; or Ring C is Ring C';

each $R^C$ is independently selected from the group consisting of halogen, —CN, —$C_{1-4}$ alkyl, —$C_{1-4}$ haloalkyl, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —N($C_{1-4}$ alkyl)$_2$, —OH, —O($C_{1-4}$ alkyl), —O($C_{1-4}$ haloalkyl), —S($C_{1-4}$ alkyl), —$SO_2C_{1-4}$ alkyl, —$SO_2NHC_{1-4}$ alkyl, substituted or unsubstituted $C_{3-6}$ cycloalkyl, or substituted or unsubstituted 3- to 6-membered heterocyclyl; or two $R^B$ taken together form a carbonyl;

m is 0 to 3;

n is 0 to 3; and

Ring C' is selected from the group consisting of:

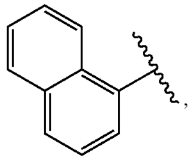,
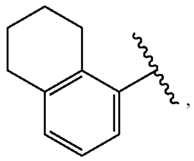,
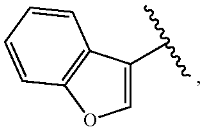, and
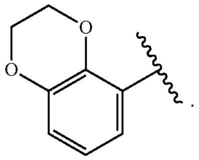.

In another embodiment is a compound having the structure of Formula (III'):

Formula (III')

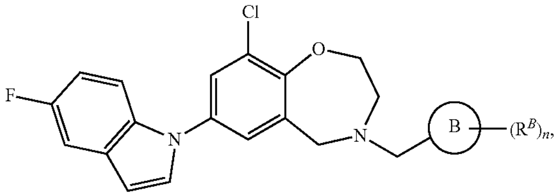, or a pharmaceutically acceptable salt thereof, wherein:

Ring B is $C_{3-6}$ cycloalkyl, phenyl, or 5-membered heteroaryl, or 6-membered heteroaryl containing two or more nitrogen atoms;

each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —NHS(O)$_2C_{1-4}$ alkyl, —OH, —O($C_{1-4}$ alkyl), —O($C_{1-4}$ haloalkyl), —SH, —S($C_{1-4}$ alkyl), —SO($C_{1-4}$ alkyl), —S(O)(NH)($C_{1-4}$ alkyl), —S(O)$_2$($C_{1-4}$ alkyl), —S(O)$_2NH_2$, —S($O_2$)$NHCH_3$, substituted or unsubstituted $C_{3-6}$ cycloalkyl, or substituted or unsubstituted 3- to 6-membered heterocyclyl; or two $R^B$ taken together form a carbonyl; and n is 0 to 3.

In another embodiment is a compound having the structure of Formula (IIIb'):

Formula (IIIb')

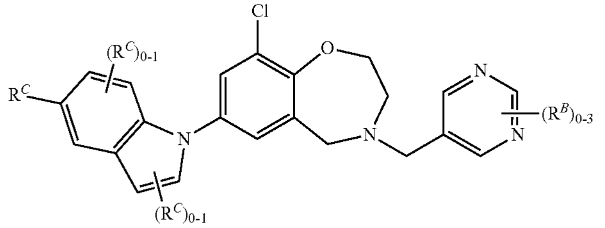

or a pharmaceutically acceptable salt thereof, or a tautomer thereof, wherein:

each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —NHS(O)$_2C_{1-4}$ alkyl, —OH, —O($C_{1-4}$ alkyl), —O($C_{1-4}$ haloalkyl), —SH, —S($C_{1-4}$ alkyl), —SO($C_{1-4}$ alkyl), —S(O)$_2$($C_{1-4}$ alkyl), —S(O)$_2NH_2$, —S($O_2$)$NHCH_3$, substituted or unsubstituted $C_{3-6}$ cycloalkyl, or substituted or unsubstituted 3- to 6-membered heterocyclyl; or two $R^B$ taken together form a carbonyl; and each $R^C$ is independently selected from the group consisting of halogen, —CN, —$C_{1-4}$ alkyl, —$C_{1-4}$ haloalkyl, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —N($C_{1-4}$ alkyl)$_2$, —OH, —O($C_{1-4}$ alkyl), —O($C_{1-4}$ haloalkyl), —S($C_{1-4}$ alkyl), —$SO_2C_{1-4}$ alkyl, —$SO_2NHC_{1-4}$ alkyl, substituted or unsubstituted $C_{3-6}$ cycloalkyl, or substituted or unsubstituted 3- to 6-membered heterocyclyl; or two $R^B$ taken together form a carbonyl.

In another embodiment is a compound having the structure of Formula (VIII):

Formula VIII

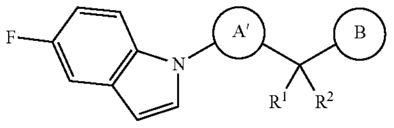

or a pharmaceutically acceptable salt thereof, wherein:

$R^1$ and $R^2$ are each independently hydrogen or deuterium;

Ring A' is selected from the group consisting of:

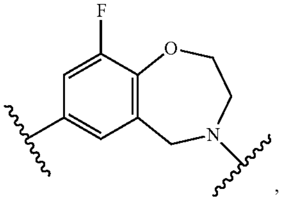
,

-continued

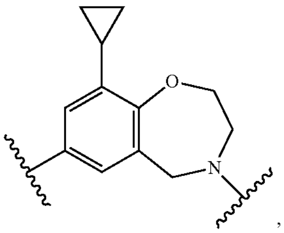
,

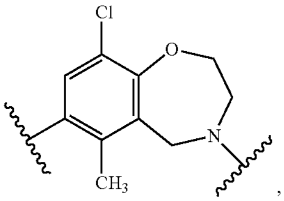
,

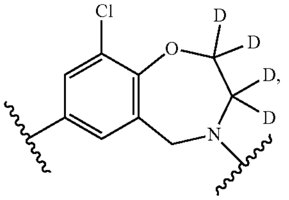

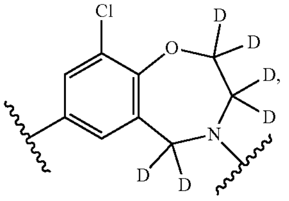

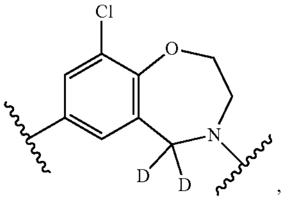
,

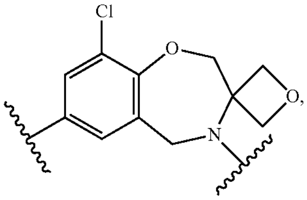

-continued
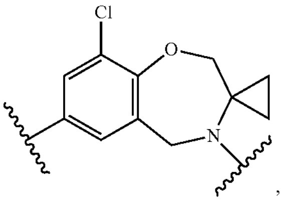
,
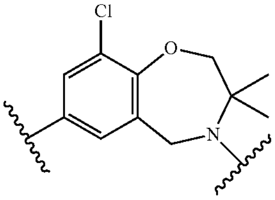
,
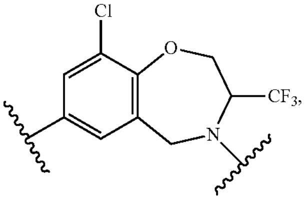
,
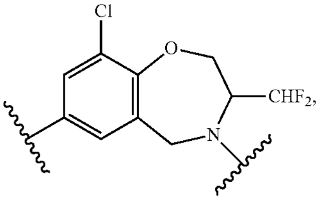
,
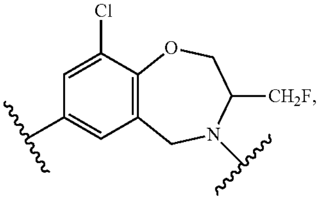
,
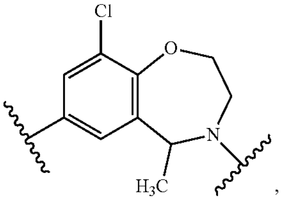
,
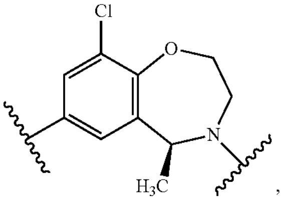
,
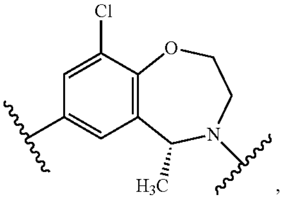
,
-continued
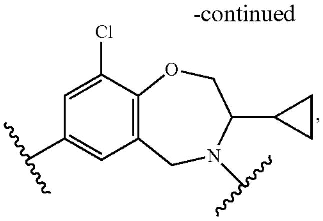
,
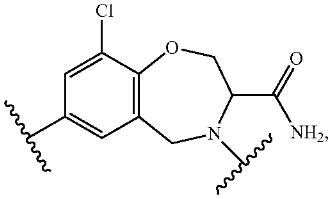
,
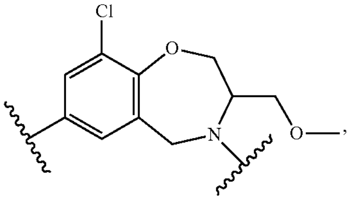
,
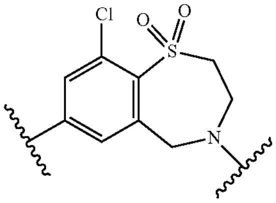
,
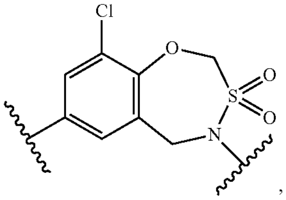
,
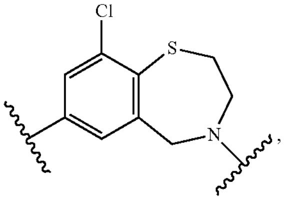
,
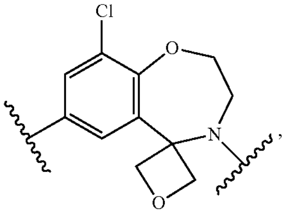
,
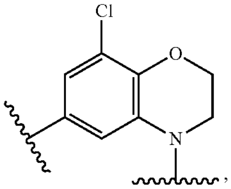
, and -continued

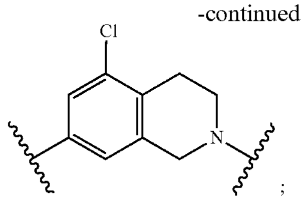

Ring B is a substituted or unsubstituted heterocycle; wherein if Ring B is substituted, it is substituted with one or more $R^B$ groups, and each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —NHS(O)$_2C_{1-4}$ alkyl, —OH, —O($C_{1-4}$ alkyl), —O($C_{1-4}$ haloalkyl), —SH, —S($C_{1-4}$ alkyl), —SO($C_{1-4}$ alkyl), —S(O)$_2$($C_{1-4}$ alkyl), —S(O)$_2NH_2$, —S($O_2$)$NHCH_3$, substituted or unsubstituted $C_{3-6}$ cycloalkyl, or substituted or unsubstituted 3- to 6-membered heterocyclyl; or two $R^B$ taken together form a carbonyl.

In another aspect, disclosed herein is a compound of Tables I, II, III, III', VII, VIII, or IX, or a tautomer thereof, or a pharmaceutically acceptable salt thereof. In another embodiment, disclosed herein is a compound of Formula I, Formula I', Formula Ia, Formula Ia', Formula Ib, Formula Ib' Formula Ic, Formula Ic', Formula ID, Formula Id', or Formula Id", or a tautomer thereof, or a pharmaceutically acceptable salt thereof. In another embodiment, disclosed herein is a compound of Formula II, Formula IIa, Formula IIb, Formula IIc, Formula IId, Formula IIe, or Formula II', or a tautomer thereof, or a pharmaceutically acceptable salt thereof. In another embodiment, disclosed herein is a compound of Formula III, Formula IIIa, Formula IIIb, Formula IIIc, Formula IIId, Formula IIIe, or Formula III', or a tautomer thereof, or a pharmaceutically acceptable salt thereof.

In another embodiment, disclosed herein is a compound of Formula IV, Formula IVa, Formula V, Formula VI, Formula VIa, Formula VIb, Formula VIc, Formula VId, Formula VII, Formula VIIa, or Formula VIIb, or a tautomer thereof, or a pharmaceutically acceptable salt thereof. In another embodiment, disclosed herein is a compound of Formula VIII or Formula IX, or a tautomer thereof, or a pharmaceutically acceptable salt thereof.

In another aspect, disclosed herein is a pharmaceutical composition comprising a compound disclosed herein, or a pharmaceutically acceptable salt, or solvate thereof, and at least one pharmaceutically acceptable excipient.

In another aspect, disclosed herein is a method of modulating the activity of the prostaglandin E2 receptor 2 (EP2) in a mammal comprising administering to the mammal a compound disclosed herein, or a pharmaceutically acceptable salt, or solvate thereof.

In another embodiment, disclosed herein is a method of treating a disease or condition that would benefit from the modulation of prostaglandin E2 receptor 2 (EP2) activity comprising administering to the mammal a compound disclosed herein, or a pharmaceutically acceptable salt, or solvate thereof.

Any combination of the groups described above for the various variables is contemplated herein. Throughout the specification, groups and substituents thereof are chosen by one skilled in the field to provide stable moieties and compounds.

In another aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, or nasal administration. In some embodiments, the pharmaceutical composition is in the form of a tablet, a pill, a capsule, a liquid, a suspension, a dispersion, a solution, or an emulsion.

In another aspect, described herein is a method of modulating the activity of the prostaglandin E2 receptor 2 (EP2) in a mammal, comprising administering to the mammal a compound described herein, or a pharmaceutically acceptable salt, or solvate thereof.

In yet another aspect, described herein is a method of treating a disease or condition that would benefit from the modulation of prostaglandin E2 receptor 2 (EP2) activity comprising administering to the mammal a compound of described herein, or a pharmaceutically acceptable salt, or solvate thereof.

Other objects, features, and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Prostaglandins act on prostaglandin receptors such as the prostaglandin DP1 receptor (DP1), prostaglandin DP2 receptor (DP2), prostaglandin EP1 receptor (EP1), prostaglandin EP2 receptor (EP2), prostaglandin EP3 receptor (EP3), prostaglandin EP4 receptor (EP4), prostaglandin F2a receptor (FP1), prostacyclin 12 receptor (IP), and thromboxane A2 receptor (TP), or a combination thereof.

Prostaglandin E2 (PGE2) is a metabolite of arachidonic acid, synthesized by the action of cyclooxygenase and prostaglandin E synthase. PGE2, which is produced in nearly all organs and tissues, has a variety of physiological effects, including mucosal protection, induction of gastric acid secretion in stomach, generation of fever, hyperalgesia, inflammation and immunity. The actions of $PGE_2$ are mediated by four receptors, EP1, EP2, EP3 and EP4. PGE2 has affinity not only for all four EP receptor subtypes but also for other prostanoid receptors, such as the PGE2 DP1 receptor.

PGE2 is a downstream product of the cyclooxy-genase 2 (COX-2) pathway and a major modulator of inflammation.

EP2 is a G-protein coupled receptor that, when bound to PGE2, mobilizes Gs proteins and initiates signaling cascades involving adenylyl cyclase (and thereby elevates cAMP) and protein kinase A (PKA). Coupling of EP2 to Gs proteins stimulates adenylate cyclase and their activation increases intracellular cAMP levels. This signaling pathway has implications on inflammation, pain, immunoregulation, mitogenesis, plasticity, and cell injury. EP2 also interacts with β-arrestin/JNK pathways, which pathway can affect proliferation and metastasis.

Expression of EP2 receptors has been demonstrated in a broad range of cell types and tissues, including lung, gastrointestinal tract, kidney, uterus, myeloid and thymus and has been linked with PGE2-mediated vasodilation and smooth muscle relaxation in pulmonary, gastrointestinal and reproductive tracts.

In some embodiments, compounds described herein modulate the activity of EP2. In some embodiments, compounds described herein inhibit or reduce the magnitude of inflammatory PGE2 signalling through the EP2 receptor. In some embodiments, compounds described herein reduce or abolish one or more symptoms associated with an EP2 mediated disease or disorder (e.g., an EP2 mediated inflammatory disease or disorder.)

Aberrant EP2 expression is observed in several forms of cancers, including cancers of the colon, prostate, liver, and breast. EP2 activity (e.g., over-activity) has also been associated with risk factors for cancer including chronic inflammation, immunoregulation, angiogenesis, metastasis, and multidrug resistance. In some embodiments, disclosed herein are methods of treating cancer with a compound disclosed herein. The term "cancer" as used herein, refers to an abnormal growth of cells that tend to proliferate in an uncontrolled way and, in some cases, to metastasize (spread).

In some embodiments, compounds described herein reduce one or more symptoms of an EP2 mediated cancer. In some embodiments, compounds described herein reduce or reverse the progression of an EP2 mediated cancer. In some embodiments, the cancer is a solid tumor. In some embodiments, the cancer is colon cancer.

In some embodiments, EP2 signaling (i.e., through activation by $PGE_2$), contributes to inflammation by enhancing edema and leukocyte infiltration from increased vascular permeability, thereby allowing more blood flow into an inflamed area of the body. In some embodiments, modulation of EP2 function has effects on B lymphocytes, T lymphocytes, cytotoxic T-cell function, or a combination thereof. I In some embodiments, disclosed herein are methods of treating inflammation with a compound disclosed herein. In some embodiments, the compounds disclosed herein are used in the reduction or suppression of inflammation in a mammal. In some embodiments, the compounds disclosed herein are used in the treatment or prevention of inflammation-related conditions (e.g., allergies, pain, and the like).

In some embodiments, disclosed herein is a method of reducing inflammation in a tissue comprising contacting an inflamed cell or tissue with a compound disclosed herein, in an amount sufficient to decrease or inhibit the inflammation. In some embodiments, the inflammation includes an inflammatory or allergic condition.

In some embodiments, the compounds disclosed herein reduce one or more symptoms of a neuroinflammatory disease or disorder comprising reducing the activity of EP2 (e.g., by contacting the inflamed tissue with an EP2 antagonist disclosed herein). In some embodiments, disclosed herein is a method of reducing or halting the progression of a neuroinflammatory disease or disorder comprising administering a compound disclosed herein to an individual (e.g., a mammal, a human, etc.) in need thereof.

In some embodiments, reducing inflammation, or treatment of an inflammatory condition, includes reducing or inhibiting the activity of EP2. In some embodiments, reducing inflammation, or treatment of an inflammatory condition, includes administering an antagonist of EP2 (e.g., an EP2 antagonist disclosed herein).

In some embodiments, the inflammatory condition is an allergic condition. In some embodiments, the inflammatory condition is asthma. In some embodiments, the inflammatory condition is anaphylaxis. In some embodiments, the inflammatory condition is chronic inflammation. In some embodiments, disclosed herein is a method of treating chronic inflammation comprising administering an EP2 antagonist (e.g., a compound disclosed herein) to the individual in need thereof.

Compounds

Compounds described herein, including pharmaceutically acceptable salts, prodrugs, active metabolites and pharmaceutically acceptable solvates thereof, are EP2 antagonists. In some embodiments, a compound of any one of the formulae described herein, or a pharmaceutically acceptable salt thereof, is an EP2 antagonist.

In one embodiment, provided herein is a compound of Formula (I) or Formula (I'):

Formula (I)

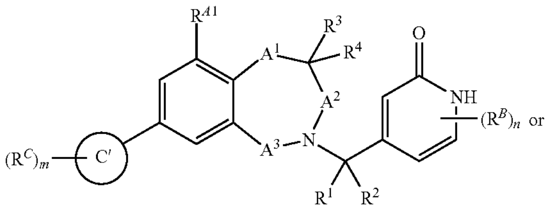

(Formula (I'))

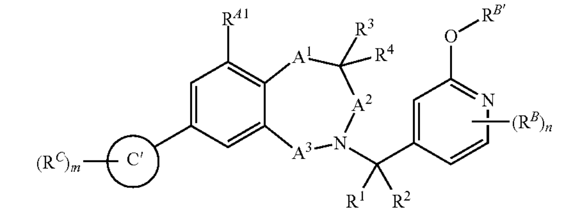

or a tautomer thereof, or a pharmaceutically acceptable salt thereof, wherein:

$R^1$ and $R^2$ are each independently hydrogen, deuterium, halogen, or $C_{1-4}$ alkyl;

$A^1$ is —O—, —$CR^5R^6$—, —S—, —S(=O)$_2$— or absent;

$A^2$ is —$CR^7R^8$— or —S(=O)$_2$—;

$A^3$ is —$CR^9R^{10}$— or absent;

$R^3$ and $R^4$ are each independently hydrogen, deuterium, halogen, or $C_{1-4}$ alkyl;

$R^5$ and $R^6$ are each independently hydrogen, deuterium, halogen, or $C_{1-4}$ alkyl; or $R^5$ and $R^6$ are taken together with the carbon atom to which they are attached to form an oxetane;

$R^7$ and $R^8$ are each independently hydrogen, deuterium, halogen, $C_{1-4}$ alkyl, or $C_{1-4}$ haloalkyl; or $R^7$ and $R^8$ are taken together with the carbon atom to which they are attached to form a cyclopropane or an oxetane;

$R^9$ and $R^{10}$ are each independently hydrogen, deuterium, halogen, or $C_{1-4}$ alkyl; or $R^9$ and $R^{10}$ are taken together with the carbon atom to which they are attached to form an oxetane;

$R^{A1}$ is halogen, $C_{1-4}$ alkyl, or cyclopropyl;

$R^B$ is halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —OH, —O($C_{1-4}$ alkyl), —O($C_{1-4}$ haloalkyl), —SH, —S($C_{1-4}$ alkyl), —SO($C_{1-4}$ alkyl), —S(O)$_2$($C_{1-4}$ alkyl), —S(O)$_2$$NH_2$, —S($O_2$)$NHCH_3$, substituted or unsubstituted $C_{3-6}$ cycloalkyl, or substituted or unsubstituted 3- to 6-membered heterocycloalkyl; or two $R^B$ taken together form a carbonyl;

$R^{B'}$ is hydrogen or $C_{1-4}$ alkyl;

$R^C$ is halogen, —CN, —$C_{1-4}$ alkyl, —$C_{1-4}$ haloalkyl, —OH, —O($C_{1-4}$ alkyl), —O($C_{1-4}$ haloalkyl), —$NH_2$, —NH($C_{1-4}$ alkyl), —N($C_{1-4}$ alkyl)$_2$, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, substituted or unsubstituted $C_{3-6}$ cycloalkyl, or substituted or unsubstituted 3- to 6-membered heterocycloalkyl; or two $R^B$ taken together form a carbonyl;

m is 0 to 3;

n is 0 to 3; and

Ring C' is selected from the group consisting of:

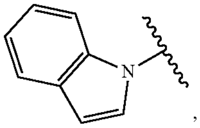
,
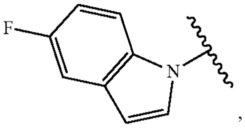
,
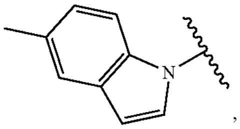
,
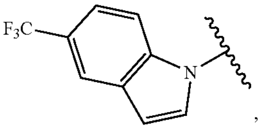
,
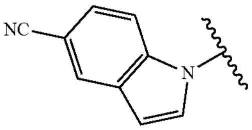
,
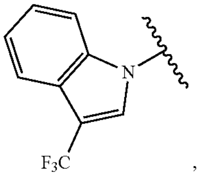
,
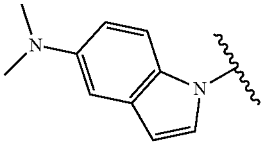
,
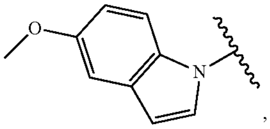
,
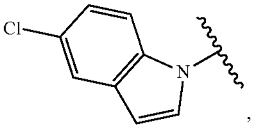
,
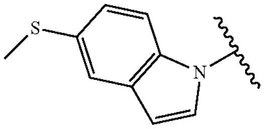
,
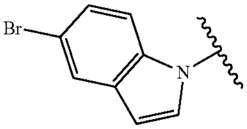
, -continued

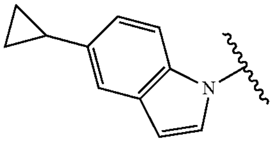
,
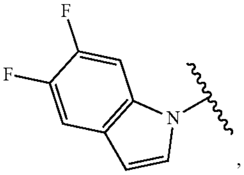
,
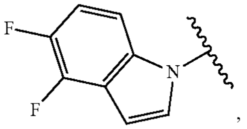
,
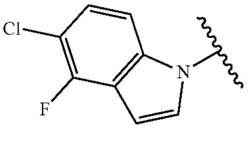
,
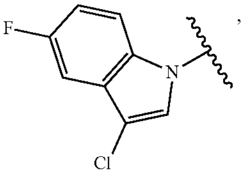
,
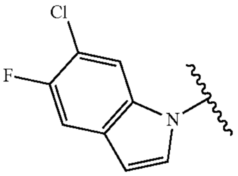
,
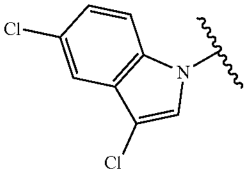
,
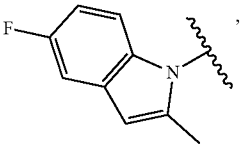
,
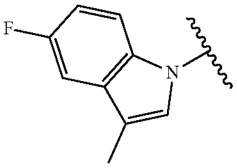
,
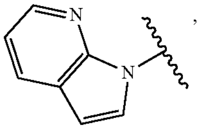
,
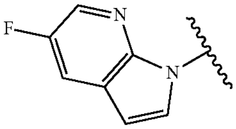
,
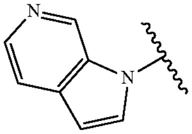
,
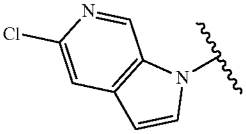
,
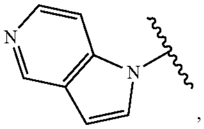
,
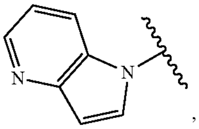
,
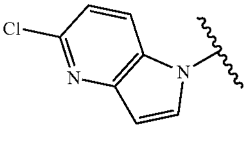
,
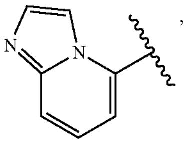
,
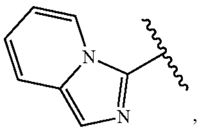
,
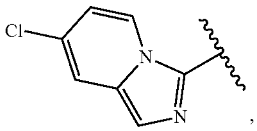
,
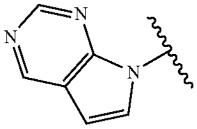
,
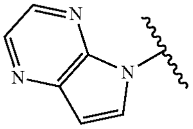
, -continued

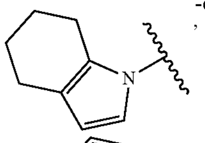,
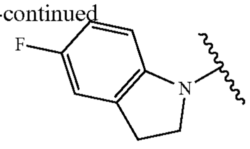,
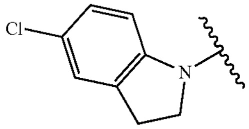,
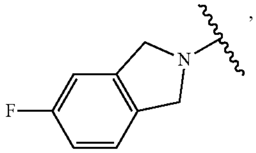,
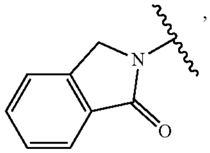,
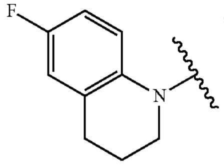,
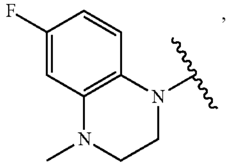,
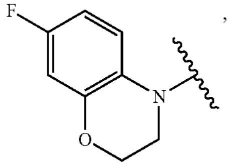,
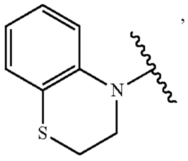,
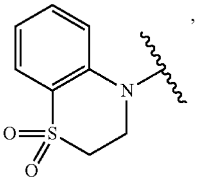,
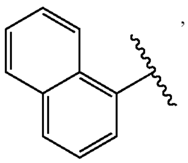,
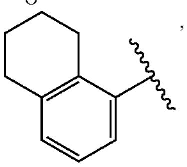,
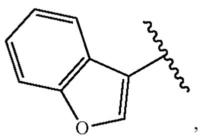, and
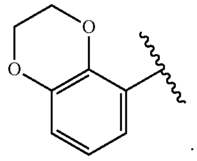.

For any and all of the embodiments, substituents are selected from among a subset of the listed alternatives. For example, $A^1$ can be —O—, —$CR^5R^6$—, —S—, —S(═O)$_2$— or absent. In some embodiments, $A^1$ is —O—. In some embodiments, $A^1$ is —$CR^5R^6$—. In some embodiments, $A^1$ is —S—. In some embodiments, $A^1$ is —S(═O)$_2$—. In some embodiments, $A^1$ is absent. Similarly, in some embodiments, $A^2$ is —$CR^7R^8$— or —S(═O)$_2$—. In some embodiments, $A^2$ is —$CR^7R^8$—. In some embodiments, $A^2$ is —S(═O)$_2$—. In some embodiments, $A^3$ is —$CR^9R^{10}$— or absent. In some embodiments, $A^3$ is —$CR^9R^{10}$—. In some embodiments, $A^3$ is absent.

In some embodiments, $A^1$ is —O—, —$CR^5R^6$—, —S—, —S(═O)$_2$, or absent; $A^2$ is —$CR^7R^8$—; and $A^3$ is —$CR^9R^{10}$—. In some embodiments, $A^1$ is —O—, —S—, or —S(═O)$_2$; $A^2$ is —$CR^7R^8$—; and $A^3$ is —$CR^9R^{10}$—. In some embodiments, $A^1$ is —O—; $A^2$ is —$CR^7R^8$—; and $A^3$ is —$CR^9R^{10}$—. In some embodiments, $A^1$ is —S—; $A^2$ is —$CR^7R^8$—; and $A^3$ is —$CR^9R^{10}$—. In some embodiments, $A^1$ is —S(═O)$_2$; $A^2$ is —$CR^7R^8$—; and $A^3$ is —$CR^9R^{10}$—. In some embodiments, $A^1$ is absent; $A^2$ is —$CR^7R^8$—; and $A^3$ is —$CR^9R^{10}$—. In some embodiments, $A^1$ is —O—; $A^2$ is —S(═O)$_2$—; and $A^3$ is —$CR^9R^{10}$—. In some embodiments, $A^1$ is —O—; $A^2$ is —$CR^7R^8$—; and $A^3$ is absent.

In some embodiments: $A^1$ is —O—, —S—, or —S(═O)$_2$—; $A^2$ is —$CR^7R^8$—; and $A^3$ is —$CR^9R^{10}$—; or $A^1$ is —O—; $A^2$ is —$CR^7R^8$— or —S(═O)$_2$—; and $A^3$ is —$CR^9R^{10}$—; or $A^1$ is absent; $A^2$ is —$CR^7R^8$—; and $A^3$ is —$CR^9R^{10}$—; or $A^1$ is —O—, —$CR^5R^6$—, or absent; $A^2$ is —$CR^7R^8$—; and $A^3$ is absent.

In some embodiments, $A^1$ is —O—, or —S(═O)$_2$—; $A^2$ is —$CR^7R^8$—; and $A^3$ is —$CR^9R^{10}$—; or A1 is —O—; $A^2$ is —$CR^7R^8$— or —S(═O)$_2$—; and $A^3$ is —$CR^9R^{10}$—. In some embodiments, $A^1$ is absent; $A^2$ is —$CR^7R^8$—; and $A^3$ is —$CR^9R^{10}$—; or $A^1$ is —O—, —$CR^5R^6$—, or absent; $A^2$ is —$CR^7R^8$—; and $A^3$ is absent.

In some embodiments, $A^1$ is —$CR^5R^6$—; and $R^5$ and $R^6$ are each independently hydrogen, deuterium, halogen, or $C_{1-4}$ alkyl; or $R^5$ and $R^6$ are taken together with the carbon atom to which they are attached to form an oxetane. In some embodiments, $R^5$ and $R^6$ are each independently hydrogen, deuterium, or —$CH_3$; or $R^5$ and $R^6$ are taken together with the carbon atom to which they are attached to form an oxetane. In some embodiments, $R^5$ and $R^6$ are each independently hydrogen, deuterium, or —$CH_3$. In some embodiments, $R^5$ is hydrogen and $R^6$ is hydrogen, deuterium, or —$CH_3$. In some embodiments, $R^5$ and $R^6$ are each independently hydrogen or deuterium. In some embodiments, $R^5$ and $R^6$ are each hydrogen. In some embodiments, $R^5$ and $R^6$ are each deuterium. In some embodiments, $R^5$ and $R^6$ are each —$CH_3$. In some embodiments, $R^5$ and $R^6$ are taken together with the carbon atom to which they are attached to form an oxetane. In some embodiments, $R^5$ and $R^6$ are each independently hydrogen or deuterium; or $R^5$ and $R^6$ are taken together with the carbon atom to which they are attached to form an oxetane.

In some embodiments, $A^2$ is —$CR^7R^8$—; and $R^7$ and $R^8$ are each independently hydrogen, deuterium, halogen, $C_{1-4}$ alkyl, or $C_{1-4}$ haloalkyl; or $R^7$ and $R^8$ are taken together with the carbon atom to which they are attached to form a cyclopropane or an oxetane. In some embodiments, $R^7$ and $R^8$ are each independently hydrogen, deuterium, —$CH_3$, or $CF_3$; or $R^7$ and $R^8$ are taken together with the carbon atom to which they are attached to form a cyclopropane or an oxetane. In some embodiments, $R^7$ and $R^8$ are each independently hydrogen, deuterium, —$CH_3$, or —$CF_3$. In some embodiments, $R^7$ and $R^8$ are each independently hydrogen, deuterium, or —$CH_3$. In some embodiments, $R^7$ is hydrogen and $R^8$ is hydrogen, deuterium, —$CH_3$, or —$CF_3$. In some embodiments, $R^7$ is hydrogen and $R^8$ is hydrogen, deuterium, or —$CH_3$. In some embodiments, $R^7$ and $R^8$ are each independently hydrogen or deuterium. In some embodiments, $R^7$ and $R^8$ are each hydrogen. In some embodiments, $R^7$ and $R^8$ are each deuterium. In some embodiments, $R^7$ and $R^8$ are each —$CH_3$. In some embodiments, $R^7$ and $R^8$ are taken together with the carbon atom to which they are attached to form an oxetane. In some embodiments, $R^7$ and $R^8$ are taken together with the carbon atom to which they are attached to form a cyclopropane. In some embodiments, $R^7$ and $R^8$ are each independently hydrogen or deuterium; or $R^7$ and $R^8$ are taken together with the carbon atom to which they are attached to form an oxetane.

In some embodiments, $A^2$ is —$CR^7R^8$— or —S(═O)$_2$. In some embodiments, $A^2$ is —S(═O)$_2$. In some embodiments, $A^2$ is —$CR^7R^8$— or —S(═O)$_2$; and $A^3$ is —$CR^9R^{10}$—. In some embodiments, $A^2$ is —S(═O)$_2$ and $A^3$ is —$CR^9R^{10}$—. In some embodiments, $A^1$ is —O— and $A^2$ is —$CR^7R^8$— or —S(═O)$_2$. In some embodiments, $A^1$ is —O— and $A^2$ is —S(═O)$_2$. In some embodiments, $A^1$ is —O—; $A^2$ is —S(═O)$_2$—; and $A^3$ is —$CR^9R^{10}$. In some embodiments, $A^1$ is —O—; $A^2$ is —$CR^7R^8$ or —S(═O)$_2$—; and $A^3$ is —$CR^9R^{10}$.

In some embodiments, $A^3$ is —$CR^9R^{10}$—; and $R^9$ and $R^{10}$ are each independently hydrogen, deuterium, halogen, or $C_{1-4}$ alkyl; or $R^9$ and $R^{10}$ are taken together with the carbon atom to which they are attached to form an oxetane. In some embodiments, $R^9$ and $R^{10}$ are each independently hydrogen, deuterium, or —$CH_3$; or $R^9$ and $R^{10}$ are taken together with the carbon atom to which they are attached to form an oxetane. In some embodiments, $R^9$ and $R^{10}$ are each independently hydrogen, deuterium, or —$CH_3$. In some embodiments, $R^9$ is hydrogen and $R^{10}$ is hydrogen, deuterium, or —$CH_3$. In some embodiments, $R^9$ and $R^{10}$ are each independently hydrogen or deuterium. In some embodiments, $R^9$ and $R^{10}$ are each hydrogen. In some embodiments, $R^9$ and $R^{10}$ are each deuterium. In some embodiments, $R^9$ and $R^{10}$ are taken together with the carbon atom to which they are attached to form an oxetane. In some embodiments, $R^9$ and $R^{10}$ are each independently hydrogen or deuterium; or $R^9$ and $R^{10}$ are taken together with the carbon atom to which they are attached to form an oxetane.

In some embodiments, $R^5$ and $R^6$ are each independently hydrogen, deuterium, or —$CH_3$; or $R^5$ and $R^6$ are taken together with the carbon atom to which they are attached to form an oxetane; $R^7$ and $R^8$ are each independently hydrogen, deuterium, or —$CH_3$; or $R^7$ and $R^8$ are taken together with the carbon atom to which they are attached to form an oxetane; and $R^9$ and $R^{10}$ are each independently hydrogen, deuterium, or —$CH_3$; or $R^9$ and $R^{10}$ are taken together with the carbon atom to which they are attached to form an oxetane.

In some embodiments, $A^3$ is —$CR^9R^{10}$— or absent. In some embodiments, $A^3$ is absent. In some embodiments, $A^1$ is —O—; and $A^3$ is —$CR^9R^{10}$— or absent. In some embodiments, $A^1$ is —O—; and $A^3$ is absent. In some embodiments, $A^2$ is —$CR^7R^8$— or —S(═O)$_2$—; and $A^3$ is —$CR^9R^{10}$— or absent. In some embodiments, $A^2$ is —$CR^7R^8$—; and $A^3$ is —$CR^9R^{10}$— or absent. In some embodiments, $A^2$ is —$CR^7R^8$—; and $A^3$ is absent. In some embodiments, $A^1$ is —O—; $A^2$ is —$CR^7R^8$— or —S(═O)$_2$—; and $A^3$ is —$CR^9R^{10}$— or absent. In some embodiments, $A^1$ is —O—; $A^2$ is —$CR^7R^8$— or —S(═O)$_2$—; and $A^3$ is absent. In some embodiments, $A^1$ is —O—; $A^2$ is —$CR^7R^8$—; and $A^3$ is absent.

In some embodiments, $R^3$ and $R^4$ are each independently hydrogen, deuterium, halogen, or $C_{1-4}$ alkyl. In some embodiments, $R^3$ and $R^4$ are each independently hydrogen, deuterium, or —$CH_3$. In some embodiments, $R^3$ and $R^4$ are each independently hydrogen or deuterium. In some embodiments, $R^3$ and $R^4$ are each independently hydrogen. In some embodiments, $R^3$ and $R^4$ are each independently deuterium.

In some embodiments, $R^{A1}$ is halogen, $C_{1-4}$ alkyl, or cyclopropyl. In some embodiments, $R^{A1}$ is halogen. In some embodiments, $R^{A1}$ is —F, —Cl, —Br, or —I. In some embodiments, $R^{A1}$ is —F or —Cl. In some embodiments, $R^{A1}$ is —F. In some embodiments, $R^{A1}$ is —Cl. In some embodiments, $R^{A1}$ is $C_{1-4}$ alkyl. In some embodiments, $R^{A1}$ is —$CH_3$, —$CH_2CH_3$, —$CH(CH_3)_2$, —$CH_2CH_2CH_3$, or —$C(CH_3)_3$. In some embodiments, $R^{A1}$ is —$CH_3$, —$CH_2CH_3$, or —$CH(CH_3)_2$. In some embodiments, $R^{A1}$ is —$CH_3$. In some embodiments, $R^{A1}$ is cyclopropyl.

In some embodiments,

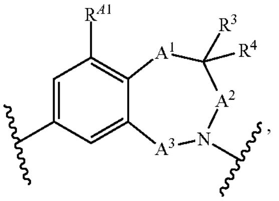

alternatively "ring A," is selected from the group consisting of:

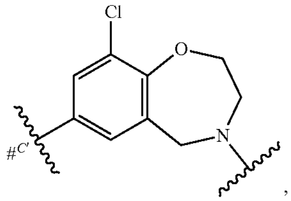

,

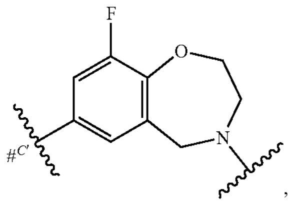

,

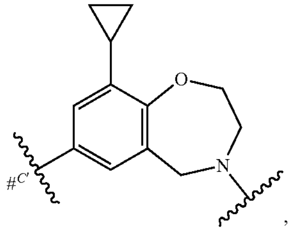

,

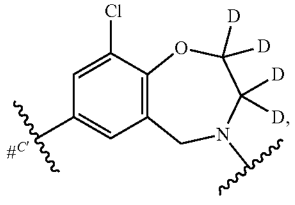

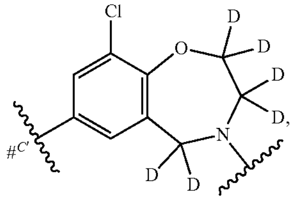

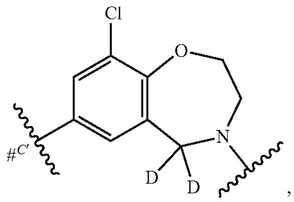

,

-continued
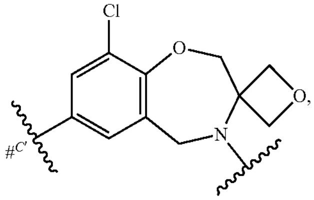
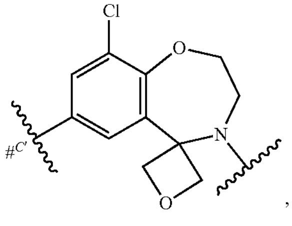
,
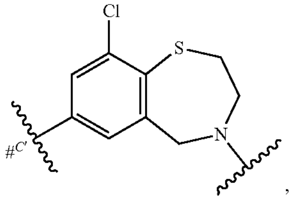
,
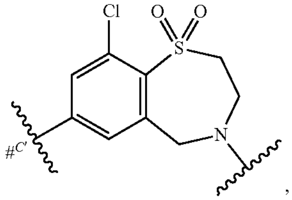
,
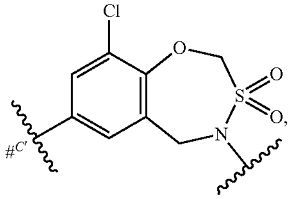
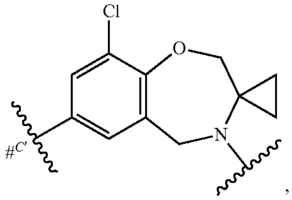
,
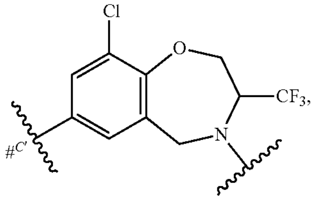
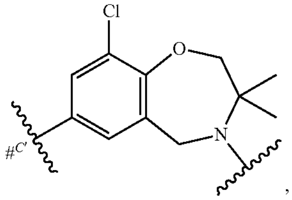
,
-continued
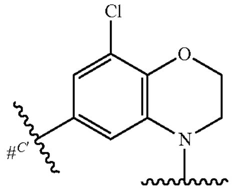
, and
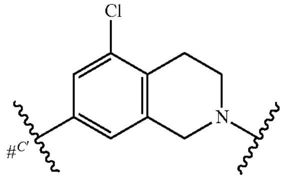
.
In some embodiments,
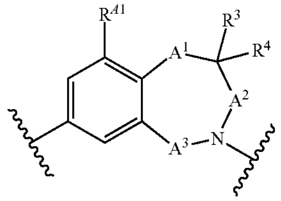
is selected from the group consisting of:
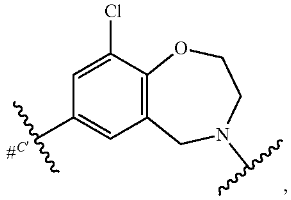
,
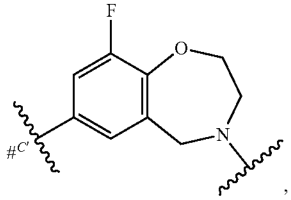
,
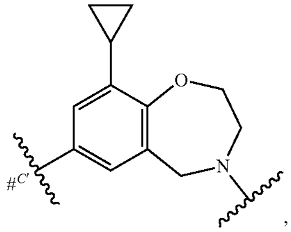
,
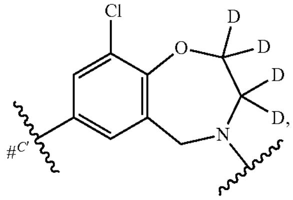

-continued

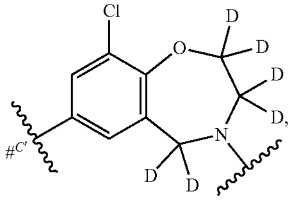

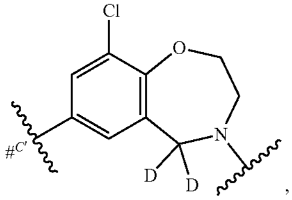

,

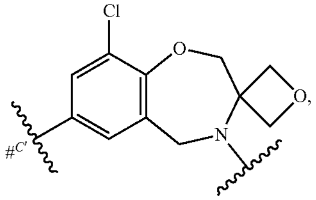

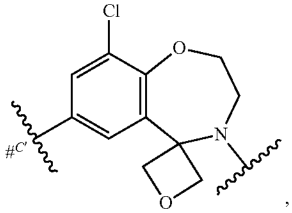

,

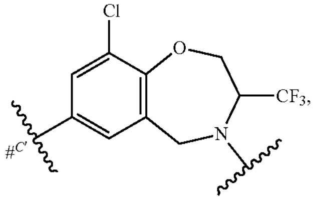

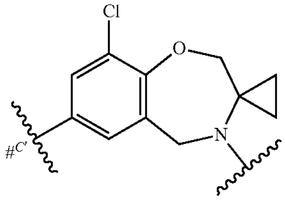

, and

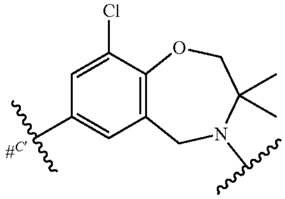

.

In some embodiments, $A^1$ is —O—; $A^2$ is —$CR^7R^8$— or —S(═O)$_2$—; and $A^3$ is —$CR^9R^{10}$—. In some embodiments, the compound of Formula (I) is a compound of Formula (Ia) or Formula (Ia'):

Formula (Ia)

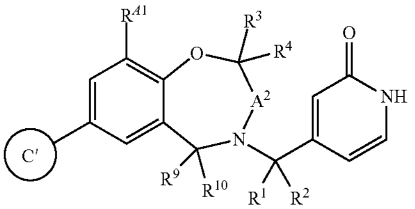

or

Formula (Ia')

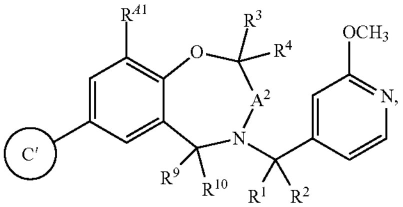

or a tautomer thereof, or a pharmaceutically acceptable salt thereof.

In some embodiments:

$R^1$, $R^2$, $R^3$, and $R^4$ are each independently hydrogen or deuterium;

$A^2$ is —$CR^7R^8$— or —S(═O)$_2$—;

$R^7$ and $R^8$ are each hydrogen or deuterium; or $R^7$ and $R^8$ are taken together with the carbon atom to which they are attached to form an oxetane;

$R^9$ and $R^{10}$ are each hydrogen or deuterium; or $R^9$ and $R^{10}$ are taken together with the carbon atom to which they are attached to form an oxetane;

$R^{A1}$ is halogen, $C_{1-4}$ alkyl, or cyclopropyl; and

Ring C' is as defined in Formula (I).

In some embodiments, the compound of Formula (I) is a compound of Formula (Ib) or Formula (Ib'):

Formula (Ib)

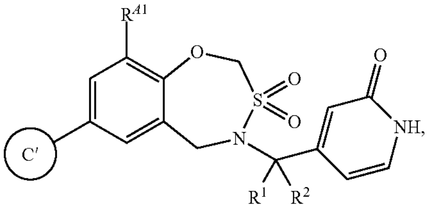

or

Formula (Ib')

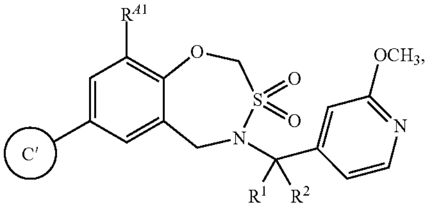

or a tautomer thereof, or a pharmaceutically acceptable salt thereof.

In some embodiments, $R^{A1}$ is halogen, $C_{1-4}$ alkyl, or cyclopropyl;

$R^1$ and $R^2$ are each independently hydrogen or deuterium; and

Ring C' is as defined in Formula (I).

In some embodiments, the compound of Formula (I) is a compound of Formula (Ic):

Formula (Ic)

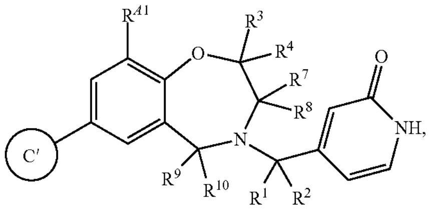

or

Formula (Ic')

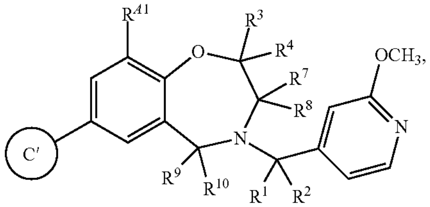

or a tautomer thereof, or a pharmaceutically acceptable salt thereof.

In some embodiments, $R^{A1}$ is halogen, $C_{1-4}$ alkyl, or cyclopropyl;

$R^1$ and $R^2$ are each independently hydrogen or deuterium; and

Ring C' is as defined in Formula (I).

In some embodiments, $R^1$, $R^2$, $R^3$, $R^4$, $R^7$, $R^8$, $R^9$, and $R^{10}$ are each independently hydrogen or deuterium;

or $R^1$, $R^2$, $R^3$, $R^4$, $R^9$, and $R^{10}$ are each independently hydrogen or deuterium; and $R^7$ and $R^8$ are taken together with the carbon atom to which they are attached to form an oxetane;

or $R^1$, $R^2$, $R^3$, $R^4$, $R^7$, and $R^8$ are each independently hydrogen or deuterium; and $R^9$ and $R^{10}$ are taken together with the carbon atom to which they are attached to form an oxetane;

and $R^{A1}$ is —F, —Cl, or cyclopropyl.

In some embodiments, $R^3$ is H; $R^4$ is H; $R^7$ is H; $R^8$ is H; $R^9$ is H; $R^{10}$ is H; and $R^{A1}$ is —F;

or $R^3$ is H; $R^4$ is H; $R^7$ is H; $R^8$ is H; $R^9$ is H; $R^{10}$ is H; and $R^{A1}$ is cyclopropyl;

or $R^3$ is D; $R^4$ is D; $R^7$ is H; $R^8$ is H; $R^9$ is H; $R^{10}$ is H; and $R^{A1}$ is —Cl;

or $R^3$ is D; $R^4$ is D; $R^7$ is D; $R^8$ is D; $R^9$ is H; $R^{10}$ is H; and $R^{A1}$ is —Cl;

or $R^3$ is H; $R^4$ is H; $R^7$ is D; $R^8$ is D; $R^9$ is H; $R^{10}$ is H; and $R^{A1}$ is —Cl;

or $R^3$ is D; $R^4$ is D; $R^7$ is D; $R^8$ is D; $R^9$ is D; $R^{10}$ is D; and $R^{A1}$ is —Cl;

or $R^3$ is H; $R^4$ is H; $R^7$ is H; $R^8$ is H; $R^9$ is D; $R^{10}$ is D; and $R^{A1}$ is —Cl;

or $R^3$ is H; $R^4$ is H; $R^7$ and $R^8$ form an oxetane; $R^9$ is H; $R^{10}$ is H; and $R^{A1}$ is —Cl;

or $R^3$ is H; $R^4$ is H; $R^7$ is H; $R^8$ is H; $R^9$ and $R^{10}$ form an oxetane; and $R^{A1}$ is —Cl.

In some embodiments, the compound of Formula (I) is a compound of Formula (Id), Formula (Id'), or Formula (Id"):

Formula (Id)

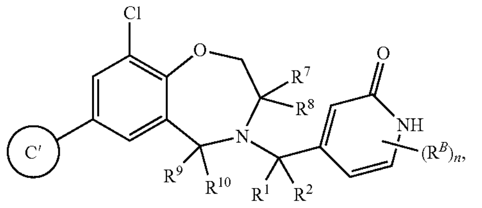

Formula (Id')

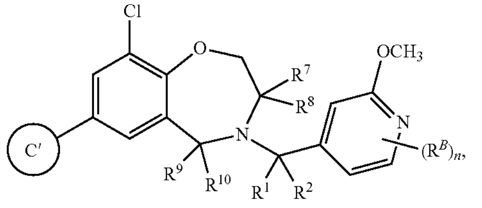

Formula (Id")

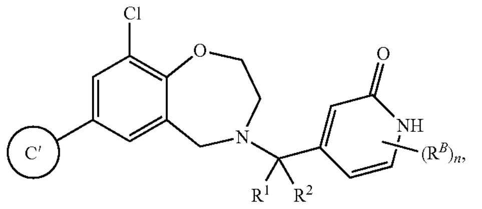

or a tautomer thereof, or a pharmaceutically acceptable salt thereof.

In some embodiments, the compound of Formula (I) is a compound of Formula (Id), Formula (Id'), or Formula (Id"), wherein:

$R^1$ and $R^2$ are each independently hydrogen, deuterium, halogen, or $C_{1-4}$ alkyl;

$R^7$ and $R^8$ are each independently hydrogen, deuterium, halogen, $C_{1-4}$ alkyl, or $C_{1-4}$ haloalkyl; or $R^7$ and $R^8$ are taken together with the carbon atom to which they are attached to form a cyclopropane or an oxetane;

$R^9$ and $R^{10}$ are each independently hydrogen, deuterium, halogen, or $C_{1-4}$ alkyl; or $R^9$ and $R^{10}$ are taken together with the carbon atom to which they are attached to form an oxetane;

$R^B$ is halogen, —CN, —$C_{1-4}$ alkyl, —$C_{1-4}$ haloalkyl, —OH, —O($C_{1-4}$ alkyl), —O($C_{1-4}$ haloalkyl), —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, substituted or unsubstituted $C_{3-6}$ cycloalkyl, or substituted or unsubstituted 3- to 6-membered heterocycloalkyl; or two $R^B$ taken together form a carbonyl;

n is 0 to 3; and

Ring C' is as defined in Formula (I).

In some embodiments: $R^1$ and $R^2$ are each independently hydrogen or deuterium; and Ring C' is selected from the group consisting of:

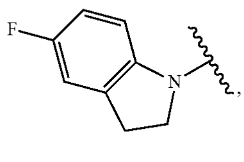,

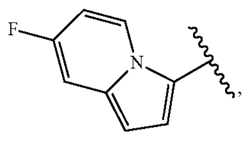,

-continued
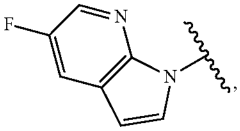, 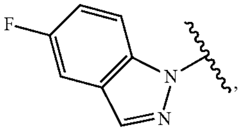, 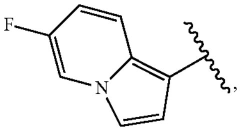, 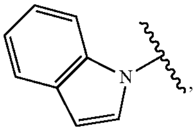, 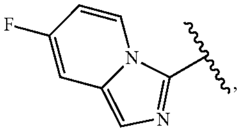, and 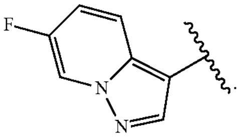.
In some embodiments, $R^1$ and $R^2$ are each hydrogen. In some embodiments, $R^1$ and $R^2$ are each deuterium.
In another embodiment is a compound of the following formula:
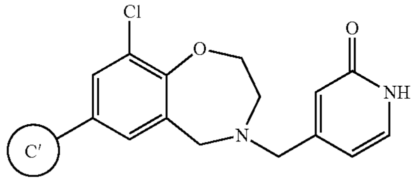
or a tautomer, or a pharmaceutically acceptable salt thereof, as disclosed in Table I.
TABLE I
Compounds 1-8.
| ID No. | Structure |  |
|---|---|---|
| 1 | 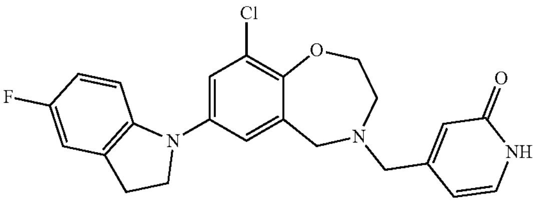 [SMILES: O=c1cc(CN2CCOc3c(Cl)cc(N4CCc5cc(F)ccc54)cc3C2)cc[nH]1] | 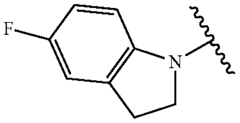 [SMILES: *N1CCc2cc(F)ccc21] |
| 2 | 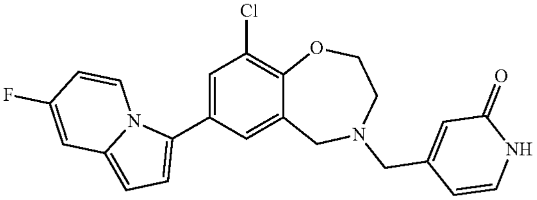 | 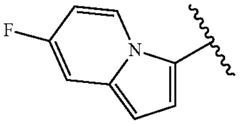 [SMILES: *c1ccc2cc(F)ccn12] |
| 3 | 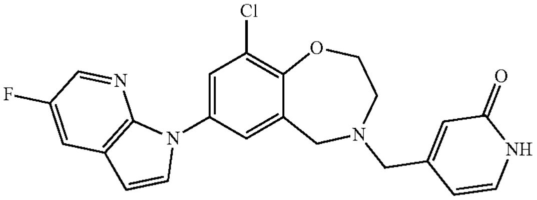 | 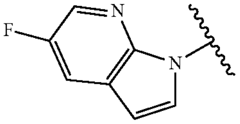 [SMILES: *n1ccc2cc(F)cnc21] |
| 4 | 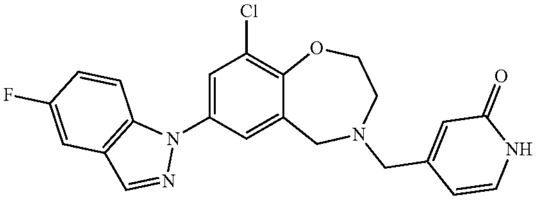 [SMILES: O=c1cc(CN2CCOc3c(Cl)cc(-n4ncc5cc(F)ccc54)cc3C2)cc[nH]1] | 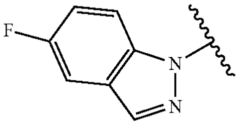 [SMILES: *n1ncc2cc(F)ccc21] |
| 5 | 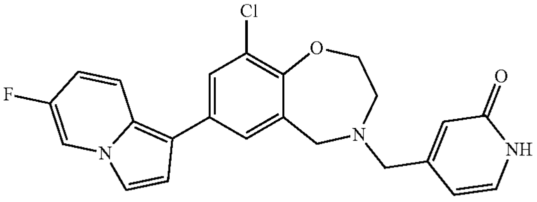 | 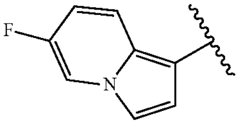 [SMILES: *c1ccn2cc(F)ccc12] |

TABLE I-continued

Compounds 1-8.

| ID No. | Structure |  |
|---|---|---|
| 6 | 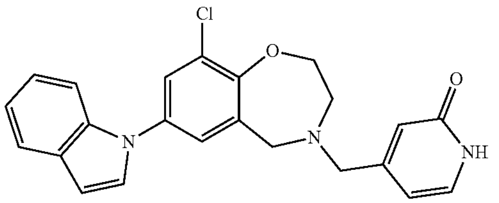 [SMILES: O=c1cc(CN2CCOc3c(Cl)cc(-n4ccc5ccccc54)cc3C2)cc[nH]1] | 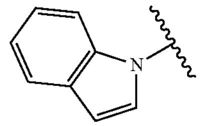 [SMILES: *n1ccc2ccccc21] |
| 7 | 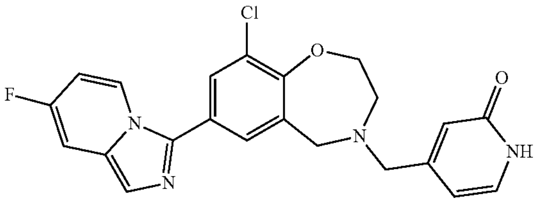 [SMILES: O=c1cc(CN2CCOc3c(Cl)cc(-c4ncc5cc(F)ccn45)cc3C2)cc[nH]1] | 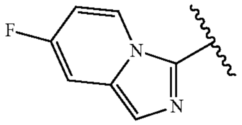 [SMILES: *c1ncc2cc(F)ccn12] |
| 8 | 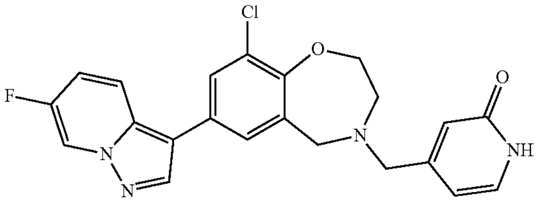 [SMILES: O=c1cc(CN2CCOc3c(Cl)cc(-c4cnn5cc(F)ccc45)cc3C2)cc[nH]1] | 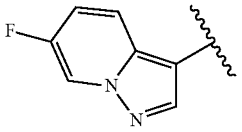 [SMILES: *c1cnn2cc(F)ccc12] |

In another embodiment, provided herein is a compound of Formula (II):

Formula (II)

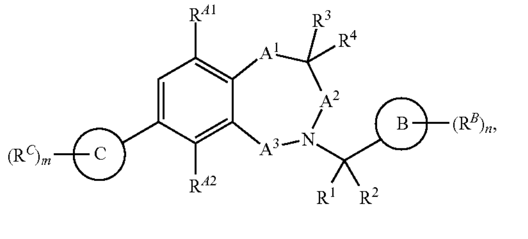

or a pharmaceutically acceptable salt thereof, wherein:

$R^1$ and $R^2$ are each independently hydrogen, deuterium, halogen, or $C_{1-4}$ alkyl;

$A^1$ is —O—, —$CR^5R^6$—, —S—, —S(═O)$_2$— or absent;

$A^2$ is —$CR^7R^8$— or —S(═O)$_2$—;

$A^3$ is —$CR^9R^{10}$— or absent;

$R^3$ and $R^4$ are each independently hydrogen, deuterium, halogen, or $C_{1-4}$ alkyl;

$R^5$ and $R^6$ are each independently hydrogen, deuterium, halogen, or $C_{1-4}$ alkyl; or $R^5$ and $R^6$ are taken together with the carbon atom to which they are attached to form an oxetane;

$R^7$ and $R^8$ are each independently hydrogen, deuterium, halogen, —CN, —$C_{1-4}$ alkyl, —$C_{1-4}$ haloalkyl, —OH, —O($C_{1-4}$ alkyl), —O($C_{1-4}$ haloalkyl), —$NH_2$, —NH($C_{1-4}$ alkyl), —N($C_{1-4}$ alkyl)$_2$, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, substituted or unsubstituted $C_{3-6}$ cycloalkyl, or substituted or unsubstituted 3- to 6-membered heterocycloalkyl; or $R^7$ and $R^8$ are taken together with the carbon atom to which they are attached to form a cyclopropane or an oxetane;

$R^9$ and $R^{10}$ are each independently hydrogen, deuterium, halogen, or $C_{1-4}$ alkyl; or $R^9$ and $R^{10}$ are taken together with the carbon atom to which they are attached to form an oxetane;

$R^{A1}$ is halogen, $C_{1-4}$ alkyl, or cyclopropyl; and $R^{A2}$ is hydrogen, deuterium, halogen, or optionally deuterated or halogenated methyl;

Ring B is $C_{3-6}$ cycloalkyl, phenyl, 5-membered heteroaryl, or 6-membered heteroaryl containing two or more nitrogen atoms; or Ring B is Ring B';

each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —NHS(O)$_2C_{1-4}$ alkyl, —OH, —O($C_{1-4}$ alkyl), —O($C_{1-4}$ haloalkyl), —SH, —S($C_{1-4}$ alkyl), —SO($C_{1-4}$ alkyl), —S(O)$_2$($C_{1-4}$ alkyl), —S(O)$_2NH_2$, —S($O_2$)$NHCH_3$, substituted or unsubstituted $C_{3-6}$ cycloalkyl, or substituted or unsubstituted 3- to 6-membered heterocyclyl; or two $R^B$ taken together form a carbonyl;

Ring C is bicyclic heterocycle having one or more nitrogen atoms; or Ring C is Ring C' each $R^C$ is independently selected from the group consisting of halogen, —CN, —$C_{1-4}$ alkyl, —$C_{1-4}$ haloalkyl, —($C_{1-4}$ alkyl)O($C_{1-4}$ alkyl), —C(O)OH, —C(O)O ($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —N($C_{1-4}$ alkyl)$_2$, —OH, —O($C_{1-4}$ alkyl), —O($C_{1-4}$ haloalkyl), —S($C_{1-4}$ alkyl), —$SO_2C_{1-4}$ alkyl, —$SO_2NHC_{1-4}$ alkyl, substituted or unsubstituted $C_{3-6}$ cycloalkyl, or substituted or unsubstituted 3- to 6-membered heterocyclyl; or two $R^B$ taken together form a carbonyl;

m is 0 to 3;

n is 0 to 3; and

Ring C' is selected from the group consisting of:

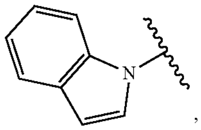,
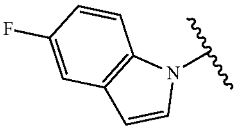,
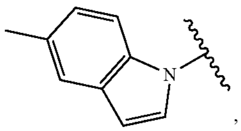,
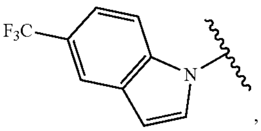,
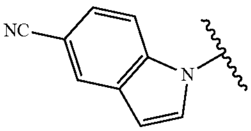,
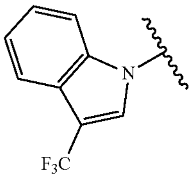,
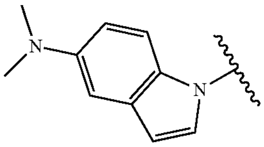,
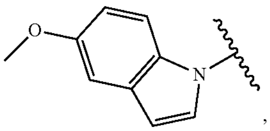,
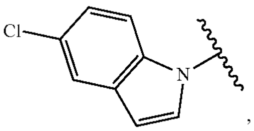,
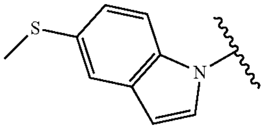,
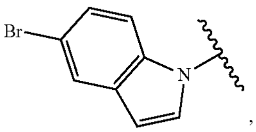,
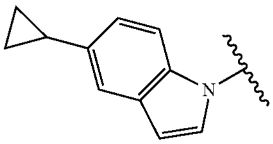,
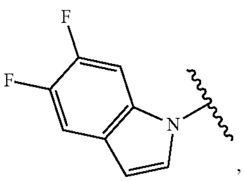,
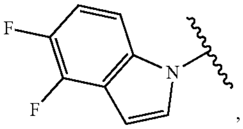, -continued

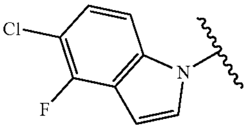,
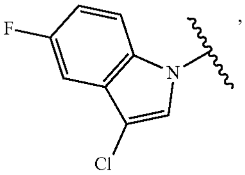,
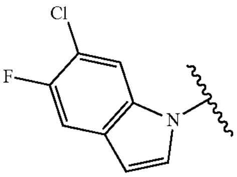,
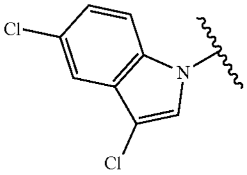,
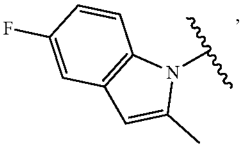,
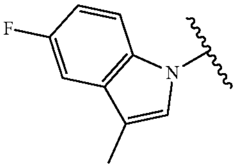,
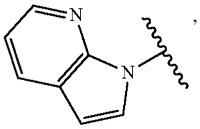,
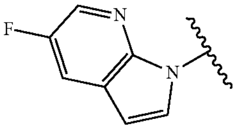,
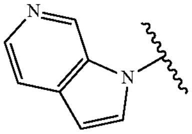,
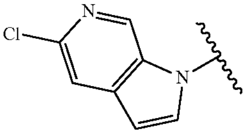,
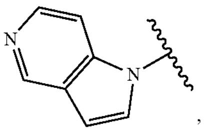,
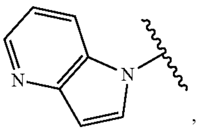,
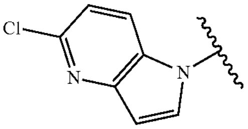,
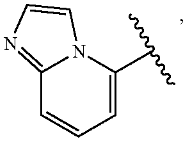,
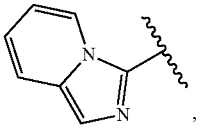,
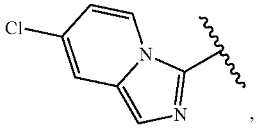,
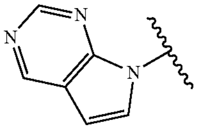,
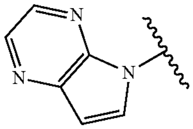,
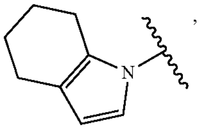,
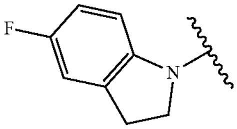,
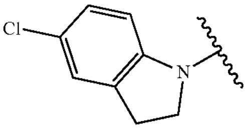,
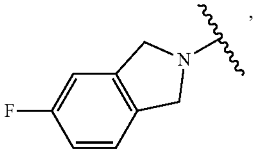

-continued

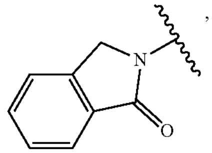, 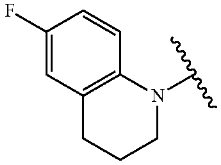,

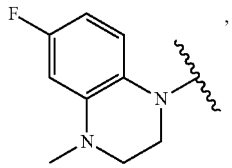, 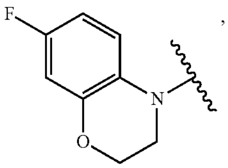,

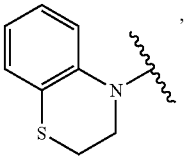, 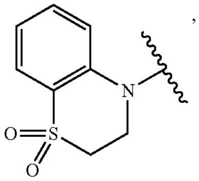,

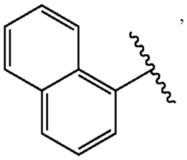, 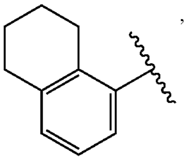,

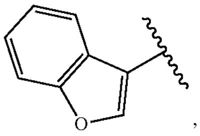, and 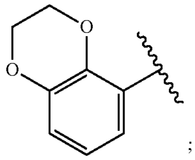;

and

In some embodiments, Ring B is $C_{3-6}$ cycloalkyl, phenyl, 5-membered heteroaryl, or 6-membered heteroaryl containing two or more nitrogen atoms; or Ring B is Ring B'. In some embodiments, Ring B is $C_{3-6}$ cycloalkyl, phenyl, 5-membered heteroaryl, or 6-membered heteroaryl containing two or more nitrogen atoms. In some embodiments, Ring B is Ring B'. In some embodiment, Ring B' is a Ring B' disclosed in Table VII. In some embodiments, Ring B' is selected from the group consisting of:

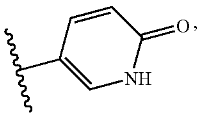 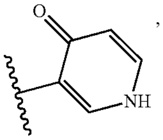,

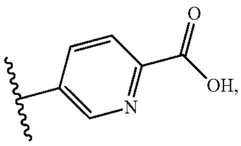

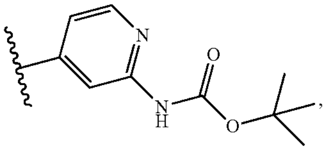

-continued

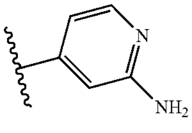 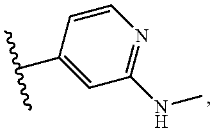

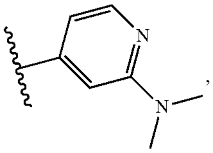 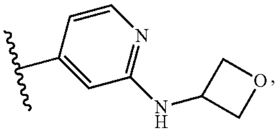

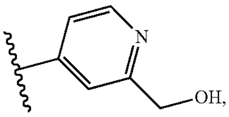 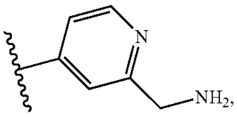

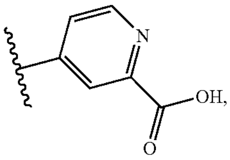 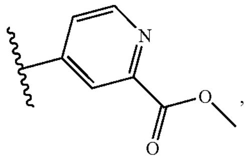

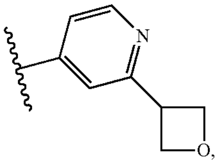 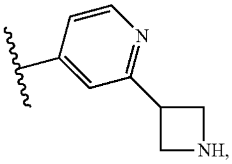

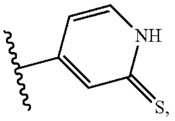 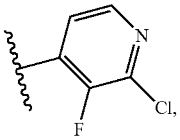

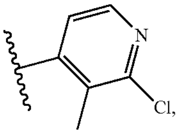 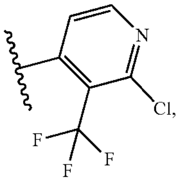

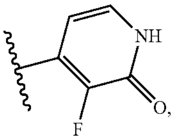 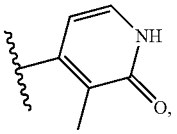

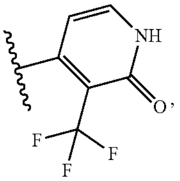 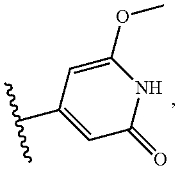

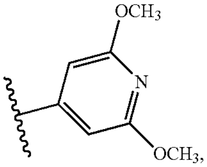 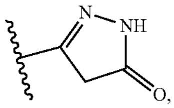

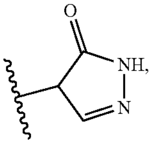 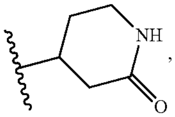 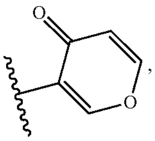

-continued

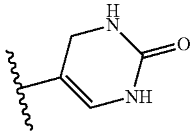,
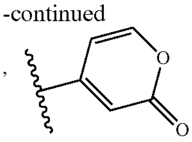,
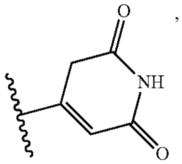,
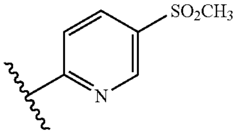,
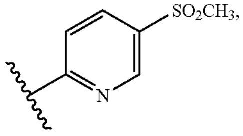,
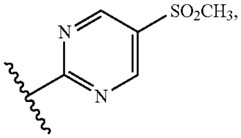,
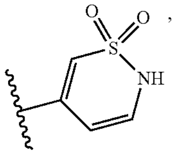,
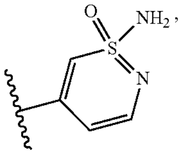,
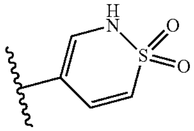,
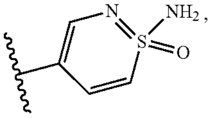,
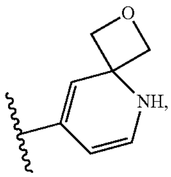,
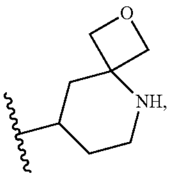,
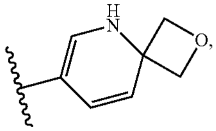,
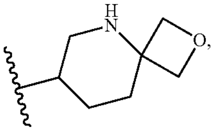 and
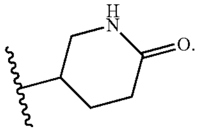.

In some embodiments, $A^1$ is —O—. In some embodiments, $A^1$ is —O—; $A^2$ is —$CR^7R^8$—; and $A^3$ is —$CR^9R^{10}$—.

In some embodiments, $A^2$ is —$CR^7R^8$—; and $R^7$ and $R^8$ are each independently hydrogen, deuterium, halogen, —CN, —$C_{1-4}$ alkyl, —$C_{1-4}$ haloalkyl, —OH, —O($C_{1-4}$ alkyl), —O($C_{1-4}$ haloalkyl), —$NH_2$, —NH($C_{1-4}$ alkyl), —N($C_{1-4}$ alkyl)$_2$, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, substituted or unsubstituted $C_{3-6}$ cycloalkyl, or substituted or unsubstituted 3- to 6-membered heterocycloalkyl; or $R^7$ and $R^8$ are taken together with the carbon atom to which they are attached to form a cyclopropane or an oxetane. In some embodiments, $A^2$ is —$CR^7R^8$—; and $R^7$ and $R^8$ are each independently hydrogen, deuterium, halogen, $C_{1-4}$ alkyl, or $C_{1-4}$ haloalkyl; or $R^7$ and $R^8$ are taken together with the carbon atom to which they are attached to form a cyclopropane or an oxetane.

In some embodiments, $A^3$ is —$CR^9R^{10}$—; and $R^9$ and $R^{10}$ are each independently hydrogen, deuterium, halogen, or $C_{1-4}$ alkyl; or $R^9$ and $R^{10}$ are taken together with the carbon atom to which they are attached to form an oxetane. In some embodiments, $A^3$ is —$CR^9R^{10}$—; and $R^9$ and $R^{10}$ are each independently hydrogen, deuterium, or methyl. In some embodiments, $R^9$ and $R^{10}$ are each independently hydrogen. In some embodiments, $R^9$ and $R^{10}$ are each independently deuterium. In some embodiments, $R^9$ is hydrogen and $R^{10}$ is methyl.

In another embodiment, is a compound of Formula (IIa):

Formula (IIa)

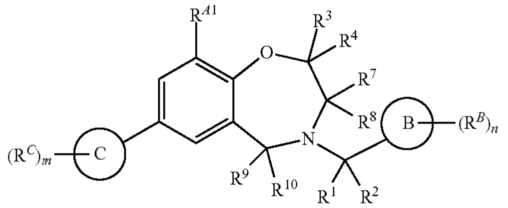

or a pharmaceutically acceptable salt thereof.

In some embodiments, Ring C is a bicyclic heteroaryl having one or more nitrogen atoms. In some embodiments, Ring C is Ring C'. In some embodiments, Ring C is a

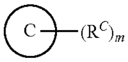

group of Table III. In some embodiments, Ring C is a substituted indole (e.g., haloindole or haloalkyl indole, (e.g., fluoroindole)).

In some embodiments, Ring B is $C_{3-6}$ cycloalkyl, phenyl, 5-membered heteroaryl, or 6-membered heteroaryl containing two or more nitrogen atoms. In some embodiments, Ring B is $C_{3-6}$ cycloalkyl, phenyl, 5- or 6-membered heteroaryl containing two or more nitrogen atoms.

In some embodiments, Ring B is $C_{3-6}$ cycloalkyl. In some embodiments, Ring B is a substituted or unsubstituted cyclopropyl. In some embodiments, Ring B is a substituted or unsubstituted cyclobutyl. In some embodiments, Ring B is a substituted or unsubstituted cyclopentyl. In some embodiments, Ring B is a substituted or unsubstituted cyclohexyl. In some embodiments, Ring B is phenyl. In some embodiments, Ring B is 5-membered heteroaryl. In some embodiments, Ring B is a 5- or 6-membered heteroaryl containing two or more nitrogen atoms. In some embodiments, Ring B is a 5-membered heteroaryl containing two or more nitrogen atoms. In some embodiments, Ring B is a 6-membered heteroaryl containing two or more nitrogen atoms.

In some embodiments, Ring B is a substituted or unsubstituted pyrazole, substituted or unsubstituted pyrazolidinone, substituted or unsubstituted imidazole, substituted or unsubstituted imidazolidinone, or a substituted or unsubstituted triazole. In some embodiments, Ring B is a substituted or unsubstituted pyrazole. In some embodiments, Ring B is a substituted or unsubstituted pyrazolidinone. In some embodiments, Ring B is a substituted or unsubstituted imidazole. In some embodiments, Ring B is a substituted or unsubstituted triazole.

In some embodiments, Ring B is a substituted or unsubstituted pyrimidine, substituted or unsubstituted pyrimidone, substituted or unsubstituted pyridazine, substituted or unsubstituted pyridazinone, substituted or unsubstituted pyrazine, substituted or unsubstituted pyrazinone, substituted or unsubstituted triazine, or a substituted or unsubstituted tetrazine. In some embodiments, Ring B is a substituted or unsubstituted pyrimidine, or a substituted or unsubstituted pyrimidone. In some embodiments, Ring B is a substituted pyrimidine. In some embodiments, Ring B is an unsubstituted pyrimidine. In some embodiments, Ring B is a substituted pyrimidone. In some embodiments, Ring B is an unsubstituted pyrimidone. In some embodiments, Ring B is a substituted or unsubstituted pyridazine. In some embodiments, Ring B is a substituted or unsubstituted pyridazinone.

In some embodiments, the compound of Formula (II) is a compound of Formula (IIb), Formula (IIc), Formula (IId), or Formula (IIe):

Formula (IIb)

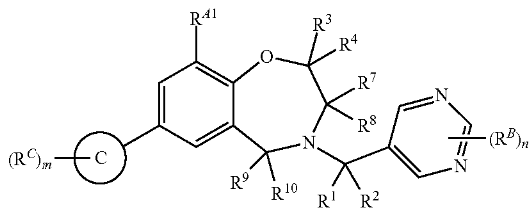

Formula (IIc)

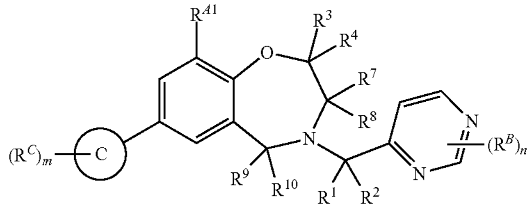

Formula (IId)

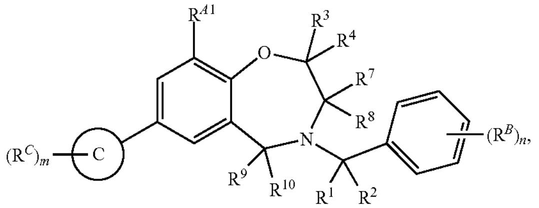

or

Formula (IIe)

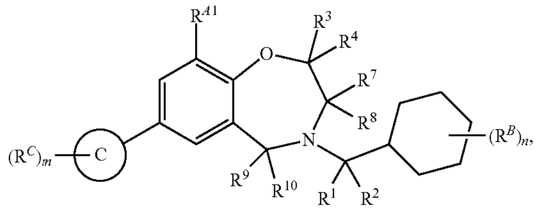

or a tautomer, or a pharmaceutically acceptable salt thereof.

In some embodiments, Ring C is a bicyclic heteroaryl having one or more nitrogen atoms. In some embodiments, Ring C is a substituted or unsubstituted indole, substituted or unsubstituted indazole, substituted or unsubstituted azaindole, substituted or unsubstituted indolizine, substituted or unsubstituted pyrrolopyridine, substituted or unsubstituted imidazopyridine, substituted or unsubstituted pyrazolopyridine, substituted or unsubstituted pyrrolopyrimidine, substituted or unsubstituted imidazopyrimidine, or substituted or unsubstituted pyrazolopyrimidine. In some embodiments, Ring C is a substituted or unsubstituted indole. In some embodiments, Ring C is a substituted or unsubstituted haloindole. In some embodiments, Ring C is a substituted or unsubstituted 5-fluoroindole. In some embodiments, Ring C is a 5-fluoroindole.

In some embodiments, Ring C is a bicyclic heterocycloalkyl having one or more nitrogen atoms. In some embodiments, Ring C is a substituted or unsubstituted indoline, substituted or unsubstituted tetrahydroquinoline, substituted or unsubstituted dihydrobenzoxazine, or substituted or unsubstituted dihydrobenzothiazine. In some embodiments, Ring C is a substituted or unsubstituted indoline. In some embodiments, Ring C is a substituted haloindoline. In some embodiments, Ring C is a substituted or unsubstituted 5-fluoroindoline. In some embodiments, Ring C is a 5-fluoroindoline. In some embodiments, Ring C is Ring C'.

In some embodiments, m is 0. In some embodiments, m is 1, and $R^C$ is -D, —F, —Cl, —Br, —$CH_3$, —$CH_2OCH_3$, —$CH_2F$, —$CHF_2$, —$CF_3$, —OH, —$OCH_3$, —$SCH_3$, —$NH_2$, —$N(CH_3)_2$, or —NHC(O)O($C_{1-4}$ alkyl). In some embodiments, m is 1, and $R^C$ is fluoro. In some embodiments, m is 1, and $R^C$ is chloro. In some embodiments, m is 1, and $R^C$ is methyl. In some embodiments, m is 1, and $R^C$ is trifluoromethyl. In some embodiments, m is 1, and $R^C$ is methoxy. In some embodiments, m is 1, and $R^C$ is dimethylamino.

In some embodiments, m is 2, and each $R^C$ is independently -D, —F, —Cl, —Br, —$CH_3$, —$CF_3$, or —$OCH_3$. In some embodiments, m is 2, and each $R^C$ is independently -D, —F, —Cl, —Br, or —$CH_3$. In some embodiments, m is 2, and each $R^C$ is halogen or $C_{1-4}$ alkyl. In some embodiments, m is 2, and each $R^C$ is halogen. In some embodiments, m is 2, and each $R^C$ is fluorine or chlorine. In some embodiments, m is 2, and each $R^C$ is fluorine. In some embodiments, m is 2, and each $R^C$ is deuterium. In some embodiments, m is 3 and each $R^C$ is halogen.

In another embodiment, is a compound of Formula (II'):

Formula (II')

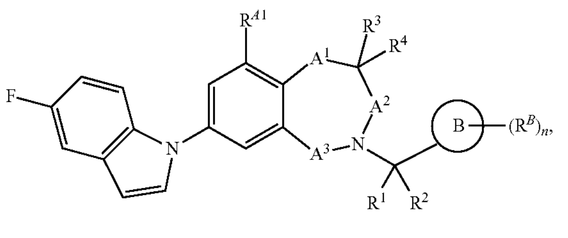

or a pharmaceutically acceptable salt thereof, wherein:

$R^1$ and $R^2$ are each independently hydrogen, deuterium, halogen, or $C_{1-4}$ alkyl;

$A^1$ is —O—, —$CR^5R^6$—, —S—, —S(=O)$_2$— or absent;

$A^2$ is —$CR^7R^8$— or —S(=O)$_2$—;

$A^3$ is —$CR^9R^{10}$— or absent;

$R^3$ and $R^4$ are each independently hydrogen, deuterium, halogen, or $C_1$ alkyl;

$R^5$ and $R^6$ are each independently hydrogen, deuterium, halogen, or $C_1$ alkyl; or $R^5$ and $R^6$ are taken together with the carbon atom to which they are attached to form an oxetane;

$R^7$ and $R^8$ are each independently hydrogen, deuterium, halogen, —CN, —$C_{1-4}$ alkyl, —$C_{1-4}$ haloalkyl, —OH, —O($C_{1-4}$ alkyl), —O($C_{1-4}$ haloalkyl), —$NH_2$, —NH $(C_{1-4}$ alkyl), $—N(C_{1-4}$ $alkyl)_2$, $—(C_{1-4}$ alkyl)O($C_{1-4}$ alkyl), —C(O)OH, —C(O)O($C_{1-4}$ alkyl), $—C(O)NH_2$, —C(O)NH($C_{1-4}$ alkyl), —C(O)N($C_{1-4}$ $alkyl)_2$, substituted or unsubstituted $C_{3-6}$ cycloalkyl, or substituted or unsubstituted 3- to 6-membered heterocycloalkyl; or $R^7$ and $R^8$ are taken together with the carbon atom to which they are attached to form a cyclopropane or an oxetane;

$R^9$ and $R^{10}$ are each independently hydrogen, deuterium, halogen, or $C_{1-4}$ alkyl; or $R^9$ and $R^{10}$ are taken together with the carbon atom to which they are attached to form an oxetane;

$R^{A1}$ is halogen, $C_{1-4}$ alkyl, or cyclopropyl;

Ring B is $C_{3-6}$ cycloalkyl, phenyl, 5-membered heteroaryl, or 6-membered heteroaryl containing two or more nitrogen atoms; or Ring B is Ring B';

each $R^B$ is independently selected from the group consisting of halogen, —CN, $—C_{1-4}$ alkyl, $—C_{1-4}$ haloalkyl, $—C_{1-4}$ aminoalkyl, $—C_{1-4}$ hydroxyalkyl, $—C_{1-4}$ methoxyalkyl, $—(C_{1-4}$ alkyl)O($C_{1-4}$ alkyl), —C(O)($C_{1-4}$ alkyl), —C(O)OH, —C(O)O($C_{1-4}$ alkyl), $—C(O)NH_2$, —C(O)NH($C_{1-4}$ alkyl), —C(O)N($C_{1-4}$ $alkyl)_2$, $—NH_2$, —NH($C_{1-4}$ alkyl), —NH($C_{3-6}$ cycloalkyl), —NH($C_{3-6}$ heterocycloalkyl), —N($C_{1-4}$ $alkyl)_2$, $—NHC(O)C_{1-4}$ alkyl, —NHC(O)O($C_{1-4}$ alkyl), $—NHS(O)_2C_{1-4}$ alkyl, —OH, —O($C_{1-4}$ alkyl), —O($C_{1-4}$ haloalkyl), —SH, —S($C_{1-4}$ alkyl), —SO($C_{1-4}$ alkyl), $—S(O)_2(C_{1-4}$ alkyl), $—S(O)_2NH_2$, $—S(O_2)NHCH_3$, substituted or unsubstituted $C_{3-6}$ cycloalkyl, or substituted or unsubstituted 3- to 6-membered heterocyclyl; or two $R^B$ taken together form a carbonyl; and n is 0 to 3.

In some embodiments, $R^{A1}$ is halogen, $C_{1-4}$ alkyl, or cyclopropyl. In some embodiments, $R^{A1}$ is halogen. In some embodiments, $R^{A1}$ is —F, —Cl, —Br, or —I. In some embodiments, $R^{A1}$ is —F or —Cl. In some embodiments, $R^{A1}$ is —F. In some embodiments, $R^{A1}$ is —Cl. In some embodiments, $R^{A1}$ is $C_{1-4}$ alkyl. In some embodiments, $R^{A1}$ is $—CH_3$, $—CH_2CH_3$, $—CH(CH_3)_2$, $—CH_2CH_2CH_3$, or $—C(CH_3)_3$. In some embodiments, $R^{A1}$ is $—CH_3$, $—CH_2CH_3$, or $—CH(CH_3)_2$. In some embodiments, $R^{A1}$ is $—CH_3$. In some embodiments, $R^{A1}$ is cyclopropyl.

In another embodiments, is a compound of the following formula:

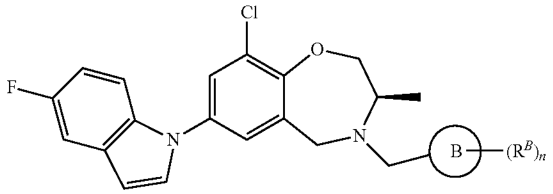

or a tautomer, or a pharmaceutically acceptable salt thereof, disclosed in Table II.

TABLE II

| ID No. | Structure | 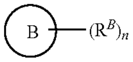 |
| --- | --- | --- |
| 9 | 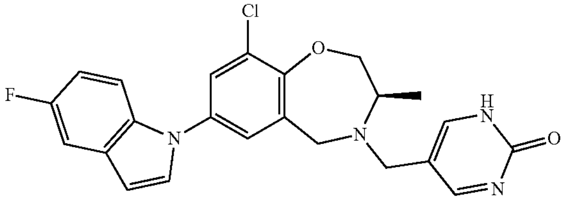 [SMILES: C[C@@H]1COc2c(Cl)cc(-n3ccc4cc(F)ccc43)cc2CN1Cc1cnc(=O)[nH]c1] | 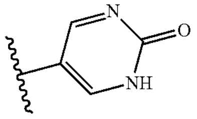 [SMILES: *c1cnc(=O)[nH]c1] |
| 10 | 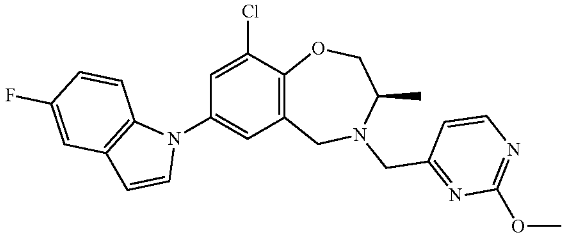 [SMILES: COc1nccc(CN2Cc3cc(-n4ccc5cc(F)ccc54)cc(Cl)c3OC[C@H]2C)n1] | 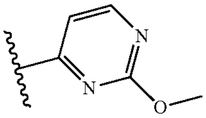 [SMILES: *c1ccnc(OC)n1] |
| 11 | 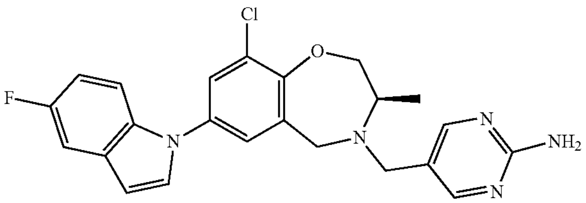 [SMILES: C[C@@H]1COc2c(Cl)cc(-n3ccc4cc(F)ccc43)cc2CN1Cc1cnc(N)nc1] | 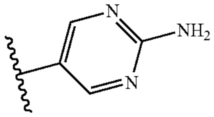 [SMILES: *c1cnc(N)nc1] |

TABLE II-continued
| ID No. | Structure | 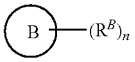 |
|---|---|---|
| 12 | 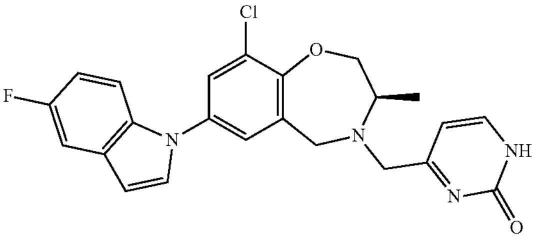 [SMILES: C[C@@H]1COc2c(Cl)cc(-n3ccc4cc(F)ccc43)cc2CN1Cc1cc[nH]c(=O)n1] | 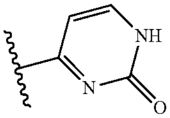 [SMILES: *c1cc[nH]c(=O)n1] |
In some embodiments,
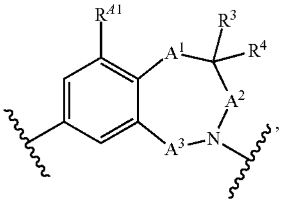
alternatively “ring A,” is selected from the group consisting of:
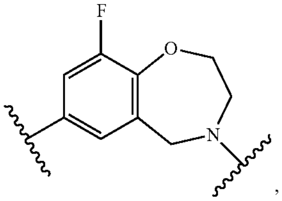
,
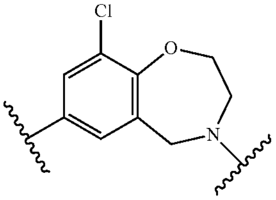
,
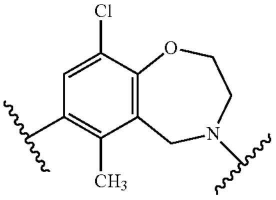
,
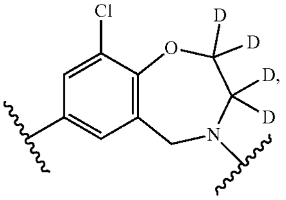
-continued
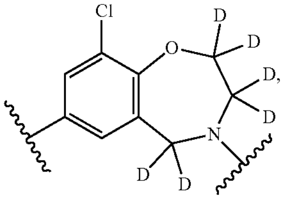
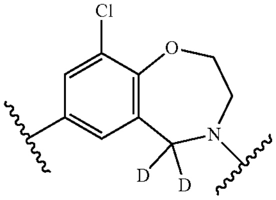
,
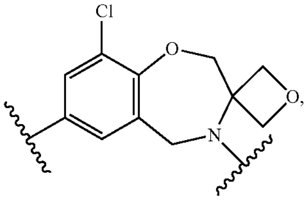
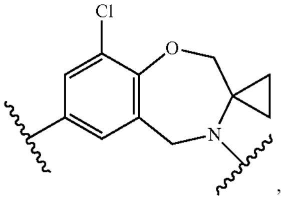
,
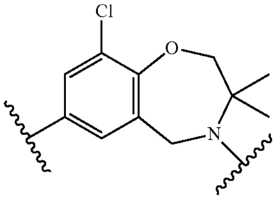
,
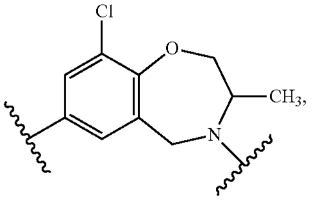

-continued
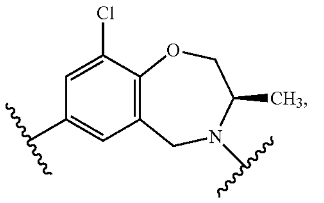
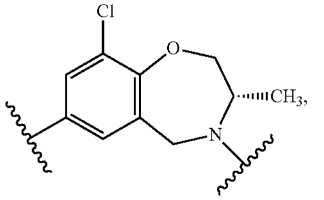
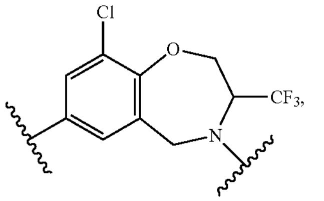
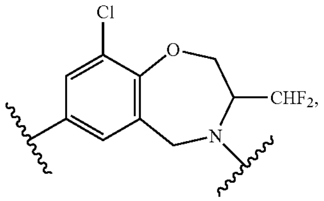
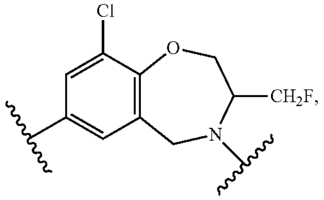
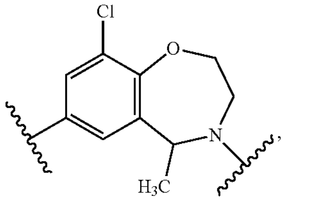
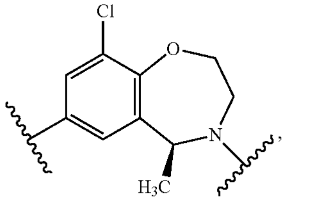
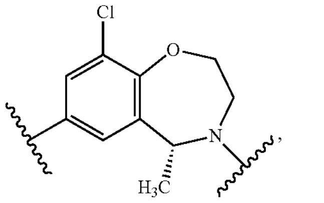
-continued
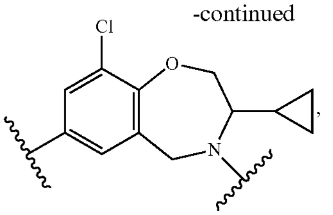
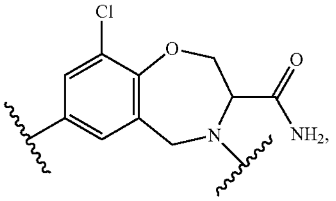
and
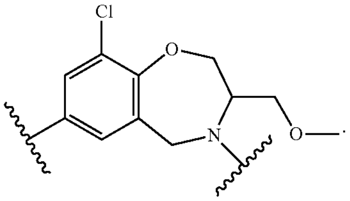
In some embodiments,
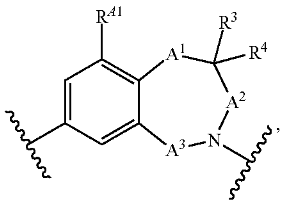
is.
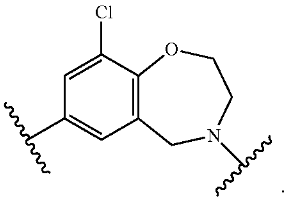 [SMILES: *c1cc(Cl)c2c(c1)CN(*)CCO2]
In some embodiments, the compound of Formula (II) is a compound of Formula (IIII):
Formula (III)
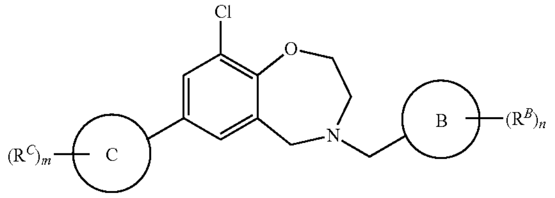
or a tautomer thereof, or a pharmaceutically acceptable salt thereof, wherein:

Ring B is $C_{3-6}$ cycloalkyl, phenyl, 5-membered heteroaryl, or 6-membered heteroaryl containing two or more nitrogen atoms; or Ring B is Ring B';

each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —NHS(O)$_2C_{1-4}$ alkyl, —OH, —O($C_{1-4}$ alkyl), —O($C_{1-4}$ haloalkyl), —SH, —S($C_{1-4}$ alkyl), —SO($C_{1-4}$ alkyl), —S(O)$_2$($C_{1-4}$ alkyl), —S(O)$_2NH_2$, —S($O_2$)$NHCH_3$, substituted or unsubstituted $C_{3-6}$ cycloalkyl, or substituted or unsubstituted 3- to 6-membered heterocyclyl; or two $R^B$ taken together form a carbonyl; Ring C is bicyclic heterocycle having one or more nitrogen atoms; or Ring C is Ring C' each $R^C$ is independently selected from the group consisting of halogen, —CN, —$C_{1-4}$ alkyl, —$C_{1-4}$ haloalkyl, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —N($C_{1-4}$ alkyl)$_2$, —OH, —O($C_{1-4}$ alkyl), —O($C_{1-4}$ haloalkyl), —S($C_{1-4}$ alkyl), —$SO_2C_{1-4}$ alkyl, —$SO_2NHC_{1-4}$ alkyl, substituted or unsubstituted $C_{3-6}$ cycloalkyl, or substituted or unsubstituted 3- to 6-membered heterocyclyl; or two $R^B$ taken together form a carbonyl;

m is 0 to 3;

n is 0 to 3; and

Ring C' is selected from the group consisting of:

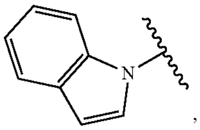,
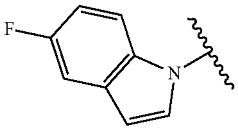,
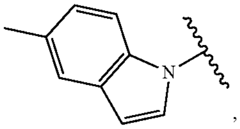,
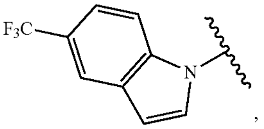,
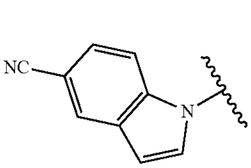,
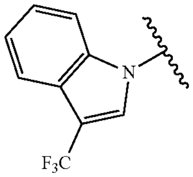,
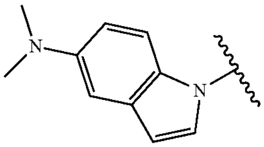,
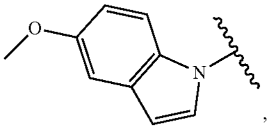,
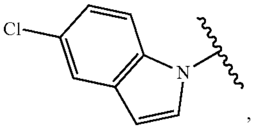,
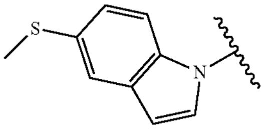, -continued

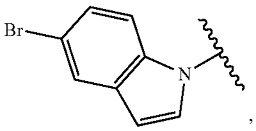,
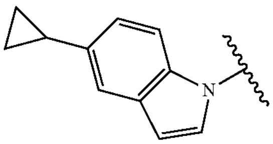,
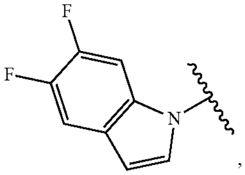,
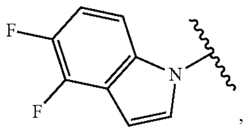,
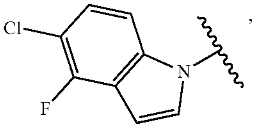,
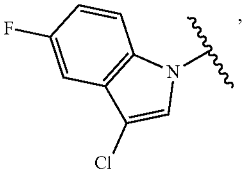,
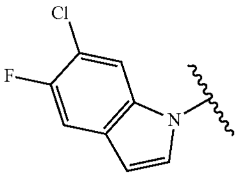,
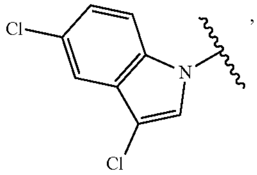,
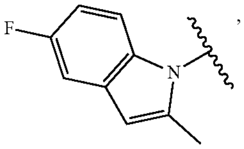,
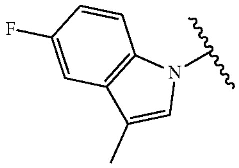,
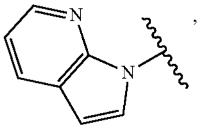,
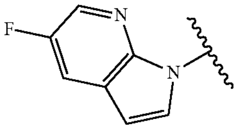,
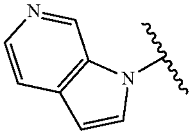,
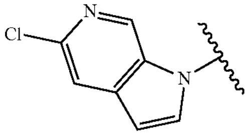,
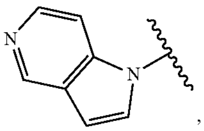,
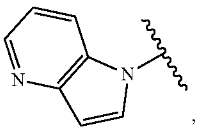,
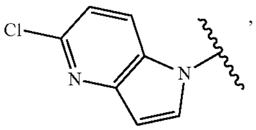,
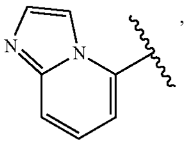,
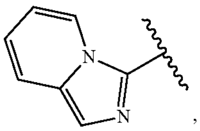,
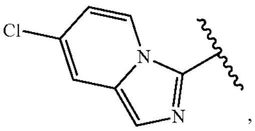, -continued

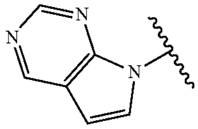, 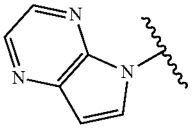,

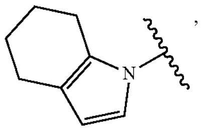, 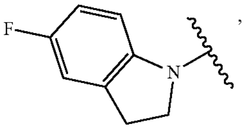,

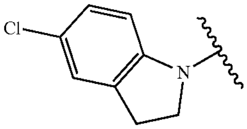, 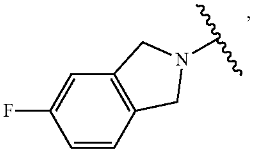,

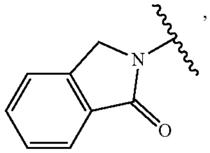, 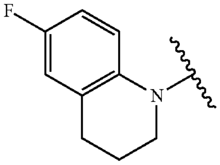,

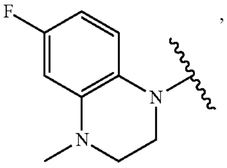, 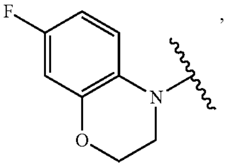,

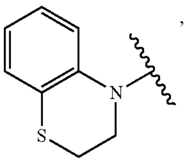, 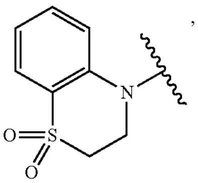,

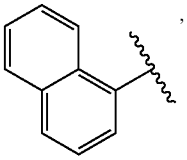, 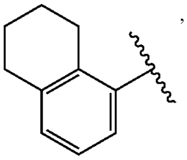,

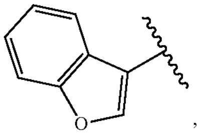, and 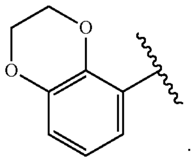.

In some embodiments, Ring B is $C_{3-6}$ cycloalkyl, phenyl, 5-membered heteroaryl, or 6-membered heteroaryl containing two or more nitrogen atoms; or Ring B is Ring B'. In some embodiments, Ring B is $C_{3-6}$ cycloalkyl, phenyl, 5-membered heteroaryl, or 6-membered heteroaryl containing two or more nitrogen atoms. In some embodiments, Ring B is Ring B'. In some embodiment, Ring B' is a Ring B' disclosed in Table VII. In some embodiments, Ring B' is selected from the group consisting of:

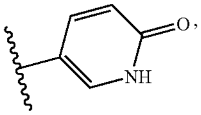, 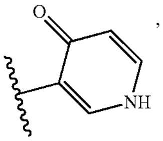,

-continued

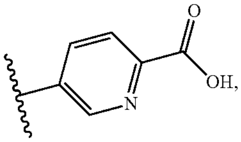

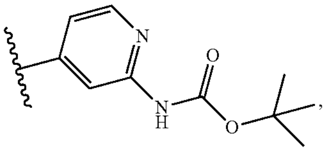

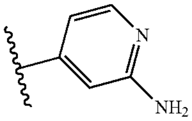 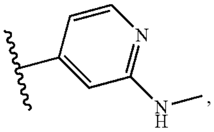

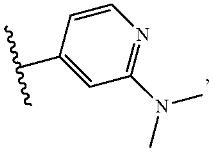 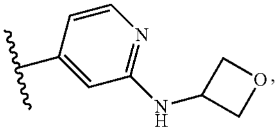

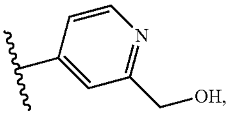 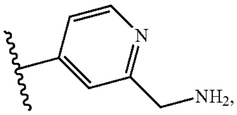

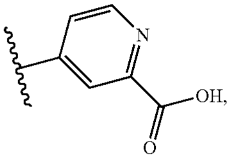 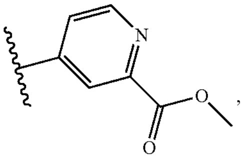

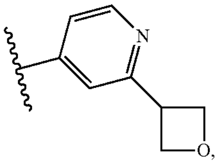 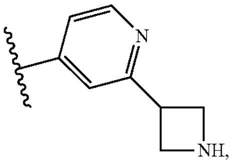

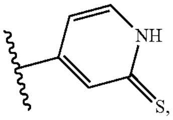 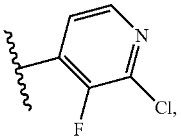

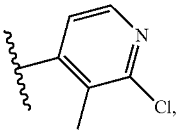 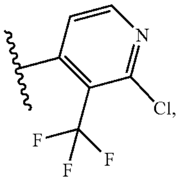

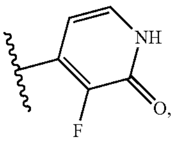 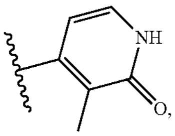

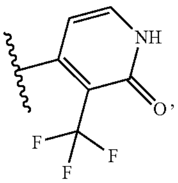 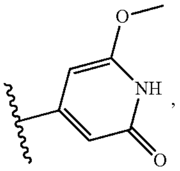

-continued

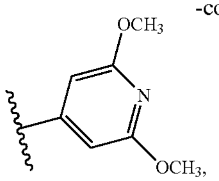
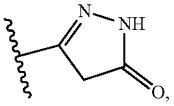
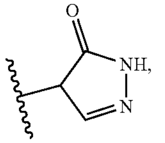
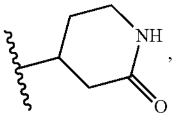
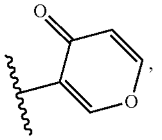
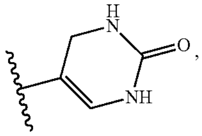
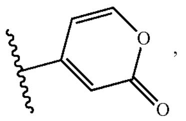
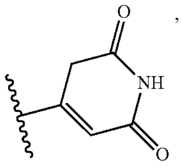
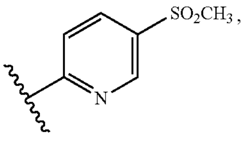
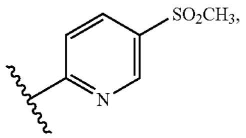
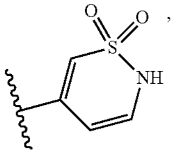
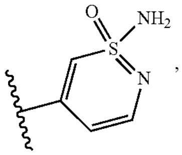
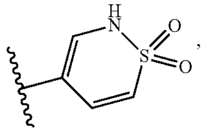
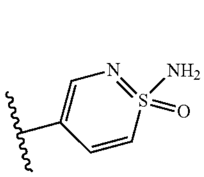
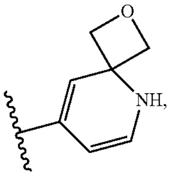
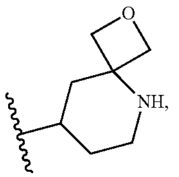
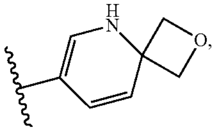
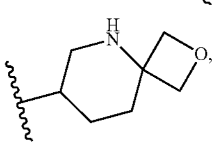
and

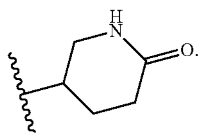

In some embodiments, Ring B is $C_{3-6}$ cycloalkyl. In some embodiments, Ring B is a substituted or unsubstituted cyclopropyl. In some embodiments, Ring B is a substituted or unsubstituted cyclobutyl. In some embodiments, Ring B is a substituted or unsubstituted cyclopentyl. In some embodiments, Ring B is a substituted or unsubstituted cyclohexyl. In some embodiments, Ring B is phenyl. In some embodiments, Ring B is a 5-membered heteroaryl. In some embodiments, Ring B is a 5- or 6-membered heteroaryl containing two or more nitrogen atoms. In some embodiments, Ring B is a 5-membered heteroaryl containing two or more nitrogen atoms. In some embodiments, Ring B is a 6-membered heteroaryl containing two or more nitrogen atoms.

In some embodiments, Ring B is a substituted or unsubstituted pyrazole, substituted or unsubstituted pyrazolidinone, substituted or unsubstituted imidazole, substituted or unsubstituted imidazolidinone, or a substituted or unsubstituted triazole. In some embodiments, Ring B is a substituted or unsubstituted pyrazole. In some embodiments, Ring B is a substituted or unsubstituted pyrazolidinone. In some embodiments, Ring B is a substituted or unsubstituted imidazole. In some embodiments, Ring B is a substituted or unsubstituted triazole.

In some embodiments, Ring B is a substituted or unsubstituted pyrimidine, substituted or unsubstituted pyrimidone, substituted or unsubstituted pyridazine, substituted or unsubstituted pyridazinone, substituted or unsubstituted pyrazine, substituted or unsubstituted pyrazinone, substituted or unsubstituted triazine, or a substituted or unsubstituted tetrazine. In some embodiments, Ring B is a substituted or unsubstituted pyrimidine, or a substituted or unsubstituted pyrimidone. In some embodiments, Ring B is a substituted pyrimidine. In some embodiments, Ring B is an unsubstituted pyrimidine. In some embodiments, Ring B is a substituted pyrimidone. In some embodiments, Ring B is an unsubstituted pyrimidone. In some embodiments, Ring B is a substituted or unsubstituted pyridazine. In some embodiments, Ring B is a substituted or unsubstituted pyridazinone.

In some embodiments, the compound of Formula (III) is a compound of Formula (IIIb), Formula (IIIc), Formula (IIId), or Formula (IIIe):

Formula (IIIb)

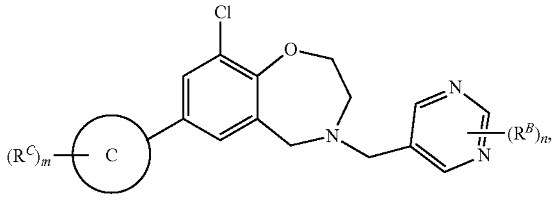

Formula (IIIc)

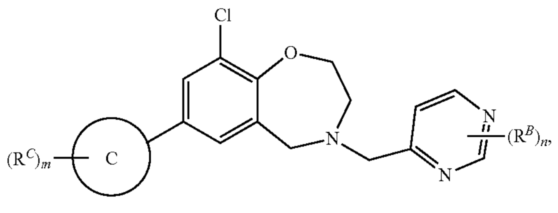

Formula (IIId)

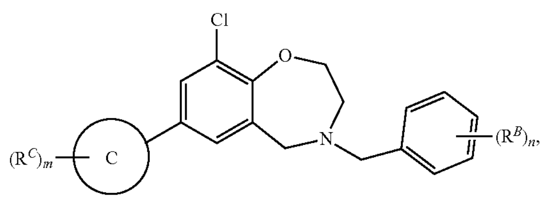

or

-continued

Formula (IIIe)

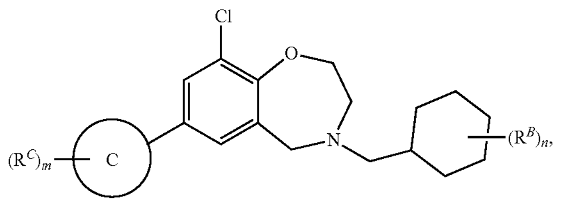

or a tautomer thereof, or a pharmaceutically acceptable salt thereof, wherein:

In some embodiments, Ring C is a bicyclic heterocycle having one or more nitrogen atoms. In some embodiments, Ring C is a bicyclic heteroaryl having one or more nitrogen atoms. In some embodiments, Ring C is a substituted or unsubstituted indole, substituted or unsubstituted indazole, substituted or unsubstituted azaindole, substituted or unsubstituted indolizine, substituted or unsubstituted pyrrolopyridine, substituted or unsubstituted imidazopyridine, substituted or unsubstituted pyrazolopyridine, substituted or unsubstituted pyrrolopyrimidine, substituted or unsubstituted imidazopyrimidine, or substituted or unsubstituted pyrazolopyrimidine. In some embodiments, Ring C is a substituted or unsubstituted indole.

In some embodiments, Ring C is

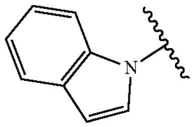
,
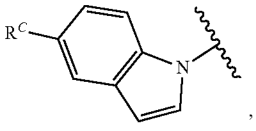
,
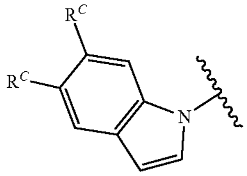
,
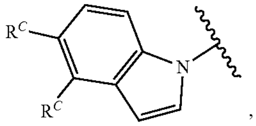
,
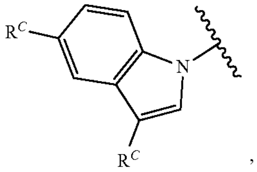
, or
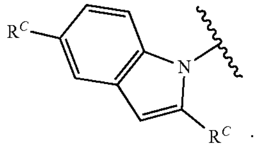
.

In some embodiments, each $R^C$ is independently selected from halogen, —CN, —$C_{1-4}$ alkyl, —$C_{1-4}$ haloalkyl, —$NH_2$, —NH($C_{1-4}$ alkyl), —N($C_{1-4}$ alkyl)$_2$, —OH, —O($C_{1-4}$ alkyl), or $C_{3-6}$ cycloalkyl; or two $R^B$ taken together form a carbonyl. In some embodiments, each $R^C$ is independently selected from halogen, —CN, —$C_{1-4}$ alkyl, —$C_{1-4}$ haloalkyl,), —$NH_2$, —NH($C_{1-4}$ alkyl), —N($C_{1-4}$ alkyl)$_2$, —OH, —O($C_{1-4}$ alkyl), or $C_{3-6}$ cycloalkyl; or two $R^B$ taken together form a carbonyl. In some embodiments, $R^C$ is —F, —Cl, —Br, —$CH_3$, —$CH_2F$, —$CHF_2$, —$CF_3$, —OH, —$OCH_3$, —$SCH_3$, —$NH_2$, —N($CH_3$)$_2$, or —NHC(O)O($C_{1-4}$ alkyl). In some embodiments, each $R^C$ is independently selected from —F, —Cl, —CN, $CH_3$, —$CF_3$, —N($CH_3$)$_2$, —$OCH_3$, —$SCH_3$, and cyclopropyl. In some embodiments, Ring C is a substituted or unsubstituted haloindole. In some embodiments, Ring C is:

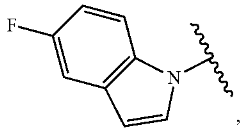
,
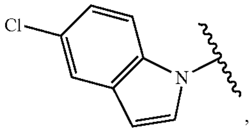
,
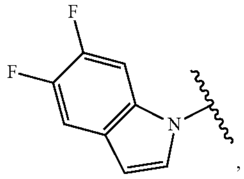
,
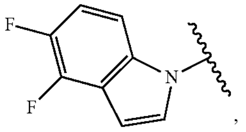
,
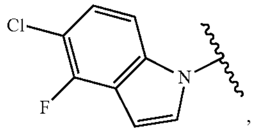
,
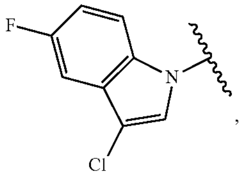
,
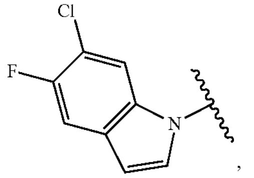
,
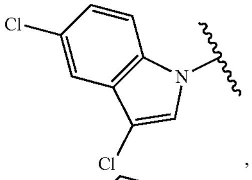
,
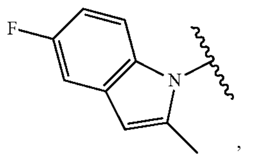
, or
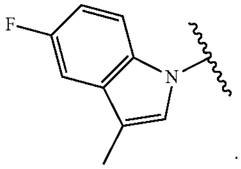
.

In some embodiments, Ring C is a substituted or unsubstituted 5-fluoroindole. In some embodiments, Ring C is a 5-fluoroindole. In some embodiments, Ring C is:

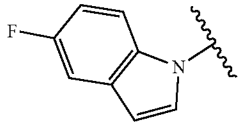
.

In some embodiments, Ring C is a bicyclic heterocycloalkyl having one or more nitrogen atoms. In some embodiments, Ring C is a substituted or unsubstituted indoline, substituted or unsubstituted tetrahydroquinoline, substituted or unsubstituted dihydrobenzoxazine, or substituted or unsubstituted dihydrobenzothiazine. In some embodiments, Ring C is a substituted or unsubstituted indoline. In some embodiments, Ring C is a substituted haloindoline. In some embodiments, Ring C is a substituted or unsubstituted 5-fluoroindoline. In some embodiments, Ring C is a 5-fluoroindoline. In some embodiments, Ring C is Ring C'.

In some embodiments, m is 0. In some embodiments, m is 1, and $R^C$ is -D, —F, —Cl, —Br, —$CH_3$, —$CH_2OCH_3$, —$CH_2F$, —$CHF_2$, —$CF_3$, —OH, —$OCH_3$, —$SCH_3$, —$NH_2$, —N($CH_3$)$_2$, or —NHC(O)O($C_{1-4}$ alkyl). In some embodiments, m is 1, and $R^C$ is fluoro. In some embodiments, m is 1, and $R^C$ is chloro. In some embodiments, m is 1, and $R^C$ is methyl. In some embodiments, m is 1, and $R^C$ is trifluoromethyl. In some embodiments, m is 1, and $R^C$ is methoxy. In some embodiments, m is 1, and $R^C$ is dimethylamino.

In some embodiments, m is 2, and each $R^C$ is independently -D, —F, —Cl, —Br, —$CH_3$, —$CF_3$, or —$OCH_3$. In some embodiments, m is 2, and each $R^C$ is independently -D, —F, —Cl, —Br, or —$CH_3$. In some embodiments, m is 2, and each $R^C$ is halogen or $C_{1-4}$ alkyl. In some embodiments, m is 2, and each $R^C$ is halogen. In some embodiments, m is 2, and each $R^C$ is fluorine or chlorine. In some embodiments, m is 2, and each $R^C$ is fluorine. In some embodiments, m is 2, and each $R^C$ is deuterium. In some embodiments, m is 3 and each $R^C$ is halogen.

In some embodiments, Ring C is a bicyclic heterocycle having one or more nitrogens, selected from the group consisting of:

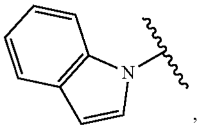, 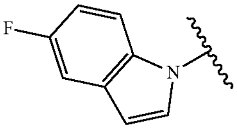,

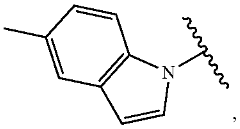, 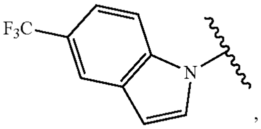,

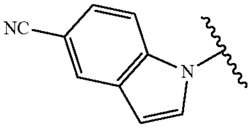, 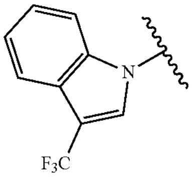,

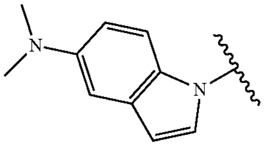,

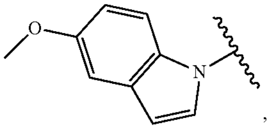, 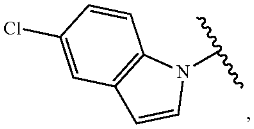,

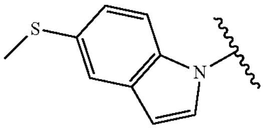,

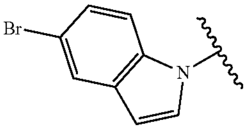,

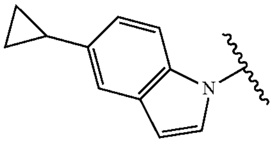,

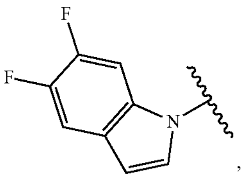, 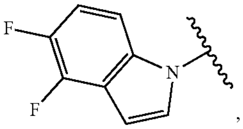,

-continued

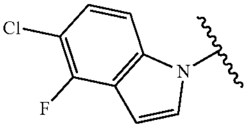, 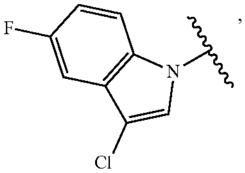,

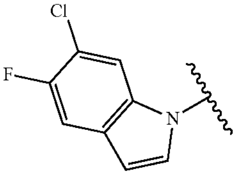, 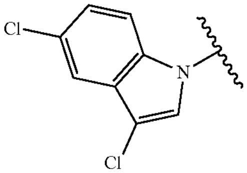,

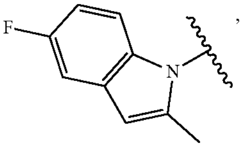, 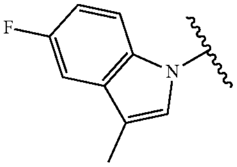,

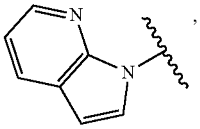, 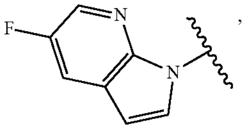,

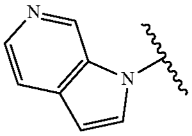, 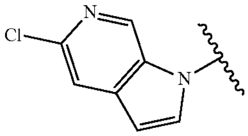,

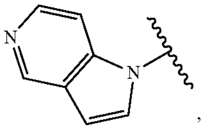, 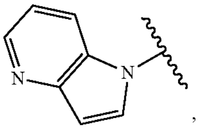,

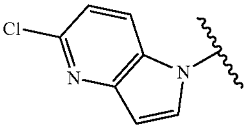, 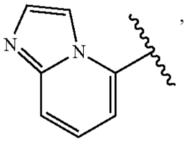,

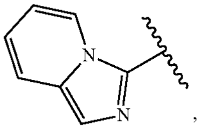, 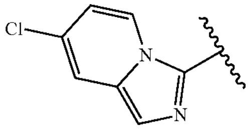,

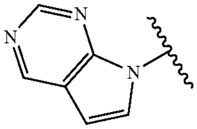, 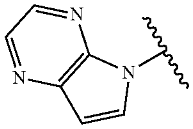,

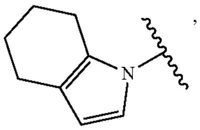, 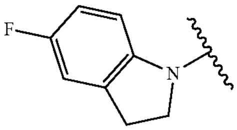,

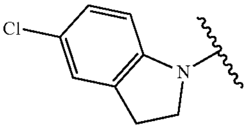, 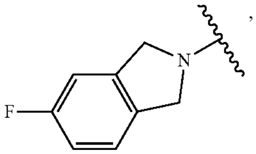,

-continued

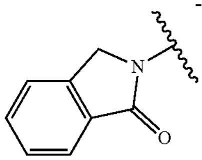,
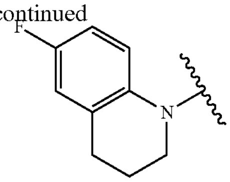,
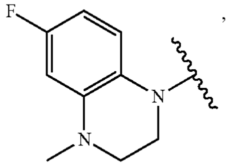,
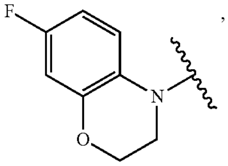,
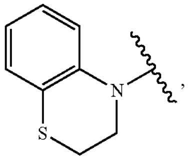, and
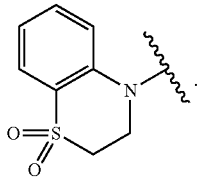.

In some embodiments, Ring C' is selected from the group consisting of:

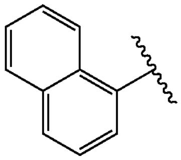,
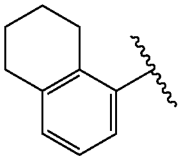,
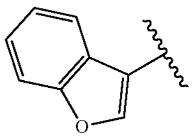, and
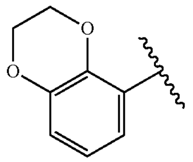.

In some embodiments, Ring B is $C_{3-6}$ cycloalkyl, phenyl, 5-membered heteroaryl, or 6-membered heteroaryl containing two or more nitrogen atoms. In some embodiments, Ring B is further substituted with 0 to 3 groups $R^B$. In some embodiments, each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —OH, —O($C_{1-4}$ alkyl), —O($C_{1-4}$ haloalkyl), —SH, —S($C_{1-4}$ alkyl), —SO($C_{1-4}$ alkyl), —S(O)$_2$($C_{1-4}$ alkyl), —S(O)$_2NH_2$, —S($O_2$)$NHCH_3$, substituted or unsubstituted $C_{3-6}$ cycloalkyl, and substituted or unsubstituted 3- to 6-membered heterocyclyl; or two $R^B$ taken together form a carbonyl.

In some embodiments, each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ heterocycloalkyl), —N($C_{1-4}$ alkyl)$_2$, —NHC(O)O($C_{1-4}$ alkyl), —OH, —O($C_{1-4}$ alkyl), —S(O)$_2$($C_{1-4}$ alkyl), and substituted or unsubstituted 3- to 6-membered heterocyclyl; or two $R^B$ taken together form a carbonyl.

In some embodiments, each $R^B$ is independently selected from the group consisting of —F, —Cl, —CN, —$CH_3$, —$CH_2F$, —$CHF_2$, —$CF_3$, —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —OH, —$OCH_3$ is —C(O)OH, —C(O)O($C_{1-4}$ alkyl), —C(O)$NH_2$, —C(O)NH($C_{1-4}$ alkyl), or —C(O)N($C_{1-4}$ alkyl)$_2$, —C(O)($C_{1-4}$ alkyl), —C(O)OH, —$NH_2$, —NH($C_{1-4}$ alkyl), —NH(oxetanyl), —N($C_{1-4}$ alkyl)$_2$, —OH—O($C_{1-4}$ alkyl), or oxo.

In some embodiments, each $R^B$ is independently selected from the group consisting of —F, —Cl, —CN, —$CH_3$, —$CH_2F$, —$CHF_2$, —$CF_3$, $CH_2NH_2$, —$CH_2$NHBoc, —$CH_2OH$, —$CH_2OCH_3$, —C(O)$NH_2$, —C(O)$NHCH_3$, —C(O)N($CH_3$)$_2$, —C(O)OH, —C(O)$OCH_3$, —$NH_2$, $NHCH_3$, —N($CH_3$)$_2$, —NH(oxetanyl), —NHC(O)$CH_3$, —NHS($O_2$)$CH_3$, —OH, —$OCH_3$, —$OCH_2CF_3$, methylpyrazolyl, pyrazolyl, and oxo.

In some embodiments, Ring B is phenyl, and n is 0. In some embodiments, Ring B is phenyl, and n is 1. In some embodiments, Ring B is phenyl, n is 1, and $R^B$ is —F, —Cl, —CN, —$CH_3$, —$CH_2F$, —$CHF_2$, —$CF_3$, —OH, or —$OCH_3$. In some embodiments, Ring B is phenyl, n is 1, and $R^B$ is —CN. In some embodiments, Ring B is phenyl, n is 1, and $R^B$ is —OH. In some embodiments, Ring B is phenyl, n is 1, and $R^B$ is —$OCH_3$. In some embodiments, Ring B is phenyl, n is 1, and $R^B$ is —F. In some embodiments, Ring B is phenyl, n is 1, and $R^B$ is —Cl. In some embodiments, Ring B is phenyl, n is 1, and $R^B$ is —$CF_3$.

In some embodiments, Ring B is cyclohexyl, and n is 0. In some embodiments, Ring B is cyclohexyl, and n is 1. In some embodiments, Ring B is cyclohexyl, n is 1, and $R^B$ is —C(O)OH, —C(O)O($C_{1-4}$ alkyl), —C(O)$NH_2$, —C(O)NH($C_{1-4}$ alkyl), or —C(O)N($C_{1-4}$ alkyl)$_2$. In some embodiments, Ring B is cyclohexyl, n is 1, and $R^B$ is —C(O)OH. In some embodiments, Ring B is cyclohexyl, n is 1, and $R^B$ is —C(O)O($C_{1-4}$ alkyl). In some embodiments, Ring B is cyclohexyl, n is 1, and $R^B$ is —C(O)$OCH_3$. In some embodiments, Ring B is cyclohexyl, n is 1, and $R^B$ is —C(O)$NH_2$. In some embodiments, Ring B is cyclohexyl, n is 1, and $R^B$ is —C(O)NH($C_{1-4}$ alkyl). In some embodiments, Ring B is cyclohexyl, n is 1, and $R^B$ is —C(O)$NHCH_3$. In some embodiments, Ring B is cyclohexyl, n is 1, and $R^B$ is —C(O)N($C_{1-4}$ alkyl)$_2$. In some embodiments, Ring B is cyclohexyl, n is 1, and $R^B$ is —C(O)N($CH_3$)$_2$.

In some embodiments, Ring B is cyclohexyl, and n is 2. In some embodiments, Ring B is cyclohexyl, n is 2, and each $R^B$ is independently halogen, $C_{1-4}$ alkyl, $C_{1-4}$ haloalkyl, —C(O)OH, —C(O)O($C_{1-4}$ alkyl), —C(O)$NH_2$, —C(O)NH($C_{1-4}$ alkyl), or —C(O)N($C_{1-4}$ alkyl)$_2$.

In some embodiments, Ring B is pyrimidinyl and n is 0. In some embodiments, Ring B is pyrimidinyl and n is 1. In some embodiments, Ring B is pyrimidinyl, n is 1, and $R^B$ is —$CH_3$, —C(O)($C_{1-4}$ alkyl), —C(O)OH, —$NH_2$, —NH($C_{1-4}$ alkyl), —NH(oxetanyl), —N($C_{1-4}$ alkyl)$_2$, —OH or —O($C_{1-4}$ alkyl). In some embodiments, Ring B is pyrimidinyl, n is 1, and $R^B$ is —C(O)OH. In some embodiments, Ring B is pyrimidinyl, n is 1, and $R^B$ is —C(O)$CH_3$. In some embodiments, Ring B is pyrimidinyl, n is 1, and $R^B$ is —OH or —O($C_{1-4}$ alkyl). In some embodiments, Ring B is pyrimidinyl, n is 1, and $R^B$ is —OH. In some embodiments, Ring B is pyrimidinyl, n is 1, and $R^B$ is —O($C_{1-4}$ alkyl). In some embodiments, Ring B is pyrimidinyl, n is 1, and $R^B$ is —$OCH_3$. In some embodiments, Ring B is pyrimidinyl, n is 1, and $R^B$ is —$NH_2$. In some embodiments, Ring B is pyrimidinyl, n is 1, and $R^B$ is —NH($C_{1-4}$ alkyl). In some embodiments, Ring B is pyrimidinyl, n is 1, and $R^B$ is —$NHCH_3$. In some embodiments, Ring B is pyrimidinyl, n is 1, and $R^B$ is —$N(C_{1-4}$ alkyl$)_2$. In some embodiments, Ring B is pyrimidinyl, n is 1, and $R^B$ is —$N(CH_3)_2$. In some embodiments, Ring B is pyrimidinyl, and n is 2. In some embodiments, Ring B is pyrimidinyl, n is 2, and two $R^B$ taken together form a carbonyl. In some embodiments, Ring B is pyrimidinonyl. In some embodiments, Ring B is pyrimidinyl, and n is 3. In some embodiments, Ring B is pyrimidinyl, n is 3, and two $R^B$ taken together form a carbonyl. In some embodiments, Ring B is an unsubstituted pyrimidinonyl. In some embodiments, Ring B is a substituted pyrimidinonyl. In some embodiments, Ring B is a methylpyrimidinonyl, aminopyrimidinonyl, hydroxypyrimidinonyl, methoxypyrimidinonyl, methoxyalkylpyrimidinonyl, halopyrimidinonyl, or $C_{1-4}$ haloalkylpyrimidinonyl. In some embodiments, Ring B is a methylpyrimidinonyl.

In some embodiments, Ring B is Ring B'. In some embodiments, Ring B' is as described in Table VII. In some embodiments, Ring B is selected from the group consisting of:

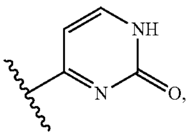 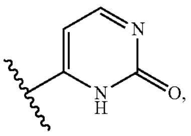

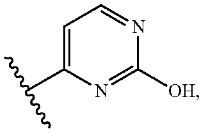 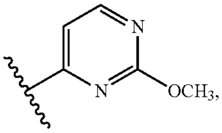

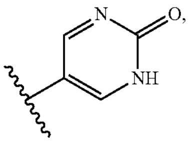 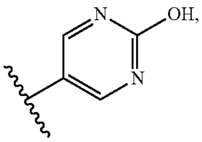

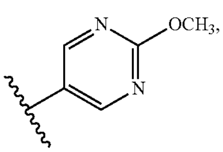 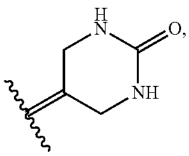

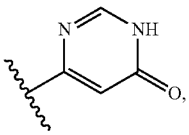 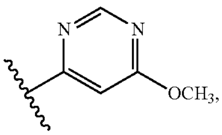

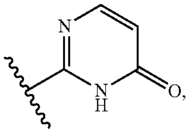 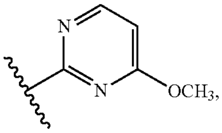

-continued

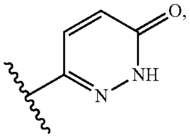 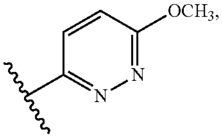

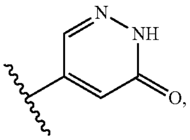 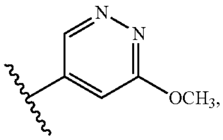

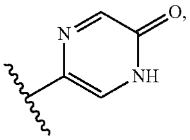 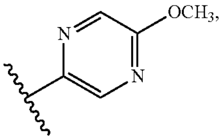

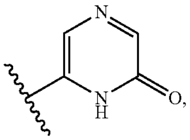 and 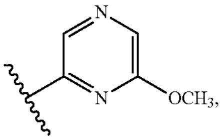

each of which is optionally further substituted with one group, $R^B$, as defined above.

In some embodiments, Ring B is selected from the group consisting of:

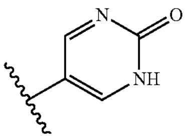 , 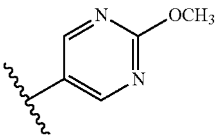 ,

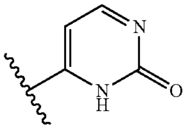 , and 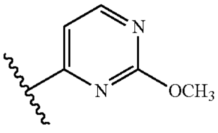 .

In some embodiments, is a compound of the following formula:

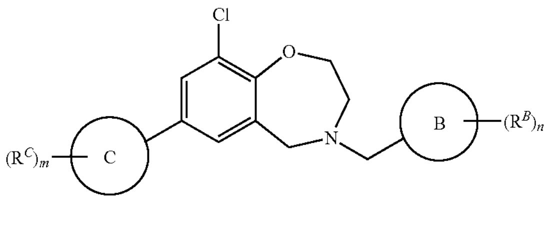

or a tautomer thereof, or a pharmaceutically acceptable salt thereof, disclosed in Table III.

TABLE III
| ID No | Structure | 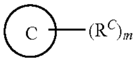 | 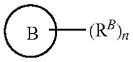 |
|---|---|---|---|
| 13 | 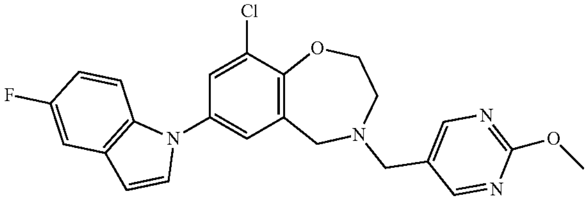 [SMILES: COc1ncc(CN2CCOc3c(Cl)cc(-n4ccc5cc(F)ccc54)cc3C2)cn1] | 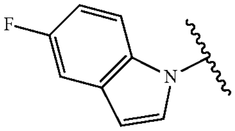 [SMILES: *n1ccc2cc(F)ccc21] | 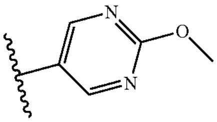 [SMILES: *c1cnc(OC)nc1] |
| 14 | 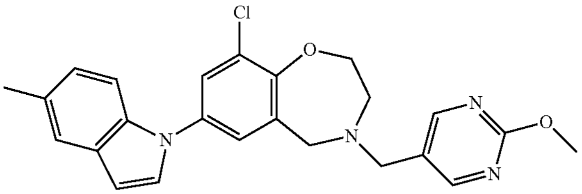 | 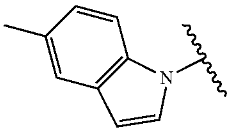 [SMILES: *n1ccc2cc(C)ccc21] | 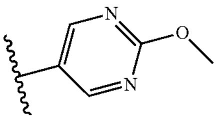 [SMILES: *c1cnc(OC)nc1] |
| 15 | 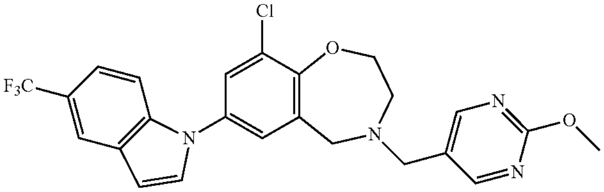 [SMILES: COc1ncc(CN2CCOc3c(Cl)cc(-n4ccc5cc(C(F)(F)F)ccc54)cc3C2)cn1] | 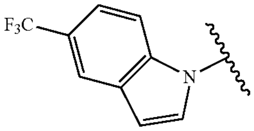 [SMILES: *n1ccc2cc(C(F)(F)F)ccc21] | 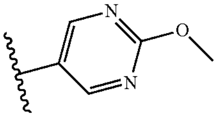 [SMILES: *c1cnc(OC)nc1] |
| 16 | 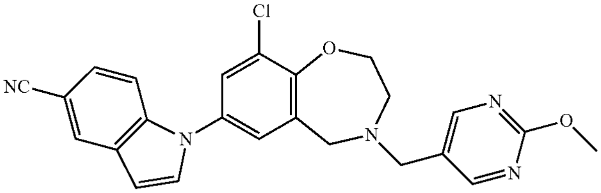 [SMILES: COc1ncc(CN2CCOc3c(Cl)cc(-n4ccc5cc(C#N)ccc54)cc3C2)cn1] | 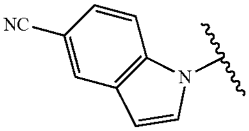 [SMILES: *n1ccc2cc(C#N)ccc21] | 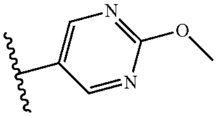 [SMILES: *c1cnc(OC)nc1] |
| 17 | 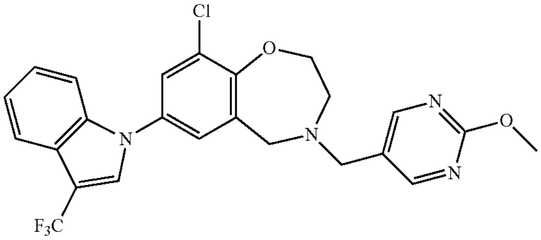 [SMILES: COc1ncc(CN2CCOc3c(Cl)cc(-n4cc(C(F)(F)F)c5ccccc54)cc3C2)cn1] | 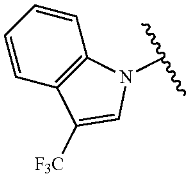 [SMILES: *n1cc(C(F)(F)F)c2ccccc21] | 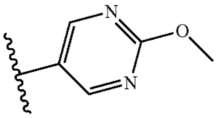 [SMILES: *c1cnc(OC)nc1] |
| 18 | 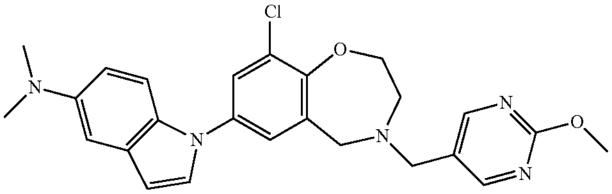 | 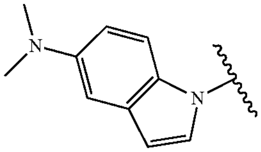 [SMILES: *n1ccc2cc(N(C)C)ccc21] | 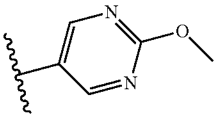 [SMILES: *c1cnc(OC)nc1] |
| 19 | 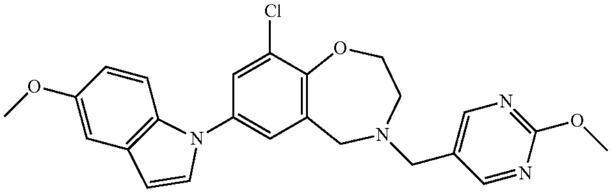 | 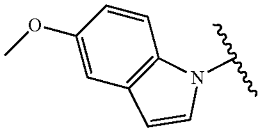 [SMILES: *n1ccc2cc(OC)ccc21] | 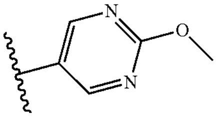 [SMILES: *c1cnc(OC)nc1] |

TABLE III-continued
| ID No | Structure | 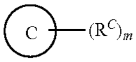 | 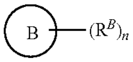 |
|---|---|---|---|
| 20 | 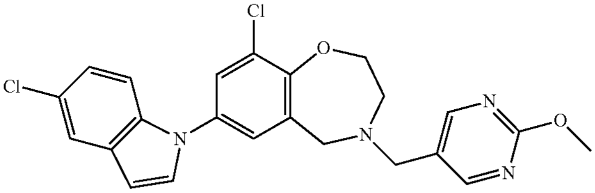 [SMILES: COc1ncc(CN2CCOc3c(Cl)cc(-n4ccc5cc(Cl)ccc54)cc3C2)cn1] | 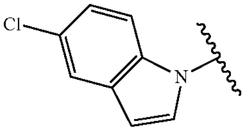 | 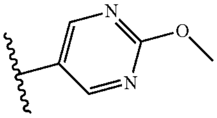 [SMILES: *c1cnc(OC)nc1] |
| 21 | 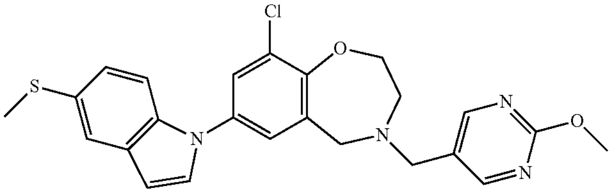 | 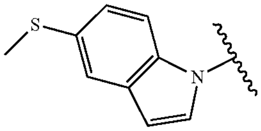 [SMILES: *n1ccc2cc(SC)ccc21] | 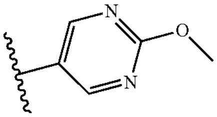 [SMILES: *c1cnc(OC)nc1] |
| 22 | 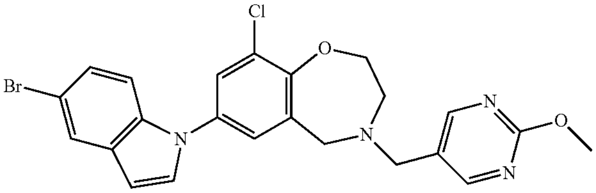 | 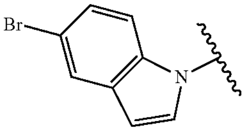 | 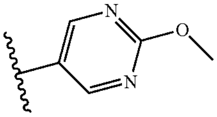 [SMILES: *c1cnc(OC)nc1] |
| 23 | 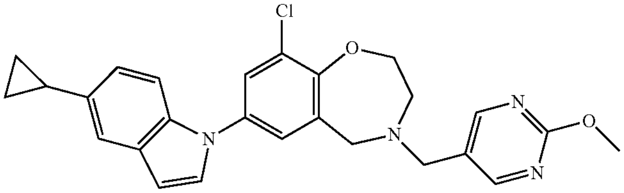 [SMILES: COc1ncc(CN2CCOc3c(Cl)cc(-n4ccc5cc(C6CC6)ccc54)cc3C2)cn1] | 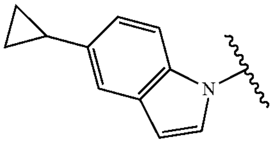 [SMILES: *n1ccc2cc(C3CC3)ccc21] | 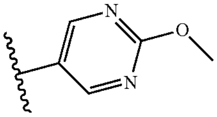 [SMILES: *c1cnc(OC)nc1] |
| 24 | 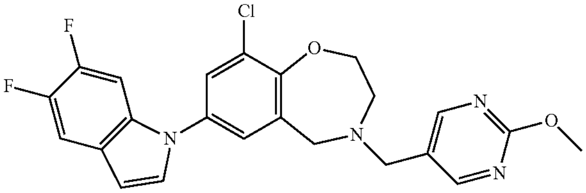 [SMILES: COc1ncc(CN2CCOc3c(Cl)cc(-n4ccc5cc(F)c(F)cc54)cc3C2)cn1] | 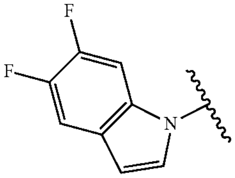 [SMILES: *n1ccc2cc(F)c(F)cc21] | 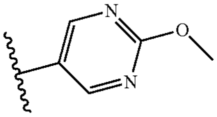 [SMILES: *c1cnc(OC)nc1] |
| 25 | 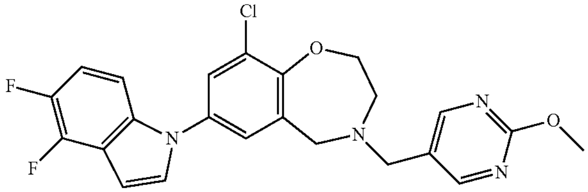 [SMILES: COc1ncc(CN2CCOc3c(Cl)cc(-n4ccc5c(F)c(F)ccc54)cc3C2)cn1] | 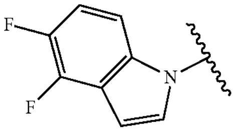 [SMILES: *n1ccc2c(F)c(F)ccc21] | 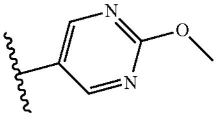 [SMILES: *c1cnc(OC)nc1] |
| 26 | 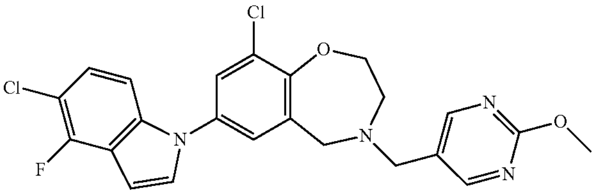 | 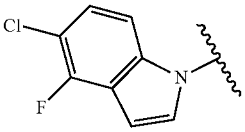 | 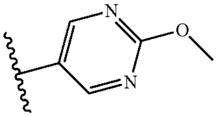 [SMILES: *c1cnc(OC)nc1] |

TABLE III-continued
| ID No | Structure | 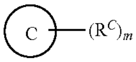 | 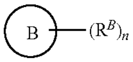 |
|---|---|---|---|
| 27 | 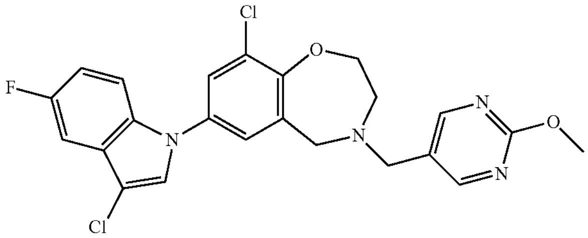 [SMILES: COc1ncc(CN2CCOc3c(Cl)cc(-n4cc(Cl)c5cc(F)ccc54)cc3C2)cn1] | 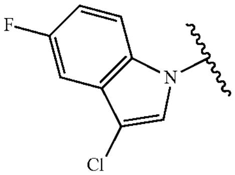 [SMILES: *n1cc(Cl)c2cc(F)ccc21] | 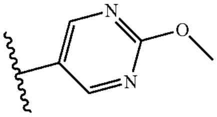 [SMILES: *c1cnc(OC)nc1] |
| 28 | 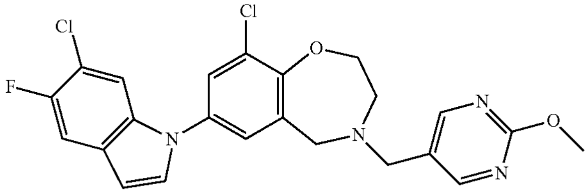 | 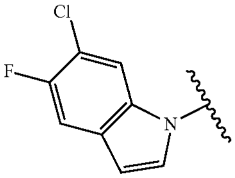 | 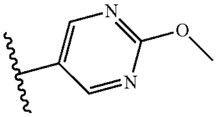 [SMILES: *c1cnc(OC)nc1] |
| 29 | 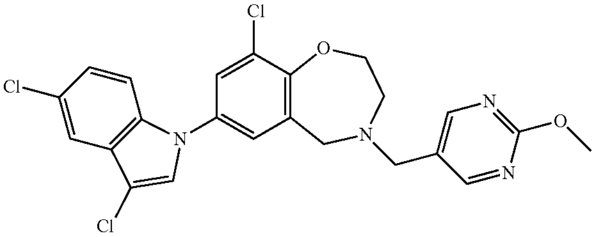 [SMILES: COc1ncc(CN2CCOc3c(Cl)cc(-n4cc(Cl)c5cc(Cl)ccc54)cc3C2)cn1] | 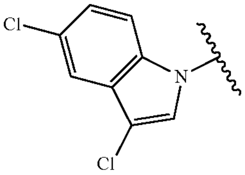 [SMILES: *n1cc(Cl)c2cc(Cl)ccc21] | 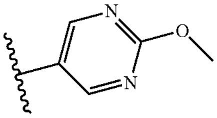 [SMILES: *c1cnc(OC)nc1] |
| 30 | 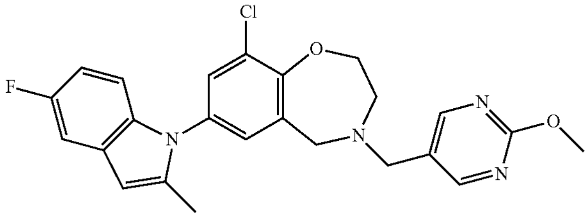 [SMILES: COc1ncc(CN2CCOc3c(Cl)cc(-n4c(C)cc5cc(F)ccc54)cc3C2)cn1] | 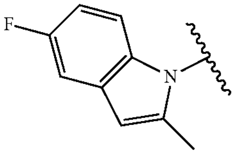 [SMILES: *n1c(C)cc2cc(F)ccc21] | 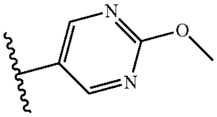 [SMILES: *c1cnc(OC)nc1] |
| 31 | 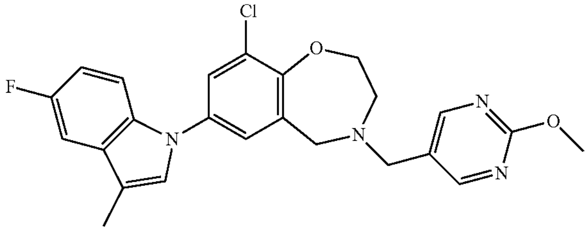 [SMILES: COc1ncc(CN2CCOc3c(Cl)cc(-n4cc(C)c5cc(F)ccc54)cc3C2)cn1] | 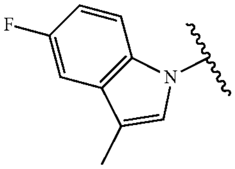 [SMILES: *n1cc(C)c2cc(F)ccc21] | 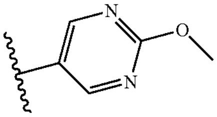 [SMILES: *c1cnc(OC)nc1] |
| 32 | 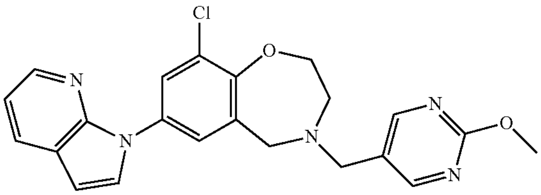 | 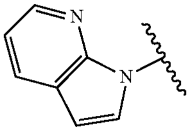 [SMILES: *n1ccc2cccnc21] | 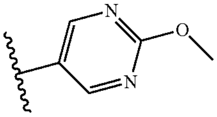 [SMILES: *c1cnc(OC)nc1] |
| 33 | 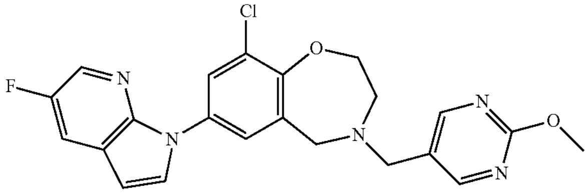 [SMILES: COc1ncc(CN2CCOc3c(Cl)cc(-n4ccc5cc(F)cnc54)cc3C2)cn1] | 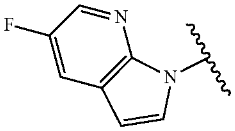 | 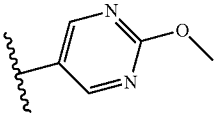 [SMILES: *c1cnc(OC)nc1] |

TABLE III-continued
| ID No | Structure | 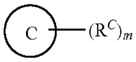 | 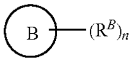 |
|---|---|---|---|
| 34 | 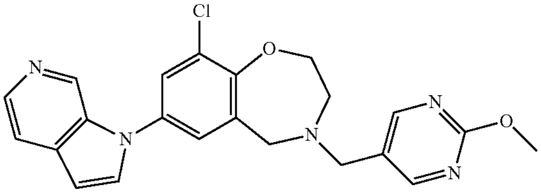 [SMILES: COc1ncc(CN2CCOc3c(Cl)cc(-n4ccc5ccncc54)cc3C2)cn1] | 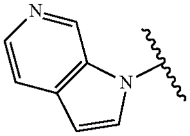 [SMILES: *n1ccc2ccncc21] | 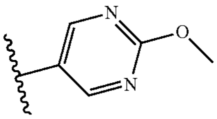 [SMILES: *c1cnc(OC)nc1] |
| 35 | 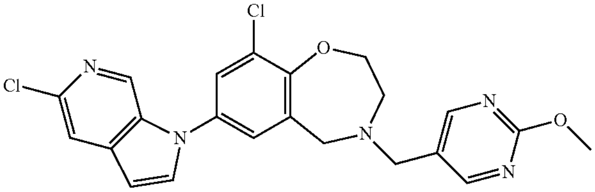 | 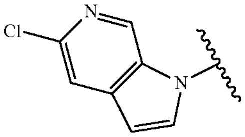 [SMILES: *n1ccc2cc(Cl)ncc21] | 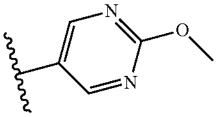 [SMILES: *c1cnc(OC)nc1] |
| 36 | 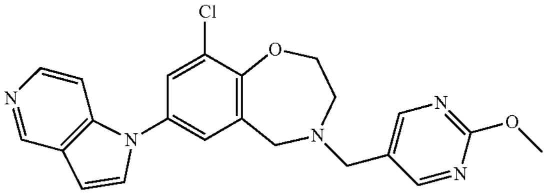 [SMILES: COc1ncc(CN2CCOc3c(Cl)cc(-n4ccc5cnccc54)cc3C2)cn1] | 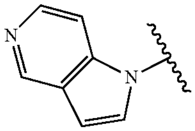 [SMILES: *n1ccc2cnccc21] | 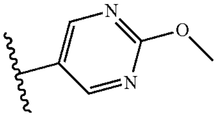 [SMILES: *c1cnc(OC)nc1] |
| 37 | 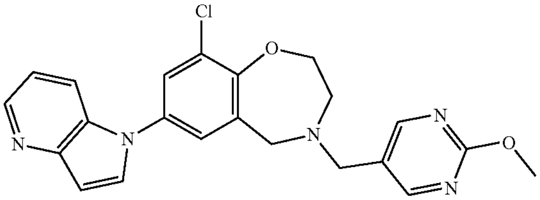 [SMILES: COc1ncc(CN2CCOc3c(Cl)cc(-n4ccc5ncccc54)cc3C2)cn1] | 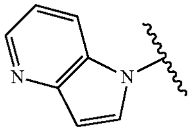 [SMILES: *n1ccc2ncccc21] | 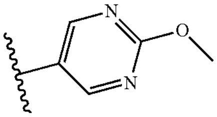 [SMILES: *c1cnc(OC)nc1] |
| 38 | 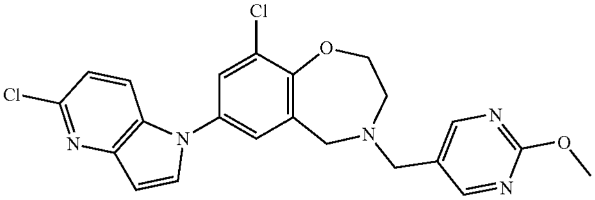 [SMILES: COc1ncc(CN2CCOc3c(Cl)cc(-n4ccc5nc(Cl)ccc54)cc3C2)cn1] | 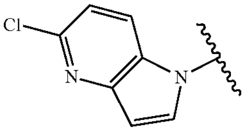 [SMILES: *n1ccc2nc(Cl)ccc21] | 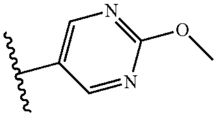 [SMILES: *c1cnc(OC)nc1] |
| 39 | 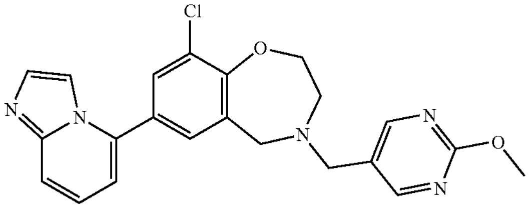 [SMILES: COc1ncc(CN2CCOc3c(Cl)cc(-c4cccc5nccn45)cc3C2)cn1] | 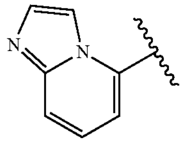 [SMILES: *c1cccc2nccn12] | 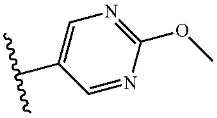 [SMILES: *c1cnc(OC)nc1] |
| 40 | 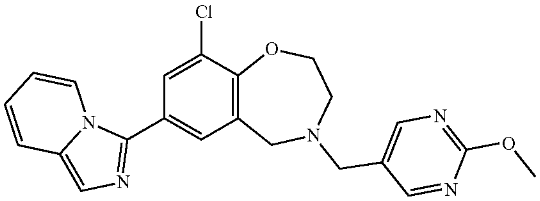 [SMILES: COc1ncc(CN2CCOc3c(Cl)cc(-c4ncc5ccccn45)cc3C2)cn1] | 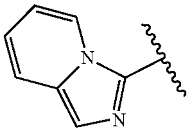 [SMILES: *c1ncc2ccccn12] | 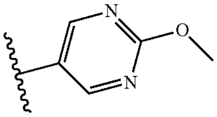 [SMILES: *c1cnc(OC)nc1] |

TABLE III-continued
| ID No | Structure | 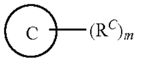 | 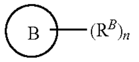 |
|---|---|---|---|
| 41 | 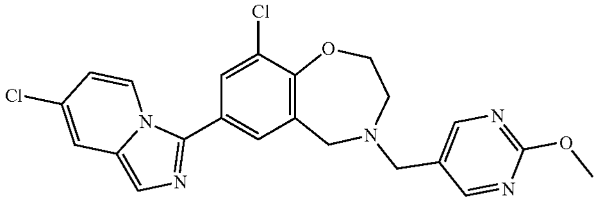 [SMILES: COc1ncc(CN2CCOc3c(Cl)cc(-c4ncc5cc(Cl)ccn45)cc3C2)cn1] | 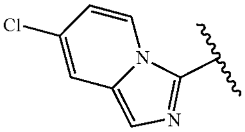 [SMILES: *c1ncc2cc(Cl)ccn12] | 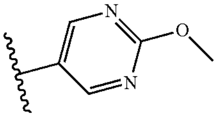 [SMILES: *c1cnc(OC)nc1] |
| 42 | 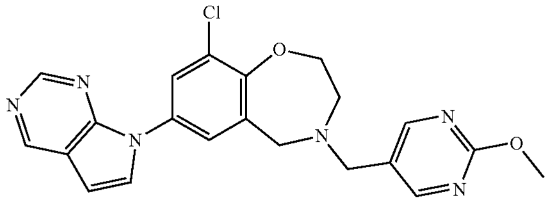 [SMILES: COc1ncc(CN2CCOc3c(Cl)cc(-n4ccc5cncnc54)cc3C2)cn1] | 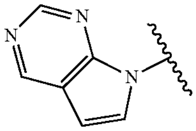 [SMILES: *n1ccc2cncnc21] | 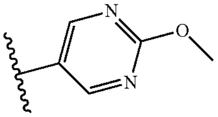 [SMILES: *c1cnc(OC)nc1] |
| 43 | 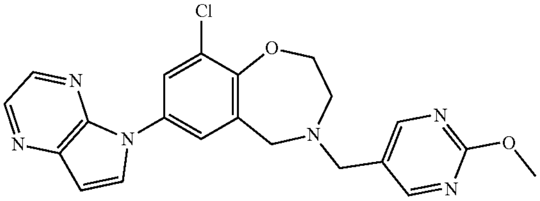 | 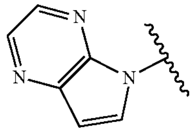 [SMILES: *n1ccc2nccnc21] | 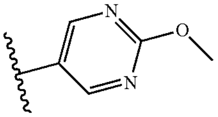 [SMILES: *c1cnc(OC)nc1] |
| 44 | 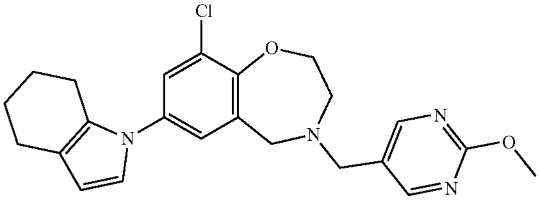 [SMILES: COc1ncc(CN2CCOc3c(Cl)cc(-n4ccc5c4CCCC5)cc3C2)cn1] | 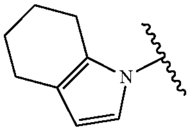 [SMILES: *n1ccc2c1CCCC2] | 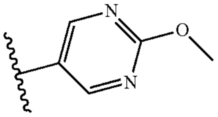 [SMILES: *c1cnc(OC)nc1] |
| 45 | 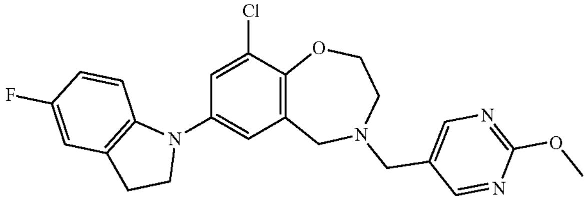 [SMILES: COc1ncc(CN2CCOc3c(Cl)cc(N4CCc5cc(F)ccc54)cc3C2)cn1] | 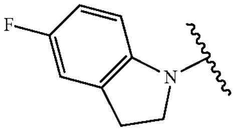 [SMILES: *N1CCc2cc(F)ccc21] | 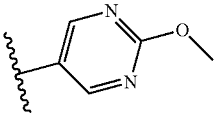 [SMILES: *c1cnc(OC)nc1] |
| 46 | 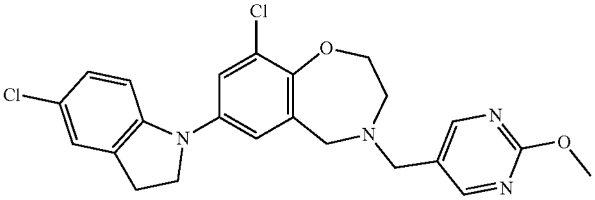 [SMILES: COc1ncc(CN2CCOc3c(Cl)cc(N4CCc5cc(Cl)ccc54)cc3C2)cn1] | 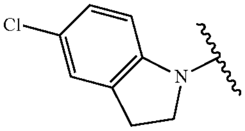 [SMILES: *N1CCc2cc(Cl)ccc21] | 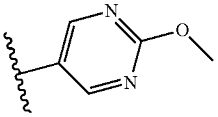 [SMILES: *c1cnc(OC)nc1] |
| 47 | 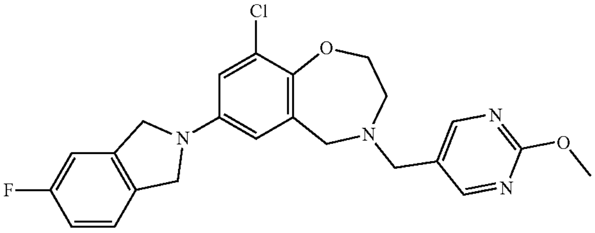 [SMILES: COc1ncc(CN2CCOc3c(Cl)cc(N4Cc5ccc(F)cc5C4)cc3C2)cn1] | 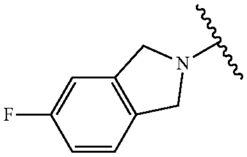 [SMILES: *N1Cc2ccc(F)cc2C1] | 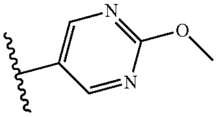 [SMILES: *c1cnc(OC)nc1] |

TABLE III-continued
| ID No | Structure | 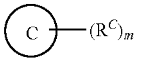 | 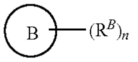 |
|---|---|---|---|
| 48 | 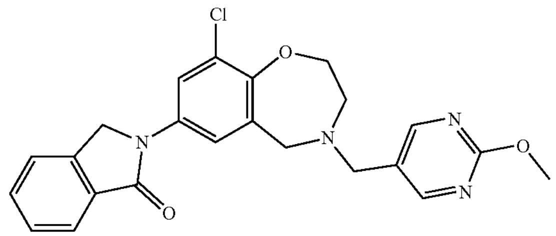 [SMILES: COc1ncc(CN2CCOc3c(Cl)cc(N4Cc5ccccc5C4=O)cc3C2)cn1] | 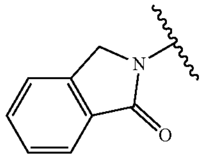 [SMILES: *N1Cc2ccccc2C1=O] | 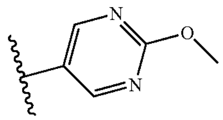 [SMILES: *c1cnc(OC)nc1] |
| 49 | 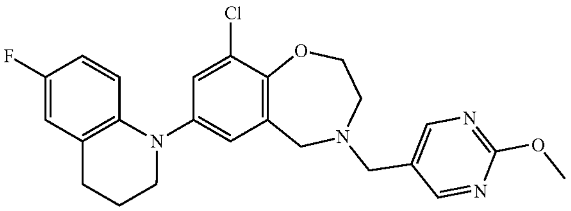 [SMILES: COc1ncc(CN2CCOc3c(Cl)cc(N4CCCc5cc(F)ccc54)cc3C2)cn1] | 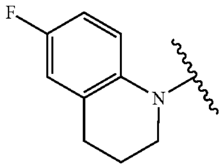 [SMILES: *N1CCCc2cc(F)ccc21] | 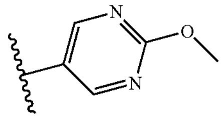 [SMILES: *c1cnc(OC)nc1] |
| 50 | 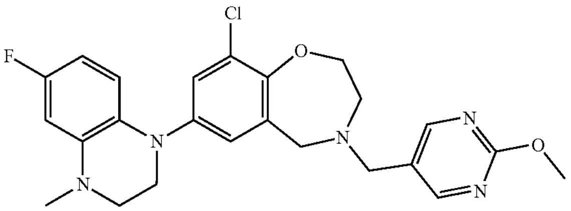 [SMILES: COc1ncc(CN2CCOc3c(Cl)cc(N4CCN(C)c5cc(F)ccc54)cc3C2)cn1] | 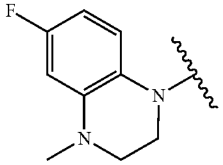 [SMILES: *N1CCN(C)c2cc(F)ccc21] | 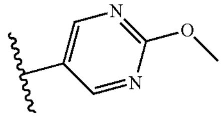 [SMILES: *c1cnc(OC)nc1] |
| 51 | 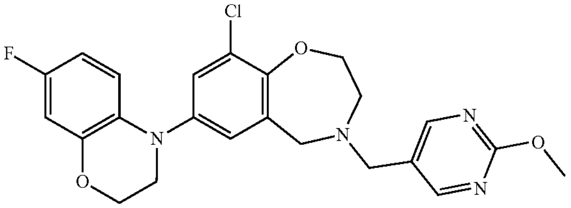 [SMILES: COc1ncc(CN2CCOc3c(Cl)cc(N4CCOc5cc(F)ccc54)cc3C2)cn1] | 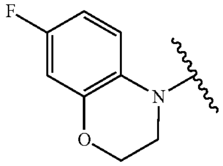 [SMILES: *N1CCOc2cc(F)ccc21] | 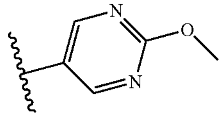 [SMILES: *c1cnc(OC)nc1] |
| 52 | 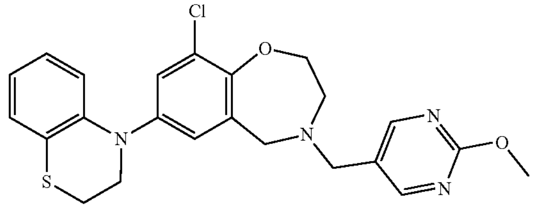 [SMILES: COc1ncc(CN2CCOc3c(Cl)cc(N4CCSc5ccccc54)cc3C2)cn1] | 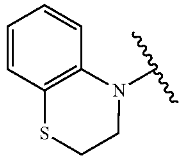 [SMILES: *N1CCSc2ccccc21] | 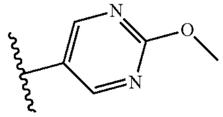 [SMILES: *c1cnc(OC)nc1] |
| 53 | 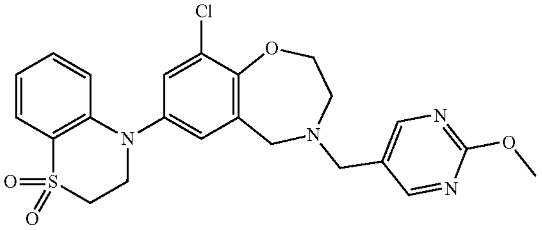 [SMILES: COc1ncc(CN2CCOc3c(Cl)cc(N4CCS(=O)(=O)c5ccccc54)cc3C2)cn1] | 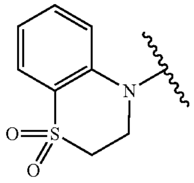 [SMILES: *N1CCS(=O)(=O)c2ccccc21] | 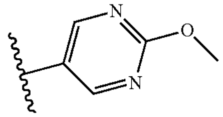 [SMILES: *c1cnc(OC)nc1] |

TABLE III-continued
| ID No | Structure | 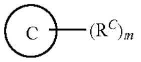 | 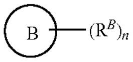 |
|---|---|---|---|
| 54 | 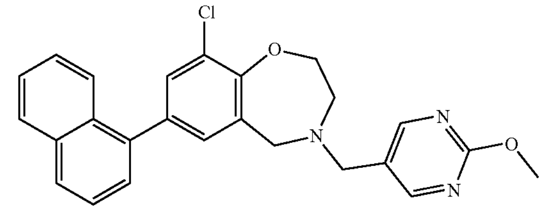 [SMILES: COc1ncc(CN2CCOc3c(Cl)cc(-c4cccc5ccccc45)cc3C2)cn1] | 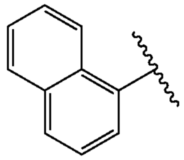 [SMILES: *c1cccc2ccccc12] | 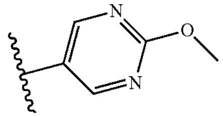 [SMILES: *c1cnc(OC)nc1] |
| 55 | 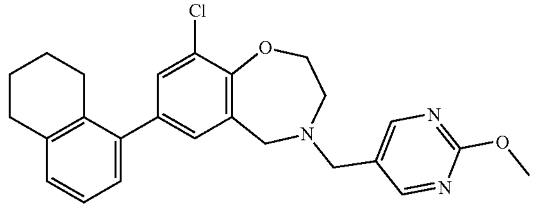 [SMILES: COc1ncc(CN2CCOc3c(Cl)cc(-c4cccc5c4CCCC5)cc3C2)cn1] | 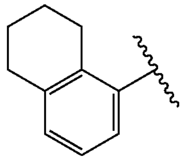 [SMILES: *c1cccc2c1CCCC2] | 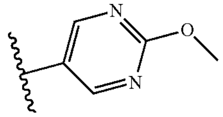 [SMILES: *c1cnc(OC)nc1] |
| 56 | 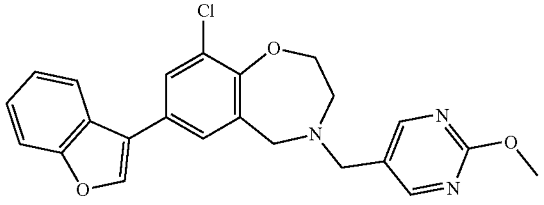 [SMILES: COc1ncc(CN2CCOc3c(Cl)cc(-c4coc5ccccc45)cc3C2)cn1] | 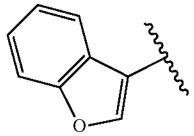 [SMILES: *c1coc2ccccc12] | 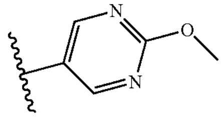 [SMILES: *c1cnc(OC)nc1] |
| 57 | 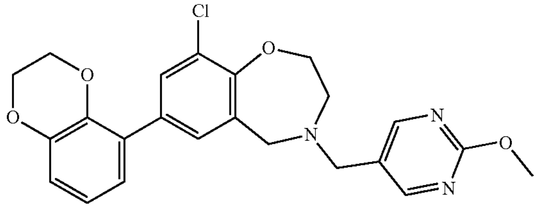 [SMILES: COc1ncc(CN2CCOc3c(Cl)cc(-c4cccc5c4OCCO5)cc3C2)cn1] | 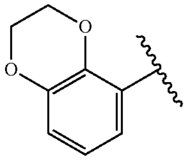 [SMILES: *c1cccc2c1OCCO2] | 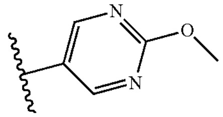 [SMILES: *c1cnc(OC)nc1] |
| 58 | 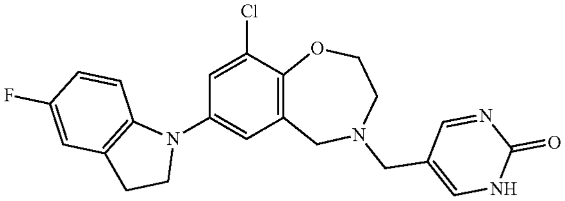 [SMILES: O=c1ncc(CN2CCOc3c(Cl)cc(N4CCc5cc(F)ccc54)cc3C2)c[nH]1] | 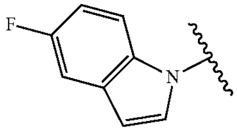 [SMILES: *n1ccc2cc(F)ccc21] | 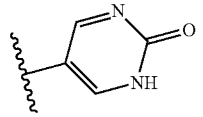 [SMILES: *c1cnc(=O)[nH]c1] |
| 59 | 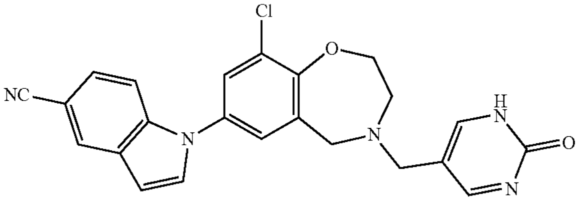 [SMILES: N#Cc1ccc2c(ccn2-c2cc(Cl)c3c(c2)CN(Cc2cnc(=O)[nH]c2)CCO3)c1] | 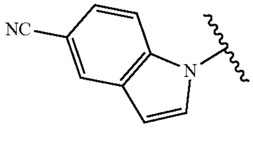 [SMILES: *n1ccc2cc(C#N)ccc21] | 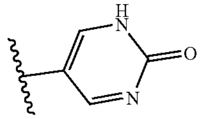 [SMILES: *c1cnc(=O)[nH]c1] |
| 60 | 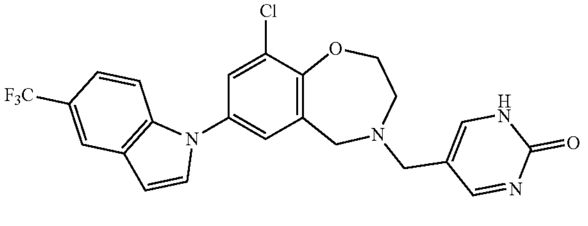 [SMILES: O=c1ncc(CN2CCOc3c(Cl)cc(-n4ccc5cc(C(F)(F)F)ccc54)cc3C2)c[nH]1] | 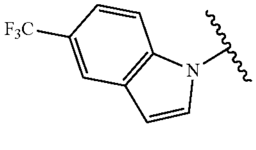 [SMILES: *n1ccc2cc(C(F)(F)F)ccc21] | 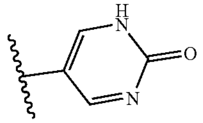 [SMILES: *c1cnc(=O)[nH]c1] |

TABLE III-continued
| ID No | Structure | —$(R^C)_m$ | —$(R^B)_n$ |
|---|---|---|---|
| 61 | 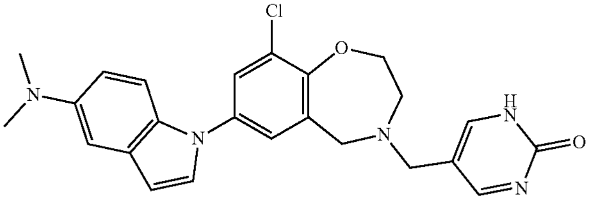 [SMILES: CN(C)c1ccc2c(ccn2-c2cc(Cl)c3c(c2)CN(Cc2cnc(=O)[nH]c2)CCO3)c1] | 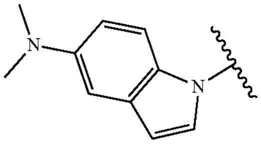 [SMILES: *n1ccc2cc(N(C)C)ccc21] | 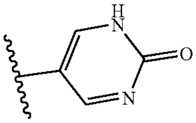 [SMILES: *c1cnc(=O)[nH]c1] |
| 62 | 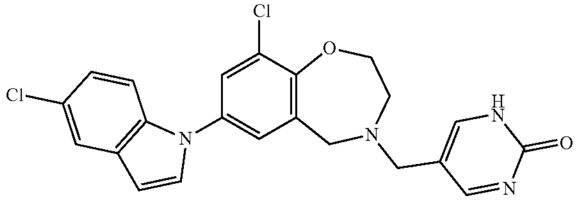 | 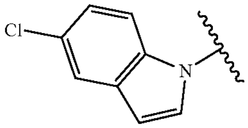 [SMILES: *n1ccc2cc(Cl)ccc21] | 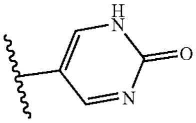 [SMILES: *c1cnc(=O)[nH]c1] |
| 63 | 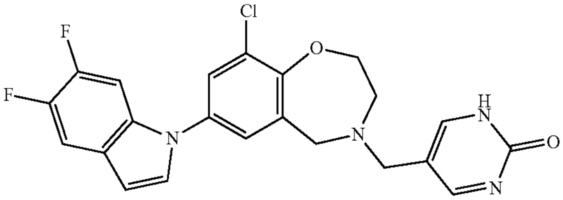 [SMILES: O=c1ncc(CN2CCOc3c(Cl)cc(-n4ccc5cc(F)c(F)cc54)cc3C2)c[nH]1] | 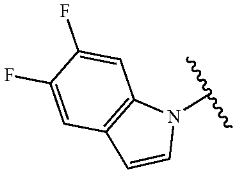 [SMILES: *n1ccc2cc(F)c(F)cc21] | 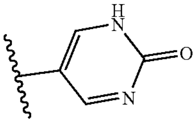 [SMILES: *c1cnc(=O)[nH]c1] |
| 64 | 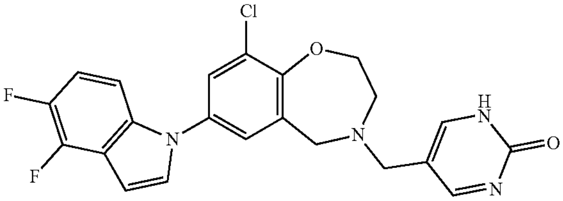 [SMILES: O=c1ncc(CN2CCOc3c(Cl)cc(-n4ccc5c(F)c(F)ccc54)cc3C2)c[nH]1] | 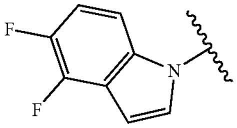 [SMILES: *n1ccc2c(F)c(F)ccc21] | 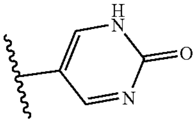 [SMILES: *c1cnc(=O)[nH]c1] |
| 65 | 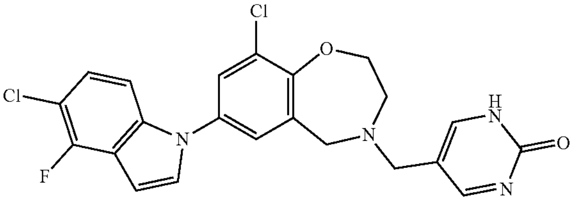 [SMILES: O=c1ncc(CN2CCOc3c(Cl)cc(-n4ccc5c(F)c(Cl)ccc54)cc3C2)c[nH]1] | 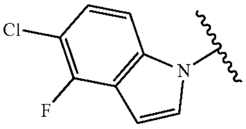 [SMILES: *n1ccc2c(F)c(Cl)ccc21] | 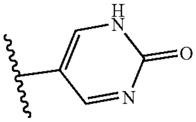 [SMILES: *c1cnc(=O)[nH]c1] |
| 66 | 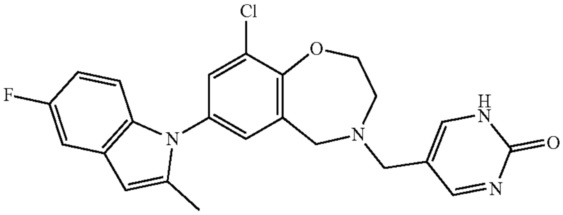 [SMILES: Cc1cc2cc(F)ccc2n1-c1cc(Cl)c2c(c1)CN(Cc1cnc(=O)[nH]c1)CCO2] | 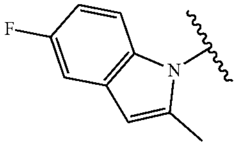 [SMILES: *n1c(C)cc2cc(F)ccc21] | 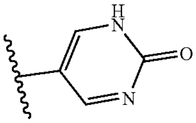 [SMILES: *c1cnc(=O)[nH]c1] |
| 67 | 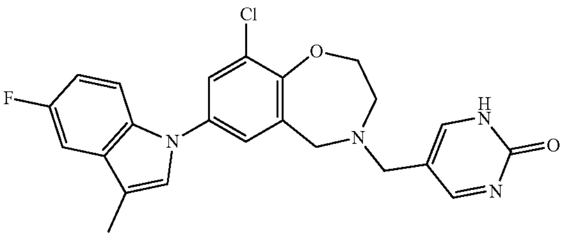 [SMILES: Cc1cn(-c2cc(Cl)c3c(c2)CN(Cc2cnc(=O)[nH]c2)CCO3)c2ccc(F)cc12] | 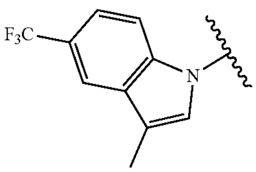 [SMILES: *n1cc(C)c2cc(C(F)(F)F)ccc21] | 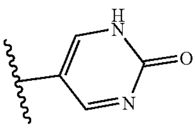 [SMILES: *c1cnc(=O)[nH]c1] |

TABLE III-continued
| ID No | Structure | 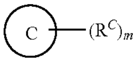 | 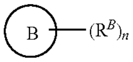 |
|---|---|---|---|
| 68 | 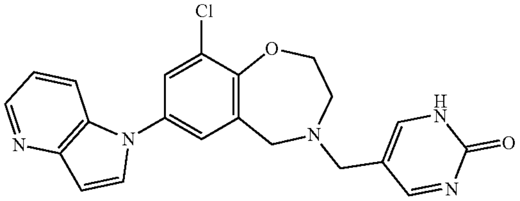 [SMILES: O=c1ncc(CN2CCOc3c(Cl)cc(-n4ccc5ncccc54)cc3C2)c[nH]1] | 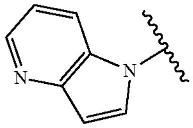 [SMILES: *n1ccc2ncccc21] | 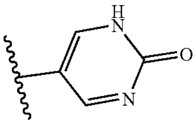 [SMILES: *c1cnc(=O)[nH]c1] |
| 69 | 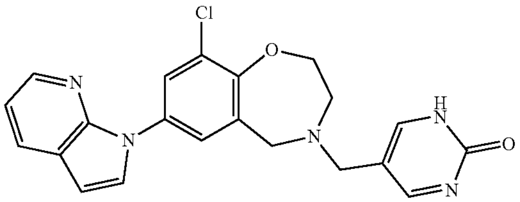 [SMILES: O=c1ncc(CN2CCOc3c(Cl)cc(-n4ccc5cccnc54)cc3C2)c[nH]1] | 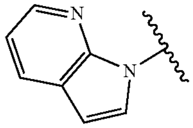 [SMILES: *n1ccc2cccnc21] | 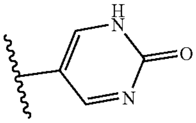 [SMILES: *c1cnc(=O)[nH]c1] |
| 70 | 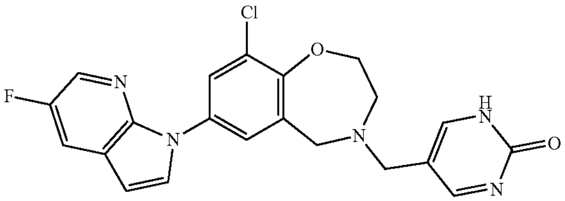 [SMILES: O=c1ncc(CN2CCOc3c(Cl)cc(-n4ccc5cc(F)cnc54)cc3C2)c[nH]1] | 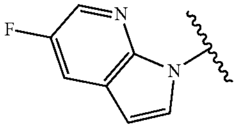 [SMILES: *n1ccc2cc(F)cnc21] | 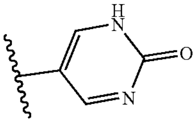 [SMILES: *c1cnc(=O)[nH]c1] |
| 71 | 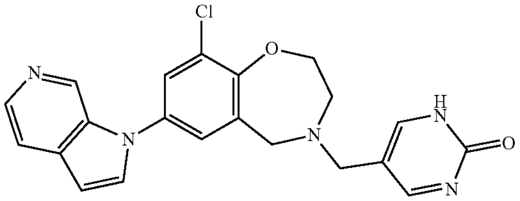 [SMILES: O=c1ncc(CN2CCOc3c(Cl)cc(-n4ccc5ccncc54)cc3C2)c[nH]1] | 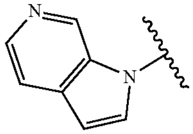 [SMILES: *n1ccc2ccncc21] | 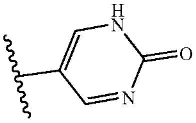 [SMILES: *c1cnc(=O)[nH]c1] |
| 72 | 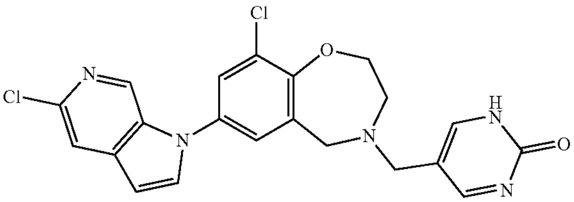 [SMILES: O=c1ncc(CN2CCOc3c(Cl)cc(-n4ccc5cc(Cl)ncc54)cc3C2)c[nH]1] | 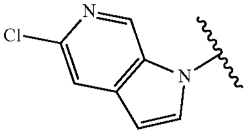 [SMILES: *n1ccc2cc(Cl)ncc21] | 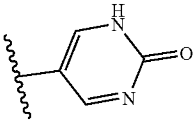 [SMILES: *c1cnc(=O)[nH]c1] |
| 73 | 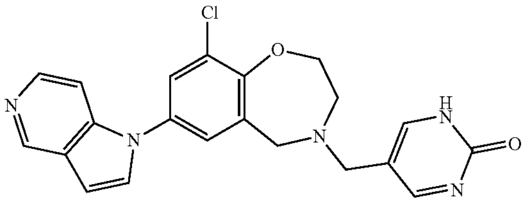 [SMILES: O=c1ncc(CN2CCOc3c(Cl)cc(-n4ccc5cnccc54)cc3C2)c[nH]1] | 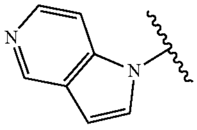 [SMILES: *n1ccc2cnccc21] | 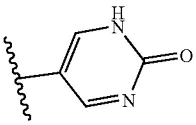 [SMILES: *c1cnc(=O)[nH]c1] |
| 74 | 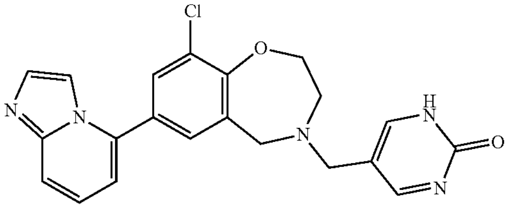 [SMILES: O=c1ncc(CN2CCOc3c(Cl)cc(-c4cccc5nccn45)cc3C2)c[nH]1] | 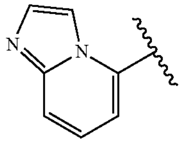 [SMILES: *c1cccc2nccn12] | 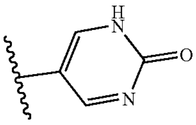 [SMILES: *c1cnc(=O)[nH]c1] |

TABLE III-continued
| ID No | Structure | 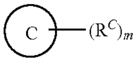 | 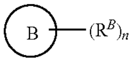 |
|---|---|---|---|
| 75 | 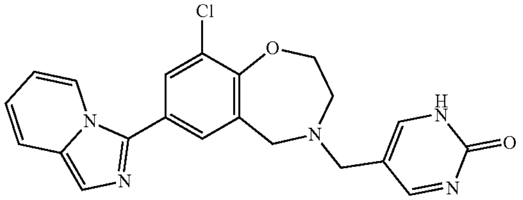 [SMILES: O=c1ncc(CN2CCOc3c(Cl)cc(-c4ncc5ccccn45)cc3C2)c[nH]1] | 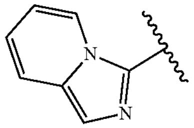 [SMILES: *c1ncc2ccccn12] | 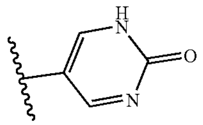 [SMILES: *c1cnc(=O)[nH]c1] |
| 76 | 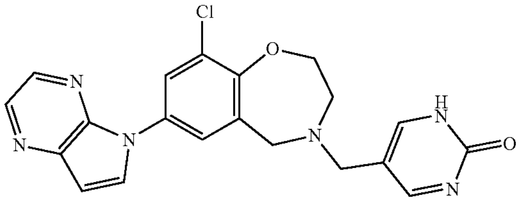 | 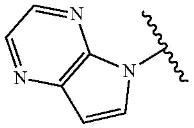 [SMILES: *n1ccc2nccnc21] | 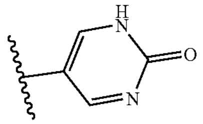 [SMILES: *c1cnc(=O)[nH]c1] |
| 77 | 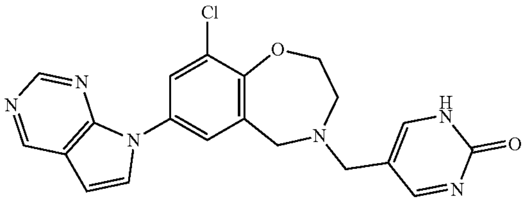 [SMILES: O=c1ncc(CN2CCOc3c(Cl)cc(-n4ccc5cncnc54)cc3C2)c[nH]1] | 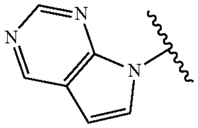 [SMILES: *n1ccc2cncnc21] | 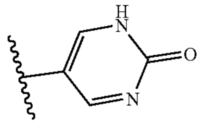 [SMILES: *c1cnc(=O)[nH]c1] |
| 78 | 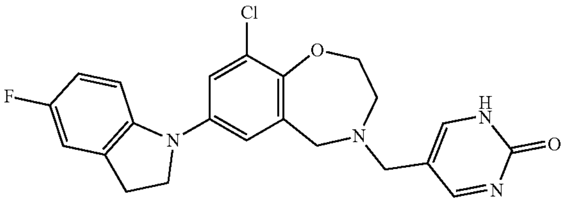 [SMILES: O=c1ncc(CN2CCOc3c(Cl)cc(N4CCc5cc(F)ccc54)cc3C2)c[nH]1] | 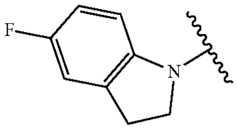 | 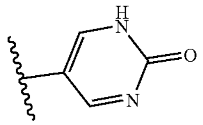 [SMILES: *c1cnc(=O)[nH]c1] |
| 79 | 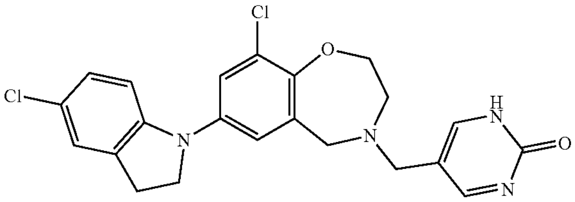 [SMILES: O=c1ncc(CN2CCOc3c(Cl)cc(N4CCc5cc(Cl)ccc54)cc3C2)c[nH]1] | 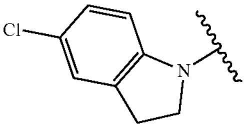 [SMILES: *N1CCc2cc(Cl)ccc21] | 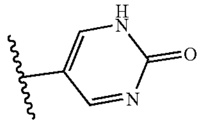 [SMILES: *c1cnc(=O)[nH]c1] |
| 80 | 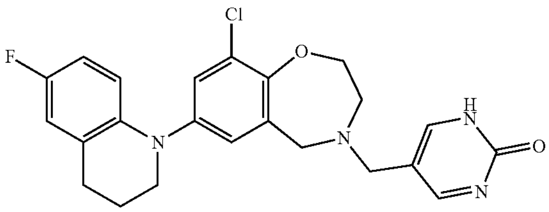 | 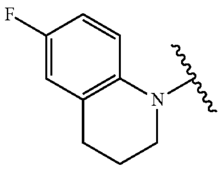 | 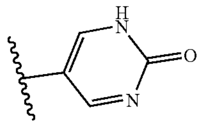 [SMILES: *c1cnc(=O)[nH]c1] |
| 81 | 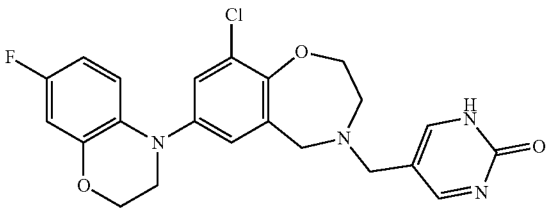 [SMILES: O=c1ncc(CN2CCOc3c(Cl)cc(N4CCOc5cc(F)ccc54)cc3C2)c[nH]1] | 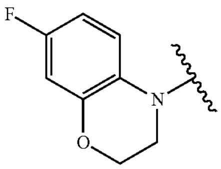 | 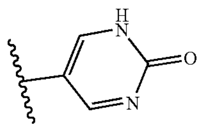 [SMILES: *c1cnc(=O)[nH]c1] |

TABLE III-continued

| ID No | Structure | 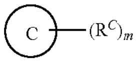 | 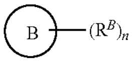 |
|---|---|---|---|
| 82 | 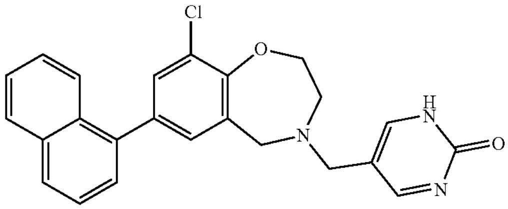 [SMILES: O=c1ncc(CN2CCOc3c(Cl)cc(-c4cccc5ccccc45)cc3C2)c[nH]1] | 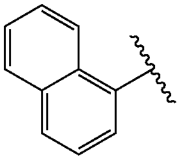 [SMILES: *c1cccc2ccccc12] | 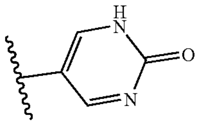 [SMILES: *c1cnc(=O)[nH]c1] |
| 83 | 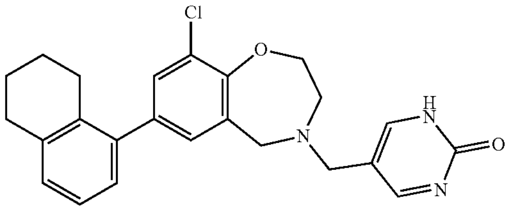 [SMILES: O=c1ncc(CN2CCOc3c(Cl)cc(-c4cccc5c4CCCC5)cc3C2)c[nH]1] | 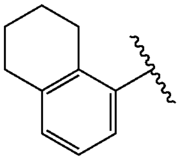 [SMILES: *c1cccc2c1CCCC2] | 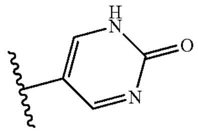 [SMILES: *c1cnc(=O)[nH]c1] |
| 84 | 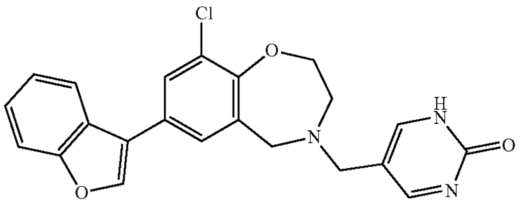 [SMILES: O=c1ncc(CN2CCOc3c(Cl)cc(-c4coc5ccccc45)cc3C2)c[nH]1] | 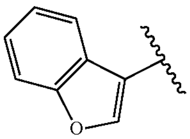 [SMILES: *c1coc2ccccc12] | 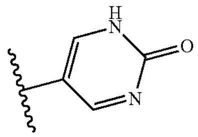 [SMILES: *c1cnc(=O)[nH]c1] |
| 85 | 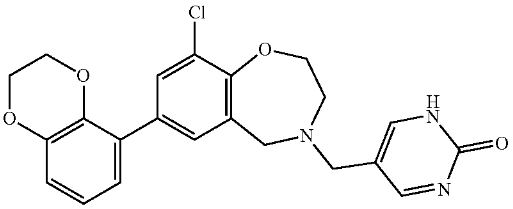 [SMILES: O=c1ncc(CN2CCOc3c(Cl)cc(-c4cccc5c4OCCO5)cc3C2)c[nH]1] | 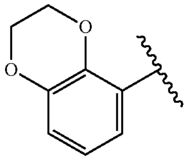 [SMILES: *c1cccc2c1OCCO2] | 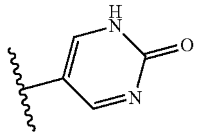 [SMILES: *c1cnc(=O)[nH]c1] |

In another embodiment, is a compound of Formula (III'):

Formula (III')

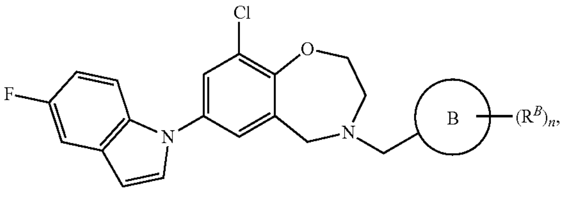

or a pharmaceutically acceptable salt thereof, wherein:

Ring B is $C_{3-6}$ cycloalkyl, phenyl, or 5-membered heteroaryl, or 6-membered heteroaryl containing two or more nitrogen atoms;

$R^B$ is halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —OH, —O($C_{1-4}$ alkyl), —O($C_{1-4}$ haloalkyl), —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, substituted or unsubstituted $C_{3-6}$ cycloalkyl, or substituted or unsubstituted 3- to 6-membered heterocycloalkyl; or two $R^B$ taken together form a carbonyl; and n is 0 to 3.

In some embodiments, each $R^B$ is independently selected from —F, —Cl, —CN, —$CH_3$, —$CH_2F$, —$CHF_2$, —$CF_3$, $CH_2NH_2$, —$CH_2$NHBoc, —$CH_2OH$, —$CH_2OCH_3$, —C(O)$NH_2$, —C(O)$NHCH_3$, —C(O)N$(CH_3)_2$, —C(O)OH, —C(O)$OCH_3$, —$NH_2$, $NHCH_3$, —N$(CH_3)_2$, —NH(oxetanyl), —NHC(O)$CH_3$, —NHS($O_2$)$CH_3$, —OH, —$OCH_3$, —$OCH_2CF_3$, methylpyrazolyl, pyrazolyl, and oxo.

In some embodiments, the compound of Formula (II) is a compound of the following formula:

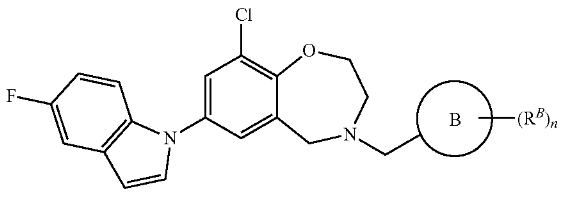

or a tautomer thereof, or a pharmaceutically acceptable salt thereof, disclosed in Table III'.

TABLE III
| ID No. | Structure | 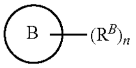 |
|---|---|---|
| 86 | 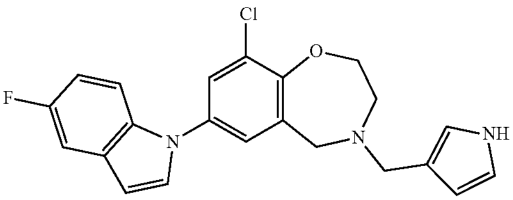 [SMILES: Fc1ccc2c(ccn2-c2cc(Cl)c3c(c2)CN(Cc2cc[nH]c2)CCO3)c1] | 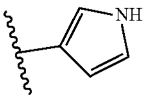 [SMILES: *c1cc[nH]c1] |
| 87 | 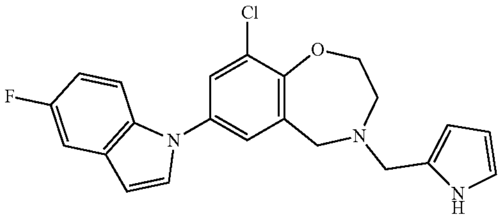 [SMILES: Fc1ccc2c(ccn2-c2cc(Cl)c3c(c2)CN(Cc2ccc[nH]2)CCO3)c1] | 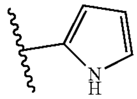 [SMILES: *c1ccc[nH]1] |
| 88 | 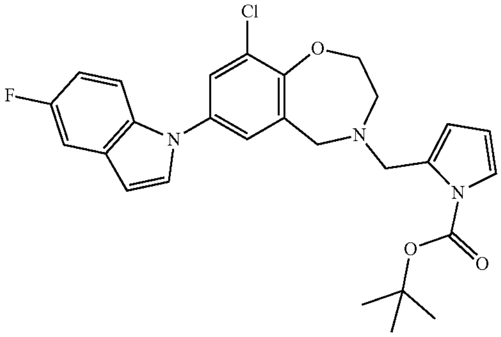 [SMILES: CC(C)(C)OC(=O)n1cccc1CN1CCOc2c(Cl)cc(-n3ccc4cc(F)ccc43)cc2C1] | 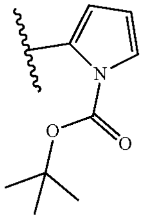 [SMILES: *c1cccn1C(=O)OC(C)(C)C] |
| 89 | 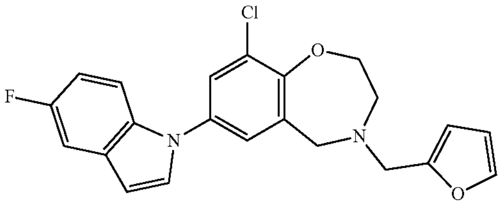 [SMILES: Fc1ccc2c(ccn2-c2cc(Cl)c3c(c2)CN(Cc2ccco2)CCO3)c1] | 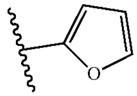 [SMILES: *c1ccco1] |
| 90 | 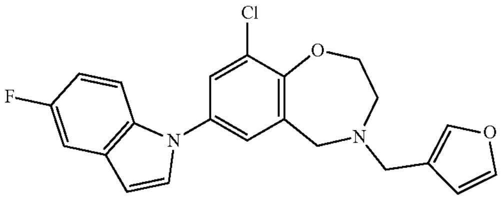 | 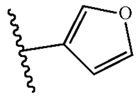 [SMILES: *c1ccoc1] |
| 91 | 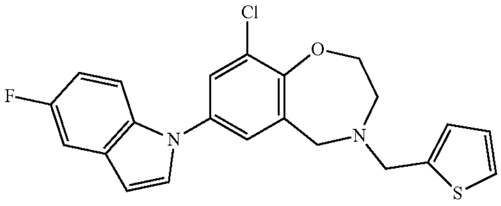 | 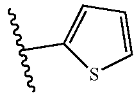 [SMILES: *c1cccs1] |

TABLE III-continued
| ID No. | Structure | 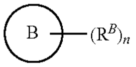 |
|---|---|---|
| 92 | 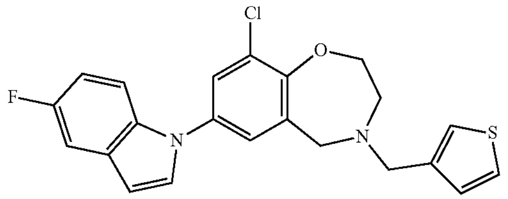 [SMILES: Fc1ccc2c(ccn2-c2cc(Cl)c3c(c2)CN(Cc2ccsc2)CCO3)c1] | 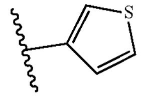 [SMILES: *c1ccsc1] |
| 93 | 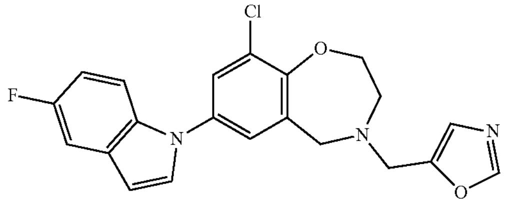 [SMILES: Fc1ccc2c(ccn2-c2cc(Cl)c3c(c2)CN(Cc2cnco2)CCO3)c1] | 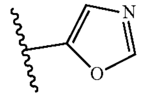 [SMILES: *c1cnco1] |
| 94 | 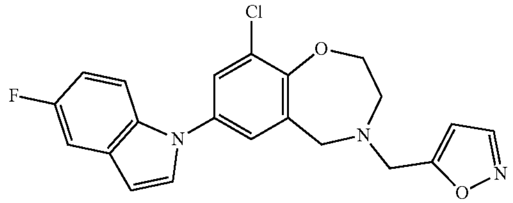 [SMILES: Fc1ccc2c(ccn2-c2cc(Cl)c3c(c2)CN(Cc2ccno2)CCO3)c1] | 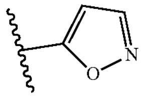 [SMILES: *c1ccno1] |
| 95 | 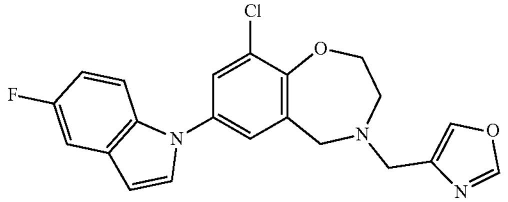 [SMILES: Fc1ccc2c(ccn2-c2cc(Cl)c3c(c2)CN(Cc2cocn2)CCO3)c1] | 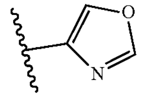 [SMILES: *c1cocn1] |
| 96 | 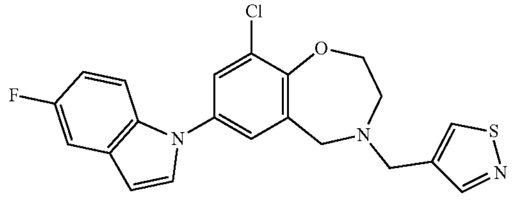 [SMILES: Fc1ccc2c(ccn2-c2cc(Cl)c3c(c2)CN(Cc2cnsc2)CCO3)c1] | 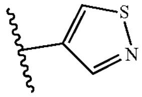 [SMILES: *c1cnsc1] |
| 97 | 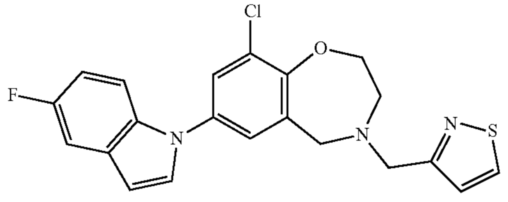 [SMILES: Fc1ccc2c(ccn2-c2cc(Cl)c3c(c2)CN(Cc2ccsn2)CCO3)c1] | 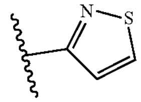 [SMILES: *c1ccsn1] |
| 98 | 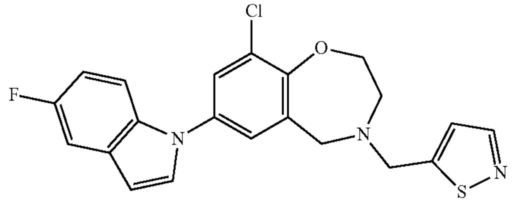 | 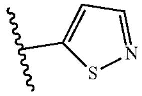 [SMILES: *c1ccns1] |

TABLE III-continued
| ID No. | Structure | 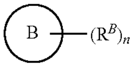 |
|---|---|---|
| 99 | 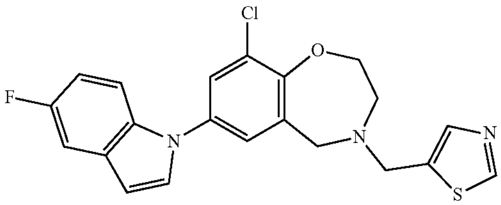 [SMILES: Fc1ccc2c(ccn2-c2cc(Cl)c3c(c2)CN(Cc2cncs2)CCO3)c1] | 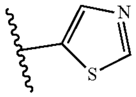 [SMILES: *c1cncs1] |
| 100 | 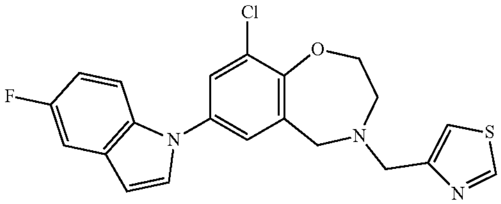 | 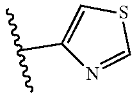 [SMILES: *c1cscn1] |
| 101 | 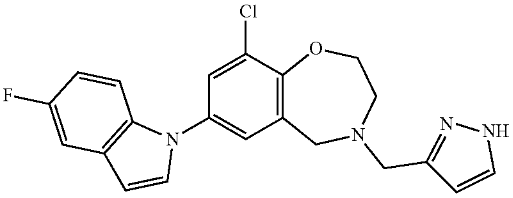 | 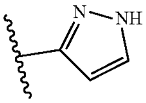 [SMILES: *c1cc[nH]n1] |
| 102 | 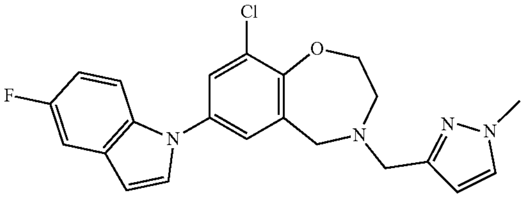 [SMILES: Cn1ccc(CN2CCOc3c(Cl)cc(-n4ccc5cc(F)ccc54)cc3C2)n1] | 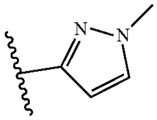 [SMILES: *c1ccn(C)n1] |
| 103 | 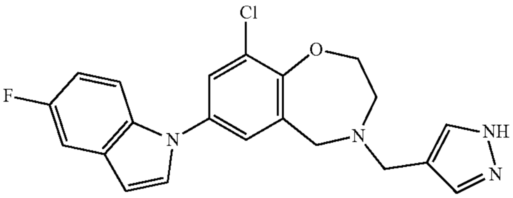 [SMILES: Fc1ccc2c(ccn2-c2cc(Cl)c3c(c2)CN(Cc2cn[nH]c2)CCO3)c1] | 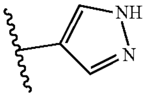 [SMILES: *c1cn[nH]c1] |
| 104 | 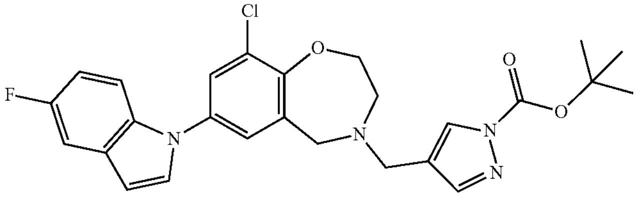 [SMILES: CC(C)(C)OC(=O)n1cc(CN2CCOc3c(Cl)cc(-n4ccc5cc(F)ccc54)cc3C2)cn1] | 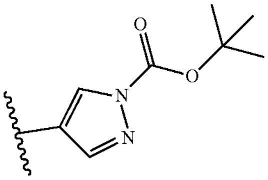 [SMILES: *c1cnn(C(=O)OC(C)(C)C)c1] |
| 105 | 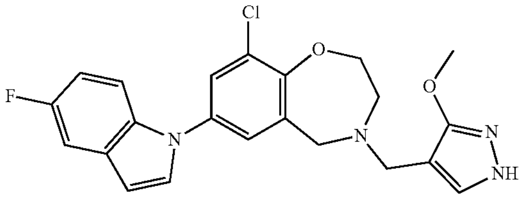 [SMILES: COc1n[nH]cc1CN1CCOc2c(Cl)cc(-n3ccc4cc(F)ccc43)cc2C1] | 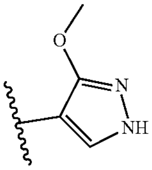 [SMILES: *c1c[nH]nc1OC] |

TABLE III-continued
| ID No. | Structure | 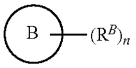 |
| --- | --- | --- |
| 106 | 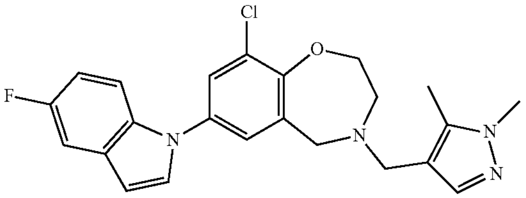 [SMILES: Cc1c(CN2CCOc3c(Cl)cc(-n4ccc5cc(F)ccc54)cc3C2)cnn1C] | 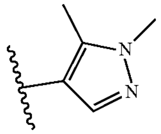 [SMILES: *c1cnn(C)c1C] |
| 107 | 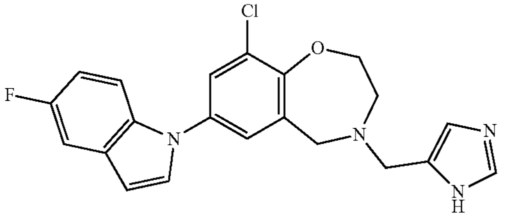 [SMILES: Fc1ccc2c(ccn2-c2cc(Cl)c3c(c2)CN(Cc2cnc[nH]2)CCO3)c1] | 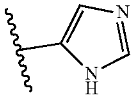 [SMILES: *c1cnc[nH]1] |
| 108 | 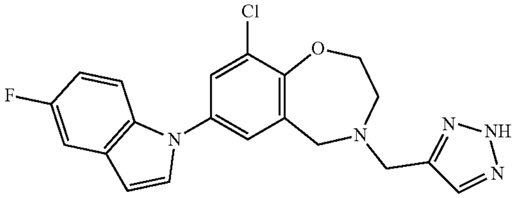 [SMILES: Fc1ccc2c(ccn2-c2cc(Cl)c3c(c2)CN(Cc2cn[nH]n2)CCO3)c1] | 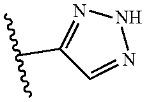 [SMILES: *c1cn[nH]n1] |
| 109 | 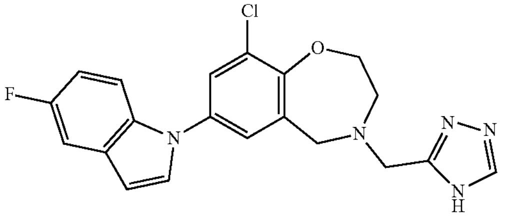 [SMILES: Fc1ccc2c(ccn2-c2cc(Cl)c3c(c2)CN(Cc2nnc[nH]2)CCO3)c1] | 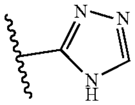 [SMILES: *c1nnc[nH]1] |
| 110 | 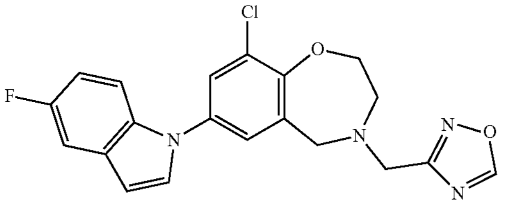 [SMILES: Fc1ccc2c(ccn2-c2cc(Cl)c3c(c2)CN(Cc2ncon2)CCO3)c1] | 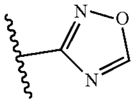 [SMILES: *c1ncon1] |
| 111 | 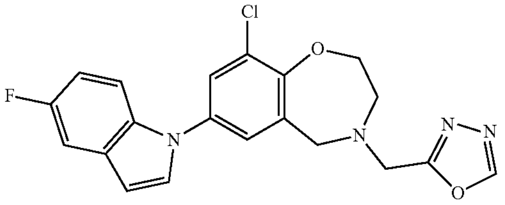 [SMILES: Fc1ccc2c(ccn2-c2cc(Cl)c3c(c2)CN(Cc2nnco2)CCO3)c1] | 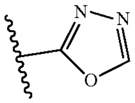 [SMILES: *c1nnco1] |
| 112 | 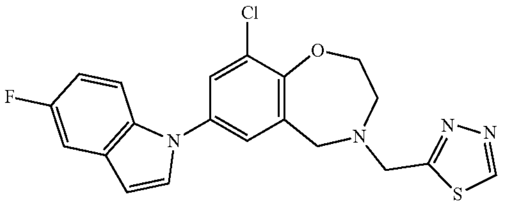 [SMILES: Fc1ccc2c(ccn2-c2cc(Cl)c3c(c2)CN(Cc2nncs2)CCO3)c1] | 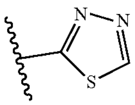 [SMILES: *c1nncs1] |

TABLE III-continued
| ID No. | Structure | 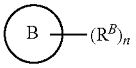 |
|---|---|---|
| 113 | 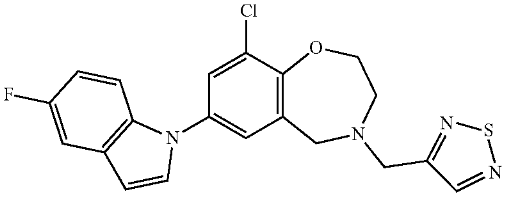 [SMILES: Fc1ccc2c(ccn2-c2cc(Cl)c3c(c2)CN(Cc2cnsn2)CCO3)c1] | 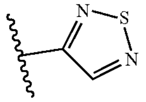 [SMILES: *c1cnsn1] |
| 114 | 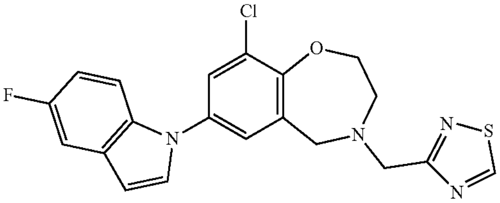 | 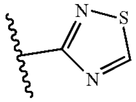 [SMILES: *c1ncsn1] |
| 115 | 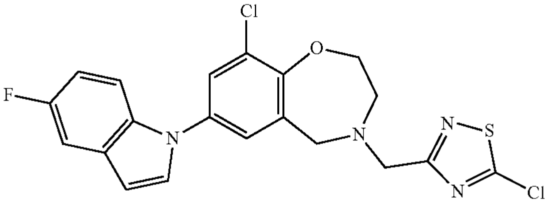 [SMILES: Fc1ccc2c(ccn2-c2cc(Cl)c3c(c2)CN(Cc2nsc(Cl)n2)CCO3)c1] | 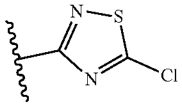 [SMILES: *c1nsc(Cl)n1] |
| 116 | 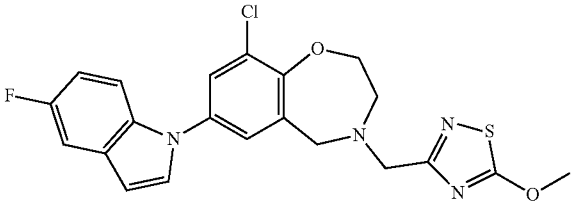 [SMILES: COc1nc(CN2CCOc3c(Cl)cc(-n4ccc5cc(F)ccc54)cc3C2)ns1] | 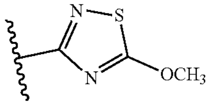 [SMILES: *c1nsc(OC)n1] |
| 117 | 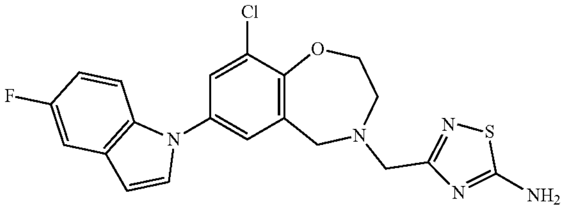 [SMILES: Nc1nc(CN2CCOc3c(Cl)cc(-n4ccc5cc(F)ccc54)cc3C2)ns1] | 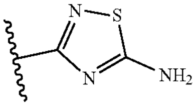 [SMILES: *c1nsc(N)n1] |
| 118 | 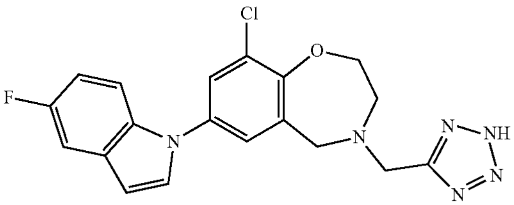 [SMILES: Fc1ccc2c(ccn2-c2cc(Cl)c3c(c2)CN(Cc2nn[nH]n2)CCO3)c1] | 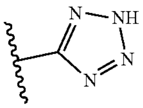 |
| 119 | 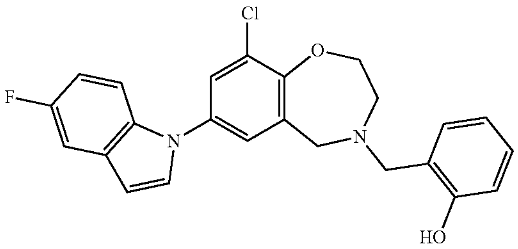 [SMILES: Oc1ccccc1CN1CCOc2c(Cl)cc(-n3ccc4cc(F)ccc43)cc2C1] | 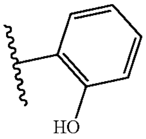 [SMILES: *c1ccccc1O] |

TABLE III-continued
| ID No. | Structure | 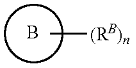 |
|---|---|---|
| 120 | 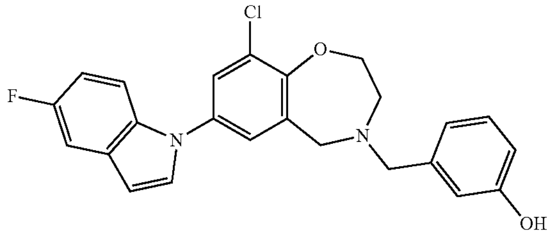 [SMILES: Oc1cccc(CN2CCOc3c(Cl)cc(-n4ccc5cc(F)ccc54)cc3C2)c1] | 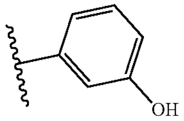 [SMILES: *c1cccc(O)c1] |
| 121 | 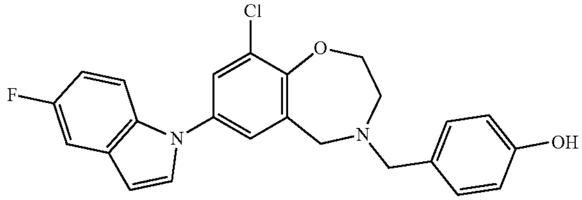 [SMILES: Oc1ccc(CN2CCOc3c(Cl)cc(-n4ccc5cc(F)ccc54)cc3C2)cc1] | 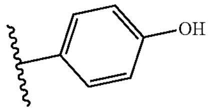 [SMILES: *c1ccc(O)cc1] |
| 122 | 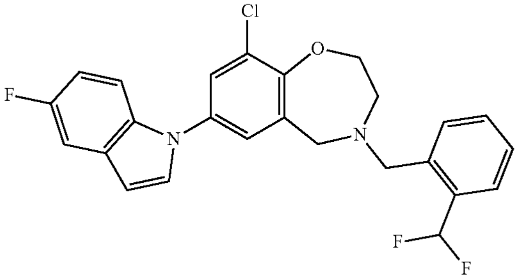 [SMILES: Fc1ccc2c(ccn2-c2cc(Cl)c3c(c2)CN(Cc2ccccc2C(F)F)CCO3)c1] | 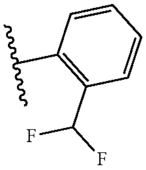 [SMILES: *c1ccccc1C(F)F] |
| 123 | 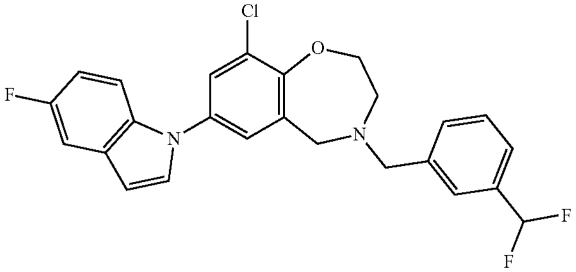 [SMILES: Fc1ccc2c(ccn2-c2cc(Cl)c3c(c2)CN(Cc2cccc(C(F)F)c2)CCO3)c1] | 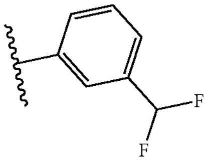 [SMILES: *c1cccc(C(F)F)c1] |
| 124 | 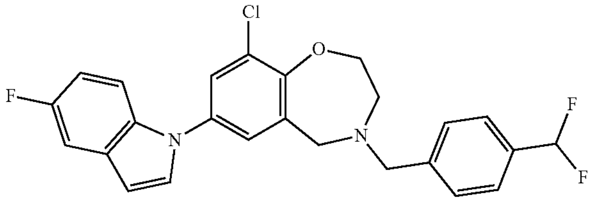 [SMILES: Fc1ccc2c(ccn2-c2cc(Cl)c3c(c2)CN(Cc2ccc(C(F)F)cc2)CCO3)c1] | 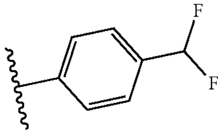 [SMILES: *c1ccc(C(F)F)cc1] |
| 125 | 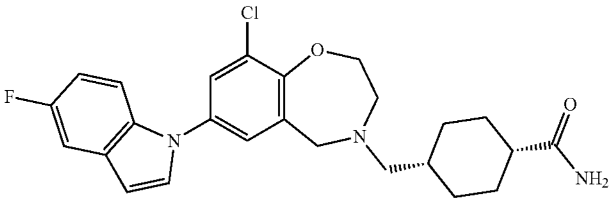 [SMILES: NC(=O)[C@H]1CC[C@@H](CN2CCOc3c(Cl)cc(-n4ccc5cc(F)ccc54)cc3C2)CC1] | 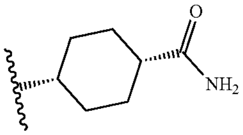 [SMILES: *[C@H]1CC[C@@H](C(N)=O)CC1] |

TABLE III-continued
| ID No. | Structure | 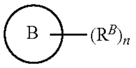 |
|---|---|---|
| 126 | 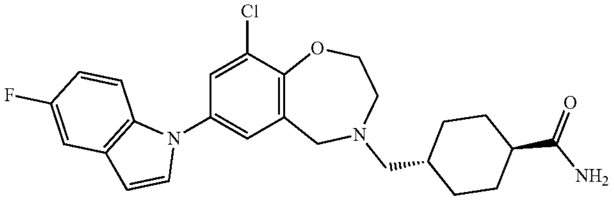 | 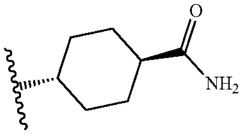 [SMILES: *[C@H]1CC[C@H](C(N)=O)CC1] |
| 127 | 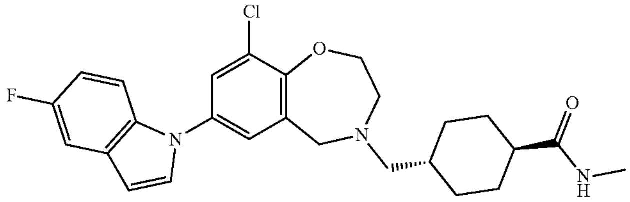 [SMILES: CNC(=O)[C@H]1CC[C@H](CN2CCOc3c(Cl)cc(-n4ccc5cc(F)ccc54)cc3C2)CC1] | 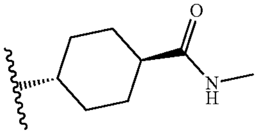 [SMILES: *[C@H]1CC[C@H](C(=O)NC)CC1] |
| 128 | 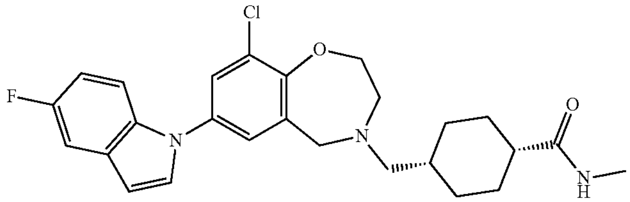 | 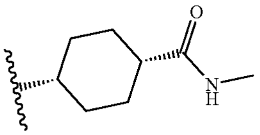 [SMILES: *[C@H]1CC[C@@H](C(=O)NC)CC1] |
| 129 | 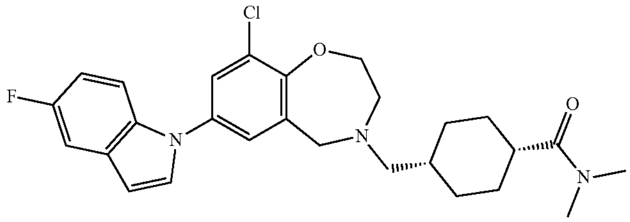 [SMILES: CN(C)C(=O)[C@H]1CC[C@@H](CN2CCOc3c(Cl)cc(-n4ccc5cc(F)ccc54)cc3C2)CC1] | 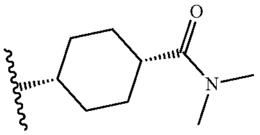 [SMILES: *[C@H]1CC[C@@H](C(=O)N(C)C)CC1] |
| 130 | 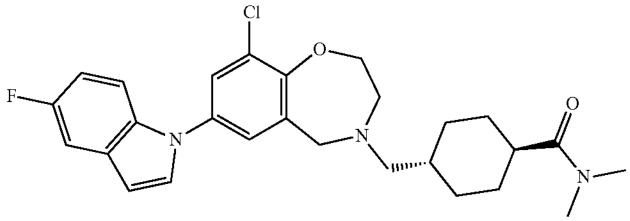 [SMILES: CN(C)C(=O)[C@H]1CC[C@H](CN2CCOc3c(Cl)cc(-n4ccc5cc(F)ccc54)cc3C2)CC1] | 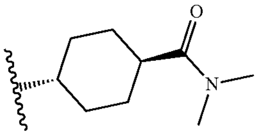 [SMILES: *[C@H]1CC[C@H](C(=O)N(C)C)CC1] |
| 131 | 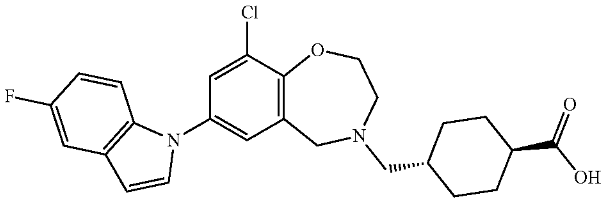 | 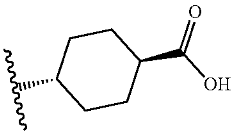 [SMILES: *[C@H]1CC[C@H](C(=O)O)CC1] |
| 132 | 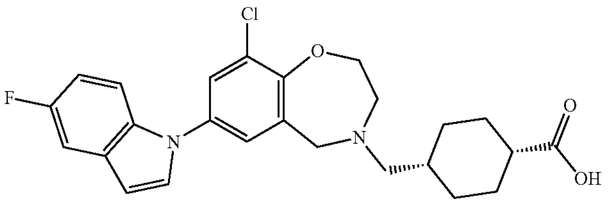 [SMILES: O=C(O)[C@H]1CC[C@@H](CN2CCOc3c(Cl)cc(-n4ccc5cc(F)ccc54)cc3C2)CC1] | 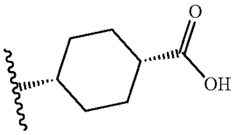 [SMILES: *[C@H]1CC[C@@H](C(=O)O)CC1] |

TABLE III-continued
| ID No. | Structure | 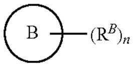 |
|---|---|---|
| 133 | 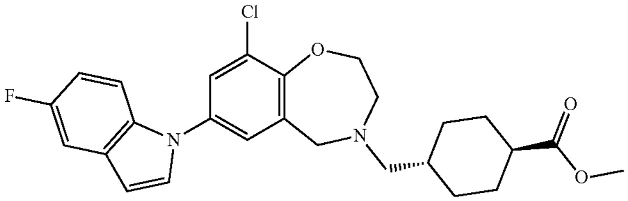 [SMILES: COC(=O)[C@H]1CC[C@H](CN2CCOc3c(Cl)cc(-n4ccc5cc(F)ccc54)cc3C2)CC1] | 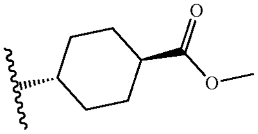 [SMILES: *[C@H]1CC[C@H](C(=O)OC)CC1] |
| 134 | 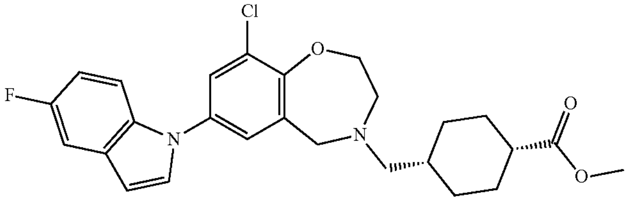 [SMILES: COC(=O)[C@H]1CC[C@@H](CN2CCOc3c(Cl)cc(-n4ccc5cc(F)ccc54)cc3C2)CC1] | 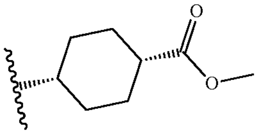 [SMILES: *[C@H]1CC[C@@H](C(=O)OC)CC1] |
| 135 | 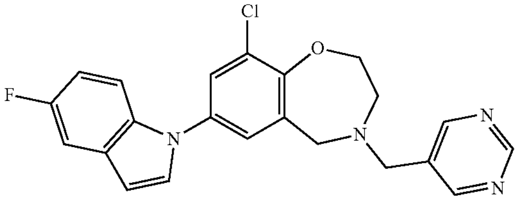 [SMILES: Fc1ccc2c(ccn2-c2cc(Cl)c3c(c2)CN(Cc2cncnc2)CCO3)c1] | 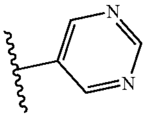 |
| 136 | 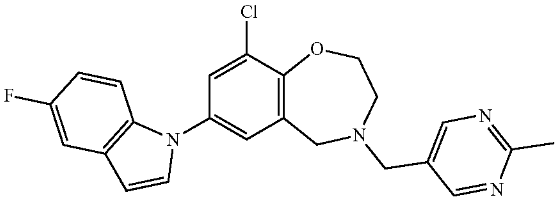 [SMILES: Cc1ncc(CN2CCOc3c(Cl)cc(-n4ccc5cc(F)ccc54)cc3C2)cn1] | 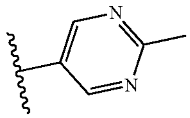 [SMILES: *c1cnc(C)nc1] |
| 137 | 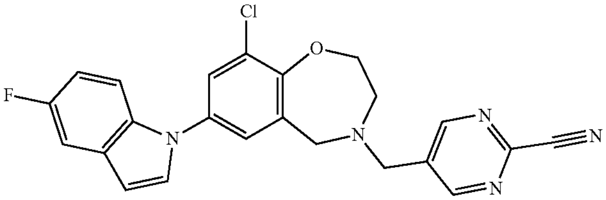 [SMILES: N#Cc1ncc(CN2CCOc3c(Cl)cc(-n4ccc5cc(F)ccc54)cc3C2)cn1] | 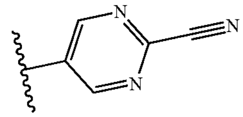 [SMILES: *c1cnc(C#N)nc1] |
| 138 | 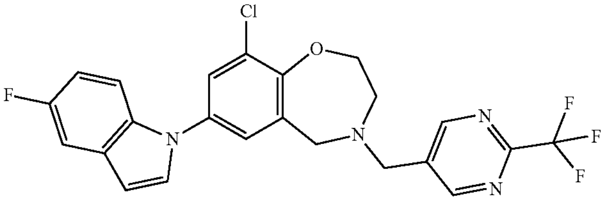 [SMILES: Fc1ccc2c(ccn2-c2cc(Cl)c3c(c2)CN(Cc2cnc(C(F)(F)F)nc2)CCO3)c1] | 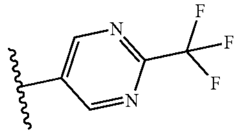 [SMILES: *c1cnc(C(F)(F)F)nc1] |
| 139 | 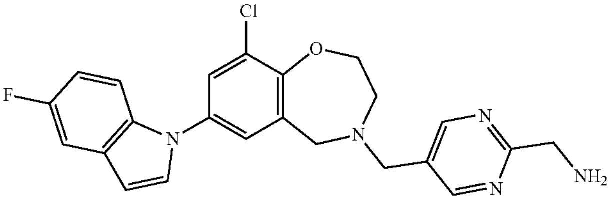 [SMILES: NCc1ncc(CN2CCOc3c(Cl)cc(-n4ccc5cc(F)ccc54)cc3C2)cn1] | 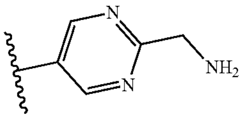 [SMILES: *c1cnc(CN)nc1] |

TABLE III-continued
| ID No. | Structure | 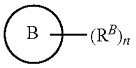 |
|---|---|---|
| 140 | 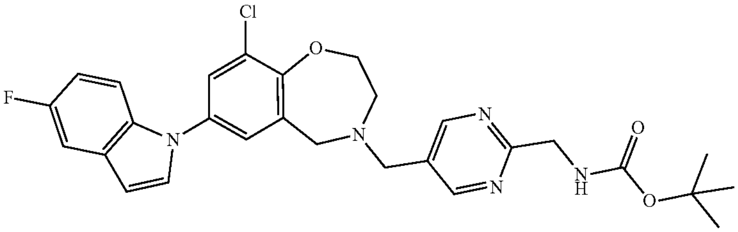 [SMILES: CC(C)(C)OC(=O)NCc1ncc(CN2CCOc3c(Cl)cc(-n4ccc5cc(F)ccc54)cc3C2)cn1] | 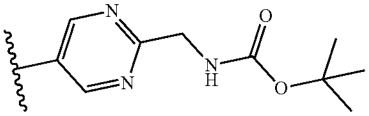 [SMILES: *c1cnc(CNC(=O)OC(C)(C)C)nc1] |
| 141 | 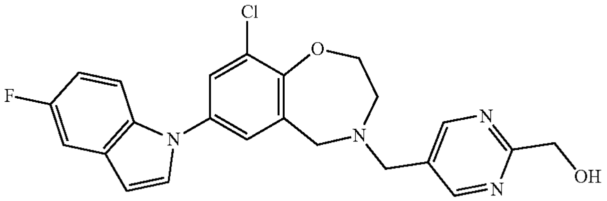 [SMILES: OCc1ncc(CN2CCOc3c(Cl)cc(-n4ccc5cc(F)ccc54)cc3C2)cn1] | 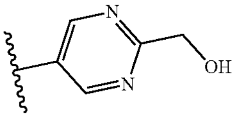 [SMILES: *c1cnc(CO)nc1] |
| 142 | 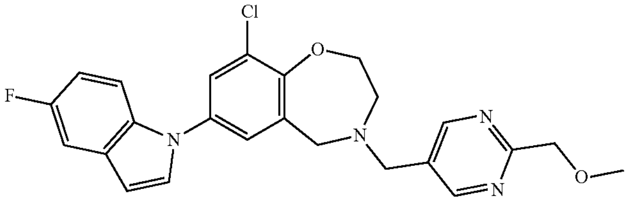 [SMILES: COCc1ncc(CN2CCOc3c(Cl)cc(-n4ccc5cc(F)ccc54)cc3C2)cn1] | 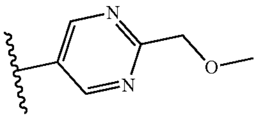 [SMILES: *c1cnc(COC)nc1] |
| 251 | 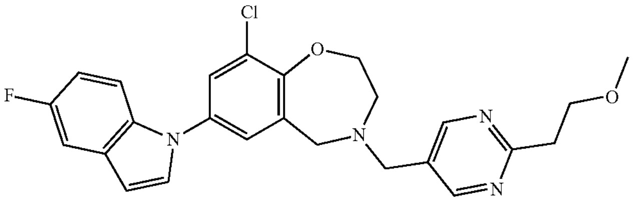 [SMILES: COCCc1ncc(CN2CCOc3c(Cl)cc(-n4ccc5cc(F)ccc54)cc3C2)cn1] | 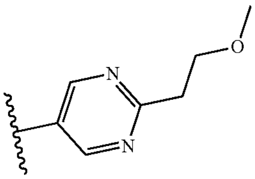 [SMILES: *c1cnc(CCOC)nc1] |
| 252 | 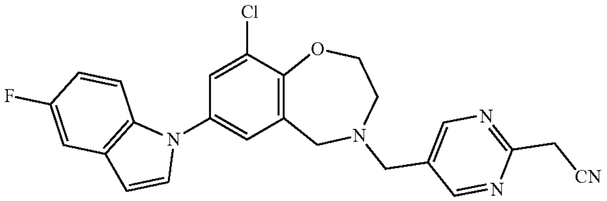 | 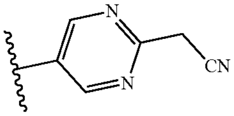 [SMILES: *c1cnc(CC#N)nc1] |
| 253 | 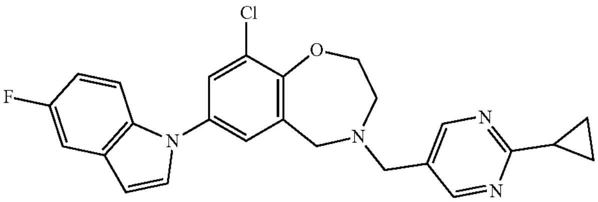 [SMILES: Fc1ccc2c(ccn2-c2cc(Cl)c3c(c2)CN(Cc2cnc(C4CC4)nc2)CCO3)c1] | 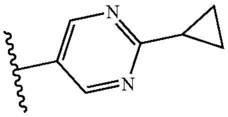 [SMILES: *c1cnc(C2CC2)nc1] |
| 143 | 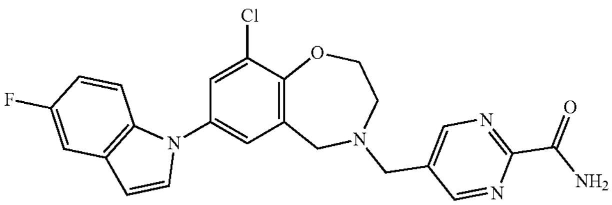 [SMILES: NC(=O)c1ncc(CN2CCOc3c(Cl)cc(-n4ccc5cc(F)ccc54)cc3C2)cn1] | 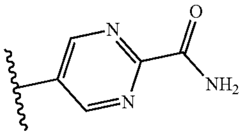 [SMILES: *c1cnc(C(N)=O)nc1] |

TABLE III-continued
| ID No. | Structure | 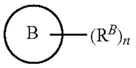 |
|---|---|---|
| 144 | 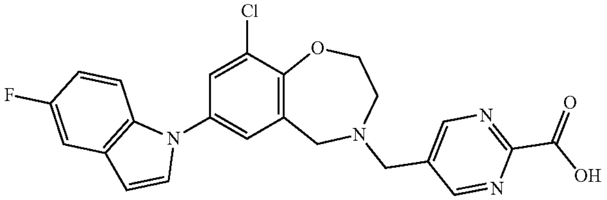 [SMILES: O=C(O)c1ncc(CN2CCOc3c(Cl)cc(-n4ccc5cc(F)ccc54)cc3C2)cn1] | 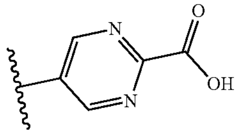 [SMILES: *c1cnc(C(=O)O)nc1] |
| 145 | 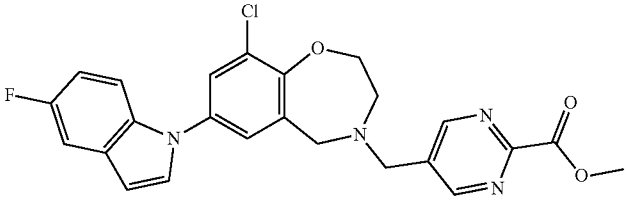 [SMILES: COC(=O)c1ncc(CN2CCOc3c(Cl)cc(-n4ccc5cc(F)ccc54)cc3C2)cn1] | 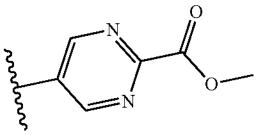 [SMILES: *c1cnc(C(=O)OC)nc1] |
| 146 | 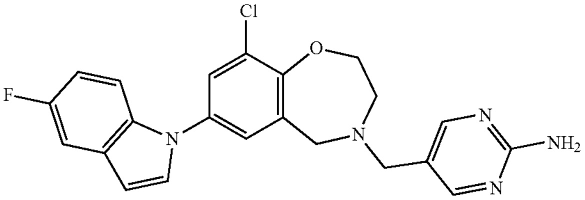 [SMILES: Nc1ncc(CN2CCOc3c(Cl)cc(-n4ccc5cc(F)ccc54)cc3C2)cn1] | 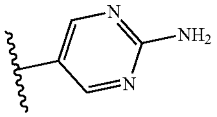 [SMILES: *c1cnc(N)nc1] |
| 147 | 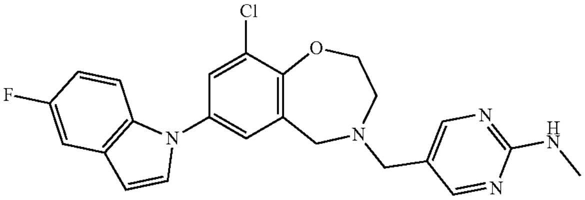 [SMILES: CNc1ncc(CN2CCOc3c(Cl)cc(-n4ccc5cc(F)ccc54)cc3C2)cn1] | 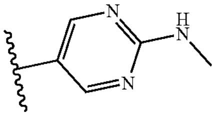 [SMILES: *c1cnc(NC)nc1] |
| 148 | 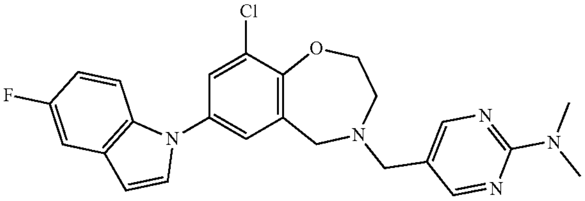 [SMILES: CN(C)c1ncc(CN2CCOc3c(Cl)cc(-n4ccc5cc(F)ccc54)cc3C2)cn1] | 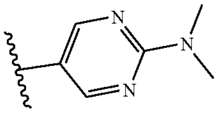 [SMILES: *c1cnc(N(C)C)nc1] |
| 149 | 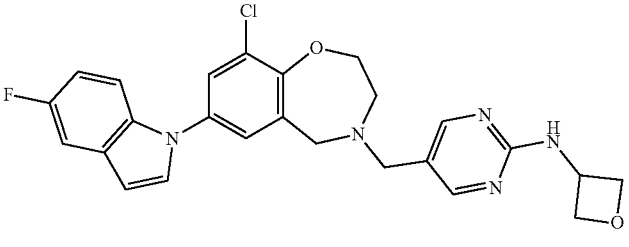 [SMILES: Fc1ccc2c(ccn2-c2cc(Cl)c3c(c2)CN(Cc2cnc(NC4COC4)nc2)CCO3)c1] | 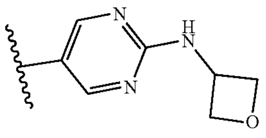 |
| 150 | 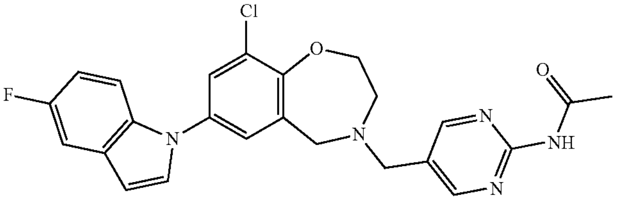 [SMILES: CC(=O)Nc1ncc(CN2CCOc3c(Cl)cc(-n4ccc5cc(F)ccc54)cc3C2)cn1] | 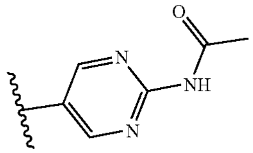 [SMILES: *c1cnc(NC(C)=O)nc1] |

TABLE III-continued
| ID No. | Structure | 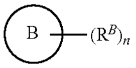 |
|---|---|---|
| 151 | 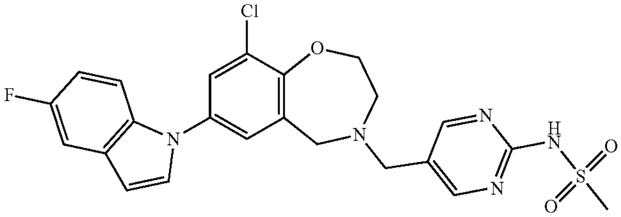 [SMILES: CS(=O)(=O)Nc1ncc(CN2CCOc3c(Cl)cc(-n4ccc5cc(F)ccc54)cc3C2)cn1] | 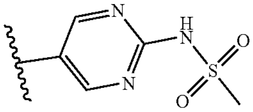 [SMILES: *c1cnc(NS(C)(=O)=O)nc1] |
| 13 | 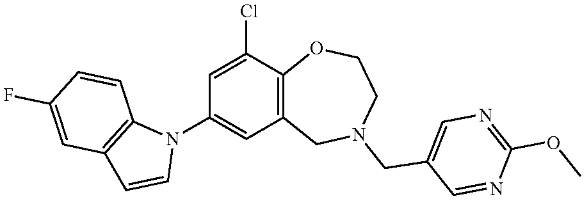 [SMILES: COc1ncc(CN2CCOc3c(Cl)cc(-n4ccc5cc(F)ccc54)cc3C2)cn1] | 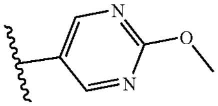 [SMILES: *c1cnc(OC)nc1] |
| 152 | 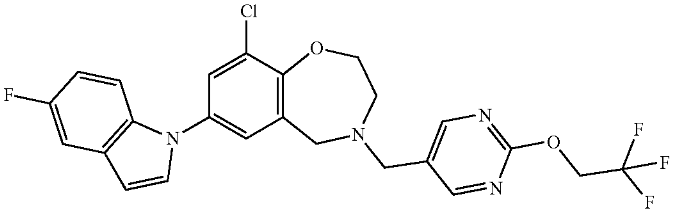 [SMILES: Fc1ccc2c(ccn2-c2cc(Cl)c3c(c2)CN(Cc2cnc(OCC(F)(F)F)nc2)CCO3)c1] | 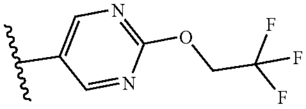 [SMILES: *c1cnc(OCC(F)(F)F)nc1] |
| 254 | 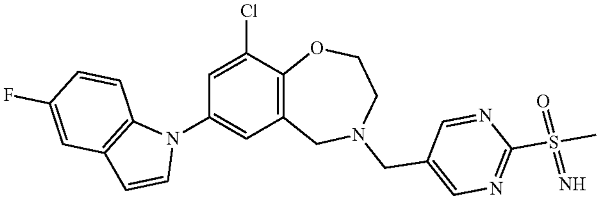 [SMILES: CS(=N)(=O)c1ncc(CN2CCOc3c(Cl)cc(-n4ccc5cc(F)ccc54)cc3C2)cn1] | 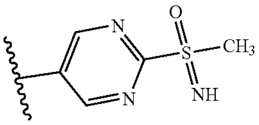 [SMILES: *c1cnc(S(C)(=N)=O)nc1] |
| 153 | 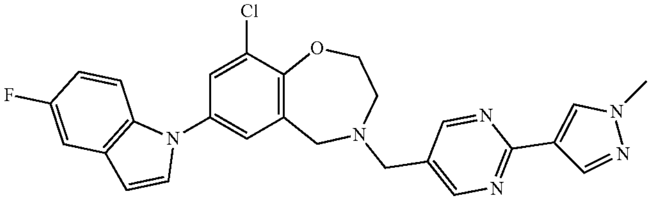 [SMILES: Cn1cc(-c2ncc(CN3CCOc4c(Cl)cc(-n5ccc6cc(F)ccc65)cc4C3)cn2)cn1] | 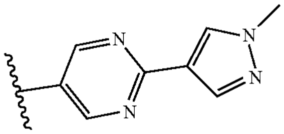 [SMILES: *c1cnc(-c2cnn(C)c2)nc1] |
| 154 | 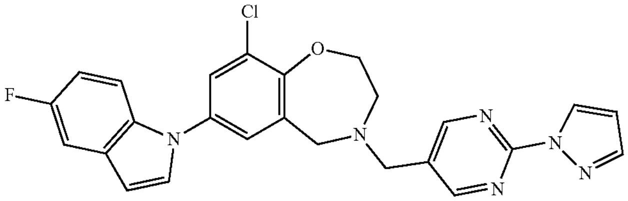 [SMILES: Fc1ccc2c(ccn2-c2cc(Cl)c3c(c2)CN(Cc2cnc(-n4cccn4)nc2)CCO3)c1] | 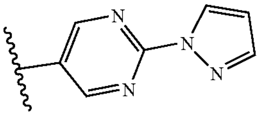 [SMILES: *c1cnc(-n2cccn2)nc1] |
| 255 | 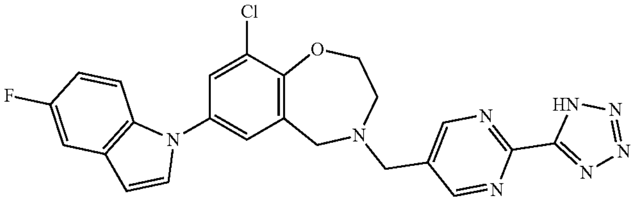 [SMILES: Fc1ccc2c(ccn2-c2cc(Cl)c3c(c2)CN(Cc2cnc(-c4nnn[nH]4)nc2)CCO3)c1] | 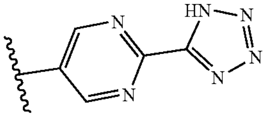 [SMILES: *c1cnc(-c2nnn[nH]2)nc1] |

TABLE III-continued
| ID No. | Structure | 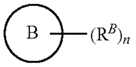 |
| --- | --- | --- |
| 58 | 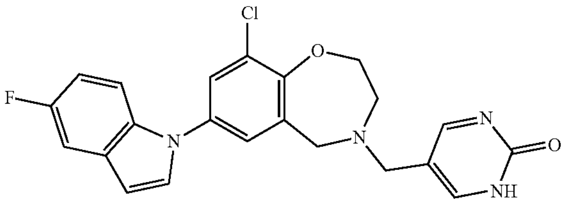 | 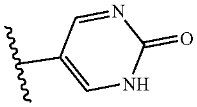 [SMILES: *c1cnc(=O)[nH]c1] |
| 155 | 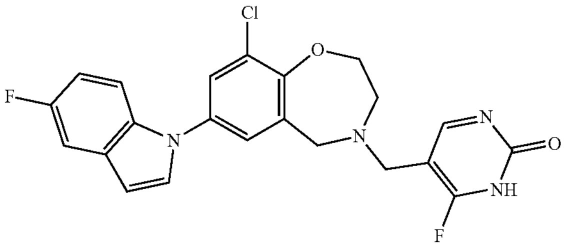 [SMILES: O=c1ncc(CN2CCOc3c(Cl)cc(-n4ccc5cc(F)ccc54)cc3C2)c(F)[nH]1] | 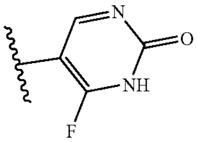 [SMILES: *c1cnc(=O)[nH]c1F] |
| 156 | 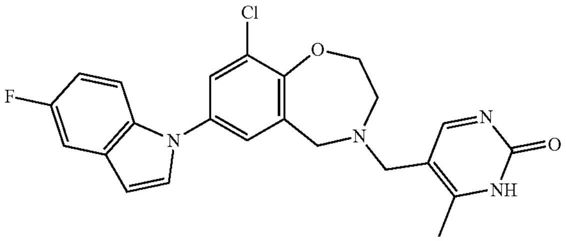 [SMILES: Cc1[nH]c(=O)ncc1CN1CCOc2c(Cl)cc(-n3ccc4cc(F)ccc43)cc2C1] | 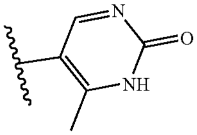 [SMILES: *c1cnc(=O)[nH]c1C] |
| 157 | 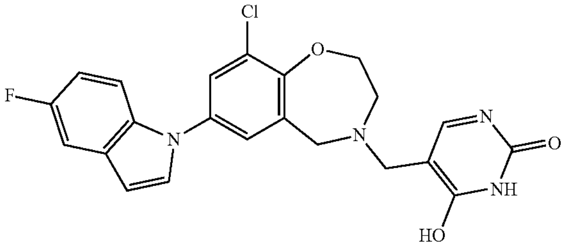 [SMILES: O=c1ncc(CN2CCOc3c(Cl)cc(-n4ccc5cc(F)ccc54)cc3C2)c(O)[nH]1] | 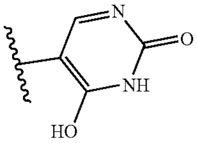 [SMILES: *c1cnc(=O)[nH]c1O] |
| 256 | 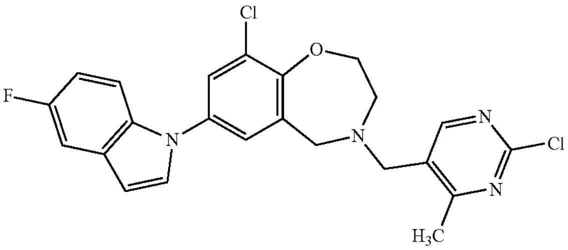 [SMILES: Cc1nc(Cl)ncc1CN1CCOc2c(Cl)cc(-n3ccc4cc(F)ccc43)cc2C1] | 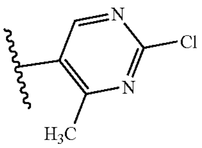 [SMILES: *c1cnc(Cl)nc1C] |
| 158 | 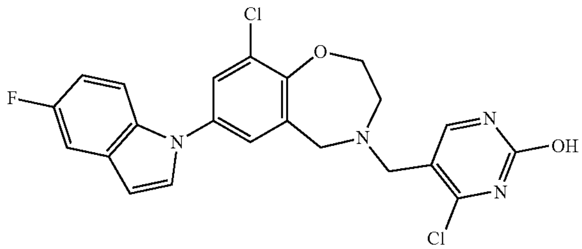 [SMILES: Oc1ncc(CN2CCOc3c(Cl)cc(-n4ccc5cc(F)ccc54)cc3C2)c(Cl)n1] | 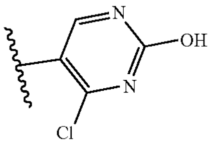 [SMILES: *c1cnc(O)nc1Cl] |

TABLE III-continued
| ID No. | Structure | 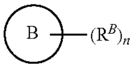 |
| --- | --- | --- |
| 159 | 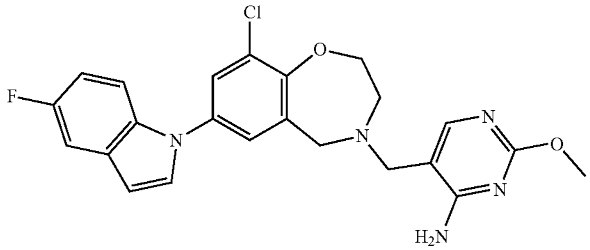 [SMILES: COc1ncc(CN2CCOc3c(Cl)cc(-n4ccc5cc(F)ccc54)cc3C2)c(N)n1] | 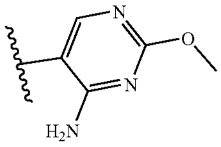 [SMILES: *c1cnc(OC)nc1N] |
| 160 | 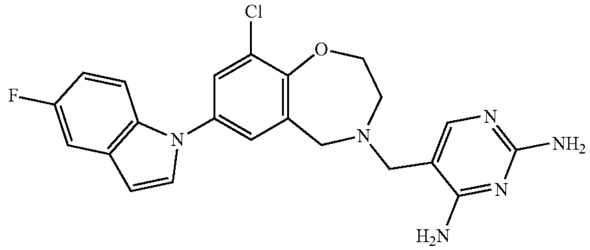 [SMILES: Nc1ncc(CN2CCOc3c(Cl)cc(-n4ccc5cc(F)ccc54)cc3C2)c(N)n1] | 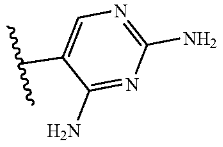 |
| 257 | 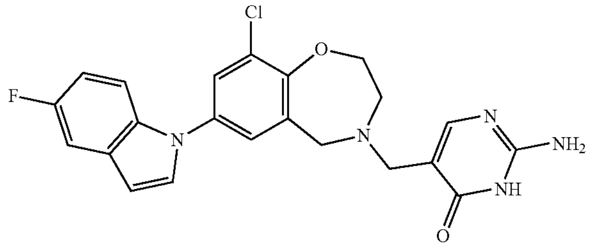 [SMILES: Nc1ncc(CN2CCOc3c(Cl)cc(-n4ccc5cc(F)ccc54)cc3C2)c(=O)[nH]1] | 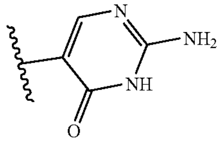 [SMILES: *c1cnc(N)[nH]c1=O] |
| 161 | 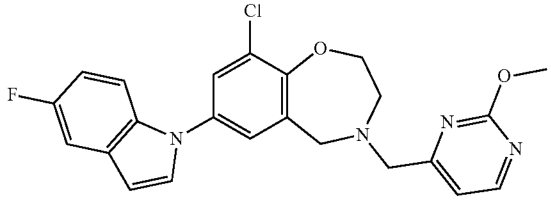 [SMILES: COc1nccc(CN2CCOc3c(Cl)cc(-n4ccc5cc(F)ccc54)cc3C2)n1] | 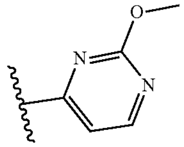 [SMILES: *c1ccnc(OC)n1] |
| 162 | 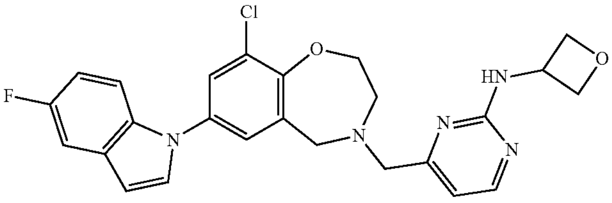 [SMILES: Fc1ccc2c(ccn2-c2cc(Cl)c3c(c2)CN(Cc2ccnc(NC4COC4)n2)CCO3)c1] | 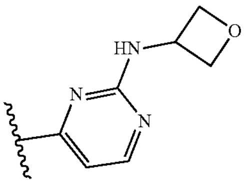 [SMILES: *c1ccnc(NC2COC2)n1] |
| 163 | 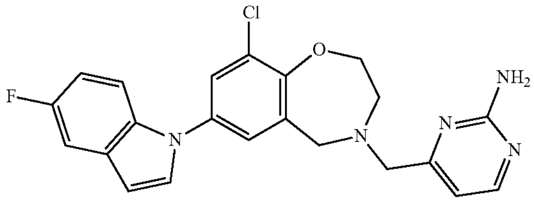 [SMILES: Nc1nccc(CN2CCOc3c(Cl)cc(-n4ccc5cc(F)ccc54)cc3C2)n1] | 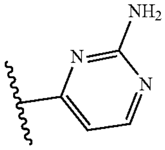 [SMILES: *c1ccnc(N)n1] |

TABLE III-continued
| ID No. | Structure | 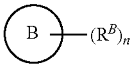 |
|---|---|---|
| 164 | 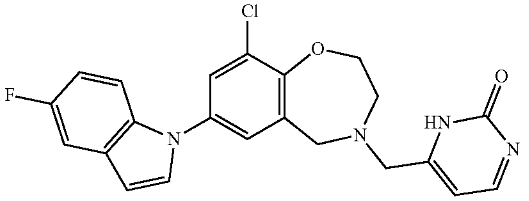 [SMILES: O=c1nccc(CN2CCOc3c(Cl)cc(-n4ccc5cc(F)ccc54)cc3C2)[nH]1] | 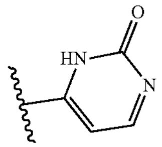 [SMILES: *c1ccnc(=O)[nH]1] |
| 165 | 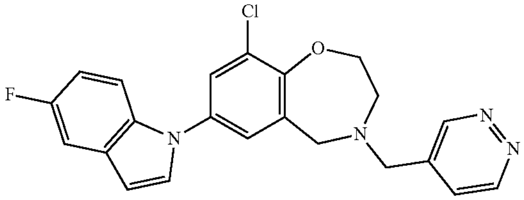 [SMILES: Fc1ccc2c(ccn2-c2cc(Cl)c3c(c2)CN(Cc2ccnnc2)CCO3)c1] | 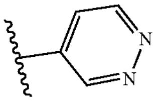 [SMILES: *c1ccnnc1] |
| 258 | 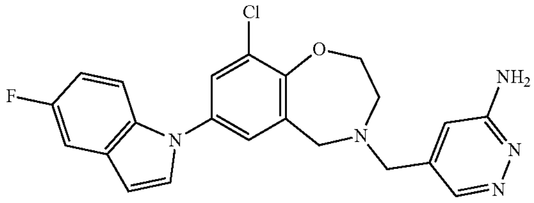 [SMILES: Nc1cc(CN2CCOc3c(Cl)cc(-n4ccc5cc(F)ccc54)cc3C2)cnn1] | 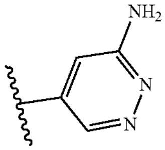 [SMILES: *c1cnnc(N)c1] |
| 259 | 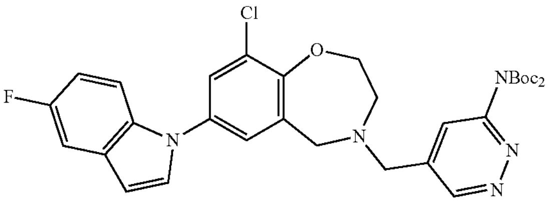 | 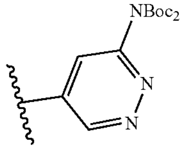 |
| 166 | 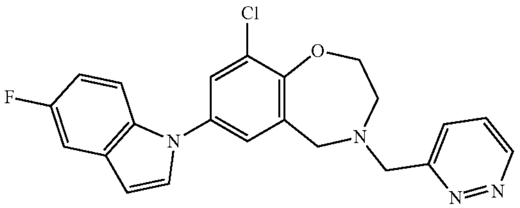 [SMILES: Fc1ccc2c(ccn2-c2cc(Cl)c3c(c2)CN(Cc2cccnn2)CCO3)c1] | 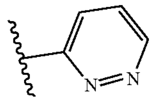 [SMILES: *c1cccnn1] |
| 167 | 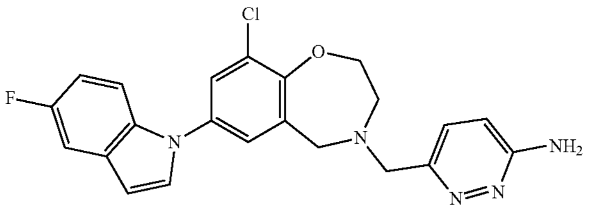 [SMILES: Nc1ccc(CN2CCOc3c(Cl)cc(-n4ccc5cc(F)ccc54)cc3C2)nn1] | 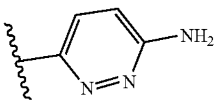 [SMILES: *c1ccc(N)nn1] |
| 168 | 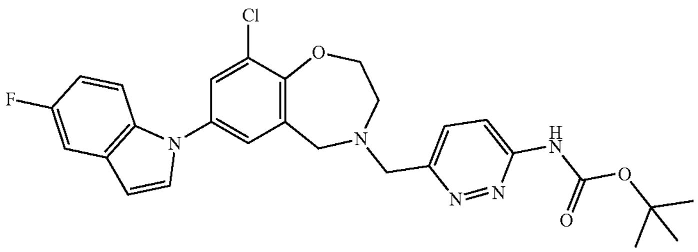 [SMILES: CC(C)(C)OC(=O)Nc1ccc(CN2CCOc3c(Cl)cc(-n4ccc5cc(F)ccc54)cc3C2)nn1] | 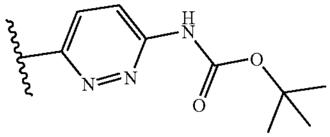 [SMILES: *c1ccc(NC(=O)OC(C)(C)C)nn1] |

TABLE III-continued
| ID No. | Structure | 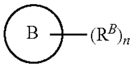 |
| --- | --- | --- |
| 169 | 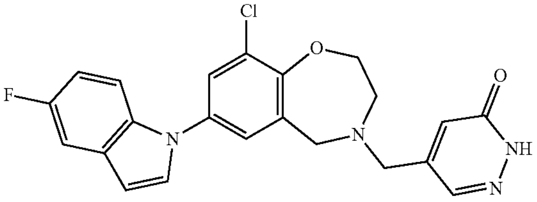 [SMILES: O=c1cc(CN2CCOc3c(Cl)cc(-n4ccc5cc(F)ccc54)cc3C2)cn[nH]1] | 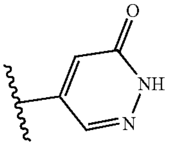 [SMILES: *c1cn[nH]c(=O)c1] |
| 170 | 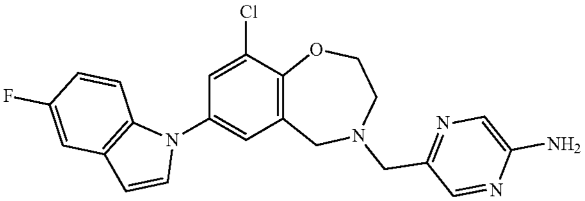 [SMILES: Nc1cnc(CN2CCOc3c(Cl)cc(-n4ccc5cc(F)ccc54)cc3C2)cn1] | 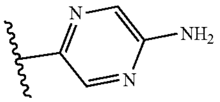 [SMILES: *c1cnc(N)cn1] |
| 171 | 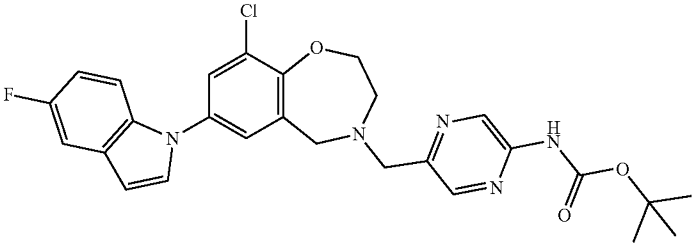 [SMILES: CC(C)(C)OC(=O)Nc1cnc(CN2CCOc3c(Cl)cc(-n4ccc5cc(F)ccc54)cc3C2)cn1] | 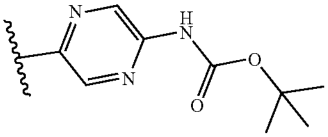 [SMILES: *c1cnc(NC(=O)OC(C)(C)C)cn1] |
| 172 | 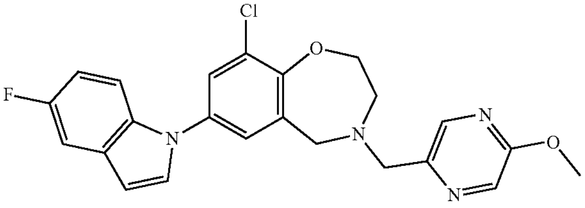 [SMILES: COc1cnc(CN2CCOc3c(Cl)cc(-n4ccc5cc(F)ccc54)cc3C2)cn1] | 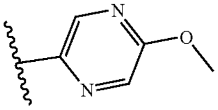 [SMILES: *c1cnc(OC)cn1] |
| 173 | 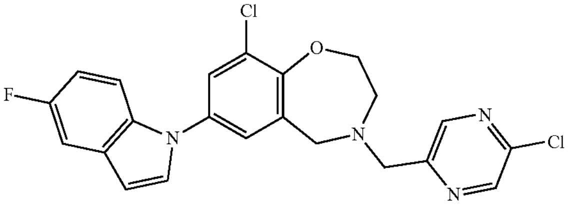 [SMILES: Fc1ccc2c(ccn2-c2cc(Cl)c3c(c2)CN(Cc2cnc(Cl)cn2)CCO3)c1] | 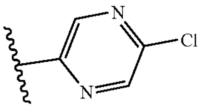 [SMILES: *c1cnc(Cl)cn1] |
| 174 | 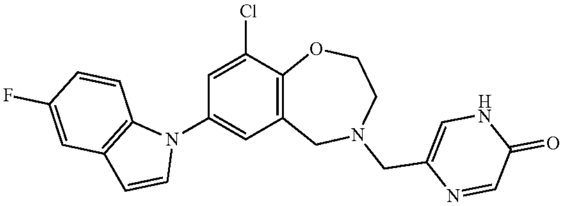 [SMILES: O=c1cnc(CN2CCOc3c(Cl)cc(-n4ccc5cc(F)ccc54)cc3C2)c[nH]1] | 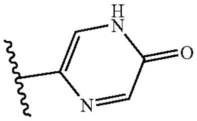 [SMILES: *c1c[nH]c(=O)cn1] |
In some embodiments, Ring B is any one of the B rings disclosed in Tables II, III, and/or III', or a salt thereof.

In another embodiment, provided herein is a compound of Formula (IV):

Formula IV

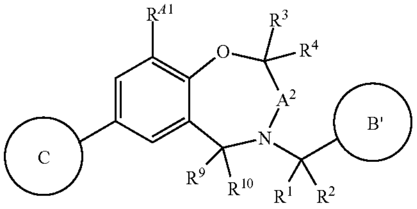

or a tautomer thereof, or a pharmaceutically acceptable salt thereof, wherein:

$R^1$ and $R^2$ are each independently hydrogen or deuterium;

$A^2$ is —$CR^7R^8$— or —$S(=O)_2$—;

$R^3$ and $R^4$ are each independently hydrogen, deuterium, halogen, or $C_{1-4}$ alkyl;

$R^7$ and $R^8$ are each independently hydrogen, deuterium, halogen, $C_{1-4}$ alkyl, or $C_{1-4}$ haloalkyl; or $R^7$ and $R^8$ are taken together with the carbon atom to which they are attached to form a cyclopropane or an oxetane;

$R^9$ and $R^{10}$ are each independently hydrogen, deuterium, halogen, or $C_{1-4}$ alkyl; or $R^9$ and $R^{10}$ are taken together with the carbon atom to which they are attached to form an oxetane;

$R^{A1}$ is halogen, $C_{1-4}$ alkyl, or cyclopropyl;

Ring C is a substituted or unsubstituted bicyclic heterocycle containing one or more nitrogen atoms; and Ring B' is selected from the group consisting of:

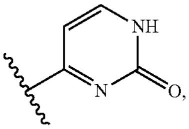
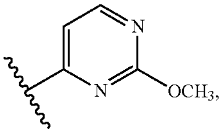
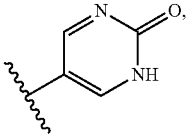
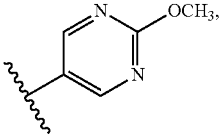
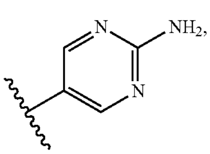
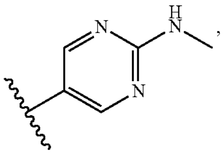
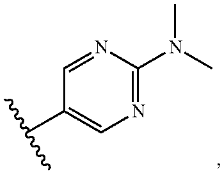
,
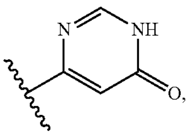
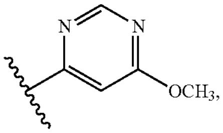
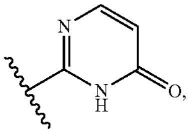

-continued

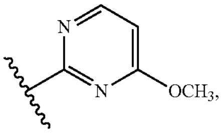
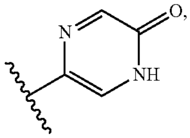
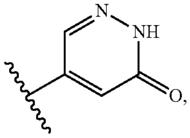
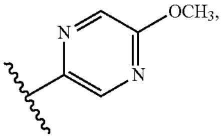
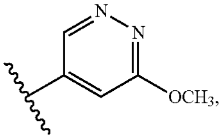
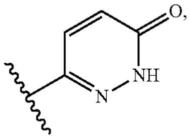
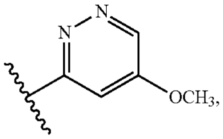
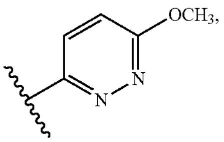
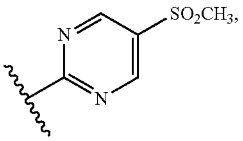
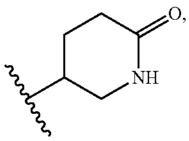
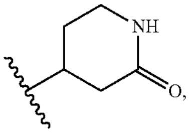
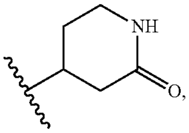
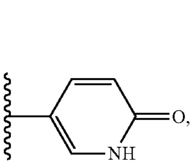
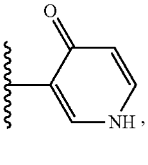
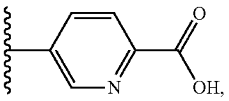
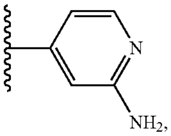
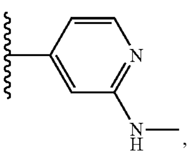
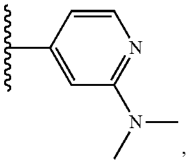

-continued

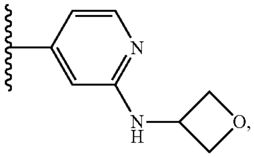
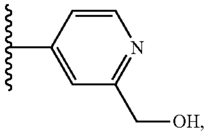
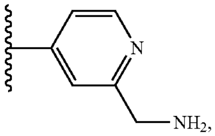
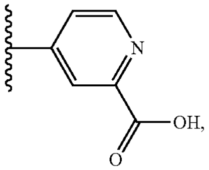
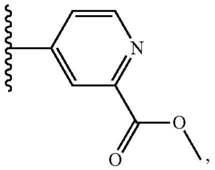
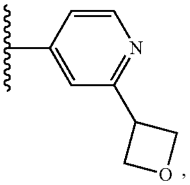
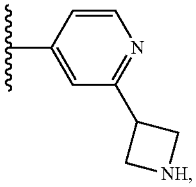
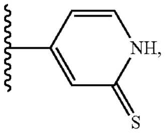
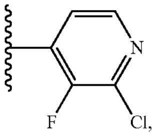
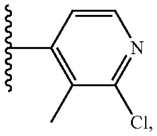
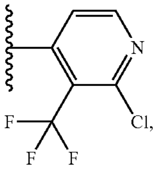
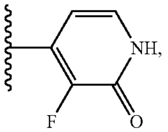
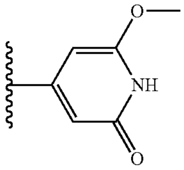
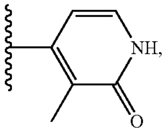
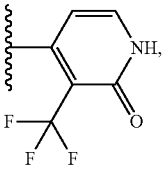
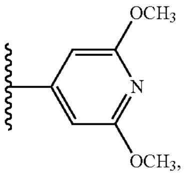
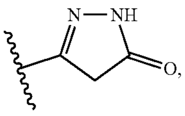
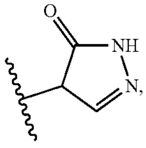
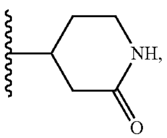
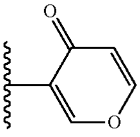
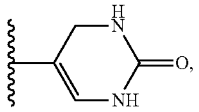

-continued

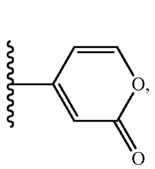
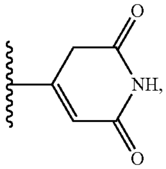
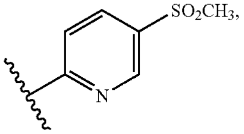
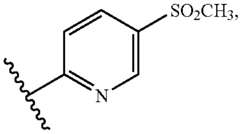
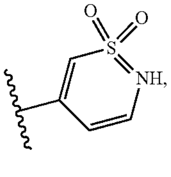
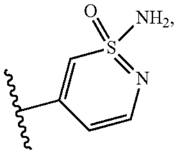
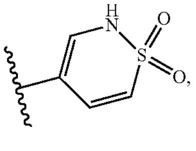
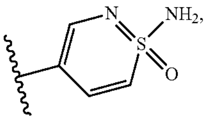
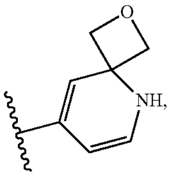
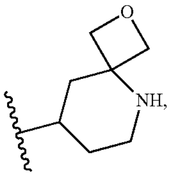
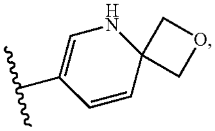
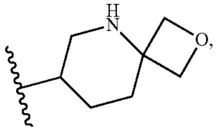
and
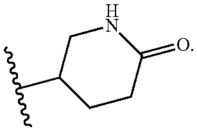

In some embodiments, $A^2$ is $—CR^7R^8—$ or $—S(=O)_2—$. In some embodiments, $A^2$ is $—S(=O)_2—$. In some embodiments, $A^2$ is $—CR^7R^8—$.

In some embodiments, $A^2$ is $—CR^7R^8—$; and $R^7$ and $R^8$ are each independently hydrogen, deuterium, halogen, or $C_{1-4}$ alkyl; or $R^7$ and $R^8$ are taken together with the carbon atom to which they are attached to form an oxetane. In some embodiments, $R^7$ and $R^8$ are each independently hydrogen or deuterium. In some embodiments, $R^7$ and $R^8$ are each hydrogen. In some embodiments, $R^7$ and $R^8$ are each deuterium. In some embodiments, $R^7$ and $R^8$ are taken together with the carbon atom to which they are attached to form an oxetane. In some embodiments, each $R^7$ and $R^8$ is independently hydrogen or deuterium; or $R^7$ and $R^8$ are taken together with the carbon atom to which they are attached to form an oxetane.

In some embodiments, the compound of Formula (IV) is a compound of Formula (IVa):

Formula IVa

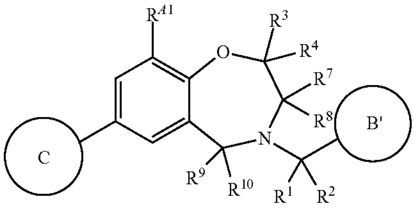

or a tautomer thereof, or a pharmaceutically acceptable salt thereof.

In some embodiments, each $R^3$ and $R^4$ is independently hydrogen, deuterium, halogen, or $C_{1-4}$ alkyl. In some embodiments, each $R^3$ and $R^4$ is independently hydrogen, deuterium, or $—CH_3$. In some embodiments, each $R^3$ and $R^4$ is independently hydrogen or deuterium. In some embodiments, each $R^3$ and $R^4$ is hydrogen. In some embodiments, each $R^3$ and $R^4$ is deuterium.

In some embodiments, $R^9$ and $R^{10}$ are each independently hydrogen, deuterium, halogen, or $C_{1-4}$ alkyl; or $R^9$ and $R^{10}$ are taken together with the carbon atom to which they are attached to form an oxetane. In some embodiments, $R^9$ and $R^{10}$ are each independently hydrogen or deuterium. In some embodiments, $R^9$ and $R^{10}$ are each hydrogen. In some embodiments, $R^9$ and $R^{10}$ are each deuterium. In some embodiments, $R^9$ and $R^{10}$ are taken together with the carbon atom to which they are attached to form an oxetane. In some embodiments, each $R^9$ and $R^{10}$ is independently hydrogen or deuterium; or $R^9$ and $R^{10}$ are taken together with the carbon atom to which they are attached to form an oxetane.

In some embodiments, each $R^3$ and $R^4$ is hydrogen; and each $R^7$ and $R^8$ is hydrogen. In some embodiments, each $R^3$, $R^4$, $R^7$, and $R^8$ is hydrogen; and each $R^9$ and $R^{10}$ is independently hydrogen or deuterium; or $R^9$ and $R^{10}$ are taken together with the carbon atom to which they are attached to form an oxetane. In some embodiments, each $R^3$ and $R^4$ is hydrogen; and each $R^9$ and $R^{10}$ is hydrogen. In some embodiments, each $R^3$, $R^4$, $R^9$, and $R^{10}$ is hydrogen; and each $R^7$ and $R^8$ is independently hydrogen or deuterium; or $R^7$ and $R^8$ are taken together with the carbon atom to which they are attached to form an oxetane. In some embodiments, each $R^7$ and $R^8$ is hydrogen; and each $R^9$ and $R^{10}$ is hydrogen. In some embodiments, each $R^7$, $R^8$, $R^9$, and $R^{10}$ is hydrogen; and each $R^3$ and $R^4$ is independently hydrogen or deuterium.

In some embodiments, the compound of Formula (IV) is a compound of Formula (V):

Formula V

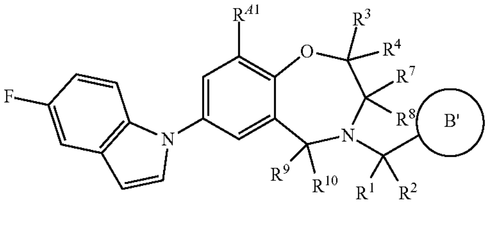

or a tautomer thereof, or a pharmaceutically acceptable salt thereof.

In some embodiments, the compound of Formula (IV) is a compound of Formula (VI):

Formula VI

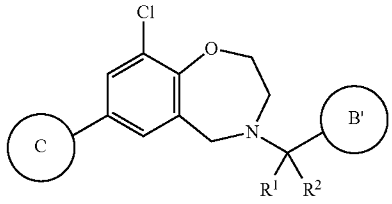

or a tautomer thereof, or a pharmaceutically acceptable salt thereof.

In some embodiments, Ring C is a substituted or unsubstituted bicyclic heterocycle containing one or more nitrogen atoms. In some embodiments, Ring C is a substituted bicyclic heterocycle containing one or two nitrogen atoms. In some embodiments, Ring C is an unsubstituted bicyclic heterocycle containing one or two nitrogen atoms. In some embodiments, Ring C is a substituted bicyclic heteroaryl containing one or two nitrogen atoms. In some embodiments, Ring C is an unsubstituted bicyclic heteroaryl containing one or two nitrogen atoms. In some embodiments, Ring C is a fused bicyclic heterocycle containing a five-membered heterocycle and a 6-membered aryl or heteroaryl.

In some embodiments, the 6-membered aryl or heteroaryl of Ring C is phenyl, pyridinyl, pyrimidinyl, pyridazinyl, or pyrazinyl. In some embodiments, the 6-membered aryl or heteroaryl of Ring C is phenyl or pyridinyl.

In some embodiments, the compound of Formula (IV) is a compound of Formula (VIa) or Formula (VIb):

Formula VIa

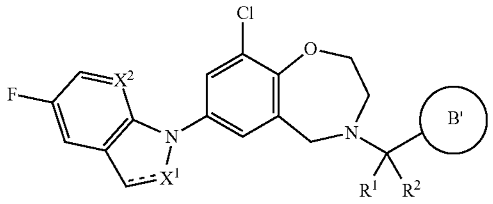

Formula VIb

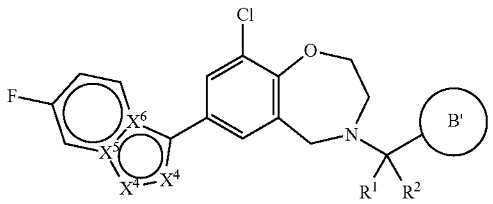

or a tautomer, or a pharmaceutically acceptable salt thereof.

In some embodiments, each $X^1$, $X^2$, $X^3$, $X^4$, $X^5$, and $X^6$ is independently C, CH, $CH_2$, N, or NH. In some embodiments, $X^1$ is —CH═; and $X^2$ is CH. In some embodiments, $X^1$ is —CH═; and $X^2$ is N. In some embodiments, $X^1$ is —N═; and $X^2$ is CH. In some embodiments, $X^1$ is $—CH_2—$; and $X^2$ is CH. In some embodiments, each $X^1$ and $X^2$ is independently CH or N; and

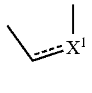

is

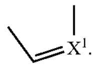

In some embodiments, the compound of Formula (VI) is a compound of Formula (VIc) or Formula (VId):

Formula VIc

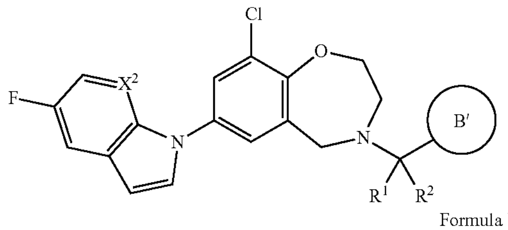

Formula VId

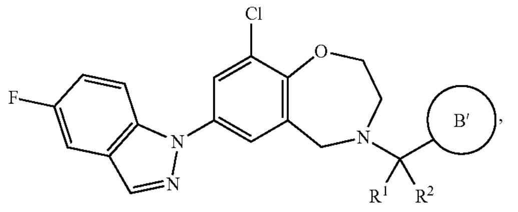

or a tautomer thereof, or a pharmaceutically acceptable salt thereof.

In some embodiments, $X^2$ is CH or N.

In some embodiments, Ring C is selected from the group consisting of substituted or unsubstituted indole, substituted or unsubstituted indoline, substituted or unsubstituted indazole, substituted or unsubstituted indolizine, substituted or unsubstituted azaindole, substituted or unsubstituted pyrrolopyridine, substituted or unsubstituted imidazopyridine, substituted or unsubstituted pyrazolopyridine, substituted or unsubstituted pyrrolopyrimidine, substituted or unsubstituted pyrazolopyrimidine, and substituted or unsubstituted imidazopyrimidine. In some embodiments, Ring C is selected from the group consisting of substituted or unsubstituted indole, substituted or unsubstituted indoline, substituted or unsubstituted indazole, substituted or unsubstituted indolizine, substituted or unsubstituted pyrrolopyridine, substituted or unsubstituted imidazopyridine, and substituted or unsubstituted pyrazolopyridine. In some embodiments, Ring C is selected from the group consisting of substituted or unsubstituted indole, substituted or unsubstituted 2,3-dihydroindole, substituted or unsubstituted indolizine, substituted or unsubstituted azaindole, and substituted or unsubstituted indazole. In some embodiments, Ring C is a substituted indole. In some embodiments, Ring C is a 5-fluoroindole.

In some embodiments, Ring C is a fused bicyclic heterocycle containing a 6-membered heterocycle and a 6-membered aryl or heteroaryl. In some embodiments, Ring C is selected from the group consisting of substituted or unsubstituted quinoline, substituted or unsubstituted isoquinoline, substituted or unsubstituted tetrahydroquinoline, substituted or unsubstituted tetrahydroisioquinoline, substituted or unsubstituted naphthyridine, substituted or unsubstituted quinone, and substituted or unsubstituted quinolizine.

In some embodiments, Ring C is substituted with one or more groups selected from deuterium, halogen, and $C_{1-4}$ alkyl. In some embodiments, Ring C is substituted with one or more groups selected from halogen and methyl. In some embodiments, Ring C is substituted with $—CH_3$.

In some embodiments, Ring C is substituted with one or more halogen atoms. In some embodiments, Ring C is substituted with one or more —F or —Cl. In some embodiments, Ring C is substituted with —F. In some embodiments, Ring C is substituted with —Cl.

In some embodiments, Ring C is selected from the group consisting of:

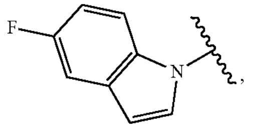
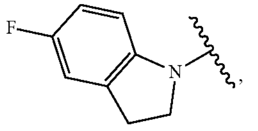
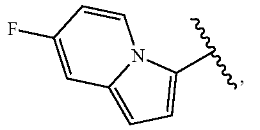
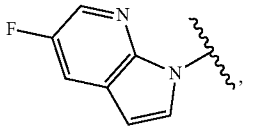
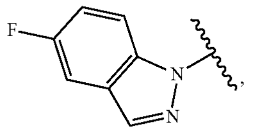
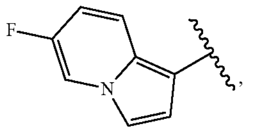
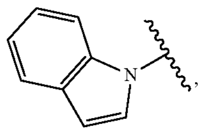
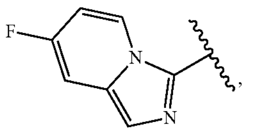
and
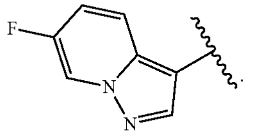

In some embodiments, Ring C is selected from the group consisting of:

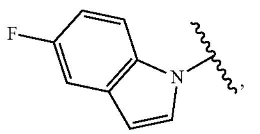
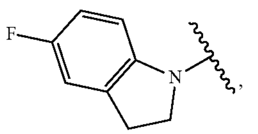
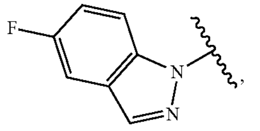
and
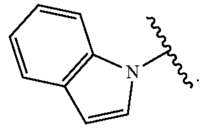

In some embodiments, Ring C is

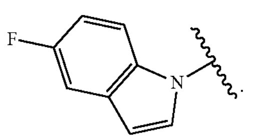 [SMILES: *n1ccc2cc(F)ccc21]

In some embodiments, Ring C is

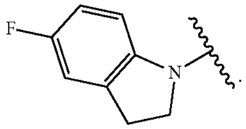 [SMILES: *N1CCc2cc(F)ccc21]

In some embodiments, Ring C is

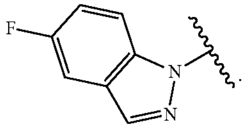 [SMILES: *n1ncc2cc(F)ccc21]

In some embodiments, Ring C is

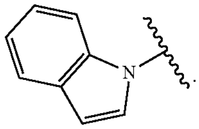 [SMILES: *n1ccc2ccccc21]

In some embodiments, the compound of Formula (IV) is a compound of Formula (VII):

Formula VII

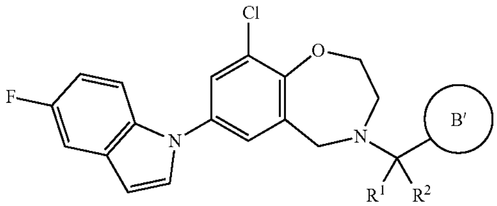

or a tautomer thereof, or a pharmaceutically acceptable salt thereof.

In some embodiments, $R^1$ and $R^2$ are each independently hydrogen or deuterium. In some embodiments, $R^1$ and $R^2$ are each hydrogen. In some embodiments, $R^1$ and $R^2$ are each deuterium. In some embodiments, $R^1$ and $R^2$ are each independently hydrogen or deuterium; and Ring B' is selected from the group consisting of:

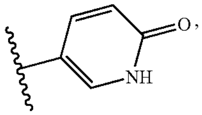

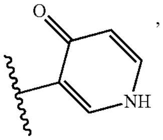

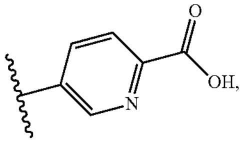

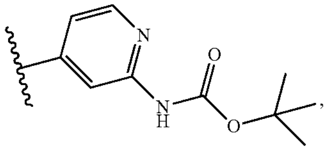

-continued

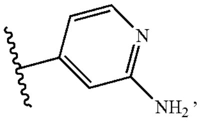

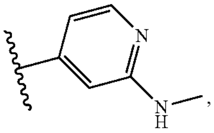

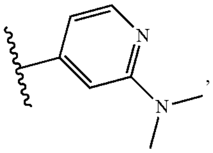

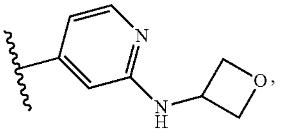

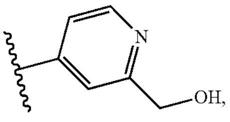

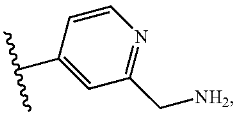

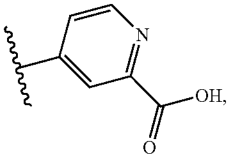

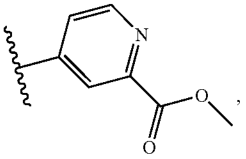

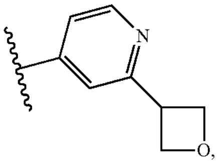

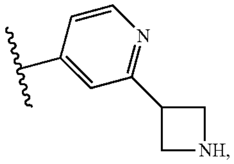

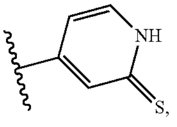

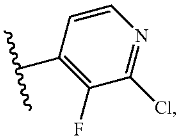

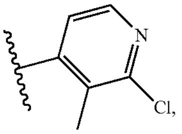

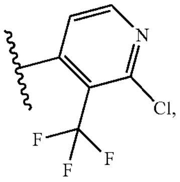

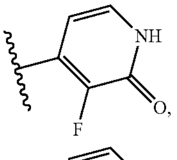

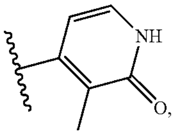

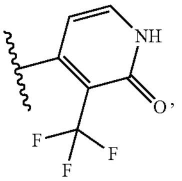

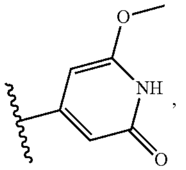

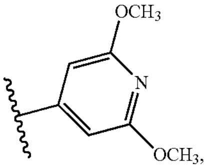

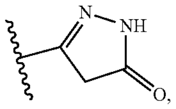

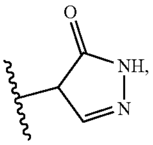

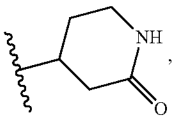

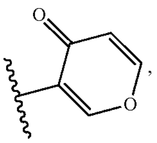

-continued

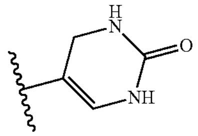, 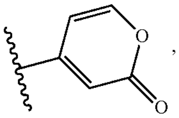,

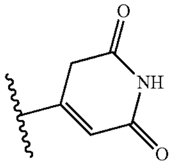, 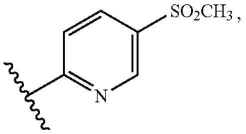

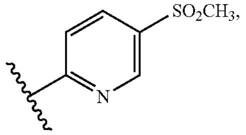 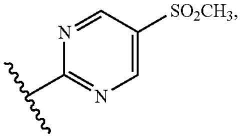

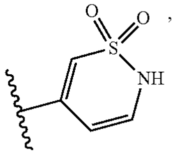, 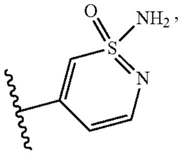

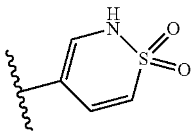, 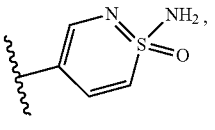

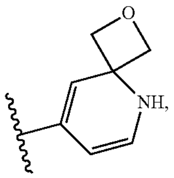 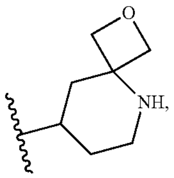

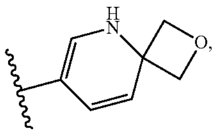 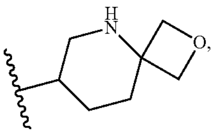 and

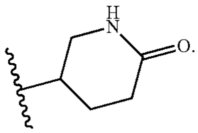

In some embodiments, the compound of Formula (VII) is a compound of Formula (VIIa):

Formula VIIa

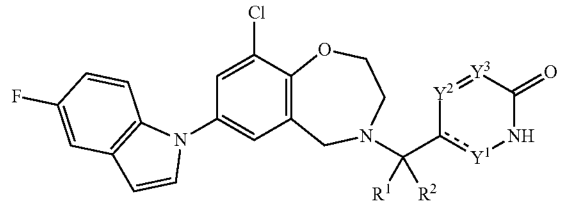

or a tautomer, or a pharmaceutically acceptable salt thereof.

wherein each $Y^1$, $Y^2$, and $Y^3$, is independently CH, $CH_2$, N, or NH.

In some embodiments, $Y^1$ is CH, $Y^2$ is CH, and $Y^3$ is N. In some embodiments, $Y^1$ is N, $Y^2$ is CH, and $Y^3$ is CH. In some embodiments, $Y^1$ is CH, $Y^2$ is N, and $Y^3$ is CH.

In some embodiments, the compound of Formula (VII) is a compound of Formula (VIIb):

Formula VIIb

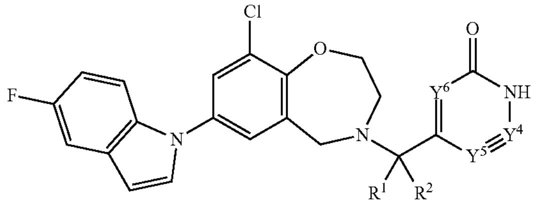

wherein $Y^4$, $Y^5$, or $Y^6$ is N, and the other members are each CH.

In some embodiments, $Y^4$ is CH, $Y^5$ is CH, and $Y^6$ is N. In some embodiments, $Y^4$ is N, $Y^5$ is CH, and $Y^6$ is CH. In some embodiments, $Y^4$ is CH, $Y^5$ is N, and $Y^6$ is CH.

In another embodiment, is a compound of the following formula:

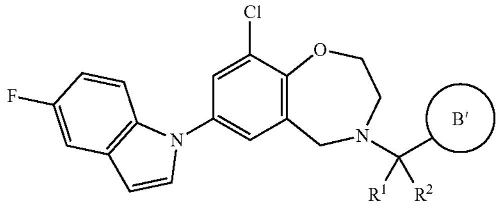

or a tautomer thereof, or a pharmaceutically acceptable salt thereof, disclosed in Table VII.

TABLE VII

| ID No. | Structure |  |
|---|---|---|
| 175 | 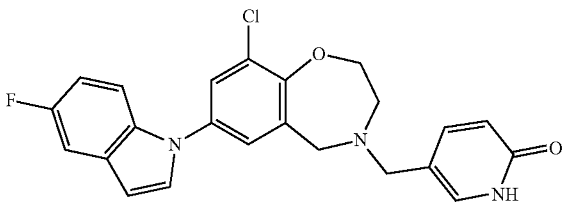 | 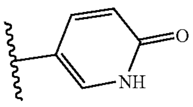 [SMILES: *c1ccc(=O)[nH]c1] |

TABLE VII-continued
| ID No. | Structure | B′ |
|---|---|---|
| 176 | 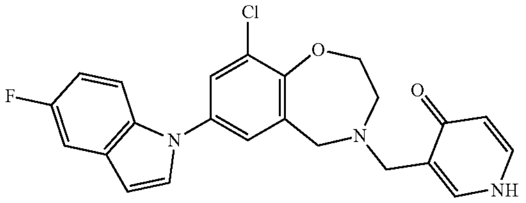 [SMILES: O=c1cc[nH]cc1CN1CCOc2c(Cl)cc(-n3ccc4cc(F)ccc43)cc2C1] | 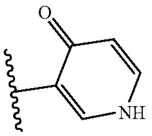 [SMILES: *c1c[nH]ccc1=O] |
| 177 | 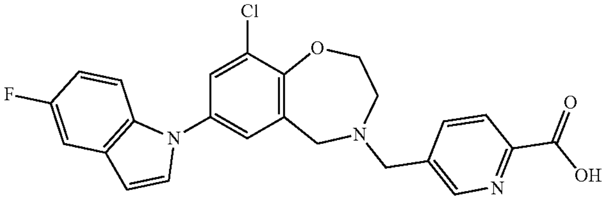 [SMILES: O=C(O)c1ccc(CN2CCOc3c(Cl)cc(-n4ccc5cc(F)ccc54)cc3C2)cn1] | 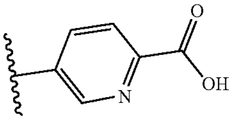 [SMILES: *c1ccc(C(=O)O)nc1] |
| 260 | 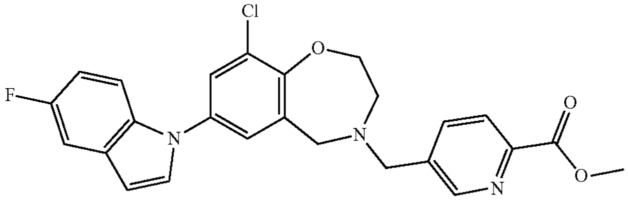 [SMILES: COC(=O)c1ccc(CN2CCOc3c(Cl)cc(-n4ccc5cc(F)ccc54)cc3C2)cn1] | 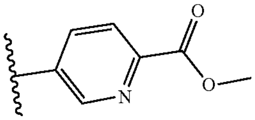 [SMILES: *c1ccc(C(=O)OC)nc1] |
| 178 | 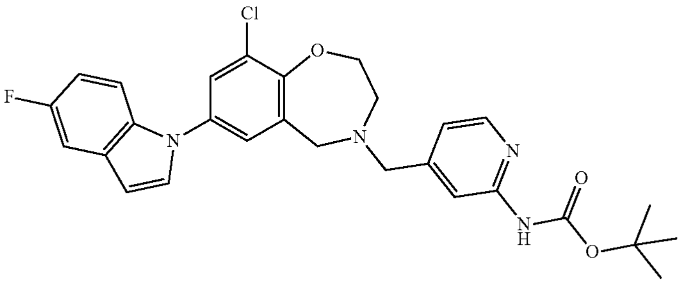 [SMILES: CC(C)(C)OC(=O)Nc1cc(CN2CCOc3c(Cl)cc(-n4ccc5cc(F)ccc54)cc3C2)ccn1] | 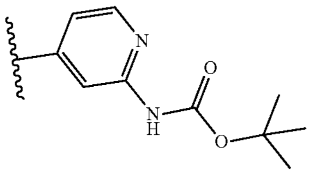 [SMILES: *c1ccnc(NC(=O)OC(C)(C)C)c1] |
| 179 | 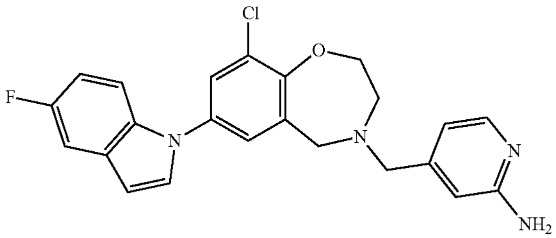 [SMILES: Nc1cc(CN2CCOc3c(Cl)cc(-n4ccc5cc(F)ccc54)cc3C2)ccn1] | 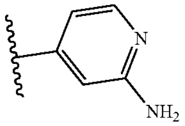 [SMILES: *c1ccnc(N)c1] |
| 180 | 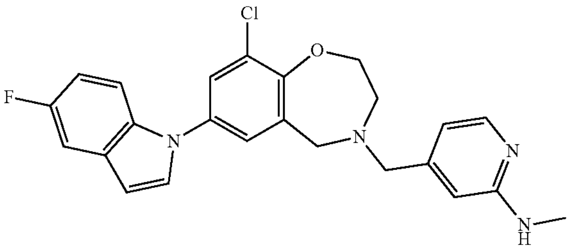 [SMILES: CNc1cc(CN2CCOc3c(Cl)cc(-n4ccc5cc(F)ccc54)cc3C2)ccn1] | 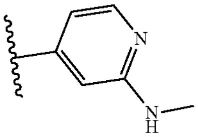 [SMILES: *c1ccnc(NC)c1] |

TABLE VII-continued
| ID No. | Structure | B′ |
|---|---|---|
| 181 | 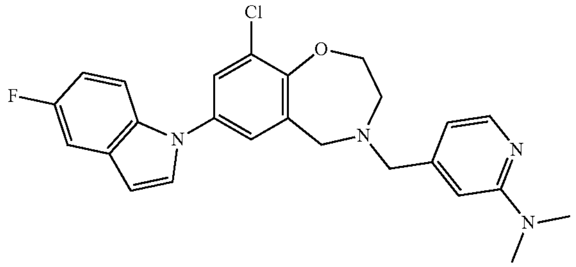 [SMILES: CN(C)c1cc(CN2CCOc3c(Cl)cc(-n4ccc5cc(F)ccc54)cc3C2)ccn1] | 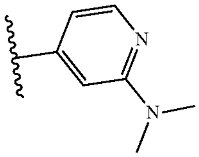 [SMILES: *c1ccnc(N(C)C)c1] |
| 182 | 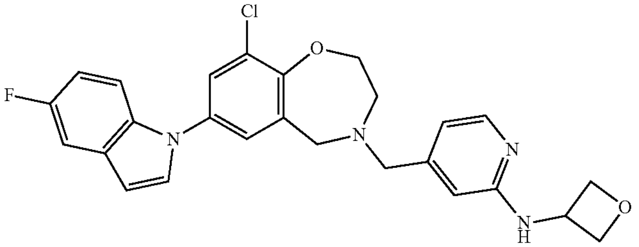 [SMILES: Fc1ccc2c(ccn2-c2cc(Cl)c3c(c2)CN(Cc2ccnc(NC4COC4)c2)CCO3)c1] | 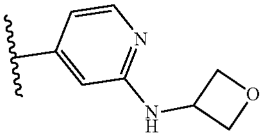 [SMILES: *c1ccnc(NC2COC2)c1] |
| 183 | 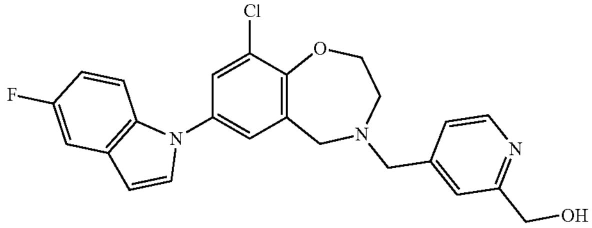 [SMILES: OCc1cc(CN2CCOc3c(Cl)cc(-n4ccc5cc(F)ccc54)cc3C2)ccn1] | 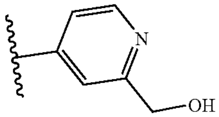 [SMILES: *c1ccnc(CO)c1] |
| 184 | 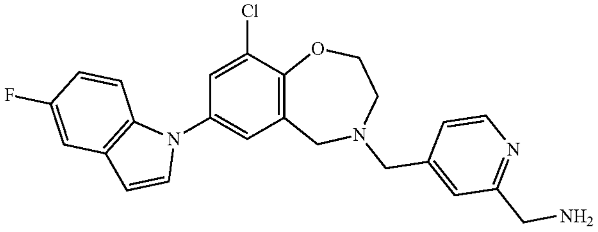 [SMILES: NCc1cc(CN2CCOc3c(Cl)cc(-n4ccc5cc(F)ccc54)cc3C2)ccn1] | 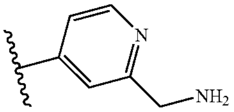 [SMILES: *c1ccnc(CN)c1] |
| 185 | 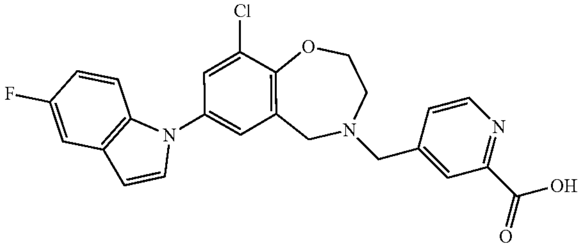 [SMILES: O=C(O)c1cc(CN2CCOc3c(Cl)cc(-n4ccc5cc(F)ccc54)cc3C2)ccn1] | 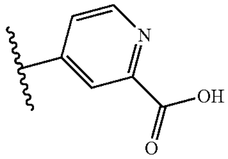 [SMILES: *c1ccnc(C(=O)O)c1] |
| 186 | 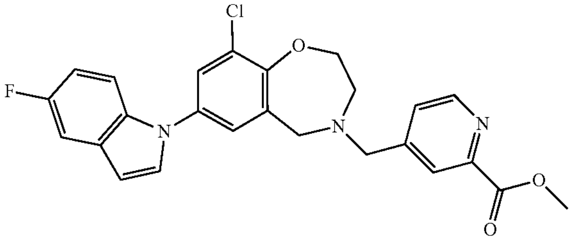 [SMILES: COC(=O)c1cc(CN2CCOc3c(Cl)cc(-n4ccc5cc(F)ccc54)cc3C2)ccn1] | 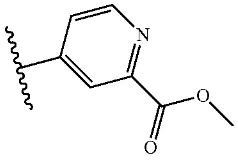 [SMILES: *c1ccnc(C(=O)OC)c1] |

TABLE VII-continued
| ID No. | Structure | B′ |
|---|---|---|
| 187 | 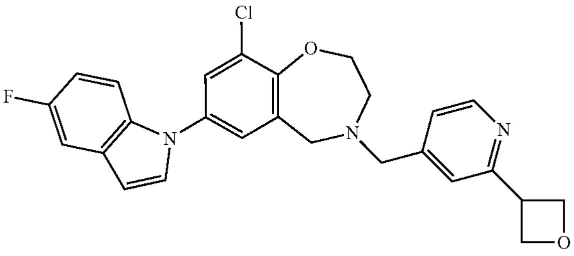 [SMILES: Fc1ccc2c(ccn2-c2cc(Cl)c3c(c2)CN(Cc2ccnc(C4COC4)c2)CCO3)c1] | 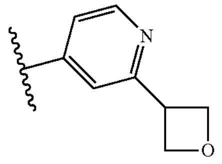 [SMILES: *c1ccnc(C2COC2)c1] |
| 188 | 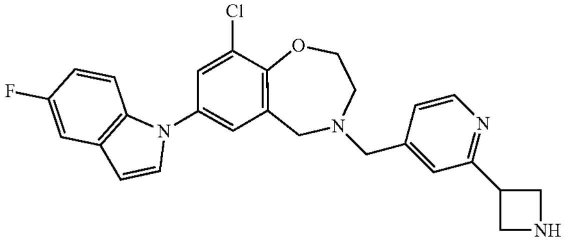 [SMILES: Fc1ccc2c(ccn2-c2cc(Cl)c3c(c2)CN(Cc2ccnc(C4CNC4)c2)CCO3)c1] | 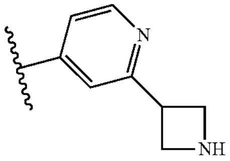 [SMILES: *c1ccnc(C2CNC2)c1] |
| 189 | 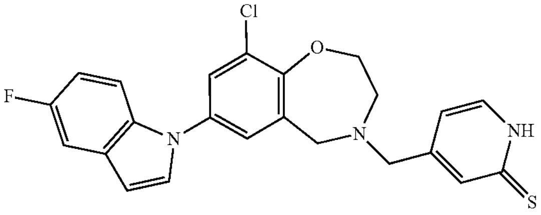 [SMILES: Fc1ccc2c(ccn2-c2cc(Cl)c3c(c2)CN(Cc2cc[nH]c(=S)c2)CCO3)c1] | 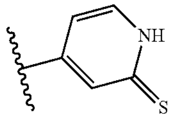 [SMILES: *c1cc[nH]c(=S)c1] |
| 190 | 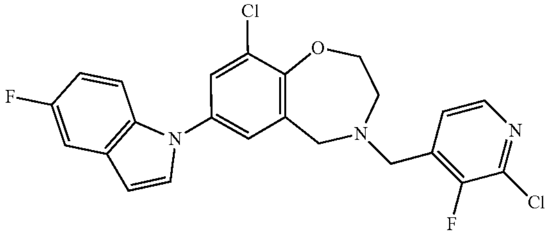 [SMILES: Fc1ccc2c(ccn2-c2cc(Cl)c3c(c2)CN(Cc2ccnc(Cl)c2F)CCO3)c1] | 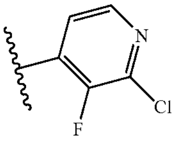 [SMILES: *c1ccnc(Cl)c1F] |
| 191 | 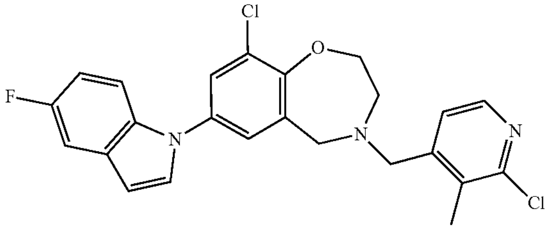 [SMILES: Cc1c(CN2CCOc3c(Cl)cc(-n4ccc5cc(F)ccc54)cc3C2)ccnc1Cl] | 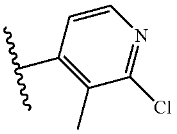 [SMILES: *c1ccnc(Cl)c1C] |
| 192 | 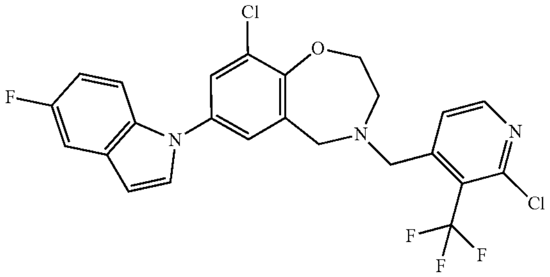 [SMILES: Fc1ccc2c(ccn2-c2cc(Cl)c3c(c2)CN(Cc2ccnc(Cl)c2C(F)(F)F)CCO3)c1] | 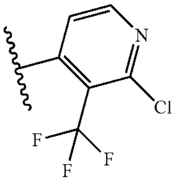 [SMILES: *c1ccnc(Cl)c1C(F)(F)F] |

TABLE VII-continued
| ID No. | Structure | B′ |
|---|---|---|
| 193 | 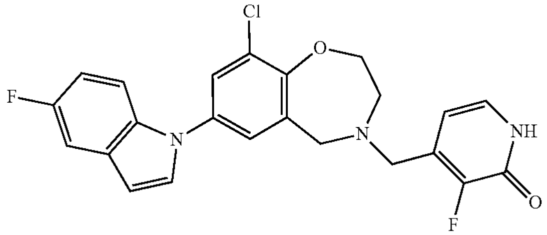 [SMILES: O=c1[nH]ccc(CN2CCOc3c(Cl)cc(-n4ccc5cc(F)ccc54)cc3C2)c1F] | 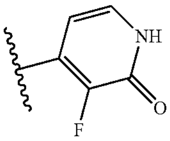 [SMILES: *c1cc[nH]c(=O)c1F] |
| 194 | 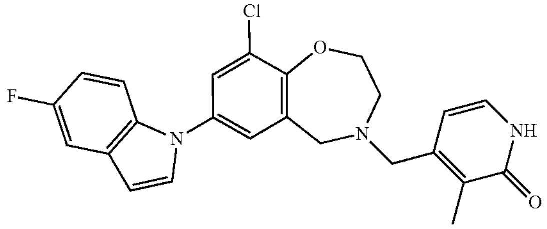 [SMILES: Cc1c(CN2CCOc3c(Cl)cc(-n4ccc5cc(F)ccc54)cc3C2)cc[nH]c1=O] | 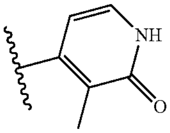 [SMILES: *c1cc[nH]c(=O)c1C] |
| 195 | 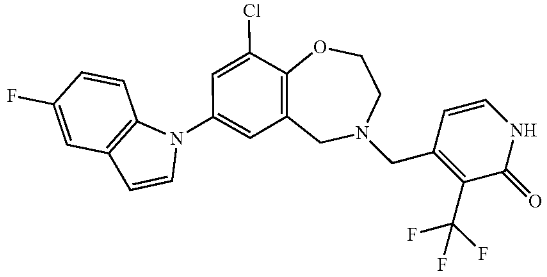 [SMILES: O=c1[nH]ccc(CN2CCOc3c(Cl)cc(-n4ccc5cc(F)ccc54)cc3C2)c1C(F)(F)F] | 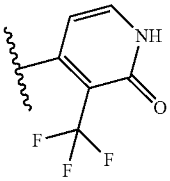 [SMILES: *c1cc[nH]c(=O)c1C(F)(F)F] |
| 196 | 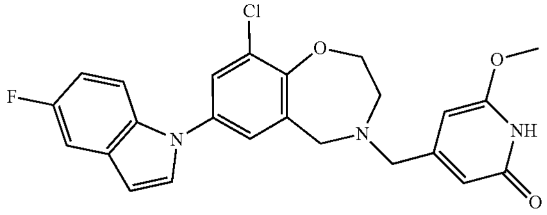 [SMILES: COc1cc(CN2CCOc3c(Cl)cc(-n4ccc5cc(F)ccc54)cc3C2)cc(=O)[nH]1] | 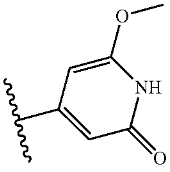 [SMILES: *c1cc(OC)[nH]c(=O)c1] |
| 197 | 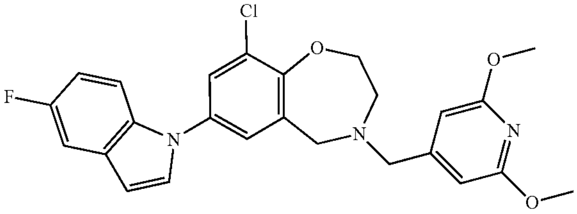 [SMILES: COc1cc(CN2CCOc3c(Cl)cc(-n4ccc5cc(F)ccc54)cc3C2)cc(OC)n1] | 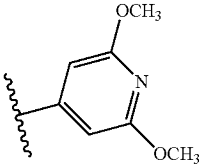 [SMILES: *c1cc(OC)nc(OC)c1] |
| 198 | 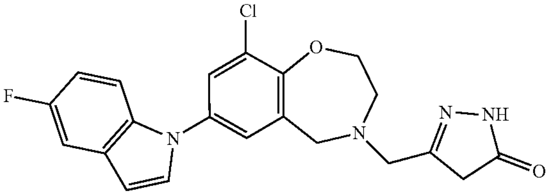 [SMILES: O=C1CC(CN2CCOc3c(Cl)cc(-n4ccc5cc(F)ccc54)cc3C2)=NN1] | 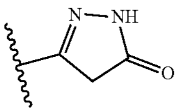 [SMILES: *C1=NNC(=O)C1] |

TABLE VII-continued
| ID No. | Structure | B′ |
|---|---|---|
| 199 | 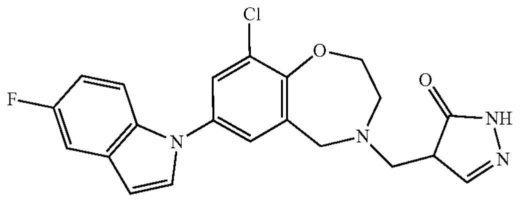 [SMILES: O=C1NN=CC1CN1CCOc2c(Cl)cc(-n3ccc4cc(F)ccc43)cc2C1] | 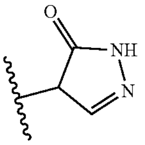 [SMILES: *C1C=NNC1=O] |
| 200 | 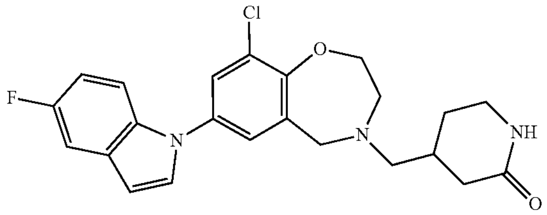 [SMILES: O=C1CC(CN2CCOc3c(Cl)cc(-n4ccc5cc(F)ccc54)cc3C2)CCN1] | 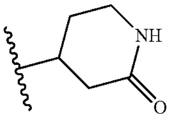 [SMILES: *C1CCNC(=O)C1] |
| 201 | 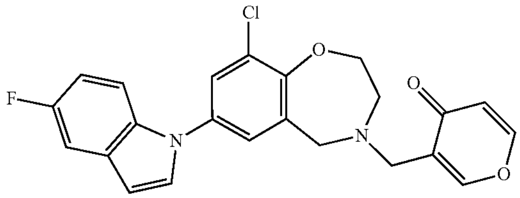 [SMILES: O=c1ccocc1CN1CCOc2c(Cl)cc(-n3ccc4cc(F)ccc43)cc2C1] | 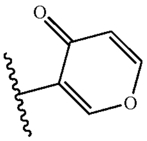 [SMILES: *c1coccc1=O] |
| 202 | 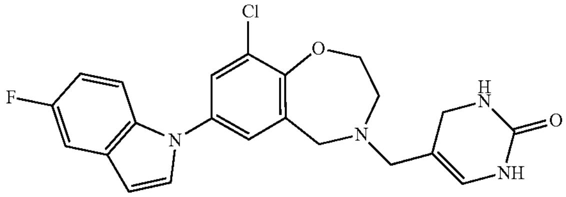 [SMILES: O=C1NC=C(CN2CCOc3c(Cl)cc(-n4ccc5cc(F)ccc54)cc3C2)CN1] | 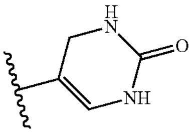 [SMILES: *C1=CNC(=O)NC1] |
| 203 | 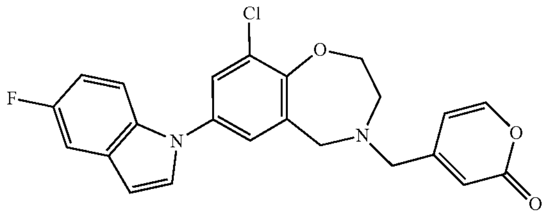 [SMILES: O=c1cc(CN2CCOc3c(Cl)cc(-n4ccc5cc(F)ccc54)cc3C2)cco1] | 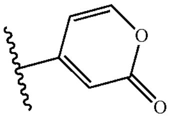 [SMILES: *c1ccoc(=O)c1] |
| 204 | 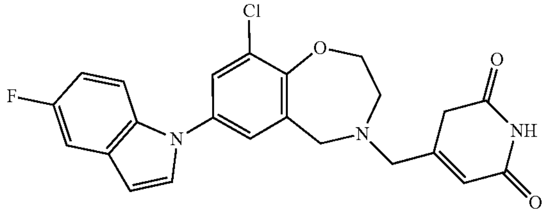 [SMILES: O=C1C=C(CN2CCOc3c(Cl)cc(-n4ccc5cc(F)ccc54)cc3C2)CC(=O)N1] | 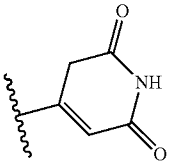 [SMILES: *C1=CC(=O)NC(=O)C1] |
| 205 | 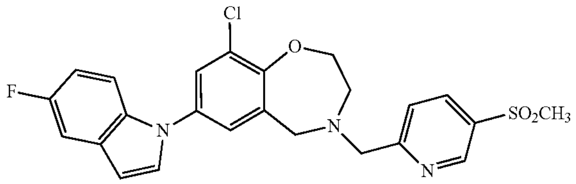 [SMILES: CS(=O)(=O)c1ccc(CN2CCOc3c(Cl)cc(-n4ccc5cc(F)ccc54)cc3C2)nc1] | 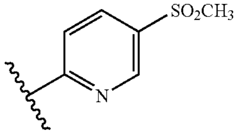 [SMILES: *c1ccc(S(C)(=O)=O)cn1] |

TABLE VII-continued
| ID No. | Structure | B′ |
|---|---|---|
| 206 | 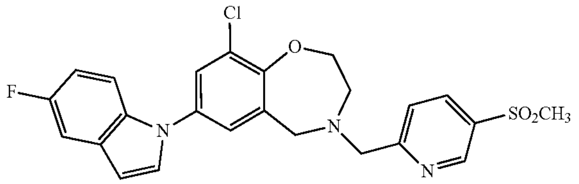 [SMILES: CS(=O)(=O)c1ccc(CN2CCOc3c(Cl)cc(-n4ccc5cc(F)ccc54)cc3C2)nc1] | 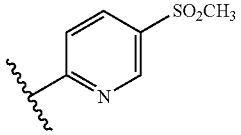 [SMILES: *c1ccc(S(C)(=O)=O)cn1] |
| 207 | 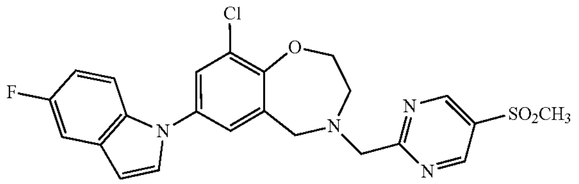 [SMILES: CS(=O)(=O)c1cnc(CN2CCOc3c(Cl)cc(-n4ccc5cc(F)ccc54)cc3C2)nc1] | 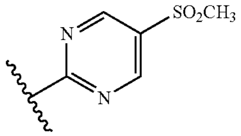 [SMILES: *c1ncc(S(C)(=O)=O)cn1] |
| 208 | 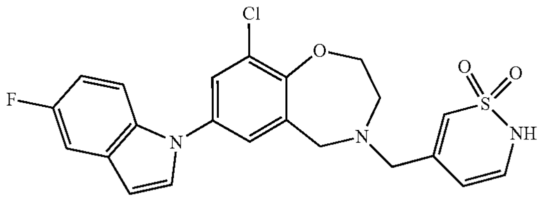 [SMILES: O=S1(=O)C=C(CN2CCOc3c(Cl)cc(-n4ccc5cc(F)ccc54)cc3C2)C=CN1] | 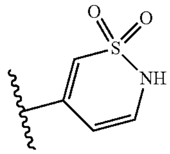 [SMILES: *C1=CS(=O)(=O)NC=C1] |
| 209 | 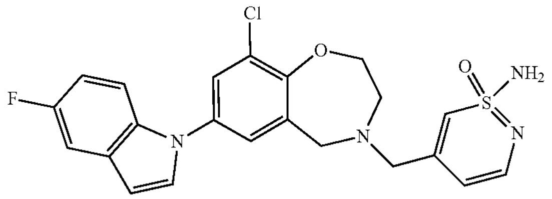 [SMILES: NS1(=O)=NC=CC(CN2CCOc3c(Cl)cc(-n4ccc5cc(F)ccc54)cc3C2)=C1] | 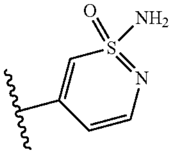 [SMILES: *C1=CS(N)(=O)=NC=C1] |
| 210 | 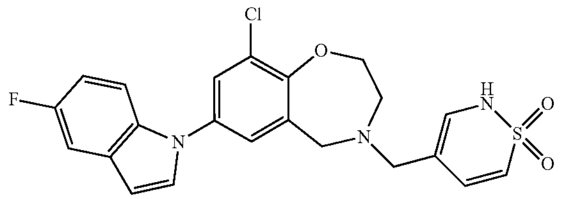 [SMILES: O=S1(=O)C=CC(CN2CCOc3c(Cl)cc(-n4ccc5cc(F)ccc54)cc3C2)=CN1] | 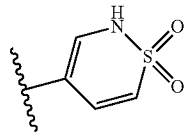 [SMILES: *C1=CNS(=O)(=O)C=C1] |
| 211 | 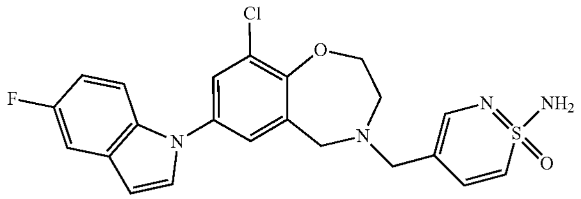 [SMILES: NS1(=O)=NC=C(CN2CCOc3c(Cl)cc(-n4ccc5cc(F)ccc54)cc3C2)C=C1] | 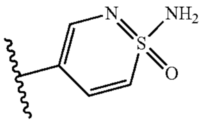 [SMILES: *C1=CN=S(N)(=O)C=C1] |
| 212 | 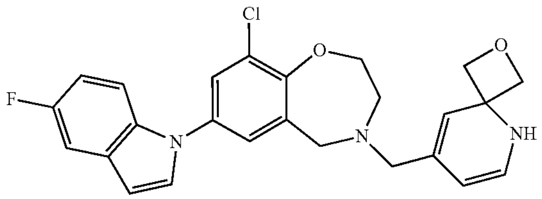 [SMILES: Fc1ccc2c(ccn2-c2cc(Cl)c3c(c2)CN(CC2=CC4(COC4)NC=C2)CCO3)c1] | 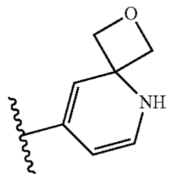 [SMILES: *C1=CC2(COC2)NC=C1] |

TABLE VII-continued
| ID No. | Structure | B' |
|---|---|---|
| 213 | 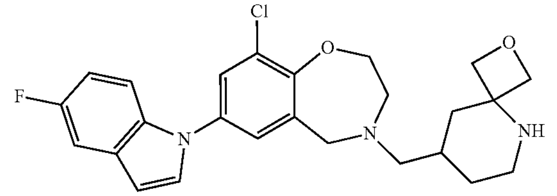 [SMILES: Fc1ccc2c(ccn2-c2cc(Cl)c3c(c2)CN(CC2CCNC4(COC4)C2)CCO3)c1] | 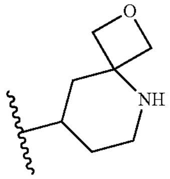 [SMILES: *C1CCNC2(COC2)C1] |
| 214 | 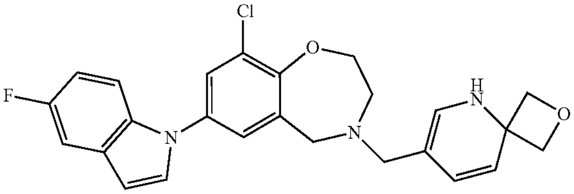 [SMILES: Fc1ccc2c(ccn2-c2cc(Cl)c3c(c2)CN(CC2=CNC4(C=C2)COC4)CCO3)c1] | 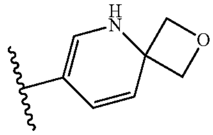 [SMILES: *C1=CNC2(C=C1)COC2] |
| 215 | 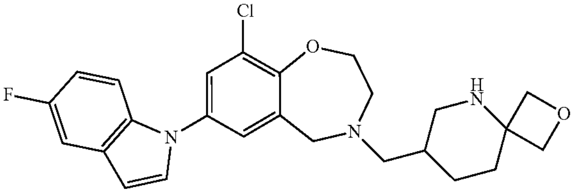 [SMILES: Fc1ccc2c(ccn2-c2cc(Cl)c3c(c2)CN(CC2CCC4(COC4)NC2)CCO3)c1] | 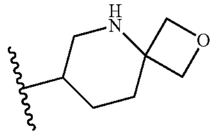 [SMILES: *C1CCC2(COC2)NC1] |
| 216 | 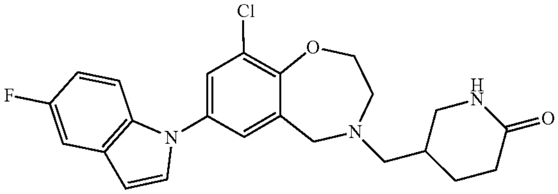 [SMILES: O=C1CCC(CN2CCOc3c(Cl)cc(-n4ccc5cc(F)ccc54)cc3C2)CN1] | 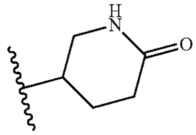 [SMILES: *C1CCC(=O)NC1] |
In another aspect, provided herein is a compound of Formula (VIII):
Formula VIII
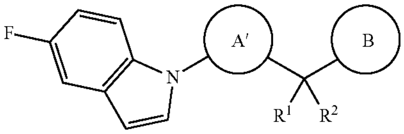
or a tautomer, or a pharmaceutically acceptable salt thereof, wherein:
$R^1$ and $R^2$ are each independently hydrogen or deuterium;
Ring A' is selected from the group consisting of:
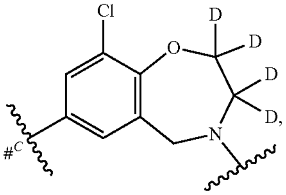
-continued
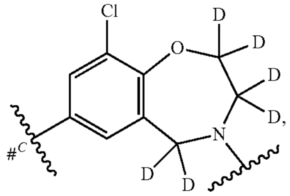
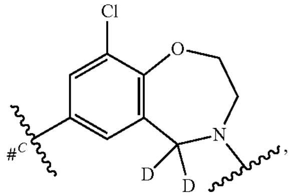
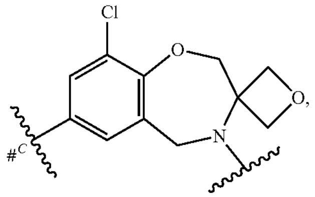

-continued

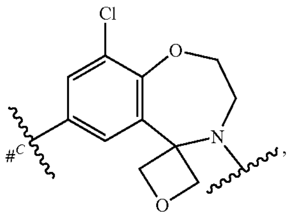

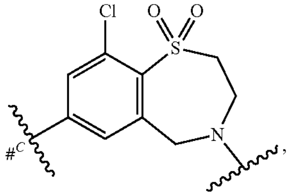

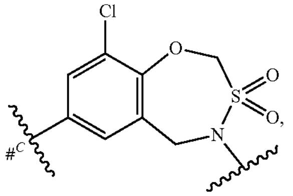

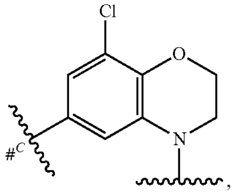

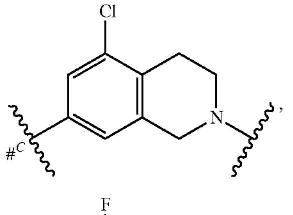

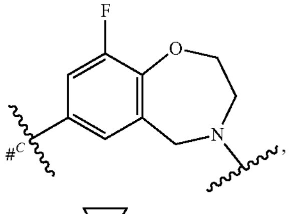

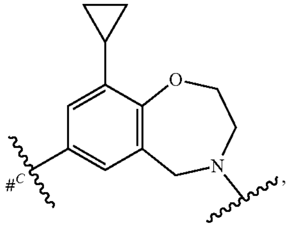

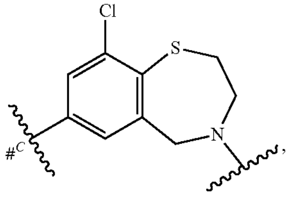

-continued

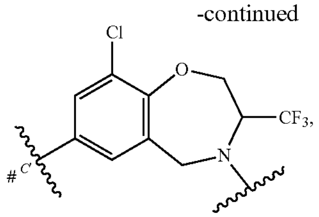

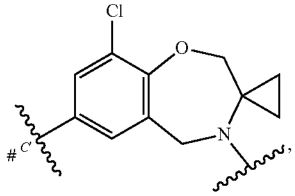

and

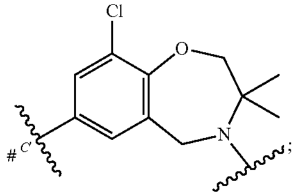

wherein #c denotes a bond to the fluoroindole ring;

Ring B is a substituted or unsubstituted heterocycle; wherein if Ring B is substituted, it is substituted with one or more $R^B$ groups, and each $R^B$ group is independently selected from the group consisting of hydrogen, deuterium, halogen, $C_{1-4}$alkyl, —CN, —C(═O)—$NH_2$, —C(═O)—$NHC_{1-4}$ alkyl, —C(═O)—N($C_{1-4}$alkyl$)_2$, —$NH_2$, —$NHC_{1-4}$ alkyl, —N($C_{1-4}$alkyl$)_2$, —NH—C(═O)—$C_{1-4}$ alkyl, —OH, —O—$C_{1-4}$alkyl, —S(═O)—$C_{1-4}$ alkyl, and —S(═O$)_2$—$C_{1-4}$alkyl; wherein two $R^B$ groups attached to the same carbon atom are optionally taken together with the carbon atom to which they are attached to form (C═O) or an oxetanyl.

In some embodiments, Ring A' is selected from the group consisting of:

In some embodiments, Ring B is a substituted or unsubstituted monocyclic heterocycle. In some embodiments, Ring B is a substituted or unsubstituted bicyclic heterocycle. In some embodiments, Ring B is a substituted or unsubstituted 5- or 6-membered heterocycle. In some embodiments, Ring B is a substituted or unsubstituted 5-membered heterocycle. In some embodiments, Ring B is a substituted 5-membered heterocycle. In some embodiments, Ring B is an unsubstituted 5-membered heterocycle.

In some embodiments, Ring B is a substituted or unsubstituted 6-membered heterocycle. In some embodiments, Ring B is a substituted 6-membered heterocycle. In some embodiments, Ring B is an unsubstituted 6-membered heterocycle. In some embodiments, Ring B is a substituted or unsubstituted pyridine, substituted or unsubstituted pyrimidine, substituted or unsubstituted pyrazine, substituted or unsubstituted pyridazine, or substituted or unsubstituted piperidine. In some embodiments, Ring B is a substituted pyridine, substituted pyrimidine, substituted pyrazine, substituted pyridazine, or substituted piperidine. In some embodiments, Ring B is an unsubstituted pyridine, unsubstituted pyrimidine, unsubstituted pyrazine, unsubstituted pyridazine, or unsubstituted piperidine.

In some embodiments, Ring B is a substituted or unsubstituted pyridine. In some embodiments, Ring B is a substituted or unsubstituted pyrimidine. In some embodiments, Ring B is a substituted or unsubstituted pyrazine. In some embodiments, Ring B is a substituted or unsubstituted pyridazine. In some embodiments, Ring B is a substituted or unsubstituted piperidine.

In some embodiments, Ring B is a substituted pyridine. In some embodiments, Ring B is a substituted pyrimidine. In some embodiments, Ring B is a substituted pyrazine.

In some embodiments, Ring B is a substituted pyridazine. In some embodiments, Ring B is a substituted piperidine. In some embodiments, Ring B is an unsubstituted pyridine. In some embodiments, Ring B is an unsubstituted pyrimidine. In some embodiments, Ring B is an unsubstituted pyrazine. In some embodiments, Ring B is an unsubstituted pyridazine. In some embodiments, Ring B is an unsubstituted piperidine.

In some embodiments, Ring B is substituted with one or more $R^B$ groups. In some embodiments, Ring B is a substituted or unsubstituted pyridone. In some embodiments, Ring B is a substituted or unsubstituted pyrimidone. In some embodiments, Ring B is a substituted or unsubstituted pyrazone. In some embodiments, Ring B is a substituted or unsubstituted pyridazone. In some embodiments, Ring B is a substituted or unsubstituted piperidone.

In some embodiments, Ring B is selected from the group consisting of:

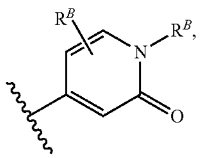
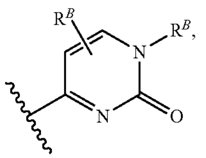
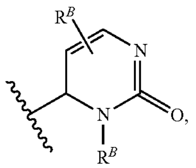
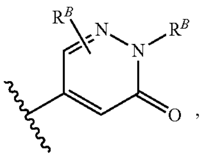
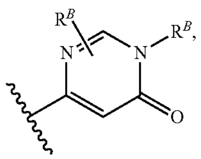
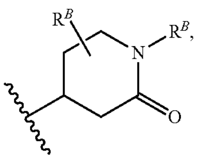
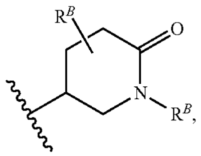
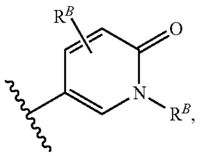
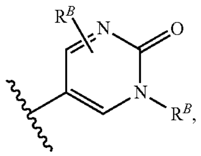
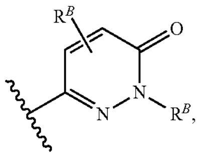
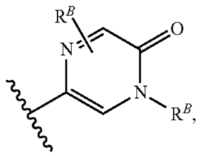
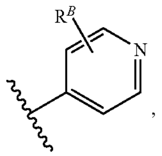

-continued

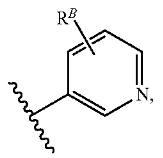
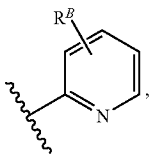
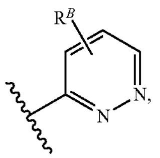
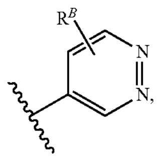
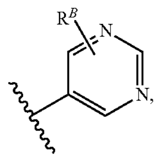
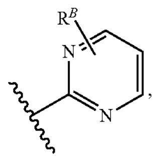
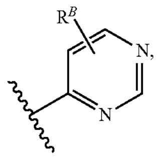
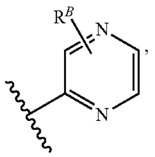
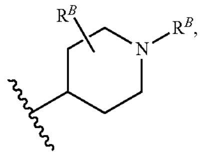
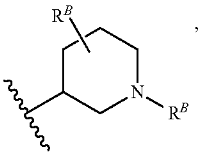
, and
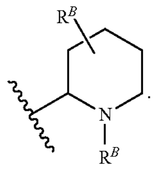

In some embodiments, Ring B is selected from the group consisting of:

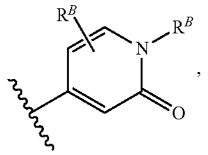
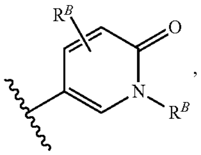
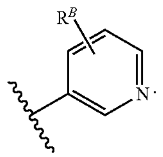
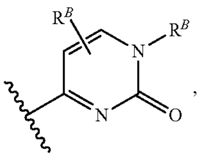
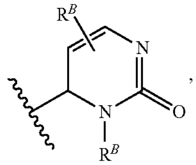
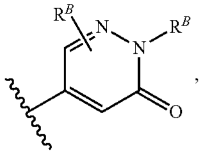
and
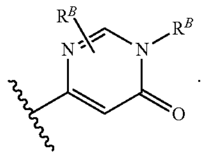

In some embodiments, Ring B is

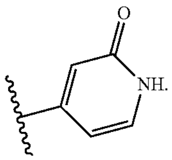 [SMILES: *c1cc[nH]c(=O)c1]

In some embodiments, each $R^B$ is independently hydrogen, deuterium, halogen, $C_{1-4}$alkyl, —$NH_2$, —$NHC_{1-4}$alkyl, —$N(C_{1-4}alkyl)_2$, —OH, —O—$C_{1-4}$alkyl, or —S(═O)$_2$—$C_{1-4}$alkyl. In some embodiments, each $R^B$ is independently hydrogen, —$NH_2$, or —S(═O)$_2$—$C_{1-4}$alkyl. In some embodiments, each $R^B$ is independently hydrogen or —S(═O)$_2$—$CH_2CH_3$. In some embodiments, each $R^B$ is independently hydrogen or —$NH_2$. In some embodiments, each $R^B$ is hydrogen and Ring B is therefore unsubstituted. In some embodiments, two $R^B$ groups are taken together to form an oxo (═O). In some embodiments, two $R^B$ groups are taken together to form an oxetanyl.

In another embodiment, is a compound of the following formula:

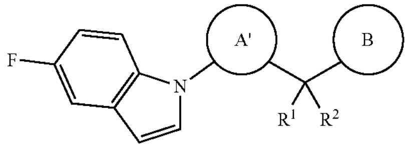

or a tautomer, or a pharmaceutically acceptable salt thereof, disclosed in Table VIII.

TABLE VIII

| ID No. | Structure | 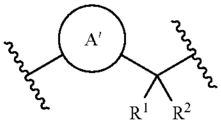 | 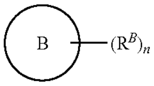 |
|---|---|---|---|
| 217 | 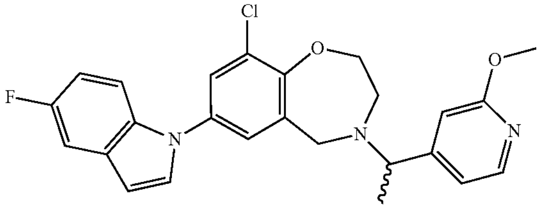 [SMILES: COc1cc(C(C)N2CCOc3c(Cl)cc(-n4ccc5cc(F)ccc54)cc3C2)ccn1] | 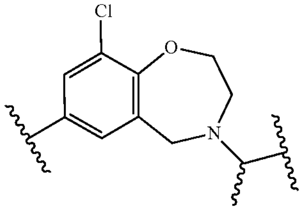 [SMILES: *c1cc(Cl)c2c(c1)CN(C(*)C)CCO2] | 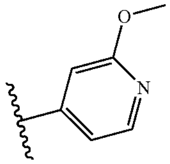 [SMILES: *c1ccnc(OC)c1] |
| 218 | 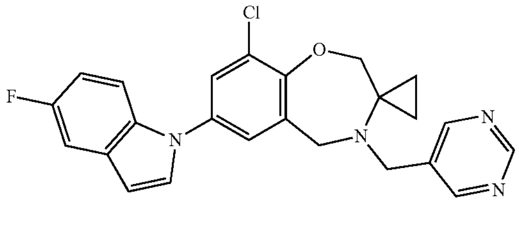 [SMILES: Fc1ccc2c(ccn2-c2cc(Cl)c3c(c2)CN(Cc2cncnc2)C2(CC2)CO3)c1] | 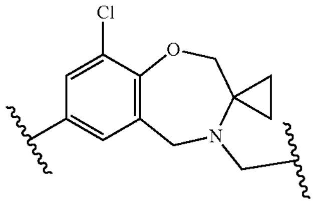 [SMILES: *CN1Cc2cc(*)cc(Cl)c2OCC12CC2] | 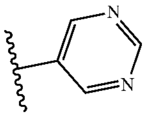 [SMILES: *c1cncnc1] |
| 219 | 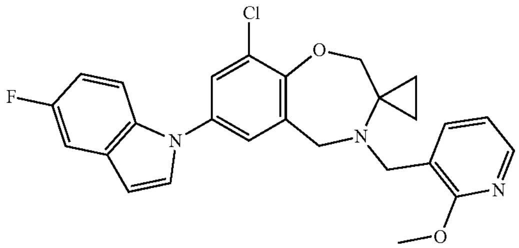 [SMILES: COc1ncccc1CN1Cc2cc(-n3ccc4cc(F)ccc43)cc(Cl)c2OCC12CC2] | 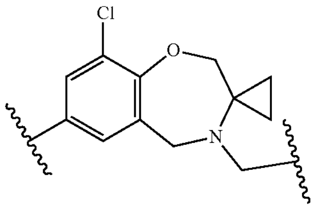 [SMILES: *CN1Cc2cc(*)cc(Cl)c2OCC12CC2] | 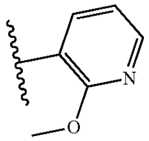 [SMILES: *c1cccnc1OC] |
| 220 | 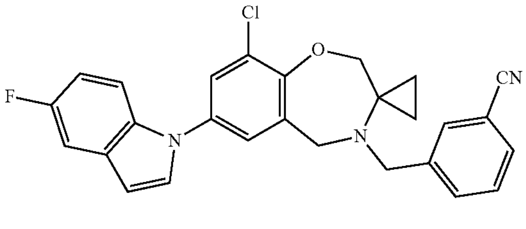 [SMILES: N#Cc1cccc(CN2Cc3cc(-n4ccc5cc(F)ccc54)cc(Cl)c3OCC23CC3)c1] | 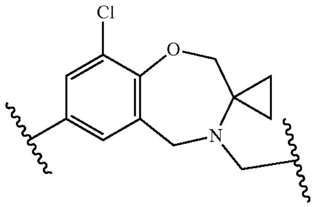 [SMILES: *CN1Cc2cc(*)cc(Cl)c2OCC12CC2] | 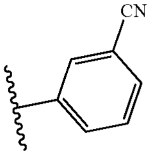 [SMILES: *c1cccc(C#N)c1] |

TABLE VIII-continued
| ID No. | Structure | 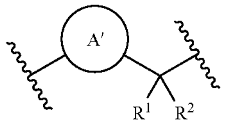 | 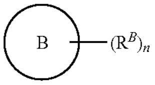 |
|---|---|---|---|
| 221 | 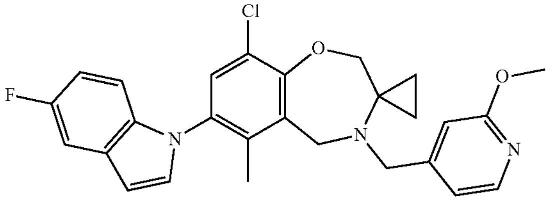 [SMILES: COc1cc(CN2Cc3c(C)c(-n4ccc5cc(F)ccc54)cc(Cl)c3OCC23CC3)ccn1] | 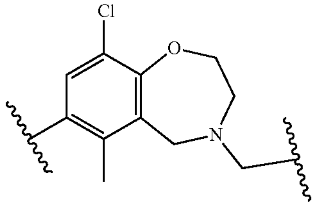 [SMILES: *CN1CCOc2c(Cl)cc(*)c(C)c2C1] | 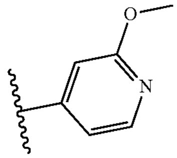 [SMILES: *c1ccnc(OC)c1] |
| 222 | 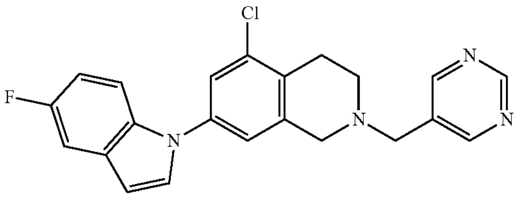 [SMILES: Fc1ccc2c(ccn2-c2cc(Cl)c3c(c2)CN(Cc2cncnc2)CC3)c1] | 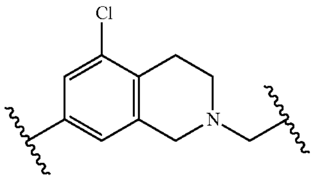 [SMILES: *CN1CCc2c(Cl)cc(*)cc2C1] | 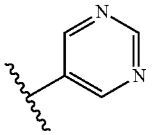 [SMILES: *c1cncnc1] |
| 223 | 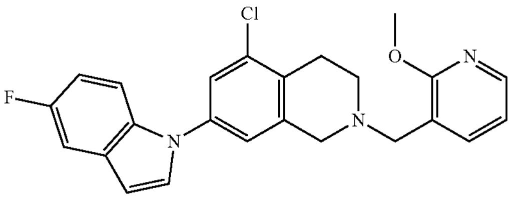 [SMILES: COc1ncccc1CN1CCc2c(Cl)cc(-n3ccc4cc(F)ccc43)cc2C1] | 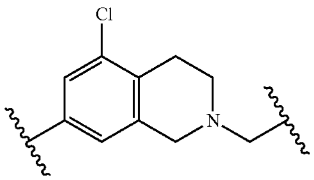 [SMILES: *CN1CCc2c(Cl)cc(*)cc2C1] | 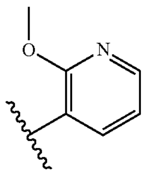 [SMILES: *c1cccnc1OC] |
| 224 | 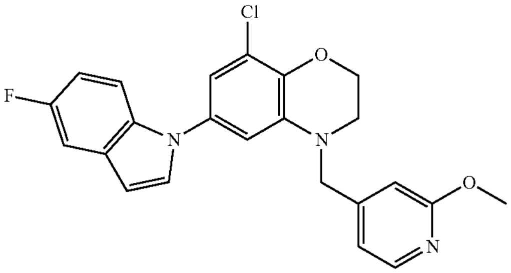 [SMILES: COc1cc(CN2CCOc3c(Cl)cc(-n4ccc5cc(F)ccc54)cc32)ccn1] | 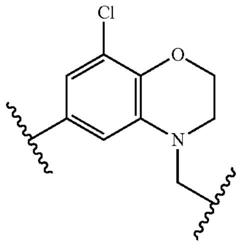 [SMILES: *CN1CCOc2c(Cl)cc(*)cc21] | 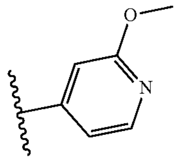 [SMILES: *c1ccnc(OC)c1] |
In some embodiments, the compound of Formula (VIII) is a compound of Formula (IX):
Formula IX
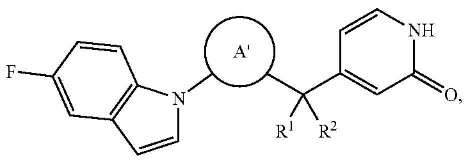
or a tautomer, or a pharmaceutically acceptable salt thereof.
In some embodiments, $R^1$ and $R^2$ are each independently hydrogen or deuterium; and Ring A' is selected from the group consisting of:
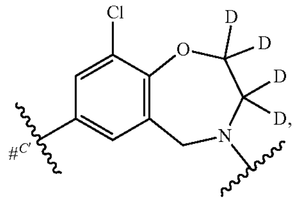
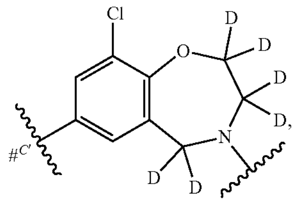

-continued
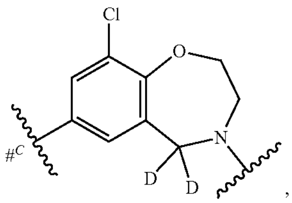
,
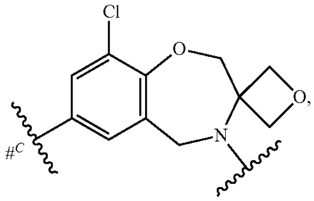
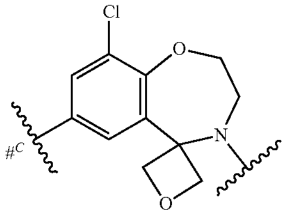
,
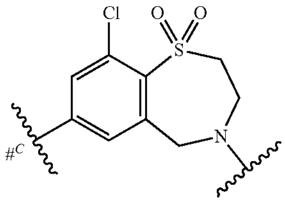
,
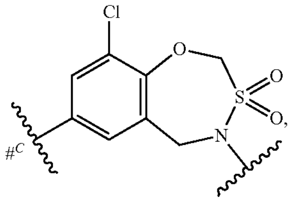
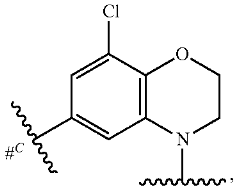
,
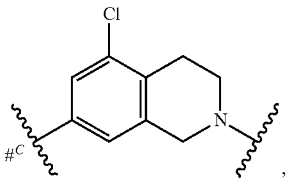
,
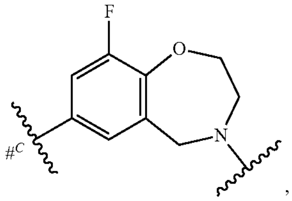
,
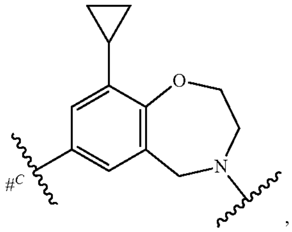
,
-continued
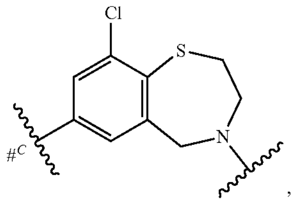
,
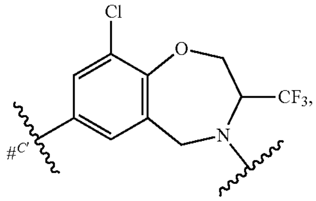
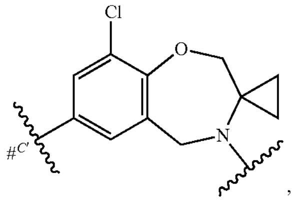
, and
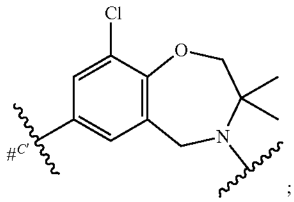
;
wherein $\#^C$ denotes a bond to the fluoroindole ring.
In some embodiments, Ring A' is selected from the group consisting of:
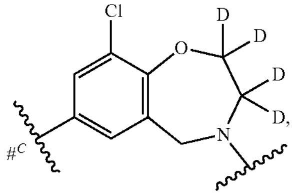
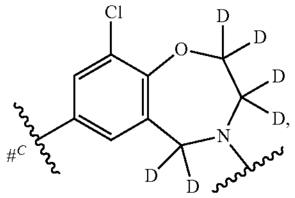
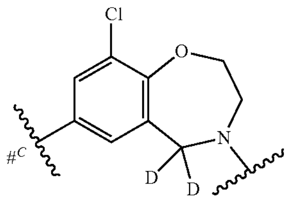
, -continued
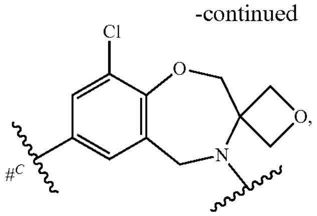
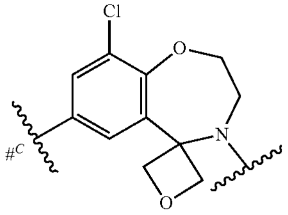
, and
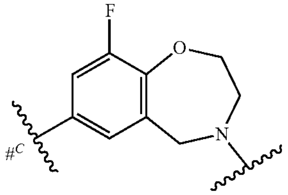
.
and
In some embodiments, Ring A' is selected from the group consisting of:
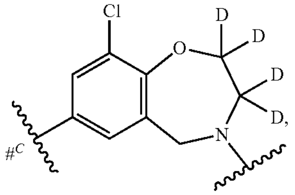
-continued
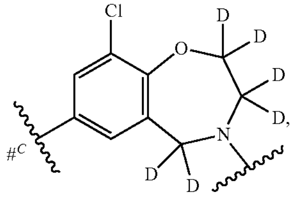
and
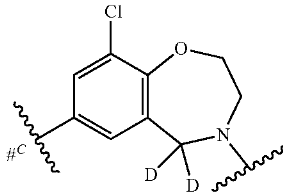
,
In another embodiment, is a compound of the following formula:
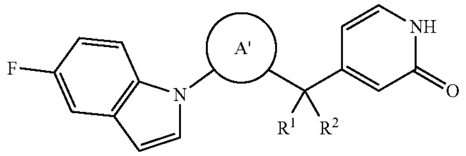
or a tautomer, or a pharmaceutically acceptable salt thereof, disclosed in Table IX.
TABLE IX
| ID No. | Structure | 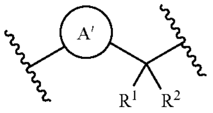 |
|---|---|---|
| 225 | 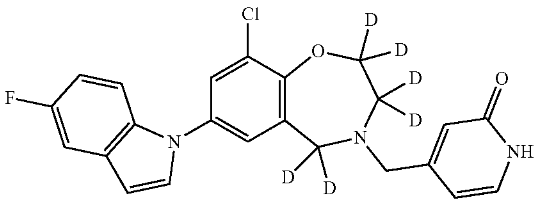 [SMILES: [2H]C1([2H])c2cc(-n3ccc4cc(F)ccc43)cc(Cl)c2OC([2H])([2H])C([2H])([2H])N1Cc1cc[nH]c(=O)c1] | 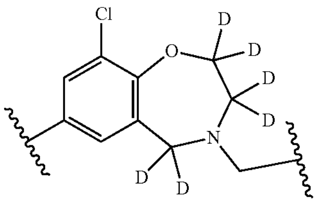 [SMILES: *CN1C([2H])([2H])c2cc(*)cc(Cl)c2OC([2H])([2H])C1([2H])[2H]] |
| 226 | 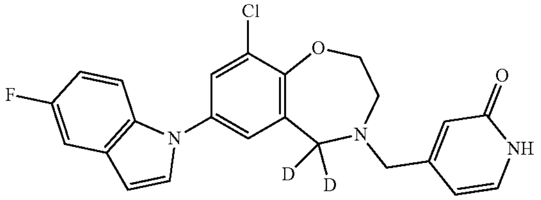 [SMILES: [2H]C1([2H])c2cc(-n3ccc4cc(F)ccc43)cc(Cl)c2OCCN1Cc1cc[nH]c(=O)c1] | 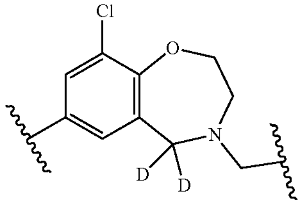 [SMILES: *CN1CCOc2c(Cl)cc(*)cc2C1([2H])[2H]] |

TABLE IX-continued
| ID No. | Structure | 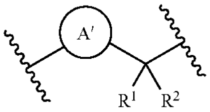 |
|---|---|---|
| 227 | 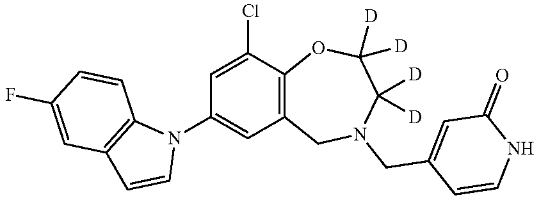 [SMILES: [2H]C1([2H])Oc2c(Cl)cc(-n3ccc4cc(F)ccc43)cc2CN(Cc2cc[nH]c(=O)c2)C1([2H])[2H]] | 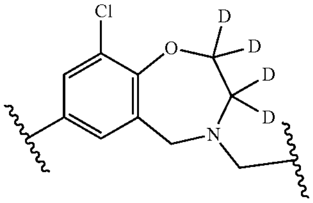 [SMILES: *CN1Cc2cc(*)cc(Cl)c2OC([2H])([2H])C1([2H])[2H]] |
| 228 | 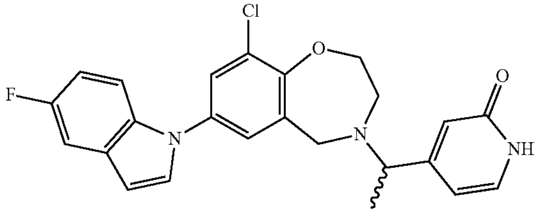 [SMILES: CC(c1cc[nH]c(=O)c1)N1CCOc2c(Cl)cc(-n3ccc4cc(F)ccc43)cc2C1] | 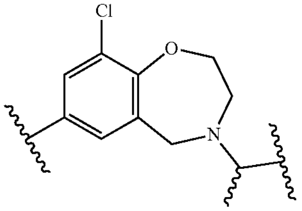 [SMILES: *c1cc(Cl)c2c(c1)CN(C(*)C)CCO2] |
| 229 | 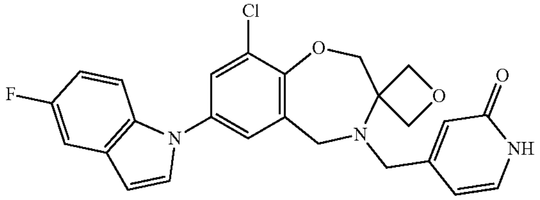 [SMILES: O=c1cc(CN2Cc3cc(-n4ccc5cc(F)ccc54)cc(Cl)c3OCC23COC3)cc[nH]1] | 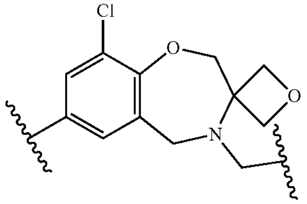 [SMILES: *CN1Cc2cc(*)cc(Cl)c2OCC12COC2] |
| 230 | 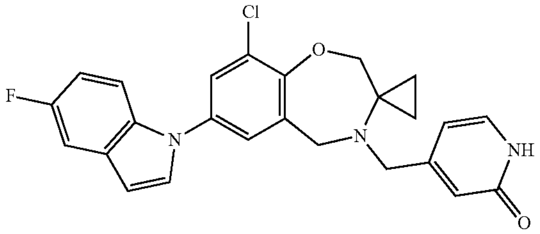 [SMILES: O=c1cc(CN2Cc3cc(-n4ccc5cc(F)ccc54)cc(Cl)c3OCC23CC3)cc[nH]1] | 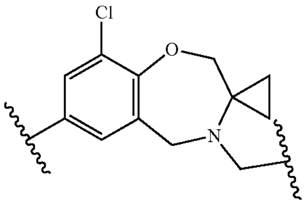 [SMILES: *CN1Cc2cc(*)cc(Cl)c2OCC12CC2] |
| 231 | 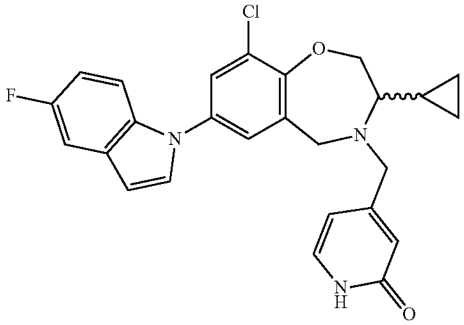 [SMILES: O=c1cc(CN2Cc3cc(-n4ccc5cc(F)ccc54)cc(Cl)c3OCC2C2CC2)cc[nH]1] | 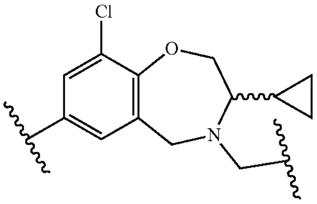 [SMILES: *CN1Cc2cc(*)cc(Cl)c2OCC1C1CC1] |
| 232 | 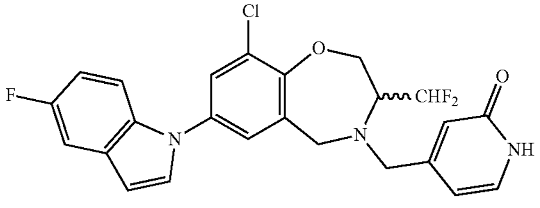 [SMILES: O=c1cc(CN2Cc3cc(-n4ccc5cc(F)ccc54)cc(Cl)c3OCC2C(F)F)cc[nH]1] | 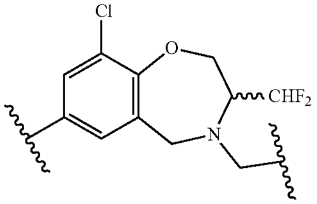 [SMILES: *CN1Cc2cc(*)cc(Cl)c2OCC1C(F)F] |

TABLE IX-continued
| ID No. | Structure | 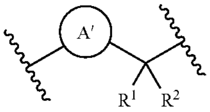 |
|---|---|---|
| 233 | 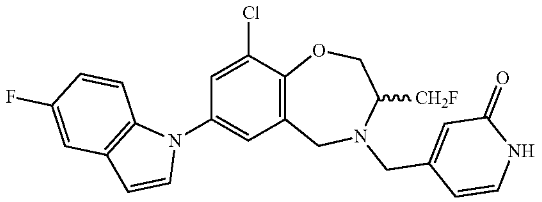 | 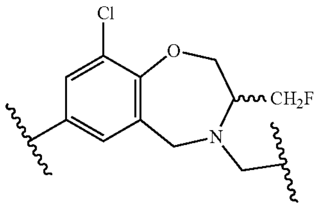 |
| 234 | 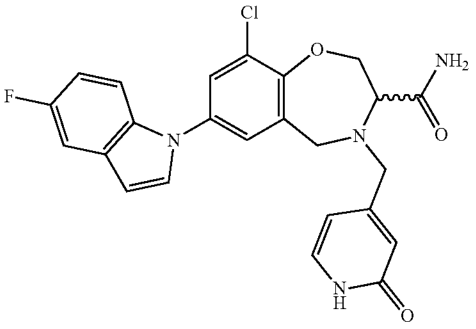 [SMILES: NC(=O)C1COc2c(Cl)cc(-n3ccc4cc(F)ccc43)cc2CN1Cc1cc[nH]c(=O)c1] | 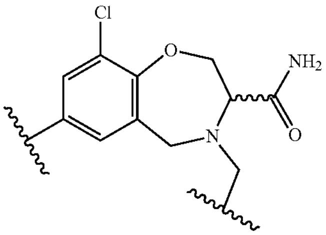 [SMILES: *CN1Cc2cc(*)cc(Cl)c2OCC1C(N)=O] |
| 235 | 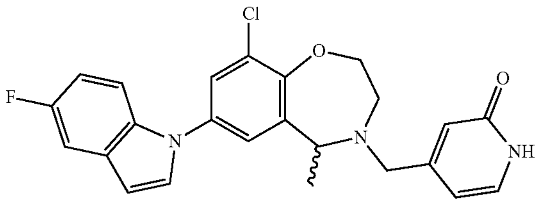 [SMILES: CC1c2cc(-n3ccc4cc(F)ccc43)cc(Cl)c2OCCN1Cc1cc[nH]c(=O)c1] | 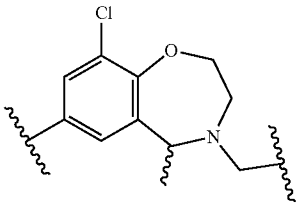 [SMILES: *CN1CCOc2c(Cl)cc(*)cc2C1C] |
| 236 | 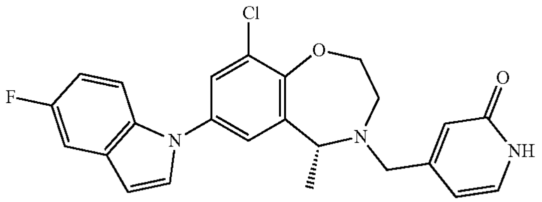 [SMILES: C[C@@H]1c2cc(-n3ccc4cc(F)ccc43)cc(Cl)c2OCCN1Cc1cc[nH]c(=O)c1] | 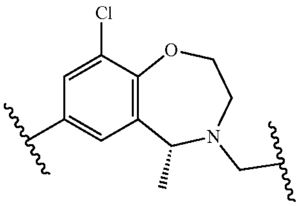 [SMILES: *CN1CCOc2c(Cl)cc(*)cc2[C@H]1C] |
| 237 | 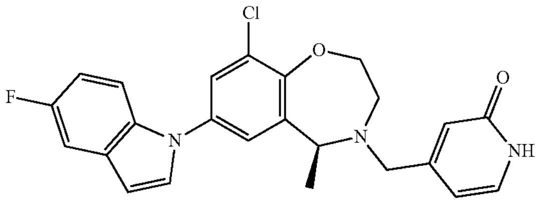 [SMILES: C[C@H]1c2cc(-n3ccc4cc(F)ccc43)cc(Cl)c2OCCN1Cc1cc[nH]c(=O)c1] | 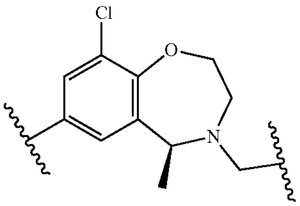 [SMILES: *CN1CCOc2c(Cl)cc(*)cc2[C@@H]1C] |
| 238 | 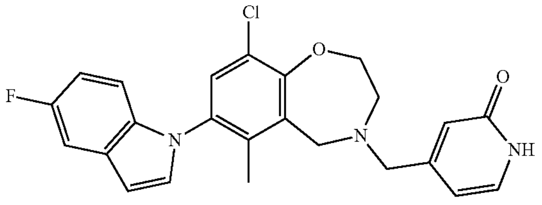 [SMILES: Cc1c(-n2ccc3cc(F)ccc32)cc(Cl)c2c1CN(Cc1cc[nH]c(=O)c1)CCO2] | 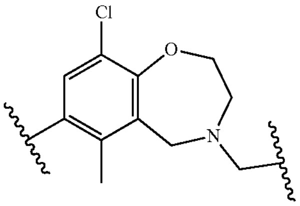 [SMILES: *CN1CCOc2c(Cl)cc(*)c(C)c2C1] |

TABLE IX-continued
| ID No. | Structure | 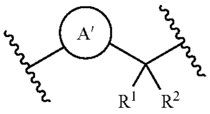 |
|---|---|---|
| 239 | 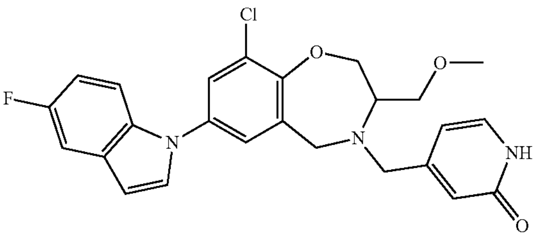 [SMILES: COCC1COc2c(Cl)cc(-n3ccc4cc(F)ccc43)cc2CN1Cc1cc[nH]c(=O)c1] | 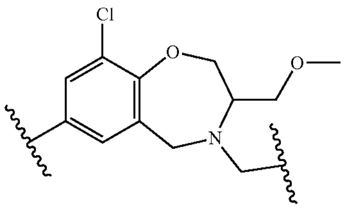 [SMILES: *CN1Cc2cc(*)cc(Cl)c2OCC1COC] |
| 240 | 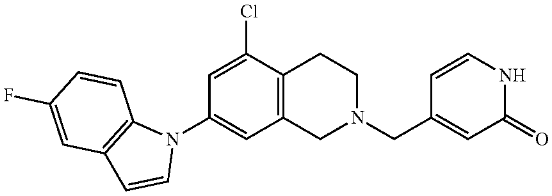 [SMILES: O=c1cc(CN2CCc3c(Cl)cc(-n4ccc5cc(F)ccc54)cc3C2)cc[nH]1] | 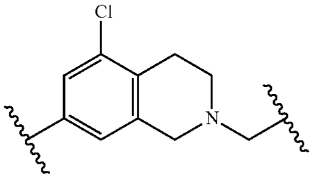 [SMILES: *CN1CCc2c(Cl)cc(*)cc2C1] |
| 241 | 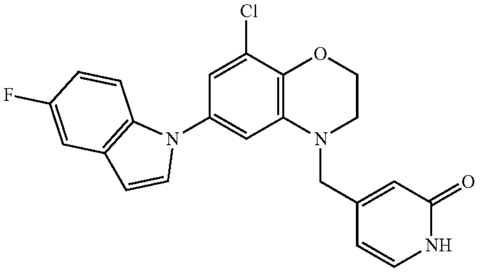 [SMILES: O=c1cc(CN2CCOc3c(Cl)cc(-n4ccc5cc(F)ccc54)cc32)cc[nH]1] | 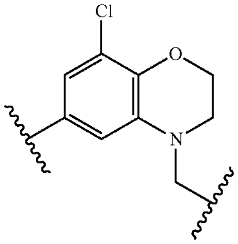 [SMILES: *CN1CCOc2c(Cl)cc(*)cc21] |
| 242 | 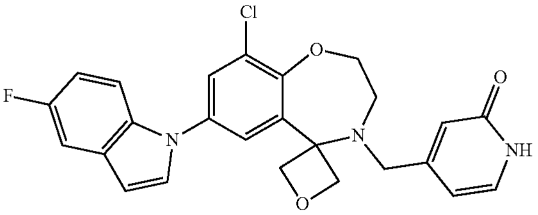 [SMILES: O=c1cc(CN2CCOc3c(Cl)cc(-n4ccc5cc(F)ccc54)cc3C23COC3)cc[nH]1] | 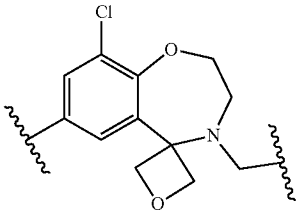 [SMILES: *CN1CCOc2c(Cl)cc(*)cc2C12COC2] |
| 243 | 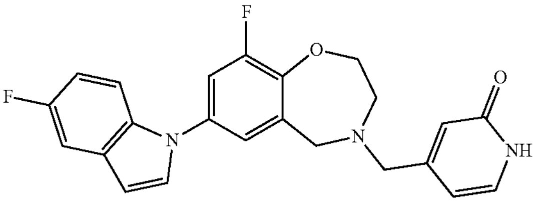 [SMILES: O=c1cc(CN2CCOc3c(F)cc(-n4ccc5cc(F)ccc54)cc3C2)cc[nH]1] | 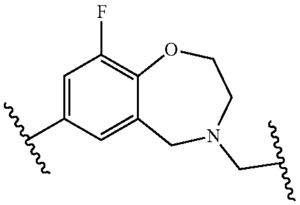 [SMILES: *CN1CCOc2c(F)cc(*)cc2C1] |
| 244 | 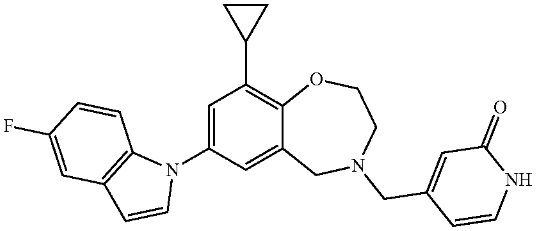 [SMILES: O=c1cc(CN2CCOc3c(cc(-n4ccc5cc(F)ccc54)cc3C3CC3)C2)cc[nH]1] | 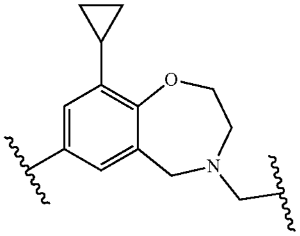 [SMILES: *CN1CCOc2c(cc(*)cc2C2CC2)C1] |

TABLE IX-continued

| ID No. | Structure | 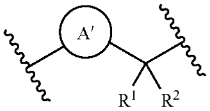 |
|---|---|---|
| 245 | 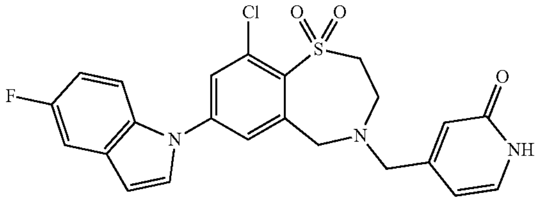 [SMILES: O=c1cc(CN2CCS(=O)(=O)c3c(Cl)cc(-n4ccc5cc(F)ccc54)cc3C2)cc[nH]1] | 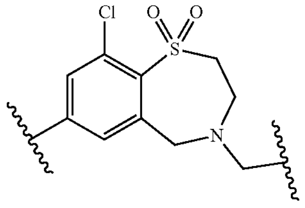 [SMILES: *CN1CCS(=O)(=O)c2c(Cl)cc(*)cc2C1] |
| 248 | 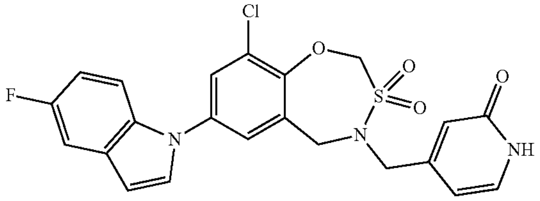 [SMILES: O=c1cc(CN2Cc3cc(-n4ccc5cc(F)ccc54)cc(Cl)c3OCS2(=O)=O)cc[nH]1] | 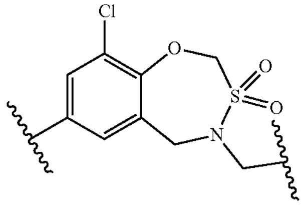 [SMILES: *CN1Cc2cc(*)cc(Cl)c2OCS1(=O)=O] |
| 249 | 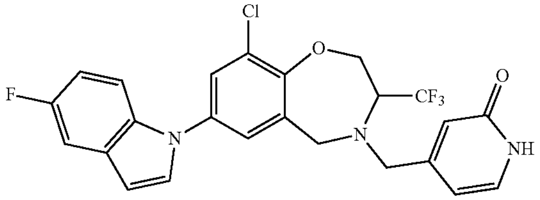 | 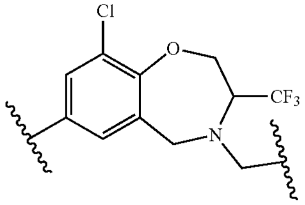 [SMILES: *CN1Cc2cc(*)cc(Cl)c2OCC1C(F)(F)F] |

| ID No. | Structure | 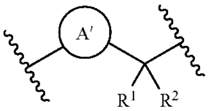 |
|---|---|---|
| 250 | 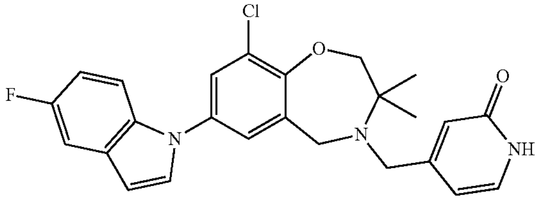 [SMILES: CC1(C)COc2c(Cl)cc(-n3ccc4cc(F)ccc43)cc2CN1Cc1cc[nH]c(=O)c1] | 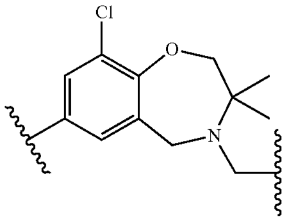 [SMILES: *CN1Cc2cc(*)cc(Cl)c2OCC1(C)C] |

Additional Forms of Compounds

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible, and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. In some instances, a prodrug may pass through membranes (e.g., cell membranes, the intestinal lumen, the blood brain barrier, and the like) whereas the active agent would not. In some instances, a charged or highly polar moiety is masked with a more permeable group which can be cleaved in vivo. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. In some embodiments, the prodrug is enzymatically metabolized to the active form in vivo via an esterase, protease, peptidase, hydrolase, etc. In some embodiments, the prodrug transforms into the active form of the compound independent of a metabolizing enzyme (e.g., via hydrolysis or pH-dependent decomposition).

Prodrugs of the compounds described herein include, but are not limited to, esters, ethers (e.g., oxymethyl ethers), carbonates, thiocarbonates, carbamates, anhydrides, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs. In some embodiments, compounds described herein are prepared as oxymethyl ether or polyoxymethylene dimethyl ether prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

In some embodiments, compounds of the present disclosure provide enhanced pharmacokinetic or pharmacodynamic profiles compared to other known EP2 antagonists. For example, a compound described herein may increase the bioavailability, volume of distribution, absorption, half-life, duration of action, receptor occupancy, cellular permeability, blood-brain barrier permeability, plasma stability, metabolic stability, excretion, or toxicity profile compared to the EP2 antagonists currently available. In some embodiments, a compound is formulated as a prodrug, wherein the active metabolite is cleaved in vivo after reaching the target cell or tissue. In other embodiments, a compound is not cleaved in vivo.

Definitions

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)=$CR_2$, wherein R refers to the remaining portions of the alkenyl group, which may be the same or different. In some embodiments, R is H or an alkyl. Non-limiting examples of an alkenyl group include —CH=$CH_2$, —C($CH_3$)=$CH_2$, —CH=$CHCH_3$, —C($CH_3$)=$CHCH_3$, and —$CH_2$CH=$CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, —C≡$CCH_3$—C≡$CCH_2CH_3$, —$CH_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C^{13}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A “heterocycloalkyl” or “heteroalicyclic” group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_2$-$C_6$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term “bond” or “single bond” refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term “moiety” refers to a specific segment or functional group of a molecule. Chemical moieties are often recognized chemical entities embedded in or appended to a molecule.

The term “optionally substituted” or “substituted” means that the referenced group is optionally substituted with one or more additional group(s) individually and independently selected from halogen, —CN, —$NH_2$, —NH(alkyl), —N(alkyl)$_2$, —OH, —$CO_2$H, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —$NH_2$, —NH($CH_3$), —N($CH_3$)$_2$, —OH, —$CO_2$H, —$CO_2$($C_1$-$C_4$alkyl), —C(=O)$NH_2$, —C(=O)NH($C_1$-$C_4$alkyl), —C(=O)N($C_1$-$C_4$alkyl)$_2$, —S(=O)$_2NH_2$, —S(=O)$_2$NH($C_1$-$C_4$alkyl), —S(=O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(=O)$C_1$-$C_4$alkyl, and —S(=O)$_2C_1$-$C_4$alkyl. In some embodiments, optional substituents are independently selected from halogen, —CN, —$NH_2$, —OH, —NH($CH_3$), —N($CH_3$)$_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (=O).

The term “acceptable” with respect to a formulation, composition or ingredient, as used herein, means having no persistent detrimental effect on the general health of the subject being treated.

The term “modulate” as used herein, means to interact with a target either directly or indirectly so as to alter the activity of the target, including, by way of example only, to enhance the activity of the target, to inhibit the activity of the target, to limit the activity of the target, or to extend the activity of the target.

The term “modulator” as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist.

The terms “administer,” “administering”, “administration,” and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms “co-administration” or the like, as used herein, are meant to encompass administration of the selected therapeutic agents to a single patient, and are intended to include treatment regimens in which the agents are administered by the same or different route of administration or at the same or different time.

The terms “effective amount” or “therapeutically effective amount,” as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an “effective amount” for therapeutic uses is the amount of the composition comprising a compound as disclosed herein required to provide a clinically significant decrease in disease symptoms. An appropriate “effective” amount in any individual case is optionally determined using techniques, such as a dose escalation study.

The terms “enhance” or “enhancing,” as used herein, means to increase or prolong either in potency or duration a desired effect. Thus, with respect to enhancing the effect of therapeutic agents, the term “enhancing” refers to the ability to increase or prolong, either in potency or duration, the effect of other therapeutic agents on a system. An “enhancing-effective amount,” as used herein, refers to an amount adequate to enhance the effect of another therapeutic agent in a desired system.

The term “pharmaceutical combination” as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be performed by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Methods of Dosing and Treatment Regimens

In one embodiment, the compounds of Formula (I) are used in the preparation of medicaments for the treatment or prevention of diseases or conditions that would benefit from or by the reduction or inhibition of EP2 activity. In addition, a method for treating any of the diseases or conditions described herein in a mammal in need of such treatment, involves administration of pharmaceutical compositions that include at least one compound of Formula (I) or Formula (X), or a pharmaceutically acceptable salt, active metabolite, prodrug, or solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

In certain instances, it is appropriate to administer at least one compound of Formula (I) or Formula (X) in combination with another therapeutic agent. In one specific embodiment, a compound of Formula (I) or Formula (X) is co-administered with a second therapeutic agent, wherein the compound of Formula (I) or Formula (X) and the second therapeutic agent modulate different aspects of the disease or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

EXAMPLES

The following examples are provided for illustrative purposes only and not to limit the scope of the claims provided herein.

Compounds described herein are synthesized using standard synthetic techniques or using methods known in the art in combination with methods described herein.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Schemes

Scheme 1. Preparation of 9-chloro-7-(5-fluoroindol-1-yl)(2,2,3,3,5,5-2H6)-4H-1,4-benzoxazepine

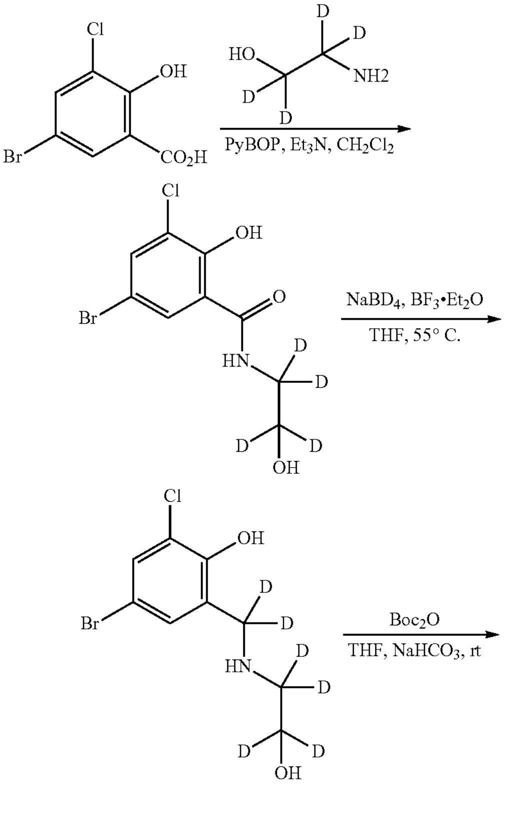

-continued

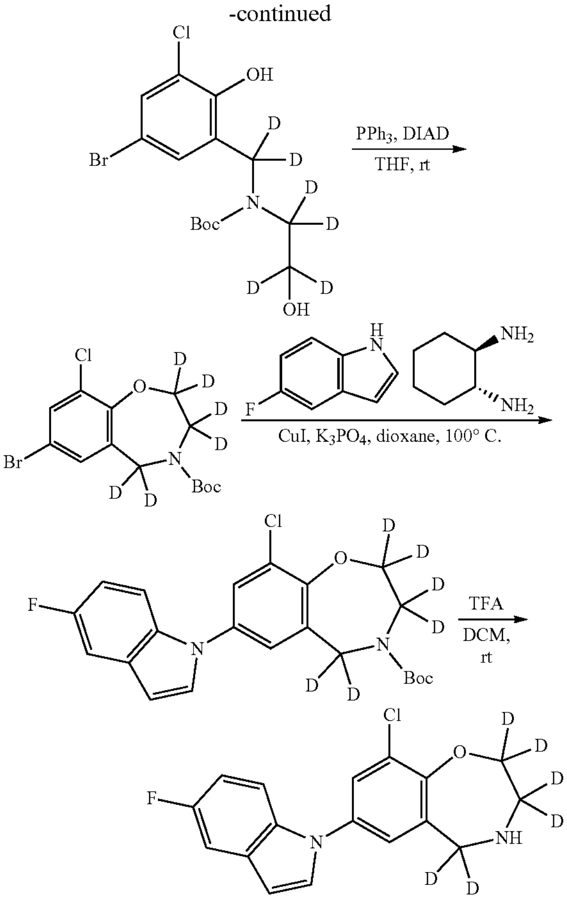

Step 1: Synthesis of 5-bromo-3-chloro-2-hydroxy-N-[2-hydroxy(1,1,2,2-2H4)ethyl]benzamide To a stirred solution of 5-bromo-3-chloro-2-hydroxybenzoic acid (2.5 g, 9.9 mmol) and 2-amino(2H4)ethanol (0.65 g, 9.9 mmol) in DCM (50 mL) were added PyBOP (5.2 g, 9.9 mmol) and $Et_3N$ (2.0 g, 19.9 mmol). The mixture was stirred overnight at rt, then concentrated under reduced pressure and the residue was purified by reverse-phase column chromatography on silican gel: column, C18 silica gel; mobile phase, $CH_3CN$ in 0.05% TFA water, 20% to 70% gradient in 10 min; detector, UV 254 nm to afford 5-bromo-3-chloro-2-hydroxy-N-[2-hydroxy(1,1,2,2-2H4)ethyl]benzamide (1.5 g, 51%) as colorless oil.

Step 2: Synthesis of 4-bromo-2-chloro-6-({[2-hydroxy(1,1,2,2-2H4)ethyl]amino}(2H2)methyl)phenol To a stirred mixture of $NaBD_4$ (1.68 g, 40.190 mmol, 10 equiv) in THF (24 mL) at 0° C. under an atmosphere of $N_2$ was added $BF_3 \cdot Et_2O$ (5.70 g, 40.2 mmol) dropwise. The mixture was stirred for 10 min at 10° C., then 5-bromo-3-chloro-2-hydroxy-N-[2-hydroxy(1,1,2,2-$2H_4$)ethyl]benzamide (1.2 g, 4.0 mmol) dropwise at 0° C. The mixture was heated to 55° C. and stirred overnight, then cooled to rt and MeOH added cautiously. The mixture was concentrated under reduced pressure and the residue was purified by reverse-phase column chromatography: column, C18; mobile phase, $CH_3CN$ in 0.05% TFA water, 10% to 50% gradient in 30 min; detector, UV 220 nm to give 4-bromo-2-chloro-6-({[2-hydroxy(1,1,2,2-2H4)ethyl]amino}(2H2)methyl)phenol (500 mg, 43%) as an oil.

Step 3: Synthesis of tert-butyl N-[(5-bromo-3-chloro-2-hydroxyphenyl)(2H2)methyl]-N-[2-hydroxy(1,1,2,2-$2H_4$)ethyl]carbamate To a stirred solution of 4-bromo-2-chloro-6-({[2-hydroxy(1,1,2,2-2H4)ethyl]amino}(2H2)methyl)phenol (550 mg, 1.9 mmol) in THE (10 mL) and saturated aqueous $NaHCO_3$ (5 mL) was added $(Boc)_2O$ (500 mg, 2.3 mmol). The mixture was stirred at rt for 16 h at rt, then extracted with EtOAc (3×10 mL). The combined organic layers were washed with brine (10 mL), dried over $Na_2SO_4$, filtered and the filtrate was concentrated under reduced pressure. The residue was purified by reverse-phase column chromatography: column, C18; mobile phase, $CH_3CN$ in 0.05% TFA water, 30% to 90% gradient in 90 min; detector, UV 220 nm to give tert-butyl N-[(5-bromo-3-chloro-2-hydroxyphenyl)(2H2)methyl]-N-[2-hydroxy(1,1,2,2-2H4)ethyl]carbamate (300 mg, 40%) as a solid.

Step 4: Synthesis of Tert-butyl 7-bromo-9-chloro(2,2,3,3,5,5-2H6)-1,4-benzoxazepine-4-carboxylate To a stirred solution of tert-butyl N-[(5-bromo-3-chloro-2-hydroxyphenyl)(2H2)methyl]-N-[2-hydroxy(1,1,2,2-2H4)ethyl]carbamate (500 mg, 1.29 mmol) and $PPh_3$ (850 mg, 3.23 mmol) in THE (5 mL) at rt under an atmosphere of $N_2$ was added DIAD (650 mg, 3.23 mmol) dropwise. The mixture was stirred at rt for 2 h, then concentrated under reduced pressure and the residue was purified by reverse-phase column chromatography: column, C18 silica gel; mobile phase, $CH_3CN$ in 0.05% TFA water, 20% to 70% gradient in 30 min; detector, UV 220 nm to give tert-butyl 7-bromo-9-chloro(2,2,3,3,5,5-2H6)-1,4-benzoxazepine-4-carboxylate (340 mg, 71%) as a solid.

Step 5: Synthesis of Tert-butyl 9-chloro-7-(5-fluoroindol-1-yl)(2,2,3,3,5,5-2H6)-1,4-benzoxazepine-4-carboxylate To a stirred solution of tert-butyl 7-bromo-9-chloro(2,2,3,3,5,5-2H6)-1,4-benzoxazepine-4-carboxylate (300 mg, 0.81 mmol) and 5-fluoro-1H-indole (170 mg, 1.22 mmol) in 1,4-dioxane (10 mL) at rt under an atmosphere of $N_2$ were added CuI (50 mg, 0.24 mmol), $K_3PO_4$ (520 mg, 2.4 mmol) and trans-cyclohexane-1,2-diamine (50 mg, 0.41 mmol). The mixture was stirred at rt for 16 h, then concentrated under reduced pressure and the residue was purified by reverse-phase column chromatography (column, C18 silica gel; mobile phase, $CH_3CN$ in 0.05% TFA water, 40% to 90% gradient in 30 min; detector, UV 220 nm to give tert-butyl 9-chloro-7-(5-fluoroindol-1-yl)(2,2,3,3,5,5-2H6)-1,4-benzoxazepine-4-carboxylate (240 mg, 70%) as a solid.

Step 6: Synthesis of 9-chloro-7-(5-fluoroindol-1-yl)(2,2,3,3,5,5-2H6)-4H-1,4-benzoxazepine To a stirred solution of tert-butyl 9-chloro-7-(5-fluoroindol-1-yl)(2,2,3,3,5,5-2H6)-1,4-benzoxazepine-4-carboxylate (120 mg, 0.28 mmol) in DCM (5 mL) was added TFA (1 mL). The mixture was stirred for 30 min at rt, then neutralized with saturated aqueous $NaHCO_3$ and extracted with DCM (3×5 mL). The combined organic layers were washed with brine (10 mL), dried over $Na_2SO_4$, filtered and the filtrate was concentrated under reduced pressure to give crude 9-chloro-7-(5-fluoroindol-1-yl)(2,2,3,3,5,5-2H6)-4H-1,4-benzoxazepine (100 mg, crude) as a solid. The solid was used for next step without further purification.

Scheme 2. Preparation of 5-chloro-7-(5-fluoroindol-1-yl)-1,2,3,4-tetrahydroisoquinoline

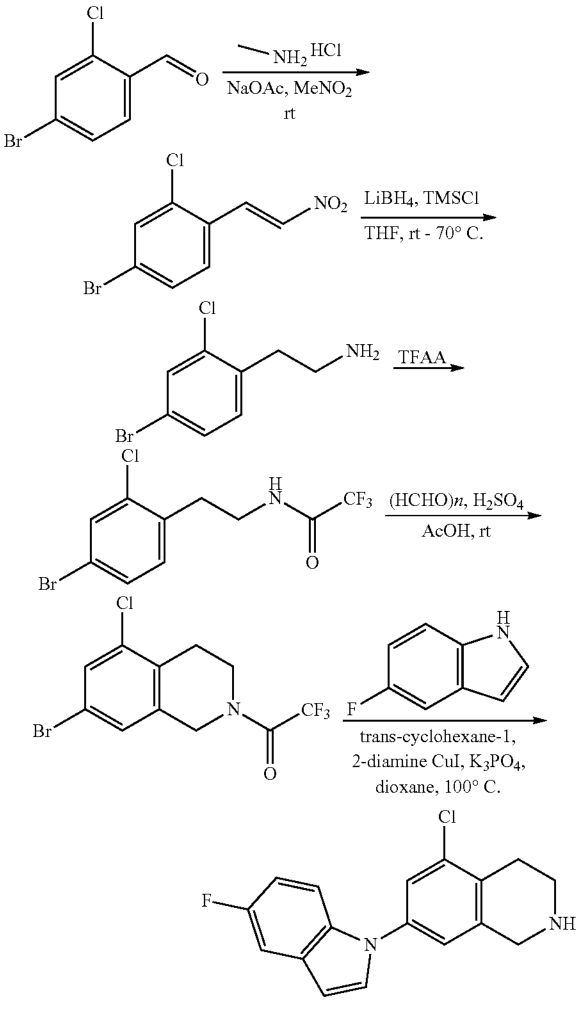

Step 1: Synthesis of 4-Bromo-2-chloro-1-(2-nitrovinyl)benzene

A mixture of 4-bromo-2-chlorobenzaldehyde (6.60 g, 30.1 mmol), $MeNH_2$·HCl (1.30 g, 19.3 mmol) and NaOAc (1.58 g, 19.3 mmol) in $MeNO_2$ (12 mL) was stirred at rt for 16 h. $H_2O$ (50 mL) was added and the mixture was extracted with DCM (50 mL×2). The combined organic layers were dried over $Na_2SO_4$, filtered and the filtrate was concentrated under reduced pressure. The residue was purified by reverse phase chromatography: column, silica gel; mobile phase, MeCN in water, 10% to 50% gradient in 10 min; detector, UV 254 nm to afford 4-bromo-2-chloro-1-(2-nitrovinyl) benzene (3.80 g, 41%) as an oil.

Step 2: Synthesis of 2-(4-Bromo-2-chlorophenyl)ethanamine

To a stirred solution of $LiBH_4$ (1.26 g, 57.9 mmol) in THE (30 mL) at rt was added TMSCl (12.58 g, 115.8 mmol) dropwise over 2 minutes. After stirring for 20 min, the mixture was sparged with $N_2$ to remove trimethylsilane that had formed. A solution of 4-bromo-2-chloro-1-[(E)-2-nitroethenyl]benzene (3.80 g, 14.5 mmol) in THE (20 mL) was added dropwise at rt over 4 min. The resulting mixture was heated to 70° C. and stitred for 2 h, then concentrated under reduced pressure to afford 2-(4-bromo-2-chlorophenyl)ethanamine (4.4 g, crude) as an oil.

Step 3: Synthesis of N-[2-(4-bromo-2-chlorophenyl) ethyl]-2,2,2-trifluoroacetamide A mixture of 2-(4-bromo-2-chlorophenyl)ethanamine (4.4 g, 18.8 mmol) in TFAA (12 mL) was stirred for 30 min at rt, then concentrated under reduced pressure. The residue was purified by column chromatography on silica gel (PE/EtOAc, 15:1) to afford N-[2-(4-bromo-2-chlorophenyl) ethyl]-2,2,2-trifluoroacetamide (2.0 g, 32%).

Step 4: Synthesis of 1-(7-Bromo-5-chloro-3,4-dihydro-1H-isoquinolin-2-yl)-2,2,2-trifluoroethanone A mixture of N-[2-(4-bromo-2-chlorophenyl)ethyl]-2,2,2-trifluoroacetamide (1.00 g, 3.0 mmol) and paraformaldehyde (0.44 g, 4.8 mmol) in AcOH (5 mL) at rt was added $H_2SO_4$ (7.5 mL) dropwise over 3 min. The mixture was stirred at rt for 8 h, then neutralized with saturated aq. $NaHCO_3$ and extracted with EtOAc (3×50 mL). The combined organic layers were washed with $H_2O$ (50 mL), brine (50 mL), dried over anhydrous $Na_2SO_4$ and filtered. The filtrate was concentrated under reduced pressure and the residue was purified by column chromatography on silica gel (PE/EtOAc, 15:1) to afford 1-(7-bromo-5-chloro-3,4-dihydro-1H-isoquinolin-2-yl)-2,2,2-trifluoroethanone (2.2 g, crude) as an oil.

Step 5: Synthesis of 5-Chloro-7-(5-fluoroindol-1-yl)-1,2,3,4-tetrahydroisoquinoline To a stirred solution of 1-(7-bromo-5-chloro-3,4-dihydro-1H-isoquinolin-2-yl)-2,2,2-trifluoroethanone (600 mg, 1.75 mmol), 5-fluoro-1H-indole (360 mg, 2.62 mmol) in 1,4-dioxane (10 mL) under an atmosphere of $N_2$ were added $K_3PO_4$ (1.1 g, 5.26 mmol), CuI (100 mg, 0.53 mmol) and trans-cyclohexane-1,2-diamine (100 mg, 0.88 mmol). The mixture was heated to 110° C. and stirred for 16 h, then filtered and the filtrate was concentrated under reduced pressure. The residue was purified by silica gel column chromatography (DCM/MeOH, 10:1) to afford 5-chloro-7-(5-fluoroindol-1-yl)-1,2,3,4-tetrahydroisoquinoline (400 mg, 76%) as a solid.

Scheme 3 Preparation of 9-chloro-7-(5-fluoroindol-1-yl)-4,5-dihydro-2H-spiro[1,4-benzoxazepine-3,1'-cyclopropane]

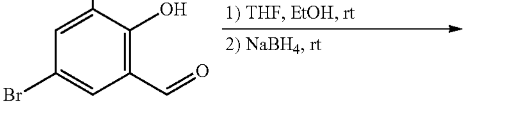

-continued

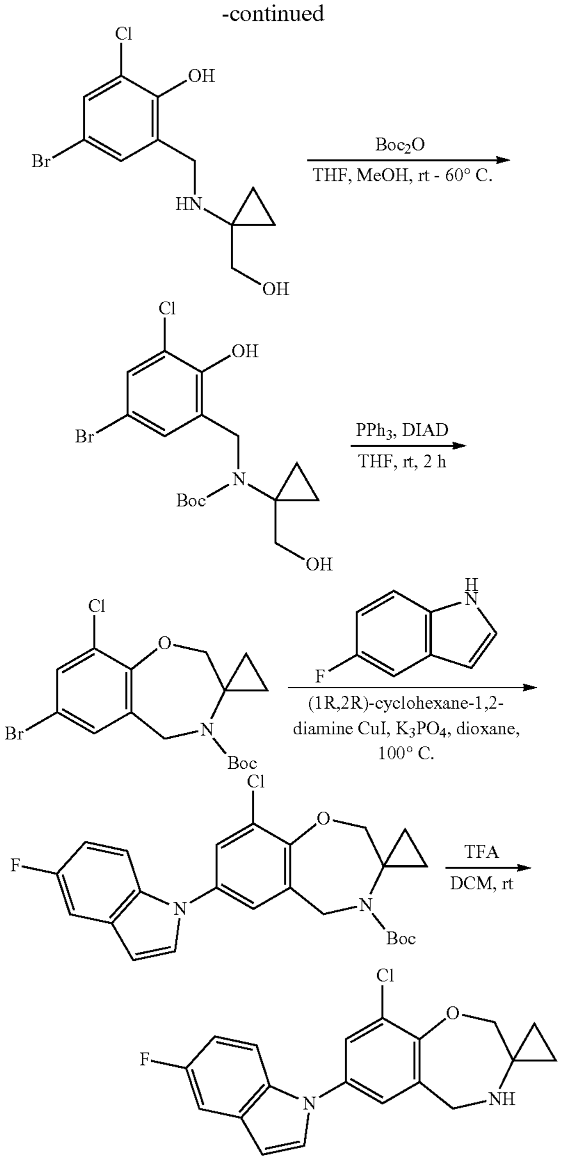

Step 1: Synthesis of 4-Bromo-2-chloro-6-(((1-(hydroxymethyl)cyclopropyl)amino)methyl)phenol A mixture of 5-bromo-3-chloro-2-hydroxybenzaldehyde (1.5 g, 6.4 mmol) and (1-aminocyclopropyl)methanol (0.67 g, 7.7 mmol) in THE (10 mL) and EtOH (10 mL) was stirred for 10 min at rt. To the above mixture was added $NaBH_4$ (0.14 g, 3.8 mmol) and the mixture was stirred at rt for 2 h, then diluted with $H_2O$ (10 mL) and aq. $NH_4Cl$ (15 mL). The emerging precipitate was collected by filtration, and dried under vacuum to give 4-bromo-2-chloro-6-({[1-(hydroxymethyl)cyclopropyl]amino}methyl)phenol (1.7 g, 87%) as a solid.

Step 2: Synthesis of Tert-butyl (5-bromo-3-chloro-2-hydroxybenzyl)(1-(hydroxymethyl)cyclopropyl) carbamate To a stirred mixture of 4-bromo-2-chloro-6-({[1-(hydroxymethyl)cyclopropyl]amino}methyl)phenol (2.0 g, 6.5 mmol) and $Boc_2O$ (1.71 g, 7.8 mmol) in THE (10 mL) and MeOH (10 mL) were added $Et_3N$ (0.99 g, 9.8 mmol). The mixture was heated to 60° C. and stirred for 2 days, then concentrated under reduced pressure and the residue was purified by reverse phase chromatography: C18; mobile phase, MeCN in water, 30% to 100% gradient in 30 min; detector, UV 220 nm to afford tert-butyl N-[(5-bromo-3-chloro-2-hydroxyphenyl)methyl]-N-[1-(hydroxymethyl)cyclopropyl]carbamate (700 mg, 26%) as an oil.

Step 3: Synthesis of Tert-butyl 7-bromo-9-chloro-2H-spiro[benzo[f][1,4]oxazepine-3,1'-cyclopropane]-4(5H)-carboxylate To a stirred solution of tert-butyl N-[(5-bromo-3-chloro-2-hydroxyphenyl)methyl]-N-[1-(hydroxymethyl) cyclopropyl]carbamate (600 mg, 1.48 mmol) and $PPh_3$ (780 mg, 2.95 mmol) in THE (10 mL) at rt under an atmosphere of $N_2$ was added DIAD (600 mg, 2.95 mmol) dropwise. The mixture was stirred at rt for 2 h, then concentrated under reduced pressure and the residue was purified by trituration with MeOH (3 mL) and filtered to give tert-butyl 7-bromo-9-chloro-2,5-dihydrospiro[1,4-benzoxazepine-3,1'-cyclopropane]-4-carboxylate (380 mg, 66%) as a solid.

Step 4: Synthesis of Tert-butyl 9-chloro-7-(5-fluoro-1H-indol-1-yl)-2H-spiro[benzo[f][1,4]oxazepine-3,1'-cyclopropane]-4(5H)-carboxylate A mixture of tert-butyl 7-bromo-9-chloro-2,5-dihydrospiro[1,4-benzoxazepine-3,1'-cyclopropane]-4-carboxylate (450 mg, 1.16 mmol), 5-fluoro-1H-indole (235 mg, 1.74 mmol), $K_3PO_4$ (740 mg, 3.47 mmol), CuI (67 mg, 0.35 mmol) and trans-cyclohexane-1,2-diamine (67 mg, 0.58 mmol) in 1,4-dioxane (15 mL) under an atmosphere of $N_2$ was heated to 100° C. and stirred overnight. The mixture was filtered, the filtrate was concentrated under reduced pressure and the residue was purified by silica gel column chromatography (DCM/MeOH, 10:1) to afford tert-butyl 9-chloro-7-(5-fluoroindol-1-yl)-2,5-dihydrospiro[1,4-benzoxazepine-3,1'-cyclopropane]-4-carboxylate (300 mg, 59%) as a solid.

Step 5: Synthesis of 9-chloro-7-(5-fluoro-1H-indol-1-yl)-4,5-dihydro-2H-spiro[benzo[f][1,4]oxazepine-3,1'-cyclopropane]

A mixture of tert-butyl 9-chloro-7-(5-fluoroindol-1-yl)-2,5-dihydrospiro[1,4-benzoxazepine-3,1'-cyclopropane]-4-carboxylate (300 mg, 0.68 mmol) in DCM (2 mL) was added TFA (0.4 mL). The mixture was stirred at rt overnight, then neutralized with saturated aqueous $NaHCO_3$ and extracted with EtOAc (3×5 mL). The combined organic layers were dried over anhydrous $MgSO_4$, filtered and the filtrate was concentrated under reduced pressure to afford 9-chloro-7-(5-fluoroindol-1-yl)-4,5-dihydro-2H-spiro[1,4-benzoxazepine-3,1'-cyclopropane] (200 mg, 86%) as a solid.

Scheme 4 Preparation of 5-[(7-bromo-9-chloro-3,5-dihydro-2H-1,4-benzoxazepin-4-yl)methyl]pyrimidin-2-ol

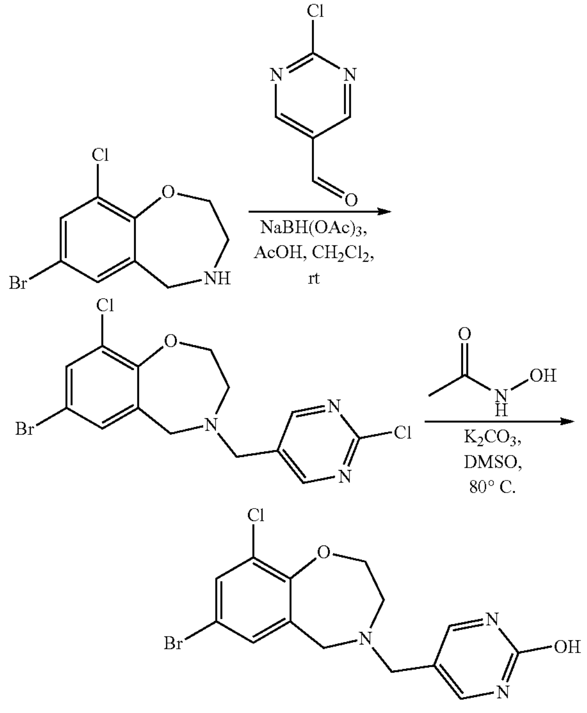

Step 1: Synthesis of 7-bromo-9-chloro-4-[(2-chloropyrimidin-5-yl)methyl]-3,5-dihydro-2H-1,4-benzoxazepine To a stirred solution of 2-chloropyrimidine-5-carbaldehyde (3.58 g, 25.1 mmol) and 7-bromo-9-chloro-2,3,4,5-tetrahydro-1,4-benzoxazepine (6.6 g, 25.1 mmol) in DCM (50 mL) was added AcOH (6.6 mL, 115.2 mmol) and $NaBH(OAc)_3$ (10.66 g, 50.3 mmol). The mixture was stirred at rt for 16 h, then neutralized with saturated sat. aq. $NaHCO_3$ and extracted with DCM (3x30 mL). The combined organic layers were washed with brine (2x30 mL), dried over anhydrous $MgSO_4$, filtered and the filtrate was concentrated under reduced pressure. The residue was purified by silica gel column chromatography (PE/EtOAc, 1:1) to afford 7-bromo-9-chloro-4-[(2-chloropyrimidin-5-yl)methyl]-3,5-dihydro-2H-1,4-benzoxazepine (3.5 g, 36%) as a solid.

Step 2: Synthesis of 5-[(7-bromo-9-chloro-3,5-dihydro-2H-1,4-benzoxazepin-4-yl)methyl]pyrimidin-2-ol To a stirred solution of 7-bromo-9-chloro-4-[(2-chloropyrimidin-5-yl)methyl]-3,5-dihydro-2H-1,4-benzoxazepine (4.4 g, 11.3 mmol) in DMSO (50 mL) at rt was added acetohydroxamic acid (2.55 g, 33.9 mmol) and $K_2CO_3$ (7.81 g, 56.6 mmol). The mixture was heated to 80° C. and for 3 h, then filtered, and the filter cake was washed with EtOAc (3x30 mL). $H_2O$ (150 mL) was added to the filtrate, and the mixture was extracted with EtOAc (3x100 mL). The combined organic layers were washed with brine (150 mL), dried over anhydrous $Na_2SO_4$, filtered and the filtrate was concentrated under reduced pressure. The residue was purified by silica gel column chromatography (DCM/MeOH, 10:1) to afford 5-[(7-bromo-9-chloro-3,5-dihydro-2H-1,4-benzoxazepin-4-yl)methyl]pyrimidin-2-ol (3.1 g, 74%) as a solid.

Scheme 5 Preparation of 7-bromo-9-chloro-4-[(2-methoxypyrimidin-5-yl)methyl]-3,5-dihydro-2H-1,4-benzoxazepine

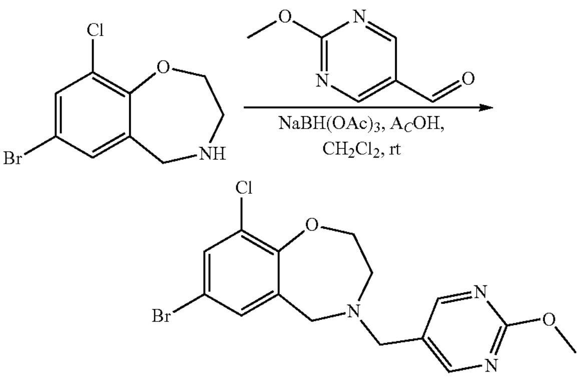

To a stirred solution of 7-bromo-9-chloro-2,3,4,5-tetrahydro-1,4-benzoxazepine (3.7 g, 14.1 mmol) and 2-methoxypyrimidine-5-carbaldehyde (2.34 g, 16.9 mmol) in DCM (50 mL) was added AcOH (4.04 mL, 70.5 mmol) and $NaBH(OAc)_3$ (5.97 g, 28.2 mmol). The mixture was stirred at rt for 16 h, then neutralized with saturated sat. aq. $NaHCO_3$ and extracted with DCM (3x30 mL). The combined organic layers were washed with brine (2x30 mL), dried over anhydrous $MgSO_4$, filtered, and the filtrate was concentrated under reduced pressure. The residue was purified by silica gel column chromatography (PE/EtOAc, 1:1) to afford 7-bromo-9-chloro-4-[(2-methoxypyrimidin-5-yl)methyl]-3,5-dihydro-2H-1,4-benzoxazepine (4 g, 74%) as an solid.

Scheme 6 Preparation of 9-chloro-7-(5-fluoroindol-1-yl)-5-methyl-2,3,4,5-tetrahydro-1,4-benzoxazepine

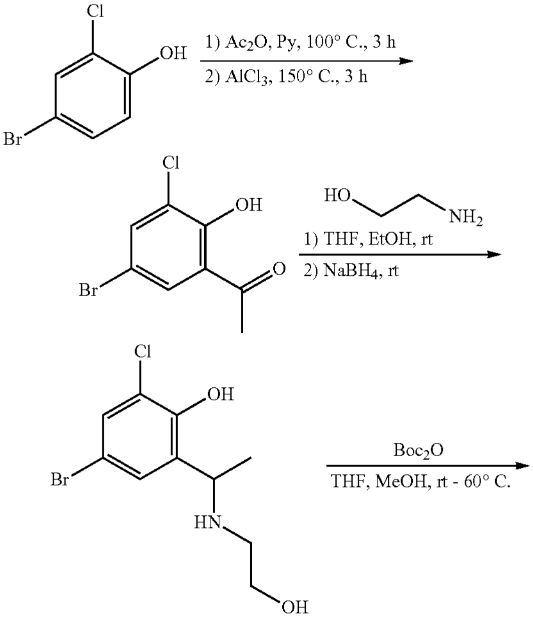

-continued

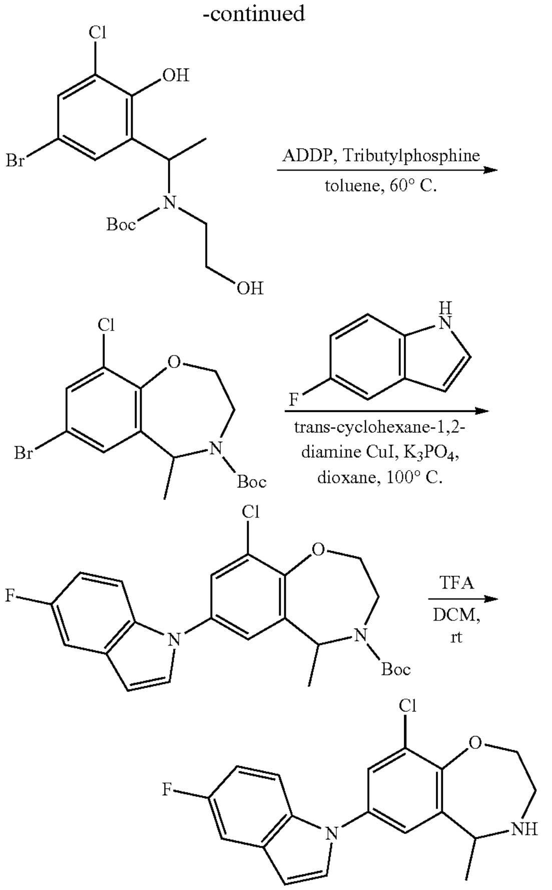

Step 1: Synthesis of 1-(5-Bromo-3-chloro-2-hydroxyphenyl)ethanone

A stirred solution of 4-bromo-2-chlorophenol (6.0 g, 28.9 mmol) and $Ac_2O$ (13.4 g, 131.3 mmol) in pyridine (10 mL) was heated to 100° C. and stirred for 3 h, then cooled to ambient temperature and poured into 6M HCl (50 mL). The mixture was extracted with EtOAc (3x20 mL), and the combined organic layers were washed with sat. aq. $NaHCO_3$ (3x20 ml), dried over $Na_2SO_4$ and filtered. The filtrate was concentrated under reduced pressure, then $AlCl_3$ (5.87 g, 44.0 mmol) added and the mixture heated at 150° C. for 3 h under an atmosphere of $N_2$. Crashed ice (20 g) was slowly added and the mixture was extracted with EtOAc (3x20 mL). The combined organic phases were washed with brine (20 mL), dried over $Na_2SO_4$, filtered and concentrated under reduced pressure. The residue was purified by trituration with MeOH (30 mL) to afford 1-(5-bromo-3-chloro-2-hydroxyphenyl)ethanone (3.2 g, 43%) as a solid.

Step 2: Synthesis of 4-Bromo-2-chloro-6-{1-[(2-hydroxyethyl)amino]ethyl}phenol

To a mixture of 1-(5-bromo-3-chloro-2-hydroxyphenyl) ethanone (1.0 g, 4.0 mmol) in EtOH (10 mL) and THF (10 mL) was added ethanolamine (489 mg, 8.0 mmol). The mixture was stirred at rt for 5 min, then $NaBH_4$ (75 mg, 2.0 mmol) added and the mixture stirred at rt for 1 h, then concentrated under reduced pressure. $H_2O$ (10 mL) and sat. aq. $NH_4Cl$ (30 mL) were added to the residue and the emerging precipitate was collected by filtration to afford 4-bromo-2-chloro-6-{1-[(2-hydroxyethyl)amino]ethyl} phenol (1 g, 85%) as a solid.

Step 3: Synthesis of Tert-butyl N-[1-(5-bromo-3-chloro-2-hydroxyphenyl)ethyl]-N-(2-hydroxyethyl) carbamate To a mixture of 4-bromo-2-chloro-6-{1-[(2-hydroxyethyl)amino]ethyl}phenol (2.7 g, 9.2 mmol) in THF (20 mL) and MeOH (5 mL) was added $Boc_2O$ (2.4 g, 11 mmol) and $Et_3N$ (2.7 g, 27.5 mmol). The mixture was heated to 45° C. and stirred for 48 h, then concentrated under reduced pressure and the residue was purified by reverse-phase column chromatography (column, C18 silica gel; mobile phase, ACN in water (0.05% TFA), 50% to 100% gradient in 30 min; detector, UV 254 nm) to afford tert-butyl N-[1-(5-bromo-3-chloro-2-hydroxyphenyl)ethyl]-N-(2-hydroxyethyl)carbamate (330 mg, 9%) as an oil.

Step 4: Synthesis of Tert-butyl 7-bromo-9-chloro-5-methyl-3,5-dihydro-2H-1,4-benzoxazepine-4-carboxylate To a mixture of tert-butyl N-[1-(5-bromo-3-chloro-2-hydroxyphenyl)ethyl]-N-(2-hydroxyethyl)carbamate (240 mg, 0.61 mmol) in toluene (5 mL) under an atmosphere of $N_2$ was added $Bu_3P$ (307 mg, 1.52 mmol) and ADDP (380 mg, 1.52 mmol). The mixture was heated to 60° C. and stirred for 16 h, then concentrated under reduced pressure and the residue was purified by reverse-phase column chromatography (column, C18 silica gel; mobile phase, ACN in water (0.05% TFA), 50% to 100% gradient in 30 min; detector, UV 254 nm) to afford tert-butyl 7-bromo-9-chloro-5-methyl-3,5-dihydro-2H-1,4-benzoxazepine-4-carboxylate (200 mg, 87%) as an oil.

Step 5: Synthesis of Tert-butyl 9-chloro-7-(5-fluoroindol-1-yl)-5-methyl-3,5-dihydro-2H-1,4-benzoxazepine-4-carboxylate To a mixture of tert-butyl 7-bromo-9-chloro-5-methyl-3,5-dihydro-2H-1,4-benzoxazepine-4-carboxylate (180 mg, 0.48 mmol), 5-fluoro-1H-indole (96 mg, 0.72 mmol), $K_3PO_4$ (304 mg, 1.43 mmol) in 1,4-dioxane (5 mL) was added trans-cyclohexane-1,2-diamine (27 mg, 0.24 mmol). The mixture was heated to 100° C. and stirred for 3 h, then filtered, and the filter cake was washed with MeOH (10 mL). The filtrate was concentrated under reduced pressure and the residue was purified by reverse-phase column chromatography (column, C18 silica gel; mobile phase, ACN in water (0.05% TFA), 50% to 100% gradient in 20 min; detector, UV 254 nm) to afford tert-butyl 9-chloro-7-(5-fluoroindol-1-yl)-5-methyl-3,5-dihydro-2H-1,4-benzoxazepine-4-carboxylate (140 mg, 68%) as an oil.

Step 6: Synthesis of 9-Chloro-7-(5-fluoroindol-1-yl)-5-methyl-2,3,4,5-tetrahydro-1,4-benzoxazepine To a mixture of tert-butyl 9-chloro-7-(5-fluoroindol-1-yl)-5-methyl-3,5-dihydro-2H-1,4-benzoxazepine-4-carboxylate (120 mg, 0.28 mmol) in DCM (2 mL) was added TFA (0.4 mL). The mixture was stirred at rt for 1 h, then aq. $NaHCO_3$ (2 mL) added and the mixture was extracted with DCM (3 mLx3). The combined organic layers were dried over $Na_2SO_4$, filtered and concentrated under reduced pressure to afford 9-chloro-7-(5-fluoroindol-1-yl)-5-methyl-2,3,4,5-tetrahydro-1,4-benzoxazepine (100 mg, crude) as an oil.

Scheme 7 Preparation of (3R)-9-chloro-7-(5-fluoroindol-1-yl)-3-methyl-2,3,4,5-tetrahydro-1,4-benzoxazepine

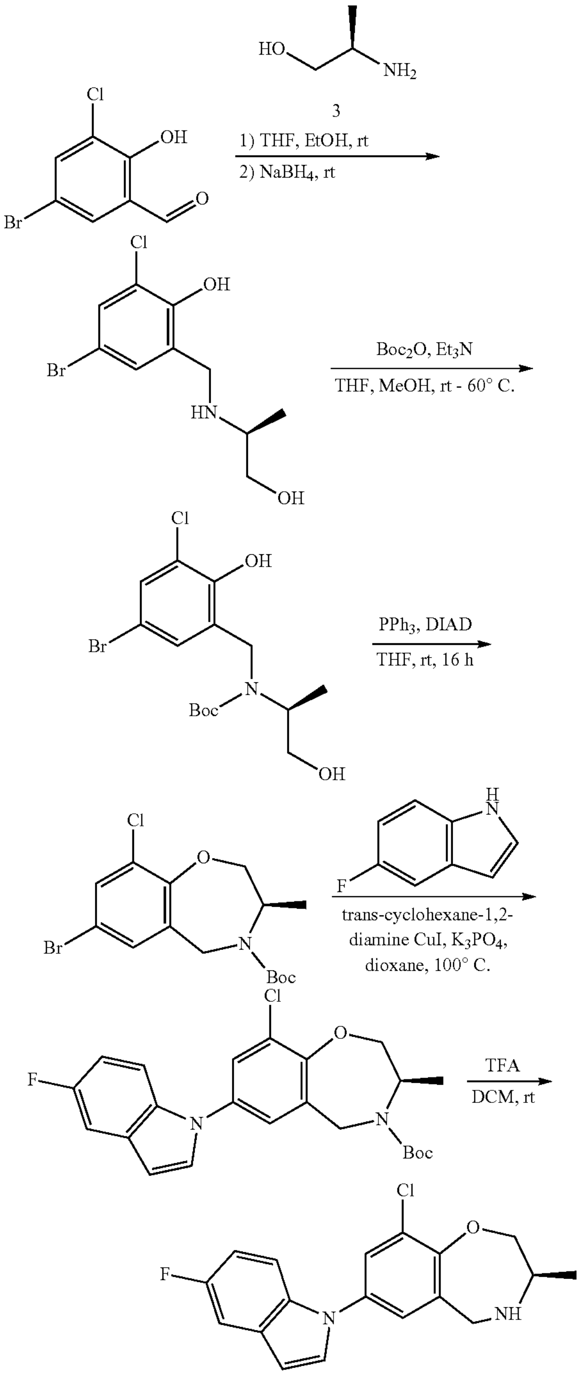

8

Step 1: Synthesis of 4-bromo-2-chloro-6-({[(2R)-1-hydroxypropan-2-yl]amino}methyl)phenol To a mixture of 5-bromo-3-chloro-2-hydroxybenzaldehyde (CAS No: 19652-33-6) (5.0 g, 21.2 mmol) in THF (25 mL) and EtOH (25 mL) at rt was added (2R)-1-aminopropan-2-ol (2.07 g, 27.6 mmol). The resulting mixture was stirred at rt for 10 min, then $NaBH_4$ (0.5 g, 13.2 mmol) was added. The mixture was concentrated under reduced pressure and the residue was diluted with $H_2O$ (30 mL) and $NH_4Cl$ (20 mL). The precipitated solids were collected by filtration and washed with $H_2O$ (2×50 mL) and dried under vacuum to afford 4-bromo-2-chloro-6-({[(2R)-1-hydroxypropan-2-yl]amino}methyl)phenol (4.0 g, 64%) as a solid.

Step 2: Synthesis of Tert-butyl N-[(5-bromo-3-chloro-2-hydroxyphenyl)methyl]-N-[(2S)-1-hydroxypropan-2-yl]carbamate A mixture of 4-bromo-2-chloro-6-({[(2S)-1-hydroxypropan-2-yl]amino}methyl)phenol (4.0 g, 13.6 mmol), $Et_3N$ (2.75 g, 27.158 mmol) and $Boc_2O$ (4.45 g, 20.4 mmol) in THF (4 mL) and MeOH (1 mL) at rt was stirred overnight. The mixture was concentrated under reduced pressure and the residue was purified by silica gel column chromatography (PE/EtOAc, 10:1) to afford tert-butyl N-[(5-bromo-3-chloro-2-hydroxyphenyl)methyl]-N-[(2S)-1-hydroxypropan-2-yl]carbamate (3.8 g, 71%) as a solid.

Step 3: Synthesis of Tert-butyl (3R)-7-bromo-9-chloro-3-methyl-3,5-dihydro-2H-1,4-benzoxazepine-4-carboxylate To a stirred solution of tert-butyl N-[(5-bromo-3-chloro-2-hydroxyphenyl)methyl]-N-[(2S)-1-hydroxypropan-2-yl] carbamate (3.8 g, 9.6 mmol) and $PPh_3$ (5.05 g, 19.3 mmol) in THF (40 mL) at rt under an atmosphere of $N_2$ was added DIAD (2.86 mL, 14.4 mmol) dropwise. The resulting mixture was stirred at rt overnight, then concentrated under reduced pressure and the residue was purified by silica gel column chromatography (PE/EtOAc, 10:1) to afford tert-butyl (3R)-7-bromo-9-chloro-3-methyl-3,5-dihydro-2H-1,4-benzoxazepine-4-carboxylate (3.5 g, 97%) as a solid.

Step 4: Synthesis of Tert-butyl (3R)-9-chloro-7-(5-fluoroindol-1-yl)-3-methyl-3,5-dihydro-2H-1,4-benzoxazepine-4-carboxylate To a stirred solution of tert-butyl (3R)-7-bromo-9-chloro-3-methyl-3,5-dihydro-2H-1,4-benzoxazepine-4-carboxylate (3.5 g, 9.3 mmol) and 5-fluoro-1H-indole (1.51 g, 11.2 mmol) in 1,4-dioxane (40 mL) at rt under an atmosphere of $N_2$ were added trans-cyclohexane-1,2-diamine (0.53 g, 4.7 mmol), CuI (0.53 g, 2.8 mmol) and $K_3PO_4$ (5.92 g, 27.9 mmol). The mixture was heated to 100° C. and stirred for 16 h, then filtered, and the filter cake was washed with DCM (2×20 mL). The filtrate was concentrated under reduced pressure and the residue was purified by silica gel column chromatography (PE/EtOAc, 10:1) to afford tert-butyl (3R)-9-chloro-7-(5-fluoroindol-1-yl)-3-methyl-3,5-dihydro-2H-1,4-benzoxazepine-4-carboxylate (1.5 g, 38%) as a solid.

Step 5: Synthesis of (3R)-9-chloro-7-(5-fluoroindol-1-yl)-3-methyl-2,3,4,5-tetrahydro-1,4-benzoxazepine To a stirred solution of tert-butyl (3R)-9-chloro-7-(5-fluoroindol-1-yl)-3-methyl-3,5-dihydro-2H-1,4-benzoxazepine-4-carboxylate (1.5 g, 3.5 mmol) in DCM (20 mL) was added TFA (6.0 mL, 80.8 mmol). The mixture was stirred at rt for 30 min, then neutralized with saturated aq. $NaHCO_3$ and extracted with DCM (3×100 mL). The combined organic layers were washed with brine (100 mL), dried over anhydrous $MgSO_4$, filtered and the filtrate was concentrated under reduced pressure to afford (3R)-9- chloro-7-(5-fluoroindol-1-yl)-3-methyl-2,3,4,5-tetrahydro-1,4-benzoxazepine (700 mg, 60%) as a solid.

Scheme 8 Preparation of 9-chloro-7-(5-fluoroindol-1-yl)-3-(methoxymethyl)-2,3,4,5-tetrahydro-1,4-benzoxazepine

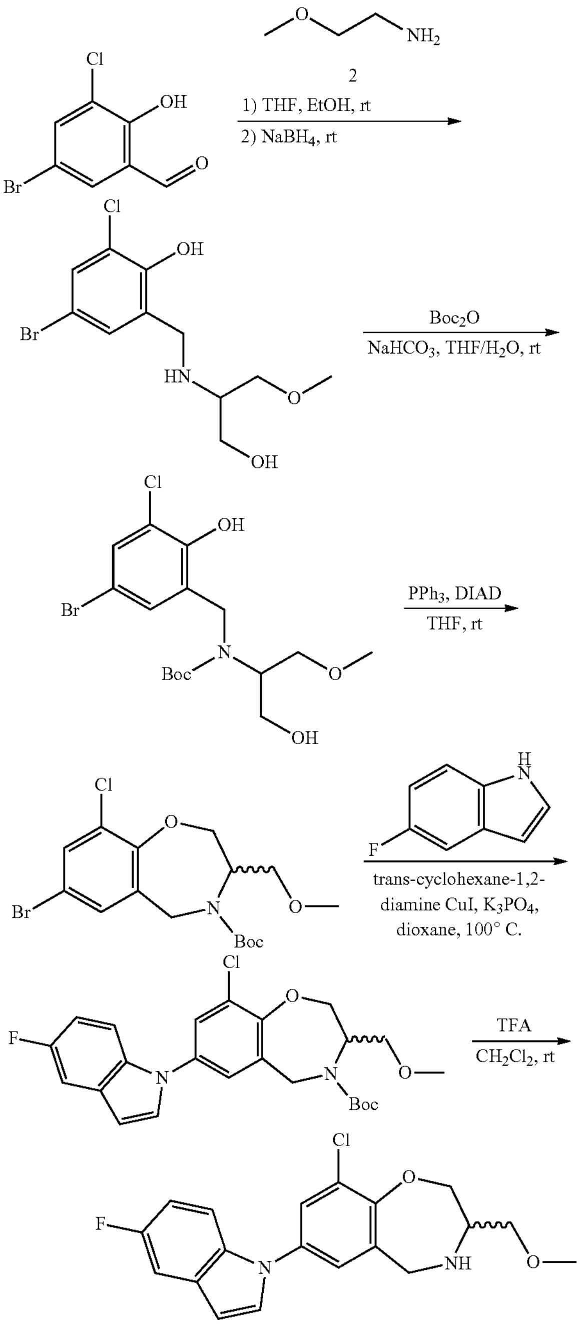

Step 1: Synthesis of 4-bromo-2-chloro-6-{[(1-hydroxy-3-methoxypropan-2-yl)amino]methyl}phenol To a mixture of 5-bromo-3-chloro-2-hydroxybenzaldehyde (3 g, 12.7 mmol) in THF (15 mL) and EtOH (15 mL) was added 2-amino-3-methoxypropan-1-ol (1.34 g, 12.7 mmol). The mixture was stirred at rt for 10 min, then $NaBH_4$ was added (0.3 g, 7.7 mmol). The mixture was stirred at rt for 1 h, then concentrated under reduced pressure and the residue was purified by reverse-phase column chromatography (column, silica gel; mobile phase, MeCN in water, 10% to 50% gradient in 10 min; detector, UV 254 nm) to afford 4-bromo-2-chloro-6-{[(1-hydroxy-3-methoxypropan-2-yl)amino]methyl}phenol (2.5 g, 54%) as an oil.

Step 2: Synthesis of Tert-butyl N-[(5-bromo-3-chloro-2-hydroxyphenyl)methyl]-N-(1,3-dihydroxypropan-2-yl)carbamate To a mixture of 4-bromo-2-chloro-6-{[(1-hydroxy-3-methoxypropan-2-yl)amino]methyl}phenol (2.6 g, 8.0 mmol) in THF (3 mL) was added $Boc_2O$ (2.62 g, 12.0 mmol) and aq. $NaHCO_3$ (12 mL). The mixture was stirred at rt for 1 h, then extracted with EtOAc (20 mL×3). The combined organic layers were washed with brine (30 mL), dried over anhydrous $Na_2SO_4$, filtered and the filtrate was concentrated under reduced pressure. The residue was purified by reverse-phase column chromatography (column, silica gel; mobile phase, MeCN in water, 10% to 50% gradient in 10 min; detector, UV 254 nm) to afford tert-butyl N-[(5-bromo-3-chloro-2-hydroxyphenyl)methyl]-N-(1,3-dihydroxypropan-2-yl)carbamate (500 mg, 15%) as a solid.

Step 3: Synthesis of Tert-butyl 7-bromo-9-chloro-3-(methoxymethyl)-3,5-dihydro-2H-1,4-benzoxazepine-4-carboxylate To a mixture of tert-butyl N-[(5-bromo-3-chloro-2-hydroxyphenyl)methyl]-N-(1-hydroxy-3-methoxypropan-2-yl)carbamate (500 mg, 1.2 mmol) and $PPh_3$ (770 mg, 2.9 mmol) in THE (10 mL) under an atmosphere of $N_2$ was added DIAD (600 mg, 2.9 mmol). The mixture was stirred at rt for 2 h, then concentrated under reduced pressure and the residue was purified by reverse-phase column chromatography (column, silica gel; mobile phase, MeCN in water, 10% to 50% gradient in 10 min; detector, UV 254 nm) to afford tert-butyl 7-bromo-9-chloro-3-(methoxymethyl)-3,5-dihydro-2H-1,4-benzoxazepine-4-carboxylate (250 mg, 48%) as an oil.

Step 4: Synthesis of Tert-butyl 9-chloro-7-(5-fluoroindol-1-yl)-3-(methoxymethyl)-3,5-dihydro-2H-1,4-benzoxazepine-4-carboxylate To a mixture of tert-butyl 7-bromo-9-chloro-3-(methoxymethyl)-3,5-dihydro-2H-1,4-benzoxazepine-4-carboxylate (230 mg, 0.57 mmol) in 1,4-dioxane (5 mL) was added 5-fluoro-1H-indole (115 mg, 0.85 mmol), CuI (32 mg, 0.17 mmol), $K_3PO_4$ (360 mg, 1.7 mmol) and trans-cyclohexane-1,2-diamine (32 mg, 0.28 mmol). The mixture was heated to 100° C. and stirred for 24 h, then filtered, and the filter cake was washed with EtOAc (3×10 mL). The filtrate was concentrated under reduced pressure and the residue was purified by reverse-phase column chromatography (column, silica gel; mobile phase, MeCN in water, 10% to 50% gradient in 10 min; detector, UV 254 nm) to afford tert-butyl 9-chloro-7-(5-fluoroindol-1-yl)-3-(methoxymethyl)-3,5-dihydro-2H-1,4-benzoxazepine-4-carboxylate (200 mg, 76%) as a solid.

Step 5: Synthesis of 9-Chloro-7-(5-fluoroindol-1-yl)-3-(methoxymethyl)-2,3,4,5-tetrahydro-1,4-benzoxazepine To a mixture of tert-butyl 9-chloro-7-(5-fluoroindol-1-yl)-3-(methoxymethyl)-3,5-dihydro-2H-1,4-benzoxazepine-4- carboxylate (200 mg, 0.43 mmol) in DCM (5 mL) was added TFA (1 mL). The mixture was stirred at rt for 1 h, then neutralized with saturated aq. $NaHCO_3$ and extracted with DCM (10 mL×3). The combined organic layers were washed with brine (10 mL), dried over anhydrous $Na_2SO_4$, filtered and the filtrate was concentrated under reduced pressure to afford 9-chloro-7-(5-fluoroindol-1-yl)-3-(methoxymethyl)-2,3,4,5-tetrahydro-1,4-benzoxazepine (140 mg, 81%) as an oil. LC/MS: mass calcd. For $C_{19}H_{18}ClFN_2O_2$: 360.1, found: 361.0 $[M+H]^+$.

Scheme 9 Preparation of 9-chloro-3-cyclopropyl-7-(5-fluoroindol-1-yl)-2,3,4,5-tetrahydro-1,4-benzoxazepine

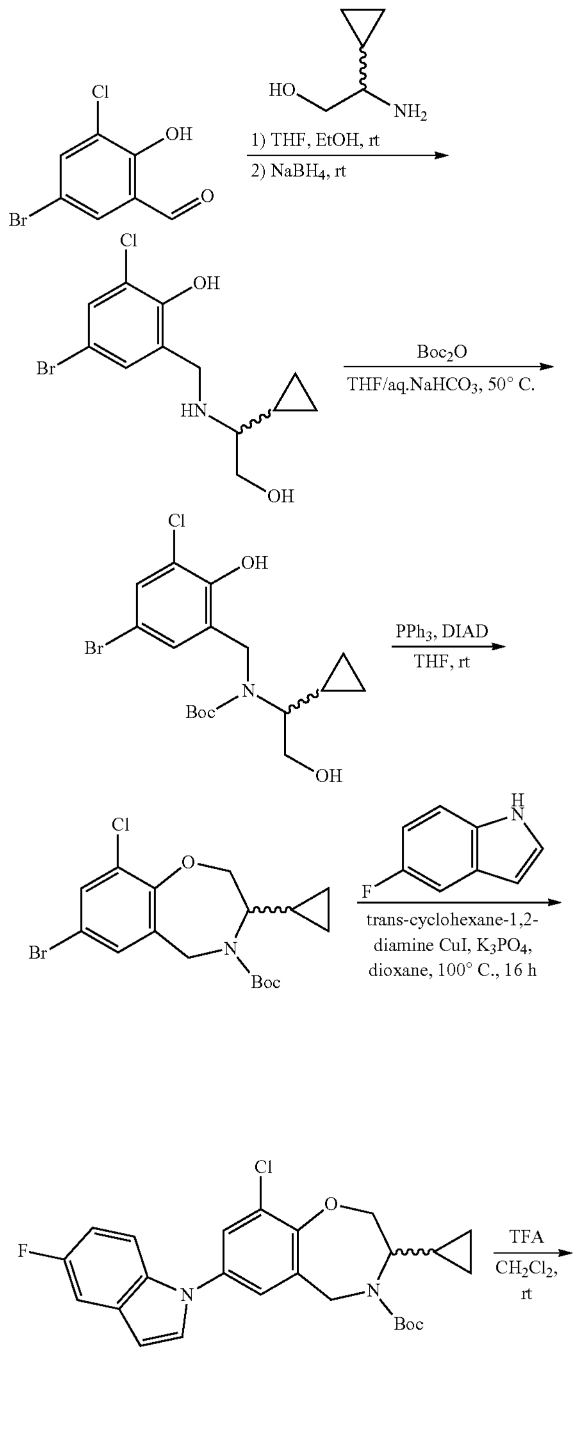

-continued

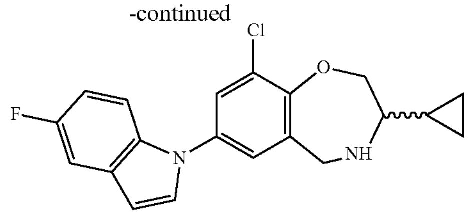

Step 1: Synthesis of 4-Bromo-2-chloro-6-{[(1-cyclopropyl-2-hydroxyethyl)amino]methyl}phenol To a stirred mixture of 5-bromo-3-chloro-2-hydroxybenzaldehyde (1.0 g, 4.3 mmol) and 2-amino-2-cyclopropylethanol (650 mg, 6.4 mmol) in THF (15 mL) at rt was added $NaBH_4$ (100 mg, 2.6 mmol). The mixture was stirred until completion of the reaction, then filtered and the filter cake was washed with H2O (2×20 mL). The filter cake was dried under vacuum to afford 4-bromo-2-chloro-6-{[(1-cyclopropyl-2-hydroxyethyl)amino]methyl}phenol (1.2 g, 27%) as a solid.

Step 2: Synthesis of Tert-butyl N-[(5-bromo-3-chloro-2-hydroxyphenyl)methyl]-N-(1-cyclopropyl-2-hydroxyethyl)carbamate To a stirred mixture of 4-bromo-2-chloro-6-{[(1-cyclopropyl-2-hydroxyethyl)amino]methyl}phenol (1.1 g, 3.4 mmol) in THF (20 mL) was added sat. $NaHCO_3$ (10 mL) and $Boc_2O$ (1.1 g, 5.2 mmol). The mixture was stirred at rt for 2 h, then concentrated under reduced pressure and the residue was purified by reverse-phase column chromatography (column, silica gel; mobile phase, MeCN in water, 20% to 100% gradient in 30 min; detector, UV 254 nm) to afford tert-butyl N-[(5-bromo-3-chloro-2-hydroxyphenyl)methyl]-N-(1-cyclopropyl-2-hydroxyethyl)carbamate (400 mg, 25%) as an oil.

Step 3: Synthesis of Tert-butyl 7-bromo-9-chloro-3-cyclopropyl-3,5-dihydro-2H-1,4-benzoxazepine-4-carboxylate To a stirred mixture of tert-butyl N-[(5-bromo-3-chloro-2-hydroxyphenyl)methyl]-N-(1-cyclopropyl-2-hydroxyethyl)carbamate (380 mg, 0.9 mmol) in THF (3 mL) at rt under an atmosphere of $N_2$ were added $PPh_3$ (616 mg, 2.4 mmol) and DIAD (475 mg, 2.4 mmol). The mixture was stirred at rt for 2 h, then concentrated under reduced pressure and the residue was purified by reverse-phase column chromatography (column, silica gel; mobile phase, MeCN in water, 30% to 100% gradient in 30 min; detector, UV 254 nm) to afford tert-butyl 7-bromo-9-chloro-3-cyclopropyl-3,5-dihydro-2H-1,4-benzoxazepine-4-carboxylate (250 mg, 62%) as an oil.

Step 4: Synthesis of Tert-butyl 9-chloro-3-cyclopropyl-7-(5-fluoroindol-1-yl)-3,5-dihydro-2H-1,4-benzoxazepine-4-carboxylate To a stirred mixture of tert-butyl 7-bromo-9-chloro-3-cyclopropyl-3,5-dihydro-2H-1,4-benzoxazepine-4-carboxylate (230 mg, 0.57 mmol) and 5-fluoro-1H-indole (125 mg, 0.93 mmol) in 1,4-dioxane (5 mL) were added trans-cyclohexane-1,2-diamine (35 mg, 0.31 mmol), CuI (35 mg, 0.19 mmol) and $K_3PO_4$ (450 mg, 2.1 mmol). The mixture was heated to 100° C. and stirred for 16 h, then filtered and the filtrate was concentrated under reduced pressure. The residue was purified by reverse-phase column chromatography (column, silica gel; mobile phase, MeCN in water, 30% to 100% gradient in 30 min; detector, UV 254 nm) to afford tert-butyl 9-chloro-3-cyclopropyl-7-(5-fluoroindol-1-yl)-3,5-dihydro-2H-1,4-benzoxazepine-4-carboxylate (180 mg, 67%) as an oil.

Step 5: Synthesis of 9-Chloro-3-cyclopropyl-7-(5-fluoroindol-1-yl)-2,3,4,5-tetrahydro-1,4-benzoxazepine To a stirred mixture of tert-butyl 9-chloro-3-cyclopropyl-7-(5-fluoroindol-1-yl)-3,5-dihydro-2H-1,4-benzoxazepine-4-carboxylate (180 mg, 0.39 mmol) in DCM (2.5 mL) was added TFA (0.5 mL). The mixture was stirred at rt for 30 min, then neutralized with sat. $NaHCO_3$ and extracted with DCM (3×10 mL). The combined organic layers were washed with brine (10 mL), dried over anhydrous MgSO4, filtered and the filtrate was concentrated under reduced pressure to afford 9-chloro-3-cyclopropyl-7-(5-fluoroindol-1-yl)-2,3,4,5-tetrahydro-1,4-benzoxazepine (126 mg, 84%) as a solid.

Scheme 10 Preparation of 7-bromo-9-chloro-4-[(2-methoxypyridin-4-yl)methyl]-6-methyl-3,5-dihydro-2H-1,4-benzoxazepine

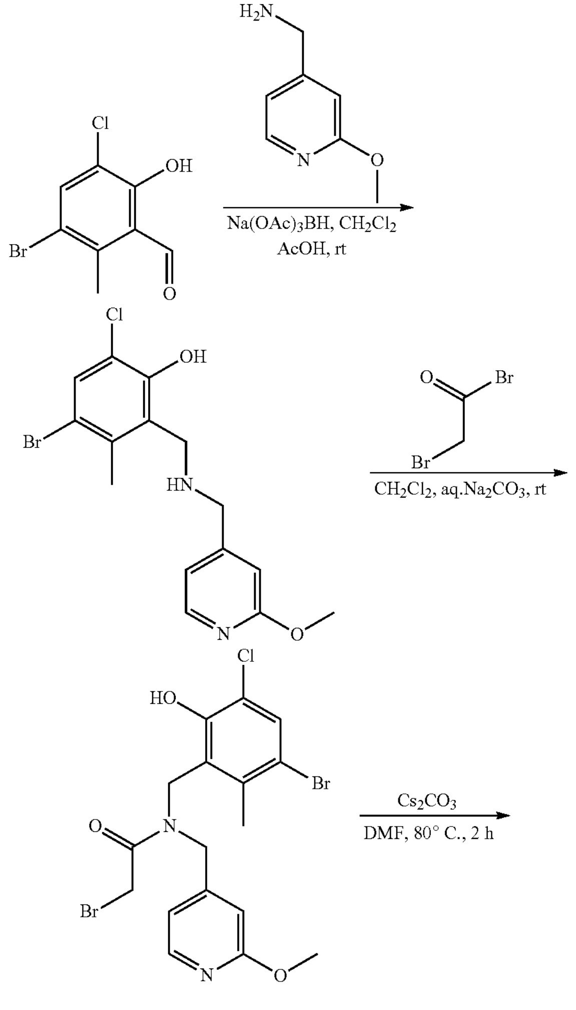

-continued

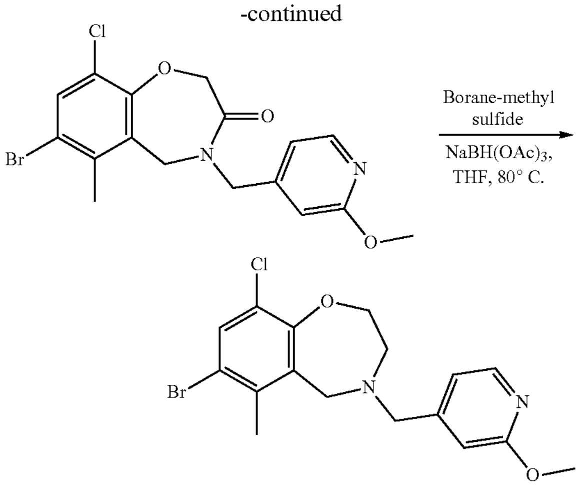

Step 1: Synthesis of 4-bromo-6-chloro-2-({[(2-methoxypyridin-4-yl)methyl]amino}methyl)-3-methylphenol To a stirred mixture of 3-bromo-5-chloro-6-hydroxy-2-methylbenzaldehyde (4.2 g, 16.8 mmol) and 1-(2-methoxypyridin-4-yl)methanamine (2.5 g, 18.1 mmol) in DCM (50 mL) was added $NaBH(OAc)_3$ (5.3 g, 25.0 mmol) and AcOH (1 mL). The mixture was stirred at rt for 3 h, then quenched with aq. $NaHCO_3$ (50 mL) and extracted with DCM (3×50 mL). The combined organic layers were washed with brine (50 mL), dried over anhydrous $Na_2SO_4$, filtered and the filtrate was concentrated under reduced pressure. The residue was purified by silica gel column chromatography (PE/EtOAc, 1:1) to afford 4-bromo-6-chloro-2-({[(2-methoxypyridin-4-yl)methyl]amino}methyl)-3-methylphenol (3.4 g, 45%) as an oil.

Step 2: Synthesis of 2-bromo-N-[(3-bromo-5-chloro-6-hydroxy-2-methylphenyl)methyl]-N-[(2-methoxypyridin-4-yl)methyl]acetamide To a stirred mixture of 4-bromo-6-chloro-2-({[(2-methoxypyridin-4-yl)methyl]amino}methyl)-3-methylphenol (3.4 g, 9.2 mmol) in DCM (42 mL) at rt were added sat. $Na_2CO_3$ (42 mL) and bromoacetyl bromide (2.18 g, 10.8 mmol). The mixture was stirred at rt for 2 h, then extracted with DCM (3×150 mL). The combined organic layers were washed with brine (150 mL), dried over anhydrous $Na_2SO_4$, filtered and the filtrate was concentrated under reduced pressure to afford 2-bromo-N-[(3-bromo-5-chloro-6-hydroxy-2-methylphenyl)methyl]-N-[(2-methoxypyridin-4-yl)methyl]acetamide (4.0 g, 57%) as an oil.

Step 3: Synthesis of 7-Bromo-9-chloro-4-[(2-methoxypyridin-4-yl)methyl]-6-methyl-2,5-dihydro-1,4-benzoxazepin-3-one To a stirred mixture of 2-bromo-N-[(3-bromo-5-chloro-6-hydroxy-2-methylphenyl)methyl]-N-[(2-methoxypyridin-4-yl)methyl]acetamide (4.0 g, 8.1 mmol) in DMF (60 mL) was added $CS_2CO_3$ (8.0 g, 24.4 mmol). The mixture was heated to 80° C. and stirred for 2 h, then filtered, and the filter cake was washed with EtOAc (3×50 mL). The filtrate was washed with $H_2O$ (3×100 mL), dried over anhydrous $Na_2SO_4$, filtered and the filtrate was concentrated under reduced pressure. The residue was purified by reverse-phase column chromatography (column, C18 silica gel; mobile phase, MeCN in Water (0.1% TFA), 10% to 70% gradient in 30 min; detector, UV 254 nm) to afford 7-bromo-9-chloro-4-[(2-methoxypyridin-4-yl)methyl]-6-methyl-2,5-dihydro-1,4-benzoxazepin-3-one (2.0 g, 60%) as an oil.

Step 4: Synthesis of 7-Bromo-9-chloro-4-[(2-methoxypyridin-4-yl)methyl]-6-methyl-3,5-dihydro-2H-1,4-benzoxazepine To a stirred mixture of $NaBH_4$ (922 mg, 24.4 mmol) in THF (10 mL) at rt under an atmosphere of $N_2$ was added $BF_3$·$Et_2O$ (3 mL, 23.7 mmol) dropwise. The mixture was stirred at rt for 10 min, then cooled to 0° C. and 7-bromo-9-chloro-4-[(2-methoxypyridin-4-yl)methyl]-6-methyl-2,5-dihydro-1,4-benzoxazepin-3-one (1.0 g, 2.4 mmol) in THF (10 mL) was added dropwise over 10 min. The mixture was heated to 55° C. and stirred for 16 h, then quenched by addition of MeOH (10 mL) and the mixture concentrated under reduced pressure. The residue was purified by reverse-phase column chromatography (column, silica gel; mobile phase, MeCN in water, 10% to 70% gradient in 20 min; detector, UV 254 nm) to afford 7-bromo-9-chloro-4-[(2-methoxypyridin-4-yl)methyl]-6-methyl-3,5-dihydro-2H-1,4-benzoxazepine (470 mg, 46%) as an oil.

Scheme 11 Preparation of lithium imidazo[1,2-a]pyridin-5-yltriisopropoxyboranuide

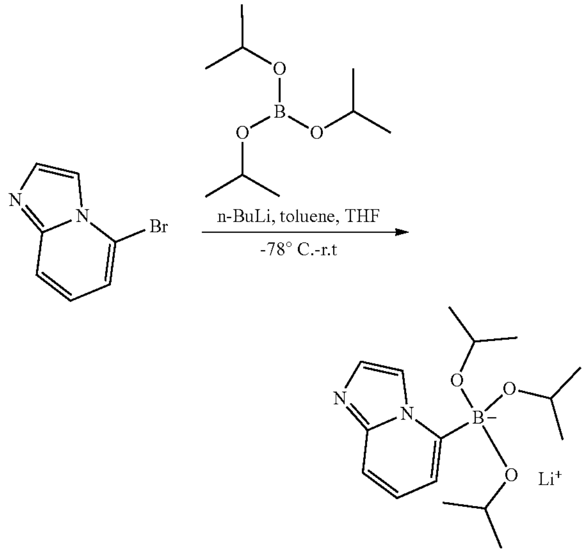

See, WO2017202742.

EP2 Inhibitors

Method A: Preparation of 9-chloro-4-((1,5-dimethyl-1H-pyrazol-4-yl)methyl)-7-(5-fluoro-1H-indol-1-yl)-2,3,4,5-tetrahydrobenzo[f][1,4]oxazepane (Compound 106)

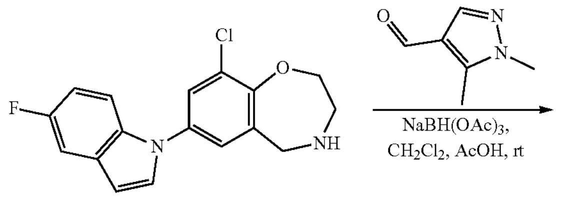

-continued

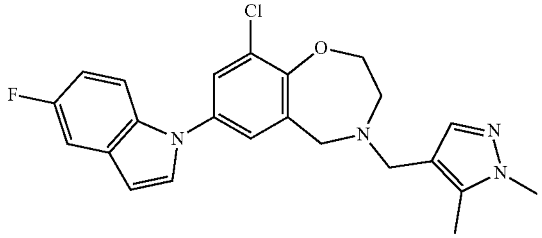

To a stirred mixture of 9-chloro-7-(5-fluoroindol-1-yl)-2,3,4,5-tetrahydro-1,4-benzoxazepine (50 mg, 0.16 mmol) and 1,5-dimethylpyrazole-4-carbaldehyde (40 mg, 0.32 mmol) in DCM (1 ml) at rt was added $NaBH(OAc)_3$ (70 mg, 0.32 mmol) and AcOH (40 μL). The mixture was stirred overnight at rt, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 51% B to 71% B in 7 min, 71% B; Wave Length: 254 nm; RT1(min): 5.82) to afford 9-chloro-4-[(1,5-dimethylpyrazol-4-yl)methyl]-7-(5-fluoroindol-1-yl)-3,5-dihydro-2H-1,4-benzoxazepine (14.4 mg, 21%) as a solid. LC/MS: mass calcd. For $C_{23}H_{23}ClFN_4O$: 424.2, found: 425.1 $[M+H]^+$; $^1H$ NMR (300 MHz, $CD_3OD$) δ 7.47 (s, 1H), 7.35-7.42 (m, 3H), 7.25-7.29 (m, 1H), 7.19 (s, 1H), 6.95 (t, J=9.3, 1H), 6.61 (d, J=3.3 Hz, 1H), 4.15-4.17 (m, 2H), 3.85 (s, 2H), 3.73 (s, 3H), 3.57 (s, 2H), 3.05 (m, 2H), 2.22 (s, 3H). $^{19}F$ NMR (282 MHz, $CD_3OD$) δ −126.0.

Method B: Preparation of 4-((1H-pyrazol-4-yl)methyl)-9-chloro-7-(5-fluoro-1H-indol-1-yl)-2,3,4,5-tetrahydrobenzo[f][1,4]oxazepane (Compound 103)

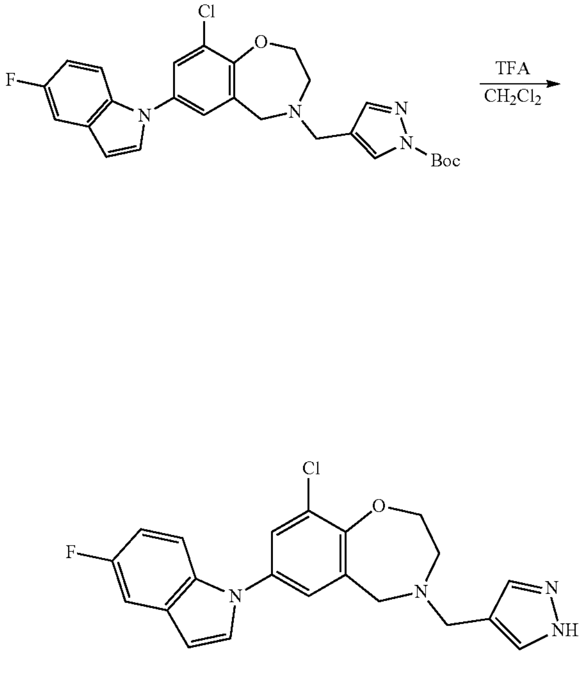

To a stirred solution of tert-butyl 4-{[9-chloro-7-(5-fluoroindol-1-yl)-3,5-dihydro-2H-1,4-benzoxazepin-4-yl]methyl}pyrazole-1-carboxylate (40 mg, 0.08 mmol) in DCM (2 mL) at rt was added TFA (0.4 mL). The resulting mixture was stirred for 1 h at rt, then concentrated under reduced pressure and the residue was purified by preparative-HPLC (Column: XBridge Prep Phenyl OBD Column, 19*250 mm, 5 μm; Mobile Phase A: Water (10 mmol/L $NH_4HCO_3$+0.1% $NH_3{\cdot}H_2O$), Mobile Phase B: ACN; Flow rate: 25 mL/min; Gradient: 45% B to 75% B in 7 min, 75% B; Wave Length: 254 nm; RT1(min): 5) to afford 9-chloro-7-(5-fluoroindol-1-yl)-4-(1H-pyrazol-4-ylmethyl)-3,5-dihydro-2H-1,4-benzoxazepine (7.2 mg, 22%) as a solid. LC/MS: mass calcd. For $C_{21}H_{18}ClFN_4O$: 396.1, found: 397.0 $[M+H]^+$; $^1H$ NMR (300 MHz, $CD_3OD$) δ 7.59-7.62 (br, 2H), 7.51 (d, J=2.7 Hz, 1H), 7.40-7.45 (m, 2H), 7.24-7.31 (m, 2H), 6.97 (t, J=9.3 Hz, 1H), 6.63 (d, J=3.3 Hz, 1H), 4.18-4.24 (m, 2H), 3.90 (s, 2H), 3.73 (s, 2H), 3.09-3.12 (m, 2H). $^{19}F$ NMR (282 MHz, $CD_3OD$) δ −126.2.

Method C: Preparation of 9-chloro-7-(5-fluoro-1H-pyrrolo[2,3-b]pyridin-1-yl)-4-((2-methoxypyrimidin-5-yl)methyl)-2,3,4,5-tetrahydrobenzo[f][1,4]oxazepine (Compound 33)

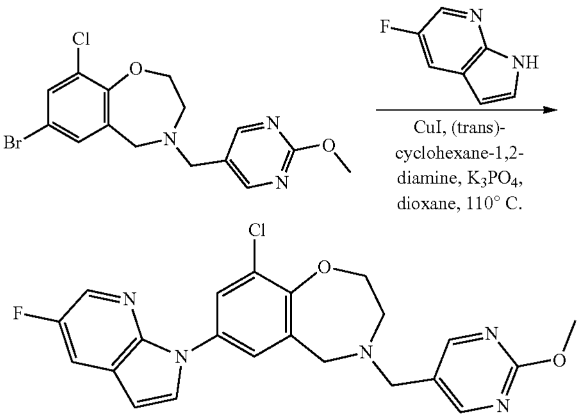

To a stirred mixture of 7-bromo-9-chloro-4-[(2-methoxypyrimidin-5-yl)methyl]-3,5-dihydro-2H-1,4-benzoxazepine (50 mg, 0.13 mmol) and 5-fluoro-1H-pyrrolo[2,3-b]pyridine (27 mg, 0.2 mmol) in 1,4-dioxane (2 mL) under an atmosphere of $N_2$ was added trans-cyclohexane-1,2-diamine (7 mg, 0.07 mmol), CuI (7 mg, 0.04 mmol) and $K_3PO_4$ (83 mg, 0.39 mmol). The resulting mixture was heated to 110° C. and stirred overnight, then filtered and the filtrate was concentrated under reduced pressure. The residue was purified by preparative-HPLC (Column: XBridge Prep OBD C18 Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 30% B to 60% B in 7 min, 60% B; Wave Length: 254 nm; RT1(min): 6.12) to afford 9-chloro-7-{5-fluoropyrrolo[2,3-b]pyridin-1-yl}-4-[(2-methoxypyrimidin-5-yl)methyl]-3,5-dihydro-2H-1,4-benzoxazepine (5.1 mg, 9%) as a solid. LC/MS: mass caled. for $C_{22}H_{19}ClFN_5O_2$, 439.1, found: 440.1. $[M+H]^+$; $^1H$ NMR (300 MHz, DMSO-$d_6$) δ 8.55 (s, 2H), 8.38 (s, 1H), 7.91-8.04 (m, 3H), 7.65 (d, J=2.7 Hz, 1H), 6.74 (d, J=3.7 Hz, 1H), 4.17-4.18 (m, 2H), 3.90-3.92 (m, 5H), 3.64 (s, 2H), 3.09-3.10 (m, 2H); $^{19}F$ NMR (282 MHz, DMSO-$d_6$) δ −173.1.

Method D: Preparation of 5-((9-chloro-7-(5-fluoro-1H-pyrrolo[2,3-b]pyridin-1-yl)-2,3-dihydrobenzo[f][1,4]oxazepin-4(5H)-yl)methyl)pyrimidin-2(1H)-one (Compound 70)

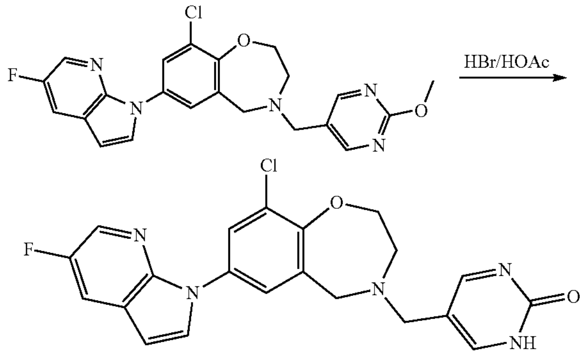

To a solution of 33% HBr in AcOH (1 mL) was added with 9-chloro-7-{5-fluoropyrrolo[2,3-b]pyridin-1-yl}-4-[(2-methoxypyrimidin-5-yl)methyl]-3,5-dihydro-2H-1,4-benzoxazepine (50 mg, 0.11 mmol). The mixture was stirred for 2 h at rt, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 25% B to 55% B in 7 min, 55% B; Wave Length: 254 nm; RT1(min): 5.87) to afford 5-[(9-chloro-7-{5-fluoropyrrolo[2,3-b]pyridin-1-yl}-3,5-dihydro-2H-1,4-benzoxazepin-4-yl)methyl]-1H-pyrimidin-2-one (5.0 mg, 10%) as a solid. LC/MS: mass caled. for $C_{21}H_{17}ClFN_5O_2$, 425.1, found: 426.0. $[M+H]^+$; $^1H$ NMR (400 MHz, $CD_3OD$) δ 8.25-8.31 (m, 3H), 7.77-7.85 (m, 3H), 7.57 (d, J=2.8 Hz, 1H), 6.70 (d, J=3.6 Hz, 1H), 4.19-4.21 (m, 2H), 3.98 (s, 2H), 3.59 (s, 2H), 3.22-3.24 (m, 2H); $^{19}F$ NMR (376 MHz, $CD_3OD$) δ −140.0.

Method E: Preparation of 7-(benzo[b]thiophen-3-yl)-9-chloro-4-((2-methoxypyrimidin-5-yl)methyl)-2,3,4,5-tetrahydrobenzo[f][1,4]oxazepine

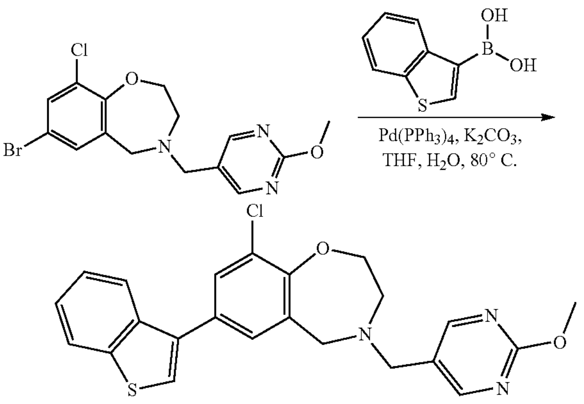

To a mixture of 7-bromo-9-chloro-4-[(2-methoxypyrimidin-5-yl)methyl]-3,5-dihydro-2H-1,4-benzoxazepine (50 mg, 0.13 mmol) and 1-benzothiophen-3-ylboronic acid (35 mg, 0.2 mmol) in THE (0.8 mL) and $H_2O$ (0.2 mL) under an atmosphere of $N_2$ was added $K_2CO_3$ (36 mg, 0.26 mmol) and $Pd(PPh_3)_4$ (15 mg, 0.013 mmol). The mixture was heated to 80° C. and stirred for 16 h, then filtered and the filtrate was concentrated under reduced pressure. The residue was purified by preparative-HPLC (Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 50% B to 80% B in 7 min, 80% B; Wave Length: 254 nm; RT1(min): 6) to afford 7-(1-benzothiophen-3-yl)-9-chloro-4-[(2-methoxypyrimidin-5-yl)methyl]-3,5-dihydro-2H-1,4-benzoxazepine (6.0 mg, 10%) as a solid. LC/MS: mass calcd. For $C_{23}H_{20}ClN_3O_2S$: 437.1, found: 438.1 $[M+H]^+$; $^1H$ NMR (300 MHz, DMSO-$d_6$) δ 8.54 (s, 2H), 8.08 (d, J=6.0 Hz, 1H), 7.56-7.94 (m, 3H), 7.34-7.53 (m, 3H), 4.18-4.19 (m, 2H), 3.95 (s, 2H), 3.90 (s, 3H), 3.67 (s, 2H), 3.05-3.06 (m, 2H).

Method F: Preparation of 9-chloro-7-(6-fluoro-3,4-dihydroquinolin-1(2H)-yl)-4-((2-methoxypyrimidin-5-yl)methyl)-2,3,4,5-tetrahydrobenzo[f][1,4]oxazepine (Compound 49)

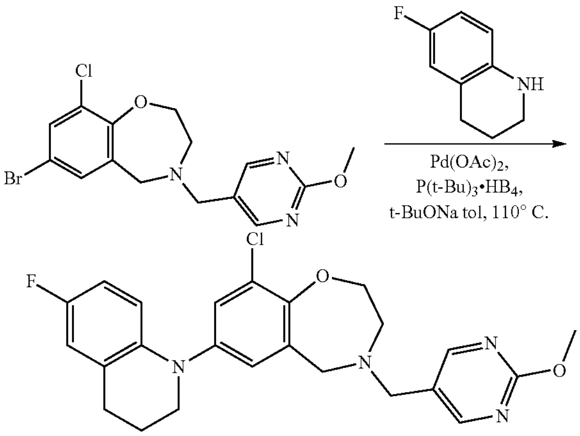

To a mixture of 7-bromo-9-chloro-4-[(2-methoxypyrimidin-5-yl)methyl]-3,5-dihydro-2H-1,4-benzoxazepine (50 mg, 0.13 mmol) in toluene (1.5 mL) under an atmosphere of nitrogen was added with 6-fluoro-1,2,3,4-tetrahydroquinoline (24 mg, 0.16 mmol), $Pd(OAc)_2$ (1 mg, 0.004 mmol), tri-tert-butylphosphamide tetrafluoroboramide (2 mg, 0.008 mmol), t-BuONa (25 mg, 0.26 mmol). The mixture was heated to 110° C. and stirred for 16 h, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 46% B to 76% B in 10 min, 76% B; Wave Length: 254 nm; RT1(min): 8.95) to afford 9-chloro-7-(6-fluoro-3,4-dihydro-2H-quinolin-1-yl)-4-[(2-methoxypyrimidin-5-yl)methyl]-3,5-dihydro-2H-1,4-benzoxazepine (7.3 mg, 12%) as a solid. LC/MS: mass calcd. For $C_{24}H_{24}ClFN_4O_2$: 454.2, found: 455.1 $[M+H]^+$; $^1H$ NMR (300 MHz, DMSO-$d_6$) δ 8.49 (s, 2H), 7.15 (d, J=2.4 Hz, 1H), 6.88-6.95 (m, 2H), 6.76-6.83 (m, 1H), 6.62-6.66 (m, 1H), 4.07-4.08 (m, 2H), 3.90 (s, 3H), 3.78 (s, 2H), 3.60 (s, 2H), 3.49 (t, J=5.7 Hz, 2H), 3.02-3.03 (m, 2H), 2.75 (t, J=5.7 Hz, 2H), 1.85-1.93 (m, 2H); $^{19}F$ (282 MHz, DMSO-$d_6$) δ −125.5.

Method G: Preparation of 9-chloro-7-(5-fluoro-1H-indol-1-yl)-4-(oxazol-5-ylmethyl)-2,3,4,5-tetrahydrobenzo[f][1,4]oxazepine (Compound 93)

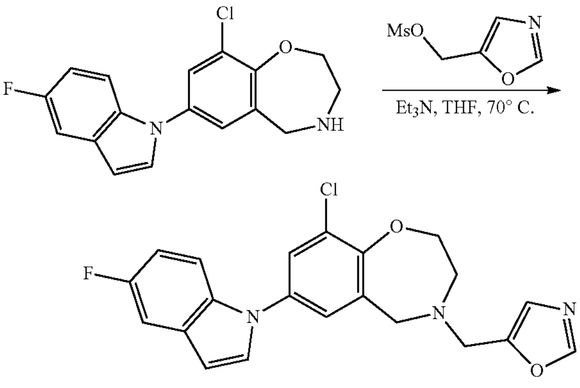

To a stirred mixture of 1,3-oxazol-5-ylmethyl methanesulfonate (56 mg, 0.32 mmol) and 9-chloro-7-(5-fluoroindol-1-yl)-2,3,4,5-tetrahydro-1,4-benzoxazepine (50 mg, 0.16 mmol) in THE (1 mL) was added $Et_3N$ (35 mg, 0.32 mmol). The mixture was heated to 70° C. and stirred for 16 h, then concentrated under reduced pressure and the residue was purified by preparative-HPLC (Column: XBridge Prep C18 OBD Column, 19*150 mm, 5 μm; Mobile Phase A: Water (10 mmol/L $NH_4HCO_3$+0.1% $NH_3 \cdot H_2O$), Mobile Phase B: ACN; Flow rate: 25 mL/min; Gradient: 47% B to 77% B in 7 min, 77% B; Wave Length: 254 nm; RT1(min): 6) to afford 9-chloro-7-(5-fluoroindol-1-yl)-4-(1,3-oxazol-5-ylmethyl)-3,5-dihydro-2H-1,4-benzoxazepine (4.2 mg, 7%) as a solid. LC/MS: mass caled. for $C_{21}H_{17}ClFN_3O_2$, 397.1, found: 398.0 $[M+H]^+$; $^1H$ NMR (300 MHz, $CD_3OD$) δ 8.20 (s, 1H), 7.50 (d, J=2.7 Hz, 1H), 7.41-7.45 (m, 2H), 7.26-7.30 (m, 2H), 7.09 (s, 1H), 6.93-6.99 (m, 1H), 6.62-6.63 (m, 1H), 4.17-4.20 (m, 2H), 3.95 (s, 2H), 3.89 (s, 2H), 3.13-3.16 (m, 2H); $^{19}F$ NMR (282 MHz, $CD_3OD$) δ −126.1.

Method I: 9-chloro-7-(5-fluoroindol-1-yl)-4-[(2-oxo-1H-pyridin-4-yl)methyl]-3-(trifluoromethyl)-2,3-dihydro-1,4-benzoxazepin-5-one (Compound 249)

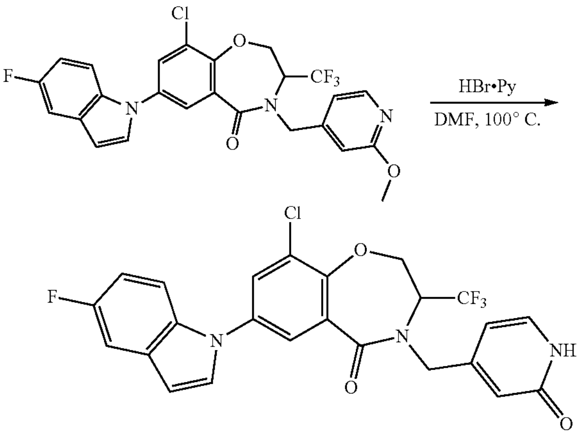

To a mixture of 9-chloro-7-(5-fluoroindol-1-yl)-4-[(2-methoxypyridin-4-yl)methyl]-3-(trifluoromethyl)-2,3-dihydro-1,4-benzoxazepin-5-one (25 mg, 0.05 mmol) in DMF (2 mL) was added pyridine hydrobromide (50 mg, 0.29 mmol). The mixture was heated to 60° C. and stirred for 24 h, then purified by preparative-HPLC (Column: XBridge Prep Phenyl OBD Column, 19*250 mm, 5 μm; Mobile Phase A: Water (10 mmol/L $NH_4HCO_3$+0.1% $NH_3$—$H_2O$), Mobile Phase B: ACN; Flow rate: 25 mL/min; Gradient: 48% B to 58% B in 10 min, 58% B; Wave Length: 254 nm; RT1(min): 8.8) to afford 9-chloro-7-(5-fluoroindol-1-yl)-4-[(2-oxo-1H-pyridin-4-yl)methyl]-3-(trifluoromethyl)-2,3-dihydro-1,4-benzoxazepin-5-one (1.8 mg, 7.26%) as an off-solid. LC/MS: mass calcd. For $C_{24}H_{16}ClF_4N_3O_3$: 505.1, found: 506.1 $[M+H]^+$; $^1H$ NMR (400 MHz, DMSO-$d_6$) δ 11.55 (br, 1H), 8.10 (d, J=4.0 Hz, 1H), 7.82-7.88 (m, 2H), 7.40-7.55 (m, 3H), 7.11 (m, 1H), 6.74 (d, J=4.0 Hz, 1H), 6.44 (s, 1H), 6.32 (d, J=8.0 Hz, 1H), 5.24 (m, 1H), 4.93 (s, 2H), 4.70 (m, 1H), 4.57 (m, 1H); $^{19}F$ NMR (376 MHz, DMSO-$d_6$) δ −74.5, −123.1.

Method J: Preparation of cis-4-{[9-chloro-7-(5-fluoroindol-1-yl)-3,5-dihydro-2H-1,4-benzoxazepin-4-yl]methyl}-N-methylcyclohexane-1-carboxamide [f][1,4]oxazepine (Compound 128)

To a stirred solution of cis-4-{[9-chloro-7-(5-fluoroindol-1-yl)-3,5-dihydro-2H-1,4-benzoxazepin-4-yl]methyl}cyclohexane-1-carboxylic acid (35 mg, 0.08 mmol) and $CH_3NH_2$—HCl (11 mg, 0.15 mmol) in DMF (1 mL) was added HATU (45 mg, 0.12 mmol) and DIPEA (25 mg, 0.19 mmol). The mixture was stirred for 2 h at rt, then concentrated under reduced pressure and the residue was purified by preparative-HPLC (Column: XBridge Prep OBD Cis Column, 30*150 mm, 5 μm; Mobile Phase A: Water (10 mmol/L $NH_4HCO_3$+0.1% $NH_3$—$H_2O$), Mobile Phase B: ACN; Flow rate: 60 mL/min; Gradient: 55% B to 85% B in 7 min, 85% B; Wave Length: 254 nm; RT1(min): 6) to afford cis-4-{[9-chloro-7-(5-fluoroindol-1-yl)-3,5-dihydro-2H-1,4-benzoxazepin-4-yl]methyl}-N-methylcyclohexane-1-carboxamide (3.3 mg, 9%) as a solid. LC/MS: mass calcd. For $C_{26}H_{29}ClFN_3O_2$: 469.1, found: 469.9 $[M+H]^+$; $^1H$ NMR (300 MHz, DMSO-$d_6$) δ 7.32-7.36 (m, 3H), 7.16-7.29 (m, 2H), 6.81-6.88 (m, 1H), 6.52-6.53 (m, 1H), 4.03-4.06 (m, 2H), 3.83 (s, 2H), 3.05-3.06 (m, 2H), 2.58 (s, 3H), 2.40 (d, J=7.8 Hz, 2H) 2.13-2.18 (m, 1H), 1.75-1.76 (m, 1H), 1.40-1.67 (m, 8H); $^{19}F$ NMR (400 MHz, $CD_3OD$) δ −126.1.

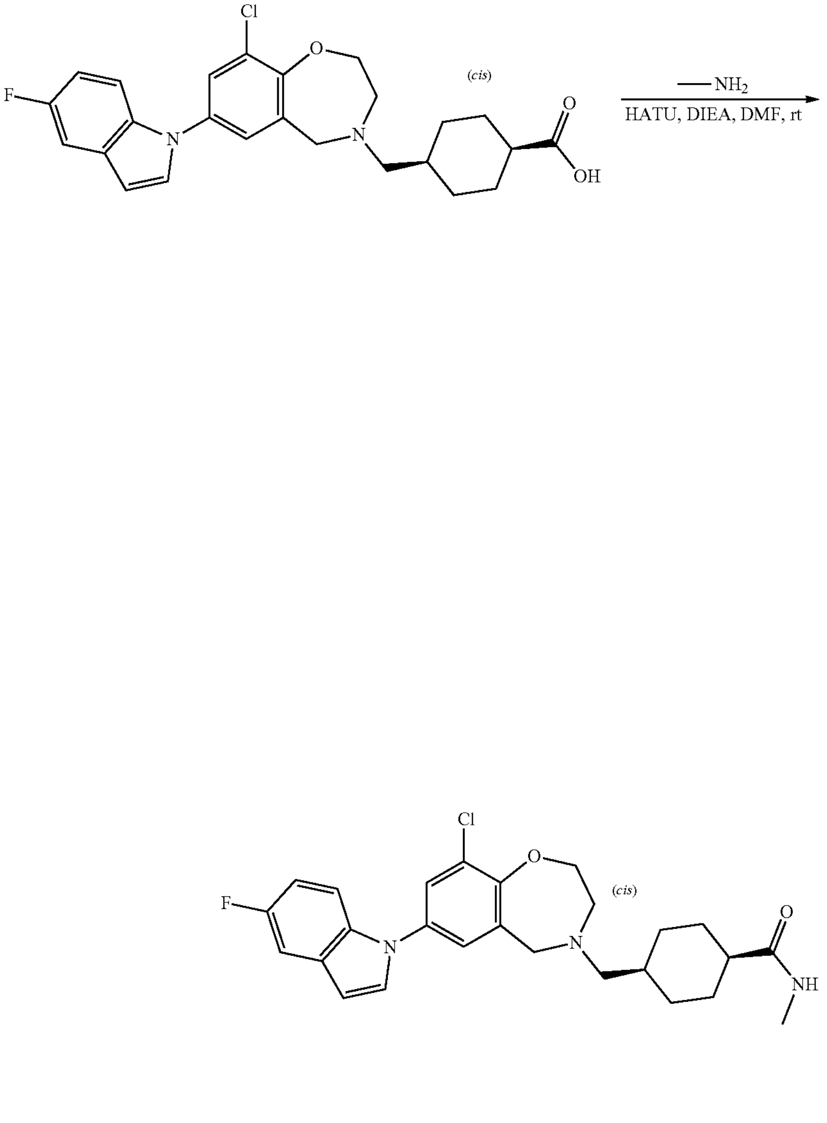

Method K: Preparation of trans-4-{[9-chloro-7-(5-fluoroindol-1-yl)-3,5-dihydro-2H-1,4-benzoxazepin-4-yl]methyl}-N-methylcyclohexane-1-carboxamide [f][1,4]oxazepane (Compound 127)

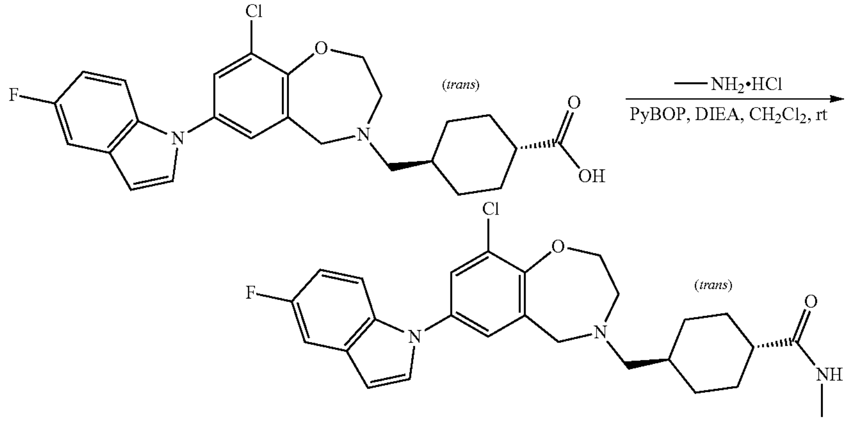

The mixture of trans-4-{[9-chloro-7-(5-fluoroindol-1-yl)-3,5-dihydro-2H-1,4-benzoxazepin-4-yl] methyl}cyclohexane-1-carboxylic acid (50 mg, 0.11 mmol) in DCM (1 mL) was added $CH_3NH_2$° HCl (15 mg, 0.22 mmol), PyBOP (86 mg, 0.16 mmol) and DIPEA (30 mg, 0.22 mmol). The mixture was stirred at rt for 16 h, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$+0.1% NH3·$H_2O$), Mobile Phase B: ACN; Flow rate: 60 mL/min; Gradient: 55% B to 85% B in 7 min, 85% B; Wave Length: 254 nm; RT1(min): 6) to afford trans-4-{[9-chloro-7-(5-fluoroindol-1-yl)-3,5-dihydro-2H-1,4-benzoxazepin-4-yl]methyl}-N-methylcyclohexane-1-carboxamide (15.5 mg, 29%) as a solid; LC/MS: mass calcd. For $C_{26}H_{29}ClFN_3O_2$: 469.1, found: 469.9 $[M+H]^+$; $^1H$ NMR (300 MHz, DMSO-$d_6$) δ 7.72 (d, J=3.2 Hz, 1H), 7.54-7.59 (m, 3H), 7.45-7.54 (m, 2H), 7.03-7.04 (m, 1H), 6.68-6.69 (m, 1H), 4.10-4.12 (m, 2H), 3.89 (s, 2H), 3.31-3.34 (m, 2H), 2.50-2.53 (m, 3H), 2.25 (d, J=6.9 Hz, 2H), 2.01-2.08 (m, 1H), 1.68-1.78 (m, 4H), 1.51-1.56 (m, 1H), 1.31-1.42 (m, 2H), 0.78-0.92 (m, 2H); $^{19}F$ NMR (400 MHz, $CD_3OD$) δ −123.5.

Method L: Preparation of 4-{[9-chloro-7-(5-fluoroindol-1-yl)-3,5-dihydro-2H-1,4-benzoxazepin-4-yl]methyl}pyran-2-one (Compound 174)

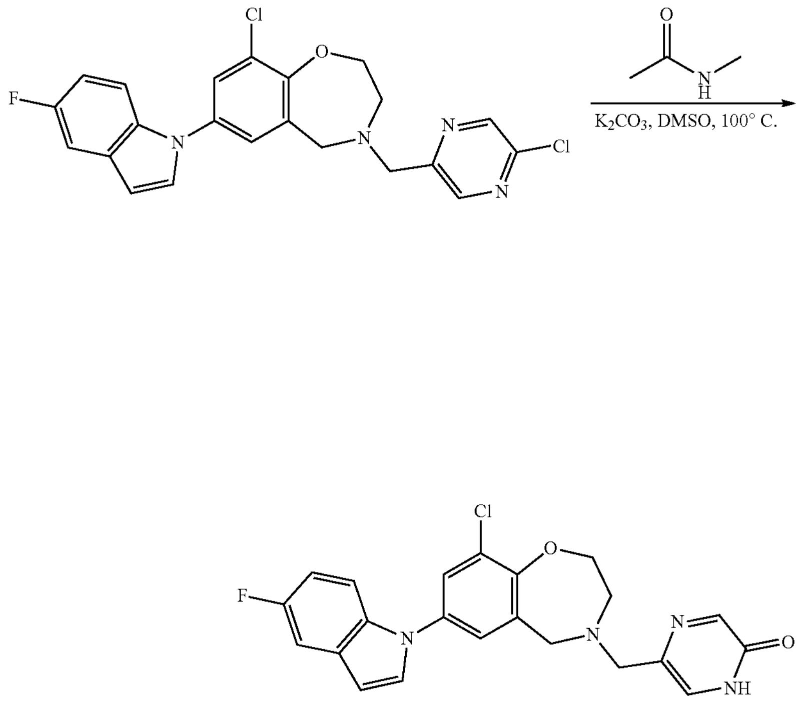

To a stirred solution of 9-chloro-4-[(5-chloropyrazin-2-yl)methyl]-7-(5-fluoroindol-1-yl)-3,5-dihydro-2H-1,4-benzoxazepine (50 mg, 0.11 mmol) and acetohydroxamic acid (25 mg, 0.34 mmol) in DMSO (1 mL) was added $K_2CO_3$ (80 mg, 0.57 mmol). The mixture was heated to 80° C. and stirred overnight, then filtered. The filtrate was purified by preparative-HPLC (Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 37% B to 67% B in 7 min, 67% B; Wave Length: 254 nm; RT1(min): 6) to afford 5-{[9-chloro-7-(5-fluoroindol-1-yl)-3,5-dihydro-2H-1,4-benzoxazepin-4-yl]methyl}-1H-pyrazin-2-one (7.9 mg, 16%) as a solid. LC/MS: mass caled. For $C_{22}H_{18}ClFN_4O_2$: 424.1, found: 425.0 $[M+H]^+$; $^1H$ NMR (300 MHz, DMSO-$d_6$) δ 12.07 (s, 1H), 7.98 (d, J=2.4 Hz, 1H), 7.71 (d, J=3.0 Hz, 1H), 7.60 (d, J=2.7 Hz, 1H), 7.54 (d, J=9.0 Hz, 1H), 7.39-7.45 (m, 3H), 7.07 (t, J=9.1 Hz, 1H), 6.69 (d, J=3.3 Hz, 1H), 4.17-4.18 (m, 2H), 3.94 (s, 2H), 3.57 (s, 2H), 3.09-3.10 (m, 2H); $^{19}F$ NMR (282 MHz, DMSO-$d_6$) δ −123.6.

Method M: 5-[(9-chloro-7-{pyrrolo[2,3-b]pyrazin-5-yl}-3,5-dihydro-2H-1,4-benzoxazepin-4-yl)methyl]-1H-pyrimidin-2-one trifluoroacetic acid (Compound 76)

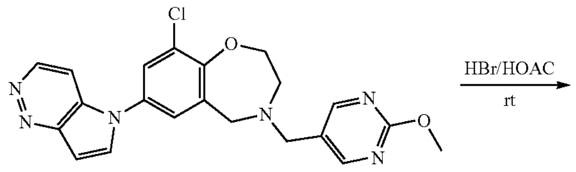

-continued

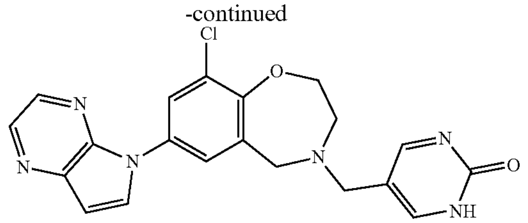

This title compound was prepared following Method D. However, the crude product was purified by preparative-HPLC (Column: Xselect CSH C18 OBD Column 30*150 mm 5 μm, n; Mobile Phase A: Water (0.05% TFA), Mobile Phase B: ACN; Flow rate: 60 mL/min; Gradient: 10% B to 40% B in 7 min, 40% B; Wave Length: 254 nm; RT1(min): 6.12) to afford 5-[(9-chloro-7-{pyrrolo[2,3-b]pyrazin-5-yl}-3,5-dihydro-2H-1,4-benzoxazepin-4-yl)methyl]-1H-pyrimidin-2-one trifluoroacetic acid (2.8 mg, 7%) as a solid. LC/MS: mass calcd. For $C_{20}H_{17}ClN_6O_2$: 408.1, found: 409.1 $[M+H]^+$; $^1H$ NMR (400 MHz, DMSO-$d_6$) δ 8.58 (d, J=2.6 Hz, 1H), 8.24-8.41 (i, 4H), 8.14 (s, 1H), 7.93 (s, 1H), 6.98 (d, J=4.0 Hz, 1H), 4.20-4.50 (m, 4H), 4.00 (br, 2H), 3.00-3.10 (m, 2H); $^{19}F$ NMR (376 MHz, DMSO-$d_6$) δ −73.8, −77.7.

The compounds in Table 1 can be prepared according to the methods described herein.

TABLE 1

| ID No. | Name, Structure, $^1H$-NMR, | MS $(M + H)^+$ | Method |
|---|---|---|---|
| 9 | 5-{[(3R)-9-chloro-7-(5-fluoroindol-1-yl)-3-methyl-3,5-dihydro-2H-1,4-benzoxazepin-4-yl]methyl}-1H-pyrimidin-2-one 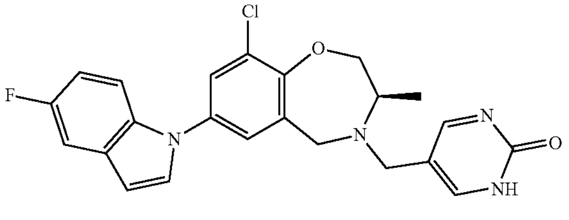 $^1H$ NMR (300 MHz, $CD_3OD$) δ 8.19 (s, 2H), 7.49 (d, J = 2.6 Hz, 1H), 7.37-7.47 (m, 2H), 7.19-7.32 (m, 2H), 6.94-7.01 (m, 1H), 6.67-6.68 (m, 1H), 4.24-4.39 (m, 2H), 4.08-4.14 (m, 1H), 3.76-3.81 (m, 1H), 3.49-3.76 (m, 2H), 3.31-3.39 (m, 1H), 1.32 (d, J = 6.9 Hz, 3H); $^{19}F$ NMR (282 MHz, $CD_3OD$) δ −126.1. | 439.1 | A |

TABLE 1-continued

| ID No. | Name, Structure, $^1$H-NMR, | MS (M + H)$^+$ | Method |
|---|---|---|---|
| 10 | (3R)-9-chloro-7-(5-fluoroindol-1-yl)-4-[(2-methoxypyrimidin-4-yl)methyl]-3-methyl-3,5-dihydro-2H-1,4-benzoxazepine 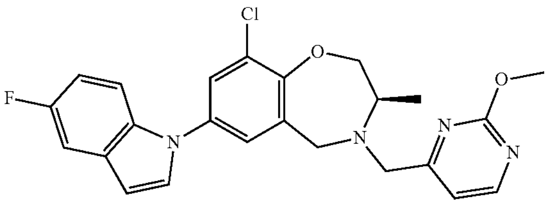 $^1$H NMR (300 MHz, DMSO-$d_6$) δ 8.56 (d, J = 5.0 Hz, 1H), 7.70 (d, J = 3.3 Hz, 1H), 7.61 (d, J = 2.6 Hz, 1H), 7.47-7.52 (m, 1H), 7.40-7.44 (m, 1H), 7.33 (d, J = 2.6 Hz, 1H), 7.24 (d, J = 5.0 Hz, 1H), 6.99-7.08 (m, 1H), 6.67 (d, J = 3.3 Hz, 1H), 4.21-4.30 (m, 2H), 4.03-4.09 (m, 1H), 3.76-3.90 (m, 5H), 3.61-3.67 (m, 1H), 3.29-3.34 (m, 1H), 1.23 (d, J = 6.8 Hz, 3H); $^{19}$F NMR (282 MHz, DMSO-$d_6$) δ −123.6. | 453.1 | A |
| 11 | See Example S1. | | |
| 12 | 4-{[(3R)-9-chloro-7-(5-fluoroindol-1-yl)-3-methyl-3,5-dihydro-2H-1,4-benzoxazepin-4-yl]methyl}-1H-pyrimidin-2-one 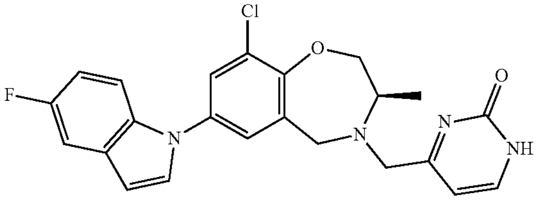 | 439.10 | L |
| | $^1$H NMR (300 MHz, DMSO-$d_6$) δ 11.7 (s, 1H), 7.86-7.89 (m, 1H), 7.72 (d, J = 3.3 Hz, 1H), 7.60 (d, J = 2.6 Hz, 2H), 7.34-7.42 (m, 2H), 7.03-7.13 (m, 1H), 6.67 (d, J = 3.3 Hz, 1H), 6.47-6.54 (m, 1H), 4.17-4.24 (m, 2H), 3.99-4.06 (m, 1H), 3.85 (d, J = 15.5 Hz, 1H), 3.43-3.63 (m, 2H), 3.34 (s, 1H), 1.23 (d, J = 6.8 Hz, 3H); $^{19}$F NMR (282 MHz, DMSO-$d_6$) δ −123.7. | 439.10 | L |
| 13 | 9-chloro-7-(5-fluoroindol-1-yl)-4-[(2-methoxypyrimidin-5-yl)methyl]-3,5-dihydro-2H-1,4-benzoxazepine 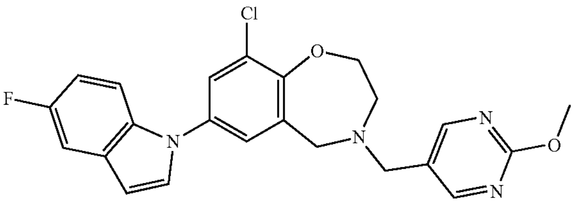 $^1$H NMR (300 MHz, DMSO-$d_6$) δ 8.53 (s, 2H), 7.71 (d, J = 3.3 Hz, 1H), 7.63 (d, J = 3.0 Hz, 1H), 7.49-7.54 (m, 3H), 7.02-7.09 (m, 1H), 6.68-6.70 (m, 1H), 4.15-4.20 (m, 2H), 3.90-3.97 (m, 5H), 3.66 (s, 2H), 3.03-3.09 (m, 2H); $^{19}$F NMR (282 MHz, DMSO-$d_6$) δ −123.6. | 439.1 | A |

TABLE 1-continued

| ID No. | Name, Structure, $^1$H-NMR, | MS (M + H)$^+$ | Method |
|---|---|---|---|
| 14 | 9-chloro-4-[(2-methoxypyrimidin-5-yl)methyl]-7-(5-methylindol-1-yl)-3,5-dihydro-2H-1,4-benzoxazepine 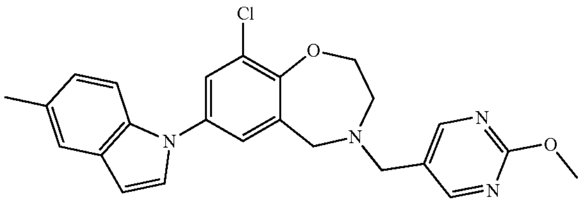 $^1$H NMR (300 MHz, DMSO-$d_6$) δ 8.53 (s, 2H), 7.58 (d, J = 3.9 Hz, 2H), 7.37-7.43 (m, 3H), 7.03 (d, J = 8.4 Hz, 1H), 6.59 (d, J = 3.0 Hz, 1H), 4.17-4.18 (m, 2H), 3.95 (s, 2H), 3.90 (s, 3H), 3.65 (s, 2H), 3.05-3.06 (m, 2H), 2.40 (s, 3H). | 435.0 | C |
| 15 | 9-chloro-7-(4,5-difluoroindol-1-yl)-4-[(2-methoxypyrimidin-5-yl)methyl]-3,5-dihydro-2H-1,4-benzoxazepine 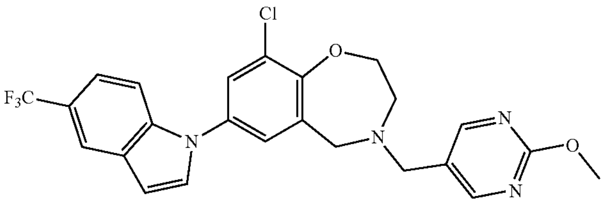 $^1$H NMR (300 MHz, DMSO-$d_6$) δ 8.53 (s, 2H), 8.07 (s, 1H), 7.82 (d, J = 3.4 Hz, 1H), 7.66-7.69 (m, 2H), 7.44-7.52 (m, 2H), 6.87 (d, J = 3.3 Hz, 1H), 4.15-4.23 (m, 2H), 3.96 (s, 2H), 3.90 (s, 3H), 3.66 (s, 2H), 3.02-3.08 (m, 2H); $^{19}$F NMR (282 MHz, DMSO-$d_6$) δ −58.5. | 489.0 | C |
| 16 | 1-{9-chloro-4-[(2-methoxypyrimidin-5-yl)methyl]-3,5-dihydro-2H-1,4-benzoxazepin-7-yl}indole-5-carbonitrile 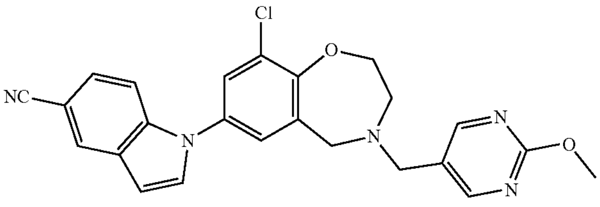 $^1$H NMR (300 MHz, DMSO-$d_6$) δ 8.53 (s, 2H), 8.22 (s, 1H), 7.85 (d, J = 3.3 Hz, 1H), 7.66-7.69 (m, 2H), 7.55 (d, J = 8.7 Hz, 1H), 7.44 (d, J = 2.7 Hz, 1H), 6.85 (d, J = 3.0 Hz, 1H), 4.18-4.19 (m, 2H), 3.96 (s, 2H), 3.89 (s, 3H), 3.66 (s, 2H), 3.05-3.06 (m, 2H). | 446.0 | C |
| 17 | See Example S2. | | |
| 18 | 1-{9-chloro-4-[(2-methoxypyrimidin-5-yl)methyl]-3,5-dihydro-2H-1,4-benzoxazepin-7-yl}-N,N-dimethylindol-5-amine 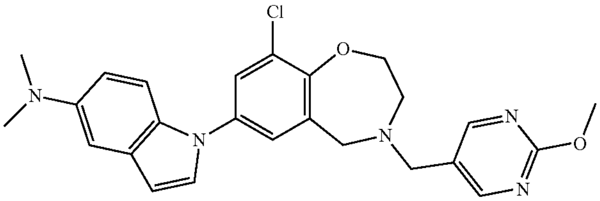 $^1$H NMR (300 MHz, DMSO-$d_6$) δ 8.53 (s, 2H), 7.49-7.59 (m, 2H), 7.33-7.45 (m, 2H), 6.80-6.96 (m, 2H), 6.53 (d, J = 3.3 Hz, 1H), 4.12-4.21 (m, 2H), 3.88-3.98 (m, 5H), 3.65 (s, 2H), 3.02-3.09 (m, 2H), 2.87 (s, 6H). | 464.2 | C |

TABLE 1-continued

| ID No. | Name, Structure, $^{1}$H-NMR, | MS $(M + H)^+$ | Method |
|---|---|---|---|
| 19 | 9-chloro-7-(5-methoxyindol-1-yl)-4-[(2-methoxypyrimidin-5-yl)methyl]-3,5-dihydro-2H-1,4-benzoxazepine<br>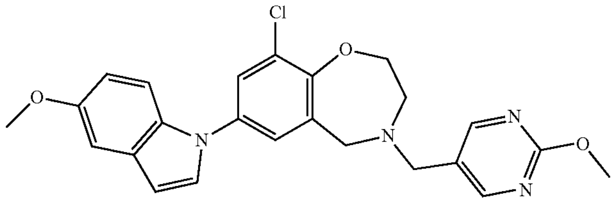<br>$^{1}$H NMR (300 MHz, DMSO-$d_6$) δ 8.53 (s, 2H), 7.59 (d, J = 6.6 Hz, 2H), 7.37-7.47 (m, 2H), 7.15 (d, J = 2.4 Hz, 1H), 6.84 (d, J = 8.7 Hz, 1H), 6.60 (d, J = 3.3 Hz, 1H), 4.16-4.22 (m, 2H), 3.96 (s, 2H), 3.90 (s, 3H), 3.78 (s, 3H), 3.66 (s, 2H), 3.05-3.06 (m, 2H). | 451.1 | C |
| 20 | 9-chloro-7-(5-chloroindol-1-yl)-4-[(2-methoxypyrimidin-5-yl)methyl]-3,5-dihydro-2H-1,4-benzoxazepine<br>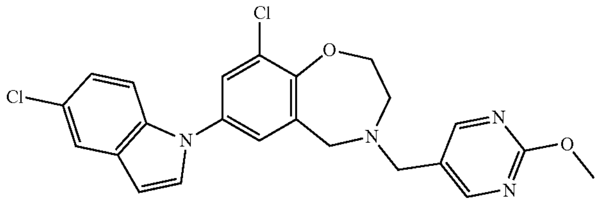<br>$^{1}$H NMR (300 MHz, DMSO-$d_6$) δ 8.53 (s, 2H), 7.71 (d, J = 3.0 Hz, 2H), 7.63 (d, J = 2.4 Hz, 1H), 7.52 (d, J = 9.0 Hz, 1H), 7.40 (d, J = 2.4 Hz, 1H), 7.20 (d, J = 8.7 Hz, 1H), 6.69 (d, J = 3.6 Hz, 1H), 4.17-4.18 (m, 2H), 3.96 (s, 2H), 3.90 (s, 3H), 3.66 (s, 2H), 3.05-3.06 (m, 2H). | 455.0 | C |
| 21 | 9-chloro-4-[(2-methoxypyrimidin-5-yl)methyl]-7-[5-(methylsulfanyl)indol-1-yl]-3,5-dihydro-2H-1,4-benzoxazepine<br>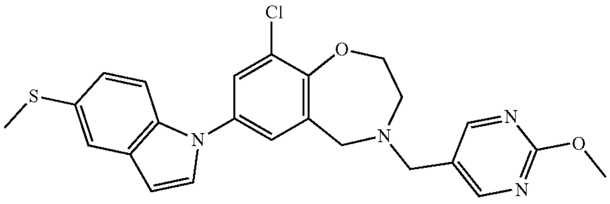<br>$^{1}$H NMR (400 MHz, DMSO-$d_6$) δ 8.53 (s, 2H), 7.58-7.67 (m, 3H), 7.48 (d, J = 8.0 Hz, 1H), 7.39 (d, J = 2.0 Hz, 1H), 7.18 (d, J = 8.8 Hz, 1H), 6.64 (d, J = 2.8 Hz, 1H), 4.17-4.18 (m, 2H), 4.06 (s, 2H), 3.96 (s, 3H), 3.66 (s, 2H), 3.05-3.06 (m, 2H), 2.50 (s, 3H). | 467.1 | C |
| 22 | 7-(5-bromoindol-1-yl)-9-chloro-4-[(2-methoxypyrimidin-5-yl)methyl]-3,5-dihydro-2H-1,4-benzoxazepine<br>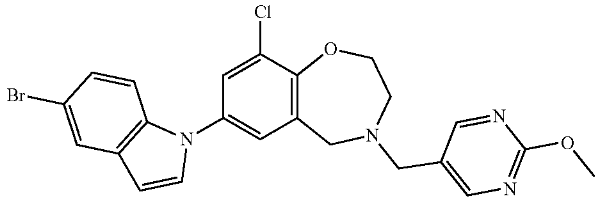<br>$^{1}$H NMR (300 MHz, DMSO-$d_6$) δ 8.53 (s, 2H), 7.86 (s, 1H), 7.70 (s, 1H), 7.63 (s, 1H), 7.48 (d, J = 8.7 Hz, 1H), 7.41 (s, 1H), 7.31-7.34 (m, 1H), 6.69 (d, J = 3.3 Hz, 1H), 4.18-4.19 (m, 2H), 3.96 (s, 2H), 3.90 (s, 3H), 3.66 (s, 2H), 3.07-3.08 (m, 2H). | 499.0 | C |

TABLE 1-continued

| ID No. | Name, Structure, $^{1}$H-NMR, | MS $(M + H)^+$ | Method |
|---|---|---|---|
| 23 | 9-chloro-N-(4-cyclopropylphenyl)-4-[(2-methoxypyrimidin-5-yl)methyl]-N-methyl-3,5-dihydro-2H-1,4-benzoxazepin-7-amine 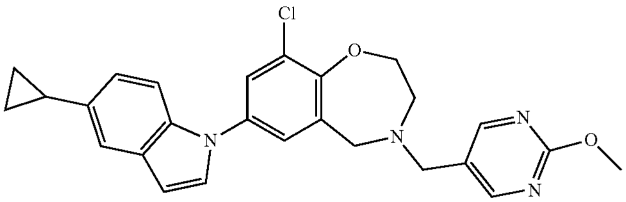 $^{1}$H NMR (300 MHz, DMSO-$d_6$) δ 8.53 (s, 2H), 7.56-7.63 (m, 2H), 7.32-7.46 (m, 3H), 6.90-6.98 (m, 1H), 6.59 (d, J = 3.0 Hz, 1H), 4.13-4.22 (m, 2H), 3.96 (s, 2H), 3.91 (s, 3H), 3.66 (s, 2H), 3.03-3.10 (m, 2H), 1.94-2.11 (m, 1H), 0.88-1.00 (m, 2H), 0.60-0.68 (m, 2H). | 461.2 | C |
| 24 | 9-chloro-7-(5,6-difluoroindol-1-yl)-4-[(2-methoxypyrimidin-5-yl)methyl]-3,5-dihydro-2H-1,4-benzoxazepine 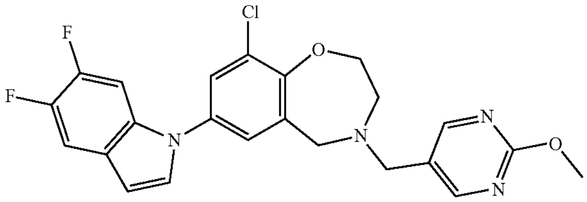 $^{1}$H NMR (300 MHz, DMSO-$d_6$) δ 8.52 (s, 2H), 7.63-7.69 (m, 3H), 7.41-7.56 (m, 1H), 7.41 (d, J = 2.7 Hz, 1H), 6.70 (d, J = 3.3 Hz, 1H), 4.12-4.23 (m, 2H), 3.97 (s, 2H), 3.90 (d, J = 2.3 Hz, 3H), 3.66 (s, 2H), 3.05-3.10 (m, 2H); $^{19}$F NMR (282 MHz, DMSO-$d_6$) δ −143.3, −147.1. | 457.0 | C |
| 25 | 9-chloro-7-(4,5-difluoroindol-1-yl)-4-[(2-methoxypyrimidin-5-yl)methyl]-3,5-dihydro-2H-1,4-benzoxazepine 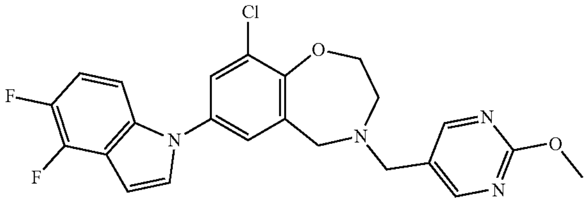 $^{1}$H NMR (300 MHz, DMSO-$d_6$) δ 8.53 (s, 2H), 7.77 (d, J = 3.4 Hz, 1H), 7.66 (d, J = 2.6 Hz, 1H), 7.43 (d, J = 2.7 Hz, 1H), 7.16-7.32 (m, 2H), 6.83 (d, J = 3.3 Hz, 1H), 4.15-4.20 (m, 2H), 3.96 (s, 2H), 3.90 (s, 3H), 3.66 (s, 2H), 3.00-3.08 (m, 2H); $^{19}$F NMR (282 MHz, DMSO-$d_6$) δ −148.5, −151.3. | 457.1 | C |
| 26 | 9-chloro-7-(5-chloro-4-fluoroindol-1-yl)-4-[(2-methoxypyrimidin-5-yl)methyl]-3,5-dihydro-2H-1,4-benzoxazepine 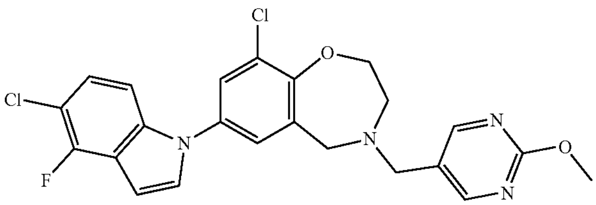 $^{1}$H NMR (300 MHz, DMSO-$d_6$) δ 8.53 (s, 2H), 7.76 (d, J = 3.4 Hz, 1H), 7.66 (d, J = 2.5 Hz, 1H), 7.42 (d, J = 2.6 Hz, 1H), 7.26-7.36 (m, 2H), 6.81 (d, J = 3.4 Hz, 1H), 4.18-4.19 (m, 2H), 3.95 (s, 2H), 3.89 (s, 3H), 3.66 (s, 2H), 3.06-3.08 (m, 2H); $^{19}$F NMR (282 MHz, DMSO-$d_6$) δ −124.6. | 473.1 | C |

TABLE 1-continued

| ID No. | Name, Structure, $^{1}$H-NMR, | MS (M + H)$^+$ | Method |
|---|---|---|---|
| 27 | 9-chloro-7-(3-chloro-5-fluoroindol-1-yl)-4-[(2-methoxypyrimidin-5-yl)methyl]-3,5-dihydro-2H-1,4-benzoxazepine<br>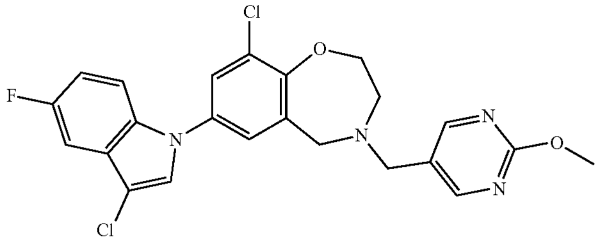<br>$^{1}$H NMR (400 MHz, DMSO-$d_6$) δ 8.52 (s, 2H), 7.96 (s, 1H), 7.65 (d, J = 2.8 Hz, 1H), 7.54-7.57 (m, 1H), 7.42 (d, J = 2.8 Hz, 1H), 7.33-7.36 (m, 1H), 7.13-7.18 (m, 1H), 4.14-4.19 (m, 2H), 3.94 (s, 2H), 3.90 (s, 3H), 3.65 (s, 2H), 3.05-3.07 (m, 2H); $^{19}$F NMR (376 MHz, DMSO-$d_6$) δ −121.6. | 473.1 | C |
| 28 | 9-chloro-7-(6-chloro-5-fluoroindol-1-yl)-4-[(2-methoxypyrimidin-5-yl)methyl]-3,5-dihydro-2H-1,4-benzoxazepine<br>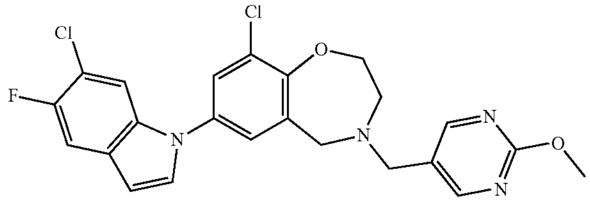<br>$^{1}$H NMR (300 MHz, DMSO-$d_6$) δ 8.52 (s, 2H), 7.74 (d, J = 3.3 Hz, 1H), 7.61-7.68 (m, 3H), 7.42 (d, J = 2.4 Hz, 1H), 6.71 (d, J = 3.3 Hz, 1H), 4.17-4.18 (m, 2H), 3.96 (s, 2H), 3.89 (s, 3H), 3.65 (s, 2H), 3.05-3.06 (m, 2H); $^{19}$F NMR (282 MHz, DMSO-$d_6$) δ −126.5. | 473.0 | C |
| 29 | 9-chloro-7-(3,5-dichloroindol-1-yl)-4-[(2-methoxypyrimidin-5-yl)methyl]-3,5-dihydro-2H-1,4-benzoxazepine<br>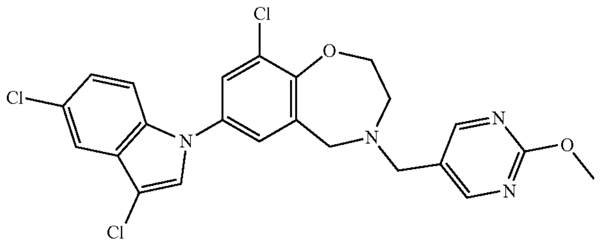<br>$^{1}$H NMR (400 MHz, DMSO-$d_6$) δ 8.53 (s, 2H), 8.01 (s, 1H), 7.69 (d, J = 4.0 Hz, 1H), 7.62 (d, J = 4.0 Hz, 1H), 7.57 (d, J = 8.0 Hz, 1H), 7.44 (d, J = 4.0 Hz, 1H), 7.32 (m, 1H), 4.18-4.19 (m, 2H), 3.95 (s, 2H), 3.90 (s, 3H), 3.65 (s, 2H), 3.06-3.07 (m, 2H). | 489.0 | C |

TABLE 1-continued

| ID No. | Name, Structure, $^1$H-NMR, | MS $(M + H)^+$ | Method |
|---|---|---|---|
| 30 | 9-chloro-7-(5-fluoro-2-methylindol-1-yl)-4-[(2-methoxypyrimidin-5-yl)methyl]-3,5-dihydro-2H-1,4-benzoxazepine 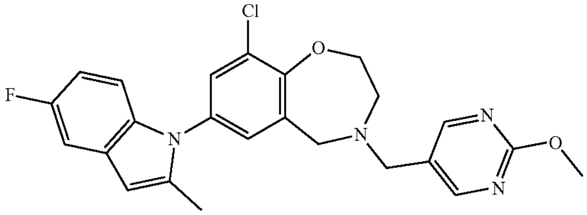 $^1$H NMR (300 MHz, DMSO-$d_6$) δ 8.51 (s, 2H), 7.55 (d, J = 2.5 Hz, 1H), 7.23-7.30 (m, 2H), 7.00-7.05 (m, 1H), 6.85-6.89 (m, 1H), 6.42 (s, 1H), 4.21-4.23 (m, 2H), 3.88-3.93 (m, 5H), 3.66 (s, 2H), 3.02-3.08 (m, 2H), 2.28 (s, 3H); $^{19}$F NMR (282 MHz, DMSO-$d_6$) δ −124.2. | 453.1 | C |
| 31 | 9-chloro-7-(5-fluoro-2-methylindol-1-yl)-4-[(2-methoxypyrimidin-5-yl)methyl]-3,5-dihydro-2H-1,4-benzoxazepine 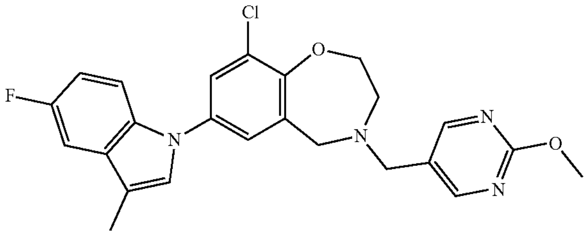 $^1$H NMR (300 MHz, DMSO-$d_6$) δ 8.53 (s, 2H), 7.57 (d, J = 2.4 Hz, 1H), 7.47-7.52 (m, 2H), 7.35-7.39 (m, 2H), 7.04 (t, J = 9.3 Hz, 1H), 4.17-4.18 (m, 2H), 3.95 (s, 2H), 3.90 (s, 3H), 3.65 (s, 2H), 3.05-3.06 (m, 2H), 2.28 (s, 3H); $^{19}$F NMR (282 MHz, DMSO-$d_6$) δ −123.7. | 453.0 | C |
| 32 | 9-chloro-4-[(2-methoxypyrimidin-5-yl)methyl]-7-{pyrrolo[2,3-b]pyridin-1-yl}-3,5-dihydro-2H-1,4-benzoxazepine 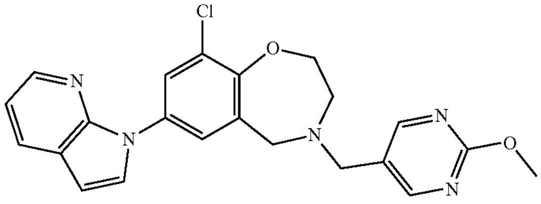 $^1$H NMR (300 MHz, DMSO-$d_6$) δ 8.57 (s, 2H), 8.39 (d, J = 4.5 Hz, 1H), 8.09 (d, J = 7.8 Hz, 1H), 8.02 (d, J = 2.4 Hz, 1H), 7.94 (d, J = 3.6 Hz, 1H), 7.69 (d, J = 2.4 Hz, 1H), 7.23 (d, J = 7.8 Hz, 1H), 6.73 (d, J = 3.9 Hz, 1H), 4.15-4.16 (m, 2H), 3.93 (s, 2H), 3.91 (s, 3H), 3.63 (s, 2H), 3.09-3.10 (m, 2H). | 422.0 | C |
| 33 | See Method C. | | |

TABLE 1-continued

| ID No. | Name, Structure, $^1$H-NMR, | MS $(M + H)^+$ | Method |
|---|---|---|---|
| 34 | 9-chloro-4-[(2-methoxypyrimidin-5-yl)methyl]-7-{pyrrolo[2,3-c]pyridin-1-yl}-3,5-dihydro-2H-1,4-benzoxazepine 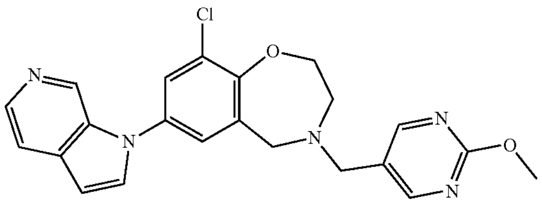 $^1$H NMR (300 MHz, DMSO-$d_6$) δ 8.89 (s, 1H), 8.53 (s, 2H), 8.24 (d, J = 5.4 Hz, 1H), 7.89 (d, J = 3.2 Hz, 1H), 7.74 (d, J = 2.6 Hz, 1H), 7.64-7.65 (m, 1H), 7.53-7.54 (m, 1H), 6.77-6.78 (m, 1H), 4.20-4.22 (m, 2H), 3.99 (s, 2H), 3.89 (s, 3H), 3.67 (s, 2H), 3.05-3.06 (m, 2H). | 440.1 | C |
| 35 | 9-chloro-7-{5-chloropyrrolo[2,3-c]pyridin-1-yl}-4-[(2-methoxypyrimidin-5-yl)methyl]-3,5-dihydro-2H-1,4-benzoxazepine 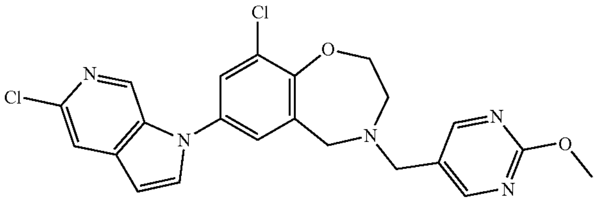 $^1$H NMR (300 MHz, DMSO-$d_6$) δ 8.67 (s, 1H), 8.52 (s, 2H), 7.99 (d, J = 3.3 Hz, 1H), 7.75 (d, J = 3.1 Hz, 2H), 7.52 (d, J = 2.7 Hz, 1H), 6.77 (d, J = 3.0 Hz, 1H), 4.18-4.19 (m, 2H), 3.97 (s, 2H), 3.90 (s, 3H), 3.66 (s, 2H), 3.05-3.06 (m, 2H). | 456.0 | C |
| 36 | 9-chloro-4-[(2-methoxypyrimidin-5-yl)methyl]-7-{pyrrolo[3,2-c]pyridin-1-yl}-3,5-dihydro-2H-1,4-benzoxazepine 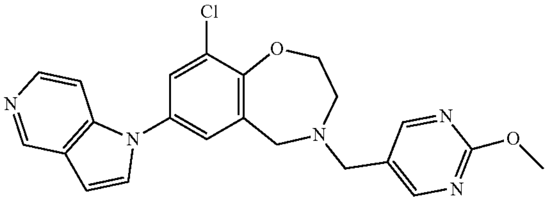 $^1$H NMR (300 MHz, DMSO-$d_6$) δ 8.94 (s, 1H), 8.54 (s, 2H), 8.29 (d, J = 5.4 Hz, 1H), 7.77 (s, 1H), 7.69 (s, 1H), 7.52 (d, J = 5.1 Hz, 1H), 7.45 (s, 1H), 6.86 (s, 1H), 4.19-4.20 (m, 2H), 3.98 (s, 2H), 3.90 (s, 3H), 3.67 (s, 2H), 3.07-3.08 (m, 2H). | 422.0 | C |
| 37 | 9-chloro-4-[(2-methoxypyrimidin-5-yl)methyl]-7-{pyrrolo[3,2-b]pyridin-1-yl}-3,5-dihydro-2H-1,4-benzoxazepine 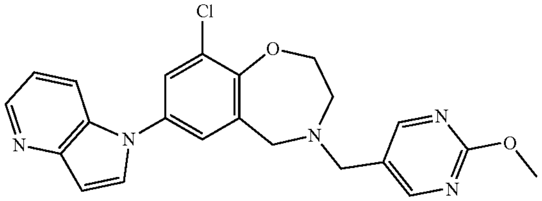 $^1$H NMR (300 MHz, DMSO-$d_6$) δ 8.54 (s, 2H), 8.45 (d, J = 4.6 Hz, 1H), 7.91-8.01 (m, 2H), 7.68 (d, J = 2.6 Hz, 1H), 7.45 (d, J = 2.7 Hz, 1H), 7.20-7.24 (m, 1H), 6.81-6.82 (m, 1H), 4.19-4.20 (m, 2H), 3.98 (s, 2H), 3.90 (s, 3H), 3.67 (s, 2H), 3.07-3.10 (m, 2H). | 422.0 | C |

TABLE 1-continued

| ID No. | Name, Structure, $^1$H-NMR, | MS $(M + H)^+$ | Method |
|---|---|---|---|
| 38 | 9-chloro-7-{5-chloropyrrolo[3,2-b]pyridin-1-yl}-4-[(2-methoxypyrimidin-5-yl)methyl]-3,5-dihydro-2H-1,4-benzoxazepine 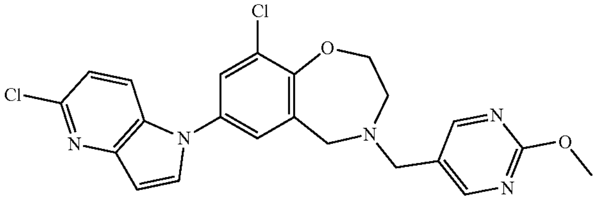 $^1$H NMR (300 MHz, DMSO-$d_6$) δ 8.53 (s, 2H), 8.05 (d, J = 3.3 Hz, 1H), 7.99 (d, J = 8.7 Hz, 1H), 7.71 (d, J = 2.7 Hz, 1H), 7.45 (d, J = 2.7 Hz, 1H), 7.25 (d, J = 8.7 Hz, 1H), 6.81 (d, J = 3.6 Hz, 1H), 4.17-4.18 (m, 2H), 3.96 (s, 2H), 3.89 (s, 3H), 3.65 (s, 2H), 3.05-3.06 (m, 2H). | 456.0 | C |
| 39 | 9-chloro-7-{imidazo[1,2-a]pyridin-5-yl}-4-[(2-methoxypyrimidin-5-yl)methyl]-3,5-dihydro-2H-1,4-benzoxazepine 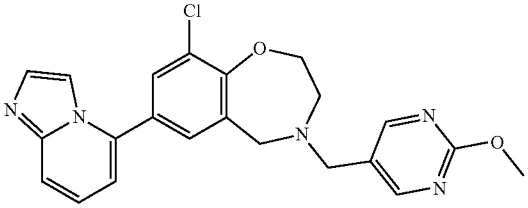 $^1$H NMR (300 MHz, DMSO-$d_6$) δ 8.52-8.54 (m, 2H), 7.74-7.80 (m, 1H), 7.60-7.68 (m, 2H), 7.43-7.51 (m, 1H), 7.29-7.36 (m, 1H), 6.90-7.00 (m, 1H), 4.16-4.19 (m, 2H), 3.89-3.95 (m, 5H), 3.65 (s, 2H), 3.06-3.07 (m, 2H). | 422.1 | E |
| 40 | See Example S3. | | |
| 41 | See Example S4. | | |
| 42 | 9-chloro-4-[(2-methoxypyrimidin-5-yl)methyl]-7-{pyrrolo[2,3-d]pyrimidin-7-yl}-3,5-dihydro-2H-1,4-benzoxazepine 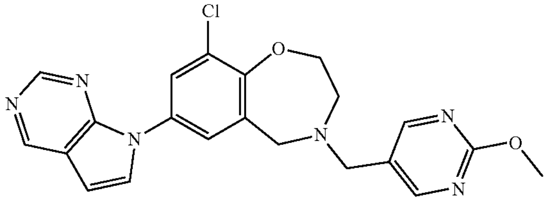 $^1$H NMR (300 MHz, DMSO-$d_6$) δ 9.13 (s, 1H), 8.92 (s, 1H), 8.56 (s, 2H), 7.99-8.03 (m, 2H), 7.68 (d, J = 2.4 Hz, 1H), 6.88 (d, J = 3.6 Hz, 1H), 4.18-4.19 (m, 2H), 3.91-3.94 (m, 5H), 3.64 (s, 2H), 3.09-3.10 (m, 2H). | 423.1 | C |

TABLE 1-continued

| ID No. | Name, Structure, $^1$H-NMR, | MS (M + H)$^+$ | Method |
|---|---|---|---|
| 43 | 9-chloro-4-[(2-methoxypyrimidin-5-yl)methyl]-7-{pyrrolo[2,3-b]pyrazin-5-yl}-3,5-dihydro-2H-1,4-benzoxazepine 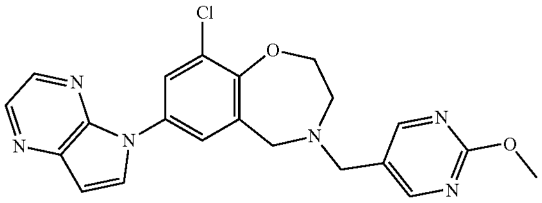 $^1$H NMR (300 MHz, DMSO-$d_6$) δ 8.56 (s, 3H), 8.41 (d, J = 4.7 Hz, 1H), 8.36 (d, J = 3.9 Hz, 1H), 8.01 (d, J = 2.7 Hz, 1H), 7.69 (d, J = 2.7 Hz, 1H), 6.93 (d, J = 3.6 Hz, 1H), 4.17-4.18 (m, 2H), 3.94 (s, 2H), 3.90 (s, 3H), 3.64 (s, 2H), 3.09-3.10 (m, 2H). | 423.0 | C |
| 44 | See Examples S5. | | |
| 45 | See Examples S6. | | |
| 46 | See Examples S7. | | |
| 47 | See Examples S8. | | |
| 48 | 2-{9-chloro-4-[(2-methoxypyrimidin-5-yl)methyl]-3,5-dihydro-2H-1,4-benzoxazepin-7-yl}-3H-isoindol-1-one 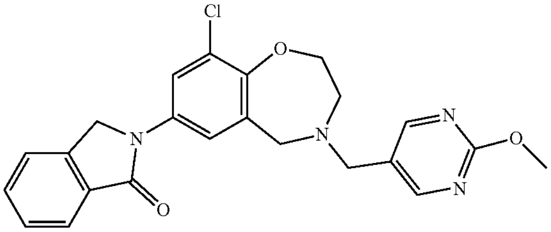 $^1$H NMR (300 MHz, DMSO-$d_6$) δ 8.53 (s, 2H), 8.04 (d, J = 2.4 Hz, 1H), 7.80 (d, J = 7.8 Hz, 1H), 7.64-7.69 (m, 2H), 7.54-7.62 (m, 2H), 5.01 (s, 2H), 4.09-4.13 (m, 2H), 3.88-3.92 (m, 5H), 3.60 (s, 2H), 2.93-3.04 (m, 2H). | 437.1 | C |
| 49 | See Method F. | | |
| 50 | See Example S9. | | |
| 51 | See Example S10. | | |
| 52 | 9-chloro-7-(2,3-dihydro-1,4-benzothiazin-4-yl)-4-[(2-methoxypyrimidin-5-yl)methyl]-3,5-dihydro-2H-1,4-benzoxazepine 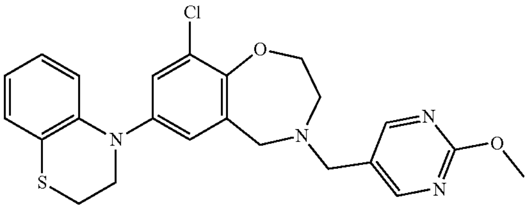 $^1$H NMR (300 MHz, DMSO-$d_6$) δ 8.49 (s, 2H), 7.08-7.13 (m, 2H), 6.90-6.95 (m, 2H), 6.69-6.81 (m, 2H), 4.08-4.14 (m, 2H), 3.90 (s, 3H), 3.78-3.84 (m, 4H), 3.59 (s, 2H), 3.09-3.12 (m, 2H), 3.01-3.02 (m, 2H). | 455.1 | F |

TABLE 1-continued

| ID No. | Name, Structure, $^1$H-NMR, | MS $(M + H)^+$ | Method |
|---|---|---|---|
| 53 | 4-{9-chloro-4-[(2-methoxypyrimidin-5-yl)methyl]-3,5-dihydro-2H-1,4-benzoxazepin-7-yl}-2,3-dihydro-1lambda6,4-benzothiazine-1,1-dione 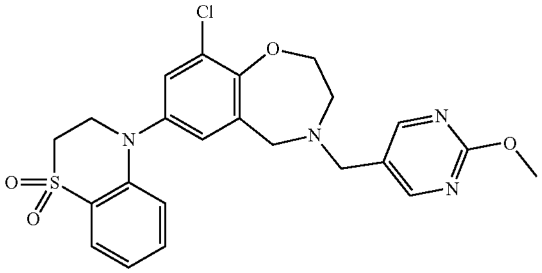 $^1$H NMR (300 MHz, DMSO-$d_6$) δ 8.50 (s, 2H), 7.67 (d, J = 7.5 Hz, 1H), 7.48 (d, J = 2.4 Hz, 1H), 7.32 (t, J = 7.8 Hz, 1H), 7.15 (d, J = 1.8 Hz, 1H), 6.89 (t, J = 4.5 Hz, 1H), 6.48 (d, J = 8.4 Hz, 1H), 4.09-4.15 (m, 4H), 3.89 (s, 3H), 3.84 (s, 2H), 3.65-3.69 (m, 2H), 3.34 (s, 2H), 3.06-3.07 (m, 2H). | 487.1 | F |
| 54 | 9-chloro-4-[(2-methoxypyrimidin-5-yl)methyl]-7-(naphthalen-1-yl)-3,5-dihydro-2H-1,4-benzoxazepine 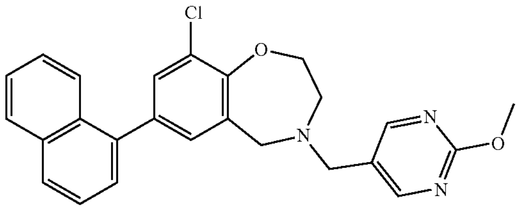 $^1$H NMR (300 MHz, DMSO-$d_6$) δ 8.53 (s, 2H), 7.93-8.06 (m, 2H), 7.77-7.87 (m, 1H), 7.51-7.63 (m, 3H), 7.42-7.50 (m, 2H), 7.23 (d, J = 3.0 Hz, 1H), 4.17-4.23 (m, 2H), 3.92 (s, 2H), 3.87 (s, 3H), 3.67 (s, 2H), 3.01-3.10 (m, 2H). | 432.1 | E |
| 55 | 9-chloro-4-[(2-methoxypyrimidin-5-yl)methyl]-7-(5,6,7,8-tetrahydronaphthalen-1-yl)-3,5-dihydro-2H-1,4-benzoxazepine 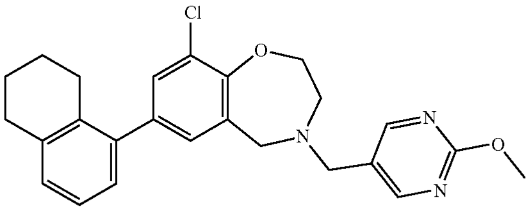 $^1$H NMR (300 MHz, DMSO-$d_6$) δ 8.50 (s, 2H), 7.27 (d, J = 3.0 Hz, 1H), 7.05-7.20 (m, 2H), 6.93-7.04 (m, 2H), 4.14-4.15 (m, 2H), 3.82-3.97 (m, 5H), 3.62 (s, 2H), 3.04-3.05 (m, 2H), 2.76-2.80 (m, 2H), 2.54 (s, 2H), 1.67-1.73 (m, 4H) | 436.1 | E |

TABLE 1-continued

| ID No. | Name, Structure, $^1$H-NMR, | MS $(M + H)^+$ | Method |
|---|---|---|---|
| 56 | 9-chloro-7-(5-fluoro-1H-indol-1-yl)-4-(thiazol-ylmethyl)-2,3,4,5-tetrahydrobenzo[f][1,4]oxazepine 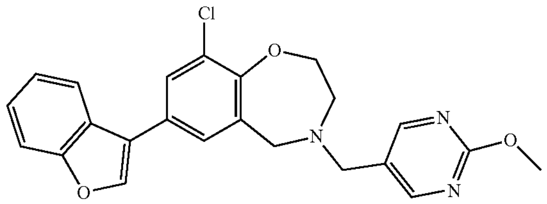 $^1$H NMR (300 MHz, DMSO-$d_6$) δ 8.54 (s, 2H), 8.40 (s, 1H), 7.92 (d, J = 6.0 Hz, 1H), 7.74 (d, J = 3.0 Hz, 1H), 7.65-7.69 (m, 1H), 7.52 (d, J = 3.0 Hz, 1H), 7.31-7.47 (m, 2H), 4.13-4.20 (m, 2H), 3.98 (s, 2H), 3.92 (s, 3H), 3.66 (s, 2H), 3.01-3.07 (m, 2H). | 422.1 | E |
| 57 | 9-chloro-7-(2,3-dihydrobenzo[b][1,4]dioxin-5-yl)-4-((2-methoxypyrimidin-5-yl)methyl)-2,3,4,5-tetrahydrobenzo[f][1,4]oxazepine 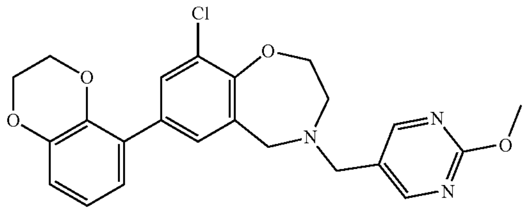 $^1$H NMR (300 MHz, DMSO-$d_6$) δ 8.51 (s, 2H), 7.49 (d, J = 2.1 Hz, 1H), 7.21 (d, J = 2.1 Hz, 1H), 6.87 (s, 3H), 4.30 (s, 4H), 4.12-4.14 (m, 2H), 3.90 (s, 3H), 3.85 (s, 2H), 3.61 (s, 2H), 3.07 (d, J = 3.0 Hz, 2H). | 440.0 | E |
| 58 | 5-{[9-chloro-7-(5-fluoroindol-1-yl)-3,5-dihydro-2H-1,4-benzoxazepin-4-yl]methyl}-1H-pyrimidin-2-one 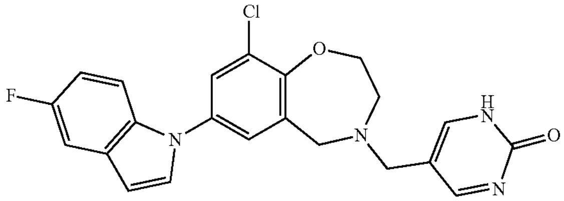 $^1$H NMR (400 MHz, $CD_3OD$) δ 8.29 (br, 2H), 7.55 (d, J = 4.0 Hz, 1H), 7.40-7.48 (m, 2H), 7.25-7.31 (m, 2H), 7.00 (m, 1H), 6.64 (s, 1H), 4.19-4.24 (m, 2H), 4.01 (s, 2H), 3.61 (s, 2H), 3.10-2.19 (m, 2H); $^{19}$F NMR (376 MHz, DMSO-$d_6$) δ −126.1. | 425.0 | A |
| 59 | 1-{9-chloro-4-[(2-oxo-1H-pyrimidin-5-yl)methyl]-3,5-dihydro-2H-1,4-benzoxazepin-7-yl}indole-5-carbonitrile 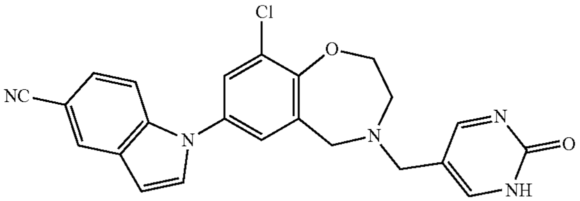 $^1$H NMR (400 MHz, $CD_3OD$) δ 8.28 (s, 2H), 8.10 (s, 1H), 7.55-7.62 (m, 3H), 7.51-7.53 (m, 1H), 7.34 (d, J = 2.6 Hz, 1H), 6.82-6.83 (m, 1H), 4.20-4.24 (m, 2H), 3.99 (s, 2H), 3.61 (s, 2H), 3.18-3.20 (m, 2H). | 432.0 | D |

TABLE 1-continued

| ID No. | Name, Structure, $^1$H-NMR, | MS $(M + H)^+$ | Method |
|---|---|---|---|
| 60 | 5-({9-chloro-7-[5-(trifluoromethyl)indol-1-yl]-3,5-dihydro-2H-1,4-benzoxazepin-4-yl}methyl)-1H-pyrimidin-2-one 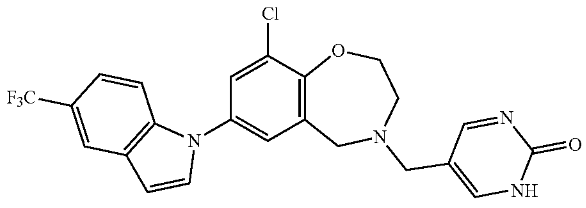 $^1$H NMR (300 MHz, $CD_3OD$) δ 8.29 (s, 2H), 7.99 (s, 1H), 7.55-7.67 (m, 3H), 7.48-7.50 (m, 1H), 7.35 (d, J = 3.0 Hz, 1H), 6.83 (d, J = 3.0 Hz, 1H), 4.19-4.28 (m, 2H), 3.99 (s, 2H), 3.61 (s, 2H), 3.15-3.24 (m, 2H); $^{19}$F NMR (282 MHz, $CD_3OD$) δ −61.6, −61.9, −62.7. | 475.1 | D |
| 61 | 5-({9-chloro-7-[5-(dimethylamino)indol-1-yl]-3,5-dihydro-2H-1,4-benzoxazepin-4-yl}methyl)-1H-pyrimidin-2-one 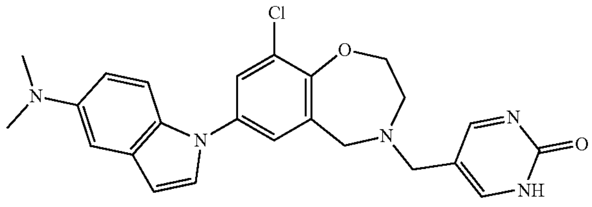 $^1$H NMR (300 MHz, DMSO-$d_6$) δ 8.16 (s, 2H), 7.49-7.58 (m, 2H), 7.37-7.45 (m, 2H), 6.84-6.97 (m, 2H), 6.53 (d, J = 3.3 Hz, 1H), 4.12-4.17 (m, 2H), 3.95 (s, 2H), 3.45 (s, 2H), 3.02-3.09 (m, 2H), 2.88 (s, 6H). | 450.1 | D |
| 62 | 5-{[9-chloro-7-(5-chloroindol-1-yl)-3,5-dihydro-2H-1,4-benzoxazepin-4-yl]methyl}-1H-pyrimidin-2-one 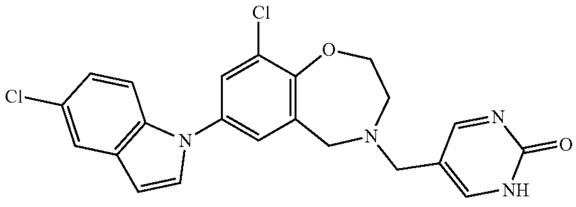 $^1$H NMR (400 MHz, $CD_3OD$) δ 8.28 (br, 2H), 7.63 (d, J = 1.6 Hz, 1H), 7.54 (d, J = 2.0 Hz, 1H), 7.44-7.48 (m, 2H), 7.31 (s, 1H), 7.20 (d, J = 8.8 Hz, 1H), 6.65 (d, J = 3.2 Hz, 1H), 4.21-4.22 (m, 2H), 3.97 (s, 2H), 3.64 (s, 2H), 3.18-3.19 (m, 2H). | 441.1 | C |

TABLE 1-continued

| ID No. | Name, Structure, $^1$H-NMR, | MS (M + H)$^+$ | Method |
|---|---|---|---|
| 63 | 5-{[9-chloro-7-(5,6-difluoroindol-1-yl)-3,5-dihydro-2H-1,4-benzoxazepin-4-yl]methyl}-1H-pyrimidin-2-one<br>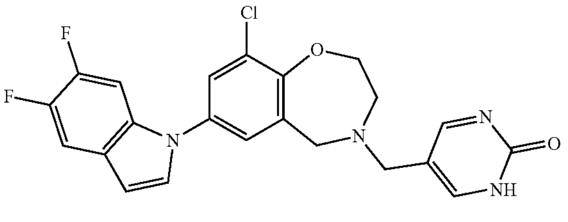<br>and/or<br>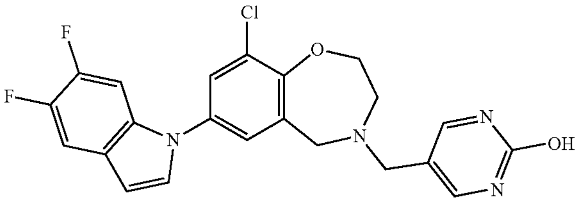<br>(A mixture of tautomers)<br>$^1$H NMR (300 MHz, $CD_3OD$) δ 8.28 (s, 1.7H), 7.97 (s, 0.3H), 7.57-7.41 (m, 2.3H), 7.41-7.26 (m, 1.7H), 7.26-7.10 (m, 0.7H), 6.80-6.63 (m, 1H), 6.45-6.31 (m, 0.3H), 4.18-4.21 (m, 2H), 3.97 (s, 1.4H), 3.87 (s, 0.6H), 3.58 (s, 1.4H), 3.54 (s, 0.6H), 3.13-3.19 (m, 2H); $^{19}$F NMR (282 MHz, $CD_3OD$) δ −145.2, −149.3. | 443.1 | D |
| 64 | 5-{[9-chloro-7-(4,5-difluoroindol-1-yl)-3,5-dihydro-2H-1,4-benzoxazepin-4-yl]methyl}-1H-pyrimidin-2-one<br>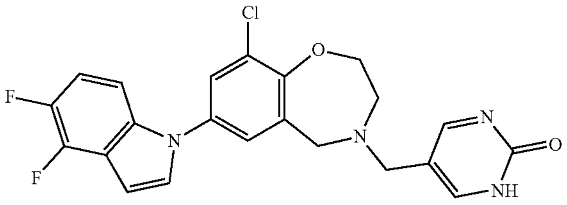<br>1H NMR (300 MHz, DMSO-$d_6$) δ 8.04 (br, 2H), 7.77 (d, J = 3.3 Hz, 1H), 7.69 (s, 1H), 7.49 (s, 1H), 7.22-7.34 (m, 2H), 6.84 (d, J = 3.3 Hz, 1H), 4.19 (s, 2H), 3.99 (br, 2H), 2.72-3.16 (m, 4H); $^{19}$F NMR (282 MHz, DMSO-$d_6$) δ −73.4, −148.5, −151.2. | 443.1 | D & M |
| 65 | 5-{[9-chloro-7-(5-chloro-4-fluoroindol-1-yl)-3,5-dihydro-2H-1,4-benzoxazepin-4-yl]methyl}-1H-pyrimidin-2-one<br>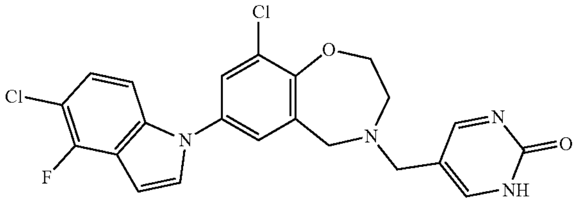<br>$^1$H NMR (400 MHz, DMSO-$d_6$) δ 11.87 (s, 1H), 8.55 (s, 1H), 7.66-7.77 (m, 3H), 7.46 (d, J = 2.4 Hz, 1H), 7.31-7.37 (m, 2H), 6.81 (d, J = 3.2 Hz, 1H), 4.16-4.18 (m, 2H), 3.94 (s, 2H), 3.46 (s, 2H), 3.06-3.08 (m, 2H); $^{19}$F NMR (376 MHz, DMSO-$d_6$) δ −124.7. | 459.0 | C |

TABLE 1-continued

| ID No. | Name, Structure, $^1$H-NMR, | MS $(M + H)^+$ | Method |
|---|---|---|---|
| 66 | 5-{[9-chloro-7-(5-fluoro-2-methylindol-1-yl)-3,5-dihydro-2H-1,4-benzoxazepin-4-yl]methyl}-1H-pyrimidin-2-one 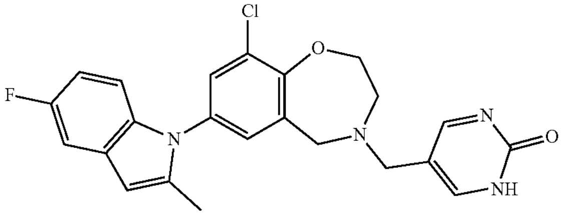 $^1$H NMR (400 MHz, $CD_3OD$) δ 8.27 (s, 2H), 7.40 (s, 1H), 7.10-7.18 (m, 2H), 6.90-7.00 (m, 1H), 6.81-6.85 (m, 1H), 6.37 (s, 1H), 4.23-4.25 (m, 2H), 3.97 (s, 2H), 3.59 (s, 2H), 3.17-3.19 (m, 2H), 2.30 (s, 3H); $^{19}$F NMR (367 MHz, $CD_3OD$) δ −126.8. | 439.1 | D |
| 67 | 5-{[9-chloro-7-(5-fluoro-3-methylindol-1-yl)-3,5-dihydro-2H-1,4-benzoxazepin-4-yl]methyl}-1H-pyrimidin-2-one 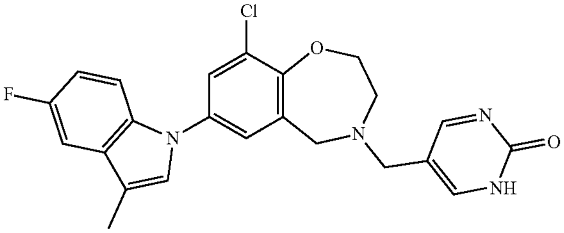 $^1$H NMR (400 MHz, $CD_3OD$) δ 8.28 (s, 2H), 7.50 (d, J = 2.4 Hz, 1H), 7.43 (m, 1H), 7.21-7.30 (m, 3H), 6.99 (t, J = 1.8 Hz, 1H), 4.17-4.24 (m, 2H), 3.97 (s, 2H), 3.60 (s, 2H), 3.15-3.22 (m, 2H), 2.34 (s, 3H); $^{19}$F NMR (376 MHz, $CD_3OD$) δ −123.5. | 439.0 | D |
| 68 | 5-[(9-chloro-7-{pyrrolo[3,2-b]pyridin-1-yl}-3,5-dihydro-2H-1,4-benzoxazepin-4-yl)methyl]-1H-pyrimidin-2-one 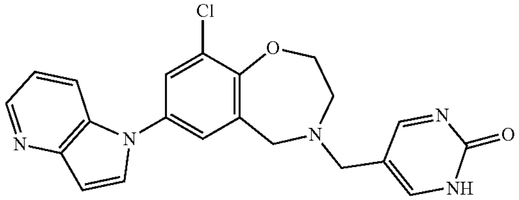 $^1$H NMR (300 MHz, DMSO-$d_6$) δ 11.78 (s, 1H), 8.44 (d, J = 4.5 Hz, 1H), 8.15 (s, 2H), 7.91-8.05 (m, 2H), 7.67 (d, J = 8.7 Hz, 1H), 7.47 (d, J = 2.7 Hz, 1H), 7.24 (d, J = 8.4 Hz, 1H), 6.82 (d, J = 3.3 Hz, 1H), 4.26-4.27 (m, 2H), 4.16 (s, 2H), 3.46 (s, 2H), 3.06-3.07 (m, 2H). | 408.0 | D |
| 69 | 5-[(9-chloro-7-{pyrrolo[2,3-b]pyridin-1-yl}-3,5-dihydro-2H-1,4-benzoxazepin-4-yl)methyl]-1H-pyrimidin-2-one 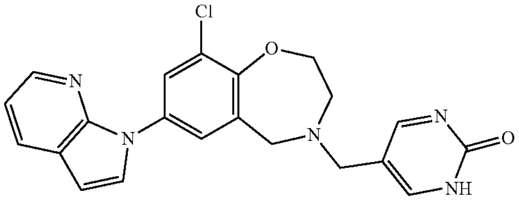 $^1$H NMR (400 MHz, $CD_3OD$) δ 8.31-8.32 (m, 3H), 8.08 (d, J = 7.8 Hz, 1H), 7.83 (d, J = 2.6 Hz, 1H), 7.68 (d, J = 3.7 Hz, 1H), 7.55 (d, J = 2.6 Hz, 1H), 7.20-7.23 (m, 1H), 6.71 (d, J = 3.7 Hz, 1H), 4.20-4.22 (m, 2H), 3.99 (s, 2H), 3.60 (s, 2H), 3.21-3.32 (m, 2H). | 408.1 | D |
| 70 | See Method D | | |

TABLE 1-continued

| ID No. | Name, Structure, $^{1}$H-NMR, | MS (M + H)$^+$ | Method |
|---|---|---|---|
| 71 | 5-[(9-chloro-7-{pyrrolo[2,3-c]pyridin-1-yl}-3,5-dihydro-2H-1,4-benzoxazepin-4-yl)methyl]-1H-pyrimidin-2-one 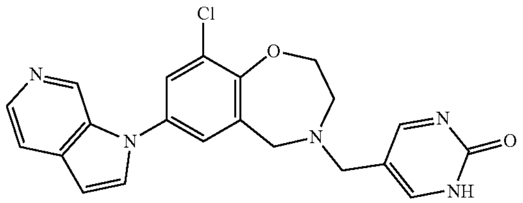 $^{1}$H NMR (300 MHz, DMSO-$d_6$) δ 8.98 (s, 1H), 8.02-8.32 (m, 4H), 7.79 (t, J = 4.8 Hz, 2H), 7.59 (d, J = 2.7 Hz, 1H), 6.88 (d, J = 3.3 Hz, 1H), 4.15-4.22 (m, 2H), 3.98 (s, 2H), 3.48 (s, 2H), 3.03-3.11 (m, 2H); $^{19}$F NMR (282 MHz, DMSO-$d_6$) δ −73.4. | 408.0 | D & M |
| 72 | 5-[(9-chloro-7-[5-chloropyrrolo[2,3-c]pyridin-1-yl}-3,5-dihydro-2H-1,4-benzoxazepin-4-yl)methyl]-1H-pyrimidin-2-one 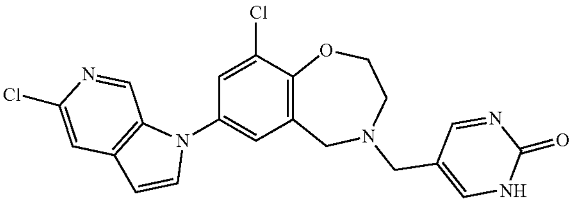 $^{1}$H NMR (400 MHz, $CD_3OD$) δ 8.58 (s, 1H), 8.29 (s, 2H), 7.80 (d, J = 3.2 Hz, 1H), 7.72 (s, 1H), 7.64 (d, J = 2.6 Hz, 1H), 7.41 (d, J = 2.7 Hz, 1H), 6.77 (d, J = 3.3 Hz, 1H), 4.20-4.27 (m, 2H), 4.00 (s, 2H), 3.61 (s, 2H), 3.24-3.17 (m, 2H). | 441.9 | D |
| 73 | 5-[(9-chloro-7-{pyrrolo[3,2-c]pyridin-1-yl}-3,5-dihydro-2H-1,4-benzoxazepin-4-yl)methyl]-1H-pyrimidin-2-one 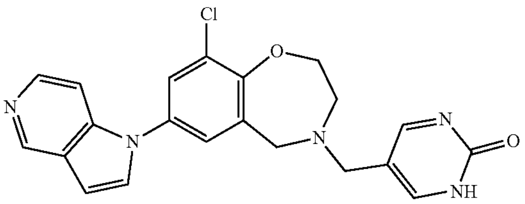 $^{1}$H NMR (300 MHz, DMSO-$d_6$) δ 9.43 (s, 1H), 8.58 (d, J = 6.9 Hz, 1H), 8.30 (s, 2H), 8.22 (d, J = 3.5 Hz, 1H), 8.06 (d, J = 6.8 Hz, 1H), 7.96 (d, J = 2.7 Hz, 1H), 7.69 (d, J = 2.7 Hz, 1H), 7.32 (d, J = 3.6 Hz, 1H), 4.34 (s, 4H), 3.93 (s, 2H), 3.43 (s, 2H). | 408.0 | D |

TABLE 1-continued

| ID No. | Name, Structure, $^1$H-NMR, | MS $(M + H)^+$ | Method |
|---|---|---|---|
| 74 | 5-[(9-chloro-7-{imidazo[1,2-a]pyridin-5-yl}-3,5-dihydro-2H-1,4-benzoxazepin-4-yl)methyl]-1H-pyrimidin-2-one 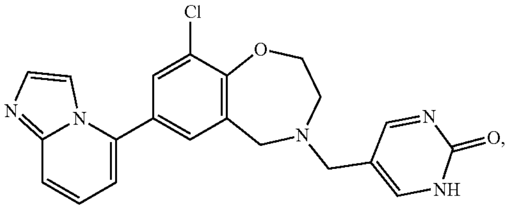 and 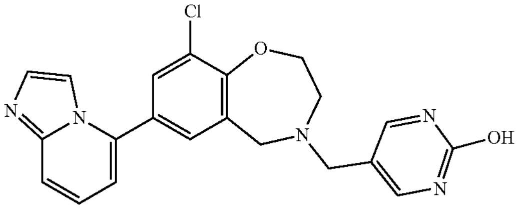 (A mixture of tautomers) $^1$H NMR (400 MHz, $CD_3OD$) δ 8.46-8.48 (m, 0.4H), 8.27 (s, 2H), 7.78 (s, 0.6H), 7.70-7.71 (m, 1H), 7.58-7.68 (m, 2H), 7.37-7.44 (m, 2H), 7.04 (t, J = 8.0 Hz, 0.4H), 6.92 (d, J = 6.8 Hz, 0.6H), 4.21-4.26 (m, 2H), 3.97 (s, 2H), 3.60 (s, 2H), 3.17-3.19 (m, 2H). | 408.0 | D |
| 75 | 5-[(9-chloro-7-{imidazo[1,5-a]pyridin-3-yl}-3,5-dihydro-2H-1,4-benzoxazepin-4-yl)methyl]-1H-pyrimidin-2-one 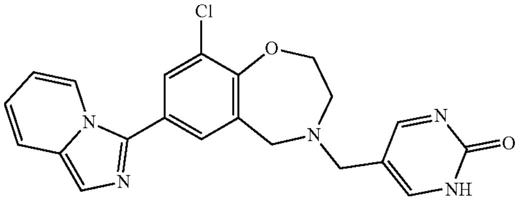 $^1$H NMR (300 MHz, DMSO-$d_6$) δ 11.86 (br, 1H), 8.44 (d, J = 6.0 Hz, 1H), 8.03-8.25 (m, 2H), 7.80 (d, J = 3.0 Hz, 1H), 7.60-7.69 (m, 2H), 7.54 (s, 1H), 6.83-6.91 (m, 1H), 6.73-6.81 (m, 1H), 4.10-4.20 (m, 2H), 3.97 (s, 2H), 3.46 (s, 2H), 2.98-3.08 (m, 2H). | 408.1 | D |
| 76 | See Method M. | | |
| 77 | 5-[(9-chloro-7-{pyrrolo[2,3-d]pyrimidin-7-yl}-3,5-dihydro-2H-1,4-benzoxazepin-4-yl)methyl]-1H-pyrimidin-2-one 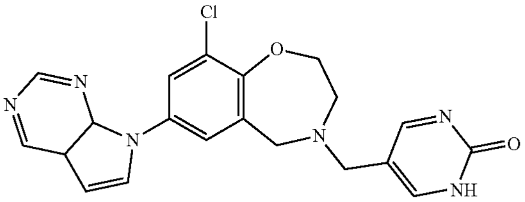 $^1$H NMR (300 MHz, DMSO-$d_6$) δ 8.52-8.54 (m, 2H), 7.74-7.80 (m, 1H), 7.60-7.68 (m, 2H), 7.43-7.51 (m, 1H), 7.29-7.36 (m, 1H), 6.90-7.00 (m, 1H), 4.16-4.19 (m, 2H), 3.89-3.95 (m, 4H), 3.65 (s, 2H), 3.06-3.07 (m, 2H). | 409.0 | D |

TABLE 1-continued

| ID No. | Name, Structure, $^1$H-NMR, | MS $(M + H)^+$ | Method |
| --- | --- | --- | --- |
| 78 | 5-{[9-chloro-7-(5-fluoro-2,3-dihydroindol-1-yl)-3,5-dihydro-2H-1,4-benzoxazepin-4-yl]methyl}-1H-pyrimidin-2-one; trifluoroacetic salt 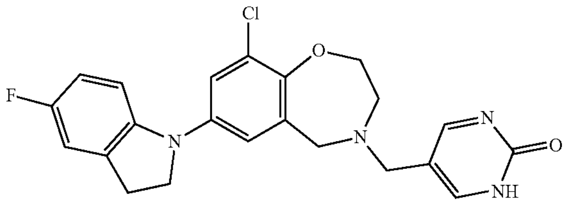 $^1$H NMR (300 MHz, DMSO-$d_6$) δ 8.33 (s, 2H), 7.26 (s, 2H), 7.02-7.14 (m, 2H), 6.84-6.97 (m, 1H), 4.02-4.80 (m, 6H), 3.88-3.99 (m, 2H), 3.60-3.70 (m, 2H), 3.05-3.17 (m, 2H); $^{19}$F (282 MHz, DMSO-$d_6$) δ −124.8. | 427.1 | D |
| 79 | 5-{[9-chloro-7-(5-chloro-2,3-dihydroindol-1-yl)-3,5-dihydro-2H-1,4-benzoxazepin-4-yl]methyl}-1H-pyrimidin-2-one 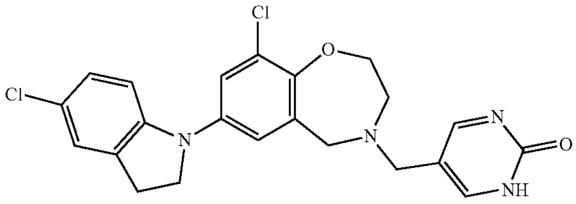 $^1$H NMR (300 MHz, DMSO-$d_6$) δ 11.89 (s, 1H), 7.69-8.43 (m, 2H), 7.21 (s, 1H), 6.91-7.17 (m, 3H), 6.96 (d, J = 12 Hz, 1H), 4.01-4.07 (m, 2H), 3.83-3.94 (m, 4H), 3.41 (s, 2H), 3.00-3.12 (m, 4H); $^{19}$F NMR (282 MHz, DMSO-$d_6$) δ −73.4. | 443.0 | D & M |
| 80 | 5-{[9-chloro-7-(6-fluoro-3,4-dihydro-2H-quinolin-1-yl)-3,5-dihydro-2H-1,4-benzoxazepin-4-yl]methyl}-1H-pyrimidin-2-one 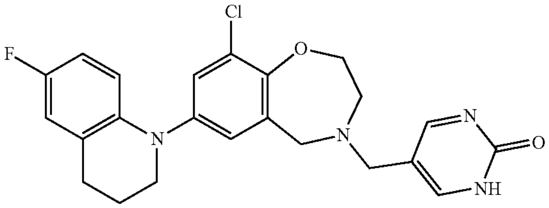 $^1$H NMR (300 MHz, DMSO-$d_6$) δ 11.88 (br, 1H), 8.13 (s, 2H), 7.14 (d, J = 2.6 Hz, 1H), 6.97 (d, J = 2.7 Hz, 1H), 6.90 (d, J = 9.4 Hz, 1H), 6.76-6.83 (m, 1H), 6.54-6.64 (m, 1H), 4.05-4.10 (m, 2H), 3.78 (s, 2H), 3.50 (t, J = 5.7 Hz, 2H), 3.48-3.50 (m, 2H), 2.99-3.02 (m, 2H), 2.76 (t, J = 5.7 Hz, 2H), 1.86-1.94 (m, 2H); $^{19}$F NMR (282 MHz, DMSO-$d_6$) δ −125.5. | 441.1 | D |
| 81 | 5-{[9-chloro-7-(7-fluoro-2,3-dihydro-1,4-benzoxazin-4-yl)-3,5-dihydro-2H-1,4-benzoxazepin-4-yl]methyl}-1H-pyrimidin-2-one 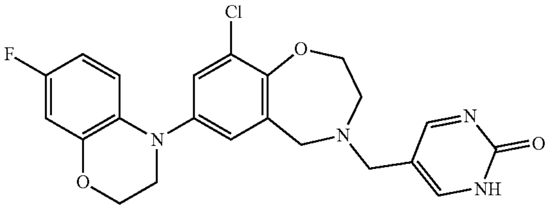 $^1$H NMR (300 MHz, DMSO-$d_6$) δ 11.85 (s, 1H), 8.12 (s, 2H), 7.17 (d, J = 2.7 Hz, 1H), 7.00 (d, J = 2.7 Hz, 1H), 6.71-6.83 (m, 2H), 6.59-6.67 (m, 1H), 4.18-4.27 (m, 2H), 4.03-4.09 (m, 2H), 3.79 (s, 2H), 3.63 (t, J = 4.2 Hz, 2H), 3.40 (s, 2H), 2.97-3.04 (m, 2H); $^{19}$F NMR (376 MHz, DMSO-$d_6$) δ −122.0. | 443.1 | D |

TABLE 1-continued

| ID No. | Name, Structure, $^1$H-NMR, | MS $(M + H)^+$ | Method |
|---|---|---|---|
| 82 | 5-{[9-chloro-7-(naphthalen-1-yl)-3,5-dihydro-2H-1,4-benzoxazepin-4-yl]methyl}-1H-pyrimidin-2-one 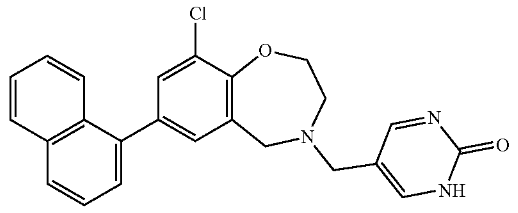 $^1$H NMR (300 MHz, $CD_3OD$) δ 8.27 (s, 2H), 7.85-7.97 (m, 2H), 7.76-7.84 (m, 1H), 7.33-7.58 (m, 5H), 7.16 (d, J = 3.0 Hz, 1H), 4.18-4.26 (m, 2H), 3.91 (s, 2H), 3.57 (s, 2H), 3.10-3.21 (m, 2H). | 418.1 | D |
| 83 | 5-{[9-chloro-7-(5,6,7,8-tetrahydronaphthalen-1-yl)-3,5-dihydro-2H-1,4-benzoxazepin-4-yl]methyl}-1H-pyrimidin-2-one 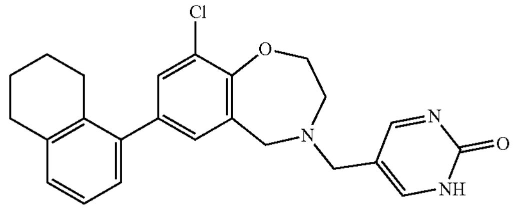 $^1$H NMR (400 MHz, $CD_3OD$) δ 8.26 (s, 2H), 7.22 (d, J = 4.0 Hz, 1H), 7.07-7.12 (m, 2H), 6.99 (d, J = 4.0 Hz, 1H), 6.93-6.99 (m, 1H), 4.14-4.21 (m, 2H), 3.92 (s, 2H), 3.56 (s, 2H), 3.19-3.11 (m, 2H), 2.84 (t, J = 6.0 Hz, 2H), 2.57 (t, J = 6.0 Hz, 2H), 1.68-1.87 (m, 4H) | 422.1 | D |
| 84 | 5-{[7-(1-benzofuran-3-yl)-9-chloro-3,5-dihydro-2H-1,4-benzoxazepin-4-yl]methyl}-1H-pyrimidin-2-one 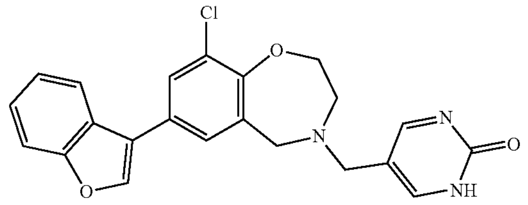 $^1$H NMR (300 MHz, $CD_3OD$) δ 8.26 (s, 2H), 8.03 (s, 1H), 7.82 (d, J = 6.0 Hz, 1H), 7.68 (d, J = 3.0 Hz, 1H), 7.53-7.65 (m, 1H), 7.33-7.45 (m, 3H), 4.17-4.25 (m, 2H), 3.98 (s, 2H), 3.59 (s, 2H), 3.10-3.19 (m, 2H). | 406.0 MS $(M - H)^-$ | D |
| 85 | 5-{[9-chloro-7-(2,3-dihydro-1,4-benzodioxin-5-yl)-3,5-dihydro-2H-1,4-benzoxazepin-4-yl]methyl}-1H-pyrimidin-2-one 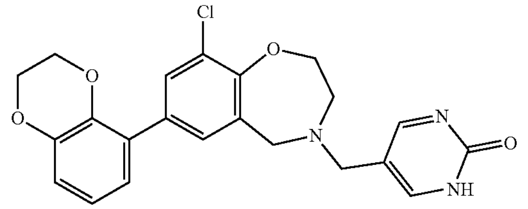 $^1$H NMR (300 MHz, DMSO-$d_6$) δ 11.85 (s, 1H), 8.13 (br, 2H), 7.49 (d, J = 3.0 Hz, 1H), 7.25 (d, J = 3.0 Hz, 1H), 6.87-6.86 (m, 3H), 4.27 (s, 4H), 4.11-4.12 (m, 2H), 3.87 (s, 2H), 3.42 (s, 2H), 3.05-3.06 (m, 2H). | 426.0 | D |

TABLE 1-continued

| ID No. | Name, Structure, $^1$H-NMR, | MS (M + H)$^+$ | Method |
|---|---|---|---|
| 86 | 9-chloro-7-(5-fluoroindol-1-yl)-4-(1H-pyrrol-3-ylmethyl)-3,5-dihydro-2H-1,4-benzoxazepine 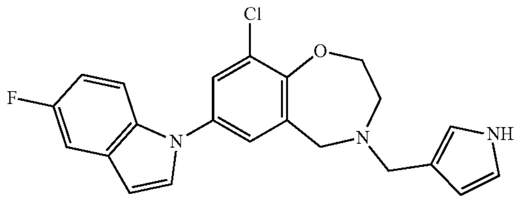 $^1$H NMR (300 MHz, $CD_3OD$) δ 7.49 (d, J = 2.4 Hz, 1H), 7.40-7.44 (m, 2H), 7.27 (d, J = 9.6 Hz, 1H), 7.21 (d, J = 2.4 Hz, 1H), 6.96 (t, J = 9.3 Hz, 1H), 6.71 (p, J = 2.1 Hz, 2H), 6.63 (d, J = 3.3 Hz, 1H), 6.13 (d, J = 2.7 Hz, 1H), 4.17-4.20 (m, 2H), 3.88 (s, 2H), 3.65 (s, 2H), 3.09-3.12 (m, 2H); $^{19}$F NMR (282 MHz, $CD_3OD$) δ 126.2. | 396.0 | A |
| 87 | 9-chloro-7-(5-fluoroindol-1-yl)-4-(1H-pyrrol-2-ylmethyl)-3,5-dihydro-2H-1,4-benzoxazepine 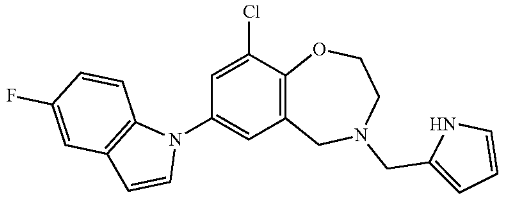 $^1$H NMR (300 MHz, $CD_3OD$) δ 7.47 (d, J = 2.7 Hz, 1H), 7.42 (q, J = 4.8 Hz, 2H), 7.28 (d, J = 9.3 Hz, 1H), 7.18 (d, J = 2.7 Hz, 1H), 6.95 (t, J = 9.3 Hz, 1H), 6.71 (d, J = 2.7 Hz, 1H), 6.60 (d, J = 3.3 Hz, 1H), 6.00-6.04 (m, 2H), 4.14-4.17 (m, 2H), 3.84 (s, 2H), 3.71 (s, 2H), 3.06-3.09 (m, 2H); $^{19}$F NMR (282 MHz, $CD_3OD$) δ −126.1. | 396.0 | A |
| 88 | tert-butyl 2-{[9-chloro-7-(5-fluoroindol-1-yl)-3,5-dihydro-2H-1,4-benzoxazepin-4-yl]methyl}pyrrole-1-carboxylate 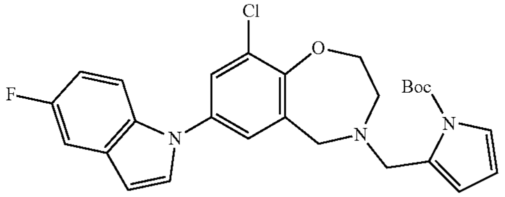 $^1$H NMR (300 MHz, $CD_3OD$) δ 7.47 (d, J = 2.7 Hz, 1H), 7.37-7.43 (m, 2H), 7.18-7.30 (m, 3H), 6.95 (t, J = 9.3, 1H), 6.62 (d, J = 3.3 Hz, 1H), 6.18 (d, J = 3.3 Hz, 1H), 6.11 (t, J = 3.3 Hz, 1H), 4.15-4.18 (m, 2H), 3.92 (m, 4H), 3.15-3.18 (m, 2H), 1.53 (s, 9H); $^{19}$F NMR (282 MHz, $CD_3OD$) δ 126.1. | 496.1 | A |
| 89 | 9-chloro-7-(5-fluoroindol-1-yl)-4-(furan-2-ylmethyl)-3,5-dihydro-2H-1,4-benzoxazepine 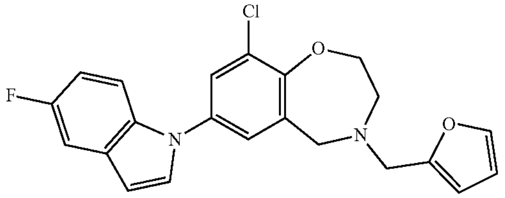 $^1$H NMR (300 MHz, $CD_3OD$) δ 7.41-7.55 (m, 4H), 7.26-7.31 (m, 2H), 6.96 (t, J = 9.3 Hz, 1H), 6.63 (d, J = 2.7 Hz, 1H), 6.39 (d, J = 3.0 Hz, 1H), 6.33 (d, J = 3.0 Hz, 1H), 4.17-4.20 (m, 2H), 3.92 (s, 2H), 3.79 (s, 2H), 3.13-3.15 (m, 2H); $^{19}$F NMR (282 MHz, DMSO-$d_6$) δ −126.1. | 397.1 | A |

TABLE 1-continued

| ID No. | Name, Structure, $^{1}$H-NMR, | MS (M + H)$^{+}$ | Method |
|---|---|---|---|
| 90 | 9-chloro-7-(5-fluoroindol-1-yl)-4-(furan-2-ylmethyl)-3,5-dihydro-2H-1,4-benzoxazepine<br>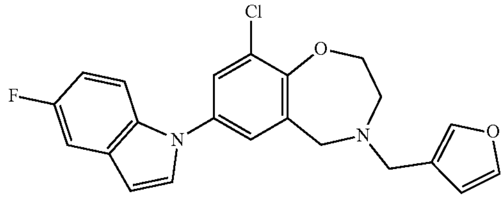<br>$^{1}$H NMR (300 MHz, $CD_3OD$) δ 7.39-7.59 (m, 5H), 7.23-7.30 (m, 2H), 6.98 (t, J = 9.0 Hz, 1H), 6.65 (d, J = 3.3 Hz, 1H), 6.48 (d, J = 1.8 Hz, 1H), 4.16-4.19 (m, 2H), 3.91 (s, 2H), 3.64 (s, 2H), 3.09-3.13 (m, 2H); $^{19}$F NMR (282 MHz, $CD_3OD$) δ −126.2. | 397.0 | A |
| 91 | $^{1}$H NMR (300 MHz, $CD_3OD$) δ 7.48 (d, J = 2.4 Hz, 1H), 7.42 (t, J = 7.2 Hz, 2H), 7.34 (d, J = 4.8 Hz, 1H), 7.28 (d, J = 9.6 Hz, 1H), 7.16 (d, J = 2.7 Hz, 1H), 6.92-6.99 (m, 3H), 6.62 (d, J = 3.3 Hz, 1H), 4.16-4.19 (m, 2H), 3.95 (s, 2H), 3.92 (s, 2H), 3.15-3.18 (m, 2H); $^{19}$F NMR (282 MHz, $CD_3OD$) δ −126.1. | | |
| 92 | 9-chloro-7-(5-fluoroindol-1-yl)-4-(thiophen-3-ylmethyl)-3,5-dihydro-2H-1,4-benzoxazepine<br>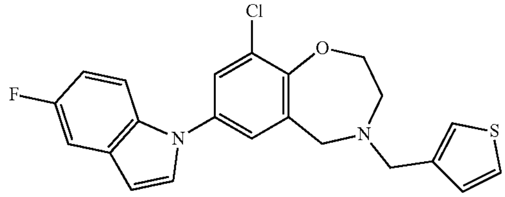<br>$^{1}$H NMR (300 MHz, $CD_3OD$) δ 7.50 (d, J = 2.7 Hz, 1H), 7.38-7.44 (m, 3H), 7.26-7.30 (m, 2H), 7.12-7.18 (m, 2H), 6.96 (t, J = 9.3 Hz, 1H), 6.63 (d, J = 3.3 Hz, 1H), 4.17-4.20 (m, 2H), 3.90 (s, 2H), 3.78 (s, 2H), 3.11-3.13 (m, 2H); $^{19}$F NMR (282 MHz, $CD_3OD$) δ 126.1. | 413.0 | A |
| 93 | Method G. | | |
| 94 | 9-chloro-7-(5-fluoro-1H-indol-1-yl)-4-(isoxazol-5-ylmethyl)-2,3,4,5-tetrahydrobenzo[f][1,4]oxazepine<br>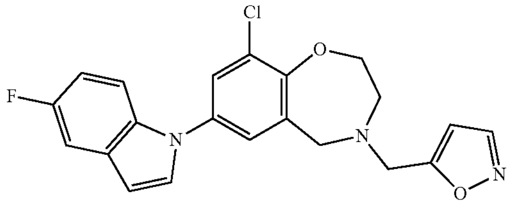<br>$^{1}$H NMR (300 MHz, $CD_3OD$) δ 8.39 (s, 1H), 7.54 (d, J = 2.7 Hz, 1H), 7.43-7.47 (m, 2H), 7.26-7.31 (m, 2H), 6.93-7.00 (m, 1H), 6.66 (d, J = 3.3 Hz, 1H), 6.43 (d, J = 1.8 Hz, 1H), 4.18-4.27 (m, 2H), 3.97-4.01 (m, 4H), 3.18-3.27 (m, 2H); $^{19}$F NMR (282 MHz, $CD_3OD$) δ −126.1. | 398.0 | G |

TABLE 1-continued

| ID No. | Name, Structure, $^{1}$H-NMR, | MS (M + H)$^{+}$ | Method |
|---|---|---|---|
| 95 | 9-chloro-7-(5-fluoro-1H-indol-1-yl)-4-(oxazol-4-ylmethyl)-2,3,4,5-tetrahydrobenzo[f][1,4]oxazepine<br>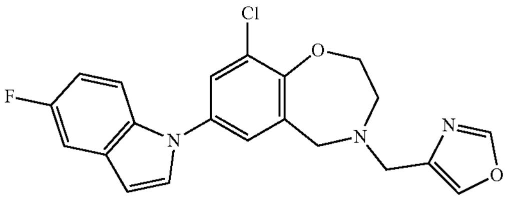<br>$^{1}$H NMR (300 MHz, $CD_3OD$) δ 8.18 (s, 1H), 7.88 (s, 1H), 7.42-7.56 (m, 3H), 7.26-7.36 (m, 2H), 6.99 (t, J = 9.2 Hz, 1H), 6.65 (d, J = 3.3 Hz, 1H), 4.13-4.20 (m, 2H), 3.97 (s, 2H), 3.72 (s, 2H), 3.12-3.18 (m, 2H); $^{19}$F NMR (300 MHz, $CD_3OD$) δ −126.2. | 398.0 | A |
| 96 | 9-chloro-7-(5-fluoro-1H-indol-1-yl)-4-(isothiazol-4-ylmethyl)-2,3,4,5-tetrahydrobenzo[f][1,4]oxazepine<br>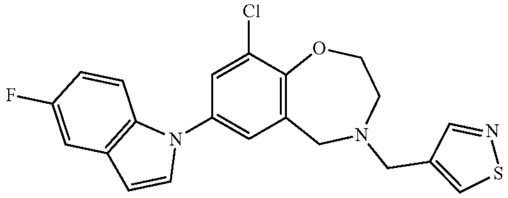<br>$^{1}$H NMR (300 MHz, $CD_3OD$) δ 8.77 (s, 1H), 8.51 (s, 1H), 7.53 (d, J = 2.6 Hz, 1H), 7.40-7.51 (m, 2H), 7.31 (d, J = 9.5 Hz, 1H), 7.23 (d, J = 2.6 Hz, 1H), 6.99 (t, J = 9.1 Hz, 1H), 6.65 (d, J = 3.3 Hz, 1H), 4.18-4.27 (m, 2H), 3.90-3.94 (m, 4H), 3.11-3.20 (m, 2H); $^{19}$F NMR (300 MHz, $CD_3OD$) δ −126.1. | 413.9 | A |
| 97 | 9-chloro-7-(5-fluoro-1H-indol-1-yl)-4-(isothiazol-3-ylmethyl)-2,3,4,5-tetrahydrofuran[f][1,4]oxazepine<br>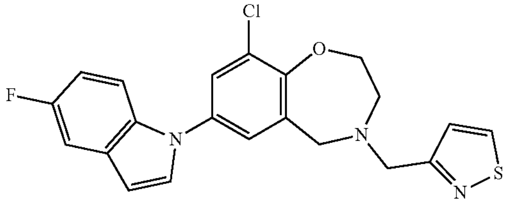<br>$^{1}$H NMR (300 MHz, $CD_3OD$) δ 8.91 (d, J = 4.7 Hz, 1H), 7.39-7.53 (m, 4H), 7.26-7.30 (m, 1H), 7.17-7.20 (m, 1H), 6.94-7.00 (m, 1H), 6.66 (d, J = 3.3 Hz, 1H), 4.19-4.22 (m, 2H), 3.95 (s, 4H), 3.20-3.29 (m, 2H); $^{19}$F NMR (300 MHz, $CD_3OD$) δ −126.2. | 414.0 | G |
| 98 | 9-chloro-7-(5-fluoro-1H-indol-1-yl)-4-(isothiazol-5-ylmethyl)-2,3,4,5-tetrahydrobenzo[f][1,4]oxazepine<br>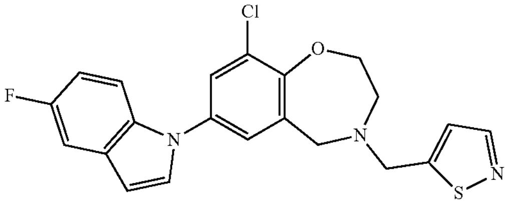<br>$^{1}$H NMR (300 MHz, $CD_3OD$) δ 8.44 (s, 1H), 7.52 (d, J = 2.6 Hz, 1H), 7.40-7.44 (m, 2H), 7.23-7.35 (m, 1H), 7.20 (d, J = 2.6 Hz, 1H), 7.18 (d, J = 2.6 Hz, 1H), 6.98 (t, J = 9.1 Hz, 1H), 6.64 (d, J = 3.3 Hz, 1H), 4.17-4.25 (m, 2H), 4.14 (s, 2H), 4.00 (s, 2H), 3.21-3.25 (m, 2H); $^{19}$F NMR (300 MHz, $CD_3OD$) δ −126.0. | 457.0 | A |

TABLE 1-continued

| ID No. | Name, Structure, $^{1}$H-NMR, | MS (M + H)$^+$ | Method |
|---|---|---|---|
| 99 | 9-chloro-7-(5-fluoro-1H-indol-1-yl)-4-(thiazol-5-ylmethyl)-2,3,4,5-tetrahydrobenzo[f][1,4]oxazepine 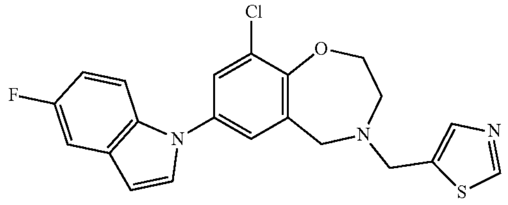 $^{1}$H NMR (300 MHz, $CD_3OD$) δ 8.95 (d, J = 3.0 Hz, 1H), 7.75 (d, J = 3.0 Hz, 1H), 7.50 (d, J = 3.0 Hz, 1H), 7.42 (m, 2H), 7.29 (m, 1H), 7.17 (d, J = 3.0 Hz, 1H), 6.92-7.03 (m, 1H), 6.63 (d, J = 3.0 Hz, 1H), 4.15-4.24 (m, 2H), 4.03 (s, 2H), 3.94 (s, 2H), 3.14-3.23 (m, 2H); $^{19}$F NMR (282 MHz, $CD_3OD$) δ −126.0. | 414.0 | A |
| 100 | See Example S11. | | |
| 101 | 9-chloro-7-(5-fluoroindol-1-yl)-4-(1H-pyrazol-3-ylmethyl)-3,5-dihydro-2H-1,4-benzoxazepine 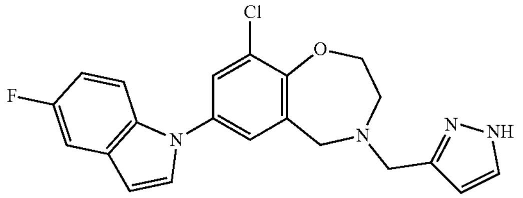 $^{1}$H NMR (300 MHz, $CD_3OD$) δ 7.63 (s, 1H), 7.40-7.49 (m, 3H), 7.28 (d, J = 9.3 Hz, 1H), 7.19 (d, J = 1.8 Hz, 1H), 6.97 (t, J = 9.3 Hz, 1H), 6.62 (d, J = 3.3 Hz, 1H), 6.35 (s, 1H), 4.14-4.20 (m, 2H), 3.92 (s, 2H), 3.81 (s, 2H), 3.12-3.15 (m, 2H); $^{19}$F NMR (282 MHz, $CD_3OD$) δ −126.1. | 397.0 | A |
| 102 | 9-chloro-7-(5-fluoroindol-1-yl)-4-[(1-methylpyrazol-3-yl)methyl]-3,5-dihydro-2H-1,4-benzoxazepine 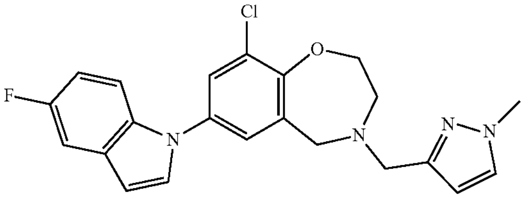 $^{1}$H NMR (300 MHz, $CD_3OD$) δ 7.54 (s, 1H), 7.42-7.53 (m, 3H), 7.23-7.30 (m, 2H), 6.96 (t, J = 9.3, 1H), 6.63 (d, J = 3.3 1H), 6.29 (d, J = 2.4 Hz, 1H), 4.17-4.20 (m, 2H), 3.92 (s, 2H), 3.84 (s, 3H), 3.74 (s, 2H), 3.12-3.15 (m, 2H); $^{19}$F NMR (282 MHz, DMSO-$d_6$) δ −126.2. | 411.0 | A |
| 103 | See Method B. | | |

TABLE 1-continued

| ID No. | Name, Structure, $^1$H-NMR, | MS (M + H)$^+$ | Method |
|---|---|---|---|
| 104 | tert-butyl 4-{[9-chloro-7-(5-fluoroindol-1-yl)-3,5-dihydro-2H-1,4-benzoxazepin-4-yl]methyl}pyrazole-1-carboxylate<br>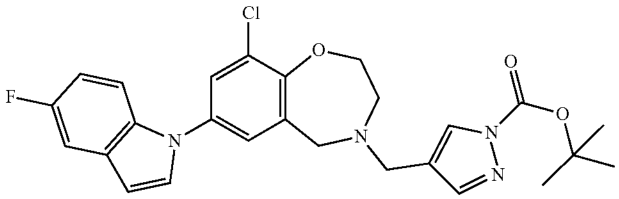<br>$^1$H NMR (300 MHz, DMSO-$d_6$) δ 8.14 (s, 1H), 7.75 (s, 1H), 7.70-7.71 (m, 1H), 7.62 (d, J = 2.5 Hz, 1H), 7.51 (d, J = 8.9 Hz, 1H), 7.40-7.44 (m, 2H), 7.05 (t, J = 9.0 Hz, 1H), 6.67 (s, 1H), 4.15-4.16 (m, 2H), 3.91 (s, 2H), 3.61 (s, 2H), 3.05-3.06 (m, 2H), 1.53 (s, 9H); $^{19}$F NMR (282 MHz, DMSO-$d_6$) δ −123.7 | 497.1 | A |
| 105 | See Example S12. | | |
| 106 | See Method A. | | |
| 107 | 9-chloro-7-(5-fluoroindol-1-yl)-4-(3H-imidazol-4-ylmethyl)-3,5-dihydro-2H-1,4-benzoxazepine<br>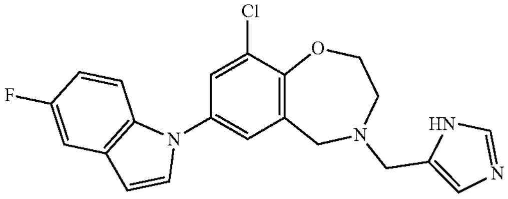<br>$^1$H NMR (300 MHz, $CD_3OD$) δ 7.65 (d, J = 1.2 Hz, 1H), 7.40-7.49 (m, 3H), 7.28 (d, J = 9.6, 1H), 7.23 (d, J = 2.4 Hz, 1H), 7.03 (d, J = 1.2 Hz, 1H), 6.96 (t, J = 9.3, 1H), 6.63 (t, J = 3.3 Hz, 1H), 4.17-4.20 (m, 2H), 3.91 (s, 2H), 3.75 (s, 2H), 3.11-3.14 (m, 2H); $^{19}$F NMR (282 MHz, $CD_3OD$) δ −126.2. | 397.0 | A |
| 108 | See Example S13. | | |
| 109 | See Example S14. | | |
| 110 | 4-((1,2,4-oxadiazol-3-yl)methyl)-9-chloro-7-(5-fluoro-1H-indol-1-yl)-2,3,4,5-tetrahydrobenzo[f][1,4]oxazepine<br>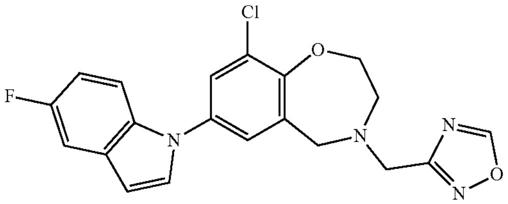<br>$^1$H NMR (300 MHz, DMSO-$d_6$) δ 9.61 (s, 1H), 7.72 (d, J = 3.3 Hz, 1H), 7.50-7.67 (m, 2H), 7.38-7.50 (m, 2H), 7.07 (t, J = 9.2 Hz, 1H), 6.69 (d, J = 3.3 Hz, 1H), 4.18-4.19 (m, 2H), 3.89-3.99 (m, 4H), 3.07-3.19 (m, 2H); $^{19}$F NMR (300 MHz, DMSO-$d_6$) δ −123.1. | 399.0 | A |
| 111 | See Example S15. | | |

TABLE 1-continued

| ID No. | Name, Structure, $^1$H-NMR, | MS $(M + H)^+$ | Method |
|---|---|---|---|
| 112 | 9-chloro-7-(5-fluoroindol-1-yl)-4-(1,3,4-thiadiazol-2-ylmethyl)-3,5-dihydro-2H-1,4-benzoxazepine 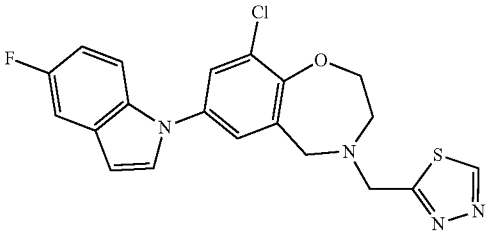 $^1$H NMR (300 MHz, $CDCl_3$) δ 9.14 (s, 1H), 7.42-7.47 (m, 2H), 7.28-7.32 (m, 2H), 7.07 (d, J = 2.4 Hz, 1H), 7.00 (t, J = 9.0 Hz, 1H), 6.62 (d, J = 3.3 Hz, 1H), 4.20-4.25 (m, 4H), 3.98 (s, 2H), 3.29-3.31 (m, 2H); $^{19}$F NMR (282 MHz, $CDCl_3$) δ −123.7. | 415.0 | G |
| 113 | 9-chloro-7-(5-fluoroindol-1-yl)-4-(1,2,5-thiadiazol-3-ylmethyl)-3,5-dihydro-2H-1,4-benzoxazepine 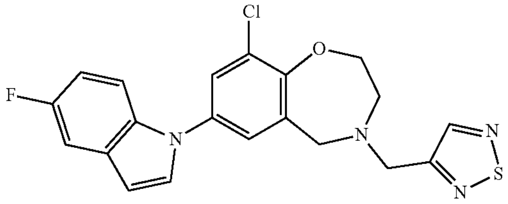 $^1$H NMR (300 MHz, DMSO-$d_6$) δ 8.85 (s, 1H), 7.72 (d, J = 3.3 Hz, 1H), 7.55-7.63 (m, 2H), 7.35-7.48 (m, 2H), 7.03-7.10 (m, 1H), 6.69 (d, J = 3, 1H), 4.18-4.21 (m, 2H), 4.06 (s, 2H), 3.97 (s, 2H), 3.12-3.21 (m, 2H); $^{19}$F NMR (282 MHz, DMSO-$d_6$) δ −123.5. | 415.1 | G |
| 114 | 4-((1,2,4-thiadiazol-3-yl)methyl)-9-chloro-7-(5-fluoro-1H-indol-1-yl)-2,3,4,5-tetrahydrobenzo[f][1,4]oxazepane 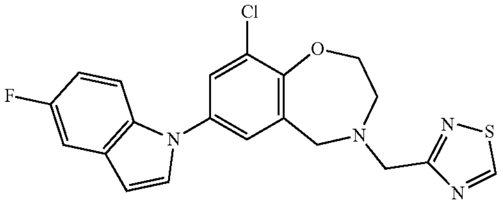 | | |
| 115 | See Example S16. | | |
| 116 | See Example S17. | | |
| 117 | See Example S18. | | |
| 118 | See Example S19. | | |

TABLE 1-continued

| ID No. | Name, Structure, $^{1}$H-NMR, | MS $(M + H)^{+}$ | Method |
|---|---|---|---|
| 119 | 2-{[9-chloro-7-(5-fluoroindol-1-yl)-3,5-dihydro-2H-1,4-benzoxazepin-4-yl]methyl}phenol 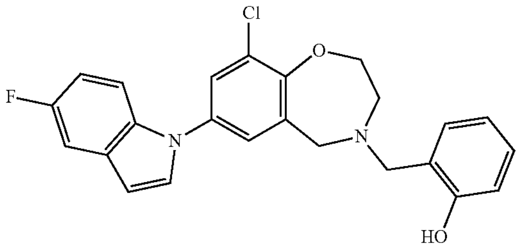 $^{1}$H NMR (300 MHz, DMSO-$d_6$) δ 9.94 (s, 1H), 7.72 (d, J = 3.3 Hz, 1H), 7.64 (d, J = 2.7 Hz, 1H), 7.48-7.57 (m, 1H), 7.38-7.47 (m, 1H), 7.33 (d, J = 2.7 Hz, 1H), 7.01-7.21 (m, 3H), 6.73-6.83 (m, 2H), 6.65-6.72 (m, 1H), 4.17-4.23 (m, 2H), 3.99 (s, 2H), 3.77 (s, 2H), 3.09-3.15 (m, 2H); $^{19}$F NMR (282 MHz, DMSO-$d_6$) δ −123.5. | 423.0 | A |
| 120 | 3-{[9-chloro-7-(5-fluoroindol-1-yl)-3,5-dihydro-2H-1,4-benzoxazepin-4-yl]methyl}phenol 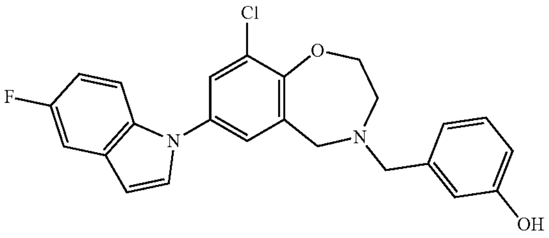 $^{1}$H NMR (300 MHz, DMSO-$d_6$) δ 9.33 (s, 1H), 7.22 (d, J = 3.3 Hz, 1H), 7.62 (d, J = 2.7 Hz, 1H), 7.47-7.55 (m, 1H), 7.38-7.46 (m, 1H), 7.27 (d, J = 2.7 Hz, 1H), 7.00-7.18 (m, 2H), 6.71-6.80 (m, 2H), 6.62-6.70 (m, 2H), 4.14-4.20 (m, 2H), 3.91 (s, 2H), 3.62 (s, 2H), 3.04-3.09 (m, 2H); $^{19}$F NMR (282 MHz, DMSO-$d_6$) δ −123.6. | 423.0 | A |
| 121 | 4-{[9-chloro-7-(5-fluoroindol-1-yl)-3,5-dihydro-2H-1,4-benzoxazepin-4-yl]methyl}phenol 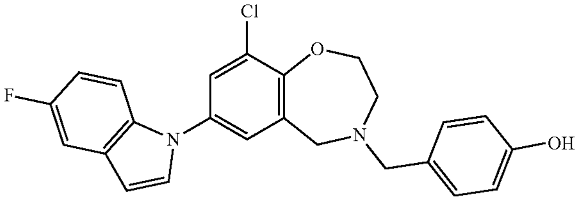 $^{1}$H NMR (300 MHz, DMSO-$d_6$) δ 9.30 (s, 1H), 7.71 (d, J = 3.3 Hz, 1H), 7.61 (d, J = 2.7 Hz, 1H), 7.38-7.54 (m, 2H), 7.26 (d, J = 2.6 Hz, 1H), 7.01-7.16 (m, 3H), 6.65-6.76 (m, 3H), 4.13-4.19 (m, 2H), 3.89 (s, 2H), 3.58 (s, 2H), 3.00-3.06 (m, 2H); $^{19}$F NMR (282 MHz, DMSO-$d_6$) δ −123.6. | 423.0 | A |
| 122 | See Example S20. | | |

TABLE 1-continued

| ID No. | Name, Structure, $^1$H-NMR, | MS (M + H)$^+$ | Method |
|---|---|---|---|
| 123 | 9-chloro-4-(3-difluoromethyl)benzyl)-7-(5-fluoro-1H-indol-1-yl)-2,3,4,5-tetrahydrobenzo[f][1,4]oxazepine 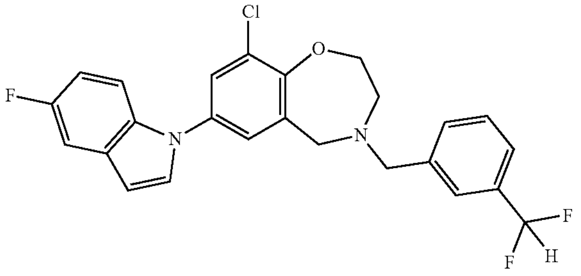 $^1$H NMR (300 MHz, $CD_3OD$) δ 7.59 (s, 1H), 7.49-7.56 (d, J = 3.0 Hz, 2H), 7.38-7.49 (m, 4H), 7.30 (m, 1H), 7.14 (d, J = 3.0 Hz, 1H), 6.91-7.04 (m, 1H), 6.75-6.64 (m, 2H), 4.18-4.27 (m, 2H), 3.93 (s, 2H), 3.82 (s, 2H), 3.13-3.22 (m, 2H); $^{19}$F NMR (282 MHz, $CD_3OD$) δ −111.6, 126.1. | 457.0 | A |
| 124 | 9-chloro-4-{[4-(difluoromethyl)phenyl]methyl}-7-(5-fluoroindol-1-yl)-3,5-dihydro-2H-1,4-benzoxazepine 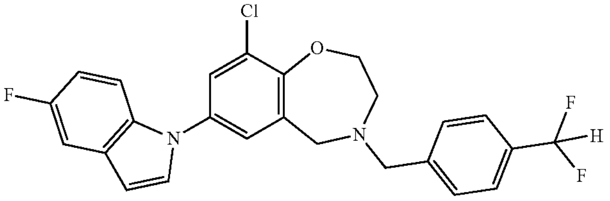 $^1$H NMR (300 MHz, $CD_3OD$) δ 7.47-7.59 (m, 5H), 7.37-7.47 (m, 2H), 7.30 (m, 1H), 7.16 (d, J = 3.0 Hz, 1H), 7.02-6.92 (m, 1H), 6.65-6.76 (m, 2H), 4.18-4.27 (m, 2H), 3.95 (s, 2H), 3.82 (s, 2H), 3.13-3.21 (m, 2H); $^{19}$F NMR (282 MHz, $CD_3OD$) δ −111.5, 128.1. | 457.0 | A |
| 125 | cis-4-{[9-chloro-7-(5-fluoroindol-1-yl)-3,5-dihydro-2H-1,4-benzoxazepin-4-yl]methyl}cyclohexane-1-carboxamide trifluoroacetic acid 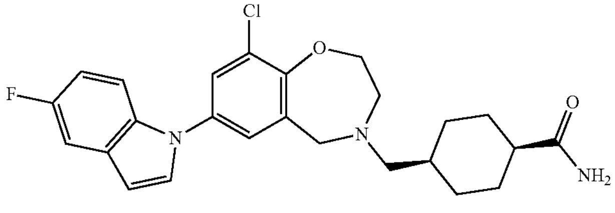 $^1$H NMR (300 MHz, DMSO-$d_6$) δ 7.59 (d, J = 2.1 Hz, 1H), 7.41-7.48 (m, 3H), 7.28-7.32 (m, 1H), 6.89-7.01 (m, 1H), 6.65 (d, J = 3.3 Hz, 1H), 4.22-4.27 (m, 4H), 3.41 (s, 2H), 2.80 (s, 2H), 2.38 (s, 1H), 1.98-2.03 (m, 1H), 1.60-1.83 (m, 2H), 1.59-1.60 (m, 6H); $^{19}$F NMR (282 MHz, $CD_3OD$) δ −76.9, −126.0. | 456.15 | J & M |

TABLE 1-continued

| ID No. | Name, Structure, $^1$H-NMR, | MS (M + H)$^+$ | Method |
|---|---|---|---|
| 126 | trans-4-{[9-chloro-7-(5-fluoroindol-1-yl)-3,5-dihydro-2H-1,4-benzoxazepin-4-yl]methyl}cyclohexane-1-carboxamide 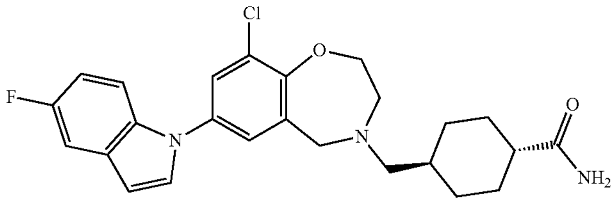 $^1$H NMR (300 MHz, DMSO-$d_6$) δ 7.72 (d, J = 3.2 Hz, 1H), 7.53-7.59 (m, 2H), 7.42-7.49 (m, 2H), 7.16 (s, 1H), 7.02-7.06 (m, 1H), 6.62-6.69 (m, 2H), 4.11-4.12 (m, 2H), 3.89 (s, 2H), 3.05-3.07 (m, 2H), 2.25 (d, J = 3.2 Hz, 2H), 1.98-2.08 (m, 1H), 1.72-1.79 (m, 4H), 1.52 (br, 1H), 1.33-1.39 (m, 2H), 0.78-0.92 (m, 2H); $^{19}$F NMR (400 MHz, $CD_3OD$) δ −123.6. | 456.1 | K |
| 127 | See Method K. | | |
| 128 | See Method J. | | |
| 129 | cis-4-{[9-chloro-7-(5-fluoroindol-1-yl)-3,5-dihydro-2H-1,4-benzoxazepin-4-yl]methyl}-N,N-dimethylcyclohexane-1-carboxamide 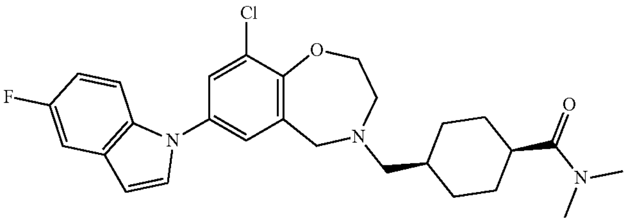 $^1$H NMR (300 MHz, DMSO-$d_6$) δ 7.28-7.36 (m, 3H), 7.16-7.29 (m, 2H), 6.81-6.88 (m, 1H), 6.52-6.53 (m, 1H), 4.03-4.06 (m, 2H), 3.83 (s, 2H), 3.19-3.22 (m, 2H), 2.97 (s, 3H), 2.79 (s, 3H), 2.62 (br, 1H), 2.43 (d, J = 7.8 Hz, 2H), 1.81-1.93 (br, 1H), 1.38-1.61 (m, 8H); $^{19}$F NMR (282 MHz, $CD_3OD$) δ −126.1. | 484.20 | J |
| 130 | trans-4-{[9-chloro-7-(5-fluoroindol-1-yl)-3,5-dihydro-2H-1,4-benzoxazepin-4-yl]methyl}-N,N-dimethylcyclohexane-1-carboxamide 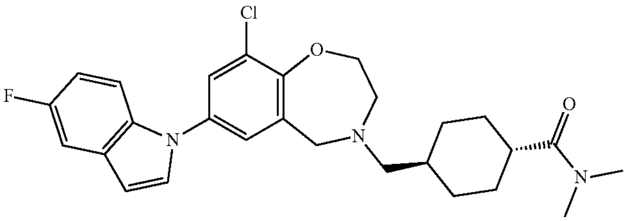 $^1$H NMR (300 MHz, DMSO-$d_6$) δ 7.71 (d, J = 3.3 Hz, 1H), 7.54-7.58 (m, 2H), 7.41-7.49 (m, 2H), 7.00-7.06 (m, 1H), 6.67 (d, J = 3 Hz, 1H), 4.11 (s, 2H), 3.89 (s, 2H), 3.06 (s, 2H), 2.98 (s, 3H), 2.78 (s, 3H), 2.52 (s, 1H), 2.25 (d, J = 6.6 Hz, 2H), 1.74-1.78 (m, 2H), 1.63-1.67 (m, 3H), 1.35-1.39 (m, 2H), 0.81-0.93 (m, 2H); $^{19}$F NMR (400 MHz, $CD_3OD$) δ −123.6. | 484.2 | K |
| 131 | See Example S21. | | |
| 132 | See Example S22. | | |

TABLE 1-continued

| ID No. | Name, Structure, $^1$H-NMR, | MS (M + H)$^+$ | Method |
|---|---|---|---|
| 133 | trans-4-{[9-chloro-7-(5-fluoroindol-1-yl)-3,5-dihydro-2H-1,4-benzoxazepin-4-yl]methyl}cyclohexane-1-carboxylic acid 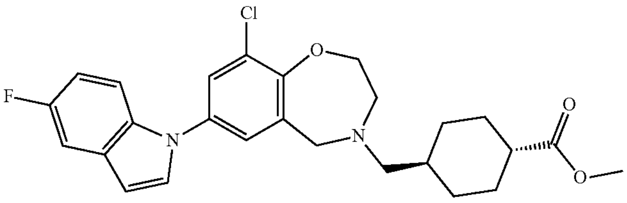 $^1$H NMR (300 MHz, DMSO-$d_6$) δ 7.40-7.47 (m, 3H), 7.30-7.38 (m, 2H), 6.92-6.99 (m, 1H), 6.63 (d, J = 3.3 Hz, 1H), 4.13-4.16 (m, 2H), 3.92 (s, 2H), 3.63 (s, 3H), 3.13-3.14 (m, 2H), 2.23-2.36 (m, 3H), 1.56-1.98 (m, 4H), 1.40-1.56 (m, 3H), 0.93-0.98 (m, 2H); $^{19}$F NMR (400 MHz, $CD_3OD$) δ −126.2. | 471.10 | A |
| 134 | methyl cis-4-{[9-chloro-7-(5-fluoroindol-1-yl)-3,5-dihydro-2H-1,4-benzoxazepin-4-yl]methyl}cyclohexane-1-carboxylate 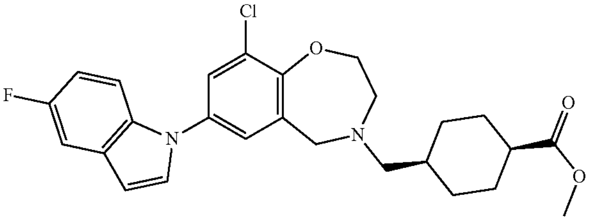 $^1$H NMR (300 MHz, $CD_3OD$) δ 7.47-7.65 (m, 2H), 7.40-7.46 (m, 1H) 7.26-7.37 (m, 2H), 6.94-7.02 (m, 1H), 6.65 (d, J = 3.0 Hz, 1H), 4.13-4.21 (m, 2H), 3.94 (s, 2H), 3.67 (s, 3H), 3.11-3.20 (m, 2H), 2.54-2.64 (m, 1H), 2.41 (d, J = 6.0 Hz, 2H), 1.90-2.03 (m, 2H), 1.54-1.80 (m, 5H), 1.19-1.31 (m, 2H); $^{19}$F NMR (282 MHz, $CD_3OD$) δ −126.2. | 471.1 | A |
| 135 | 9-chloro-7-(5-fluoroindol-1-yl)-4-(pyrimidin-5-ylmethyl)-3,5-dihydro-2H-1,4-benzoxazepine 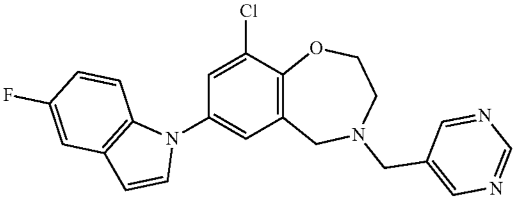 $^1$H NMR (300 MHz, DMSO-$d_6$) δ 9.01 (s, 2H), 7.71 (d, J = 3.0 Hz, 1H), 7.64 (d, J = 2.7 Hz, 1H), 7.40-7.64 (m, 3H), 7.03 (t, J = 9.3 Hz, 1H), 6.69 (d, J = 3.0 Hz, 1H), 4.19-4.21 (m, 2H), 4.02 (s, 2H), 3.86 (s, 2H), 3.12-3.14 (m, 2H); $^{19}$F NMR (282 MHz, DMSO-$d_6$) δ −123.6. | 409.1 | A |

TABLE 1-continued

| ID No. | Name, Structure, $^{1}$H-NMR, | MS (M + H)$^{+}$ | Method |
|---|---|---|---|
| 136 | 9-chloro-7-(5-fluoro-1H-indol-1-yl)-4-((2-methoxypyrimidin-5-yl)methyl)-2,3,4,5-tetrahydrobenzo[f][1,4]oxazepine 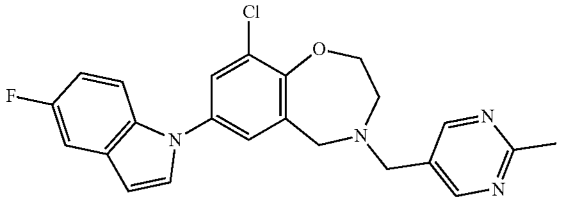 $^{1}$H NMR (400 MHz, DMSO-$d_6$) δ 8.62 (s, 2H), 7.71 (d, J = 3.3 Hz, 1H), 7.63 (d, J = 2.6 Hz, 1H), 7.49-7.51 (m, 1H), 7.38-7.44 (m, 2H), 7.05 (t, J = 9.2 Hz, 1H), 6.69 (d, J = 3.3 Hz, 1H), 4.15-4.22 (m, 2H), 3.97 (s, 2H), 3.70 (s, 2H), 3.03-3.10 (m, 2H), 2.60 (s, 3H); $^{19}$F NMR (376 MHz, DMSO-$d_6$) δ −123.4. | 423.0 | A |
| 137 | 5-((9-chloro-7-(5-fluoro-1H-indol-1-yl)-2,3-dihydrobenzo[f][1,4]oxazepin-4(5H)-yl)methyl)pyrimidine-2-carbonitrile 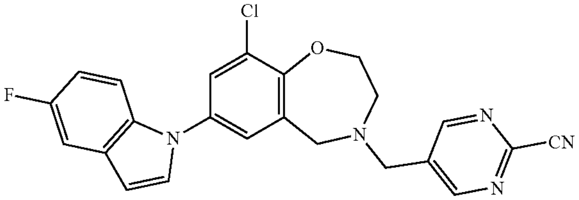 $^{1}$H NMR (400 MHz, DMSO-$d_6$) δ 8.96 (s, 2H), 7.70 (d, J = 3.3 Hz, 1H), 7.64 (d, J = 2.6 Hz, 1H), 7.48-7.49 (m, 1H), 7.41-7.44 (m, 2H), 7.05 (t, J = 9.2 Hz, 1H), 6.69 (d, J = 3.2 Hz, 1H), 4.19-4.21 (m, 2H), 3.98 (s, 2H), 3.85 (s, 2H), 3.12-3.14 (m, 2H); $^{19}$F NMR (376 MHz, DMSO-$d_6$) δ −123.4. | 434.0 | A |
| 138 | 9-chloro-7-(5-fluoroindol-1-yl)-4-{[2-(trifluoromethyl)pyrimidin-5-yl]methyl}-3,5-dihydro-2H-1,4-benzoxazepine 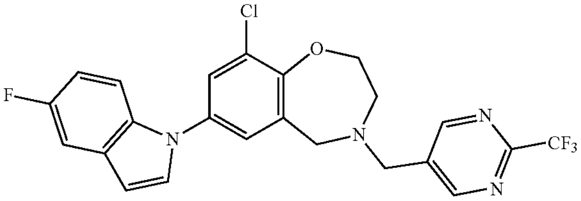 $^{1}$H NMR (300 MHz, DMSO-$d_6$) δ 9.01 (s, 2H), 7.71 (d, J = 3.0 Hz, 1H), 7.64 (d, J = 2.7 Hz, 1H), 7.40-7.64 (m, 3H), 7.03 (t, J = 9.3 Hz, 1H), 6.69 (d, J = 3.0 Hz, 1H), 4.19-4.21 (m, 2H), 4.02 (s, 2H), 3.86 (s, 2H), 3.12-3.14 (m, 2H); $^{19}$F NMR (282 MHz, DMSO-$d_6$) δ −68.8, −123.6. | 477.1 | A |
| 139 | See Example S23. | | |
| 140 | See Example S23. | | |
| 141 | See Example S24. | | |

TABLE 1-continued

| ID No. | Name, Structure, $^1$H-NMR, | MS (M + H)$^+$ | Method |
|---|---|---|---|
| 142 | 9-chloro-7-(5-fluoroindol-1-yl)-4-{[2-(methoxymethyl)pyrimidin-5-yl]methyl}-3,5-dihydro-2H-1,4-benzoxazepine 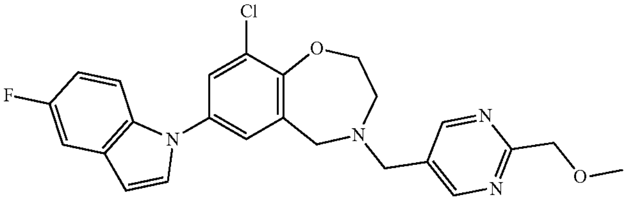 $^1$H NMR (300 MHz, DMSO-$d_6$) δ 8.74 (s, 2H), 7.71 (d, J = 3.3 Hz, 1H), 7.64 (d, J = 2.7 Hz, 1H), 7.49-7.56 (m, 1H), 7.47-7.37 (m, 2H), 7.00-7.10 (m, 1H), 6.69 (d, J = 3.3 Hz, 1H), 4.56 (s, 2H), 4.16-4.23 (m, 2H), 3.99 (s, 2H), 3.75 (s, 2H), 3.35 (s, 3H), 3.05-3.11 (m, 2H); $^{19}$F NMR (282 MHz, DMSO-$d_6$) δ −123.6. | 453.1 | A |
| 143 | See Example S25. | | |
| 144 | See Example S26. | | |
| 145 | See Example S26. | | |
| 146 | 5-{[9-chloro-7-(5-fluoroindol-1-yl)-3,5-dihydro-2H-1,4-benzoxazepin-4-yl]methyl}pyrimidin-2-amine 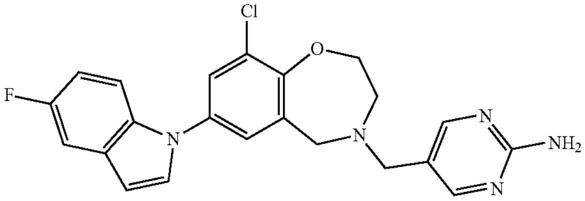 $^1$H NMR (300 MHz, $CD_3OD$) δ 8.24 (s, 2H), 7.51 (s, 1H), 7.43-7.48 (m, 2H), 7.29 (d, J = 9.5 Hz, 1H), 7.21 (s, 1H), 6.99 (t, J = 9.1 Hz, 1H), 6.64 (s, 1H), 4.16-4.25 (m, 2H), 3.91 (s, 2H), 3.60 (s, 2H), 3.10-3.19 (m, 2H); $^{19}$F NMR (282 MHz, $CD_3OD$) δ −126.1. | 424.0 | A |
| 147 | 5-{[9-chloro-7-(5-fluoroindol-1-yl)-3,5-dihydro-2H-1,4-benzoxazepin-4-yl]methyl}-N-methylpyrimidin-2-amine; trifluoroacetic acid 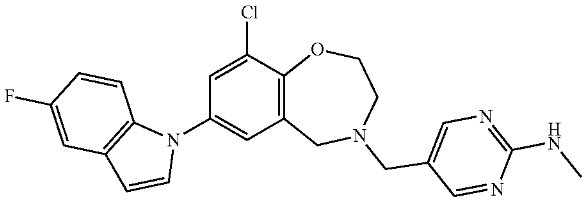 $^1$H NMR (300 MHz, DMSO-$d_6$) δ 8.25 (s, 2H), 7.72 (d, J = 3.3 Hz, 1H), 7.41-7.46 (m, 2H), 7.25-7.30 (m, 2H), 6.90-7.01 (m, 1H), 6.63 (d, J = 3.2 Hz, 1H), 4.20-4.23 (m, 2H), 3.98 (s, 2H), 3.67 (s, 2H), 3.19-3.30 (m, 2H), 2.90 (s, 3H); $^{19}$F NMR (282 MHz, $CD_3OD$) δ −78.9, −126.1. | 138.15 | A & M |

TABLE 1-continued

| ID No. | Name, Structure, $^1$H-NMR, | MS (M + H)$^+$ | Method |
|---|---|---|---|
| 148 | 5-{[9-chloro-7-(5-fluoroindol-1-yl)-3,5-dihydro-2H-1,4-benzoxazepin-4-yl]methyl}-N,N-dimethylpyrimidin-2-amine; trifluoroacetic acid 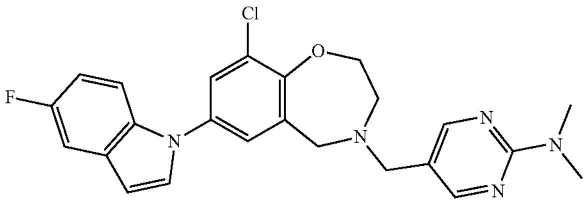 $^1$H NMR (300 MHz, DMSO-$d_6$) δ 8.26 (s, 2H), 7.72 (d, J = 3.3 Hz, 1H), 7.63 (s, 1H), 7.49-7.52 (m, 1H), 7.39-7.45 (m, 2H), 7.01-7.08 (m, 1H), 6.68 (m, 1H), 4.16-4.18 (m, 2H), 3.93 (s, 2H), 3.52 (s, 2H), 3.09 (s, 6H), 3.02-3.03 (m, 2H); $^{19}$F NMR (282 MHz, $CD_3OD$) δ −73.4, −123.6. | 452.15 | A & M |
| 149 | See Example S27. | | |
| 150 | See Example S28. | | |
| 151 | See Example S29. | | |
| 152 | 9-chloro-7-(5-fluoro-1H-indol-1-yl)-4-((2-(2,2,2-trifluoroethoxy)pyrimidin-5-yl)methyl)-2,3,4,5-tetrahydrobenzo[f][1,4]oxazepine 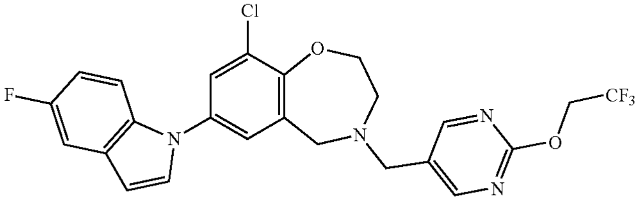 $^1$H NMR (400 MHz, DMSO-$d_6$) δ 8.61 (s, 2H), 7.71 (d, J = 3.2 Hz, 1H), 7.63 (d, J = 2.6 Hz, 1H), 7.49-7.51 (m, 1H), 7.41-7.44 (m, 2H), 7.02-7.05 (m, 1H), 6.69 (d, J = 3.3 Hz, 1H), 4.98-5.05 (m, 2H), 4.17-4.19 (m, 2H), 3.98 (s, 2H), 3.71 (s, 2H), 3.06-3.08 (m, 2H); $^{19}$F NMR (376 MHz, DMSO-$d_6$) δ −72.4, −123.6. | 507.0 | A |
| 153 | See Example S30. | | |
| 154 | See Example S31. | | |
| 155 | See Example S32. | | |
| 156 | 5-{[9-chloro-7-(5-fluoroindol-1-yl)-3,5-dihydro-2H-1,4-benzoxazepin-4-yl]methyl}-4-methyl-3H-pyrimidin-2-one 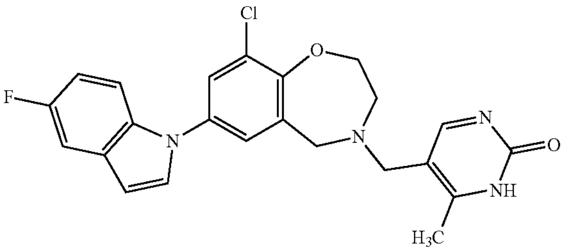 $^1$H NMR (300 MHz, DMSO-$d_6$) δ 11.65 (s, 1H), 7.86 (s, 1H), 7.71 (d, J = 3.3 Hz, 1H), 7.63 (d, J = 2.7 Hz, 1H), 7.38-7.56 (m, 3H), 7.01-7.14 (m, 1H), 6.69 (d, J = 3.3 Hz, 1H), 4.14-4.19 (m, 2H), 3.95 (s, 2H), 3.43 (s, 2H), 3.01-3.06 (s, 2H), 2.29 (s, 3H); $^{19}$F NMR (282 MHz, DMSO-$d_6$) δ −123.6. | 439.1 | L |
| 157 | See Example S33. | | |
| 158 | See Example S32. | | |

TABLE 1-continued

| ID No. | Name, Structure, $^1$H-NMR, | MS (M + H)$^+$ | Method |
|---|---|---|---|
| 159 | 5-((9-chloro-7-(5-fluoro-1H-indol-1-yl)-2,3-dihydrobenzo[f][1,4]oxazepin-4(5H)-yl)methyl)-2-methoxypyrimidin-4-amine 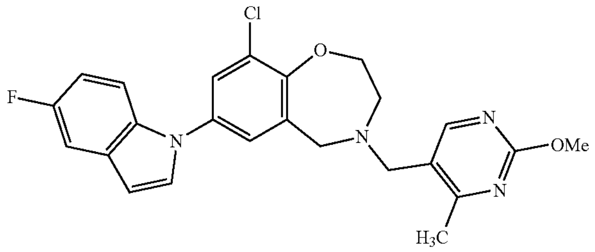 $^1$H NMR (300 MHz, DMSO-d$_6$) δ 7.77 (s, 1H), 7.72 (d, J = 3.3 Hz, 1H), 7.63 (d, J = 2.6 Hz, 1H), 7.52-7.55 (m, 1H), 7.37-7.43 (m, 2H), 7.02-7.06 (m, 1H), 6.84 (br, 2H), 6.69 (d, J = 3.3 Hz, 1H), 7.15-4.17 (m, 2H), 3.92 (s, 2H), 3.75 (s, 3H), 3.51 (s, 2H), 3.01-3.04 (m, 2H); $^{19}$F NMR (376 MHz, DMSO-d$_6$) δ −123.6. | 454.0 | A |
| 160 | 5-((9-chloro-7-(5-fluoro-1H-indol-1-yl)-2,3-dihydrobenzo[f][1,4]oxazepin-4(5H)-yl)methyl)pyrimidine-2,4-diamine 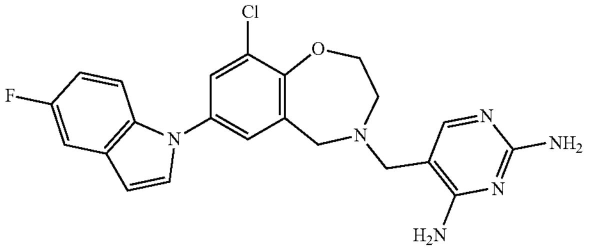 $^1$H NMR (300 MHz, CD$_3$OD) δ 7.54 (d, J = 2.7 Hz, 2H), 7.42-7.46 (m, 2H), 7.26-7.31 (m, 1H), 7.24 (d, J = 2.6 Hz, 1H), 6.95-7.07 (m, 1H), 6.65 (d, J = 3.3 Hz, 1H), 4.20-4.23 (m, 2H), 3.94 (s, 2H), 3.58 (s, 2H), 3.13-3.19 (m, 2H); $^{19}$F NMR (376 MHz, DMSO-d$_6$) δ −123.6. | 439.1 | A |
| 161 | 9-chloro-7-(5-fluoroindol-1-yl)-4-[(2-methoxypyrimidin-4-yl)methyl]-3,5-dihydro-2H-1,4-benzoxazepine 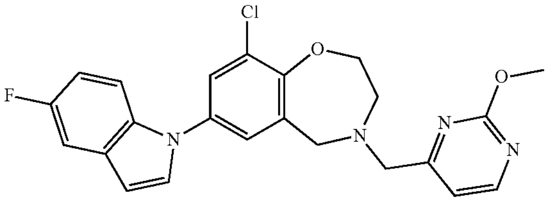 $^1$H NMR (300 MHz, DMSO-d$_6$) δ 8.57 (d, J = 6.0 Hz, 1H), 7.71 (d, J = 3.3 Hz, 1H), 7.63 (d, J = 3.0 Hz, 1H), 7.48-7.53 (m, 1H), 7.38-7.45 (m, 2H), 7.23 (d, J = 6.0 Hz, 1H), 7.01-7.08 (m, 1H), 6.67-6.69 (m, 1H), 4.17-4.21 (m, 2H), 3.97 (s, 2H), 3.87 (s, 3H), 3.75 (s, 2H), 3.15-3.22 (m, 2H); $^{19}$F NMR (282 MHz, DMSO-d$_6$) δ −123.6. | 439.1 | A |
| 162 | See Example S34 | | |
| 163 | See Example S35 | | |

TABLE 1-continued

| ID No. | Name, Structure, $^1$H-NMR, | MS $(M + H)^+$ | Method |
|---|---|---|---|
| 164 | 4-{[9-chloro-7-(5-fluoroindol-1-yl)-3,5-dihydro-2H-1,4-benzoxazepin-4-yl]methyl}-1H-pyrimidin-2-one<br>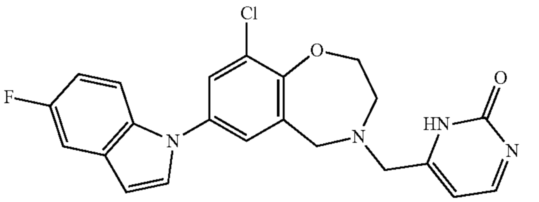<br>$^1$H NMR (300 MHz, DMSO-$d_6$) δ 11.28 (s, 1H), 8.15 (s, 2H), 7.70 (d, J = 3.0 Hz, 1H), 7.61 (d, J = 2.4 Hz, 1H), 7.40-7.52 (m, 3H), 7.06 (t, J = 9.0 Hz, 1H), 6.67 (d, J = 3.3 Hz, 1H), 4.15-4.16 (m, 2H), 3.94 (s, 2H), 3.45 (s, 2H), 3.05-3.06 (m, 2H); $^{19}$F NMR (282 MHz, DMSO-$d_6$) δ −123.6. | 425.0 | I |
| 165 | 9-chloro-7-(5-fluoro-1H-indol-1-yl)-4-(pyridazin-4-ylmethyl)-2,3,4,5-tetrahydrobenzo[f][1,4]oxazepine<br>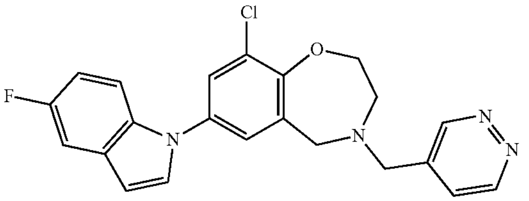<br>$^1$H NMR (300 MHz, $CD_3OD$) δ 9.21 (s, 1H), 9.14 (d, J = 5.3 Hz, 1H), 7.74-7.80 (m, 1H), 7.55 (d, J = 2.7 Hz, 1H), 7.38-7.44 (m, 2H), 7.30 (d, J = 9.4 Hz, 1H), 7.23 (d, J = 2.6 Hz, 1H), 6.99 (t, J = 9.2 Hz, 1H), 6.65 (s, 1H), 4.20-4.28 (m, 2H), 4.00 (s, 2H), 3.89 (s, 2H), 3.17-3.26 (m, 2H); $^{19}$F NMR (300 MHz, $CD_3OD$) δ −126.1. | 409.0 | A |
| 166 | 9-chloro-7-(5-fluoro-1H-indol-1-yl)-4-(pyridazin-3-ylmethyl)-2,3,4,5-tetrahydrobenzo[f][1,4]oxazepine<br>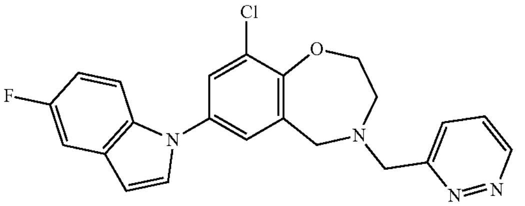<br>$^1$H NMR (300 MHz, DMSO-$d_6$) δ 9.17 (s, 1H), 7.60-7.78 (m, 5H), 7.43 (d, J = 9.6 Hz, 1H), 7.32 (s, 1H), 7.08 (t, J = 9.2 Hz, 1H), 6.68 (d, J = 3.3 Hz, 1H), 4.19-4.21 (m, 2H), 3.99 (s, 2H), 3.93 (s, 2H), 3.16-3.19 (m, 2H); $^{19}$F NMR (282 MHz, DMSO-$d_6$) δ −123.6. | 409.0 | A |
| 167 | 6-{[9-chloro-7-(5-fluoroindol-1-yl)-3,5-dihydro-2H-1,4-benzoxazepin-4-yl]methyl}pyridazin-3-amine<br>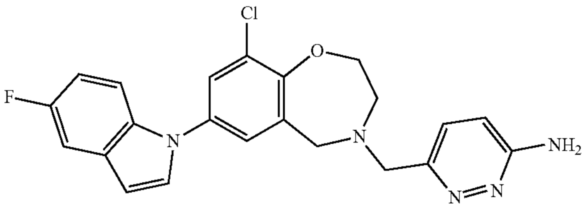<br>$^1$H NMR (300 MHz, DMSO-$d_6$) δ 7.72 (d, J = 3.3 Hz, 1H), 7.62-7.69 (m, 1H), 7.61 (d, J = 3.0 Hz, 1H), 7.37-7.46 (m, 1H), 7.25-7.37 (m, 2H), 7.06-7.18 (m, 1H), 6.79 (d, J = 9.0 Hz, 1H), 6.64-6.71 (m, 1H), 6.30 (s, 2H), 4.13-4.21 (m, 2H), 3.88 (s, 2H), 3.74 (s, 2H), 3.08-3.17 (m, 2H); $^{19}$F NMR (282 MHz, DMSO-$d_6$) δ −123.5. | 424.1 | B |

TABLE 1-continued

| ID No. | Name, Structure, $^{1}$H-NMR, | MS (M + H)$^{+}$ | Method |
|---|---|---|---|
| 168 | tert-butyl N-(6-{[9-chloro-7-(5-fluoroindol-1-yl)-3,5-dihydro-2H-1,4-benzoxazepin-4-yl]methyl}pyridazin-3-yl)carbamate 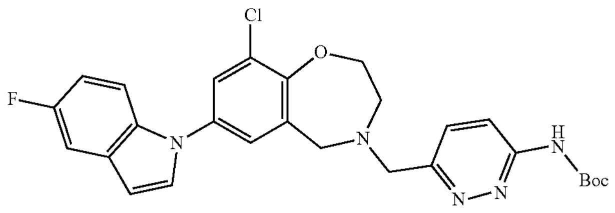 $^{1}$H NMR (300 MHz, DMSO-$d_6$) δ 10.46 (s, 1H), 8.11 (d, J = 9.0 Hz, 1H), 7.69-7.72 (m, 2H), 7.61-7.67 (m, 2H), 7.41 (d, J = 9.6 Hz, 1H), 7.30 (d, J = 2.7 Hz, 1H), 7.17 (t, J = 9.3 Hz, 1H), 6.67 (d, J = 3.0 Hz, 1H), 4.19-4.20 (m, 2H), 3.89-3.90 (m, 4H), 3.18-3.19 (m, 2H), 1.49 (s, 9H); $^{19}$F NMR (282 MHz, DMSO-$d_6$) δ −123.5. | 524.1 | A |
| 169 | See Example S36. | | |
| 170 | 5-{[9-chloro-7-(5-fluoroindol-1-yl)-3,5-dihydro-2H-1,4-benzoxazepin-4-yl]methyl}pyrazin-2-amine 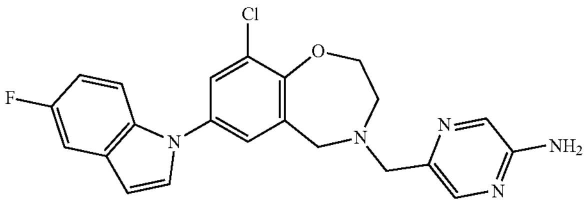 $^{1}$H NMR (300 MHz, $CD_3OD$) δ 7.93-8.54 (m, 2H), 7.45-7.50 (m, 3H), 7.23-7.30 (m, 2H), 7.01 (t, J = 9.3 Hz, 1H), 6.63 (d, J = 3.3 Hz, 1H), 4.19-4.22 (m, 2H), 3.95 (s, 2H), 3.71 (s, 2H), 3.18-3.21 (m, 2H); $^{19}$F NMR (282 MHz, $CD_3OD$) δ −126.2. | 424.0 | B |
| 171 | tert-butyl N-(5-{[9-chloro-7-(5-fluoroindol-1-yl)-3,5-dihydro-2H-1,4-benzoxazepin-4-yl]methyl}pyrazin-2-yl)carbamate 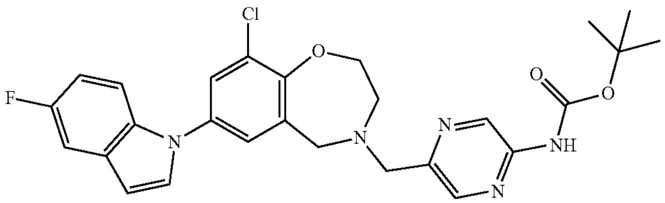 $^{1}$H NMR (300 MHz, DMSO-$d_6$) δ 10.16 (s, 1H), 9.03 (d, J = 1.2 Hz, 1H), 8.35 (d, J = 1.5 Hz, 1H), 7.71 (d, J = 3.0 Hz, 1H), 7.55-7.61 (m, 2H), 7.35-7.44 (m, 2H), 7.10 (t, J = 9.3 Hz, 1H), 6.68 (d, J = 3.3 Hz, 1H), 4.19-4.20 (m, 2H), 3.93 (s, 2H), 3.80 (s, 2H), 3.16-3.17 (m, 2H), 1.48 (s, 9H); $^{19}$F NMR (282 MHz, DMSO-$d_6$) δ 123.6. | 524.1 | A |

TABLE 1-continued

| ID No. | Name, Structure, $^{1}$H-NMR, | MS (M + H)$^{+}$ | Method |
|---|---|---|---|
| 172 | 9-chloro-7-(5-fluoroindol-1-yl)-4-[(5-methoxypyrazin-2-yl)methyl]-3,5-dihydro-2H-1,4-benzoxazepine 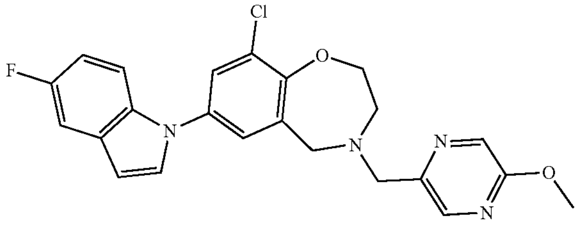 $^{1}$H NMR (300 MHz, $CD_3OD$) δ 8.18-8.22 (m, 2H), 7.45-7.51 (m, 3H), 7.24-7.31 (m, 2H), 6.97 (t, J = 9.3 Hz, 1H), 6.63 (d, J = 3.3 Hz, 1H), 4.20-4.23 (m, 2H), 3.84-3.98 (m, 5H), 3.84 (s, 2H), 3.07-3.29 (m, 2H); $^{19}$F NMR (282 MHz, $CD_3OD$) δ −126.1. | 439.0 | A |
| 173 | 9-chloro-4-[(5-chloropyrazin-2-yl)methyl]-7-(5-fluoroindol-1-yl)-3,5-dihydro-2H-1,4-benzoxazepine 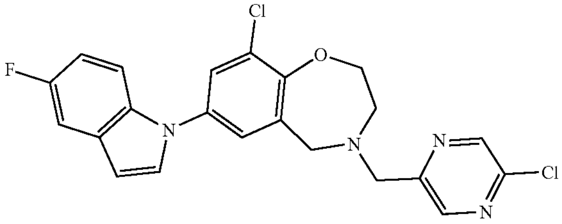 $^{1}$H NMR (400 MHz, DMSO-$d_6$) δ 8.76 (d, J = 1.2 Hz, 1H), 8.57 (d, J = 1.2 Hz, 1H), 7.71 (d, J = 3.2 Hz, 1H), 7.62 (d, J = 2.8 Hz, 1H), 7.54 (d, J = 8.8 Hz, 1H), 7.41-7.45 (m, 2H), 7.09 (t, J = 7.2 Hz, 1H), 6.68 (d, J = 3.2 Hz, 1H), 4.19-4.21 (m, 2H), 3.97 (s, 2H), 3.89 (s, 2H), 3.18-3.20 (m, 2H); $^{19}$F NMR (376 MHz, DMSO-$d_6$) δ −123.6. | 443.0 | A |
| 174 | See Method L. | | |
| 175 | 5-{[9-chloro-7-(5-fluoroindol-1-yl)-3,5-dihydro-2H-1,4-benzoxazepin-4-yl]methyl}-1H-pyridin-2-one 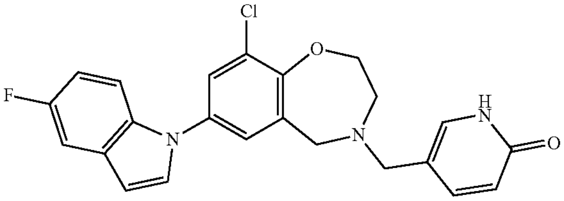 $^{1}$H NMR (300 MHz, $CD_3OD$) δ 7.61-7.72 (m, 1H), 7.51 (d, J = 2.7 Hz, 1H), 7.39-7.48 (m, 2H), 7.20-7.36 (m, 3H), 6.91-7.04 (m, 1H), 6.63 (d, J = 3.3 Hz, 1H), 6.55 (d, J = 9.3 Hz, 1H), 4.12-4.23 (m, 2H), 3.93 (s, 2H), 3.54 (s, 2H), 3.10-3.19 (m, 2H). $^{19}$F NMR (282 MHz, $CD_3OD$) δ −126.1 | 424.1 | A |

TABLE 1-continued

| ID No. | Name, Structure, $^1$H-NMR, | MS (M + H)$^+$ | Method |
|---|---|---|---|
| 176 | 3-((9-chloro-7-(5-fluoro-1H-indol-1-yl)-2,3-dihydrobenzo[f][1,4] oxazepin-4(5H)-yl)methyl)pyridin-4(1H)-one 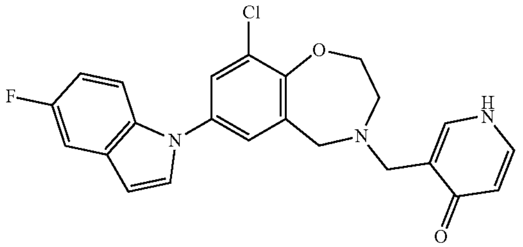 $^1$H NMR (300 MHz, $CD_3OD$) δ 7.92 (s, 1H), 7.76 (d, J = 9.0 Hz, 1H), 7.53 (d, J = 3.0 Hz, 1H), 7.40-7.51 (m, 2H), 7.26-7.34 (m, 2H), 6.99 (m, 1H), 6.65 (m, 1H), 6.48 (d, J = 9.0 Hz, 1H), 4.20-4.29 (m, 2H), 4.01 (s, 2H), 3.66 (s, 2H), 3.16-3.25 (m, 2H); $^{19}$F NMR (282 MHz, $CD_3OD$) δ −126.1. | 423.1 | A |
| 177 | See Example S37. | | |
| 178 | tert-butyl N-(4-{[9-chloro-7-(5-fluoroindol-1-yl)-3,5-dihydro-2H-1,4-benzoxazepin-4-yl]methyl}pyridin-2-yl)carbamate 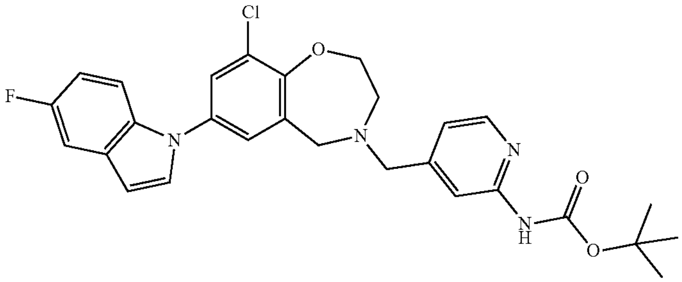 $^1$H NMR (300 MHz, DMSO-$d_6$) δ 9.75 (s, 1H), 8.19 (d, J = 4.8 Hz, 1H), 7.81 (s, 1H), 7.71 (d, J = 3.3 Hz, 1H), 7.63 (d, J = 2.4 Hz, 1H), 7.43-7.46 (m, 2H), 7.30 (d, J = 2.4 Hz, 1H), 6.99-7.08 (m, 2H), 6.66 (d, J = 3.0 Hz, 1H), 4.19-4.20 (m, 2H), 3.93 (s, 2H), 3.70 (s, 2H), 3.13-3.14 (m, 2H), 1.40 (s, 9H); $^{19}$F NMR (282 MHz, DMSO-$d_6$) δ −123.7. | 523.1 | A |
| 179 | See Example S38. | | |
| 180 | See Example S39. | | |
| 181 | See Example S40. | | |
| 182 | See Example S41. | | |
| 183 | 4-{[9-chloro-7-(5-fluoroindol-1-yl)-3,5-dihydro-2H-1,4-benzoxazepin-4-yl]methyl}pyridin-2-yl 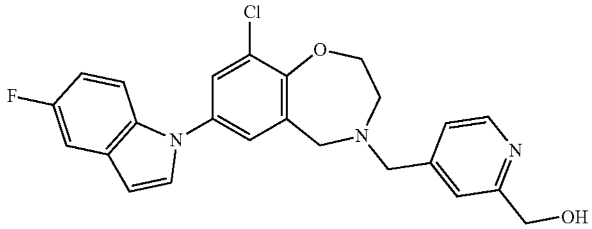 $^1$H NMR (400 MHz, $CD_3OD$) δ 8.40 (d, J = 4.8 Hz, 1H), 7.61 (s, 1H), 7.51 (d, J = 2.8 Hz, 1H), 7.45 (d, J = 3.2 Hz, 1H), 7.40 (d, J = 9.2 Hz, 1H), 7.29-7.33 (m, 1H), 7.28 (d, J = 9.6 Hz, 1H), 7.16 (d, J = 2.4 Hz, 1H), 6.93-6.99 (m, 1H), 6.62 (d, J = 3.6 Hz, 1H), 4.68 (s, 2H), 4.19-4.21 (m, 2H), 3.94 (s, 2H), 3.82 (s, 2H), 3.16-3.19 (m, 2H); $^{19}$F NMR (376 MHz, $CD_3OD$) δ −126.1. | 438.2 | A |
| 184 | See Example S42. | | |
| 185 | See Example S43. | | |

TABLE 1-continued

| ID No. | Name, Structure, $^1$H-NMR, | MS $(M + H)^+$ | Method |
|---|---|---|---|
| 186 | 4-{[9-chloro-7-(5-fluoroindol-1-yl)-3,5-dihydro-2H-1,4-benzoxazepin-4-yl]methyl}pyridine-2-carboxylate<br>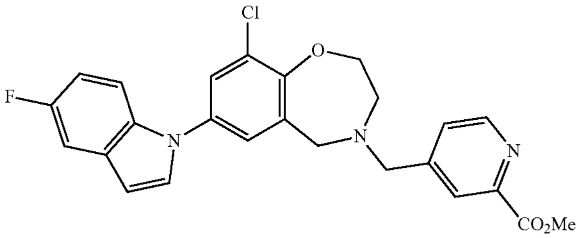<br>$^1$HNMR (300 MHz, $CD_3OD$) δ 8.63 (d, J = 5.1 Hz, 1H), 8.18-8.24 (m, 1H), 7.68 (d, J = 3.9 Hz, 1H), 7.55 (d, J = 3.0 Hz, 1H), 7.37-7.51 (m, 2H), 7.30 (d, J = 6.9 Hz, 1H), 7.15 (d, J = 2.7 Hz, 1H), 6.98 (t, J = 9.0 Hz, 1H), 6.62 (d, J = 3.0 Hz, 1H), 4.21-4.23 (m, 2H), 3.93 (s, 2H), 3.88-3.90 (m, 5H), 3.19-3.22 (m, 2H); $^{19}$F NMR (282 MHz, $CD_3OD$) δ −126.1. | 466.1 | A |
| 187 | See Example S44. | | |
| 188 | See Example S45. | | |
| 189 | See Example S46. | | |
| 190 | 9-chloro-4-[(2-chloro-3-fluoropyridin-4-yl)methyl]-7-(5-fluoroindol-1-yl)-3,5-dihydro-2H-1,4-benzoxazepine<br>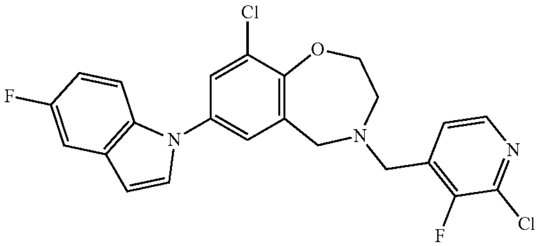<br>$^1$H NMR (300 MHz, DMSO-$d_6$) δ 8.26 (d, J = 4.8 Hz, 1H), 7.70 (d, J = 3.3 Hz, 1H), 7.63 (d, J = 3.0 Hz, 1H), 7.57 (t, J = 6.0 Hz, 1H), 7.47-7.54 (m, 1H), 7.38-7.45 (m, 2H), 6.99-7.11 (m, 1H), 6.65-6.72 (m, 1H), 4.16-4.25 (m, 2H), 3.96 (s, 2H), 3.85 (s, 2H), 3.09-3.20 (m, 2H); $^{19}$F NMR (282 MHz, DMSO-$d_6$) δ −123.6 | 460.0 | A |
| 191 | 9-chloro-4-[(2-chloro-3-methylpyridin-4-yl)methyl]-7-(5-fluoroindol-1-yl)-3,5-dihydro-2H-1,4-benzoxazepine<br>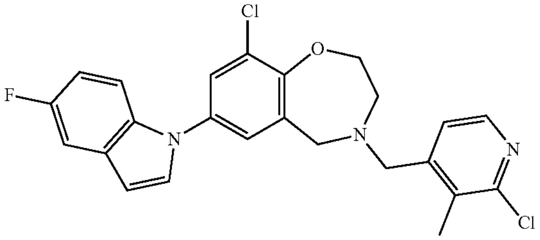<br>$^1$H NMR (300 MHz, DMSO-$d_6$) δ 8.24-8.17 (m, 1H), 7.72 (d, J = 3.3 Hz, 1H), 7.64 (d, J = 2.7 Hz, 1H), 7.48-7.54 (m, 1H), 7.34-7.48 (m, 2H), 7.38 (d, J = 3.0 Hz, 1H), 7.00-7.11 (m, 1H), 6.66-6.72 (m, 1H), 4.17-4.25 (m, 2H), 3.97 (s, 2H), 3.75 (s, 2H), 3.03-3.11 (m, 2H), 2.33 (s, 3H); $^{19}$F NMR (282 MHz, DMSO-$d_6$) δ −123.6. | 456.0 | A |

TABLE 1-continued

| ID No. | Name, Structure, $^1$H-NMR, | MS $(M + H)^+$ | Method |
|---|---|---|---|
| 192 | 9-chloro-4-{[2-chloro-3-(trifluoromethyl)pyridin-4-yl]methyl}-7-(5-fluoroindol-1-yl)-3,5-dihydro-2H-1,4-benzoxazepine 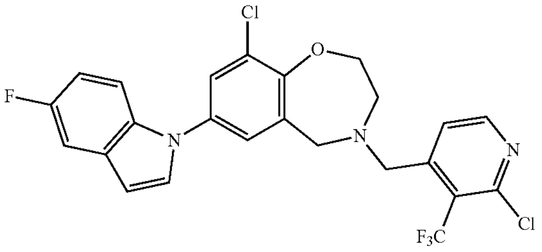 $^1$H NMR (300 MHz, DMSO-$d_6$) δ 8.61-8.62 (m, 1H), 7.80 (d, J = 5.1 Hz, 1H), 7.71 (d, J = 3.3 Hz, 1H), 7.62 (d, J = 2.7 Hz, 1H), 7.41-7.52 (m, 3H), 7.05 (t, J = 9.3 Hz, 1H), 6.69 (d, J = 2.7 Hz, 1H), 4.13-4.15 (m, 2H), 3.96-4.00 (m, 4H), 2.98-3.00 (m, 2H); $^{19}$F NMR (282 MHz, DMSO-$d_6$) δ −59.0, −123.6. | 510.0 | A |
| 193 | 4-{[9-chloro-7-(5-fluoroindol-1-yl)-3,5-dihydro-2H-1,4-benzoxazepin-4-yl]methyl}-3-fluoro-1H-pyridin-2-one 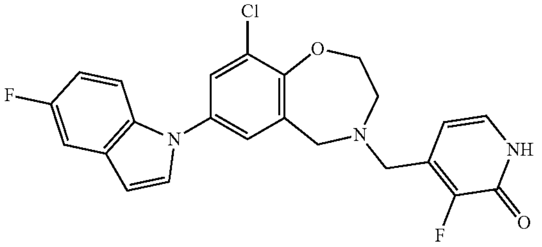 $^1$H NMR (300 MHz, $CD_3OD$) δ 7.53 (d, J = 2.7 Hz, 1H), 7.39-7.50 (m, 2H), 7.21-7.34 (m, 3H), 6.95-7.07 (m, 1H), 6.62-6.68 (m, 1H), 6.55-6.61 (m, 1H), 4.18-4.27 (m, 2H), 3.96 (s, 2H), 3.78 (d, J = 2.1 Hz, 2H), 3.19-3.28 (m, 2H); $^{19}$F NMR (282 MHz, $CD_3OD$) δ −126.2, −141.1. | 442.0 | L |
| 194 | See Example S47. | | |
| 195 | 4-{[9-chloro-7-(5-fluoroindol-1-yl)-3,5-dihydro-2H-1,4-benzoxazepin-4-yl]methyl}-3-(trifluoromethyl)-1H-pyridin-2-one 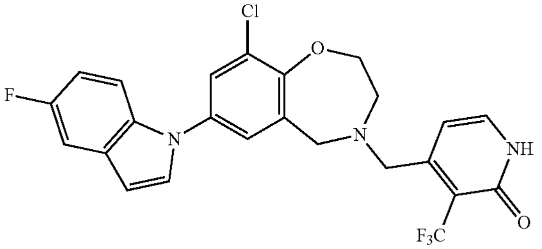 $^1$H NMR (300 MHz, DMSO-$d_6$) δ 12.25 (s, 1H), 7.74 (d, J = 3.3 Hz, 1H), 7.55-7.62 (m, 3H), 7.40-7.47 (m, 2H), 7.07 (t, J = 9.3 Hz, 1H), 6.69 (d, J = 3.3 Hz, 1H), 6.39 (d, J = 6.9 Hz, 1H), 4.17-4.18 (m, 2H), 3.98 (s, 2H), 3.65 (s, 2H), 3.02-3.03 (m, 2H); $^{19}$F NMR (282 MHz, DMSO-$d_6$) δ −60.3, −123.7. | 492.0 | L |
| 196 | See Example S48 | | |

TABLE 1-continued

| ID No. | Name, Structure, $^1$H-NMR, | MS $(M + H)^+$ | Method |
|---|---|---|---|
| 197 | 9-chloro-4-[(2,6-dimethoxypyridin-4-yl)methyl]-7-(5-fluoroindol-1-yl)-3,5-dihydro-2H-1,4-benzoxazepine 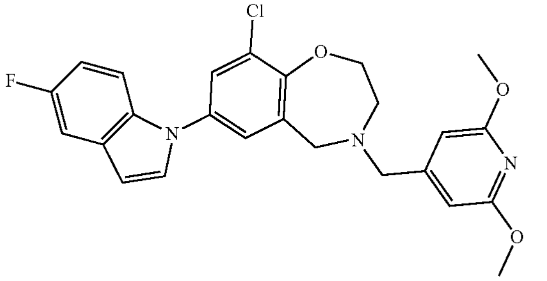 $^1$H NMR (300 MHz, $CD_3OD$) δ 7.50 (d, J = 2.7 Hz, 1H), 7.40-7.45 (m, 2H), 7.28 (d, J = 9.6 Hz, 1H), 7.15 (d, J = 2.7 Hz, 1H), 6.96 (t, J = 9.3 Hz, 1H), 6.65 (d, J = 3.0 Hz, 1H), 6.36 (s, 2H), 4.18-4.21 (m, 2H), 3.88-3.91 (m, 8H), 3.68 (s, 2H), 3.16-3.19 (m, 2H); $^{19}$F NMR (282 MHz, $CD_3OD$) δ −126.2. | 468.0 | A |
| 198 | See Example S49. | | |
| 200 | See Example S50 | | |
| 202 | 5-((9-chloro-7-(5-fluoro-1H-indol-1-yl)-2,3-dihydrobenzo[f][1,4]oxazepin-4(5H)-yl)methyl)-3,5-dihydropyrimidin-2(1H)-one 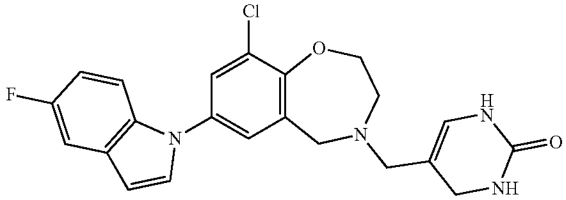 $^1$H NMR (300 MHz, $CD_3OD$) δ 7.40-7.55 (m, 4H), 7.26-7.36 (m, 2H), 7.00 (t, J = 9.1 Hz, 1H), 6.65 (d, J = 3.3 Hz, 1H), 6.02 (s, 1H), 4.13-4.22 (m, 2H), 3.81-3.93 (m, 4H), 3.13 (s, 4H); $^{19}$F NMR (300 MHz, $CD_3OD$) δ −126.1. | 427.0 | A |
| 203 | See Example S51. | | |
| 204 | See Example S48 | | |
| 217 | See Example S52. | | |
| 218 | 9-chloro-7-(5-fluoro-1H-indol-1-yl)-4-(pyrimidin-5-ylmethyl)-4,5-dihydro-2H-spiro[benzo[f][1,4]oxazepine-3,1′-cyclopropane] 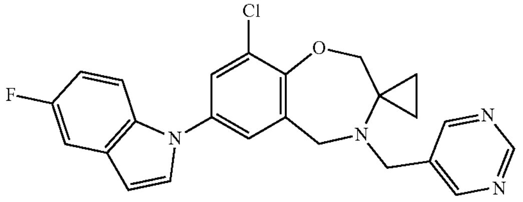 $^1$H NMR (400 MHz, $CD_3OD$) δ 9.05 (s, 1H), 8.67 (s, 2H), 7.57 (s, 1H), 7.40-7.45 (m, 2H), 7.27 (d, J = 6.8 Hz, 1H), 7.06 (s, 1H), 6.98 (t, J = 9.1 Hz, 1H), 6.62-6.64 (m, 1H), 4.11 (s, 2H), 4.02 (s, 2H), 3.86 (s, 2H), 0.88-0.97 (m, 4H); $^{19}$F NMR (376 MHz, $CD_3OD$) δ −77.4, −126.0. | 435.2 | A & M |

TABLE 1-continued

| ID No. | Name, Structure, $^1$H-NMR, | MS $(M + H)^+$ | Method |
|---|---|---|---|
| 219 | 9-chloro-7-(5-fluoro-1H-indol-1-yl)-4-((2-methoxypyridin-3-yl)methyl)-4,5-dihydro-2H-spiro[benzo[f][1,4]oxazepine-3,1′-cyclopropane] 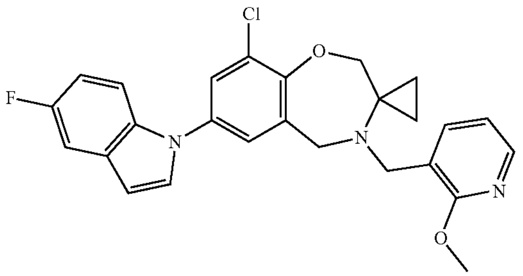 $^1$H NMR (400 MHz, $CD_3OD$) δ 8.01 (s, 1H), 7.64-7.66 (m, 1H), 7.53-7.54 (m, 1H), 7.44 (s, 1H), 7.30-7.36 (m, 1H), 7.27-7.30 (m, 1H), 7.02 (s, 1H), 6.92-6.98 (m, 2H), 6.62-6.63 (m, 1H), 4.02-4.08 (m, 4H), 3.81 (s, 5H), 0.81-0.91 (m, 4H); $^{19}$F NMR (376 MHz, $CD_3OD$) δ −126.1. | 467.1 | A |
| 220 | 3-((9-chloro-7-(5-fluoro-1H-indol-1-yl)-2H-spiro[benzo[f][1,4]oxazepine-3,1′-cyclopropan]-4(5H)-yl)methyl)benzonitrile 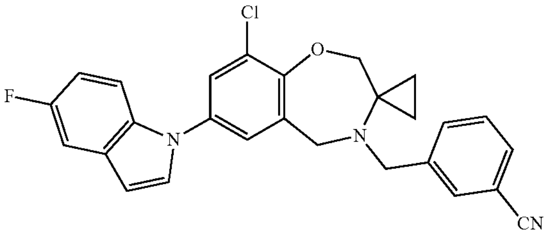 $^1$H NMR (400 MHz, $CD_3OD$) δ 7.79-7.89 (m, 4H), 7.62-7.72 (m, 2H), 7.56-7.69 (m, 2H), 7.15 (s, 1H), 7.09 (t, J = 8.4 Hz, 1H), 6.67 (d, J = 2.4 Hz, 1H), 4.08 (s, 2H), 3.92 (s, 2H), 3.77 (s, 2H), 0.81-0.84 (m, 4H); $^{19F}$ NMR (376 MHz, $CD_3OD$) δ −123.5. | 458.1 | A |
| 221 | 9-chloro-7-(5-fluoroindol-1-yl)-4-[(2-methoxypyridin-4-yl)methyl]-6-methyl-3,5-dihydro-2H-1,4-benzoxazepine 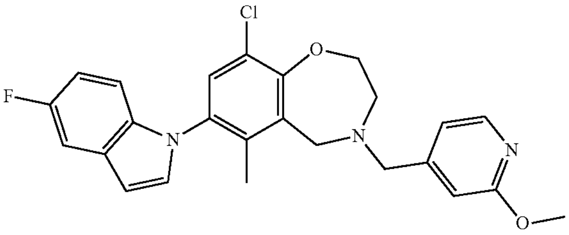 $^1$H NMR (300 MHz, DMSO-$d_6$) δ 8.10 (d, J = 3 Hz, 1H), 7.49 (d, J = 3.3 Hz, 1H), 7.39-7.43 (m, 2H), 6.99-7.00 (m, 3H), 6.79 (s, 1H), 6.65 (m, 1H), 4.17-4.21 (m, 2H), 4.16 (s, 2H), 3.81 (s, 3H), 3.71 (s, 2H), 3.09-3.13 (m, 2H), 1.50 (s, 3H); $^{19}$F NMR (300 MHz, DMSO-$d_6$) δ −124.3. | 452.1 | C |

TABLE 1-continued

| ID No. | Name, Structure, $^1$H-NMR, | MS (M + H)$^+$ | Method |
|---|---|---|---|
| 222 | 5-chloro-7-(5-fluoro-1H-indol-1-yl)-2-(pyrimidin-5-ylmethyl)-1,2,3,4-tetrahydroisoquinoline 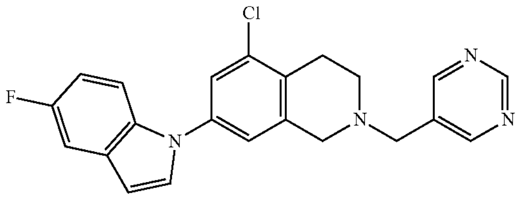 $^1$H NMR (400 MHz, $CD_3OD$) δ 9.12 (s, 1H), 8.88 (s, 2H), 7.44-7.52 (m, 3H), 7.31 (d, J = 9.2 Hz, 1H), 7.25 (d, J = 2.0 Hz, 1H), 6.98 (t, J = 9.2 Hz, 1H), 6.65 (d, J = 3.6 Hz, 1H), 3.77-3.82 (m, 4H), 2.88-3.00 (m, 4H); $^{19}$F NMR (376 MHz, CD3OD) δ −126.1. | 393.2 | A |
| 223 | 5-chloro-7-(5-fluoro-1H-indol-1-yl)-2-((2-methoxypyridin-3-yl)methyl)-1,2,3,4-tetrahydroisoquinoline 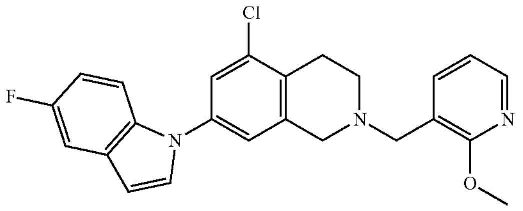 $^1$H NMR (400 MHz, $CD_3OD$) δ 8.10 (d, J = 4.8 Hz, 1H), 7.80 (d, J = 7.2 Hz, 1H), 7.44-7.52 (m, 3H), 7.31 (d, J = 9.6 Hz, 1H), 7.25 (d, J = 2.4 Hz, 1H), 6.93-7.04 (m, 2H), 6.65 (d, J = 3.2 Hz, 1H), 3.98 (s, 3H), 3.69-3.77 (m, 4H), 2.73-3.06 (m, 4H); $^{19}$F NMR (376 MHz, $CD_3OD$) δ −126.1 | 422.1 | A |
| 225 | 4-{[9-chloro-7-(5-fluoroindol-1-yl)(2,2,3,3,5,5-2H6)-1,4-benzoxazepin-4-yl]methyl}-1H-pyridin-2-one 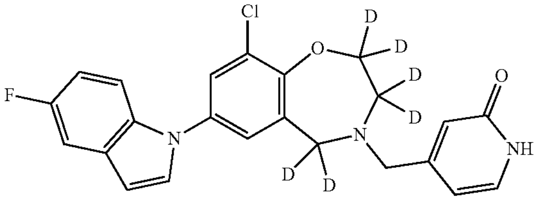 $^1$H NMR (300 MHz, DMSO-$d_6$) δ 11.41 (s, 1H), 7.71 (d, J = 3.3 Hz, 1H), 7.62 (d, J = 2.7 Hz, 1H), 7.51 (d, J = 8.9 Hz 1H), 7.42 (d, J = 9.6 Hz, 1H), 7.27-7.38 (m, 2H), 7.09 (t, J = 9.5 Hz, 1H), 6.67 (s, 1H), 6.26 (s, 1H), 6.18 (d, J = 6.5 Hz, 1H), 3.51 (s, 2H). | 430.2 | A |

TABLE 1-continued

| ID No. | Name, Structure, $^{1}$H-NMR, | MS $(M + H)^+$ | Method |
|---|---|---|---|
| 228 | 4-{1-[9-chloro-7-(5-fluoroindol-1-yl)-3,5-dihydro-2H-1,4-benzoxazepin-4-yl]ethyl}-1H-pyridin-2-one 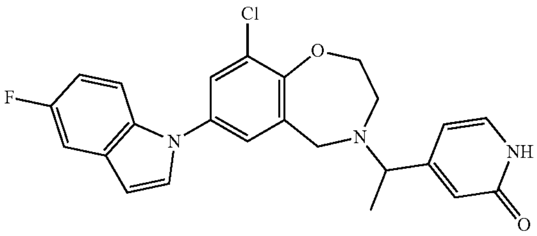 $^{1}$H NMR (300 MHz, DMSO-$d_6$) δ 11.43 (s, 1H), 7.70 (d, J = 3.3 Hz, 1H), 7.60 (d, J = 2.6 Hz, 1H), 7.47-7.49 (m, 1H), 7.40-7.42 (m, 1H), 7.27-7.37 (m, 2H), 7.10 (d, J = 9.2 Hz, 1H), 6.67 (s, 1H), 6.19-6.29 (m, 2H), 4.03-4.19 (m, 2H), 3.95 (d, J = 14.6 Hz, 1H), 3.78 (d, J = 14.6 Hz, 1H), 3.65 (d, J = 6.6 Hz, 1H), 3.02-3.19 (m, 2H), 1.26 (d, J = 6.5 Hz, 3H); $^{19}$F NMR (300 MHz, DMSO-$d_6$) δ −126.1. | 438.2 | I |
| 230 | 4-((9-chloro-7-(5-fluoro-1H-indol-1-yl)-2H-spiro[benzo[f][1,4]oxazepine-3,1′-cyclopropan]-4(5H)-yl)methyl)pyridin-2(1H)-one 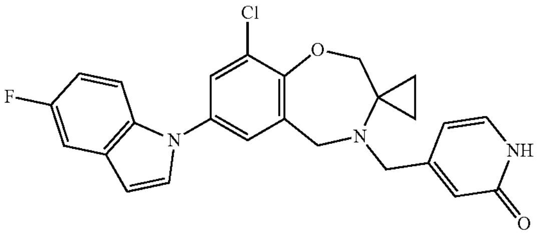 $^{1}$H NMR (400 MHz, $CD_3OD$) δ 7.56-7.58 (m, 2H), 7.40-7.45 (m, 2H), 7.27 (d, J = 6.8 Hz, 1H), 7.17 (s, 1H), 6.99 (t, J = 9.1 Hz, 1H), 6.62-6.64 (m, 3H), 4.09 (s, 4H), 3.79 (s, 2H), 0.91-1.02 (m, 4H); $^{19}$F NMR (376 MHz, $CD_3OD$) δ −126.0. | 450.2 | A |
| 231 | 4-{[9-chloro-3-cyclopropyl-7-(5-fluoroindol-1-yl)-3,5-dihydro-2H-1,4-benzoxazepin-4-yl]methyl}-1H-pyridin-2-one 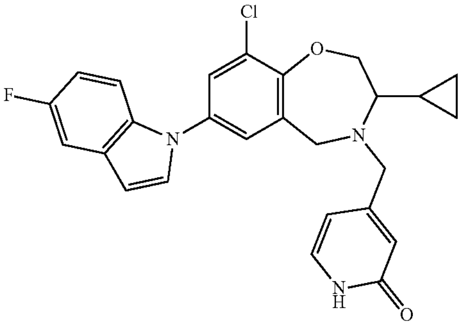 $^{1}$H NMR (300 MHz, DMSO-$d_6$) δ 11.40 (s, 1H), 7.69 (d, J = 3.3 Hz, 1H), 7.60 (d, J = 2.6 Hz, 1H), 7.47-7.52 (m, 1H), 7.36-7.45 (m, 1H), 7.24-7.36 (m, 2H), 7.05-7.13 (m, 1H), 6.67 (d, J = 3.3 Hz, 1H), 6.16-6.27 (m, 2H), 4.15-4.35 (m, 3H), 3.79 (d, J = 12 Hz, 1H), 3.63 (d, J = 15 Hz, 1H), 3.48 (d, J = 15 Hz, 1H), 2.28 (s, 1H), 1.14-1.23 (m, 1H), 0.32-0.36 (m, 2H), 0.29-0.39 (m, 2H); $^{19}$F NMR (300 MHz, DMSO-$d_6$) δ −123.6. | 464.1 | A |

TABLE 1-continued

| ID No. | Name, Structure, $^1$H-NMR, | MS (M + H)$^+$ | Method |
|---|---|---|---|
| 235 | 4-{[9-chloro-7-(5-fluoroindol-1-yl)-5-methyl-3,5-dihydro-2H-1,4-benzoxazepin-4-yl]methyl}-1H-pyridin-2-one 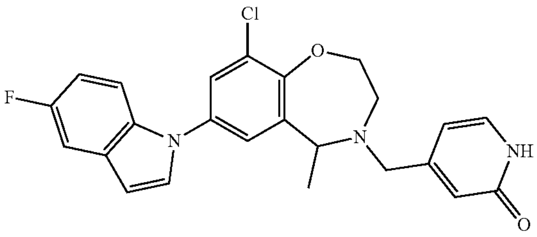 $^1$H NMR (400 MHz, $CD_3OD$) δ 7.52-7.55 (m, 2H), 7.42-7.49 (m, 1H), 7.41 (d, J = 4.0 Hz, 1H), 7.29-7.32 (m, 1H), 7.22 (d, J = 4.0 Hz, 1H), 6.99-7.05 (m, 1H), 6.65 (d, J = 4.0 Hz, 1H), 6.49-6.57 (m, 2H), 4.24-4.29 (m, 1H), 4.08-4.18 (m, 2H), 3.56-3.71 (m, 3H), 2.94-3.02 (m, 1H), 1.63 (d, J = 8.0 Hz, 3H); $^{19}$F NMR (376 MHz, $CD_3OD$) δ −126.1 | 438.1 | A |
| 238 | 4-{[9-chloro-7-(5-fluoroindol-1-yl)-6-methyl-3,5-dihydro-2H-1,4-benzoxazepin-4-yl]methyl}-1H-pyridin-2-one 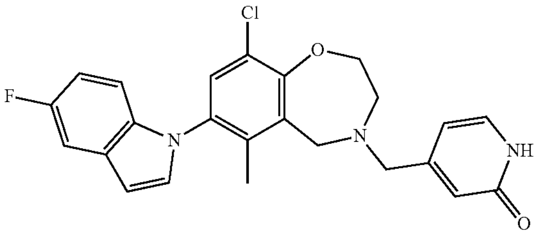 $^1$H NMR (300 MHz, DMSO-$d_6$) δ 11.38 (s, 1H), 7.50 (d, J = 3 Hz, 1H), 7.40-7.44 (m, 2H), 7.30 (d, J = 6 Hz, 1H), 7.00-7.33 (m, 2H), 6.65-6.66 (m, 1H), 6.28 (s, 1H), 6.17-6.20 (m, 1H), 4.13-4.24 (m, 2H), 3.89 (s, 2H), 3.53 (s, 2H), 3.09-3.16 (m, 2H), 1.61 (s, 3H); $^{19}$F NMR (300 MHz, DMSO-$d_6$) δ −124.3. | 438.1 | I |
| 239 | 4-{[9-chloro-7-(5-fluoroindol-1-yl)-3-(methoxymethyl)-3,5-dihydro-2H-1,4-benzoxazepin-4-yl]methyl}-1H-pyridin-2-one 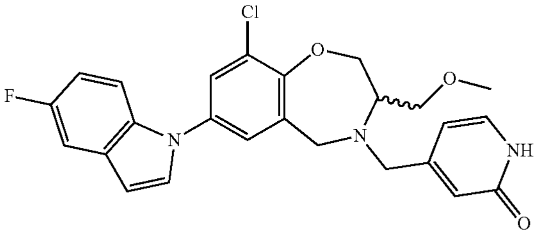 $^1$HNMR (400 MHz, DMSO-$d_6$) δ 7.71 (d, J = 3.6 Hz, 2H), 7.51-7.54 (m, 1H), 7.42-7.47 (m, 3H), 7.06-7.12 (m, 1H), 6.69 (d, J = 3.6 Hz, 1H), 6.47 (d, J = 1.6 Hz, 2H), 4.40-4.50 (m, 3H), 3.76-4.05 (m, 6H), 3.34 (s, 3H); $^{19}$F (376 MHz, DMSO-$d_6$) δ −123.5. | 468.0 | A |

TABLE 1-continued

| ID No. | Name, Structure, $^1$H-NMR, | MS (M + H)$^+$ | Method |
|---|---|---|---|
| 240 | 4-((5-chloro-7-(5-fluoro-1H-indol-1-yl)-3,4-dihydroisoquinolin-2(1H)-yl)methyl)pyridin-2(1H)-one<br>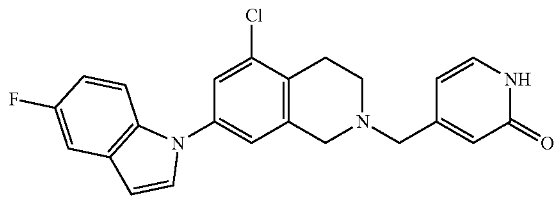<br>$^1$H NMR (400 MHz, $CD_3OD$) δ 7.40-7.56 (m, 4H), 7.31 (d, J = 9.2 Hz, 1H), 7.25 (d, J = 2.4 Hz, 1H), 6.98 (t, J = 9.2 Hz, 1H), 6.53-6.68 (m, 3H), 3.77 (s, 2H), 3.67 (s, 2H), 2.98 (t, J = 6.0 Hz, 2H), 2.89 (t, J = 5.6 Hz, 2H). $^{19}$F NMR (282 MHz, DMSO-$d_6$) δ −126.1. | 408.1 | A |
| 249 | See Method I. | | |
| 251 | 9-chloro-7-(5-fluoro-1H-indol-1-yl)-4-((2-(2-methoxyethyl)pyrimidin-5-yl)methyl)-2,3,4,5-tetrahydrobenzo[f][1,4]oxazepine<br>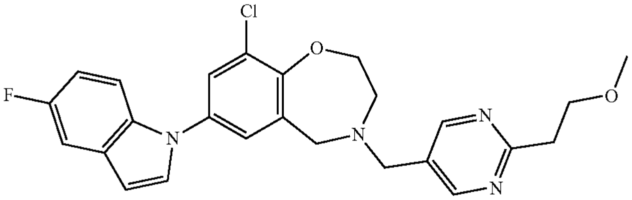<br>$^1$H NMR (300 MHz, DMSO-$d_6$) δ 8.66 (s, 2H), 7.71 (d, J = 3.3 Hz, 1H), 7.63 (d, J = 2.6 Hz, 1H), 7.49-7.51 (m, 1H), 7.38-7.47 (m, 2H), 7.01-7.05 (m, 1H), 6.69 (d, J = 3.3 Hz, 1H), 4.17-4.19 (m, 2H), 3.98 (s, 2H), 3.79 (t, J = 6.6 Hz, 2H), 3.71 (s, 2H), 3.21 (s, 3H), 3.03-3.14 (m, 4H); $^{19}$F NMR (282 MHz, DMSO-$d_6$) δ −123.6. | 467.1 | A |
| 252 | See Example S53. | | |
| 253 | 9-chloro-4-((2-cyclopropylpyrimidin-5-yl)methyl)-7-(5-fluoro-1H-indol-1-yl)-2,3,4,5-tetrahydrobenzo[f][1,4]oxazepine<br>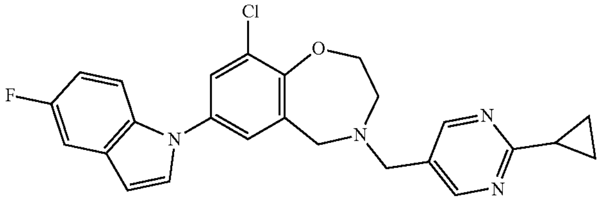<br>$^1$H NMR (300 MHz, DMSO-$d_6$) δ 8.56 (s, 2H), 7.72 (d, J = 3.3 Hz, 1H), 7.63 (d, J = 2.6 Hz, 1H), 7.39-7.47 (m, 3H), 7.01-7.05 (m, 1H), 6.69 (d, J = 3.3 Hz, 1H), 4.16-4.19 (m, 2H), 3.97 (s, 2H), 3.67 (s, 2H), 3.01-3.05 (m, 2H), 2.11-2.15 (m, 1H), 0.94-1.06 (m, 4H); $^{19}$F NMR (282 MHz, DMSO-$d_6$) δ −123.6. | 449.0 | A |
| 254 | See Example S54. | | |
| 255 | See Example S55. | | |
| 256 | See Example S56. | | |
| 257 | See Example S57. | | |

TABLE 1-continued

| ID No. | Name, Structure, $^1$H-NMR, | MS (M + H)$^+$ | Method |
|---|---|---|---|
| 258 | 5-{[9-chloro-7-(5-fluoroindol-1-yl)-3,5-dihydro-2H-1,4-benzoxazepin-4-yl]methyl}pyridazin-3-amine 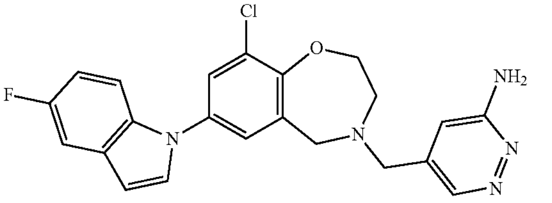 | 425.1 | B |
| | $^1$H NMR (400 MHz, DMSO-$d_6$) δ 8.36 (d, J = 1.8 Hz, 1H), 7.71 (d, J = 3.3 Hz, 1H), 7.63 (d, J = 2.6 Hz, 1H), 7.48-7.55 (m, 1H), 7.39-7.46 (m, 1H), 7.37 (d, J = 2.7 Hz, 1H), 7.02-7.11 (m, 1H), 6.74 (d, J = 1.8 Hz, 1H), 6.66-6.71 (m, 1H), 6.31 (s, 2H), 4.15-4.21 (m, 2H), 3.93 (s, 2H), 3.61 (s, 2H), 3.35 (s, 2H), 3.05-3.12 (m, 2H); $^{19}$F NMR (376 MHz, DMSO-$d_6$) δ −123.6. | 425.1 | B |
| 259 | See Example S58. | | |
| 260 | methyl 5-((9-chloro-7-(5-fluoro-1H-indol-1-yl)-2,3-dihydrobenzo[f][1,4]oxazepin-4(5H)-yl)methyl)picolinate 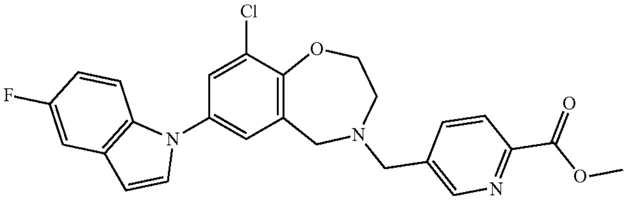 $^1$H NMR (300 MHz, DMSO-$d_6$) δ 8.66 (s, 1H), 8.04-8.06 (m, 1H), 7.91-7.95 (m, 1H), 7.71 (d, J = 3.3 Hz, 1H), 7.63 (d, J = 2.6 Hz, 1H), 7.40-7.48 (m, 2H), 7.34 (d, J = 2.7 Hz, 1H), 7.01-7.06 (m, 1H), 6.68 (d, J = 3.3 Hz, 1H), 4.17-4.19 (m, 2H), 3.96 (s, 2H), 3.87 (s, 3H), 3.85 (s, 2H), 3.09-3.11 (m, 2H); $^{19}$F NMR (282 MHz, DMSO-$d_6$) δ −123.2. | 466.0 | A |
| 300 | 5-{[7-(1-benzothiophen-3-yl)-9-chloro-3,5-dihydro-2H-1,4-benzoxazepin-4-yl]methyl}-1H-pyrimidin-2-one 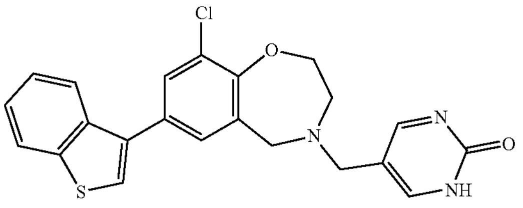 $^1$H NMR (300 MHz, $CD_3OD$) δ 8.25 (s, 2H), 7.95-8.01 (m, 1H), 7.82-7.88 (m, 1H), 7.55-7.60 (m, 2H), 7.39-7.49 (m, 2H), 7.31 (d, J = 2.1 Hz, 1H), 4.20-4.24 (m, 2H), 3.96 (s, 2H), 3.58 (t, 2H), 3.15-3.19 (m, 2H). | 424.1 | D |

Synthesis of Additional Compounds

Example S1. Preparation of 5-{[9-chloro-7-(5-fluoroindol-1-yl)-3-methyl-3,5-dihydro-2H-1,4-benzoxazepin-4-yl]methyl}pyrimidin-2-amine (Compound 11)

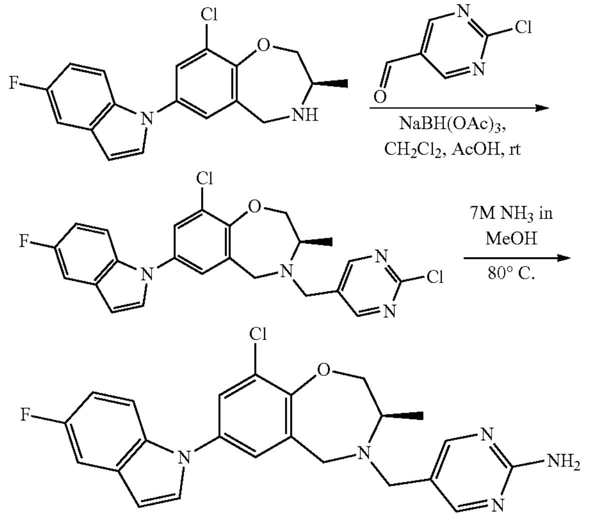

9-chloro-4-[(2-chloropyrimidin-5-yl)methyl]-7-(5-fluoroindol-1-yl)-3-methyl-3,5-dihydro-2H-1,4-benzoxazepine To a stirred mixture of 9-chloro-7-(5-fluoroindol-1-yl)-13-methyl-2,3,4,5-tetrahydro-1,4-benzoxazepine (75 mg, 0.23 mmol) in DCM (2 mL) were added 2-chloropyrimidine-5-carbaldehyde (64 mg, 0.45 mmol), $NaBH(OAc)_3$ (96 mg, 0.45 mmol) and AcOH (0.08 mg, 0.001 mmol). The mixture was stirred at rt for 2 h, then concentrated under vacuum and the residue was purified by reverse-phase column chromatography (column, C18 silica gel; mobile phase, MeCN in Water (10 mmol/L $NH_4HCO_3$), 10% to 80% gradient in 20 min; detector, UV 254 nm) to afford 9-chloro-4-[(2-chloropyrimidin-5-yl)methyl]-7-(5-fluoroindol-1-yl)-3-methyl-3,5-dihydro-2H-1,4-benzoxazepine (35 mg, 32%) as an oil.

5-{[9-chloro-7-(5-fluoroindol-1-yl)-3-methyl-3,5-dihydro-2H-1,4-benzoxazepin-4-yl]methyl}pyrimidin-2-amine A stirred mixture of 9-chloro-4-[(2-chloropyrimidin-5-yl)methyl]-7-(5-fluoroindol-1-yl)-3-methyl-3,5-dihydro-2H-1,4-benzoxazepine (30 mg, 0.066 mmol) in 7M $NH_3$ in MeOH (3 mL) was heated to 80° C. and stirred for 16 h. The mixture was concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 51% B to 71% B in 7 min, 71% B; Wave Length: 254 nm; RT1(min): 5.40) to afford 5-{[9-chloro-7-(5-fluoroindol-1-yl)-3-methyl-3,5-dihydro-2H-1,4-benzoxazepin-4-yl]methyl}pyrimidin-2-amine (2 mg, 7%) as a solid. LC/MS: mass calcd. For $C_{23}H_{21}ClFN_5O$: 437.1, found: 438.2 $[M+H]^+$; $^1H$ NMR (300 MHz, $CD_3OD$) δ 8.19 (s, 2H), 7.39-7.55 (m, 3H), 7.25-7.39 (m, 1H), 7.14 (d, J=2.7 Hz, 1H), 6.92-7.07 (m, 1H), 6.61-6.68 (m, 1H), 4.25-4.48 (m, 2H), 4.04-4.20 (m, 1H), 3.59-3.82 (m, 3H), 3.43-3.59 (m, 1H), 1.35 (d, J=6.9 Hz, 3H); $^{19}F$ NMR (282 MHz, $CD_3OD$) δ -126.2.

Example S2. Preparation of 9-chloro-4-[(2-methoxypyrimidin-5-yl)methyl]-7-[3-(trifluoromethyl)indol-1-yl]-3,5-dihydro-2H-1,4-benzoxazepine (Compound 17)

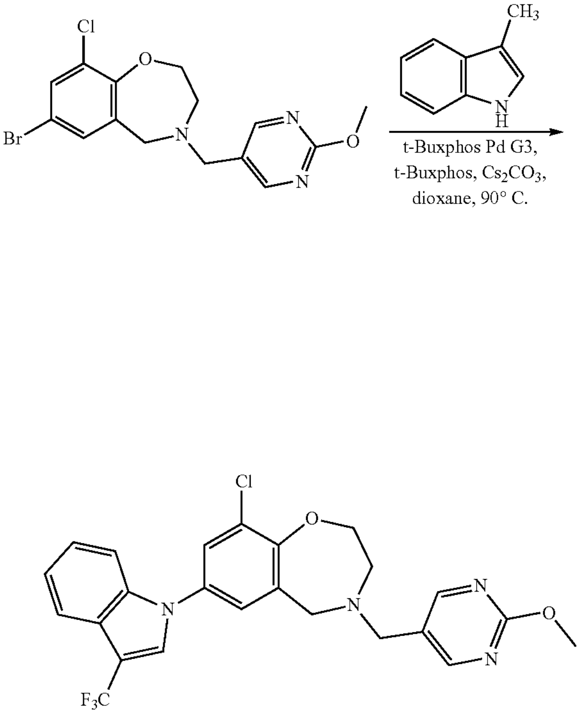

To a mixture of 7-bromo-9-chloro-4-[(2-methoxypyrimidin-5-yl)methyl]-3,5-dihydro-2H-1,4-benzoxazepine (50 mg, 0.13 mmol) and 3-(trifluoromethyl)-1H-indole (24 mg, 0.13 mmol) in 1,4-dioxane (1 mL) under an atmosphere of $N_2$ were added di-tert-butyl[2',4',6'-tris(propan-2-yl)-[1,1'-biphenyl]-2-yl]phosphane (6 mg), tBuxphos Pd G3 (10 mg, 0.013 mmol) and $Cs_2CO_3$ (85 mg, 0.26 mmol). The mixture was heated to 90° C. and stirred for 16 h, then filtered and the filtrate was concentrated under vacuum. The residue was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 55% B to 85% B in 7 min, 85% B; Wave Length: 254 nm; RT1(min): 6.55) to afford 9-chloro-4-[(2-methoxypyrimidin-5-yl)methyl]-7-[3-(trifluoromethyl)indol-1-yl]-3,5-dihydro-2H-1,4-benzoxazepine (4.9 mg, 8%) as a solid. LC/MS: mass calcd. For $C_{24}H_{20}ClF_3N_4O_2$: 488.1, found: 489.0$[M+H]^+$; $^1H$ NMR (300 MHz, DMSO-$d_6$) δ 8.54 (s, 2H), 8.31 (s, 1H), 7.80-7.67 (m, 2H), 7.57 (d, J=8.1 Hz, 1H), 7.49 (d, J=2.6 Hz, 1H), 7.27-7.44 (m, 2H), 4.19-4.22 (m, 2H), 3.97 (s, 2H), 3.90 (s, 3H), 3.66 (s, 2H), 3.06-3.09 (m, 2H); $^{19}F$ NMR (376 MHz, DMSO-$d_6$) δ -55.0.

Example S3. Preparation of 9-chloro-7-{imidazo[1,5-a]pyridin-3-yl}-4-[(2-methoxypyrimidin-5-yl)methyl]-3,5-dihydro-2H-1,4-benzoxazepine (Compound 40)

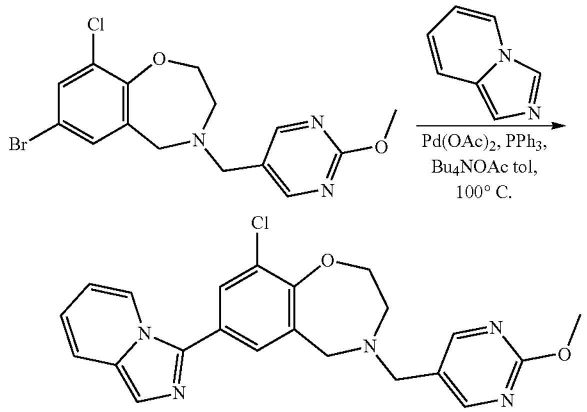

A mixture of 7-bromo-9-chloro-4-[(2-methoxypyrimidin-5-yl)methyl]-3,5-dihydro-2H-1,4-benzoxazepine (100 mg, 0.26 mmol) and imidazo[1,5-a]pyridine (31 mg, 0.260 mmol), $PPh_3$ (7 mg, 0.03 mmol), $Bu_4NOAc$ (157 mg, 0.52 mmol) in toluene (3 mL) under an atmosphere of $N_2$ was heated to 100° C. and stirred for 16 h. The mixture was concentrated under reduced pressure and the residue was purified by reverse-phase column chromatography and preparative-HPLC (Column: XBridge Prep Phenyl OBD Column, 19*250 mm, 5 μm; Mobile Phase A: Water (10 mmol/L $NH_4HCO_3$+0.1% $NH_3 \cdot H_2O$), Mobile Phase B: ACN; Flow rate: 25 mL/min; Gradient: 40% B to 63% B in 10 min, 63% B; Wave Length: 254 nm; RT1(min): 8.36) to afford 9-chloro-7-{imidazo[1,5-a]pyridin-3-yl}-4-[(2-methoxypyrimidin-5-yl)methyl]-3,5-dihydro-2H-1,4-benzoxazepine (5.2 mg, 5%) as a solid. LC/MS: mass calcd. For $C_{22}H_{20}ClN_5O_2$: 421.1, found: 422.1 $[M+H]^+$; $^1H$ NMR (300 MHz, $CD_3OD$) δ 8.56 (s, 2H), 8.30-8.36 (m, 1H), 7.76 (d, J=3.0 Hz, 1H), 7.58-7.65 (m, 1H), 7.50 (s, 1H), 7.45-7.48 (d, J=3.0 Hz, 1H), 6.83-6.94 (m, 1H), 6.74-6.81 (m, 1H), 4.21-4.28 (m, 2H), 4.02 (s, 3H), 3.98 (s, 2H), 3.75 (s, 2H), 3.15-3.21 (m, 2H).

Example S4. Preparation of 9-chloro-7-{7-chloroimidazo[1,5-a]pyridin-3-yl}-4-[(2-methoxypyrimidin-5-yl)methyl]-3,5-dihydro-2H-1,4-benzoxazepine (Compound 41)

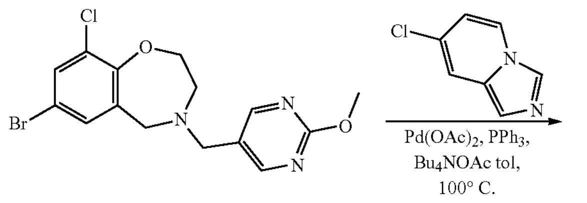

-continued

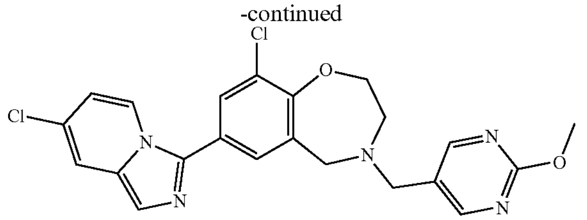

To a mixture of 7-bromo-9-chloro-4-[(2-methoxypyrimidin-5-yl)methyl]-3,5-dihydro-2H-1,4-benzoxazepine (50 mg, 0.13 mmol) and 7-chloroimidazo[1,5-a]pyridine (20 mg, 0.13 mmol) in toluene (1 mL) under an atmosphere of $N_2$ were added $Pd(OAc)_2$ (2 mg, 0.007 mmol), $PPh_3$ (4 mg, 0.013 mmol) and $Bu_4NOAc$ (78 mg, 0.26 mmol). The mixture was heated to 100° C. and stirred for 16 h, then concentrated under vacuum and the residue was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 35% B to 65% B in 7 min, 65% B; Wave Length: 254 nm; RT1(min): 5.25) to afford 9-chloro-7-{7-chloroimidazo[1,5-a]pyridin-3-yl}-4-[(2-methoxypyrimidin-5-yl)methyl]-3,5-dihydro-2H-1,4-benzoxazepine (7.3 mg, 12%) as a solid. LC/MS: mass calcd. For $C_{22}H_{19}C_{12}N_5O_2$: 455.0, found: 456.1$[M+H]^+$; $^1H$ NMR (400 MHz, DMSO-$d_6$) δ 8.53 (s, 2H), 8.43-8.45 (m, 1H), 7.81-7.83 (m, 2H), 7.60 (d, J=2.7 Hz, 1H), 7.52 (d, J=2.1 Hz, 1H), 6.72-6.74 (m, 1H), 4.17-4.20 (m, 2H), 3.97 (s, 2H), 3.90 (s, 3H), 3.65 (s, 2H), 3.01-3.08 (m, 2H).

Example S5. Preparation of 9-chloro-4-[(2-methoxypyrimidin-5-yl)methyl]-7-(4,5,6,7-tetrahydroindol-1-yl)-3,5-dihydro-2H-1,4-benzoxazepine (Compound 44)

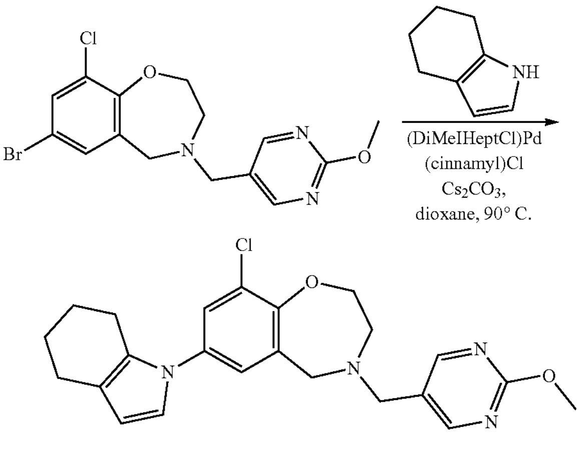

To a mixture of 7-bromo-9-chloro-4-[(2-methoxypyrimidin-5-yl)methyl]-3,5-dihydro-2H-1,4-benzoxazepine (50 mg, 0.13 mmol) and 4,5,6,7-tetrahydro-1H-indole (19 mg, 0.16 mmol) in 1,4-dioxane (1 mL) under an atmosphere of $N_2$ were added $Cs_2CO_3$ (4 mg, 0.013 mmol) and (prop-2-en-1-yl)benzene; {1-[2,6-bis(2,6-dimethylheptan-4-yl)phenyl]-4,5-dichloro-3-{2-[2,8-dimethyl-3,7-bis(propan-2-yl)nonan-5-yl]-6-(2,6-dimethylheptan-4-yl)phenyl}-2,3-dihydro-1H-imidazol-2-yl}(chloro)palladium (14 mg). The mixture was heated to 90° C. and stirred for 16 h, then filtered and the filtrate was concentrated under vacuum. The residue was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 47% B to 77% B in 10 min, 77% B; Wave Length: 254 nm; RT1(min): 9.12) to afford 9-chloro-4-[(2-methoxypyrimidin-5-yl) methyl]-7-(4,5,6,7-tetrahydroindol-1-yl)-3,5-dihydro-2H-1,4-benzoxazepine (3.5 mg, 6%) as a solid. LC/MS: mass calcd. For $C_{23}H_{25}ClN_4O_2$: 424.1, found: 425.1[M+H]$^+$; $^1$H NMR (300 MHz, DMSO-$d_6$) δ 8.50 (s, 2H), 7.37 (d, J=2.4 Hz, 1H), 7.13 (d, J=2.7 Hz, 1H), 6.82 (d, J=3 Hz, 1H), 5.96 (d, J=3 Hz, 1H), 4.11-4.13 (m, 2H), 3.90 (d, J=3 Hz, 5H), 3.61 (s, 2H), 3.36 (s, 2H), 3.04 (d, J=5.2 Hz, 2H), 2.47-2.51 (m, 2H), 1.70 (s, 4H).

Example S6. Preparation of 9-chloro-7-(5-fluoro-2, 3-dihydroindol-1-yl)-4-[(2-methoxypyrimidin-5-yl) methyl]-3,5-dihydro-2H-1,4-benzoxazepine (Compound 45)

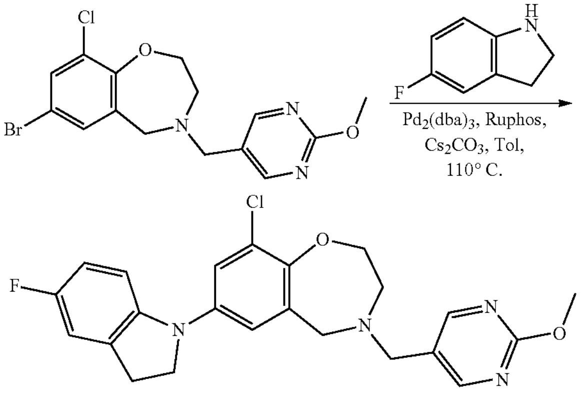

A mixture of 7-bromo-9-chloro-4-[(2-methoxypyrimidin-5-yl)methyl]-3,5-dihydro-2H-1,4-benzoxazepine (50 mg, 0.13 mmol) in toluene (1 mL) under an atmosphere of $N_2$ was added 5-fluoro-1H,2H,3H-pyrrolo[2,3-b]pyridine (27 mg, 0.2 mmol), $Pd_2(dba)_3$ (6 mg, 0.007 mmol), Ruphos (6 mg, 0.013 mmol) and $Cs_2CO_3$ (127 mg, 0.39 mmol) were heated to 110° C. and stirred for 12 h. The mixture was filtered, the filtrate was concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 45% B to 75% B in 9 min, 75% B; Wave Length: 254 nm; RT1(min): 8) to afford 9-chloro-7-(5-fluoro-2,3-dihydroindol-1-yl)-4-[(2-methoxypyrimidin-5-yl)methyl]-3,5-dihydro-2H-1,4-benzoxazepine (13.1 mg, 23%) as a solid. LC/MS: mass calcd. For $C_{23}H_{22}ClFN_4O_2$: 440.1, found: 441.1 [M+H]$^+$; $^1$H NMR (300 MHz, DMSO-$d_6$) δ 8.50 (s, 2H), 7.10 (d, J=3.2 Hz, 1H), 7.02-7.06 (m, 1H), 6.92-6.98 (m, 2H), 6.79-6.86 (m, 1H), 4.02-4.05 (m, 2H), 3.85-3.90 (m, 7H), 3.59 (s, 2H), 2.99-3.08 (m, 4H); $^{19}$F (282 MHz, DMSO-$d_6$) δ −125.3.

Example S7. Preparation of 9-chloro-7-(5-chloro-2, 3-dihydroindol-1-yl)-4-[(2-methoxypyrimidin-5-yl) methyl]-3,5-dihydro-2H-1,4-benzoxazepine (Compound 46)

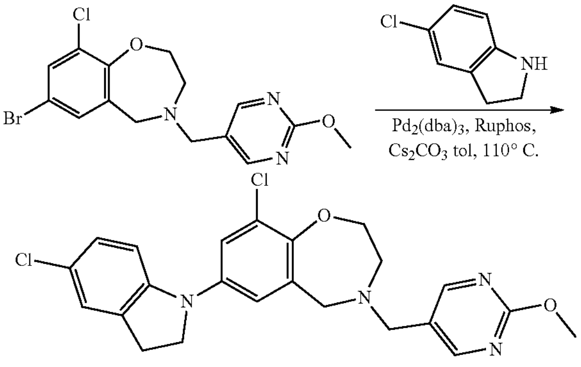

To a mixture of 7-bromo-9-chloro-4-[(2-methoxypyrimidin-5-yl)methyl]-3,5-dihydro-2H-1,4-benzoxazepine (50 mg, 0.13 mmol) and 5-chloro-2,3-dihydro-1H-indole (30 mg, 0.2 mmol) in toluene (1 mL) under an atmosphere of $N_2$ were added $Pd_2(dba)_3$ (6 mg, 0.007 mmol), Ruphos (6 mg, 0.013 mmol) and $Cs_2CO_3$ (127 mg, 0.39 mmol). The mixture was heated to 110° C. and stirred for 16 h, then filtered and the filtrate was concentrated under vacuum. The residue was purified by preparative-HPLC (Column: Xselect CSH F-Phenyl OBD column, 19*250 mm, 5 μm; Mobile Phase A: Water (0.1% FA), Mobile Phase B: ACN; Flow rate: 25 mL/min; Gradient: 30% B to 55% B in 9 min, 55% B; Wave Length: 254 nm; RT1(min): 7.32) to afford 9-chloro-7-(5-chloro-2,3-dihydroindol-1-yl)-4-[(2-methoxypyrimidin-5-yl)methyl]-3,5-dihydro-2H-1,4-benzoxazepine (16 mg, 26%) as a solid. LC/MS: mass calcd. For $C_{23}H_{22}Cl_2N_4O_2$: 456.1, found: 457.0[M+H]$^+$; $^1$H NMR (300 MHz, DMSO-$d_6$) δ 8.52 (s, 2H), 7.18 (d, J=3 Hz, 2H), 7.15-7.08 (m, 3H), 4.05-4.08 (m, 2H), 3.86-3.94 (m, 7H), 3.61 (s, 2H), 3.01-3.12 (m, 4H).

Example S8. Preparation of 9-chloro-7-(5-fluoro-1, 3-dihydroisoindol-2-yl)-4-[(2-methoxypyrimidin-5-yl)methyl]-3,5-dihydro-2H-1,4-benzoxazepine (Compound 47)

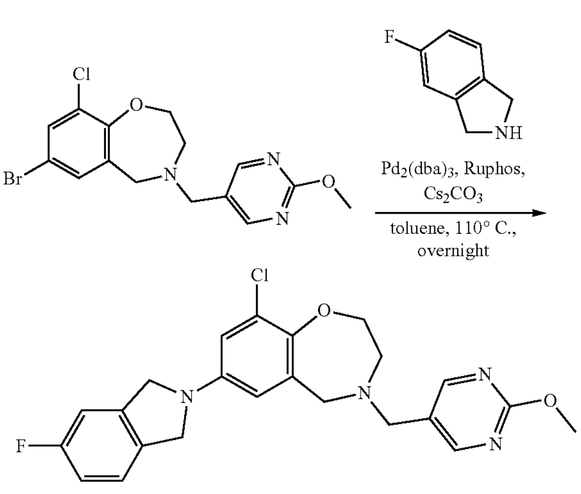

To a mixture of 5-fluoro-2,3-dihydro-1H-isoindole (27 mg, 0.2 mmol) and 7-bromo-9-chloro-4-[(2-methoxypyrimidin-5-yl)methyl]-3,5-dihydro-2H-1,4-benzoxazepine (50 mg, 0.13 mmol) in toluene under an atmosphere of $N_2$ were added $Pd_2(dba)_3$ (6 mg, 0.007 mmol), RuPhos (6 mg, 0.013 mmol) and $Cs_2CO_3$ (127 mg, 0.39 mmol). The mixture was heated to 110° C. and stirred overnight, then filtered, and the filtrate was concentrated under reduced pressure. The residue was purified by preparative-HPLC (Column: XBridge Prep OBD C18 Column, 30*150 mm, 5 µm; Mobile Phase A: Water (10 mmol/L $NH_4HCO_3$+0.1% $NH_3 \cdot H_2O$), Mobile Phase B: ACN; Flow rate: 60 mL/min; Gradient: 50% B to 80% B in 7 min, 80% B; Wave Length: 254 nm; RT1(min): 6.12) to afford 9-chloro-7-(5-fluoro-1,3-dihydroisoindol-2-yl)-4-[(2-methoxypyrimidin-5-yl)methyl]-3,5-dihydro-2H-1,4-benzoxazepine (5.7 mg, 10%) as a solid. LC/MS: mass caled. For $C_{23}H_{22}ClFN_4O_2$: 440.1, found: 441.1 $[M+H]^+$; $^1$H NMR (300 MHz, DMSO-$d_6$) δ 8.51 (s, 2H), 7.39-7.44 (m, 1H), 7.25 (d, J=8.4 Hz, 1H), 7.15 (t, J=9.0 Hz, 1H), 6.58 (d, J=2.4 Hz, 1H), 6.39 (d, J=2.4 Hz, 1H), 4.54 (d, J=8.7 Hz, 4H), 3.98-3.99 m, 2H), 3.92 (s, 3H), 3.83 (s, 2H), 3.58 (s, 2H), 3.00-3.01 (m, 2H); $^{19}$F NMR (282 MHz, DMSO-d6) δ −115.9.

Example S9. Preparation of 9-chloro-7-(6-fluoro-4-methyl-2,3-dihydroquinoxalin-1-yl)-4-[(2-methoxypyrimidin-5-yl)methyl]-3,5-dihydro-2H-1,4-benzoxazepine (Compound 50)

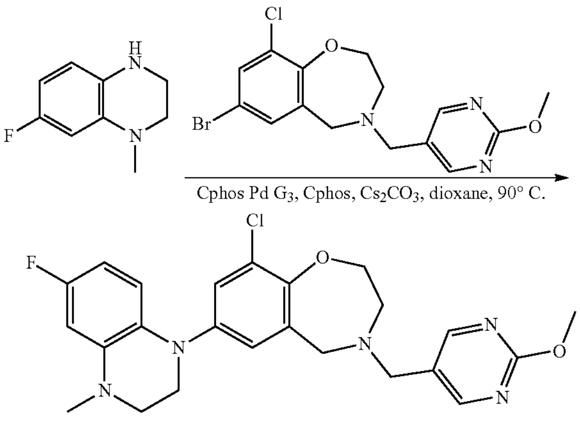

To a stirred mixture of 7-fluoro-1-methyl-3,4-dihydro-2H-quinoxaline [CAS No: 1354953-50-6] (36 mg, 0.22 mmol) and 7-bromo-9-chloro-4-[(2-methoxypyrimidin-5-yl)methyl]-3,5-dihydro-2H-1,4-benzoxazepine (100 mg, 0.26 mmol) in 1,4-dioxane (2 mL) under an atmosphere of $N_2$ was added Cphos pd $G_3$ (18 mg, 0.02 mmol), Cphos (10 mg, 0.02 mmol) and $Cs_2CO_3$ (141 mg, 0.43 mmol). The mixture was heated to 90° C. and stirred for 16 h, then filtered, and the filtrate was concentrated under reduced pressure. The residue was purified by preparative-HPLC (Column: XBridge Prep OBD C18 Column, 30*150 mm, 5 µm; Mobile Phase A: H2O (10 mmol/L NH4HCO3+0.1% NH3·H2O), Mobile Phase B: ACN; Flow rate: 60 mL/min; Gradient: 50% B to 80% B in 7 min, 80% B; Wave Length: 254 nm; RT1(min): 5.87) to afford 9-chloro-7-(6-fluoro-4-methyl-2,3-dihydroquinoxalin-1-yl)-4-[(2-methoxypyrimidin-5-yl)methyl]-3,5-dihydro-2H-1,4-benzoxazepine (3.5 mg, 3%) as a solid. LC/MS: mass calcd. For $C_{24}H_{25}ClFN_5O_2$: 469.2, found: 470.1 $[M+H]^+$; $^1$H NMR (300 MHz, DMSO-$d_6$) δ 8.49 (s, 2H), 7.03 (d, J=3.0 Hz, 1H), 6.80 (d, J=3.0 Hz, 1H), 6.60-6.65 (m, 1H), 6.46-6.51 (m, 1H), 6.25-6.32 (m, 1H), 4.03-4.06 (m, 2H), 3.91 (d, J=6.0 Hz, 3H), 3.76 (s, 2H), 3.56-3.58 (m, 4H), 3.23-3.31 (m, 2H), 3.02 (s, 2H), 2.89 (s, 3H); $^{19}$F (282 MHz, DMSO-$d_6$) δ −120.7.

Example S10. Preparation of 9-chloro-7-(7-fluoro-2,3-dihydro-1,4-benzoxazin-4-yl)-4-[(2-methoxypyrimidin-5-yl)methyl]-3,5-dihydro-2H-1,4-benzoxazepine (Compound 51)

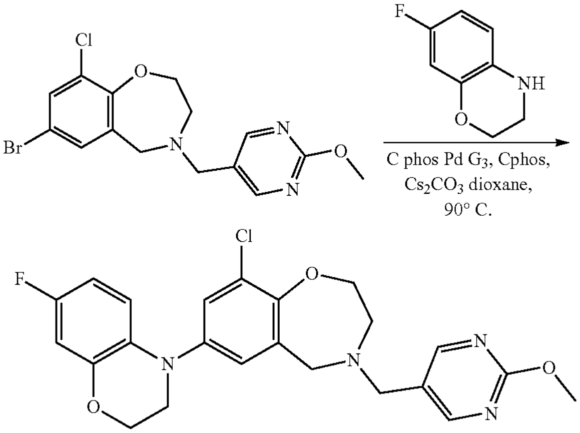

To a mixture of 7-bromo-9-chloro-4-[(2-methoxypyrimidin-5-yl)methyl]-3,5-dihydro-2H-1,4-benzoxazepine (50 mg, 0.13 mmol) and 7-fluoro-3,4-dihydro-2H-1,4-benzoxazine (24 mg, 0.16 mmol) in 1,4-dioxane (1 mL) under an atmosphere of $N_2$ was added Cphos pd G3 (11 mg, 0.013 mmol), Cphos (6 mg, 0.013 mmol) and $Cs_2CO_3$ (85 mg, 0.26 mmol). The mixture was heated to 90° C. and stirred for 16 h, then filtered and the filtrate was concentrated under vacuum. The residue was purified by preparative-HPLC (Column: XBridge Prep OBD C18 Column, 30*150 mm, 5 µm; Mobile Phase A: Water (10 mmol/L $NH_4HCO_3$+0.1% $NH_3 \cdot H_2O$), Mobile Phase B: ACN; Flow rate: 60 mL/min; Gradient: 45% B to 75% B in 7 min, 75% B; Wave Length: 254 nm; RT1(min): 5.25) to afford 9-chloro-7-(7-fluoro-2,3-dihydro-1,4-benzoxazin-4-yl)-4-[(2-methoxypyrimidin-5-yl)methyl]-3,5-dihydro-2H-1,4-benzoxazepine (6.4 mg, 11%) as a solid. LC/MS: mass calcd. For $C_{23}H_{22}ClFN_4O_3$: 456.1, found: 457.1$[M+H]^+$; $^1$H NMR (400 MHz, DMSO-$d_6$) δ 8.50 (s, 2H), 7.18 (d, J=2.8 Hz, 1H), 6.94 (d, J=2.8 Hz, 1H), 6.79-6.83 (m, 1H), 6.72-6.75 (m, 1H), 6.59-6.65 (m, 1H), 4.21-4.23 (m, 2H), 4.05-4.11 (m, 2H), 3.90 (s, 3H), 3.79 (s, 2H), 3.58-3.66 (m, 4H), 3.06-2.99 (m, 2H); $^{19}$F NMR (376 MHz, DMSO-$d_6$) δ −122.0.

Example S11. Preparation of 9-chloro-7-(5-fluoroindol-1-yl)-4-(1,3-thiazol-4-ylmethyl)-3,5-dihydro-2H-1,4-benzoxazepine (Compound 100)

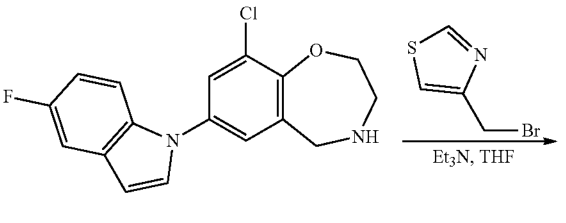

-continued

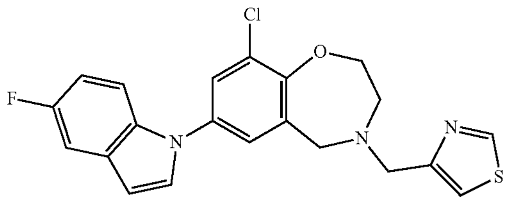

To a stirred mixture of 9-chloro-7-(5-fluoroindol-1-yl)-2,3,4,5-tetrahydro-1,4-benzoxazepine (50 mg, 0.16 mmol) in THF (1 mL) was added 4-(bromomethyl)-1,3-thiazole (61 mg) and $Et_3N$ (32 mg, 0.32 mmol). The mixture was heated to 70° C. and stirred for 2 h, then concentrated under vacuum and the residue was purified by preparative-HPLC (Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 55% B to 85% B in 7 min, 85% B; Wave Length: 254 nm; RT1(min): 6) to afford 9-chloro-7-(5-fluoroindol-1-yl)-4-(1,3-thiazol-4-ylmethyl)-3,5-dihydro-2H-1,4-benzoxazepine (8.3 mg, 13%) as a solid. LC/MS: mass calcd. For $C_{21}H_{17}ClFN_3OS$: 413.1, found: 414.1 $[M+H]^+$; $^1H$ NMR (300 MHz, DMSO-$d_6$) δ 9.09 (d, J=2.1 Hz, 1H), 7.72 (d, J=3.3 Hz, 1H), 7.53-7.61 (m, 3H), 7.37-7.45 (m, 2H), 7.04-7.10 (m, 1H), 6.68 (d, J=3.3 Hz, 1H), 4.14-4.22 (m, 2H), 3.97 (s, 2H), 3.88 (s, 2H), 3.07-3.15 (m, 2H); $^{19}F$ NMR (282 MHz, DMSO-$d_6$) δ −123.6.

Example S12. Preparation of 9-chloro-7-(5-fluoroindol-1-yl)-4-[(3-methoxy-1H-pyrazol-4-yl)methyl]-3,5-dihydro-2H-1,4-benzoxazepine (Compound 105)

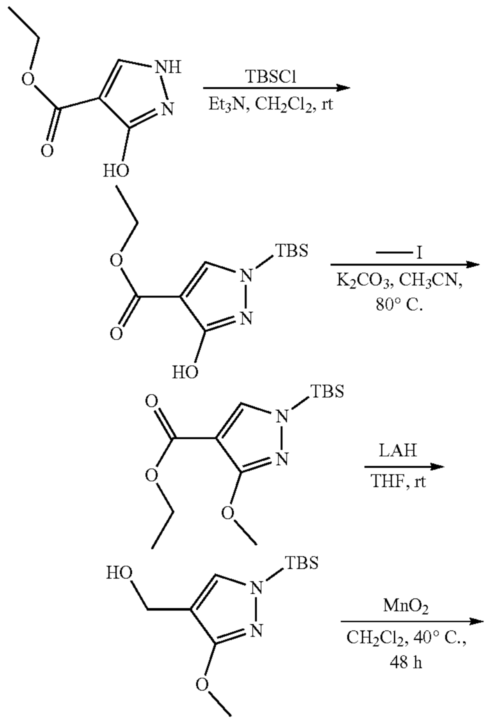

-continued

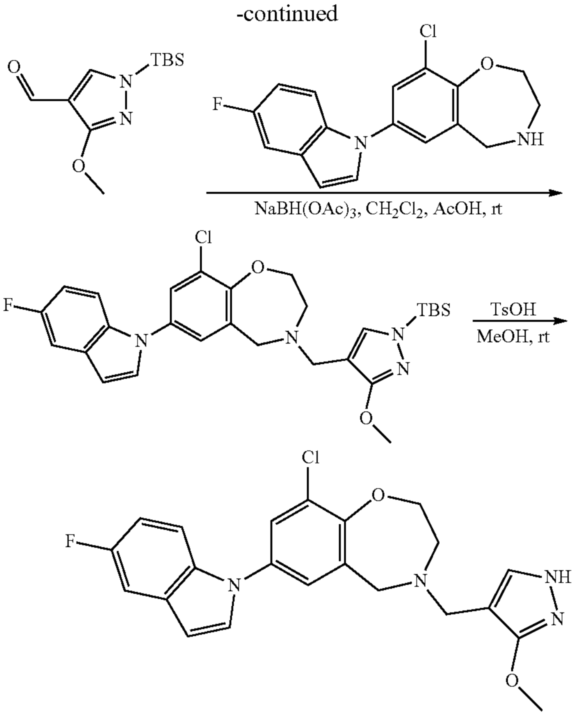

Ethyl 1-(tert-butyldimethylsilyl)-3-hydroxypyrazole-4-carboxylate

To a stirred mixture of ethyl 3-hydroxy-1H-pyrazole-4-carboxylate (1.0 g, 6.4 mmol) and TBSCl (1.45 g, 9.6 mmol) in DCM was added $Et_3N$ (1.78 mL, 12.8 mmol) dropwise at rt. The mixture was stirred for 1 h, then concentrated under reduced pressure and the residue was purified by silica gel column chromatography (PE/EtOAc, 10:1) to afford ethyl 1-(tert-butyldimethylsilyl)-3-hydroxypyrazole-4-carboxylate (1.3 g, 75%) as a solid.

Ethyl 1-(tert-butyldimethylsilyl)-3-methoxypyrazole-4-carboxylate

To a stirred mixture of ethyl 1-(tert-butyldimethylsilyl)-3-hydroxypyrazole-4-carboxylate (300 mg, 1.1 mmol) and $K_2CO_3$ (300 mg, 2.22 mmol) in MeCN (2 mL) was added MeI (0.21 mL, 3.37 mmol). The mixture was heated to 60° C. and stirred for 6 h, then concentrated under reduced pressure and the residue was purified by silica gel column chromatography (PE/EtOAc, 12:1) to afford ethyl 1-(tert-butyldimethylsilyl)-3-methoxypyrazole-4-carboxylate (120 mg, 38%) as an oil.

[1-(tert-butyldimethylsilyl)-3-methoxypyrazol-4-yl]methanol

To a stirred solution of ethyl 1-(tert-butyldimethylsilyl)-3-methoxypyrazole-4-carboxylate (460 mg, 1.62 mmol) in THE at 0° C. was added $LiAlH_4$ (160 mg, 4.2 mmol). The mixture was warmed to rt and stirred for 2 h, then re-cooled to 0° C. and quenched with $Na_2SO_4 \cdot 10H_2O$. The mixture was filtered, and the filter cake was washed with THE (3×5 mL). The filtrate was concentrated under reduced pressure to give the title compound (110 mg, crude), which was used directly in the next step without further purification.

1-(tert-butyldimethylsilyl)-3-methoxypyrazole-4-carbaldehyde

To a stirred solution of [1-(tert-butyldimethylsilyl)-3-methoxypyrazol-4-yl]methanol (70 mg, 0.29 mmol) in DCM was added $MnO_2$ (250 mg, 2.9 mmol). The mixture was heated to 40° C. and stirred overnight, then filtered, and the filter cake was washed with DCM (3×5 mL). The filtrate was concentrated under reduced pressure and the residue was purified by preparative-TLC (PE/EtOAc, 2:1) to afford 1-(tert-butyldimethylsilyl)-3-methoxypyrazole-4-carbaldehyde (32 mg, 44%) as an oil.

4-{[1-(tert-butyldimethylsilyl)-3-methoxypyrazol-4-yl]methyl}-9-chloro-7-(5-fluoroindol-1-yl)-3,5-dihydro-2H-1,4-benzoxazepine To a stirred solution of 9-chloro-7-(5-fluoroindol-1-yl)-2,3,4,5-tetrahydro-1,4-benzoxazepine (42 mg, 0.13 mmol), 1-(tert-butyldimethylsilyl)-3-methoxypyrazole-4-carbaldehyde (32 mg, 0.13 mmol) and $NaBH(OAc)_3$ (28 mg, 0.13 mmol) in DCM (2 mL) was added AcOH (0.76 uL, 0.013 mmol). The mixture was stirred at rt for 5 h, then concentrated under reduced pressure and the residue was purified by preparative-TLC (PE/EtOAc, 1:1) to afford 4-{[1-(tert-butyldimethylsilyl)-3-methoxypyrazol-4-yl]methyl}-9-chloro-7-(5-fluoroindol-1-yl)-3,5-dihydro-2H-1,4-benzoxazepine (20 mg, 28%) as a solid.

9-chloro-7-(5-fluoroindol-1-yl)-4-[(3-methoxy-1H-pyrazol-4-yl)methyl]-3,5-dihydro-2H-1,4-benzoxazepine To a stirred solution of 4-{[1-(tert-butyldimethylsilyl)-3-methoxypyrazol-4-yl]methyl}-9-chloro-7-(5-fluoroindol-1-yl)-3,5-dihydro-2H-1,4-benzoxazepine (20 mg, 0.037 mmol) in MeOH (1 mL) was added p-TsOH (20 mg, 0.11 mmol). The mixture was stirred at rt for 4 h, then concentrated under reduced pressure and the residue was purified by preparative-HPLC (Column: XSelect CSH Prep C18 OBD Column, 19*250 mm, 5 μm; Mobile Phase A: Water (0.05% HCl), Mobile Phase B: ACN; Flow rate: 25 mL/min; Gradient: 25% B to 48% B in 10 min, 48% B; Wave Length: 254 nm; RT1(min): 7.3) to afford 9-chloro-7-(5-fluoroindol-1-yl)-4-[(3-methoxy-1H-pyrazol-4-yl)methyl]-3,5-dihydro-2H-1,4-benzoxazepine (4.1 mg, 26%) as a solid. LC/MS: mass calcd. $C_{22}H_{20}ClFN_4O_2$: 426.1, found: 427.1 $[M+H]^+$; $^1H$ NMR (300 MHz, $CDCl_3$) δ 7.38-7.45 (m, 2H), 7.28-7.32 (m, 2H), 7.13 (d, J=2.4 Hz, 1H), 6.94-7.05 (m, 2H), 6.58-6.61 (m, 1H), 4.21-4.24 (m, 2H), 3.93 (s, 2H), 3.64-3.67 (m, 5H), 3.17-3.22 (m, 2H); $^{19}F$ NMR (282 MHz, $CDCl_3$) δ −123.7.

Example S13. Preparation of 9-chloro-7-(5-fluoroindol-1-yl)-4-(2H-1,2,3-triazol-4-ylmethyl)-3,5-dihydro-2H-1,4-benzoxazepine (Compound 108)

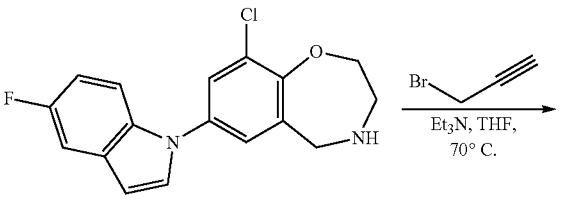

-continued

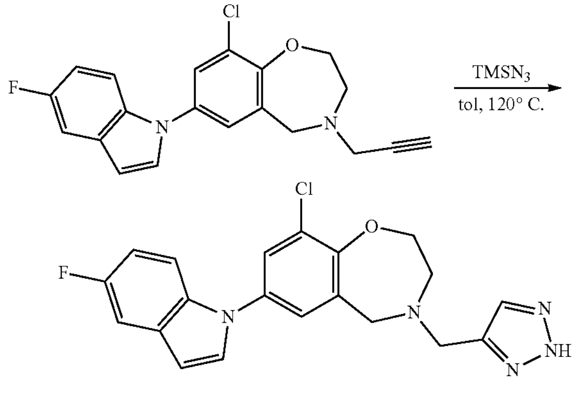

9-Chloro-7-(5-fluoroindol-1-yl)-4-(prop-2-yn-1-yl)-3,5-dihydro-2H-1,4-benzoxazepine To a stirred mixture of 9-chloro-7-(5-fluoroindol-1-yl)-2,3,4,5-tetrahydro-1,4-benzoxazepine (100 mg, 0.32 mmol) in THF (1 mL) were added propargyl bromide (56 mg, 0.47 mmol) and $Et_3N$ (65 mg, 0.63 mmol). The mixture was heated to 70° C. and stirred for 2 h, then concentrated under reduced pressure to afford 9-chloro-7-(5-fluoroindol-1-yl)-4-(prop-2-yn-1-yl)-3,5-dihydro-2H-1,4-benzoxazepine (150 mg, crude) as an oil.

9-Chloro-7-(5-fluoroindol-1-yl)-4-(2H-1,2,3-triazol-4-ylmethyl)-3,5-dihydro-2H-1,4-benzoxazepine To a stirred mixture of 9-chloro-7-(5-fluoroindol-1-yl)-4-(prop-2-yn-1-yl)-3,5-dihydro-2H-1,4-benzoxazepine (150 mg, crude) in toluene (3 mL) was added $TMSN_3$ (635 mg, 5.5 mmol). The mixture was heated to 120° C. and stirred for 35 h, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 45% B to 65% B in 7 min, 65% B; Wave Length: 254 nm; RT1(min): 5.17) to afford 9-chloro-7-(5-fluoroindol-1-yl)-4-(2H-1,2,3-triazol-4-ylmethyl)-3,5-dihydro-2H-1,4-benzoxazepine (29.6 mg, 24% over two steps) as a solid. LC/MS: mass calcd. For $C_{20}H_{17}ClFN_5O$: 397.1, found: 398.0 $[M+H]^+$; $^1H$ NMR (300 MHz, DMSO-$d_6$) δ 11.20 (br, 1H), 7.78 (s, 1H), 7.73 (d, J=3 Hz, 1H), 7.52-7.65 (m, 2H), 7.40-7.45 (m, 1H), 7.37 (d, J=3 Hz, 1H), 7.05-7.12 (m, 1H), 6.69 (d, J=3.3 Hz, 1H), 4.14-4.19 (m, 2H), 3.92 (s, 2H), 3.81 (s, 2H), 3.04-3.11 (m, 2H); $^{19}F$ NMR (300 MHz, DMSO-$d_6$) δ −123.6.

Example S14. Preparation of 9-chloro-7-(5-fluoroindol-1-yl)-4-(4H-1,2,4-triazol-3-ylmethyl)-3,5-dihydro-2H-1,4-benzoxazepine (Compound 109)

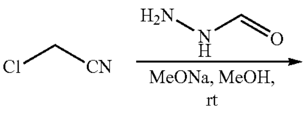

-continued

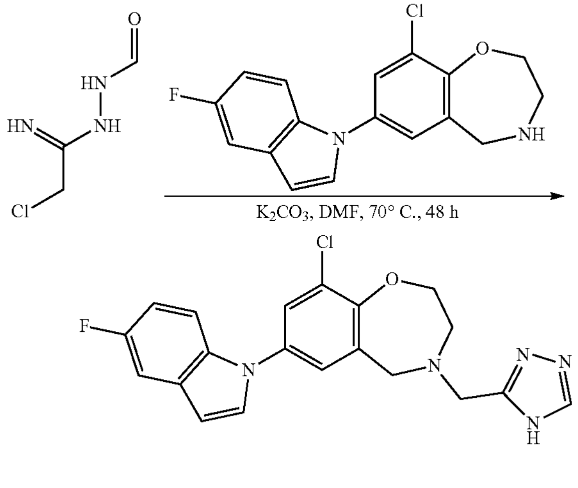

2-Chloro-N'-formylacetimidohydrazide

MeONa (0.03 g, 0.6 mmol) was added to an ice-cold solution of chloroacetonitrile (1.5 g, 19.9 mmol) in MeOH (15 mL). After stirring for 45 min, AcOH (0.04 g, 0.6 mmol) was added (to neutralize the methoxide), followed by N-formylhydrazine (1.19 g, 19.9 mmol). The mixture was stirred at rt for 1 h, then concentrated under reduced pressure and the crude product was triturated with ethanol (10 mL) and filtered to give N-(2-chloroethanimidoyl) formohydrazide (400 mg, 15%) as a solid.

9-chloro-7-(5-fluoroindol-1-yl)-4-(4H-1,2,4-triazol-3-ylmethyl)-3,5-dihydro-2H-1,4-benzoxazepine To a stirred mixture of 9-chloro-7-(5-fluoroindol-1-yl)-2,3,4,5-tetrahydro-1,4-benzoxazepine (50 mg, 0.16 mmol) and N-(2-chloroethanimidoyl)formohydrazide (33 mg, 0.24 mmol) in DMF (1 mL) was added $K_2CO_3$ (670 mg, 0.47 mmol). The mixture was heated to 70° C. and stirred for 48 h, then filtered and the filtrate was purified by preparative-HPLC (Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 40% B to 58% B in 7 min, 58% B; Wave Length: 254 nm; RT1(min): 5.43) to afford 9-chloro-7-(5-fluoroindol-1-yl)-4-(4H-1,2,4-triazol-3-ylmethyl)-3,5-dihydro-2H-1,4-benzoxazepine (15.7 mg, 24%) as a solid. LC/MS: mass caled. for $C_{20}H_{17}ClFN_5O$: 397.1, found: 398.1[M+H]$^+$; $^1$H NMR (300 MHz, DMSO-$d_6$) δ 13.90 (s, 1H), 7.95-8.51 (m, 1H), 7.73 (d, J=3.3 Hz, 1H), 7.59-7.69 (m, 2H), 7.36-7.48 (m, 2H), 7.02-7.15 (m, 1H), 6.69 (d, J=3.3 Hz, 1H), 4.17 (s, 2H), 3.96 (s, 2H), 3.81 (s, 2H), 3.14 (s, 2H); $^{19}$F NMR (300 MHz, $CD_3OD$) δ −123.6.

Example S15. Preparation of 9-chloro-7-(5-fluoroindol-1-yl)-4-(1,3,4-oxadiazol-2-ylmethyl)-3,5-dihydro-2H-1,4-benzoxazepine (Compound 111)

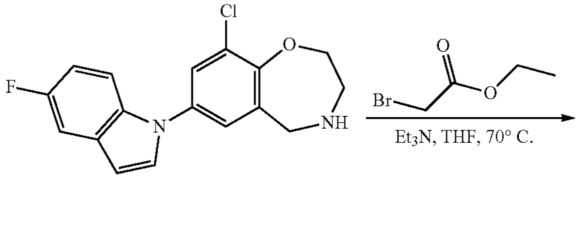

-continued

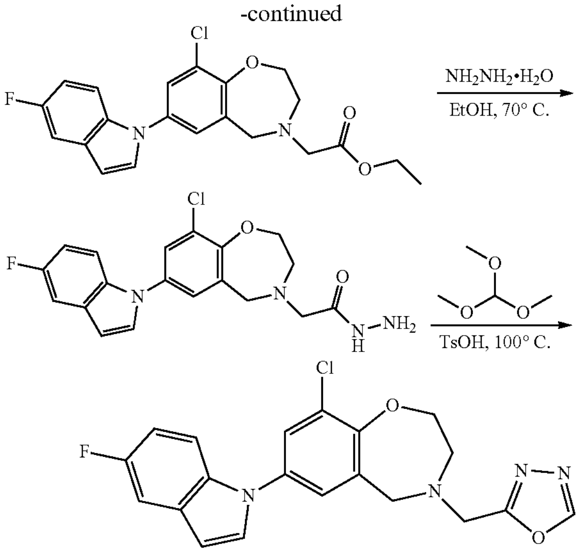

Ethyl 2-[9-chloro-7-(5-fluoroindol-1-yl)-3,5-dihydro-2H-1,4-benzoxazepin-4-yl]acetate To a stirred mixture of 9-chloro-7-(5-fluoroindol-1-yl)-2,3,4,5-tetrahydro-1,4-benzoxazepine (200 mg, 0.63 mmol) in THF (2 mL) were added ethyl bromoacetate (210 mg, 1.3 mmol) and $Et_3N$ (127 mg, 1.3 mmol). The mixture was heated to 70° C. and stirred for 2 h, then concentrated under reduced pressure and the residue was purified by silica gel column chromatography (PE/EtOAc, 1:1) to afford ethyl 2-[9-chloro-7-(5-fluoroindol-1-yl)-3,5-dihydro-2H-1,4-benzoxazepin-4-yl]acetate (170 mg, 61%) as an oil.

2-[9-Chloro-7-(5-fluoroindol-1-yl)-3,5-dihydro-2H-1,4-benzoxazepin-4-yl]acetohydrazide To a stirred mixture of ethyl 2-[9-chloro-7-(5-fluoroindol-1-yl)-3,5-dihydro-2H-1,4-benzoxazepin-4-yl]acetate (170 mg, 0.42 mmol) in EtOH (1.5 mL) were added hydrazine hydrate (54 mg, 1.1 mmol). The mixture was heated to 90° C. and stirred for 4 h, then concentrated under reduced pressure to afford 2-[9-chloro-7-(5-fluoroindol-1-yl)-3,5-dihydro-2H-1,4-benzoxazepin-4-yl]acetohydrazide (137 mg, 81%) as an oil.

9-Chloro-7-(5-fluoroindol-1-yl)-4-(1,3,4-oxadiazol-2-ylmethyl)-3,5-dihydro-2H-1,4-benzoxazepine To a stirred mixture of 2-[9-chloro-7-(5-fluoroindol-1-yl)-3,5-dihydro-2H-1,4-benzoxazepin-4-yl]acetohydrazide (127 mg, 0.33 mmol) in trimethyl orthoformate (1 mL) was added p-TsOH (13 mg). The mixture was heated to 100° C. and stirred for 10 h, then concentrated under reduced pressure and the residue was purified by preparative-HPLC (Column: XBridge Shield RP18 OBD Column, 30*150 mm, 5 μm; Mobile Phase A: Water (0.1% FA), Mobile Phase B: ACN; Flow rate: 60 mL/min; Gradient: 42% B to 62% B in 7 min, 62% B; Wave Length: 254 nm; RT1(min): 5.95) to afford 9-chloro-7-(5-fluoroindol-1-yl)-4-(1,3,4-oxadiazol-2-ylmethyl)-3,5-dihydro-2H-1,4-benzoxazepine (6.3 mg, 5%) as a solid. LC/MS: mass calcd. For $C_{20}H_{16}ClFN_4O_2$: 398.0, found: 399.0 [M+H]$^+$; $^1$H NMR (400 MHz, DMSO-$d_6$) δ 9.24 (s, 1H), 7.71 (d, J=4 Hz, 1H), 7.57-7.65 (m, 2H), 7.55

(s, 2H), 7.03-7.08 (m, 1H), 6.69 (d, J=3.2 Hz, 1H), 4.16-4.21 (m, 2H), 4.06 (s, 2H), 3.98 (s, 2H), 3.15-3.21 (m, 2H); $^{19}$F NMR (376 MHz, DMSO-$d_6$) δ −123.6.

Example S16. Preparation of 9-chloro-4-[(5-chloro-1,2,4-thiadiazol-3-yl)methyl]-7-(5-fluoroindol-1-yl)-3,5-dihydro-2H-1,4-benzoxazepine (Compound 115)

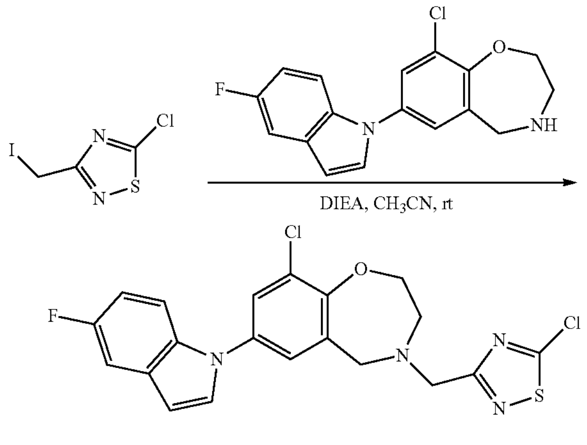

9-Chloro-4-[(5-chloro-1,2,4-thiadiazol-3-yl)methyl]-7-(5-fluoroindol-1-yl)-3,5-dihydro-2H-1,4-benzoxazepine To a stirred mixture of 9-chloro-7-(5-fluoroindol-1-yl)-2,3,4,5-tetrahydro-1,4-benzoxazepine (20 mg, 0.06 mmol) in $CH_3CN$ (1 mL) was added 5-iodo-3-(iodomethyl)-1,2,4-thiadiazole (CAS No: 115443-43-1) (45 mg, 0.13 mmol) and DIPEA (20 mg, 0.16 mmol). The mixture was stirred at rt for 18 h, then concentrated under vacuum and the residue was purified by preparative-HPLC (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 55% B to 75% B in 7 min, 75% B; Wave Length: 254 nm; RT1(min): 6.05) to afford 9-chloro-4-[(5-chloro-1,2,4-thiadiazol-3-yl)methyl]-7-(5-fluoroindol-1-yl)-3,5-dihydro-2H-1,4-benzoxazepine (1.5 mg, 5%) as a solid. LC/MS: mass calcd. For $C_{20}H_{15}Cl_2FN_4OS$: 448.0, found: 449.0 $[M+H]^+$; $^1$H NMR (300 MHz, DMSO-$d_6$) δ 7.72 (d, J=3.3 Hz, 1H), 7.52-7.65 (m, 2H), 7.38-7.49 (m, 2H), 7.03-7.10 (m, 1H), 6.69 (d, J=3.3 Hz, 1H), 4.14-4.23 (m, 2H), 4.00 (s, 4H), 3.17-3.26 (m, 2H); $^{19}$F NMR (282 MHz, DMSO-$d_6$) δ −123.5.

Example S17. Preparation of 9-chloro-7-(5-fluoroindol-1-yl)-4-[(5-methoxy-1,2,4-thiadiazol-3-yl)methyl]-3,5-dihydro-2H-1,4-benzoxazepine (Compound 116)

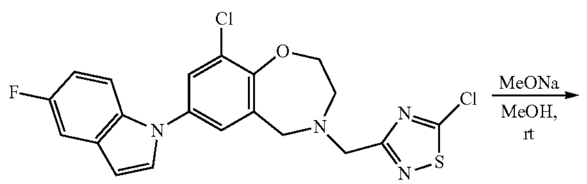

-continued

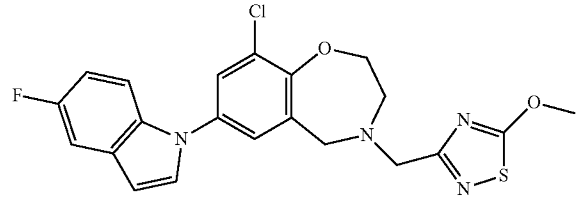

To a mixture of 9-chloro-4-[(5-chloro-1,2,4-thiadiazol-3-yl)methyl]-7-(5-fluoroindol-1-yl)-3,5-dihydro-2H-1,4-benzoxazepine (30 mg, 0.07 mmol) in MeOH (1 mL) was added $CH_{30}Na$ (12 mg, 0.22 mmol). The mixture was stirred at rt for 2 h, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 59% B to 79% B in 7 min, 79% B; Wave Length: 254 nm; RT1(min): 6.27) to afford 9-chloro-7-(5-fluoroindol-1-yl)-4-[(5-methoxy-1,2,4-thiadiazol-3-yl)methyl]-3,5-dihydro-2H-1,4-benzoxazepine (1.6 mg, 5%) as an oil. LC/MS: mass caled. For $C_{21}H_{18}ClFN_4O_2S$: 444.0, found: 445.0 $[M+H]^+$; $^1$H NMR (300 MHz, DMSO-$d_6$) δ 7.72 (d, J=3.3 Hz, 1H), 7.54-7.64 (m, 2H), 7.37-7.49 (m, 2H), 7.02-7.09 (m, 1H), 6.69 (d, J=3.3 Hz, 1H), 4.00-4.18 (m, 5H), 3.99 (s, 2H), 3.80 (s, 2H), 3.16-3.25 (m, 2H); $^{19}$F NMR (282 MHz, DMSO-$d_6$) δ −123.6.

Example S18. Preparation of 3-{[9-chloro-7-(5-fluoroindol-1-yl)-3,5-dihydro-2H-1,4-benzoxazepin-4-yl]methyl}-1,2,4-thiadiazol-5-amine (Compound 117)

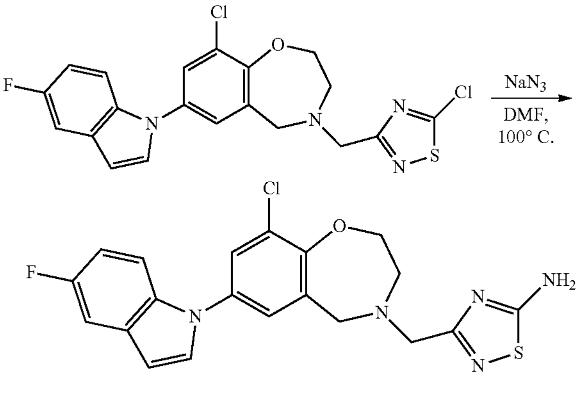

To a stirred mixture of 9-chloro-4-[(5-chloro-1,2,4-thiadiazol-3-yl)methyl]-7-(5-fluoroindol-1-yl)-3,5-dihydro-2H-1,4-benzoxazepine (75 mg, 0.17 mmol) in DMF (1 mL) was added $NaN_3$ (22 mg, 0.34 mmol). The mixture was heated to 100° C. and stirred for 2 h, then purified by preparative-HPLC directly (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 45% B to 65% B in 10 min, 65% B; Wave Length: 254 nm; RT1(min): 6.03) to afford 3-{[9-chloro-7-(5-fluoroindol-1-yl)-3,5-dihydro-2H-1,4-benzoxazepin-4-yl]methyl}-1,2,4-thiadiazol-5-amine (3.2 mg, 4%) as a solid. LC/MS: mass caled. For $C_{20}H_{17}ClFN_5OS$: 429.1, found: 430.1 $[M+H]^+$; $^1$H NMR (300 MHz, DMSO-$d_6$) δ 7.89 (s, 2H), 7.72 (d, J=3.3 Hz, 1H), 7.52-7.63 (m, 2H), 7.34-7.48 (m, 2H), 7.02-7.09 (m, 1H), 6.69 (d, J=3.3 Hz, 1H), 4.12-4.18 (m, 2H), 3.98 (s, 2H), 3.66 (s, 2H), 3.14-3.19 (m, 2H); $^{19}$F NMR (282 MHz, DMSO-$d_6$) δ −123.6.

Example S19. Preparation of 9-chloro-7-(5-fluoroindol-1-yl)-4-(2H-1,2,3,4-tetrazol-5-ylmethyl)-3,5-dihydro-2H-1,4-benzoxazepine (Compound 118)

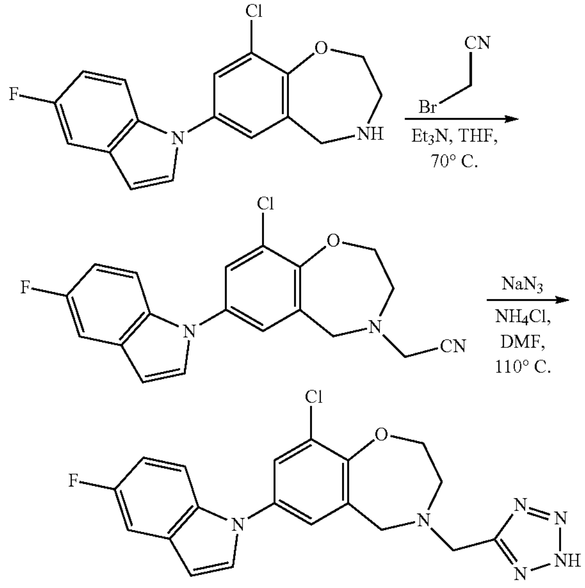

2-[9-chloro-7-(5-fluoroindol-1-yl)-3,5-dihydro-2H-1,4-benzoxazepin-4-yl]acetonitrile To a stirred mixture of 9-chloro-7-(5-fluoroindol-1-yl)-2,3,4,5-tetrahydro-1,4-benzoxazepine (100 mg, 0.32 mmol) in THF (1 mL) was added 2-bromoacetonitrile (57 mg, 0.47 mmol) and $Et_3N$ (64 mg, 0.63 mmol). The mixture was heated to 70° C. and stirred for 1 h, then concentrated under vacuum and the residue was purified by reverse-phase column chromatography (column, C18 silica gel; mobile phase, MeCN in Water (10 mmol/L $NH_4HCO_3$), 10% to 50% gradient in 10 min; detector, UV 254 nm) to afford 2-[9-chloro-7-(5-fluoroindol-1-yl)-3,5-dihydro-2H-1,4-benzoxazepin-4-yl]acetonitrile (60 mg, 54%) as a solid.

9-chloro-7-(5-fluoroindol-1-yl)-4-(2H-1,2,3,4-tetrazol-5-ylmethyl)-3,5-dihydro-2H-1,4-benzoxazepine To a stirred mixture of 2-[9-chloro-7-(5-fluoroindol-1-yl)-3,5-dihydro-2H-1,4-benzoxazepin-4-yl]acetonitrile (60 mg, 0.169 mmol) in DMF (1 mL) were added $NaN_3$ (109 mg, 1.7 mmol) and $NH_4Cl$ (89 mg, 1.7 mmol). The mixture was heated to 100° C. was stirred for 2 h, then purified by preparative-HPLC (Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 23% B to 53% B in 7 min, 53% B; Wave Length: 254 nm; RT1(min): 6) to afford 9-chloro-7-(5-fluoroindol-1-yl)-4-(2H-1,2,3,4-tetrazol-5-ylmethyl)-3,5-dihydro-2H-1,4-benzoxazepine (18 mg, 27%) as a solid. LC/MS: mass calcd. For $C_{19}H_{16}ClFN_6O$: 398.1, found: 399.0 [M+H]$^+$; $^1$H NMR (300 MHz, DMSO-$d_6$) δ 7.72 (d, J=3.3 Hz, 1H), 7.58-7.68 (m, 2H), 7.36-7.48 (m, 2H), 7.02-7.09 (m, 1H), 6.65-6.73 (m, 1H), 4.16-4.19 (m, 2H), 3.92-4.02 (m, 4H), 3.08-3.17 (m, 2H); $^{19}$F NMR (282 MHz, DMSO-$d_6$) δ −123.6.

Example S20. Preparation of 9-chloro-4-(2-(difluoromethyl)benzyl)-7-(5-fluoro-1H-indol-1-yl)-2,3,4,5-tetrahydrobenzo[f][1,4]oxazepane (Compound 122)

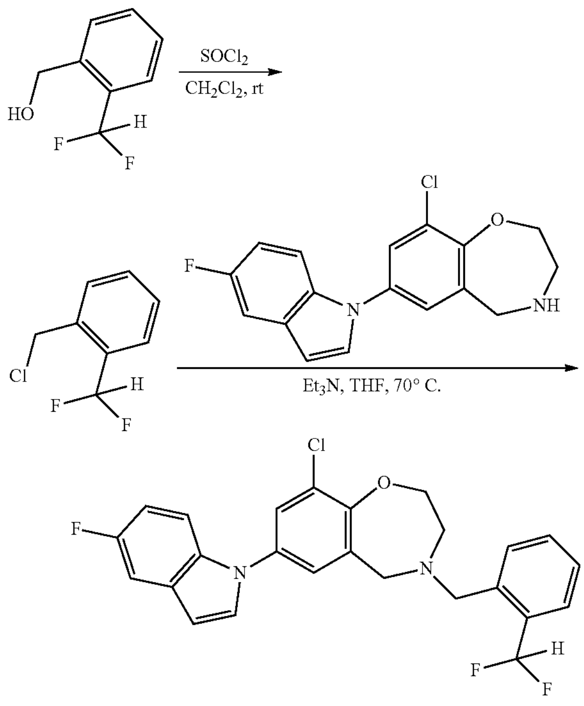

1-(Chloromethyl)-2-(difluoromethyl)benzene

To a stirred solution of [2-(difluoromethyl)phenyl]methanol (50 mg, 0.32 mmol) in DCM (1 mL) was added $SOCl_2$ (0.1 mL, 1.4 mmol). The mixture was stirred at rt for 2 h, then concentrated under reduced pressure to afford 1-(chloromethyl)-2-(difluoromethyl)benzene (60 mg, crude) as an oil.

9-Chloro-4-{[2-(difluoromethyl)phenyl]methyl}-7-(5-fluoroindol-1-yl)-3,5-dihydro-2H-1,4-benzoxazepine To a stirred solution of 1-(chloromethyl)-2-(difluoromethyl)benzene (45 mg, 0.24 mmol) and 9-chloro-7-(5-fluoroindol-1-yl)-2,3,4,5-tetrahydro-1,4-benzoxazepine (50 mg, 0.16 mmol) in THF (1 mL) was added $Et_3N$ (30 mg, 0.32 mmol). The mixture was heated to 70° C. and stirred for 4 h, then concentrated under reduced pressure and the residue was purified by preparative-HPLC (Column: XBridge Prep C18 OBD Column, 19*150 mm, 5 μm; Mobile Phase A: Water (10 mmol/L $NH_4HCO_3$+0.1% $NH_3 \cdot H_2O$), Mobile Phase B: ACN; Flow rate: 25 mL/min; Gradient: 47% B to 77% B in 7 min, 77% B; Wave Length: 254 nm; RT1(min): 6) to afford 9-chloro-4-{[2-(difluoromethyl)phenyl]

methyl}-7-(5-fluoroindol-1-yl)-3,5-dihydro-2H-1,4-benzoxazepine (5.1 mg, 7%) as a solid. LC/MS: mass calcd. for $C_{25}H_{20}ClF_3N_2O$, 456.1, found: 457.0 $[M+H]^+$; $^1H$ NMR (300 MHz, $CD_3OD$) δ 7.59-7.63 (m, 1H), 7.41-7.46 (m, 1H), 7.36-7.40 (m, 5H), 7.23-7.29 (m, 2H), 7.04-7.13 (m, 1H), 6.98 (t, J=9.1 Hz, 1H), 6.64 (d, J=3.3 Hz, 1H), 4.16-4.25 (m, 2H), 3.90 (d, J=6.8 Hz, 4H), 3.11-3.20 (m, 2H); $^{19}F$ NMR (300 MHz, $CD_3OD$) δ −114.0, −126.2.

Example S21. Preparation of trans-4-{[9-chloro-7-(5-fluoroindol-1-yl)-3,5-dihydro-2H-1,4-benzoxazepin-4-yl] methylcyclohexane-1-carboxylic acid (Compound 131)

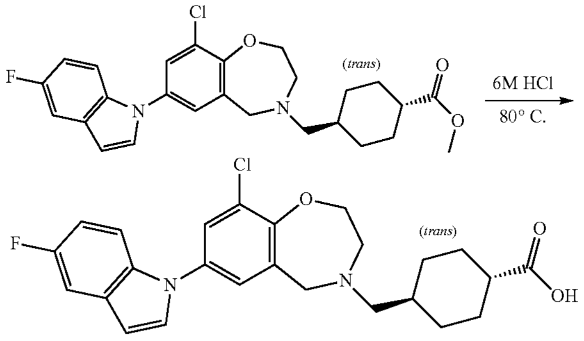

Trans-4-{[9-chloro-7-(5-fluoroindol-1-yl)-3,5-dihydro-2H-1,4-benzoxazepin-4-yl]methylcyclohexane-1-carboxylic acid A solution of methyl trans-4-{[9-chloro-7-(5-fluoroindol-1-yl)-3,5-dihydro-2H-1,4-benzoxazepin-4-yl] methyl}cyclohexane-1-carboxylate (50 mg, 0.11 mmol) in 6M HCl (5 mL) was stirred at 80° C. for 2 h. The mixture was concentrated under reduced pressure and the residue was purified by preparative-HPLC (Column: XBridge Prep OBD C18 Column, 19*250 mm, 5 μm; Mobile Phase A: Water (10 mmol/L $NH_4HCO_3$), Mobile Phase B: ACN; Flow rate: 25 mL/min; Gradient: 37% B to 57% B in 7 min, 57% B; Wave Length: 254 nm; RT1(min): 5.8) to afford trans-4-{[9-chloro-7-(5-fluoroindol-1-yl)-3,5-dihydro-2H-1,4-benzoxazepin-4-yl]methylcyclohexane-1-carboxylic acid (9 mg, 18%) as a solid. LC/MS: mass calcd. for $C_{25}H_{26}ClFN_2O_3$: 456.2, found: 457.1$[M+H]^+$; $^1H$ NMR (300 MHz, $CD_3OD$) δ 7.42-7.47 (m, 3H), 7.26-7.39 (m, 2H), 6.92-6.99 (m, 1H), 6.62-6.64 (m, 1H), 4.14-4.17 (m, 2H), 3.93 (s, 2H), 3.14-3.16 (m, 2H), 2.10-2.42 (m, 3H), 1.91-2.10 (m, 3H), 1.54-1.62 (m, 2H), 0.93-1.46 (m, 4H); $^{19}F$ NMR (282 MHz, $CD_3OD$) δ −126.2.

Example S22. Preparation of cis-4-{[9-chloro-7-(5-fluoroindol-1-yl)-3,5-dihydro-2H-1,4-benzoxazepin-4-yl]methyl}cyclohexane-1-carboxylic acid (Compound 132)

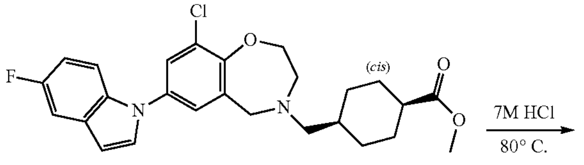

-continued

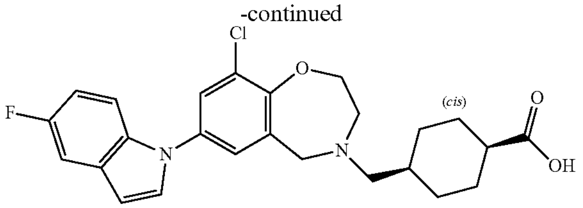

A mixture of methyl cis-4-{[9-chloro-7-(5-fluoroindol-1-yl)-3,5-dihydro-2H-1,4-benzoxazepin-4-yl] methyl}cyclohexane-1-carboxylate (50 mg, 0.11 mmol) in aq. HCl (7M) (10 mL) was stirred at 80° C. for 16 h. The mixture was concentrated under reduced pressure and the residue was purified by preparative-HPLC (Column: XBridge Prep Phenyl OBD Column, 19*250 mm, 5 μm; Mobile Phase A: Water (10 mmol/L $NH_4HCO_3$+0.1% $NH_3 \cdot H_2O$), Mobile Phase B: ACN; Flow rate: 25 mL/min; Gradient: 33% B to 63% B in 7 min, 63% B; Wave Length: 254 nm; RT1(min): 5) to afford cis-4-{[9-chloro-7-(5-fluoroindol-1-yl)-3,5-dihydro-2H-1,4-benzoxazepin-4-yl] methyl}cyclohexane-1-carboxylic acid (10.7 mg, 21%) as a solid. LC/MS: mass calcd. For $C_{25}H_{26}ClFN_2O_3$: 456.1, found: 457.1 $[M+H]^+$; $^1H$ NMR (300 MHz, $CD_3OD$) δ 7.46-7.50 (m, 2H), 7.38-7.47 (m, 1H), 7.38 (d, J=3.0 Hz, 1H), 7.28-7.34 (m, 1H), 6.90-6.70 (m, 1H), 6.65 (d, J=3.0 Hz, 1H), 4.13-4.22 (m, 2H), 3.96 (s, 2H), 3.13-3.22 (m, 2H), 2.48-2.56 (m, 1H), 2.44 (d, J=6.0 Hz, 2H), 1.90-2.00 (m, 2H), 1.69-1.76 (m, 1H), 1.50-1.65 (m, 3H), 1.54-1.65 (m, 1H), 1.35 (m, 2H); $^{19}F$ NMR (282 MHz, $CD_3OD$) δ −126.2.

Example S23. Preparation of 5-{[9-chloro-7-(5-fluoroindol-1-yl)-3,5-dihydro-2H-1,4-benzoxazepin-4-yl]methyl}pyrimidine-2-carboxylate (Compound 140) & 1-(5-{[9-chloro-7-(5-fluoroindol-1-yl)-3,5-dihydro-2H-1,4-benzoxazepin-4-yl] methyl}pyrimidin-2-yl)methanamine (Compound 139)

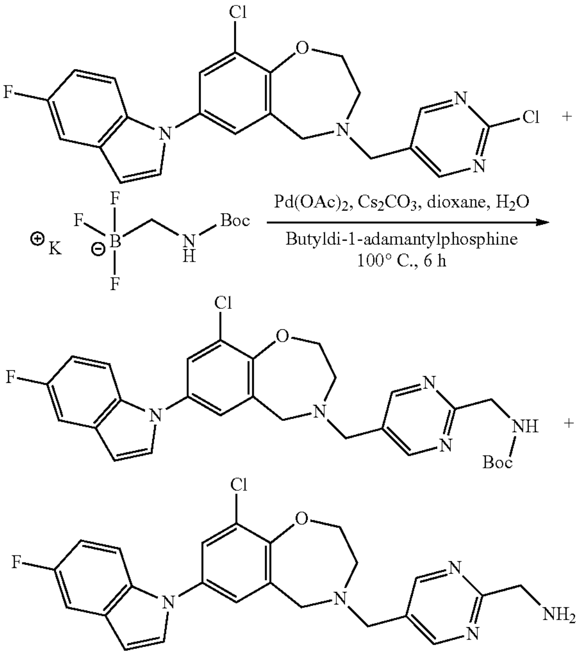

To a mixture of 9-chloro-4-[(2-chloropyrimidin-5-yl)methyl]-7-(5-fluoroindol-1-yl)-3,5-dihydro-2H-1,4-benzoxazepine (50 mg, 0.11 mmol) and potassium tert-butyl N-[(trifluoroboranuidyl)methyl]carbamate (40 mg, 0.17 mmol) in 1,4-dioxane (2 mL) and $H_2O$ (0.2 mL) under an atmosphere of $N_2$ was added $Pd(OAc)_2$ (3 mg, 0.011 mmol), butylbis[(3R,5S,7s)-adamantan-1-yl]phosphane (20 mg, 0.057 mmol) and $Cs_2CO_3$ (110 mg, 0.34 mmol). The mixture was heated to 100° C. and stirred for 6 h, then filtered and the filtrate was concentrated under reduced pressure. The residue was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 50% B to 80% B in 10 min, 80% B; Wave Length: 254 nm; RT1(min): 8.67) to afford tert-butyl N-[(5-{[9-chloro-7-(5-fluoroindol-1-yl)-3,5-dihydro-2H-1,4-benzoxazepin-4-yl]methyl}pyrimidin-2-yl)methyl]carbamate (7.3 mg, 12%) as a solid and 1-(5-{[9-chloro-7-(5-fluoroindol-1-yl)-3,5-dihydro-2H-1,4-benzoxazepin-4-yl]methyl}pyrimidin-2-yl)methanamine (3.2 mg, 3%) as a solid.

5-{[9-chloro-7-(5-fluoroindol-1-yl)-3,5-dihydro-2H-1,4-benzoxazepin-4-yl]methyl}pyrimidine-2-carboxylate LC/MS: mass calcd. For $C_{28}H_{29}ClFN_5O_3$: 537.1, found: 538.1 $[M+H]^+$; $^1H$ NMR (300 MHz, DMSO-$d_6$) δ 8.69 (s, 2H), 7.71 (d, J=3.3 Hz, 1H), 7.63 (d, J=2.7 Hz, 1H), 7.51 (d, J=9.3 Hz, 1H), 7.39-7.45 (m, 2H), 7.21 (s, 1H), 7.05 (t, J=9.3 Hz, 1H), 6.68 (d, J=3.3 Hz, 1H), 4.30 (d, J=6.0 Hz, 2H), 4.19-4.20 (m, 2H), 3.98 (s, 2H), 3.72 (s, 2H), 3.05-3.06 (m, 2H), 1.37 (s, 9H); $^{19}F$ NMR (282 MHz, DMSO-$d_6$) δ −123.5.

1-(5-{[9-chloro-7-(5-fluoroindol-1-yl)-3,5-dihydro-2H-1,4-benzoxazepin-4-yl]methyl}pyrimidin-2-yl)methanamine LC/MS: mass caled. For $C_{23}H_{21}ClFN_5O$: 437.1, found: 438.0 $[M+H]^+$; $^1H$ NMR (300 MHz, DMSO-$d_6$) δ 8.19 (s, 2H), 7.71 (d, J=3.3 Hz, 1H), 7.61 (d, J=2.4 Hz, 1H), 7.49-7.53 (m, 1H), 7.37-7.45 (m, 2H), 7.01-7.06 (m, 2H), 6.68 (d, J=3.0 Hz, 1H), 4.16-4.17 (m, 2H), 3.92 (s, 2H), 3.50 (s, 2H), 3.03-3.04 (m, 2H), 2.77 (d, J=4.5 Hz, 2H); $^{19}F$ NMR (282 MHz, DMSO-$d_6$) δ −123.6.

Example S24. Preparation of (5-{[9-chloro-7-(5-fluoroindol-1-yl)-3,5-dihydro-2H-1,4-benzoxazepin-4-yl]methyl}pyrimidin-2-yl)methanol (Compound 141)

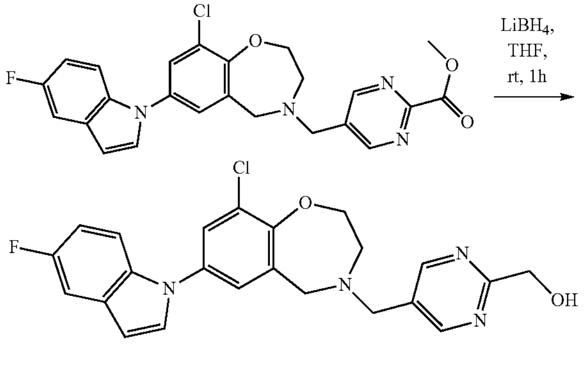

To a stirred mixture of methyl 5-{[9-chloro-7-(5-fluoroindol-1-yl)-3,5-dihydro-2H-1,4-benzoxazepin-4-yl]methyl}pyrimidine-2-carboxylate (90 mg, 0.19 mmol) in THE (2 mL) was added $LiBH_4$ (8 mg, 0.39 mmol). The mixture was stirred at rt for 1 h, then $H_2O$ (10 mL) added and extracted with EtOAc (3×10 mL). The combined organic layers were washed with brine (20 mL), dried over anhydrous $Na_2SO_4$ and filtered. The filtrate was concentrated under reduced pressure and the residue was purified by preparative-HPLC (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 36% B to 66% B in 7 min, 66% B; Wave Length: 254 nm; RT1(min): 5.67) to afford (5-{[9-chloro-7-(5-fluoroindol-1-yl)-3,5-dihydro-2H-1,4-benzoxazepin-4-yl]methyl}pyrimidin-2-yl)methanol (2.8 mg, 3%) as a solid. LC/MS: mass calcd. For $C_{23}H_{20}ClFN_4O_2$: 438.1, found: 439.0 $[M+H]^+$; $^1H$ NMR (300 MHz, DMSO-$d_6$) δ 8.72 (s, 2H), 7.72 (d, J=3.3 Hz, 1H), 7.64 (d, J=2.6 Hz, 1H), 7.48-7.55 (m, 1H), 7.37-7.47 (m, 2H), 7.00-7.13 (m, 1H), 6.69 (d, J=3.3 Hz, 1H), 5.29 (t, J=6.3 Hz, 1H), 4.60 (d, J=6.0 Hz, 2H), 4.16-4.22 (m, 2H), 3.99 (s, 2H), 3.74 (s, 2H), 3.04-3.10 (m, 2H); $^{19}F$ NMR (282 MHz, DMSO-$d_6$) δ −123.5.

Example S25. Preparation of 5-{[9-chloro-7-(5-fluoroindol-1-yl)-3,5-dihydro-2H-1,4-benzoxazepin-4-yl]methyl}pyrimidine-2-carboxamide (Compound 143)

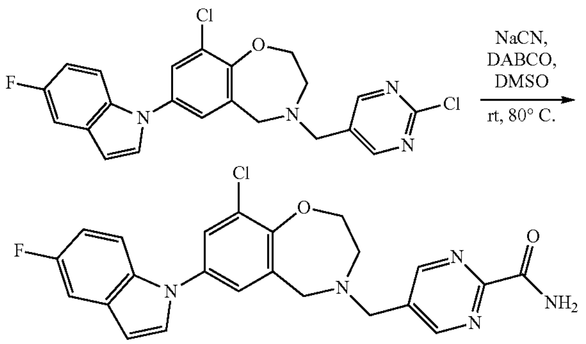

To an 8 mL vial containing NaCN (25 mg, 0.51 mmol), 1,4-diazabicyclo[2.2.2]octane (2 mg, 0.02 mmol) and DMSO (2 mL) was added 9-chloro-4-[(2-chloropyrimidin-5-yl)methyl]-7-(5-fluoroindol-1-yl)-3,5-dihydro-2H-1,4-benzoxazepine (150 mg, 0.34 mmol) in DMSO (1 mL) dropwise over 5 min at rt. The mixture was heated to 80° C. and stirred for 16 h, then purified by preparative-HPLC directly (Column: XBridge Prep Phenyl OBD Column, 19*250 mm, 5 μm; Mobile Phase A: Water (10 mmol/L $NH_4HCO_3$+0.1% $NH_3 \cdot H_2O$), Mobile Phase B: MeOH—HPLC; Flow rate: 25 mL/min; Gradient: 65% B to 95% B in 7 min, 95% B; Wave Length: 25 nm; RT1(min): 6) to afford 5-{[9-chloro-7-(5-fluoroindol-1-yl)-3,5-dihydro-2H-1,4-benzoxazepin-4-yl]methyl}pyrimidine-2-carboxamide (4.6 mg, 3.0%) as a solid. LC/MS: mass calcd. For $C_{23}H_{19}ClFN_5O_2$: 451.1, found: 452.1 $[M+H]^+$; $^1H$ NMR (400 MHz, DMSO-$d_6$) δ 8.87 (s, 2H), 8.21 (s, 1H), 7.62-7.79 (m, 3H), 7.39-7.54 (m, 3H), 7.04-7.12 (m, 1H), 6.66-6.71 (m, 1H), 4.18-4.24 (m, 2H), 4.00 (s, 2H), 3.83 (s, 2H), 3.09-3.15 (m, 2H); $^{19}F$ NMR (376 MHz, DMSO-$d_6$) δ −123.7.

Example S26. Preparation of 5-{[9-chloro-7-(5-fluoroindol-1-yl)-3,5-dihydro-2H-1,4-benzoxazepin-4-yl]methyl}pyrimidine-2-carboxylic acid (Compound 144) & Methyl 5-{[9-chloro-7-(5-fluoroindol-1-yl)-3,5-dihydro-2H-1,4-benzoxazepin-4-yl]methyl}pyrimidine-2-carboxylate (Compound 145)

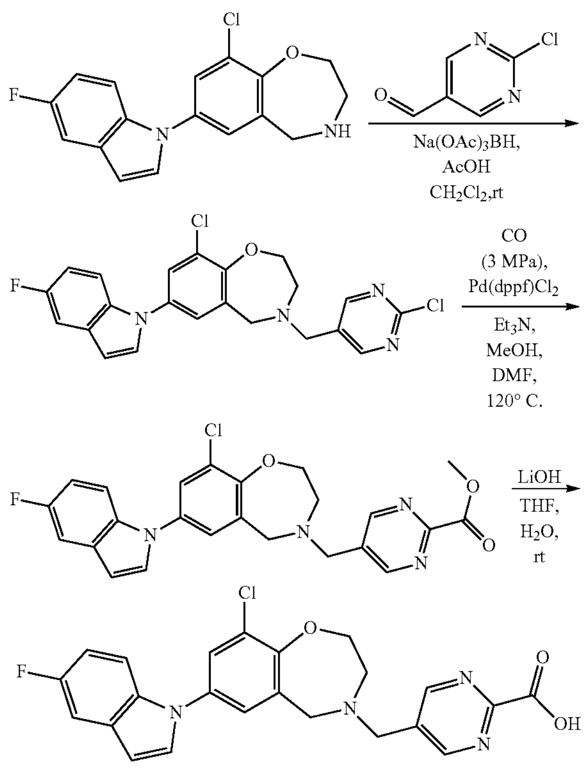

9-chloro-4-[(2-chloropyrimidin-5-yl)methyl]-7-(5-fluoroindol-1-yl)-3,5-dihydro-2H-1,4-benzoxazepine To a stirred mixture of 9-chloro-7-(5-fluoroindol-1-yl)-2,3,4,5-tetrahydro-1,4-benzoxazepine (200 mg, 0.63 mmol) and 2-chloropyrimidine-5-carbaldehyde (135 mg, 0.95 mmol) in DCM (3 mL) were added $NaBH(OAc)_3$ (267 mg, 1.26 mmol) and AcOH (0.08 mg, 0.001 mmol). The reaction was stirred at rt for 3 h, then concentrated under reduced pressure and the residue was purified by reverse-phase column chromatography (column, C18 silica gel; mobile phase, MeCN in Water (0.1% TFA), 10% to 50% gradient in 20 min; detector, UV 254 nm) to afford 9-chloro-4-[(2-chloropyrimidin-5-yl)methyl]-7-(5-fluoroindol-1-yl)-3,5-dihydro-2H-1,4-benzoxazepine (180 mg, 61%) as an oil.

Methyl 5-{[9-chloro-7-(5-fluoroindol-1-yl)-3,5-dihydro-2H-1,4-benzoxazepin-4-yl]methyl}pyrimidine-2-carboxylate To a stirred mixture of 9-chloro-4-[(2-chloropyrimidin-5-yl)methyl]-7-(5-fluoroindol-1-yl)-3,5-dihydro-2H-1,4-benzoxazepine (200 mg, 0.45 mmol) in MeOH (5 mL) and DMF (1 mL) were added $Pd(dppf)Cl_2$ (49 mg, 0.068 mmol) and $Et_3N$ (137 mg, 1.35 mmol). The mixture was placed under an atmosphere of CO (3 MPa), heated to 120° C. and stirred for 24 h, then concentrated under vacuum and the residue was purified by reverse-phase column chromatography (column, C18 silica gel; mobile phase, MeCN in Water (0.1% TFA), 10% to 70% gradient in 15 min; detector, UV 254 nm) to afford methyl 5-{[9-chloro-7-(5-fluoroindol-1-yl)-3,5-dihydro-2H-1,4-benzoxazepin-4-yl]methyl}pyrimidine-2-carboxylate (130 mg, 59%) as a solid. LC/MS: mass calcd. For $C_{24}H_{20}ClFN_4O_3$: 466.1, found: 467.0 $[M+H]^+$; $^1H$ NMR (300 MHz, DMSO-$d_6$) δ 8.92 (s, 2H), 7.71 (d, J=3.3 Hz, 1H), 7.64 (d, J=2.7 Hz, 1H), 7.50 (d, J=9.0 Hz, 1H), 7.40-7.45 (m, 2H), 7.06 (t, J=9.3 Hz, 1H), 6.68 (d, J=3.3 Hz, 1H), 4.21 (d, J=4.8 Hz, 2H), 3.99 (s, 2H), 3.91 (s, 3H), 3.84 (s, 2H), 3.13 (d, J=5.7 Hz, 2H); $^{19}F$ NMR (282 MHz, DMSO-$d_6$) δ −123.6.

5-{[9-chloro-7-(5-fluoroindol-1-yl)-3,5-dihydro-2H-1,4-benzoxazepin-4-yl]methyl}pyrimidine-2-carboxylic acid To a stirred mixture of methyl 5-{[9-chloro-7-(5-fluoroindol-1-yl)-3,5-dihydro-2H-1,4-benzoxazepin-4-yl]methyl}pyrimidine-2-carboxylate (15 mg, 0.032 mmol) in THE (0.75 mL) was added 2M LiOH (0.5 mL). The mixture was stirred at rt for 2 h, then concentrated under reduced pressure and the residue was purified by preparative-HPLC (Column: XBridge Prep Phenyl OBD Column, 19*250 mm, 5 μm; Mobile Phase A: Water (10 mmol/L $NH_4HCO_3$+0.1% $NH_3 \cdot H_2O$), Mobile Phase B: ACN; Flow rate: 25 mL/min; Gradient: 30% B to 60% B in 7 min, 60% B; Wave Length: 254 nm; RT1(min): 6) to afford 5-{[9-chloro-7-(5-fluoroindol-1-yl)-3,5-dihydro-2H-1,4-benzoxazepin-4-yl]methyl}pyrimidine-2-carboxylic acid (4.5 mg, 31%) as a solid. LC/MS: mass calcd. For $C_{23}H_{18}ClFN_4O_3$: 452.1, found: 453.0 $[M+H]^+$; $^1H$ NMR (300 MHz, DMSO-$d_6$) δ 8.77 (s, 2H), 7.72 (d, J=3.3 Hz, 1H), 7.64 (d, J=2.7 Hz, 1H), 7.47-7.56 (m, 1H), 7.38-7.47 (m, 2H), 7.02-7.13 (m, 1H), 6.69 (d, J=3.3 Hz, 1H), 4.14-4.23 (m, 2H), 3.99 (s, 2H), 3.78 (s, 2H), 3.05-3.14 (m, 2H); $^{19}F$ NMR (282 MHz, DMSO-$d_6$) δ −123.5.

Example S27. Preparation of 5-{[9-chloro-7-(5-fluoroindol-1-yl)-3,5-dihydro-2H-1,4-benzoxazepin-4-yl]methyl}-N-(oxetan-3-yl)pyrimidin-2-amine (Compound 149)

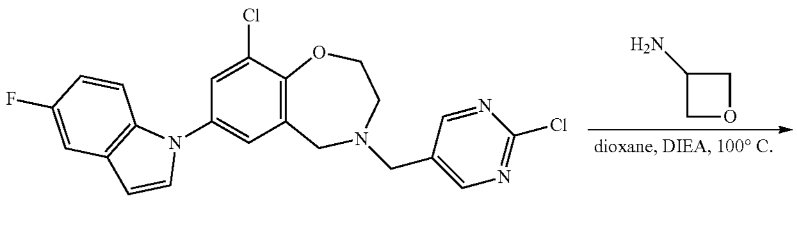

-continued

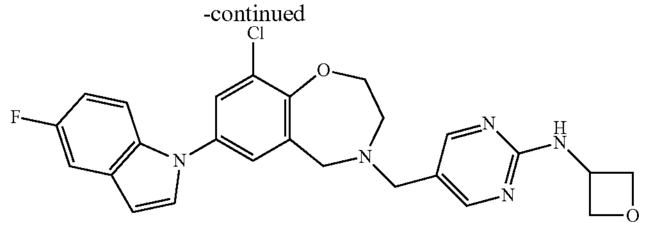

To a stirred mixture of 9-chloro-4-[(2-chloropyrimidin-5-yl)methyl]-7-(5-fluoroindol-1-yl)-3,5-dihydro-2H-1,4-benzoxazepine (10 mg, 0.023 mmol) and in 1,4-dioxane (1 mL) was added oxetan-3-amine (3 mg, 0.05 mmol) and DIPEA (6 mg, 0.05 mmol). The mixture was heated to 100° C. and stirred for 6 h, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 49% B to 69% B in 7 min, 69% B; Wave Length: 254 nm; RT1(min): 5.25) to afford 5-{[9-chloro-7-(5-fluoroindol-1-yl)-3,5-dihydro-2H-1,4-benzoxazepin-4-yl]methyl}-N-(oxetan-3-yl)pyrimidin-2-amine (3.6 mg, 33%) as a solid. LC/MS: mass calcd. For $C_{25}H_{23}ClFN_5O_2$:479.1, found: 480.1 $[M+H]^+$; $^1H$ NMR (300 MHz, $CD_3OD$) δ 8.28 (s, 2H), 7.53 (d, J=2.7 Hz, 1H), 7.39-7.50 (m, 2H), 7.27-7.35 (m, 1H), 7.23 (d, J=2.7 Hz, 1H), 6.93-7.05 (m, 1H), 6.62-6.69 (m, 1H), 4.97-5.11 (m, 1H), 4.94 (d, J=6.3 Hz, 2H), 4.63 (t, J=6.3 Hz, 2H), 4.17-4.26 (m, 2H), 3.93 (s, 2H), 3.62 (s, 2H), 3.11-3.20 (m, 2H); $^{19}F$ NMR (282 MHz, $CD_3OD$) δ −126.1.

Example S28. Preparation of N-(5-{[9-chloro-7-(5-fluoroindol-1-yl)-3,5-dihydro-2H-1,4-benzoxazepin-4-yl]methyl}pyrimidin-2-yl)acetamide (Compound 150)

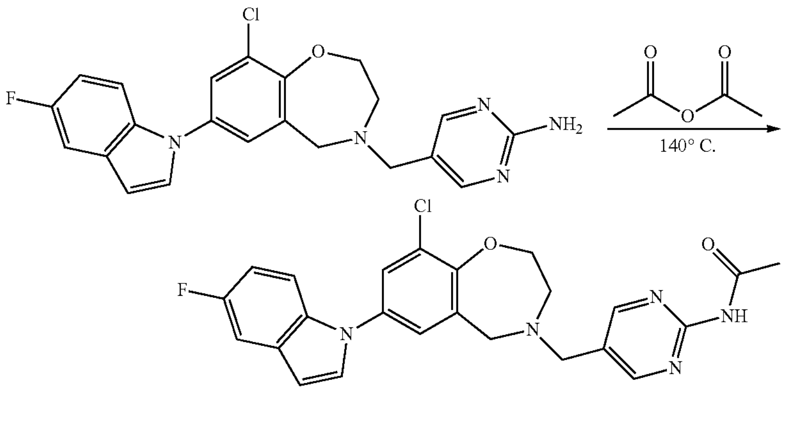

A solution of 5-{[9-chloro-7-(5-fluoroindol-1-yl)-3,5-dihydro-2H-1,4-benzoxazepin-4-yl]methyl}pyrimidin-2-amine (50 mg, 0.12 mmol) in $Ac_2O$ (1 mL) was heated to 140° C. and stirred for overnight, then concentrated under reduced pressure. Aq. $NH_3$—$H_2O$ (2 mL) was added, and the mixture was stirred at rt for 1 h, then extracted with DCM (3×2 mL). The combined organic layers were washed with brine (2 mL), dried over anhydrous $Na_2SO_4$ and filtered. The filtrate was concentrated under reduced pressure and the residue was purified by preparative-HPLC (Column: XBridge Prep Phenyl OBD Column, 19*250 mm, 5 μm; Mobile Phase A: H2O (10 mmol/L $NH_4HCO_3$+0.1% $NH_3 \cdot H_2O$), Mobile Phase B: ACN; Flow rate: 25 mL/min; Gradient: 30% B to 60% B in 9 min, 60% B; Wave Length: 254 nm; RT1(min): 8.23) to afford N-(5-{[9-chloro-7-(5-fluoroindol-1-yl)-3,5-dihydro-2H-1,4-benzoxazepin-4-yl]methyl}pyrimidin-2-yl)methanesulfonamide (9.0 mg, 14%) as a solid. LC/MS: mass caled. For $C_{24}H_{21}ClFN_5O_2$: 465.1, found: 466.0 $[M+H]^+$; $^1H$ NMR (300 MHz, DMSO-$d_6$) δ 10.54 (s, 1H), 8.57 (s, 2H), 7.71 (d, J=3.3 Hz, 1H), 7.63 (d, J=2.6 Hz, 1H), 7.51 (d, J=9.0 Hz, 1H), 7.47-7.37 (m, 2H), 7.07 (t, J=9.2 Hz, 1H), 6.69 (d, J=3.2 Hz, 1H), 4.18-4.19 (m, 2H), 3.97 (s, 2H), 3.67 (s, 2H), 3.07-3.08 (m, 2H), 2.17 (s, 3H); $^{19}F$ NMR (282 MHz, DMSO-$d_6$) δ −123.6.

Example S29. Preparation of N-(5-{[9-chloro-7-(5-fluoroindol-1-yl)-3,5-dihydro-2H-1,4-benzoxazepin-4-yl]methyl}pyrimidin-2-yl)methanesulfonamide (Compound 151)

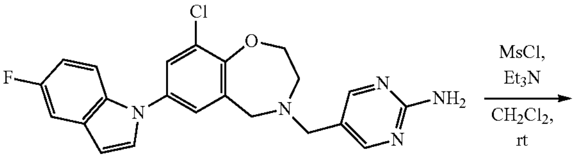

-continued

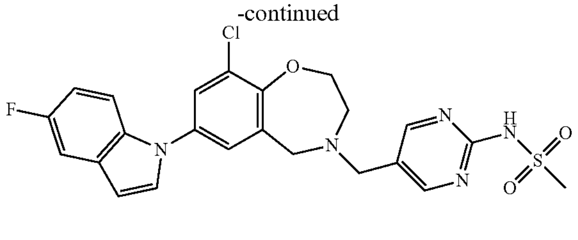

To a stirred solution of 5-{[9-chloro-7-(5-fluoroindol-1-yl)-3,5-dihydro-2H-1,4-benzoxazepin-4-yl]methyl}pyrimidin-2-amine (50 mg, 0.118 mmol) in DCM (1 mL) at 0° C. was added MsCl (20 uL, 0.24 mmol) and $Et_3N$ (33 uL, 0.24 mmol). The mixture was warmed to rt and stirred for 2 h at rt, then concentrated under reduced pressure and the residue was purified by preparative-HPLC (Column: XBridge Prep Phenyl OBD Column, 19*250 mm, 5 μm; Mobile Phase A: H2O (10 mmol/L $NH_4HCO_3$+0.1% $NH_3·H_2O$), Mobile Phase B: ACN; Flow rate: 25 mL/min; Gradient: 30% B to 60% B in 9 min, 60% B; Wave Length: 254 nm; RT1(min): 8.23) to afford N-(5-{[9-chloro-7-(5-fluoroindol-1-yl)-3,5-dihydro-2H-1,4-benzoxazepin-4-yl]methyl}pyrimidin-2-yl)methanesulfonamide (4.4 mg, 7%) as a solid. LC/MS: mass calcd. For $C_{23}H_{21}ClFN_5O_3S$: 501.1, found: 502.1 $[M+H]^+$; $^1H$ NMR (300 MHz, DMSO-$d_6$) δ 11.31 (s, 1H), 8.50 (s, 2H), 7.72 (d, J=3.3 Hz, 1H), 7.64 (d, J=2.6 Hz, 1H), 7.49-7.53 (m 1H), 7.42-7.45 (m, 2H), 7.02-7.14 (m, 1H), 6.69 (d, J=3.2 Hz, 1H), 4.17-4.18 (m, 2H), 3.98 (s, 2H), 3.64 (s, 2H), 3.27 (s, 3H), 3.05-3.06 (m, 2H); $^{19}F$ NMR (282 MHz, DMSO-$d_6$) δ −123.6.

Example S30. Preparation of 9-chloro-7-(5-fluoroindol-1-yl)-4-{[2-(1-methylpyrazol-4-yl)pyrimidin-5-yl]methyl}-3,5-dihydro-2H-1,4-benzoxazepine (Compound 153)

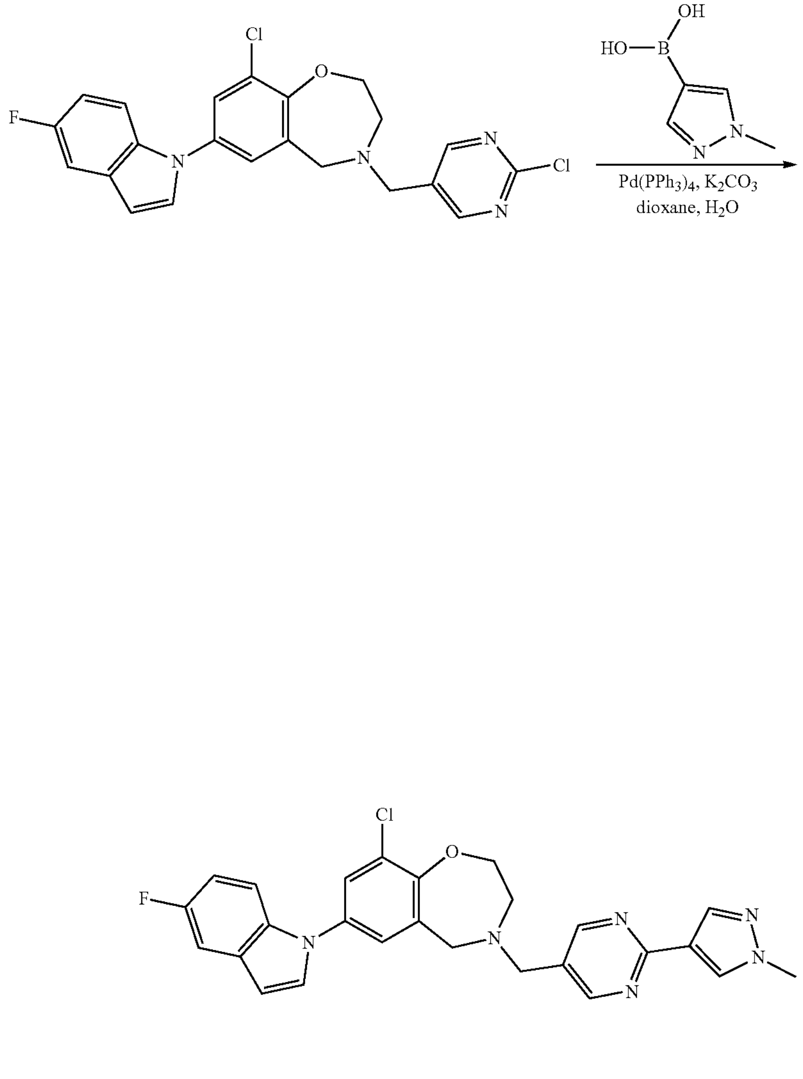

To a mixture of 9-chloro-4-[(2-chloropyrimidin-5-yl)methyl]-7-(5-fluoroindol-1-yl)-3,5-dihydro-2H-1,4-benzoxazepine (50 mg, 0.11 mmol) and 1-methylpyrazol-4-ylboronic acid (28 mg, 0.23 mmol) in 1,4-dioxane (1 mL) and $H_2O$ (0.2 mL) under an atmosphere of $N_2$ was added $K_2CO_3$ (31 mg, 0.23 mmol) and $Pd(PPh_3)_4$ (13 mg, 0.011 mmol). The mixture was heated to 80° C. and stirred overnight, then concentrated under reduced pressure and the residue was purified by preparative-HPLC (Column: XBridge Prep OBD C18 Column, 30*150 mm, 5 μm; Mobile Phase A: H2O (10 mmol/L $NH_4HCO_3$), Mobile Phase B: ACN; Flow rate: 60 mL/min; Gradient: 58% B to 88% B in 7 min, 88% B; Wave Length: 254 nm; RT1(min): 5.98) to afford 9-chloro-7-(5-fluoroindol-1-yl)-4-{[2-(1-methylpyrazol-4-yl)pyrimidin-5-yl]methyl}-3,5-dihydro-2H-1,4-benzoxazepine (14.1 mg, 23%) as a solid. LC/MS: mass calcd. For $C_{26}H_{22}ClFN_6O$: 488.1, found: 489.1 $[M+H]^+$; $^1H$ NMR (300 MHz, DMSO-$d_6$) δ 8.66 (s, 2H), 8.35 (s, 1H), 8.00 (d, J=0.6 Hz, 1H), 7.71 (d, J=3.3 Hz, 1H), 7.62 (d, J=2.4 Hz, 1H), 7.50 (d, J=9.0 Hz, 1H), 7.42 (d, J=7.5 Hz, 2H), 7.02 (t, J=6.9 Hz, 1H), 6.68 (d, J=2.7 Hz, 1H), 4.19-4.20 (m, 2H), 43.99 (s, 2H), 3.89 (s, 3H), 3.70 (s, 2H), 3.08-3.09 (m, 2H); $^{19}F$ NMR (282 MHz, DMSO-$d_6$) δ −123.6.

Example S31. Preparation of 9-chloro-7-(5-fluoroindol-1-yl)-4-{[2-(pyrazol-1-yl)pyrimidin-5-yl]methyl}-3,5-dihydro-2H-1,4-benzoxazepine (Compound 154)

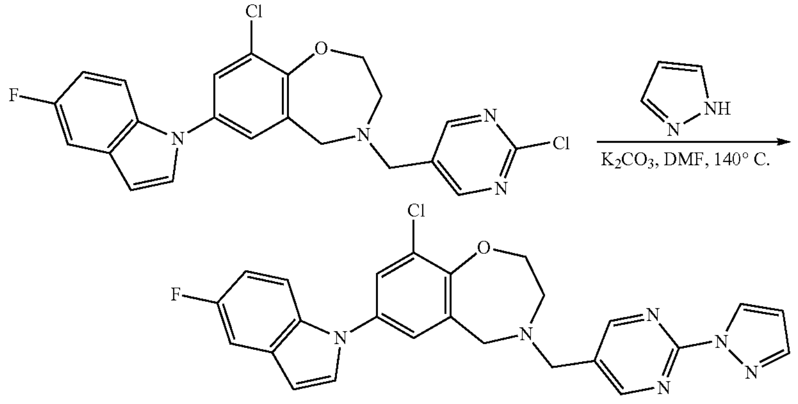

To a stirred mixture of 9-chloro-4-[(2-chloropyrimidin-5-yl)methyl]-7-(5-fluoroindol-1-yl)-3,5-dihydro-2H-1,4-benzoxazepine (50 mg, 0.11 mmol) and pyrazole (15 mg, 0.23 mmol) in DMF was added $K_2CO_3$ (31 mg, 0.23 mmol). The mixture was heated to 140° C. and stirred overnight, then filtered, and the filtrate was purified by preparative-HPLC (Column: XBridge Prep OBD C18 Column, 30*150 mm, 5 μm; Mobile Phase A: H2O (10 mmol/L $NH_4HCO_3$), Mobile Phase B: ACN; Flow rate: 60 mL/min; Gradient: 48% B to 78% B in 7 min, 78% B; Wave Length: 254 nm; RT1(min): 6.23) to afford 9-chloro-7-(5-fluoroindol-1-yl)-4-{[2-(pyrazol-1-yl)pyrimidin-5-yl]methyl}-3,5-dihydro-2H-1,4-benzoxazepine (11.5 mg, 22%) as a solid. LC/MS: mass calcd. For $C_{25}H_{20}ClFN_6O$: 474.1, found: 475.1 $[M+H]^+$; $^1H$ NMR (300 MHz, DMSO-$d_6$) δ 8.79 (s, 2H), 8.66 (d, J=2.1 Hz, 1H), 7.85 (s, 1H), 7.70 (d, J=3.3 Hz, 1H), 7.63 (d, J=2.4 Hz, 1H), 7.51 (d, J=9.0 Hz, 1H), 7.42-7.44 (m, 2H), 7.05 (t, J=9.3 Hz, 1H), 6.66 (d, J=3.3 Hz, 1H), 6.59 (d, J=2.7 Hz, 1H), 4.20-4.21 (m, 2H), 4.00 (s, 2H), 3.78 (s, 2H), 3.14-3.15 (m, 2H); $^{19}F$ NMR (282 MHz, DMSO-$d_6$) δ −123.7.

Example S33. Preparation of 5-{[9-chloro-7-(5-fluoroindol-1-yl)-3,5-dihydro-2H-1,4-benzoxazepin-4-yl]methyl}-4-fluoro-3H-pyrimidin-2-one (Compound 155) and 4-chloro-5-{[9-chloro-7-(5-fluoroindol-1-yl)-3,5-dihydro-2H-1,4-benzoxazepin-4-yl]methyl}-3H-pyrimidin-2-one & (Compound 158)

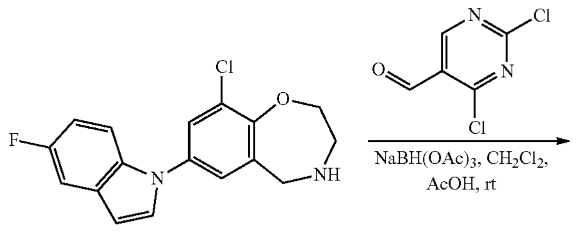

-continued

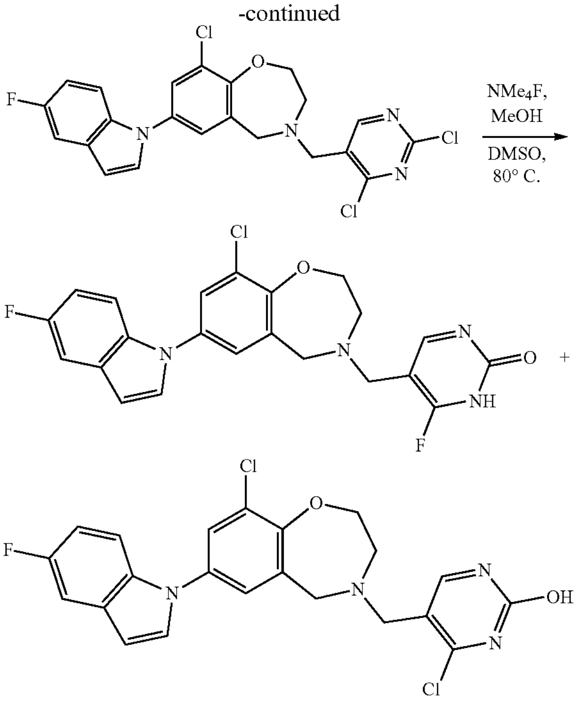

9-chloro-4-[(2,4-dichloropyrimidin-5-yl)methyl]-7-(5-fluoroindol-1-yl)-3,5-dihydro-2H-1,4-benzoxazepine To a stirred mixture of 9-chloro-7-(5-fluoroindol-1-yl)-2,3,4,5-tetrahydro-1,4-benzoxazepine (200 mg, 0.63 mmol) and 2,4-dichloropyrimidine-5-carbaldehyde (223 mg, 1.26 mmol) in DCM (4 mL) at rt was added $NaBH(OAc)_3$ (267 mg, 1.26 mmol) and AcOH (0.04 mL). The mixture was stirred at rt for 16 h, then concentrated under reduced pressure and the residue was purified by silica gel column chromatography (PE/EtOAc, 3:1) to afford 9-chloro-4-[(2,4-dichloropyrimidin-5-yl)methyl]-7-(5-fluoroindol-1-yl)-3,5-dihydro-2H-1,4-benzoxazepine (116 mg, 39%) as a solid.

5-{[9-chloro-7-(5-fluoroindol-1-yl)-3,5-dihydro-2H-1,4-benzoxazepin-4-yl]methyl}-4-fluoro-3H-pyrimidin-2-one and 4-chloro-5-{[9-chloro-7-(5-fluoroindol-1-yl)-3,5-dihydro-2H-1,4-benzoxazepin-4-yl]methyl}-3H-pyrimidin-2-one A mixture of dry $Me_4NF$ (389 mg, 4.2 mmol) in MeOH (5 mL) was stirred at rt for 16 h. The mixture was concentrated under reduced pressure and the residue was dissolved with 2-Methyl-2-butanol (5 mL) and concentrated under reduced pressure—this process was repeated four times. The residue and 9-chloro-4-[(2,4-dichloropyrimidin-5-yl)methyl]-7-(5-fluoroindol-1-yl)-3,5-dihydro-2H-1,4-benzoxazepine (100 mg, 0.21 mmol) were dissolved in DMSO (2 mL), heated to 80° C. and stirred for 16 h. Part of mixture was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 24% B to 54% B in 7 min, 54% B; Wave Length: 254 nm; RT1(min): 5.38) to afford 5-{[9-chloro-7-(5-fluoroindol-1-yl)-3,5-dihydro-2H-1,4-benzoxazepin-4-yl]methyl}-4-fluoro-3H-pyrimidin-2-one (1.3 mg, 1%) as a solid. LC/MS: mass calcd. For $C_{22}H_{17}ClF_2N_4O_2$: 442.1, found: 443.1[M+H]$^+$; $^1$H NMR (400 MHz, $CD_3OD$) δ 7.97 (d, J=4.0 Hz, 1H), 7.71 (d, J=4.0 Hz, 1H), 7.45-7.60 (m, 3H), 7.30-7.37 (m, 1H), 6.94-7.03 (m, 1H), 6.68 (d, J=4.0 Hz, 1H), 4.49 (s, 2H), 4.26-4.39 (m, 2H), 4.13 (s, 2H), 3.62 (m, 2H); $^{19}$F NMR (282 MHz, $CD_3OD$) δ −50.6, 126.2. Another part of mixture was purified by preparative-HPLC (Column: Xselect CSH C18 OBD Column 30*150 mm 5 μm, n; Mobile Phase A: Water (0.1% FA), Mobile Phase B: ACN; Flow rate: 60 mL/min; Gradient: 22% B to 52% B in 10 min, 52% B; Wave Length: 254 nm; RT1(min): 8.65) to afford 4-chloro-5-{[9-chloro-7-(5-fluoroindol-1-yl)-3,5-dihydro-2H-1,4-benzoxazepin-4-yl]methyl}-3H-pyrimidin-2-one (1.3 mg, 1%) as a solid. LC/MS: mass caled. For $C_{22}H_{17}Cl_2FN_4O_2$: 458.0, found: 459.1[M+H]$^+$; $^1$H NMR (400 MHz, $CD_3OD$) δ 7.95 (s, 1H), 7.64 (d, J=4.0 Hz, 1H), 7.39-7.55 (m, 3H), 7.26-7.35 (m, 1H), 6.96-7.03 (m, 1H), 6.67 (d, J=4.0 Hz, 1H), 4.30-4.37 (m, 2H), 4.28 (s, 2H), 3.90 (s, 2H), 3.40-3.48 (m, 2H); $^{19}$F NMR (376 MHz, $CD_3OD$) δ −126.0.

Example S33. Preparation of 5-{[9-chloro-7-(5-fluoroindol-1-yl)-3,5-dihydro-2H-1,4-benzoxazepin-4-yl]methyl}-4-hydroxy-3H-pyrimidin-2-one (Compound 157)

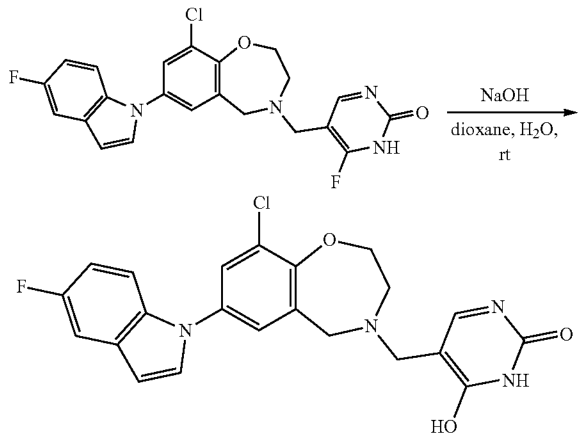

To a mixture of 5-{[9-chloro-7-(5-fluoroindol-1-yl)-3,5-dihydro-2H-1,4-benzoxazepin-4-yl]methyl}-4-fluoro-3H-pyrimidin-2-one (30 mg, 0.07 mmol) in 1,4-dioxane (1 mL) was added NaOH (4 mg, 0.1 mmol) in $H_2O$ (0.5 mL). The mixture was stirred at rt for 4 h, then acidified with 2 M HCl (drops) and purified by preparative-HPLC directly (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 30% B to 60% B in 7 min, 60% B; Wave Length: 254 nm; RT1(min): 5.87) to afford 5-{[9-chloro-7-(5-fluoroindol-1-yl)-3,5-dihydro-2H-1,4-benzoxazepin-4-yl]methyl}-4-hydroxy-3H-pyrimidin-2-one (8.3 mg, 28%) as a solid. LC/MS: mass calcd. For $C_{22}H_{18}ClFN_4O_3$: 440.1, found: 441.1 [M+H]$^+$; $^1$H NMR (300 MHz, $CD_3OD$) a 7.42-7.56 (m, 4H), 7.26-7.39 (m, 2H), 6.90-7.00 (m, 1H), 6.65 (d, J=3.0 Hz, 1H), 4.17-4.26 (m, 2H), 3.98 (s, 2H), 3.46 (s, 2H), 3.10-3.18 (m, 2H); $^{19}$F NMR (282 MHz, $CD_3OD$) δ −126.2.

Example S34. Preparation of 4-{[9-chloro-7-(5-fluoroindol-1-yl)-3,5-dihydro-2H-1,4-benzoxazepin-4-yl]methyl}-N-(oxetan-3-yl)pyrimidin-2-amine (Compound 162)

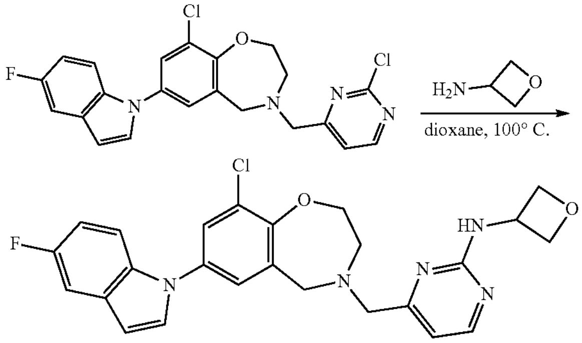

To a stirred mixture of 9-chloro-4-[(2-chloropyrimidin-4-yl)methyl]-7-(5-fluoroindol-1-yl)-3,5-dihydro-2H-1,4-benzoxazepine (50 mg, 0.11 mmol) in 1,4-dioxane (1 mL) were added oxetan-3-amine (16 mg, 0.23 mmol) and DIPEA (29 mg, 0.23 mmol). The reaction was heated to 100° C. and stirred for 24 h, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 48% B to 68% B in 7 min, 68% B; Wave Length: 254 nm; RT1(min): 6.32) to afford 4-{[9-chloro-7-(5-fluoroindol-1-yl)-3,5-dihydro-2H-1,4-benzoxazepin-4-yl]methyl}-N-(oxetan-3-yl) pyrimidin-2-amine (6.2 mg, 11%) as a solid. LC/MS: mass calcd. For $C_{25}H_{23}ClFN_5O_2$:479.1, found: 480.1 [M+H]$^+$; $^1$H NMR (300 MHz, $CD_3OD$) δ 8.25 (d, J=5.1 Hz, 1H), 7.54 (d, J=2.7 Hz, 1H), 7.39-7.51 (m, 2H), 7.27-7.35 (m, 1H), 7.23 (d, J=2.7 Hz, 1H), 6.92-7.04 (m, 1H), 6.85 (d, J=5.1 Hz, 1H), 6.62-6.69 (m, 1H), 4.95-5.07 (m, 1H), 4.85 (t, J=6.9 Hz, 2H), 4.58 (t, J=6.3 Hz, 2H), 4.18-4.27 (m, 2H), 4.02 (s, 2H), 3.69 (s, 2H), 3.21-3.30 (m, 2H); $^{19}$F NMR (282 MHz, $CD_3OD$) δ −126.1.

Example S35. Preparation of 4-{[9-chloro-7-(5-fluoroindol-1-yl)-3,5-dihydro-2H-1,4-benzoxazepin-4-yl]methyl}pyrimidin-2-amine (Compound 163)

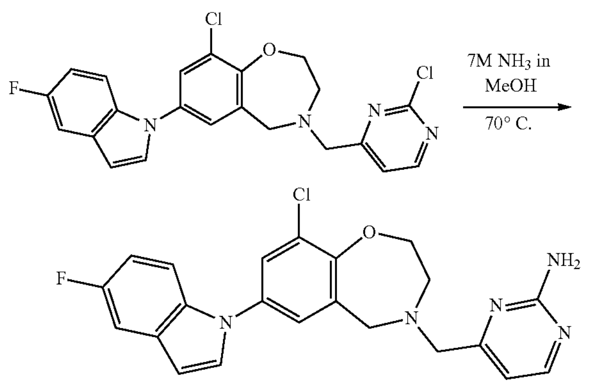

A stirred mixture of 9-chloro-4-[(2-chloropyrimidin-4-yl)methyl]-7-(5-fluoroindol-1-yl)-3,5-dihydro-2H-1,4-benzoxazepine (100 mg, 0.23 mmol) in 7M $NH_3$ in MeOH (3 mL) was heated to 70° C. and stirred for 12 h. The mixture was concentrated under reduced pressure and the residue was purified by preparative-HPLC (Column: XBridge Prep Phenyl OBD Column, 19*250 mm, 5 μm; Mobile Phase A: Water (10 mmol/L $NH_4HCO_3$+0.1% $NH_3 \cdot H_2O$), Mobile Phase B: ACN; Flow rate: 25 mL/min; Gradient: 46% B to 76% B in 7 min, 76% B; Wave Length: 254 nm; RT1(min): 6) to afford 4-{[9-chloro-7-(5-fluoroindol-1-yl)-3,5-dihydro-2H-1,4-benzoxazepin-4-yl]methyl}pyrimidin-2-amine (16.4 mg, 16%) as a solid. LC/MS: mass calcd. For $C_{22}H_{19}ClFN_5O$: 423.1, found: 424.1 $[M+H]^+$; $^1H$ NMR (300 MHz, $CD_3OD$) δ 8.21 (d, J=5.1 Hz, 1H), 7.37-7.53 (m, 3H), 7.18-7.33 (m, 2H), 6.92-7.03 (m, 1H), 6.82 (d, J=5.1 Hz, 1H), 6.59-6.66 (m, 1H), 4.11-4.25 (m, 2H), 3.99 (s, 2H), 3.66 (s, 2H), 3.18-3.27 (m, 2H); $^{19}F$ NMR (282 MHz, $CD_3OD$) δ −126.1.

Example S36. Preparation of 5-{[9-chloro-7-(5-fluoroindol-1-yl)-3,5-dihydro-2H-1,4-benzoxazepin-4-yl]methyl}-2H-pyridazin-3-one (Compound 169)

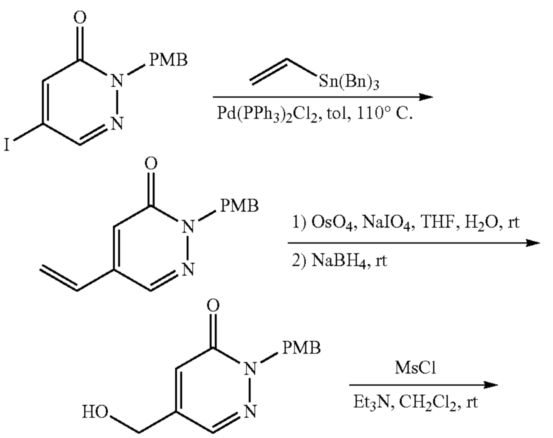

-continued

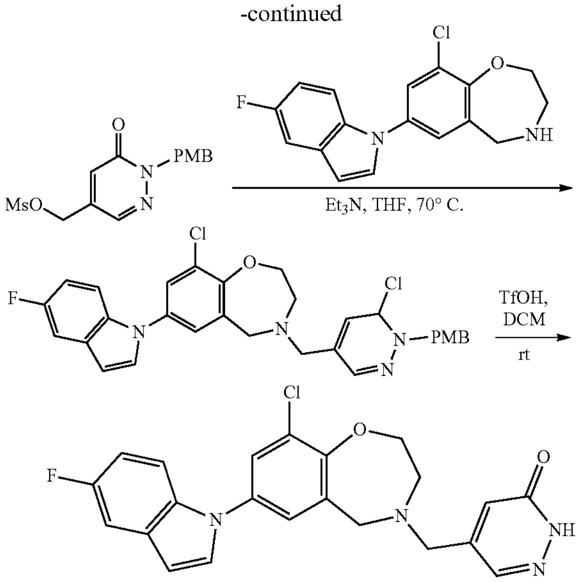

5-ethenyl-2-[(4-methoxyphenyl)methyl]pyridazin-3-one

To a stirred mixture of 5-iodo-2-[(4-methoxyphenyl)methyl]pyridazin-3-one (700 mg, 2.1 mmol) in methylbenzene (1 mL) under an atmosphere of $N_2$ were added tributyl(ethenyl)stannane (649 mg, 2.1 mmol) and $Pd(dppf)Cl_2$ (72 mg, 0.1 mmol). The mixture was heated to 110° C. and stirred for 2 h, then $H_2O$ (100 mL) added and extracted with EtOAc (3×100 mL). The combined organic layers were washed with $H_2O$ (100 mL), dried over anhydrous $Na_2SO_4$, filtered and the filtrate was concentrated under reduced pressure. The residue was purified by silica gel column chromatography (PE/EtOAc, 2:1) to afford 5-ethenyl-2-[(4-methoxyphenyl)methyl] pyridazin-3-one (400 mg, 77%) as a solid.

5-(Hydroxymethyl)-2-[(4-methoxyphenyl)methyl]pyridazin-3-one

To a stirred mixture of 5-ethenyl-2-[(4-methoxyphenyl)methyl]pyridazin-3-one (400 mg, 1.7 mmol) in THF (3 mL) and $H_2O$ (3 mL) was added $OSO_4$ (4 mg, 0.02 mmol) and $NaIO_4$ (705 mg, 3.3 mmol) over a period of 2 min. The mixture was stirred at rt for 6 h, then $NaBH_4$ (125 mg, 3.3 mmol) was added. The reaction was stirred at rt for 15 min, then $H_2O$ (15 mL) added and extracted with EtOAc (3×20 mL). The combined organic layers were washed with brine (20 mL), dried over anhydrous $Na_2SO_4$, filtered and the filtrate was concentrated under reduced pressure to afford 5-(hydroxymethyl)-2-[(4-methoxyphenyl)methyl] pyridazin-3-one (360 mg, 89%) as an oil.

{1-[(4-Methoxyphenyl)methyl]-6-oxopyridazin-4-yl}methyl methanesulfonate

To a stirred mixture of 5-(hydroxymethyl)-2-[(4-methoxyphenyl)methyl]pyridazin-3-one (360 mg, 1.5 mmol) in DCM (5 mL) were added MsCl (335 mg, 2.924 mmol) and $Et_3N$ (300 mg, 2.9 mmol). The reaction was stirred at rt for 2 h, then $H_2O$ (20 mL) was added and the mixture extracted with DCM (3×50 mL). The combined organic layers were washed with $H_2O$ (10 mL), dried over anhydrous $Na_2SO_4$, filtered and the filtrate was concentrated under reduced pressure to afford {1-[(4-methoxyphenyl)methyl]-6-oxopyridazin-4-yl}methyl methanesulfonate (430 mg, 86%) as an oil.

5-{[9-Chloro-7-(5-fluoroindol-1-yl)-3,5-dihydro-2H-1,4-benzoxazepin-4-yl]methyl}-2-[(4-methoxyphenyl)methyl]pyridazin-3-one To a stirred mixture of 9-chloro-7-(5-fluoroindol-1-yl)-2,3,4,5-tetrahydro-1,4-benzoxazepine (100 mg, 0.32 mmol) in THF (10 mL) were added {1-[(4-methoxyphenyl)methyl]-6-oxopyridazin-4-yl}methyl methanesulfonate (205 mg, 0.63 mmol) and $Et_3N$ (64 mg, 0.63 mmol). The mixture was stirred at rt for 2 h, then concentrated under reduced pressure and the residue was purified by reverse-phase column chromatography (column, C18 silica gel; mobile phase, MeCN in Water (0.1% TFA), 10% to 50% gradient in 10 min; detector, UV 254 nm) to afford 5-{[9-chloro-7-(5-fluoroindol-1-yl)-3,5-dihydro-2H-1,4-benzoxazepin-4-yl]methyl}-2-[(4-methoxyphenyl)methyl]pyridazin-3-one (170 mg, 94%) as an oil.

5-{[9-Chloro-7-(5-fluoroindol-1-yl)-3,5-dihydro-2H-1,4-benzoxazepin-4-yl]methyl}-2H-pyridazin-3-one To a stirred mixture of 5-{[9-chloro-7-(5-fluoroindol-1-yl)-3,5-dihydro-2H-1,4-benzoxazepin-4-yl]methyl}-2-[(4-methoxyphenyl)methyl]pyridazin-3-one (50 mg, 0.09 mmol) in DCM (1 mL) was added $CF_3SO_3H$ (2 mg, 0.01 mmol). The mixture was stirred at rt for 1 h, then concentrated under vacuum and the residue was purified by preparative-HPLC (Column: Xselect CSH C18 OBD Column 30*150 mm 5 μm, n; Mobile Phase A: Water (0.1% FA), Mobile Phase B: ACN; Flow rate: 60 mL/min; Gradient: 37% B to 67% B in 7 min, 67% B; Wave Length: 254 nm; RT1(min): 6.33) to afford 5-{[9-chloro-7-(5-fluoroindol-1-yl)-3,5-dihydro-2H-1,4-benzoxazepin-4-yl]methyl}-2H-pyridazin-3-one (3.7 mg, 9%) as a solid. LC/MS: mass calcd. For $C_{22}H_{18}ClFN_4O_2$: 424.1, found: 425.1[M+H]$^+$; $^1$H NMR (300 MHz, DMSO-$d_6$) δ 12.94 (s, 1H), 7.84 (d, J=1.8 Hz, 1H), 7.71 (d, J=3.3 Hz, 1H), 7.64 (d, J=2.7 Hz, 1H), 7.49-7.57 (m, 1H), 7.38-7.48 (m, 2H), 7.01-7.13 (m, 1H), 6.77 (s, 1H), 6.69 (d, J=3.3 Hz, 1H), 4.16-4.23 (m, 2H), 4.00 (s, 2H), 3.64 (s, 2H), 3.13-3.19 (m, 2H); $^{19}$F NMR (282 MHz, DMSO-$d_6$) δ −80.1, −126.0.

Example S37. Preparation of 5-{[9-chloro-7-(5-fluoroindol-1-yl)-3,5-dihydro-2H-1,4-benzoxazepin-4-yl]methyl}pyridine-2-carboxylic acid (Compound 177)

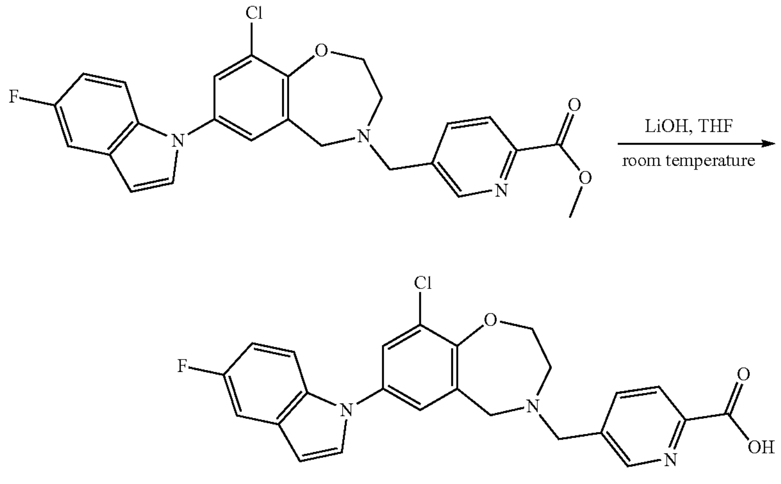 [SMILES: COC(=O)c1ccc(CN2CCOc3c(Cl)cc(-n4ccc5cc(F)ccc54)cc3C2)cn1 ; O=C(O)c1ccc(CN2CCOc3c(Cl)cc(-n4ccc5cc(F)ccc54)cc3C2)cn1]

To a stirred solution of methyl 5-{[9-chloro-7-(5-fluoroindol-1-yl)-3,5-dihydro-2H-1,4-benzoxazepin-4-yl]methyl}pyridine-2-carboxylate (50 mg, 0.11 mmol) in THF (1 mL) at rt was added 1M aq LiOH (0.5 mL, 0.5 mmol). The mixture was stirred at rt for 2 h at rt, then acidified to pH ~6 with 1M HCl and extracted with DCM (3×2 mL). The combined organic layers were washed with brine (2 mL), dried over anhydrous $Na_2SO_4$ and filtered. The filtrate was concentrated under reduced pressure and the residue was purified by preparative-HPLC (Column: XBridge Prep OBD C18 Column, 30*150 mm, 5 μm; Mobile Phase A: H2O (10 mmol/L $NH_4HCO_3$), Mobile Phase B: ACN; Flow rate: 60 mL/min; Gradient: 27% B to 57% B in 7 min, 57% B; Wave Length: 254 nm; RT1(min): 5.87) to afford 5-{[9-chloro-7-(5-fluoroindol-1-yl)-3,5-dihydro-2H-1,4-benzoxazepin-4-yl]methyl}pyridine-2-carboxylic acid (7.3 mg, 15%) as a solid. LC/MS: mass calcd. For $C_{24}H_{19}ClFN_3O_3$: 451.1, found: 452.1 [M+H]$^+$; $^1$H NMR (300 MHz, DMSO-$d_6$) δ 8.57 (s, 1H), 7.97 (d, J=8.0 Hz, 1H), 7.85 (d, J=8.1 Hz, 1H), 7.72 (d, J=3.3 Hz, 1H), 7.64 (d, J=2.6 Hz, 1H), 7.39-7.51 (m, 2H), 7.35 (d, J=2.7 Hz, 1H), 7.14-7.02 (m, 1H), 6.68 (d, J=3.3 Hz, 1H), 4.18-4.19 (m, 2H), 3.96 (s, 2H), 3.80 (s, 2H), 3.08-3.09 (m, 2H); $^{19}$F NMR (282 MHz, DMSO-$d_6$) δ −123.5.

Example S38. Preparation of 4-{[9-chloro-7-(5-fluoroindol-1-yl)-3,5-dihydro-2H-1,4-benzoxazepin-4-yl] methyl}pyridin-2-amine (Compound 179)

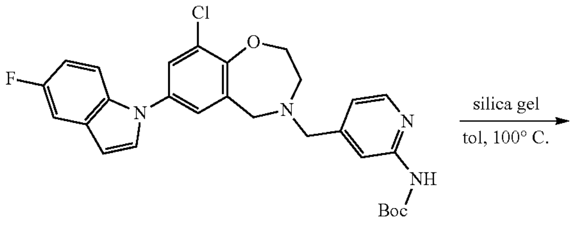

-continued

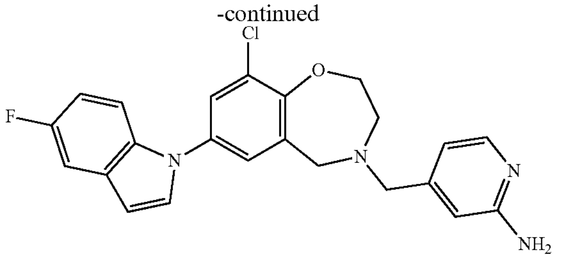

To a stirred solution of tert-butyl N-(4-{[9-chloro-7-(5-fluoroindol-1-yl)-3,5-dihydro-2H-1,4-benzoxazepin-4-yl]methyl}pyridin-2-yl)carbamate (60 mg, 0.12 mmol) in toluene (2 mL) was added silica gel (70 mg, 1.2 mmol). The mixture was heated to 100° C. and stirred for 3 h, then filtered, and the filter cake was washed with DCM (3x3 mL). The filtrate was concentrated under reduced pressure and the residue was purified by preparative-HPLC (Column: XSelect CSH Prep C18 OBD Column, 19*250 mm, 5 μm; Mobile Phase A: Water (10 mmol/L NH4HCO3), Mobile Phase B: ACN; Flow rate: 25 mL/min; Gradient: 65% B to 85% B in 7 min, 85% B; Wave Length: 254 nm; RT1(min): 5.32) to afford 4-{[9-chloro-7-(5-fluoroindol-1-yl)-3,5-dihydro-2H-1,4-benzoxazepin-4-yl]methyl}pyridin-2-amine (3.7 mg, 8%) as a solid. LC/MS: mass caled. For $C_{23}H_{20}ClFN_4O$: 422.1, found: 423.1 $[M+H]^+$; $^1H$ NMR (300 MHz, $CDCl_3$) δ 7.89 (d, J=5.7 Hz, 1H), 7.46 (d, J=2.6 Hz, 1H), 7.26-7.40 (m, 3H), 6.94-7.09 (m, 2H), 6.67-6.77 (m, 2H), 6.64 (d, J=3.4 Hz, 1H), 5.47 (s, 1H), 4.20-4.29 (m, 2H), 3.92 (s, 2H), 3.67 (s, 2H), 3.16-3.25 (m, 2H); $^{19}F$ NMR (376 MHz, $CDCl_3$) −126.1.

Example S39. Preparation of 4-{[9-chloro-7-(5-fluoroindol-1-yl)-3,5-dihydro-2H-1,4-benzoxazepin-4-yl]methyl}-N-methylpyridin-2-amine (Compound 180)

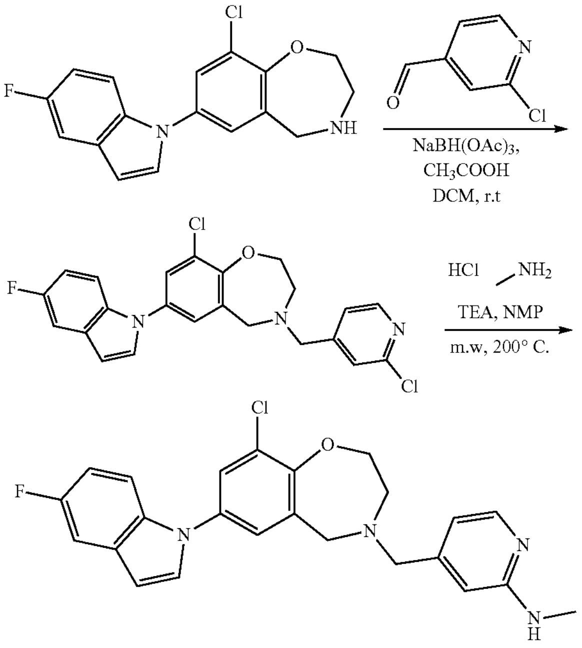

9-chloro-4-[(2-chloropyridin-4-yl)methyl]-7-(5-fluoroindol-1-yl)-3,5-dihydro-2H-1,4-benzoxazepine To a stirred mixture of 9-chloro-7-(5-fluoroindol-1-yl)-2,3,4,5-tetrahydro-1,4-benzoxazepine (100 mg, 0.32 mmol) and 2-chloropyridine-4-carbaldehyde (90 mg, 0.63 mmol) in DCM were added $NaBH(OAc)_3$ (134 mg, 0.63 mmol) and AcOH (2 mg, catalytic quantity). The mixture was stirred at rt overnight, then concentrated under reduced pressure and the residue was purified by preparative-TLC (PE/EtOAc, 2:1) to afford 9-chloro-4-[(2-chloropyridin-4-yl)methyl]-7-(5-fluoroindol-1-yl)-3,5-dihydro-2H-1,4-benzoxazepine (80 mg, 57%) as a solid.

4-{[9-chloro-7-(5-fluoroindol-1-yl)-3,5-dihydro-2H-1,4-benzoxazepin-4-yl]methyl}-N-methylpyridin-2-amine To a stirred mixture of 9-chloro-4-[(2-chloropyridin-4-yl)methyl]-7-(5-fluoroindol-1-yl)-3,5-dihydro-2H-1,4-benzoxazepine (50 mg, 0.11 mmol) and $MeNH_2$·HCl (23 mg, 0.34 mmol) in NMP (1 mL) was added $Et_3N$ (47 uL, 0.34 mmol). The mixture was heated to 200° C. under microwave irradiation and stirred for 2 h, then filtered and the filtrate was concentrated under reduced pressure. The residue was purified by preparative-HPLC (Column: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 50% B to 80% B in 8 min, 80% B; Wave Length: 254 nm; RT1(min): 7) to afford 4-{[9-chloro-7-(5-fluoroindol-1-yl)-3,5-dihydro-2H-1,4-benzoxazepin-4-yl]methyl}-N-methylpyridin-2-amine (2.0 mg, 4%) as a solid. LC/MS: mass caled. For $C_{24}H_{22}ClFN_4O$: 436.1, found: 437.0 $[M+H]^+$; $^1H$ NMR (300 MHz, $CDCl_3$) δ 7.89 (d, J=5.7 Hz, 1H), 7.47 (d, J=2.7 Hz, 1H), 7.29-7.40 (m, 3H), 6.91-7.03 (m, 2H), 6.61-6.65 (m, 2H), 6.54 (s, 1H), 6.12 (s, 1H), 4.22-4.24 (m, 2H), 3.90 (s, 2H), 3.66 (s, 2H), 3.18-3.22 (m, 2H), 2.89 (d, J=5.1 Hz, 3H); $^{19}F$ NMR (282 MHz, $CDCl_3$) δ −123.0.

Example 40. Preparation of 4-{[9-chloro-7-(5-fluorindol-1-yl)-3,5-dihydro-2H-1,4-benzoxazepin-4-yl]methyl}-N,N-dimethylpyridin-2-amine) (Compound 181)

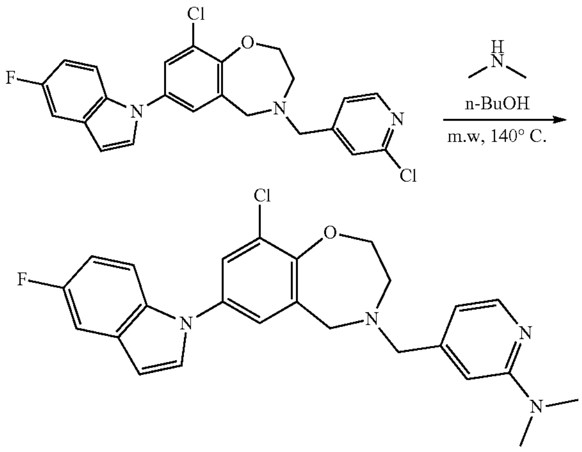

A mixture of 9-chloro-4-[(2-chloropyridin-4-yl)methyl]-7-(5-fluoroindol-1-yl)-3,5-dihydro-2H-1,4-benzoxazepine (50 mg, 0.11 mmol) and $Me_2NH$ (15 mg, 0.34 mmol) in n-butanol (2 mL) was heated to 140° C. under microwave radiation and stirred for 30 min, then concentrated under reduced pressure and the residue was purified by reparative-HPLC (Column: XSelect CSH Prep C18 OBD Column, 19*250 mm, 5 μm; Mobile Phase A: Water (0.05% TFA), Mobile Phase B: ACN; Flow rate: 25 mL/min; Gradient: 30% B to 53% B in 7 min, 53% B; Wave Length: 254 nm; RT1(min): 5.15) to afford 4-{[9-chloro-7-(5-fluoroindol-1-yl)-3,5-dihydro-2H-1,4-benzoxazepin-4-yl]methyl}-N,N-dimethylpyridin-2-amine) as a solid. LC/MS: mass calcd. For $C_{25}H_{24}ClFN_4O$: 450.1, found: 451.1 $[M+H]^+$; $^1H$ NMR (300 MHz, $CDCl_3$) δ 8.13 (s, 1H), 7.56 (s, 1H), 7.37-7.41 (m, 1H), 7.29-7.33 (m, 3H), 7.16 (s, 1H), 7.00 (t, J=8.4 Hz, 1H), 6.80 (s, 1H), 6.64 (d, J=3.0 Hz, 1H), 4.34-4.35 (m, 2H), 4.19 (s, 2H), 4.01 (s, 2H), 3.38-3.39 (m, 2H), 3.31 (s, 6H); $^{19}F$ NMR (282 MHz, $CDCl_3$) δ −75.7, −123.2.

Example S41. Preparation of 4-{[9-chloro-7-(5-fluoroindol-1-yl)-3,5-dihydro-2H-1,4-benzoxazepin-4-yl]methyl}-N-(oxetan-3-yl)pyridin-2-amine (Compound 182)

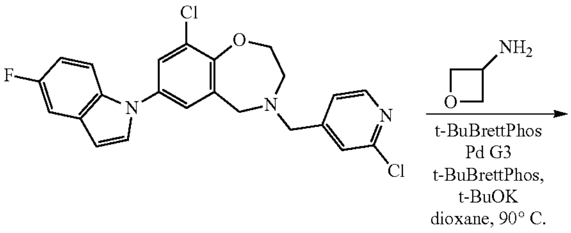

-continued

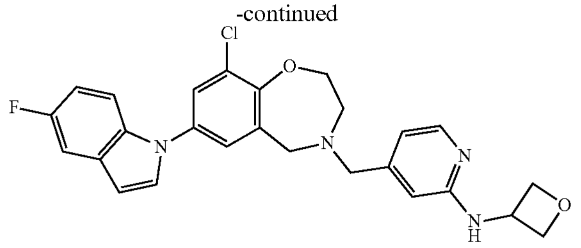

To a stirred mixture of 9-chloro-4-[(2-chloropyridin-4-yl)methyl]-7-(5-fluoroindol-1-yl)-3,5-dihydro-2H-1,4-benzoxazepine (50 mg, 0.11 mmol) and oxetan-3-amine (25 mg, 0.34 mmol) in 1,4-dioxane were added t-BuBrettPhos Pd G3 (20 mg, 0.023 mmol), t-BuBrettPhos (11 mg, 0.023 mmol) and t-BuOK (25 mg, 0.23 mmol). The mixture was stirred at 90° C. for 16 h, then filtered and the filtrate was concentrated under reduced pressure. The residue was purified by preparative-HPLC (Column: XSelect CSH Prep C18 OBD Column, 19*250 mm, 5 μm; Mobile Phase A: Water (0.05% TFA), Mobile Phase B: ACN; Flow rate: 25 mL/min; Gradient: 30% B to 53% B in 7 min, 53% B; Wave Length: 254 nm; RT1(min): 5.15) to afford 4-{[9-chloro-7-(5-fluoroindol-1-yl)-3,5-dihydro-2H-1,4-benzoxazepin-4-yl]methyl}-N-(oxetan-3-yl)pyridin-2-amine (2.2 mg, 4%) as a solid. LC/MS: mass calcd. For $C_{26}H_{24}ClFN_4O_2$: 478.1, found: 479.1 $[M+H]^+$; $^1H$ NMR (300 MHz, $CD_3OD$) δ 7.88 (d, J=5.4 Hz, 1H), 7.51 (d, J=2.7 Hz, 1H), 7.43 (d, J=10.5 Hz, 2H), 7.28 (d, J=9.3 Hz, 1H), 7.15 (d, J=2.4 Hz, 1H), 6.96 (t, J=9.3, 2.6 Hz, 1H), 6.56-6.66 (m, 2H), 6.54 (s, 1H), 4.91 (m, 3H), 4.53 (m, 2H), 4.18-4.21 (m, 2H), 3.92 (s, 2H), 3.64 (s, 2H), 3.15-3.18 (m, 2H); $^{19}F$ NMR (282 MHz, $CD_3OD$) δ −126.1.

Example S42. Preparation of 1-(4-{[9-chloro-7-(5-fluoroindol-1-yl)-3,5-dihydro-2H-1,4-benzoxazepin-4-yl]methyl}pyridin-2-yl)methanamine (Compound 184)

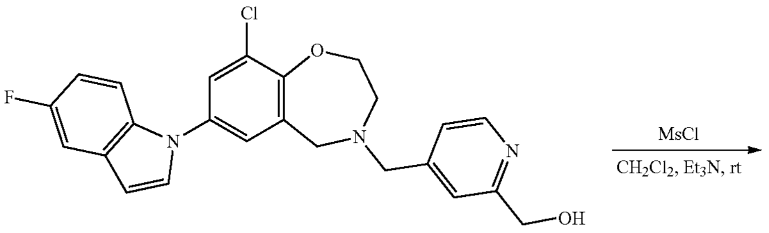

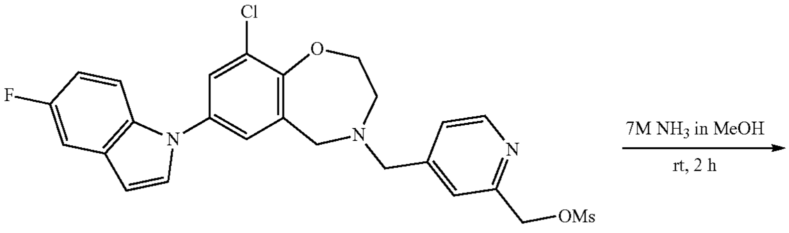

-continued

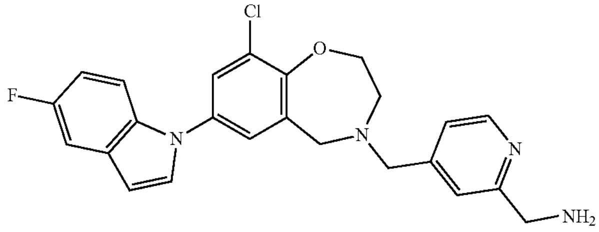

(4-{[9-chloro-7-(5-fluoroindol-1-yl)-3,5-dihydro-2H-1,4-benzoxazepin-4-yl]methyl}pyridin-2-yl) methyl methanesulfonate To a mixture of (4-{[9-chloro-7-(5-fluoroindol-1-yl)-3,5-dihydro-2H-1,4-benzoxazepin-4-yl]methyl}pyridin-2-yl) methanol (40 mg, 0.09 mmol) in DCM (4 mL) at 0° C. was added MsCl (20 mg, 0.18 mmol) and $Et_3N$ (18 mg, 0.18 mmol). The mixture was warmed to rt and stirred for 1 h, then concentrated under reduced pressure and the residue was used directly in the next step.

1-(4-{[9-chloro-7-(5-fluoroindol-1-yl)-3,5-dihydro-2H-1,4-benzoxazepin-4-yl]methyl}pyridin-2-yl) methanamine A mixture of (4-{[9-chloro-7-(5-fluoroindol-1-yl)-3,5-dihydro-2H-1,4-benzoxazepin-4-yl]methyl}pyridin-2-yl) methyl methanesulfonate (40 mg, 0.08 mmol) in 7M $NH_3$ in MeOH (3 mL) was stirred at rt for 2 h. The mixture was concentrated under reduced pressure and the residue was purified by preparative-HPLC (Column: XSelect CSH Prep C18 OBD Column, 19*150 mm, 5 μm; Mobile Phase A: Water (10 mmol/L $NH_4HCO_3$), Mobile Phase B: ACN; Flow rate: 25 mL/min; Gradient: 42% B to 72% B in 7 min, 72% B to 72% B in 9 min, 72% B; Wave Length: 254 nm; RT1(min): 6.47) to afford 1-(4-{[9-chloro-7-(5-fluoroindol-1-yl)-3,5-dihydro-2H-1,4-benzoxazepin-4-yl]methyl}pyridin-2-yl)methanamine (3.3 mg, 10%) as a solid. LC/MS: mass calcd. For $C_{24}H_{22}ClFN_4O$: 436.1, found: 437.1 $[M+H]^+$; $^1H$ NMR (300 MHz, DMSO-$d_6$) δ 8.42 (d, J=6.0 Hz, 1H), 7.71 (d, J=3.0 Hz, 1H), 7.63 (d, J=3.0 Hz, 1H), 7.46-7.53 (m, 1H), 7.38-7.48 (m, 2H), 7.34 (d, J=3.0 Hz, 1H), 7.18 (d, J=9.0 Hz, 1H), 6.98-7.10 (m, 1H), 6.68 (d, J=3.0 Hz, 1H), 4.14-4.27 (m, 2H), 3.96 (s, 2H), 3.76 (s, 2H), 3.73 (s, 2H) 3.04-3.12 (m, 2H); $^{19}F$ NMR (282 MHz, DMSO-$d_6$) δ −123.6.

Example S43. Preparation of 4-{[9-chloro-7-(5-fluoroindol-1-yl)-3,5-dihydro-2H-1,4-benzoxazepin-4-yl]methyl}pyridine-2-carboxylic acid (Compound 185)

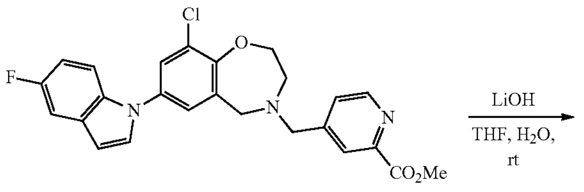

-continued

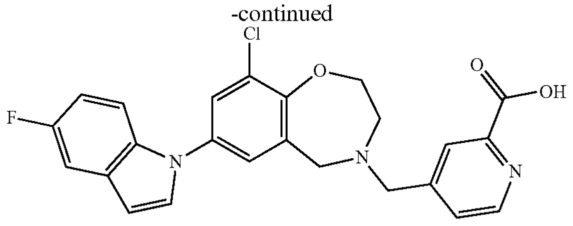

To a mixture of methyl 4-{[9-chloro-7-(5-fluoroindol-1-yl)-3,5-dihydro-2H-1,4-benzoxazepin-4-yl]methyl}pyridine-2-carboxylate (40 mg, 0.09 mmol) in THF (0.2 mL) and MeOH (0.8 mL) was added LiOH·$H_2O$ (12 mg, 0.29 mmol) in $H_2O$ (0.1 mL). The mixture was stirred at rt for 3 h, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$+0.1% $NH_3$·$H_2O$), Mobile Phase B: ACN; Flow rate: 60 mL/min; Gradient: 50% B to 80% B in 7 min, 80% B; Wave Length: 254 nm; RT1(min): 6) to afford 4-{[9-chloro-7-(5-fluoroindol-1-yl)-3,5-dihydro-2H-1,4-benzoxazepin-4-yl]methyl}pyridine-2-carboxylic acid (16.1 mg, 38%) as a solid. LC/MS: mass calcd. For $C_{24}H_{19}ClFN_3O_3$: 451.1, found: 452.0 $[M+H]^+$; $^1H$ NMR (300 MHz, DMSO-$d_6$) δ 8.62 (d, J=6.0 Hz, 1H), 7.95-8.06 (m, 2H), 7.70-7.75 (m, 1H), 7.60-7.68 (m, 1H), 7.25-7.57 (m, 4H), 6.98-7.10 (m, 1H), 6.60-6.70 (m, 1H), 4.11-4.24 (m, 2H), 3.88-3.96 (m, 2H), 3.78-3.81 (m, 2H), 3.04-3.16 (m, 2H); $^{19}F$ NMR (282 MHz, DMSO-$d_6$) δ −123.5.

Example S44. Preparation of 9-chloro-7-(5-fluoroindol-1-yl)-4-{[2-(oxetan-3-yl)pyridin-4-yl]methyl}-3,5-dihydro-2H-1,4-benzoxazepine (Compound 187)

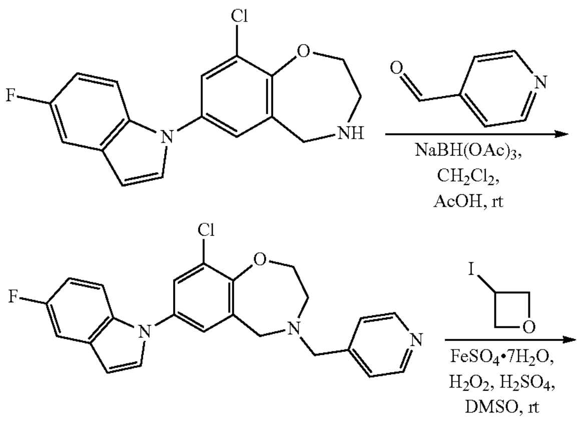

-continued

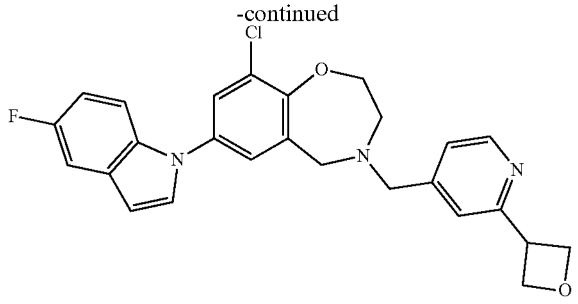

9-chloro-7-(5-fluoroindol-1-yl)-4-(pyridin-4-ylmethyl)-3,5-dihydro-2H-1,4-benzoxazepine To a mixture of 9-chloro-7-(5-fluoroindol-1-yl)-2,3,4,5-tetrahydro-1,4-benzoxazepine (300 mg, 0.95 mmol) and 4-formylpyridine (131 mg, 1.23 mmol) in DCM (5 mL) was added $NaBH(OAc)_3$ (400 mg, 1.9 mmol) and AcOH (0.2 mL). The mixture was stirred at rt for 2 h, then quenched with aq. $NaHCO_3$ (5 mL) and extracted with EtOAc (3×5 mL). The combined organic layers were washed with brine (5 mL), dried over anhydrous $Na_2SO_4$, filtered and the filtrate was concentrated under reduced pressure. The residue was purified by silica gel column chromatography (PE/EtOAc, 10:1) to afford 9-chloro-7-(5-fluoroindol-1-yl)-4-(pyridin-4-ylmethyl)-3,5-dihydro-2H-1,4-benzoxazepine (370 mg, 96%) as an oil.

9-chloro-7-(5-fluoroindol-1-yl)-4-{[2-(oxetan-3-yl)pyridin-4-yl]methyl}-3,5-dihydro-2H-1,4-benzoxazepine $H_2O_2$, 30% in $H_2O$ (57 uL, 0.74 mmol) was added dropwise slowly to a stirred mixture of 9-chloro-7-(5-fluoroindol-1-yl)-4-(pyridin-4-ylmethyl)-3,5-dihydro-2H-1,4-benzoxazepine (100 mg, 0.25 mmol), $H_2SO_4$ (27 uL, 0.49 mmol), 3-iodooxetane (90 mg, 0.49 mmol), $FeSO_4·7H_2O$ (20.5 mg, 0.07 mmol) in DMSO (2 mL) at 40° C. After 2 min, a further portion $FeSO_4·7H_2O$ (20 mg, 0.07 mmol) was added and the mixture was stirred at 40° C. for 30 min. Further $H_2O_2$, 30% in $H_2O$ (57 uL, 0.74 mmol) and $FeSO_4·7H_2O$ (20 mg, 0.07 mmol) was added, and the mixture was stirred at 40° C. for 1 h, then diluted with EtOAc (10 mL) and poured in to sat.aq. $NaHCO_3$ (5 mL). The separated organic layer was washed with brine (5 mL), dried over $Na_2SO_4$, filtered and concentrated under reduced pressure. The residue was purified by preparative-HPLC (Column: XBridge Shield RP18 OBD Column, 19*250 mm, 10 μm; Mobile Phase A: Water (0.1% FA), Mobile Phase B: ACN; Flow rate: 25 mL/min; Gradient: 44% B to 74% B in 7 min, 74% B; Wave Length: 254 nm; RT1(min): 5) to afford 9-chloro-7-(5-fluoroindol-1-yl)-4-{[2-(oxetan-3-yl)pyridin-4-yl]methyl}-3,5-dihydro-2H-1,4-benzoxazepine (4.0 mg, 4%) as a solid. LC/MS: mass calcd. For $C_{26}H_{23}ClFN_3O_2$: 463.1, found: 464.1 $[M+H]^+$; $^1H$ NMR (300 MHz, DMSO-$d_6$) δ 8.55 (d, J=6.0 Hz, 1H), 7.71 (d, J=3.0 Hz, 1H), 7.64 (d, J=3.0 Hz, 1H), 7.43-7.50 (m, 2H), 7.34 (d, J=3.0 Hz, 1H), 7.22-7.31 (m, 2H), 7.00-7.10 (m, 1H), 6.68 (d, J=3.0 Hz, 1H), 4.80-4.88 (m, 2H), 4.70-4.78 (m, 2H), 4.28-4.44 (m, 1H), 4.12-4.20 (m, 2H), 3.96 (s, 2H), 3.73 (s, 2H), 3.02-3.09 (m, 2H); $^{19}F$ NMR (282 MHz, DMSO-$d_6$) δ −123.8.

Example S45. Preparation of 4-{[2-(azetidin-3-yl)pyridin-4-yl]methyl}-9-chloro-7-(5-fluoroindol-1-yl)-3,5-dihydro-2H-1,4-benzoxazepine; trifluoroacetic acid (Compound 188)

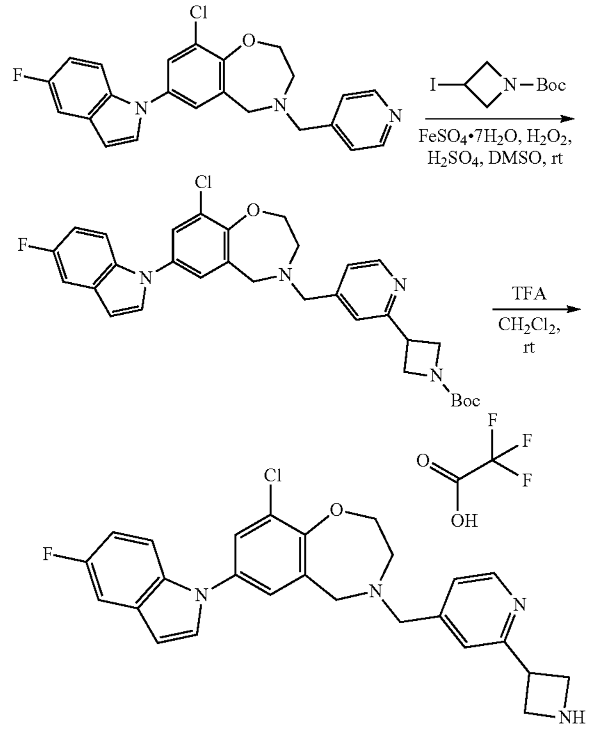

Tert-butyl 3-(4-{[9-chloro-7-(5-fluoroindol-1-yl)-3,5-dihydro-2H-1,4-benzoxazepin-4-yl]methyl}pyridin-2-yl)azetidine-1-carboxylate $H_2O_2$, 30% in $H_2O$ (50 uL, 1.5 mmol) was added to a stirred mixture of 9-chloro-7-(5-fluoroindol-1-yl)-4-(pyridin-4-ylmethyl)-3,5-dihydro-2H-1,4-benzoxazepine (200 mg, 0.49 mmol), $H_2SO_4$ (96 mg, 0.98 mmol), tert-butyl 3-iodoazetidine-1-carboxylate (277 mg, 0.98 mmol) and $FeSO_4·7H_2O$ (40 mg, 0.15 mmol) in DMSO (5 mL) at 60° C. slowly. After 2 min, a further portion of $FeSO_4·7H_2O$ (41 mg, 0.15 mmol) and $H_2O_2$, 30% in $H_2O$ (50 uL, 1.5 mmol) was added. The mixture was stirred at 60° C. for 1 h, then poured into 0.1 M NaOH (10 mL) and extracted with EtOAc (3×10 mL). The combined organic layers were washed with brine (20 mL×3), dried over $Na_2SO_4$, filtered and concentrated under reduced pressure. The residue was purified by reverse-phase column chromatography (column, C18 silica gel; mobile phase, MeCN in Water (0.05% TFA), 20% to 100% gradient in 40 min; detector, UV 254 nm) to afford tert-butyl 3-(4-{[9-chloro-7-(5-fluoroindol-1-yl)-3,5-dihydro-2H-1,4-benzoxazepin-4-yl]methyl}pyridin-2-yl)azetidine-1-carboxylate (40 mg, 15%) as an oil.

4-{[2-(azetidin-3-yl)pyridin-4-yl]methyl}-9-chloro-7-(5-fluoroindol-1-yl)-3,5-dihydro-2H-1,4-benzoxazepine To a mixture of tert-butyl 3-(4-{[9-chloro-7-(5-fluoroindol-1-yl)-3,5-dihydro-2H-1,4-benzoxazepin-4-yl]

methyl}pyridin-2-yl)azetidine-1-carboxylate (50 mg, 0.089 mmol) in DCM (1 mL) was added TFA (0.2 mL). The mixture was stirred at rt for 1 h, then concentrated under reduced pressure and the residue was purified by preparative-HPLC (Column: XSelect CSH Prep C18 OBD Column, 19*250 mm, 5 μm; Mobile Phase A: Water (0.1% TFA), Mobile Phase B: ACN; Flow rate: 25 mL/min; Gradient: 25% B to 51% B in 7 min, 51% B; Wave Length: 254 nm; RT1(min): 6.02) to afford 4-{[2-(azetidin-3-yl)pyridin-4-yl]methyl}-9-chloro-7-(5-fluoroindol-1-yl)-3,5-dihydro-2H-1,4-benzoxazepine (6.2 mg, 11%) as a solid. LC/MS: mass calcd. For $C_{26}H_{23}ClFN_3O_2$: 462.1, found: 463.1 $[M+H]^+$; $^1H$ NMR (400 MHz, $CD_3OD$) δ 8.69 (d, J=4.0 Hz, 1H), 7.60 (d, J=4.0 Hz, 1H), 7.38-7.52 (m, 4H), 7.31-7.36 (m, 1H), 7.26 (d, J=4.0 Hz, 1H), 6.95-7.02 (m, 1H), 6.67 (d, J=8.0 Hz, 1H), 4.21-4.42 (m, 7H), 4.16 (s, 2H), 4.03 (s, 2H), 3.36-3.42 (m, 2H); $^{19}F$ NMR (376 MHz, $CD_3OD$) δ −76.8, −126.0.

Example S46. Preparation of 4-{[9-chloro-7-(5-fluoroindol-1-yl)-3,5-dihydro-2H-1,4-benzoxazepin-4-yl] methyl}-1H-pyridine-2-thione (Compound 189)

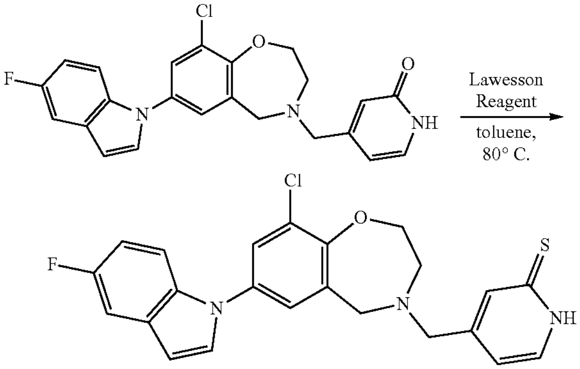

5-Bromo-3-chloro-2-hydroxy-N-[2-hydroxy(1,1,2,2-$^2H_4$) ethyl]benzamide

A solution of 4-{[9-chloro-7-(5-fluoroindol-1-yl)-3,5-dihydro-2H-1,4-benzoxazepin-4-yl]methyl}-1H-pyridin-2-one (20 mg, 0.05 mmol) in toluene (1 mL) at 80° C. was treated with Lawesson's Reagent (11.0 mg, 0.03 mmol). The resulting mixture was heated to 80° C. and stirred for 16 h, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$+0.1% $NH_3{\cdot}H2O$), Mobile Phase B: ACN; Flow rate: 60 mL/min; Gradient: 44% B to 74% B in 7 min, 74% B; Wave Length: 254 nm; RT1(min): 6) to afford 4-{[9-chloro-7-(5-fluoroindol-1-yl)-3,5-dihydro-2H-1,4-benzoxazepin-4-yl]methyl}-1H-pyridine-2-thione (8.9 mg, 42%) as a solid. LC/MS: mass calcd. for $C_{23}H_{19}ClFN_3OS$: 439.1, found: 440.1 $[M+H]^+$; $^1H$ NMR (400 MHz, DMSO-$d_6$) δ 13.33 (s, 1H), 7.73 (d, J=3.3 Hz, 1H), 7.67-7.60 (m, 2H), 7.50-7.54 (m, 1H), 7.37-7.43 (m, 2H), 7.28 (s, 1H), 7.08-7.13 (m, 1H), 6.73-6.75 (m, 1H), 6.65-6.67 (m, 1H), 4.16-4.22 (m, 2H), 3.91 (s, 2H), 3.60 (s, 2H), 3.10-3.11 (m, 2H); $^{19}F$ NMR (376 MHz, DMSO-$d_6$) δ −123.6.

Example S47. Preparation of 4-{[9-chloro-7-(5-fluoroindol-1-yl)-3,5-dihydro-2H-1,4-benzoxazepin-4-yl]methyl}-3-methyl-1H-pyridin-2-one (Compound 194)

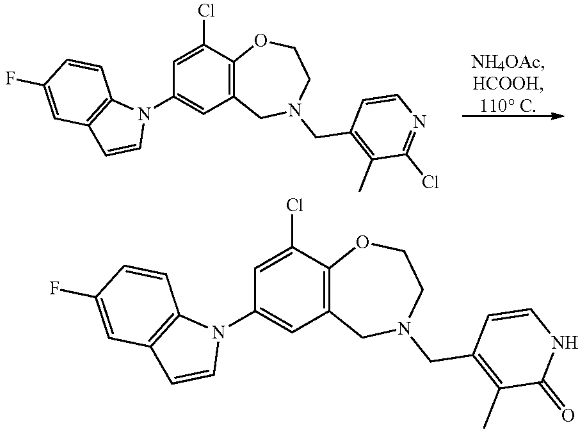

To a stirred mixture of 9-chloro-4-[(2-chloro-3-methylpyridin-4-yl)methyl]-7-(5-fluoroindol-1-yl)-3,5-dihydro-2H-1,4-benzoxazepine (40 mg, 0.09 mmol) in HCOOH (1 mL) was added $CH_3COONH_4$ (67 mg, 0.9 mmol). The mixture was heated to 110° C. and stirred for 12 h, then concentrated under vacuum and the residue was purified by preparative-HPLC (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 40% B to 70% B in 7 min, 70% B; Wave Length: 254 nm; RT1(min): 5.88) to afford 4-{[9-chloro-7-(5-fluoroindol-1-yl)-3,5-dihydro-2H-1,4-benzoxazepin-4-yl]methyl}-3-methyl-1H-pyridin-2-one (5.8 mg, 15%) as solid. LC/MS: mass calcd. For $C_{24}H_{21}ClFN_3O_2$: 437.1, found: 438.1 $[M+H]^+$; $^1H$ NMR (300 MHz, DMSO-$d_6$) δ 11.37 (s, 1H), 7.70 (d, J=3.3 Hz, 1H), 7.62 (d, J=2.7 Hz, 1H), 7.38-7.53 (m, 2H), 7.35 (d, J=2.7 Hz, 1H), 7.17 (d, J=6.9 Hz, 1H), 7.01-7.12 (m, 1H), 6.65-6.71 (m, 1H), 6.26 (d, J=6.9 Hz, 1H), 4.14-4.22 (m, 2H), 3.90 (s, 2H), 3.55 (s, 2H), 3.05-3.11 (m, 2H), 1.91 (s, 3H); $^{19}F$ NMR (282 MHz, DMSO-$d_6$) δ −123.6.

Example S48. Preparation of 4-{[9-chloro-7-(5-fluoroindol-1-yl)-3,5-dihydro-2H-1,4-benzoxazepin-4-yl]methyl}-1,3-dihydropyridine-2,6-dione (Compound 204 & 4-{[9-chloro-7-(5-fluoroindol-1-yl)-3,5-dihydro-2H-1,4-benzoxazepin-4-yl]methyl}-6-methoxy-1H-pyridin-2-one (Compound 196)

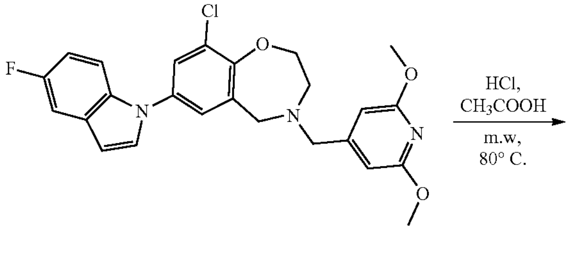

-continued

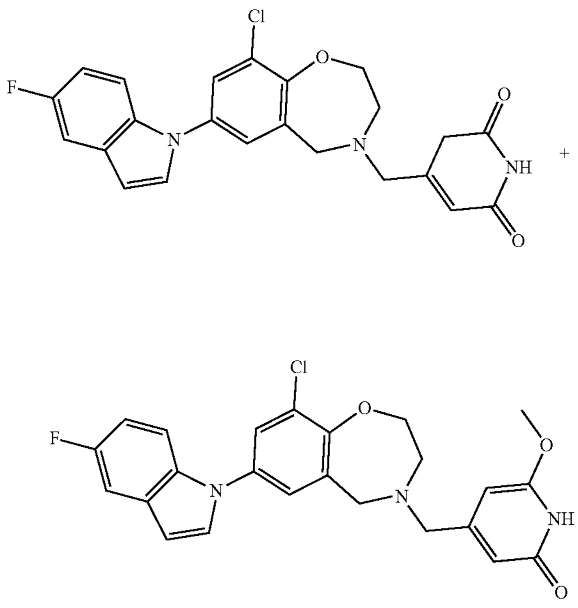

To a 10 cc glass sealed tube was added 9-chloro-4-[(2,6-dimethoxypyridin-4-yl)methyl]-7-(5-fluoroindol-1-yl)-3,5-dihydro-2H-1,4-benzoxazepine (100 mg, 0.21 mmol), HCl (1 mL, 32.9 mmol) and AcOH (0.5 mL). The mixture was heated to 80° C. under microwave radiation and stirred for 10 min, then concentrated under reduced pressure and the residue was purified by preparative-HPLC (Column: XSelect CSH Prep C18 OBD Column, 19*250 mm, 5 μm; Mobile Phase A: Water (0.05% TFA), Mobile Phase B: ACN; Flow rate: 25 mL/min; Gradient: 30% B to 53% B in 7 min, 53% B; Wave Length: 254 nm; RT1(min): 5.15) to afford 4-{[9-chloro-7-(5-fluoroindol-1-yl)-3,5-dihydro-2H-1,4-benzoxazepin-4-yl]methyl}-1,3-dihydropyridine-2,6-dione (2.1 mg, 2%) as a solid and 4-{[9-chloro-7-(5-fluoroindol-1-yl)-3,5-dihydro-2H-1,4-benzoxazepin-4-yl]methyl}-6-methoxy-1H-pyridin-2-one (1.8 mg, 2%) as a solid.

4-{[9-chloro-7-(5-fluoroindol-1-yl)-3,5-dihydro-2H-1,4-benzoxazepin-4-yl]methyl}-1,3-dihydropyridine-2,6-dione LC/MS: mass caled. For $C_{23}H_{19}ClFN_3O_3$: 439.1, found: 440.1 $[M+H]^+$; $^1H$ NMR (300 MHz, $CD_3OD$) δ 7.79 (d, J=2.4 Hz, 1H), 7.50-7.63 (m, 4H), 7.31 (d, J=9.3 Hz, 1H), 7.01 (t, J=9.1 Hz, 1H), 6.68 (d, J=3.3 Hz, 1H), 4.69 (s, 2H), 4.47 (s, 2H), 4.39 (s, 2H), 3.75-3.78 (m, 3H), 3.29 (m, 1H); $^{19}F$ NMR (282 MHz, $CD_3OD$) δ −125.6.

4-{[9-chloro-7-(5-fluoroindol-1-yl)-3,5-dihydro-2H-1,4-benzoxazepin-4-yl]methyl}-6-methoxy-1H-pyridin-2-one LC/MS: mass caled. For $C_{24}H_{21}ClFN_3O_3$: 453.1, found: 454.1 $[M+H]^+$; $^1H$ NMR (300 MHz, $CD_3OD$) δ 7.78 (d, J=2.4 Hz, 1H), 7.50-7.55 (m, 3H), 7.30 (d, J=9.3 Hz, 1H), 7.01 (t, J=9.3 Hz, 1H), 6.68 (d, J=3.3 Hz, 1H), 6.35 (s, 2H), 4.74-4.75 (m, 2H), 4.57-4.67 (m, 4H), 3.89 (s, 3H), 3.75-3.78 (m, 2H); $^{19}F$ NMR (282 MHz, $CD_3OD$) δ −125.6.

Example S49. Preparation of 5-{[9-chloro-7-(5-fluoroindol-1-yl)-3,5-dihydro-2H-1,4-benzoxazepin-4-yl]methyl}-2,4-dihydropyrazol-3-one (Compound 198)

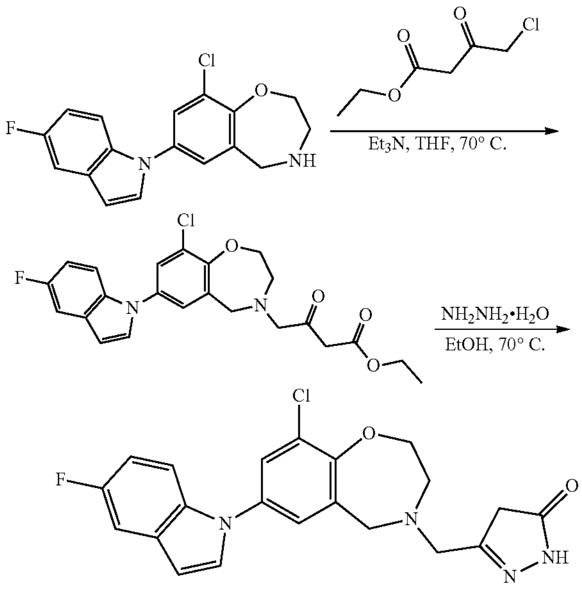

Ethyl 4-[9-chloro-7-(5-fluoroindol-1-yl)-3,5-dihydro-2H-1,4-benzoxazepin-4-yl]-3-oxobutanoate To a stirred mixture of 9-chloro-7-(5-fluoroindol-1-yl)-2,3,4,5-tetrahydro-1,4-benzoxazepine (50 mg, 0.16 mmol) in THF (1 mL) was added ethyl 4-chloro-3-oxobutanoate (40 mg, 0.24 mmol) and $Et_3N$ (35 mg, 0.32 mmol). The mixture was heated to 70° C. and stirred for 16 h, then concentrated under reduced pressure and the residue was purified by preparative-TLC (PE/EtOAc, 1:1) to afford ethyl 4-[9-chloro-7-(5-fluoroindol-1-yl)-3,5-dihydro-2H-1,4-benzoxazepin-4-yl]-3-oxobutanoate (50 mg, 64%) as an oil.

5-{[9-Chloro-7-(5-fluoroindol-1-yl)-3,5-dihydro-2H-1,4-benzoxazepin-4-yl]methyl}-2,4-dihydropyrazol-3-one To a stirred mixture of ethyl 4-[9-chloro-7-(5-fluoroindol-1-yl)-3,5-dihydro-2H-1,4-benzoxazepin-4-yl]-3-oxobutanoate (50 mg, 0.11 mmol) in THF (1 mL) was added $NH_2NH_2{\cdot}H_2O$ (12 mg, 0.23 mmol). The mixture was stirred at rt for 4 h, then concentrated under reduced pressure and the residue was purified by preparative-HPLC (Column: XBridge Prep OBD C18 Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 26% B to 56% B in 7 min, 56% B; Wave Length: 254 nm; RT1(min): 6) to afford 5-{[9-chloro-7-(5-fluoroindol-1-yl)-3,5-dihydro-2H-1,4-benzoxazepin-4-yl]methyl}-2,4-dihydropyrazol-3-one (8.9 mg, 19%) as an oil. LC/MS: mass calcd. For $C_{21}H_{18}ClFN_4O_2$:412.1, found: 413.0 $[M+H]^+$; $^1H$ NMR (300 MHz, DMSO-$d_6$) δ 11.43 (br, 1H), 9.45 (br, 1H), 7.72 (d, J=3 Hz, 1H), 7.62 (d, J=3 Hz, 1H), 7.51-7.56 (m, 1H), 7.41-7.45 (m, 1H), 7.35 (d, J=3 Hz 1H), 7.04-7.11 (m, 1H), 6.69 (d, J=3.3 Hz, 1H), 5.38 (s, 1H), 4.10-4.19 (m, 2H), 3.92 (s, 2H), 3.58 (s, 2H), 3.01-3.06 (m, 2H); $^{19}F$ NMR (376 MHz, DMSO-$d_6$) δ −123.6.

Example S50. Preparation of 4-{[9-chloro-7-(5-fluoroindol-1-yl)-3,5-dihydro-2H-1,4-benzoxazepin-4-yl]methyl}piperidin-2-one (Compound 200)

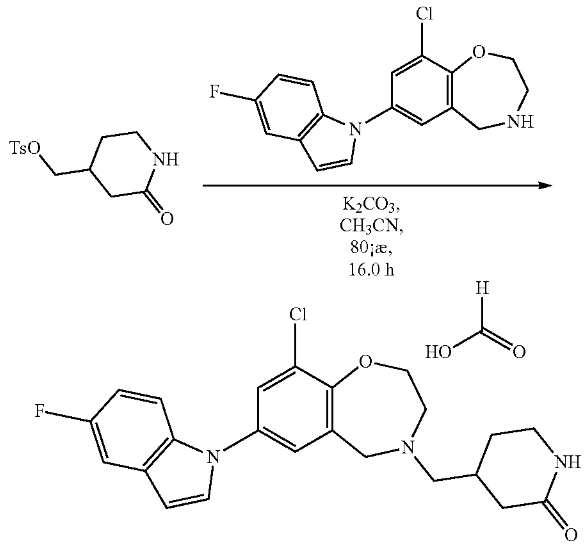

4-{[9-chloro-7-(5-fluoroindol-1-yl)-3,5-dihydro-2H-1,4-benzoxazepin-4-yl]methyl}piperidin-2-one (2-Oxopiperidin-4-yl)methyl 4-methylbenzenesulfonate (CAS No: 2629362-45-2) (100 mg, 0.35 mmol) was added to a mixture of 9-chloro-7-(5-fluoroindol-1-yl)-2,3,4,5-tetrahydro-1,4-benzoxazepine (67 mg, 0.21 mmol) and $Et_3N$ (48 mg, 0.48 mmol) in DMF (10 mL). The mixture was heated to 80° C. and stirred for 16 h, then $H_2O$ (10 mL) added and the mixture was extracted with EtOAc (3×10 mL). The combined organic layers were dried over anhydrous $Na_2SO_4$, filtered and the filtrate was concentrated under reduced pressure. The residue was purified by preparative-HPLC (Column: XSelect CSH Prep C18 OBD Column, 19*150 mm, 5 μm; Mobile Phase A: Water (0.05% FA), Mobile Phase B: ACN; Flow rate: 25 mL/min; Gradient: 23% B to 33% B in 10 min, 33% B; Wave Length: 254 nm; RT1(min): 8.6) to afford 4-{[9-chloro-7-(5-fluoroindol-1-yl)-3,5-dihydro-2H-1,4-benzoxazepin-4-yl] methyl}piperidin-2-one (30.9 mg, 20%) as a solid. LC/MS: mass caled. For $C_{23}H_{23}ClFN_3O_2$: 427.1, found: 428.2 $[M+H]^+$; $^1H$ NMR (400 MHz, DMSO-$d_6$) δ 7.72 (d, J=4.0 Hz, 1H), 7.54-7.62 (m, 2H), 7.40-7.48 (m, 3H), 7.17 (br, 1H), 7.05 (m, 1H), 6.69 (d, J=4.0 Hz, 1H), 4.08-4.16 (m, 2H), 3.92 (s, 2H), 3.14-3.20 (m, 5H), 2.36-2.61 (m, 2H), 2.08-2.10 (m, 1H), 2.03-2.25 (m, 1H), 1.78 (m, 2H); $^{19}F$ NMR (376 MHz, DMSO-$d_6$) δ −123.6.

Example S51. Preparation of 4-{[9-chloro-7-(5-fluoroindol-1-yl)-3,5-dihydro-2H-1,4-benzoxazepin-4-yl]methyl}pyran-2-one (Compound 203)

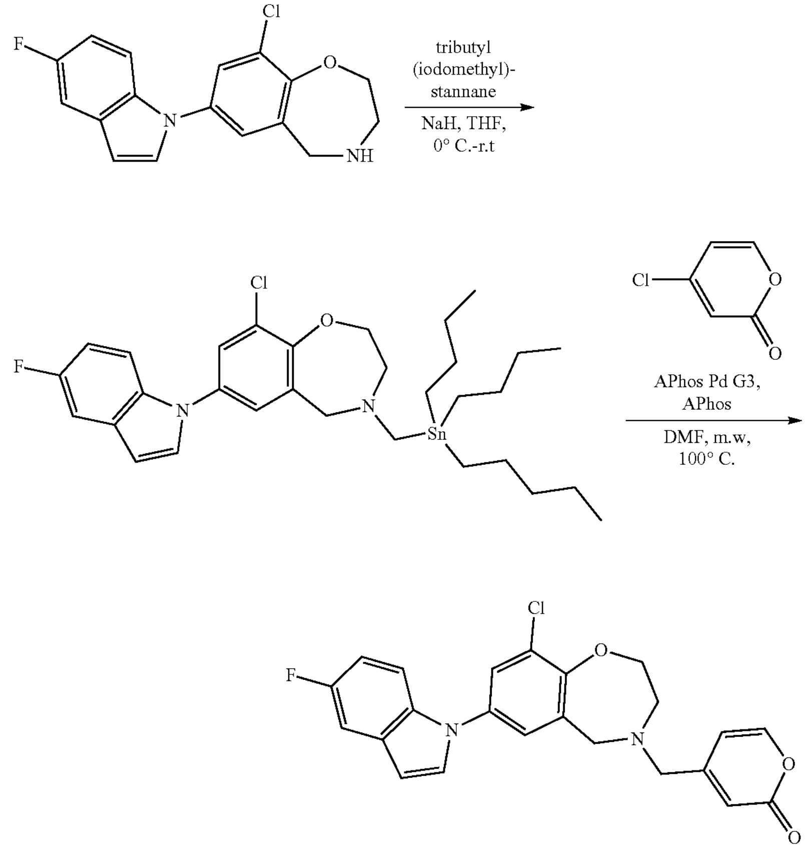

9-chloro-7-(5-fluoroindol-1-yl)-4-[(tributylstannyl) methyl]-3,5-dihydro-2H-1,4-benzoxazepine To a stirred mixture of 9-chloro-7-(5-fluoroindol-1-yl)-2,3,4,5-tetrahydro-1,4-benzoxazepine (100 mg, 0.32 mmol) in THE (2 mL) at 0° C. was added NaH, 60% in oil (65 mg, 1.58 mmol). The mixture was stirred for 30 min, then warmed to rt and tributyl(iodomethyl)stannane (680 mg, 1.58 mmol) was addd. The mixture was stirred at rt for 24 h, then cooled to 0° C., $H_2O$ added and the mixture was extracted with EtOAc (3x50 mL). The combined organic layers were washed with $H_2O$ (3x10 mL), dried over anhydrous $Na_2SO_4$ and filtered. The filtrate was concentrated under reduced pressure and the residue was purified by preparative-TLC (PE/EtOAc, 5:1) to afford 9-chloro-7-(5-fluoroindol-1-yl)-4-[(tributylstannyl)methyl]-3,5-dihydro-2H-1,4-benzoxazepine (150 mg, 63%) as an oil.

4-{[9-chloro-7-(5-fluoroindol-1-yl)-3,5-dihydro-2H-1,4-benzoxazepin-4-yl]methyl}pyran-2-one To a stirred mixture of 9-chloro-7-(5-fluoroindol-1-yl)-4-[(tributylstannyl)methyl]-3,5-dihydro-2H-1,4-benzoxazepine (50 mg, 0.08 mmol) in DMF (1.67 mL, 21.6 mmol) were added 4-chloropyran-2-one (16 mg, 0.12 mmol), [4-(N,N-dimethylamino)phenyl]di-tert-butylphosphine (2 mg, 0.008 mmol) and methanesulfonato([4-(N,N-dimethylamino)Phenyl]di-tert-butylphosphino)(2.-amino-1,1-biphenyl-2-yl)palladium (II) (5 mg, 0.008 mmol). The mixture was heated to 100° C. under microwave irradiation and stirred for 10 min, then filtered. $H_2O$ (10 mL) was added to the filtrate and the mixture was extracted with EtOAc (3x15 mL). The combined organic layers were washed with brine (15 mL), dried over anhydrous $Na_2SO_4$, filtered and the filtrate was concentrated under reduced pressure. The residue was purified by preparative-HPLC (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 47% B to 67% B in 7 min, 67% B; Wave Length: 254 nm; RT1(min): 6.33) to afford 4-{[9-chloro-7-(5-fluoroindol-1-yl)-3,5-dihydro-2H-1,4-benzoxazepin-4-yl]methyl}pyran-2-one (10.8 mg, 31%) as a solid. LC/MS: mass caled. For $C_{23}H_{18}ClFN_2O_3$: 424.1, found: 425.0 $[M+H]^+$; $^1H$ NMR (300 MHz, $CD_3OD$) δ 7.62 (d, J=5.4 Hz, 1H), 7.50 (d, J=2.4 Hz, 1H), 7.42 (d, J=7.8 Hz, 2H), 7.19-7.29 (m, 2H), 6.98 (t, J=9.0 Hz, 1H), 6.62 (d, J=3.3 Hz, 1H), 6.48 (d, J=5.4 Hz, 1H), 6.33-6.37 (m, 1H), 4.17-4.20 (m, 2H), 3.92 (s, 2H), 3.61 (d, J=1.2 Hz, 2H), 3.17-3.20 (m, 2H); $^{19}F$ NMR (282 MHz, $CD_3OD$) δ −126.0.

Example S52. Preparation of 9-chloro-7-(5-fluoroindol-1-yl)-4-[1-(2-methoxypyridin-4-yl)ethyl]-3,5-dihydro-2H-1,4-benzoxazepine (Compound 217)

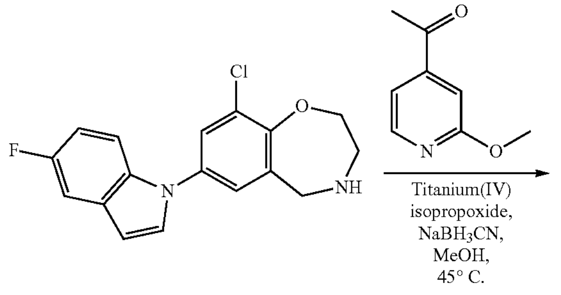

-continued

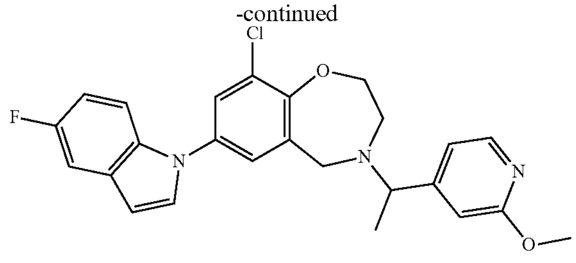

9-chloro-7-(5-fluoroindol-1-yl)-4-[1-(2-methoxypyridin-4-yl)ethyl]-3,5-dihydro-2H-1,4-benzoxazepine A mixture of 1-(2-methoxypyridin-4-yl)ethanone (143 mg, 0.95 mmol), 9-chloro-7-(5-fluoroindol-1-yl)-2,3,4,5-tetrahydro-1,4-benzoxazepine (200 mg, 0.63 mmol) and titanium(IV) isopropoxide (500 uL) were heated to 45° C. and stirred for 4 h. Then mixture was cooled, diluted with MeOH (4 mL), and $NaBH_3CN$ (158 mg, 2.5 mmol) was added. The resulting mixture was heated to 45° C. and stirred for 4 h, the overnight at rt. The mixture was concentrated under reduced pressure and purified by preparative-HPLC (Column: YMC-Actus Triart C18, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 70% B to 90% B in 7 min, 90% B; Wave Length: 254 nm; RT1(min): 6.4) to afford 9-chloro-7-(5-fluoroindol-1-yl)-4-[1-(2-methoxypyridin-4-yl)ethyl]-3,5-dihydro-2H-1,4-benzoxazepine (70 mg, 24%) as a solid. LC/MS: mass calcd. For $C_{25}H_{23}ClFN_3O_2$: 451.1, found: 452.2 $[M+H]^+$; $^1H$ NMR (400 MHz, $CD_3OD$) δ 8.08 (d, J=5.2 Hz, 1H), 7.49 (d, J=2.7 Hz, 1H), 7.35-7.45 (m, 2H), 7.29 (m, 1H), 6.97-7.03 (m, 3H), 6.81 (s, 1H), 6.63 (d, J=3.6 Hz, 1H), 4.26-4.11 (m, 2H), 3.95-4.04 (m, 1H), 3.80-3.87 (m, 5H), 3.15-3.27 (m, 2H), 1.40 (d, J=6.8 Hz, 3H); $^{19}F$ NMR (376 MHz, $CD_3OD$) δ −126.2.

Example S53. Preparation of 4-{[(5S)-9-chloro-7-(5-fluoroindol-1-yl)-5-methyl-3,5-dihydro-2H-1,4-benzoxazepin-4-yl]methyl}-1H-pyridin-2-one (Compound 236 and 237)

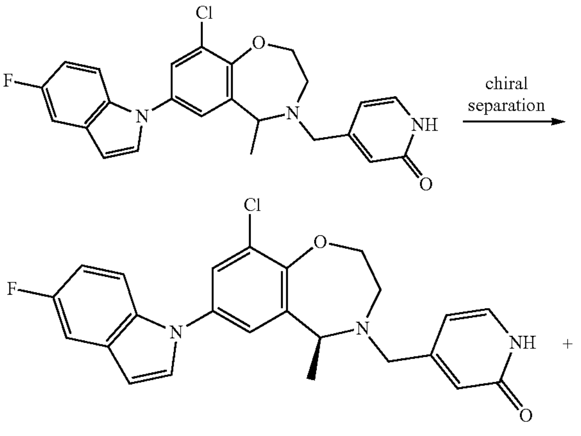

assumed

-continued

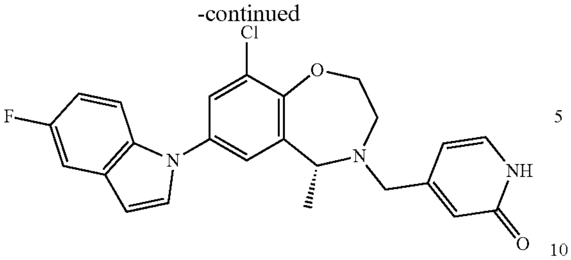

assumed

The racemates of 4-{[9-chloro-7-(5-fluoroindol-1-yl)-5-methyl-3,5-dihydro-2H-1,4-benzoxazepin-4-yl]methyl}-1H-pyridin-2-one (20 mg, 0.046 mmol) were separated by preparative-chiral-HPLC (Column:(R, R)-WHELK-O1-Kromasil, 2.11*25 cm, 5 μm; Mobile Phase A: Hex(0.5% 2M NH3-MeOH)—HPLC, Mobile phase B: EtOH—HPLC; Flow rate; 20 mL/min; Gradient: 35% B to 35% B in 21 min; Wave length: 220/254 nm; RT1(min): 16.49; RT2(min) 18.91; Sample Solvent: EtOH—HPLC; InJection Volume: 0.5 mL; Number Of Runs: 4) to afford two compounds:

Example P1 (first eluting isomer): 4-{[(5R)-9-chloro-7-(5-fluoroindol-1-yl)-5-methyl-3,5-dihydro-2H-1,4-benzoxazepin-4-yl]methyl}-1H-pyridin-2-one (5.2 mg, 26%) as a solid. LC/MS: mass caled. For $C_{24}H_{21}ClFN_3O_2$: 437.1, found: 438.1 $[M+H]^+$; $^1H$ NMR (300 MHz, $CD_3OD$) δ 7.36-7.54 (m, 4H), 7.29-7.33 (m, 1H), 7.20 (d, J=3.0 Hz, 1H), 6.96-7.03 (m, 1H), 6.64 (d, J=6.0 Hz, 1H), 6.47-6.57 (m, 2H), 4.21-4.29 (m, 1H), 4.01-4.14 (m, 2H), 3.52-3.76 (m, 3H), 2.94-3.01 (m, 1H), 1.61 (d, J=6.0 Hz, 3H); $^{19}F$ NMR (282 MHz, $CD_3OD$) δ -126.1.

Example P2 (second eluting isomer): 4-{[(5S)-9-chloro-7-(5-fluoroindol-1-yl)-5-methyl-3,5-dihydro-2H-1,4-benzoxazepin-4-yl]methyl}-1H-pyridin-2-one (4.6 mg, 23%) as a solid. LC/MS: mass calcd. For $C_{24}H_{21}ClFN_3O_2$: 437.1, found: 438.1 $[M+H]^+$; $^1H$ NMR (300 MHz, $CD_3OD$) δ 7.36-7.51 (m, 4H), 7.26-7.31 (m, 1H), 7.20 (d, J=3.0 Hz, 1H), 6.95-7.02 (m, 1H), 6.64 (d, J=3.0 Hz, 1H), 6.47-6.58 (m, 2H), 4.20-4.28 (m, 1H), 4.02-4.15 (m, 2H), 3.53-3.77 (m, 3H), 2.94-3.01 (m, 1H), 1.62 (d, J=6.0 Hz, 3H); $^{19}F$ NMR (282 MHz, $CD_3OD$) δ -126.1.

Example S53. Preparation of 2-(5-{[9-chloro-7-(5-fluoroindol-1-yl)-3,5-dihydro-2H-1,4-benzoxazepin-4-yl]methyl}pyrimidin-2-yl)acetonitrile (Compound 252)

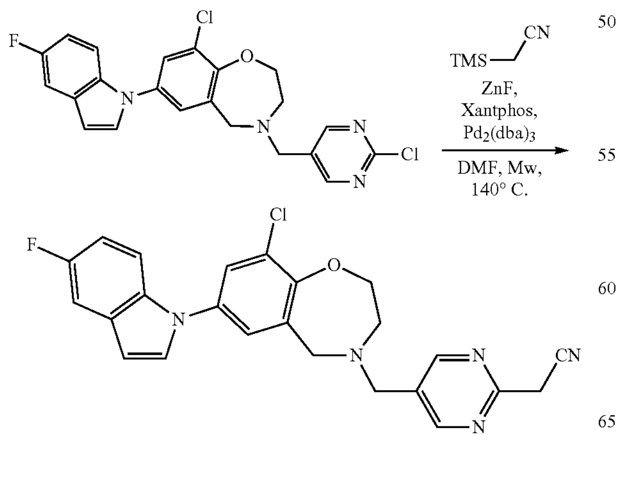

To a mixture of 9-chloro-4-[(2-chloropyrimidin-5-yl)methyl]-7-(5-fluoroindol-1-yl)-3,5-dihydro-2H-1,4-benzoxazepine (100 mg, 0.23 mmol) in DMF (2 mL) under an atmosphere of $N_2$ was added 2-(trimethylsilyl)acetonitrile (38 mg, 0.34 mmol), Xantphos (5 mg, 0.009 mmol), $Pd_2(dba)_3$ (4 mg, 0.005 mmol) and $ZnF_2$ (14 mg, 0.14 mmol). The mixture was heated to 140° C. under microwave irradiation and stirred for 30 min, then the mixture was filtered and the filtrate was concentrated under reduced pressure. The residue was purified by preparative-HPLC (Column: XBridge Prep OBD C18 Column, 30*150 mm, 5 μm; Mobile Phase A: H2O(Column: XBridge Prep Phenyl OBD Column, 19*250 mm, 5 μm; Mobile Phase A: H2O (10 mmol/L $NH_4HCO_3$+0.1% $NH_3 \cdot H_2O$), Mobile Phase B: ACN; Flow rate: 25 mL/min; Gradient: 60% B to 80% B in 8 min, 80% B; Wave Length: 254 nm; RT1(min): 7.23) to afford 2-(5-{[9-chloro-7-(5-fluoroindol-1-yl)-3,5-dihydro-2H-1,4-benzoxazepin-4-yl]methyl}pyrimidin-2-yl)acetonitrile (3.3 mg, 3%) as a solid. LC/MS: mass calcd. For $C_{24}H_{19}ClFN_5O$: 447.1, found: 448.0 $[M+H]^+$; $^1H$ NMR (300 MHz, DMSO-$d_6$) δ 8.77 (s, 2H), 7.71 (d, J=3.3 Hz, 1H), 7.64 (d, J=2.7 Hz, 1H), 7.54-7.59 (m, 1H), 7.41-7.45 (m, 2H), 7.03-7.10 (m, 1H), 6.69 (d, J=3.3 Hz, 1H), 4.40 (s, 2H), 4.18-4.20 (m, 2H), 3.99 (s, 2H), 3.75 (s, 2H), 3.06-3.09 (m, 2H); $^{19}F$ NMR (282 MHz, DMSO-$d_6$) δ -123.6.

Example S54. Preparation of (5-{[9-chloro-7-(5-fluoroindol-1-yl)-3,5-dihydro-2H-1,4-benzoxazepin-4-yl]methyl}pyrimidin-2-yl)(imino)methyl-lambda6-sulfanone (Compound 254)

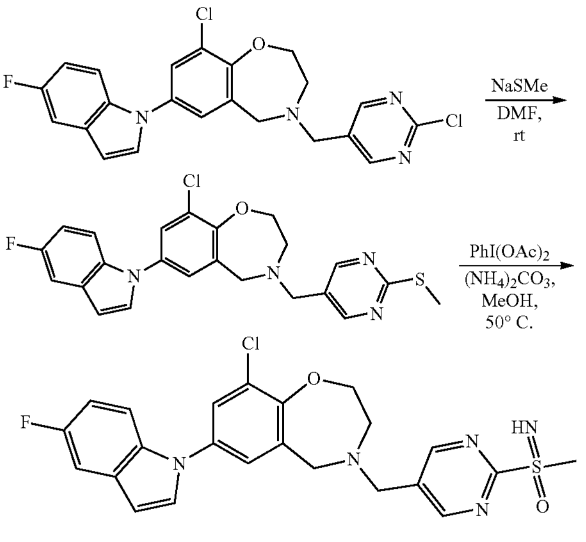

9-chloro-7-(5-fluoroindol-1-yl)-4-{[2-(methylsulfanyl)pyrimidin-5-yl]methyl}-3,5-dihydro-2H-1,4-benzoxazepine To a mixture of 9-chloro-4-[(2-chloropyrimidin-5-yl)methyl]-7-(5-fluoroindol-1-yl)-3,5-dihydro-2H-1,4-benzoxazepine (100 mg, 0.23 mmol) in DMF (3 mL) was added (methylsulfanyl)sodium (32 mg, 0.45 mmol). The mixture was heated to 80° C. and stirred for 12 h, then purified directly by reversed-phase flash chromatography (column, C18 silica gel; mobile phase, MeCN in H2O (0.1% TFA), 10% to 50% gradient in 10 min; detector, UV 254 nm) to afford 9-chloro-7-(5-fluoroindol-1-yl)-4-{[2-(methylsulfanyl)pyrimidin-5-yl]methyl}-3,5-dihydro-2H-1,4-benzoxazepine (60 mg, 58%) as an oil.

(5-{[9-chloro-7-(5-fluoroindol-1-yl)-3,5-dihydro-2H-1,4-benzoxazepin-4-yl]methyl}pyrimidin-2-yl)(imino)methyl-lambda6-sulfanone A mixture of 9-chloro-7-(5-fluoroindol-1-yl)-4-{[2-(methylsulfanyl)pyrimidin-5-yl]methyl}-3,5-dihydro-2H-1,4-benzoxazepine (60 mg, 0.13 mmol) in MeOH (1.5 mL) was added $(NH_4)_2CO_3$ (25 mg, 0.26 mmol) and $PhI(OAc)_2$ (149 mg, 0.46 mmol). The mixture was heated to 50° C. and stirred for 3 h, then purified directly by preparative-HPLC with followed conditions (Column: XBridge Prep OBD C18 Column, 30*150 mm, 5 μm; Mobile Phase A: H2O (10 mmol/L $NH_4HCO_3$+0.1% $NH_3 \cdot H_2O$), Mobile Phase B: ACN; Flow rate: 60 mL/min; Gradient: 35% B to 65% B in 10 min, 65% B; Wave Length: 254 nm; RT1(min): 8.25) to afford (5-{[9-chloro-7-(5-fluoroindol-1-yl)-3,5-dihydro-2H-1,4-benzoxazepin-4-yl]methyl}pyrimidin-2-yl)(imino)methyl-lambda6-sulfanone (9.1 mg, 14%) as a solid. LC/MS: mass calcd. For $C_{23}H_{21}ClFN_5O_2S$: 485.1, found: 486.0 $[M+H]^+$; $^1H$ NMR (300 MHz, DMSO-$d_6$) δ 8.95 (s, 2H), 7.72 (d, J=3.3 Hz, 1H), 7.65 (d, J=2.7 Hz, 1H), 7.42-7.55 (m, 3H), 7.01-7.13 (m, 1H), 6.69 (d, J=3.3 Hz, 1H), 4.59 (s, 1H), 4.19-4.22 (m, 2H), 4.04 (s, 2H), 3.84 (s, 2H), 3.29 (d, J=2.7 Hz, 3H), 3.09-3.12 (m, 2H); $^{19}F$ NMR (282 MHz, DMSO-$d_6$) δ −123.5.

Example S55. Preparation of 9-chloro-7-(5-fluoroindol-1-yl)-4-{[2-(1H-1,2,3,4-tetrazol-5-yl)pyrimidin-5-yl]methyl}-3,5-dihydro-2H-1,4-benzoxazepine (Compound 255)

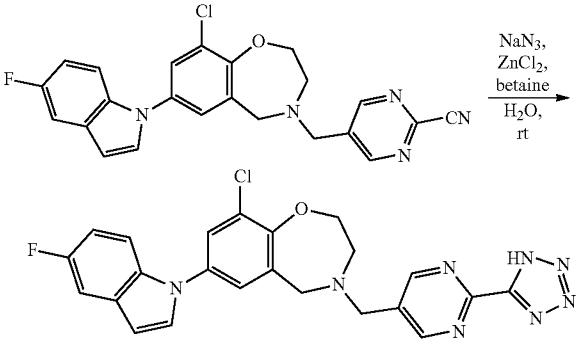

To a stirred mixture of 5-{[9-chloro-7-(5-fluoroindol-1-yl)-3,5-dihydro-2H-1,4-benzoxazepin-4-yl]methyl}pyrimidine-2-carbonitrile (50 mg, 0.12 mmol) and $NaN_3$ (22 mg, 0.35 mmol) in $H_2O$ (2 mL) at rt was added $ZnCl_2$ (47 mg, 0.35 mmol) and 2-(trimethylazaniumyl)acetate (2 mg, 0.012 mmol). The mixture was stirred at rt for 3 days, and the precipitated solids were collected by filtration and the filter cake was washed with $H_2O$ (3×2 mL). The crude product (30 mg) was purified by preparative-HPLC (Column: XBridge Prep OBD C18 Column, 30*150 mm, 5 μm; Mobile Phase A: H2O (10 mmol/L $NH_4HCO_3$+0.1% $NH_3 \cdot H_2O$), Mobile Phase B: ACN; Flow rate: 60 mL/min; Gradient: 25% B to 55% B in 7 min, 55% B; Wave Length: 254 nm; RT1(min): 5.87) to afford 9-chloro-7-(5-fluoroindol-1-yl)-4-{[2-(1H-1,2,3,4-tetrazol-5-yl)pyrimidin-5-yl]methyl}-3,5-dihydro-2H-1,4-benzoxazepine (3.6 mg, 6%) as a solid. LC/MS: mass calcd. For $C_{23}H_{18}ClFN_8O$: 476.1, found: 477.1 $[M+H]^+$; $^1H$ NMR (300 MHz, DMSO-$d_6$) δ 8.76 (s, 2H), 7.69 (d, J=3.2 Hz, 1H), 7.61 (d, J=2.6 Hz, 1H), 7.51 (d, J=9.0 Hz, 1H), 7.41 (d, J=9.4 Hz, 2H), 7.08 (t, J=9.2 Hz, 1H), 6.68 (d, J=3.4 Hz, 1H), 4.19-4.20 (m, 2H), 4.00 (s, 2H), 3.76 (s, 2H), 3.10-3.11 (m, 2H); $^{19}F$ NMR (282 MHz, DMSO-$d_6$) δ −123.5.

Example S56. Preparation of 9-chloro-4-[(2-chloro-4-methylpyrimidin-5-yl)methyl]-7-(5-fluoroindol-1-yl)-3,5-dihydro-2H-1,4-benzoxazepine (Compound 256)

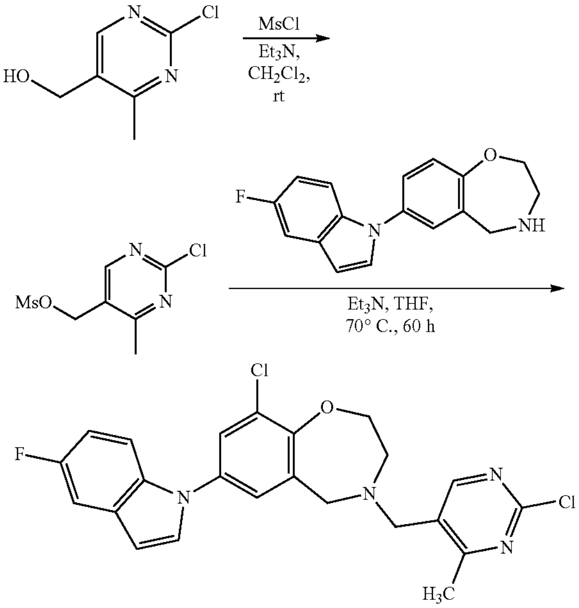

(2-chloro-4-methylpyrimidin-5-yl)methyl methanesulfonate

To a stirred mixture of (2-chloro-4-methylpyrimidin-5-yl)methanol (30 mg, 0.19 mmol) in DCM (1 mL) was added MsCl (43 mg, 0.38 mmol) and $Et_3N$ (38 mg, 0.38 mmol). The mixture was stirred at rt for 2 h, then concentrated under reduced pressure to afford (2-chloro-4-methylpyrimidin-5-yl)methyl methanesulfonate (30 mg, crude) as a solid.

9-chloro-4-[(2-chloro-4-methylpyrimidin-5-yl)methyl]-7-(5-fluoroindol-1-yl)-3,5-dihydro-2H-1,4-benzoxazepine To a stirred mixture of (2-chloro-4-methylpyrimidin-5-yl)methyl methanesulfonate (30 mg, crude) and 9-chloro-7-(5-fluoroindol-1-yl)-2,3,4,5-tetrahydro-1,4-benzoxazepine (40 mg, 0.13 mmol) in THF (1 mL) was added $Et_3N$ (26 mg, 0.25 mmol). The mixture was heated to 80° C. and stirred overnight, then purified by silica gel column chromatography (PE/EtOAc, 5:1) to afford 9-chloro-4-[(2-chloro-4-methylpyrimidin-5-yl)methyl]-7-(5-fluoroindol-1-yl)-3,5-dihydro-2H-1,4-benzoxazepine (30 mg, 19%) as a solid.

Example S57. Preparation of 2-amino-5-{[9-chloro-7-(5-fluoroindol-1-yl)-3,5-dihydro-2H-1,4-benzoxazepin-4-yl]methyl}-3H-pyrimidin-4-one (Compound 257)

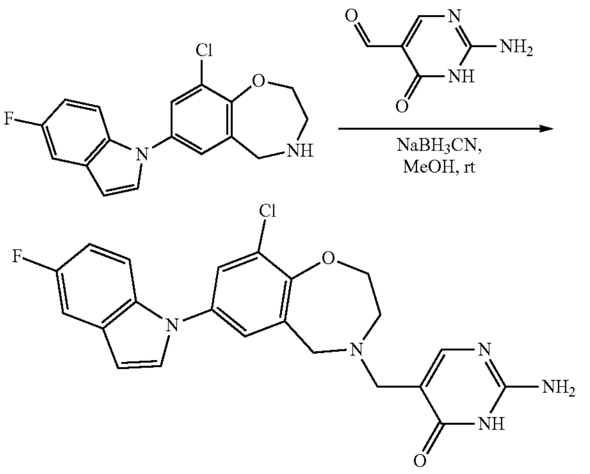

To a stirred mixture of 9-chloro-7-(5-fluoroindol-1-yl)-2,3,4,5-tetrahydro-1,4-benzoxazepine (30 mg, 0.1 mmol) and 2-amino-4-oxo-3H-pyrimidine-5-carbaldehyde (20 mg, 0.14 mmol) in MeOH (1 mL) was added $NaBH_3CN$ (12 mg, 0.190 mmol). The mixture was stirred at rt for 12 h, then concentrated under vacuum and the crude product was purified by preparative-HPLC (Column: XBridge Shield RP18 OBD Column, 19*250 mm, 10 μm; Mobile Phase A: H2O (10 mmol/L $NH_4HCO_3$+0.1% $NH_3{\cdot}H_2O$), Mobile Phase B: ACN; Flow rate: 25 mL/min; Gradient: 45% B to 75% B in 9 min, 75% B; Wave Length: 254 nm; RT1(min): 8.23) to afford 2-amino-5-{[9-chloro-7-(5-fluoroindol-1-yl)-3,5-dihydro-2H-1,4-benzoxazepin-4-yl]methyl}-3H-pyrimidin-4-one (1.1 mg, 3%) as a solid. LC/MS: mass caled. For $C_{22}H_{19}ClFN_5O_2$: 439.1, found: 424.1 $[M+H]^+$; $^1H$ NMR (300 MHz, DMSO-$d_6$) δ 10.89 (s, 1H), 7.73 (d, J=3.3 Hz, 1H), 7.48-7.67 (m, 3H), 7.38-7.48 (m, 2H), 7.00-7.13 (m, 1H), 6.68 (d, J=3.3 Hz, 1H), 6.47 (s, 2H), 4.12-4.18 (m, 2H), 3.91 (s, 2H), 3.34 (s, 2H), 3.01-3.06 (m, 2H); $^{19}F$ NMR (282 MHz, DMSO-$d_6$) δ −123.6.

Example S58. Preparation of tert-butyl N-(tert-butoxycarbonyl)-N-(5-{[9-chloro-7-(5-fluoroindol-1-yl)-3,5-dihydro-2H-1,4-benzoxazepin-4-yl]methyl}pyridazin-3-yl)carbamate (Compound 259)

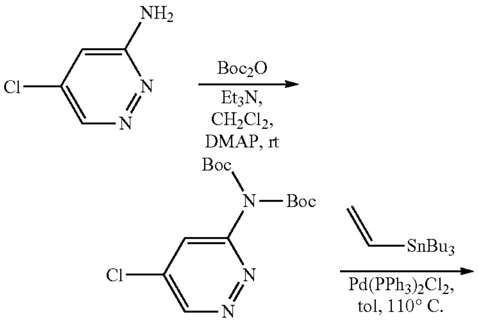

-continued

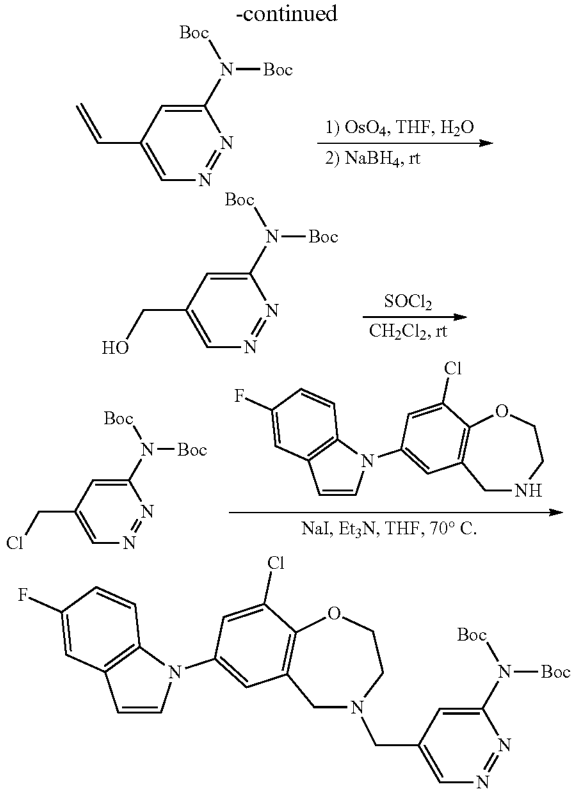

Tert-butyl N-(tert-butoxycarbonyl)-N-(5-chloropyridazin-3-yl)carbamate

To a stirred mixture of 5-chloropyridazin-3-amine (500 mg, 3.9 mmol) and $Boc_2O$ (1.26 g, 5.8 mmol) in DCM (10 mL) was added $Et_3N$ (590 mg, 5.8 mmol) and DMAP (47 mg, 0.39 mmol). The mixture was stirred at 40° C. for 2 h, then $H_2O$ (50 mL) added and the mixture was extracted with DCM (3×50 mL). The combined organic layers were washed with $H_2O$ (10 mL), dried over anhydrous $MgSO_4$ and filtered. The filtrate was concentrated under reduced pressure and the residue was purified by silica gel column chromatography (PE/EtOAc, 20:1) to afford tert-butyl N-(tert-butoxycarbonyl)-N-(5-chloropyridazin-3-yl)carbamate (350 mg, 40%) as a solid.

Tert-butyl N-(tert-butoxycarbonyl)-N-(5-ethenylpyridazin-3-yl)carbamate

To a stirred mixture of tert-butyl N-(tert-butoxycarbonyl)-N-(5-chloropyridazin-3-yl)carbamate (300 mg, 0.91 mmol) in toluene (3 mL) under an atmosphere of $N_2$ was added tributyl(vinyl)stannane (763 mg, 1.82 mmol) and $Pd(pph_3)_2Cl_2$ (64 mg, 0.09 mmol). The mixture was heated to 110° C. and stirred for 2 h, then filtered, and the filter cake was washed with EtOAc (3×10 mL). The filtrate was concentrated under vacuum and the residue was purified by silica gel column chromatography (PE/EtOAc, 5:1) to afford tert-butyl N-(tert-butoxycarbonyl)-N-(5-ethenylpyridazin-3-yl)carbamate (280 mg, 91%) as an oil.

Tert-butyl N-(tert-butoxycarbonyl)-N-[5-(hydroxymethyl)pyridazin-3-yl]carbamate

To a stirred mixture of tert-butyl N-(tert-butoxycarbonyl)-N-(5-ethenylpyridazin-3-yl)carbamate (270 mg, 0.84 mmol)

in THE (2.5 mL) and $H_2O$ (2.5 mL) at rt was added $OSO_4$ (22 mg, 0.084 mmol), then $NaIO_4$ (361 mg, 1.69 mmol). The mixture was stirred at rt for 5 h, and cooled to 0° C., then $NaBH_4$ (81 mg, 2.14 mmol) added. The mixture was warmed to rt and stirred for 15 min, then $H_2O$ (30 mL) added and the mixture was extracted with EtOAc (3×30 mL). The combined organic layers were washed with $H_2O$ (10 mL), dried over anhydrous $Na_2SO_4$ and filtered. The filtrate was concentrated under reduced pressure and the residue was purified by silica gel column chromatography (PE/EtOAc, 5:1) to afford tert-butyl N-(tert-butoxycarbonyl)-N-[5-(hydroxymethyl)pyridazin-3-yl]carbamate (160 mg, 53%) as an oil.

Tert-butyl N-(tert-butoxycarbonyl)-N-[5-(chloromethyl)pyridazin-3-yl]carbamate To a stirred mixture of tert-butyl N-(tert-butoxycarbonyl)-N-[5-(hydroxymethyl)pyridazin-3-yl]carbamate (100 mg, 0.31 mmol) in DCM (2 mL) at 0° C. was added $SOCl_2$ (44 mg, 0.37 mmol). The mixture was warmed to rt and stirred for 1 h, then concentrated under vacuum to afford tert-butyl N-(tert-butoxycarbonyl)-N-[5-(chloromethyl)pyridazin-3-yl]carbamate (100 mg, 85%) as an oil, that was used in the next step without further purification.

Tert-butyl N-(tert-butoxycarbonyl)-N-(5-{[9-chloro-7-(5-fluoroindol-1-yl)-3,5-dihydro-2H-1,4-benzoxazepin-4-yl]methyl}pyridazin-3-yl)carbamate To a stirred mixture of 9-chloro-7-(5-fluoroindol-1-yl)-2,3,4,5-tetrahydro-1,4-benzoxazepine (70 mg, 0.22 mmol) in THE (1 mL) was added tert-butyl N-(tert-butoxycarbonyl)-N-[5-(chloromethyl)pyridazin-3-yl]carbamate (76 mg, 0.22 mmol), $Et_3N$ (45 mg, 0.44 mmol) and NaI (66 mg, 0.44 mmol). The mixture was heated to 70° C. and stirred for 2 h, then concentrated under vacuum and the residue was purified by reversed-phase column chromatography (column, C18 silica gel; mobile phase, MeCN in H2O (0.05% $NH_4HCO_3$), 20% to 100% gradient in 10 min; detector, UV 254 nm) to afford tert-butyl N-(tert-butoxycarbonyl)-N-(5-{[9-chloro-7-(5-fluoroindol-1-yl)-3,5-dihydro-2H-1,4-benzoxazepin-4-yl]methyl}pyridazin-3-yl)carbamate (75 mg, 52%) as a solid.

BIOLOGY EXAMPLES

Example B1: EP2 Potency Assay

Compounds of the present disclosure are EP2 antagonists with half-max inhibitory concentration ($IC_{50}$) values below 25 μM. Compound potency was measured using a cAMP TR-FRET assay.

CHO-K1 cells (ATCC) were seeded at a density of $9.75\times10^5$ in 6 cm plates, and then on the following day cell media was changed to Opti-Mem I reduced serum media (Gibco), and transfected with a plasmid for expression of the EP2 receptor (the target receptor of interest), using the FuGENE 6 Transfection reagent (Promega). After 6 hours incubation, the cell media was replaced with F12 medium supplemented with 10% FBS and 100 U/ml Pen-Strep. 24 hours after transfection, cells were harvested and seeded at a density of 3000 cells/well in a 384 well plate to perform the cAMP assay, using the LANCE Ultra cAMP assay kit (PerkinElmer).

For each test compound of interest, 10 nl/well of serially diluted test compound was added to each well, resulting in a range of 10 serially diluted compound concentrations from 10000 nM to 0.038 nM, with duplicate wells for each concentration. Plates were then centrifuged at 1000 rpm for 1 min, agitated at 600 rpm at R.T. for 2 min, and incubated at 25° C. for 5 min. The reference agonist, prostaglandin E2 (MCE), was added to each well at the appropriate concentration to reach its EC80 value. Plates were then centrifuged at 1000 rpm for 1 min, agitated at 600 rpm at R.T. for 2 min, and incubated at 25° C. for 30 min.

To measure levels of cAMP, 5 μl/well of Eu-cAMP working solution and 5 μl/well of Ulight-anti-cAMP working solution were added to each well, and plate was centrifuged at 1000 rpm for 1 min, agitated at 600 rpm at R.T. for 2 min, and incubated at 25° C. for 15 min. Levels of TR-FRET fluorescence were measured in each well using an EnVision microplate reader (excitation wavelength=337 nm and emission wavelength=615 and 665 nm). A dose-response curve was prepared by plotting percent inhibition for each compound concentration, and then IC50 was calculated by fitting a curve to the plotted values and extrapolating the IC50 concentration.

The potency for compounds disclosed herein are as shown in Table B1. Potency data is grouped into categories of AA ($IC_{50}$<100 nM); A ($IC_{50}$=100 to 500 nM); B ($IC_{50}$=500 nM to 1 μM); C ($IC_{50}$=1 μM to 5 μM); and D ($IC_{50}$>5 μM).

TABLE B1

| | EP2 Potency |
|---|---|
| ID | Potency |
| (Compound ID No. 9-182) | |
| 9 | A |
| 10 | B |
| 11 | AA |
| 12 | B |
| 13 | A |
| 14 | B |
| 15 | D |
| 16 | B |
| 17 | C |
| 18 | D |
| 19 | D |
| 20 | B |
| 21 | D |
| 22 | D |
| 24 | C |
| 25 | A |
| 26 | B |
| 27 | B |
| 28 | D |
| 29 | D |
| 30 | C |
| 31 | B |
| 32 | C |
| 33 | C |
| 34 | D |
| 35 | D |
| 36 | D |
| 37 | B |
| 38 | C |
| 39 | C |
| 40 | C |
| 41 | B |
| 42 | D |
| 43 | D |
| 44 | C |
| 45 | B |
| 46 | B |
| 47 | C |
| 48 | D |
| 49 | D |
| 51 | D |
| 52 | D |

TABLE B1-continued

| EP2 Potency | |
|---|---|
| ID | Potency |
| 53 | D |
| 54 | C |
| 55 | D |
| 56 | C |
| 57 | D |
| 58 | AA |
| 59 | C |
| 60 | C |
| 61 | D |
| 62 | A |
| 64 | AA |
| 65 | B |
| 66 | C |
| 67 | A |
| 68 | B |
| 69 | D |
| 70 | C |
| 71 | D |
| 72 | D |
| 73 | D |
| 74 | C |
| 75 | B |
| 76 | D |
| 77 | D |
| 78 | A |
| 79 | A |
| 80 | C |
| 81 | C |
| 82 | C |
| 83 | D |
| 84 | A |
| 85 | D |
| 86 | D |
| 87 | D |
| 88 | D |
| 89 | D |
| 90 | D |
| 91 | D |
| 92 | D |
| 93 | B |
| 94 | C |
| 95 | D |
| 96 | C |
| 97 | D |
| 98 | C |
| 99 | B |
| 100 | D |
| 101 | D |
| 102 | D |
| 103 | C |
| 104 | D |
| 105 | D |
| 106 | B |
| 107 | D |
| 108 | C |
| 109 | D |
| 110 | D |
| 111 | C |
| 112 | C |
| 113 | C |
| 115 | D |
| 117 | D |
| 118 | D |
| 119 | D |
| 120 | D |
| 121 | D |
| 122 | D |
| 123 | D |
| 124 | D |
| 125 | C |
| 126 | B |
| 127 | B |
| 128 | C |
| 129 | C |
| 130 | C |
| 131 | B |
| 132 | C |

TABLE B1-continued

| EP2 Potency | |
|---|---|
| ID | Potency |
| 133 | D |
| 134 | D |
| 139 | A |
| 140 | C |
| 141 | B |
| 142 | A |
| 143 | C |
| 144 | AA |
| 145 | AA |
| 146 | AA |
| 147 | A |
| 148 | B |
| 149 | A |
| 155 | C |
| 156 | AA |
| 157 | C |
| 158 | C |
| 161 | B |
| 162 | C |
| 163 | C |
| 164 | D |
| 166 | B |
| 167 | C |
| 168 | D |
| 169 | AA |
| 170 | B |
| 171 | D |
| 172 | C |
| 173 | C |
| 174 | A |
| 175 | A |
| 176 | C |
| 178 | D |
| 179 | C |
| 180 | C |
| 181 | C |
| 182 | C |
| (Compound ID No. 183-241) | |
| 183 | A |
| 184 | C |
| 185 | A |
| 186 | A |
| 187 | A |
| 188 | D |
| 189 | A |
| 190 | C |
| 191 | C |
| 192 | A |
| 193 | AA |
| 194 | AA |
| 195 | D |
| 197 | D |
| 198 | C |
| 199 | C |
| 200 | C |
| 202 | B |
| 203 | A |
| 217 | D |
| 218 | D |
| 219 | D |
| 220 | D |
| 221 | D |
| 222 | D |
| 223 | D |
| 224 | D |
| 225 | A |
| 226 | A |
| 227 | AA |
| 228 | D |
| 229 | D |
| 230 | D |
| 231 | D |
| 235 | B |
| 236 | D |
| 238 | C |
| 239 | C |

TABLE B1-continued

| EP2 Potency | |
|---|---|
| ID | Potency |
| 240 | D |
| 241 | D |

Example B2: Human Liver Microsome Stability

The tested compound was incubated in duplicate with human liver microsomes (0.5 mg/mL) at 37° C. These incubations were carried out at a final test article concentration of 2 μM over a total incubation period of 60 minutes. Samples were taken at 0, 15, 30, 45 and 60 min and the reaction terminated by addition of 4 volumes of acetonitrile containing internal standard (100 nM alprazolam, 200 nM imipramine, 200 nM labetalol and 2 μM ketoprofen). Diclofenac was used as a positive control in this study. The samples were analyzed by UPLC-MS/MS to determine the concentration of the test compound and the percent remaining, intrinsic clearance (in vitro $CL_{int}$) and half-life ($T_{1/2}$) values were calculated.

Chromatographic analyses were performed on a Shimadzu UPLC apparatus (Kyoto, Japan) consisting of a gradient pump (model LC-30AD), an automatic injector (model HTC PAL System) and an on-line degasser (model DGU-20A5R). Detection was a triple quadrupole tandem mass spectrometer equipped with a turbo ion spray interface (API 4000/Triple Quad 4500/Triple Quad 5500/Triple Quad 6500). Data acquisition and integration were carried out with LC-MS software (Analyst 1.6) linked directly to the LC-MS/MS system. Chromatographic separations were achieved on a XSelect Hss T3 2.5μ (2.1×30 mm) Column. The mobile phase was 0.1% formic acid in water (A) and 0.1% formic acid in acetonitrile (B). The flow rate was 1.0 mL/min and column was maintained at 40° C.

The stability data for compounds disclosed herein are as shown in Table B2. Half-life ($T_{1/2}$) data is measured in minutes, and in Table B2, the data is grouped into categories of by the following rules:

$T_{1/2}$ (microsomal): A=100+; B=50 to 100; C=20 to 50; D<20.

In vitro clearance ($CL_{int}$) data is measured in μL/min/mg prot, and in Table B2, the data is grouped into categories of by the following rules:

$CL_{int}$ (microsomal): A<20; B=20 to 50; C=50 to 100; and D=100+.

TABLE B2

| Half-life and intrinsic clearance (microsomal assay) | | |
|---|---|---|
| ID No. | $T_{1/2}$ (microsomal) | in vitro $CL_{int}$ (microsomal) |
| 9 | B | B |
| 11 | D | D |
| 13 | D | C |
| 58 | A | A |
| 106 | D | D |
| 146 | D | C |
| 170 | C | B |
| 187 | D | D |
| 198 | C | C |
| 200 | C | B |
| 202 | B | B |

TABLE B2-continued

| Half-life and intrinsic clearance (microsomal assay) | | |
|---|---|---|
| ID No. | $T_{1/2}$ (microsomal) | in vitro $CL_{int}$ (microsomal) |
| 203 | D | C |
| Ref | C | B |

The reference compound ("Ref") of Tables B2 and B3 is 4-((9-chloro-7-(5-fluoro-1H-indol-1-yl)-2,3-dihydrobenzo[f][1,4]oxazepin-4(5H)-yl)methyl)pyridin-2(1H)-one, which has the structure:

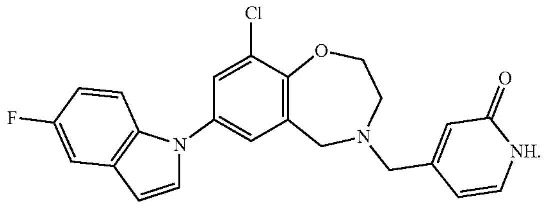 [SMILES: O=c1cc(CN2CCOc3c(Cl)cc(-n4ccc5cc(F)ccc54)cc3C2)cc[nH]1]

Example B3: Human Hepatocyte Stability

The tested compound was incubated in duplicate with incubation media (Williams' Medium E with 1× GlutaMAX) containing human hepatocytes ($0.5\times10^6$ cells/mL). These incubations were carried out at a final test concentration of 1 μM over a total incubation period of 120 minutes. Samples were taken at 0, 15, 30, 60, 90 and 120 min and the reaction was terminated by addition of acetonitrile containing internal standard (100 nM alprazolam, 200 nM labetalol, 200 nM caffeine and 200 nM diclofenac). Verapamil was used as the positive control in this study. The samples were analyzed by UPLC-MS/MS to determine the concentration of the tested compound and the percentage remaining, intrinsic clearance (in vitro $CL_{int}$) and half-life (t½) values were calculated.

Chromatographic analyses were performed on a Shimadzu UPLC apparatus (Kyoto, Japan) consisting of a gradient pump (model LC-30AD), an automatic injector (model HTC PAL System) and an on-line degasser (model DGU-20A5R). Detection was a triple quadrupole tandem mass spectrometer equipped with a turbo ion spray interface (API 4000/Triple Quad 4500/Triple Quad 5500/Triple Quad 6500). Data acquisition and integration were carried out with LC-MS software (Analyst 1.6) linked directly to the LC-MS/MS system. Chromatographic separations were achieved on a XSelect Hss T3 2.5μ (2.1×30 mm) Column. The mobile phase was 0.1% formic acid in water (A) and 0.1% formic acid in acetonitrile (B). The flow rate was 1.0 mL/min and column was maintained at 40° C.

The stability data for compounds disclosed herein are as shown in Table B3. Half-life ($T_{1/2}$) data is measured in minutes, and in Table B2, the data is grouped into categories of by the following rules:

$T_{1/2}$ (hepatic): A=200+; B=100 to 200; C=50 to 100; and D<50.

In vitro clearance ($CL_{int}$) data is measured in μL/min/mg prot, and in Table B3, the data is grouped into categories of by the following rules:

$CL_{int}$ (microsomal): A<5; B=5 to 10; C=10 to 20; and D=20+.

TABLE B3

| Half-life and intrinsic clearance (hepatic assay) | | |
|---|---|---|
| ID No. | $T_{1/2}$ (hepatic) | in vitro $CL_{int}$ (hepatic) |
| 9 | D | D |
| 11 | C | D |
| 25 | B | C |
| 58 | A | B |
| 142 | A | B |
| 144 | A | A |
| 146 | B | C |
| 156 | B | B |
| 169 | B | B |
| 185 | A | A |
| 187 | D | D |
| 189 | C | D |
| 193 | C | C |
| 194 | B | C |
| Ref | B | B |

COMPOSITION EXAMPLES

Example C-1: Parenteral Pharmaceutical Composition

To prepare a parenteral pharmaceutical composition suitable for administration by injection (subcutaneous, intravenous, and the like), 100 mg of a water-soluble salt of a compound of Formula (I) or Formula (X), or a pharmaceutically acceptable salt or solvate thereof, is dissolved in sterile water and then mixed with 10 mL of 0.9% sterile saline. The mixture is incorporated into a dosage unit form suitable for administration by injection

Example C-2: Oral Pharmaceutical Composition

To prepare a pharmaceutical composition for oral delivery, 100 mg of a compound of Formula (I) or Formula (X), or a pharmaceutically acceptable salt or solvate thereof, is mixed with 750 mg of starch. The mixture is incorporated into an oral dosage unit for, such as a hard gelatin capsule, which is suitable for oral administration.

Example C-3: Topical Gel Pharmaceutical Composition

To prepare a pharmaceutical topical gel composition, 100 mg of a compound of Formula (I) or Formula (X), or a pharmaceutically acceptable salt or solvate thereof, is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example C-4: Ophthalmic Solution

To prepare a pharmaceutical ophthalmic solution composition, 100 mg of a compound of Formula (I) or Formula (X), or a pharmaceutically acceptable salt or solvate thereof, is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and various modifications or changes suggested to persons skilled in the art are to be included within the spirit and purview of this application and scope of the appended claims.

What is claimed is:

1. A compound having the structure of Formula (II):

Formula (IIb)

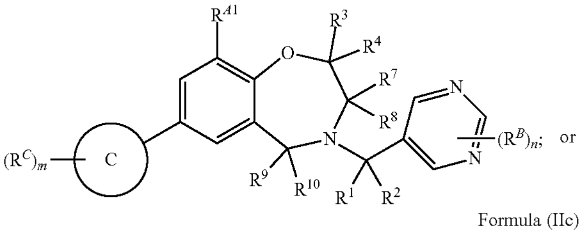

or

Formula (IIc)

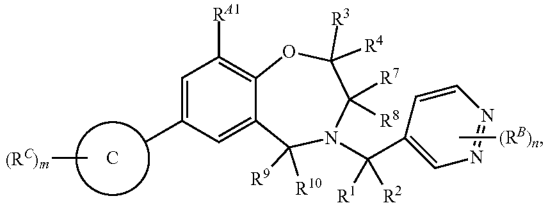

, or a pharmaceutically acceptable salt thereof, wherein:

$R^1$ and $R^2$ are each independently hydrogen, deuterium, halogen, or $C_{1-4}$ alkyl;

$R^3$ and $R^4$ are each independently hydrogen, deuterium, halogen, or $C_{1-4}$ alkyl;

$R^5$ and $R^6$ are each independently hydrogen, deuterium, halogen, or $C_{1-4}$ alkyl; or $R^5$ and $R^6$ are taken together with the carbon atom to which they are attached to form an oxetane;

$R^7$ and $R^8$ are each independently hydrogen, deuterium, halogen, —CN, —$C_{1-4}$ alkyl, —$C_{1-4}$ haloalkyl, —OH, —O($C_{1-4}$ alkyl), —O($C_{1-4}$ haloalkyl), —$NH_2$, —NH($C_{1-4}$ alkyl), —N($C_{1-4}$ alkyl)$_2$, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, substituted or unsubstituted $C_{3-6}$ cycloalkyl, or substituted or unsubstituted 3- to 6-membered heterocycloalkyl; or $R^7$ and $R^8$ are taken together with the carbon atom to which they are attached to form a cyclopropane or an oxetane;

$R^9$ and $R^{10}$ are each independently hydrogen, deuterium, halogen, or $C_{1-4}$ alkyl; or $R^9$ and $R^{10}$ are taken together with the carbon atom to which they are attached to form an oxetane;

$R^{A1}$ is halogen, $C_{1-4}$ alkyl, or cyclopropyl; and $R^{A2}$ is hydrogen, deuterium, halogen, or optionally deuterated or halogenated methyl;

each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)O($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —NHS(O)$_2C_{1-4}$ alkyl, —OH, —O($C_{1-4}$ alkyl), —O($C_{1-4}$ haloalkyl), —SH, —S($C_{1-4}$ alkyl), —S(O)($C_{1-4}$ alkyl), —S(O)(NH)($C_{1-4}$ alkyl), —S(O)$_2$($C_{1-4}$ alkyl), —S(O)$_2$ $NH_2$, —$S(O_2)NHCH_3$, substituted or unsubstituted $C_{3-6}$ cycloalkyl, or substituted or unsubstituted 3- to 6-membered heterocyclyl;

Ring C is bicyclic heterocycle having one or more nitrogen atoms; or Ring C is Ring C';

each $R^C$ is independently selected from the group consisting of halogen, —CN, —$C_{1-4}$ alkyl, —$C_{1-4}$ haloalkyl, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —N($C_{1-4}$ alkyl)$_2$, —OH, —O($C_{1-4}$ alkyl), —O($C_{1-4}$ haloalkyl), —S($C_{1-4}$ alkyl), —$SO_2C_{1-4}$ alkyl, —$SO_2NHC_{1-4}$ alkyl, substituted or unsubstituted $C_{3-6}$ cycloalkyl, or substituted or unsubstituted 3- to 6-membered heterocyclyl; or two $R^C$ taken together form a carbonyl;

m is 0 to 3;

n is 1, 2 or 3; and

Ring C' is selected from the group consisting of:

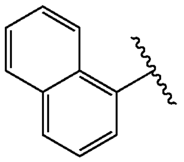
,
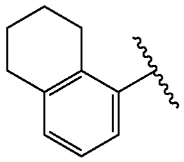
,
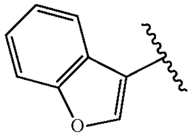
, and
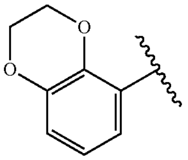
.

2. The compound of claim 1, or a pharmaceutically acceptable salt thereof, wherein $R^{A1}$ is halogen.

3. The compound of claim 1, or a pharmaceutically acceptable salt thereof, wherein $R^{A1}$ is —Cl.

4. The compound of claim 1, or a pharmaceutically acceptable salt thereof, wherein

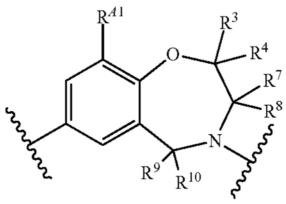

is selected from the group consisting of:

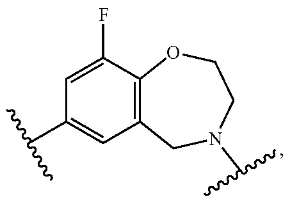

-continued

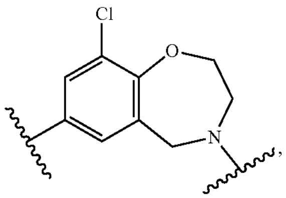

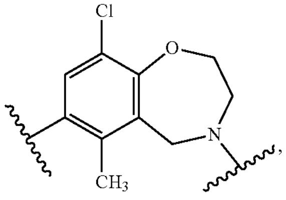

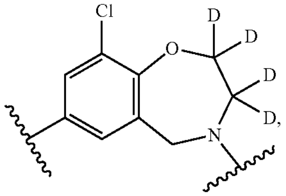

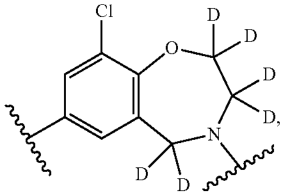

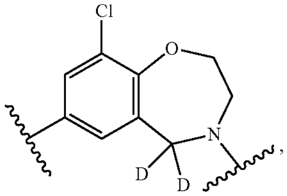

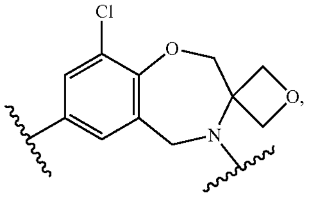

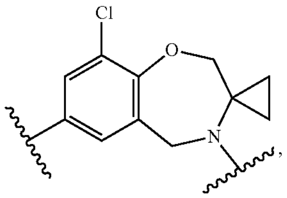

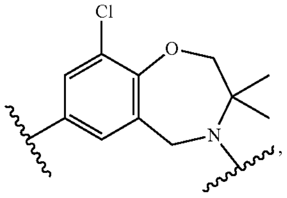

-continued
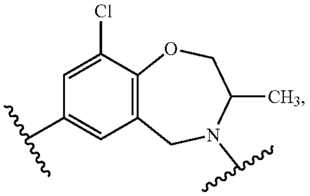
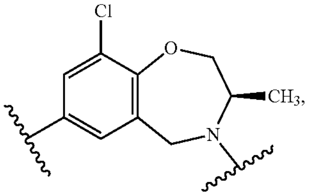
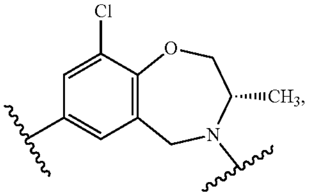
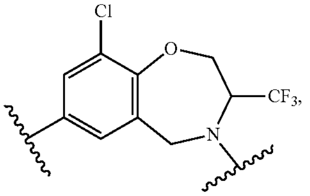
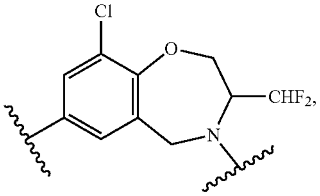
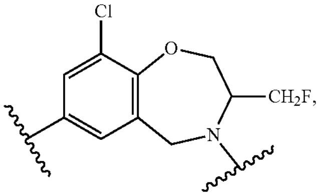
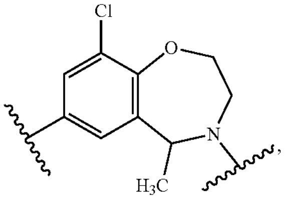
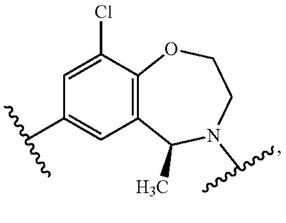
-continued
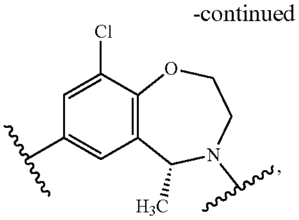
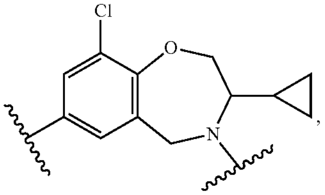
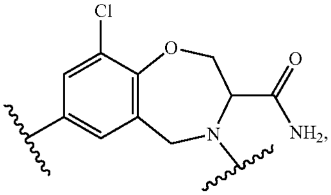
and
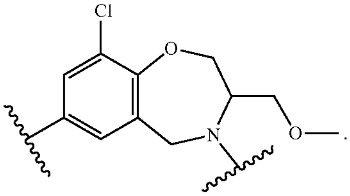
5. The compound of claim 1, having the structure:
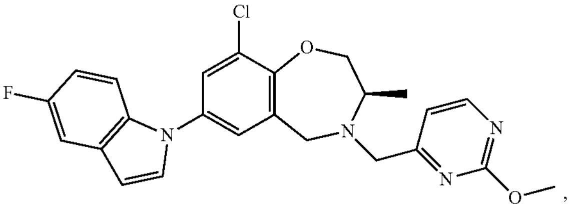
or
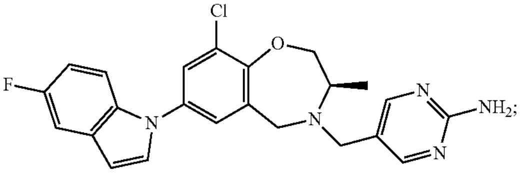
or a pharmaceutically acceptable salt thereof.
6. The compound of claim 1, or a pharmaceutically acceptable salt thereof, having the structure:
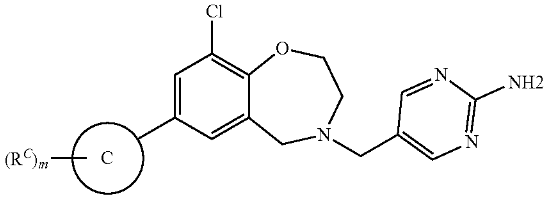

or a pharmaceutically acceptable salt thereof, wherein:

Ring C is bicyclic heterocycle having one or more nitrogen atoms; or Ring C is Ring C';

each $R^C$ is independently selected from the group consisting of halogen, —CN, —$C_{1-4}$ alkyl, —$C_{1-4}$ haloalkyl, —($C_{1-4}$ alkyl)O($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —N($C_{1-4}$ alkyl)$_2$, —OH, —O($C_{1-4}$ alkyl), —O($C_{1-4}$ haloalkyl), —S($C_{1-4}$ alkyl), —$SO_2C_{1-4}$ alkyl, —$SO_2NHC_{1-4}$ alkyl, substituted or unsubstituted $C_{3-6}$ cycloalkyl, or substituted or unsubstituted 3- to 6-membered heterocyclyl; or two $R^C$ taken together form a carbonyl;

m is 0 to 3;

n is 1, 2 or 3; and

Ring C' is selected from the group consisting of:

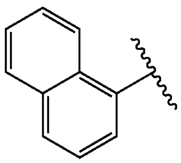
,
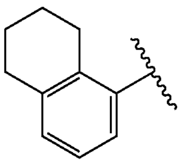
,
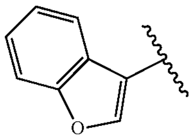
, and
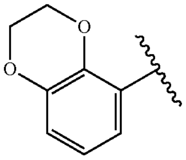
.

7. The compound of claim 1, or a pharmaceutically acceptable salt thereof, wherein Ring C is bicyclic heteroaryl having one, two or three nitrogen atoms.

8. The compound of claim 1, or a pharmaceutically acceptable salt thereof, wherein Ring C is bicyclic heteroaryl consisting of a pyrrole ring or pyrazole ring fused to a phenyl ring, a pyridine ring, or a pyrimidine ring.

9. The compound of claim 1, or a pharmaceutically acceptable salt thereof, wherein Ring C is a substituted or unsubstituted indole, or a substituted or unsubstituted azaindole.

10. The compound of claim 1, or a pharmaceutically acceptable salt thereof, wherein Ring C is a substituted or unsubstituted indole.

11. The compound of claim 1, wherein Ring C is a bicyclic heterocycle having one or more nitrogens, selected from the group consisting of:

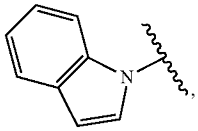
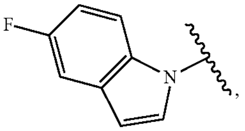
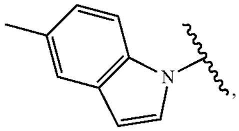
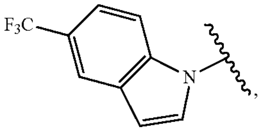
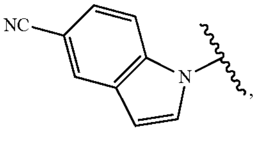
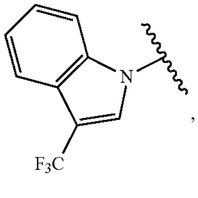
,

-continued

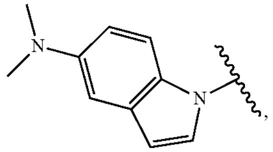
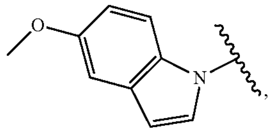
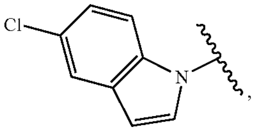
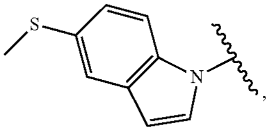
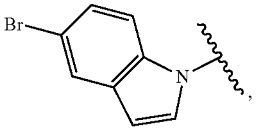
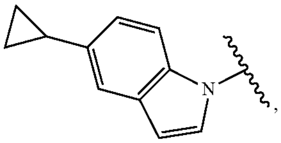
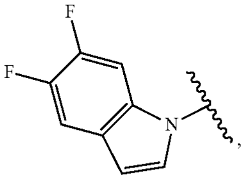
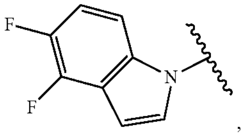
,
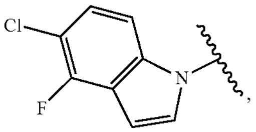
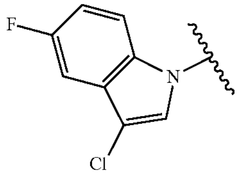
,
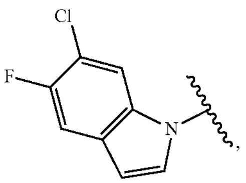
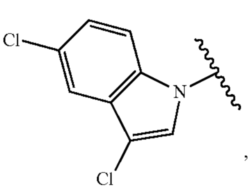
,
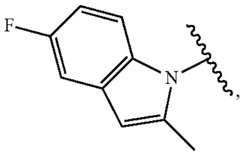
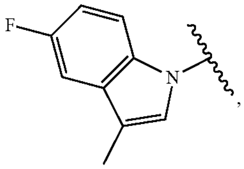
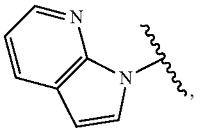
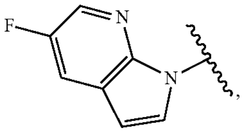

-continued

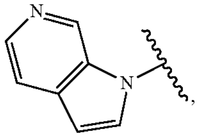, 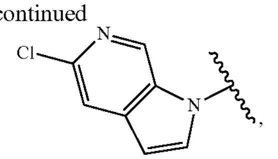, 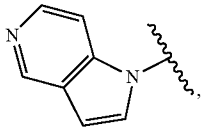, 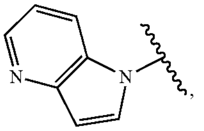, 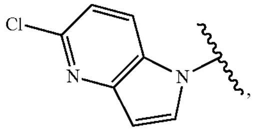, 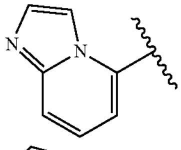, 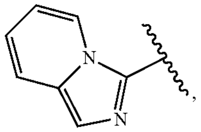, 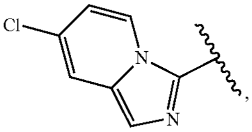, 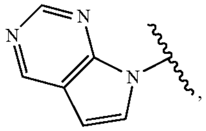, 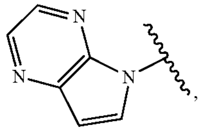, 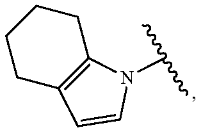, 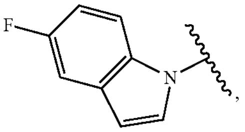, 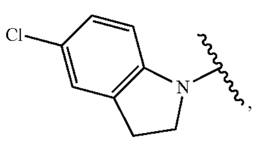, 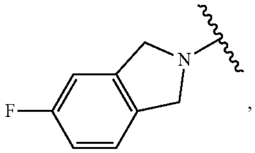, 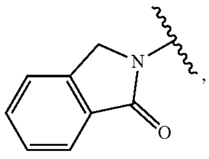, 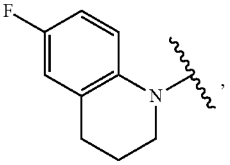, 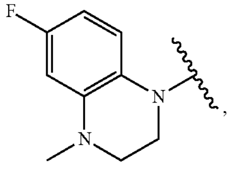, 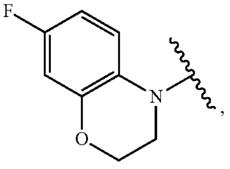, 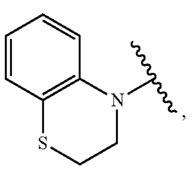, and 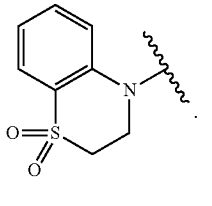.

12. The compound of claim 1, or a pharmaceutically acceptable salt thereof, wherein $R^C$ is halogen, and m is 0, 1, or 2.

13. The compound of claim 1, or a pharmaceutically acceptable salt thereof, wherein Ring C is indole; Re is halogen, and m is 1.

14. The compound of claim 1, or a pharmaceutically acceptable salt thereof, wherein each $R^B$ is independently halogen, $C_{1-4}$ alkyl, $C_{1-4}$ haloalkyl, —C(O)OH, —C(O)O($C_{1-4}$ alkyl), —C(O)$NH_2$, —C(O)NH($C_{1-4}$ alkyl), or —C(O)N($C_{1-4}$ alkyl)$_2$.

15. The compound of claim 1, or a pharmaceutically acceptable salt thereof, wherein each $R^B$ is independently selected from the group consisting of —F, —Cl, —CN, —$CH_3$, —$CH_2F$, —$CHF_2$, —$CF_3$, —OH, and —$OCH_3$.

16. The compound of claim 1, or a pharmaceutically acceptable salt thereof, wherein each $R^B$ is independently selected from the group consisting of —F, —Cl, —CN, —$CH_3$, —$CH_2F$, —$CHF_2$, —$CF_3$, $CH_2NH_2$, —$CH_2$NHBoc, —$CH_2OH$, —$CH_2OCH_3$, —C(O)$NH_2$, —C(O)$NHCH_3$, —C(O)N($CH_3$)$_2$, —C(O)OH, —C(O)$OCH_3$, —$NH_2$, —$NHCH_3$, —N($CH_3$)$_2$, —NH(oxetanyl), —NHC(O)$CH_3$, —NHS(O)$_2CH_3$, —OH, —$OCH_3$, —$OCH_2CF_3$, —S(O)(NH)$CH_3$, methylpyrazolyl, and pyrazolyl.

17. The compound of claim 1, having the structure:

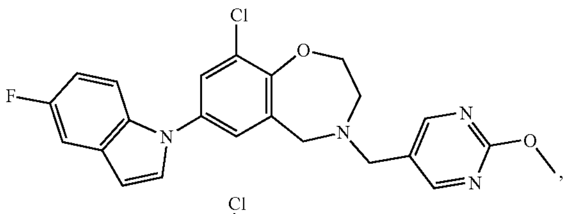,

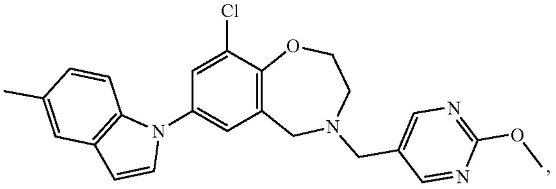,

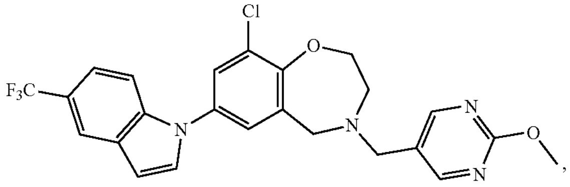,

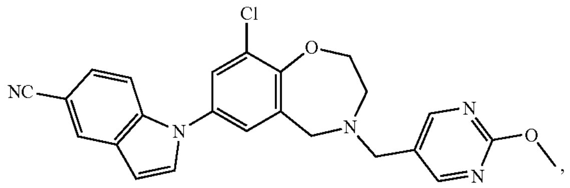,

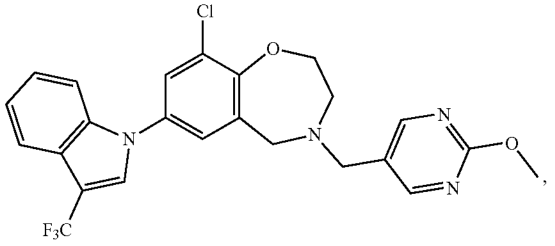,

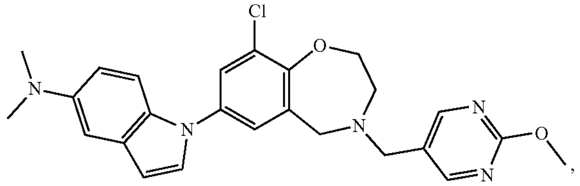,

-continued
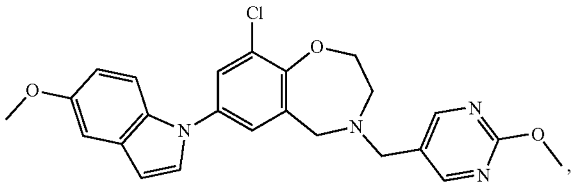
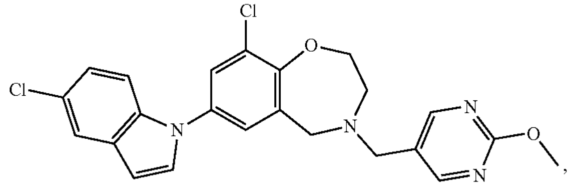
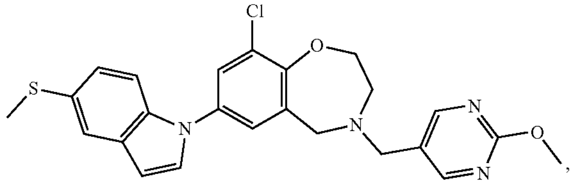
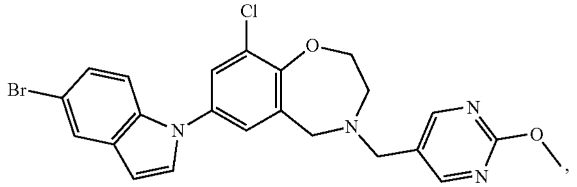
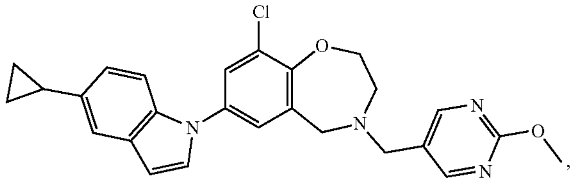
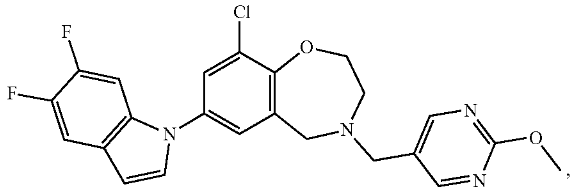
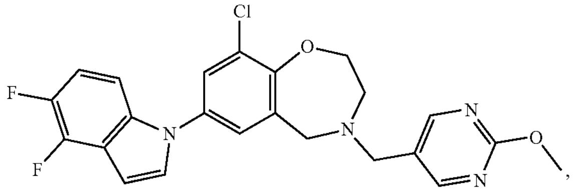
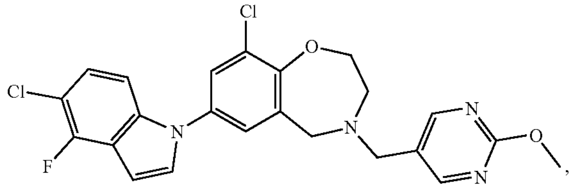
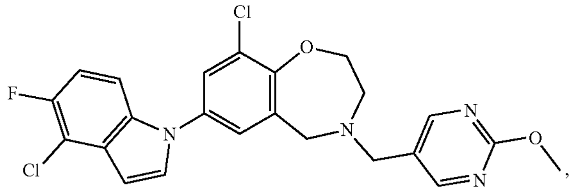
-continued
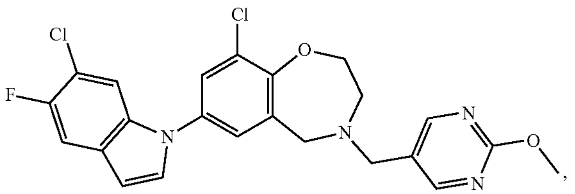
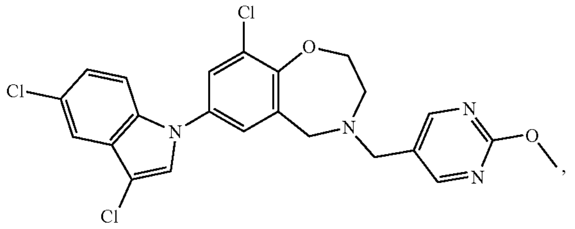
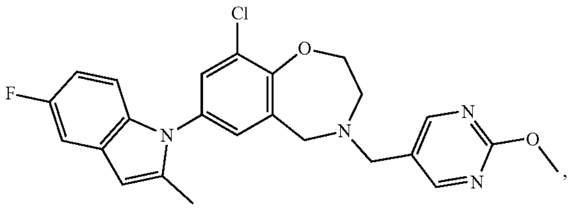
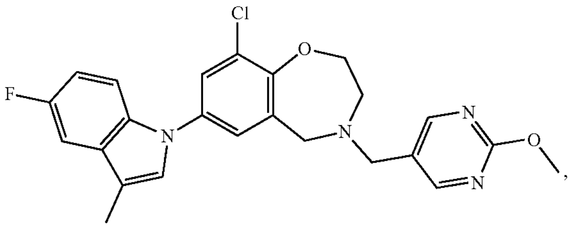
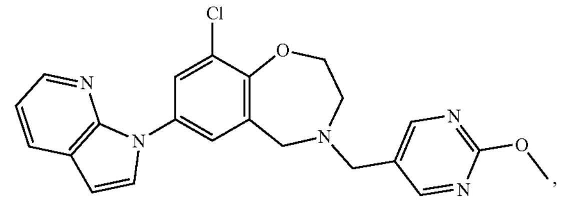
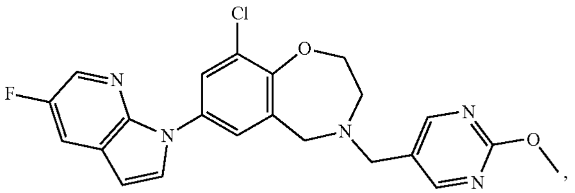
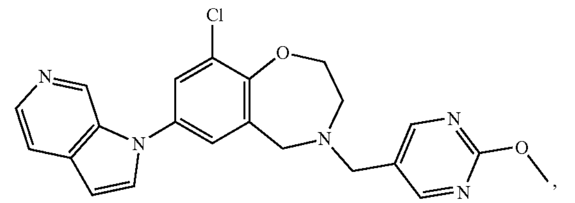
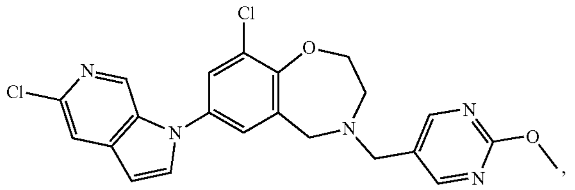

-continued
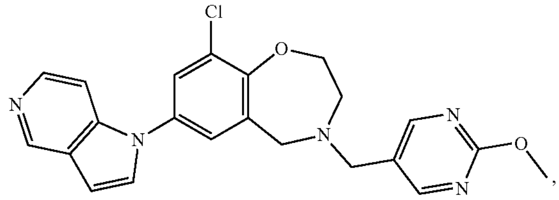,
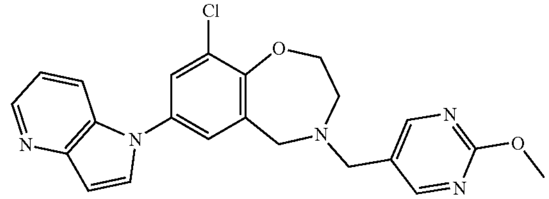,
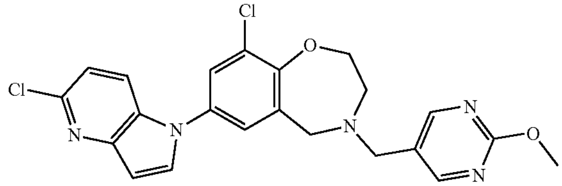,
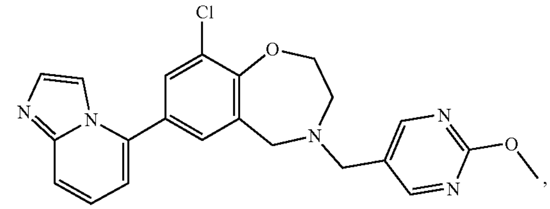,
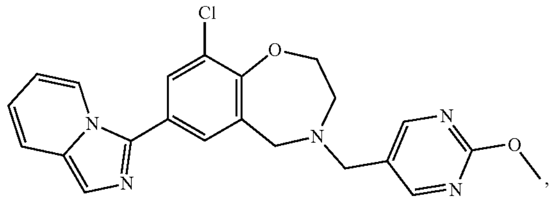,
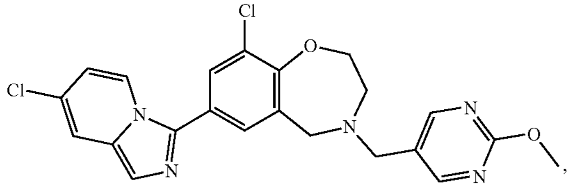,
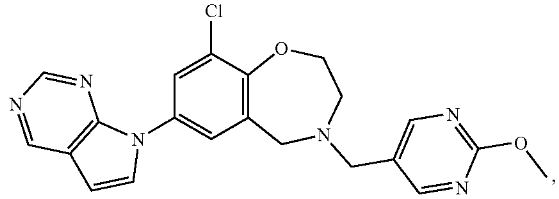,
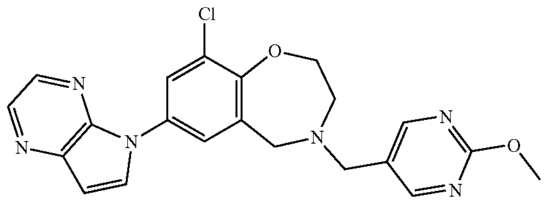,
-continued
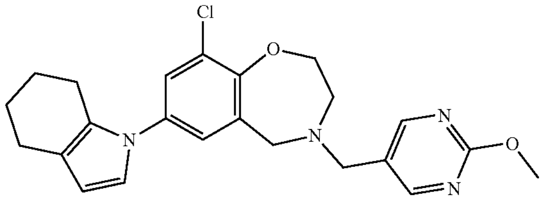,
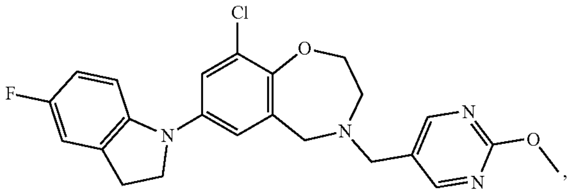,
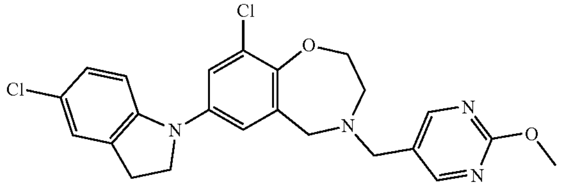,
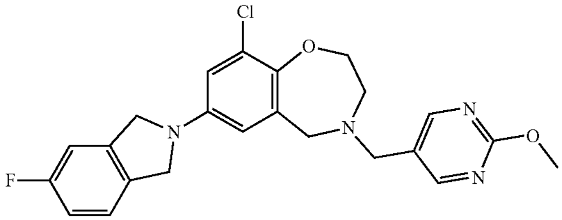,
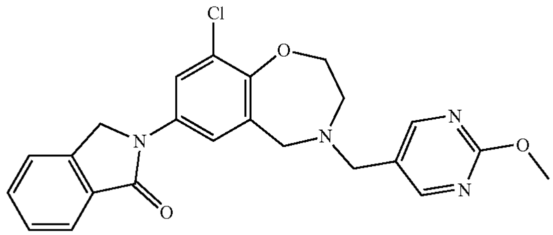,
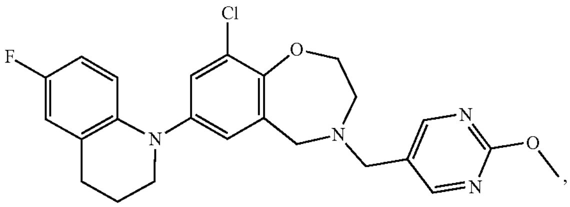,
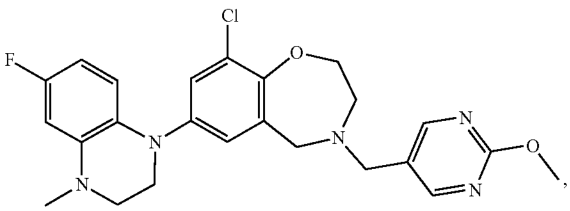,
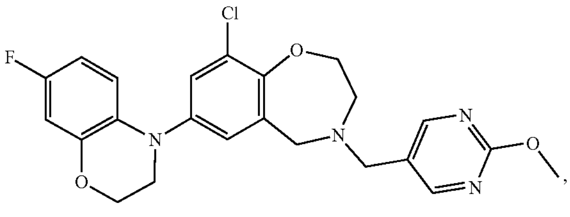, -continued
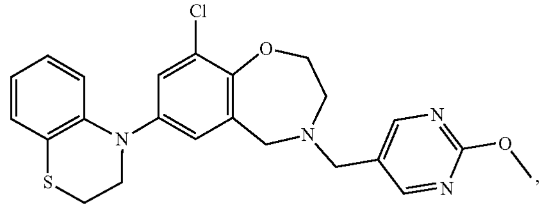
,
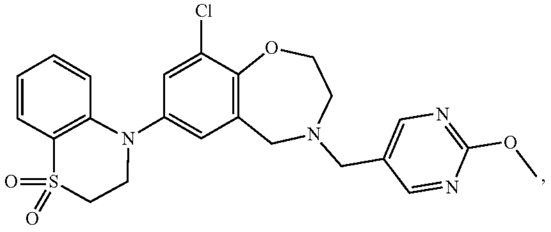
,
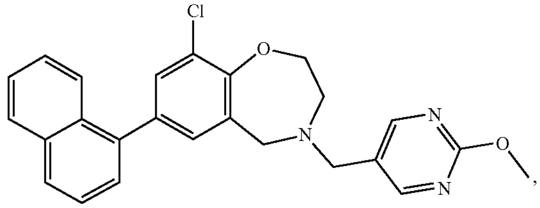
,
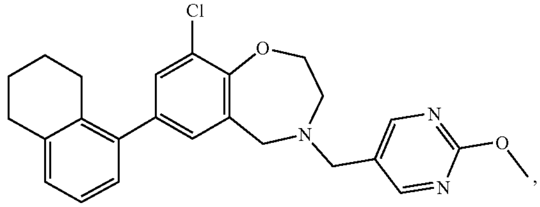
,
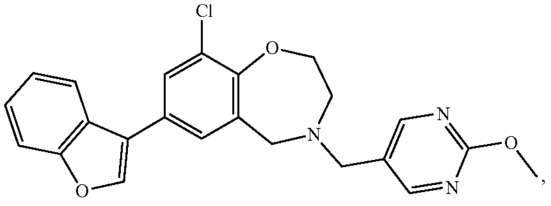
,
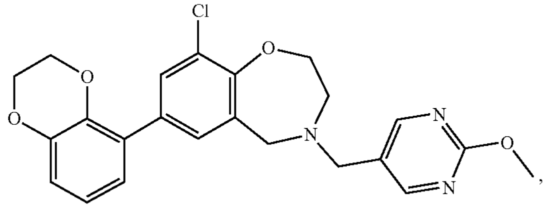
,
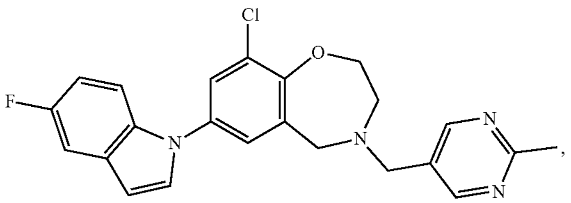
,
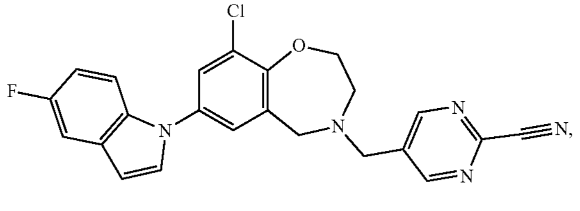
,
-continued
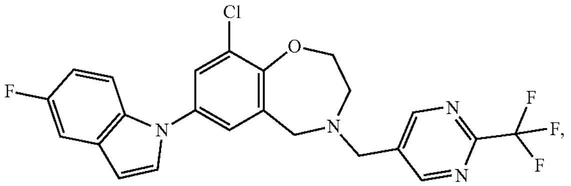
,
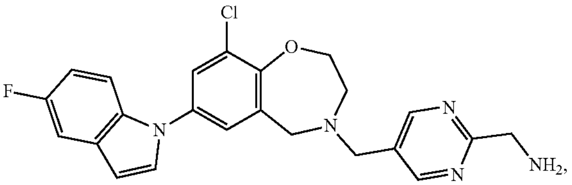
,
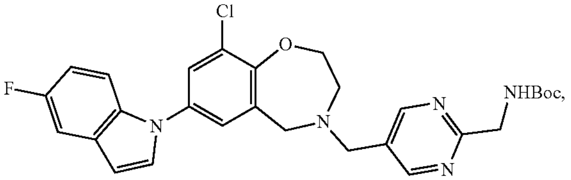
,
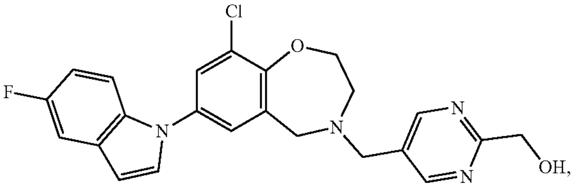
,
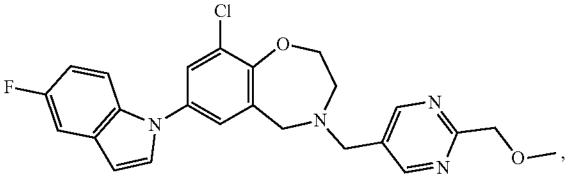
,
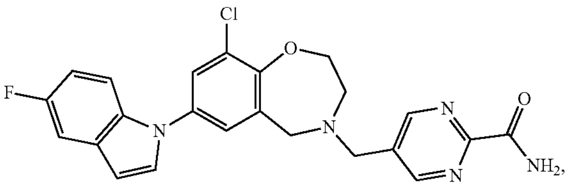
,
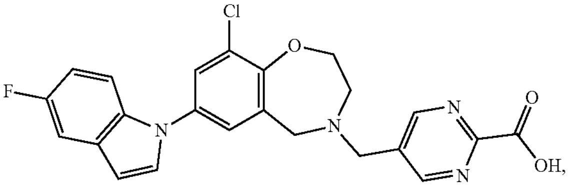
,
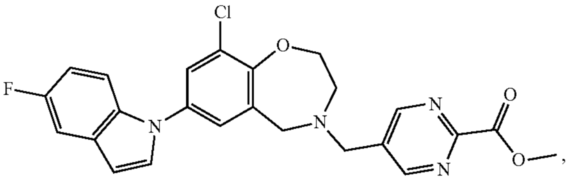
,
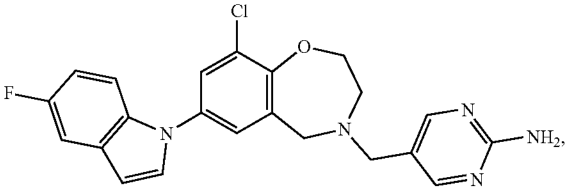
, -continued
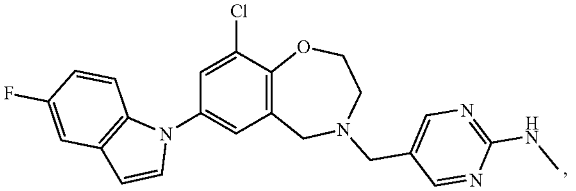
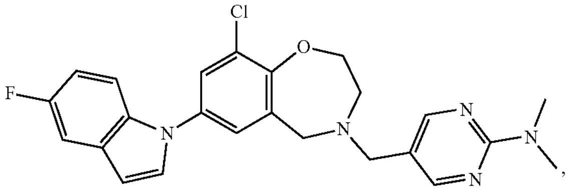
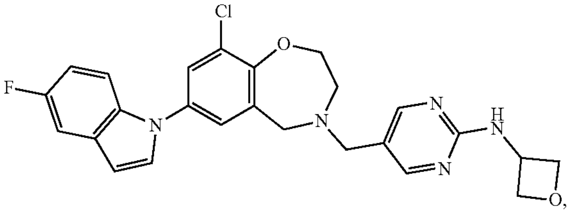
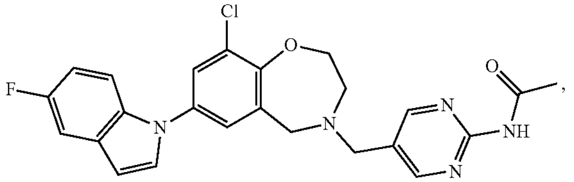
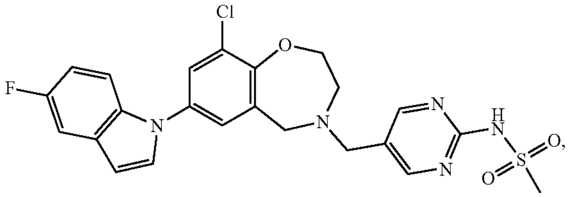
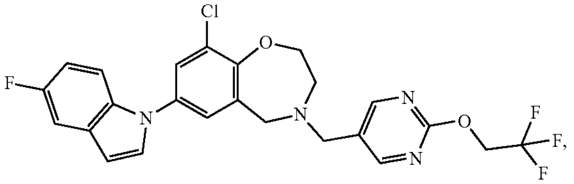
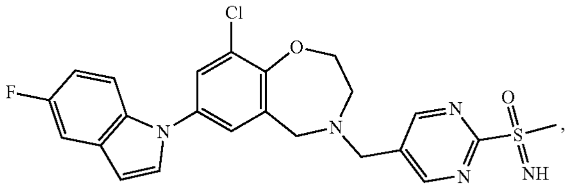
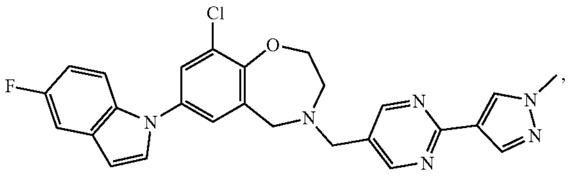
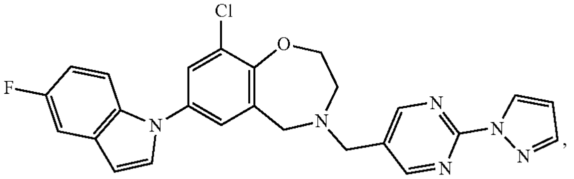
-continued
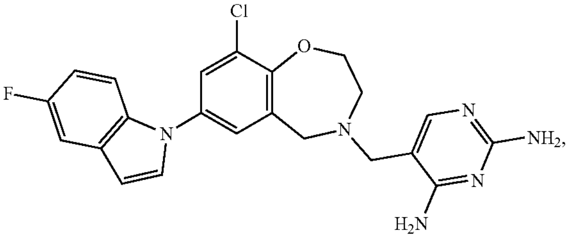
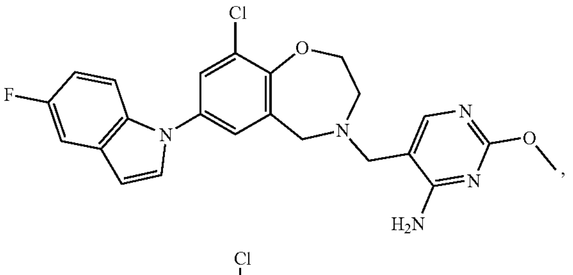
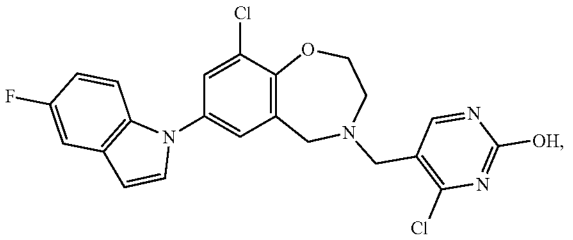
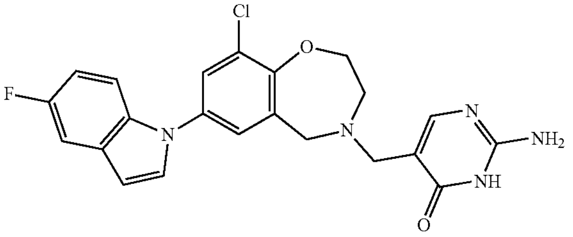
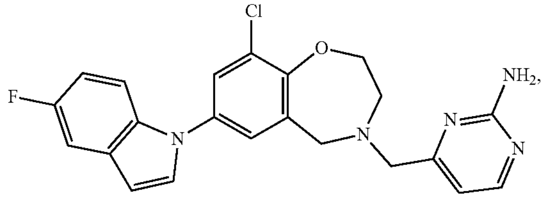
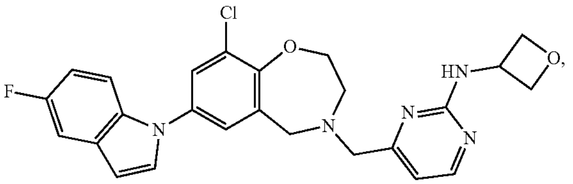
and
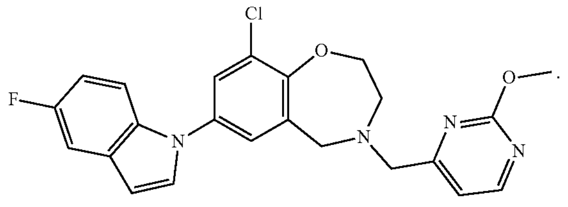 [SMILES: COc1nccc(CN2CCOc3c(Cl)cc(-n4ccc5cc(F)ccc54)cc3C2)n1]
or a pharmaceutically acceptable salt thereof.

18. The compound of claim 1, having the structure:

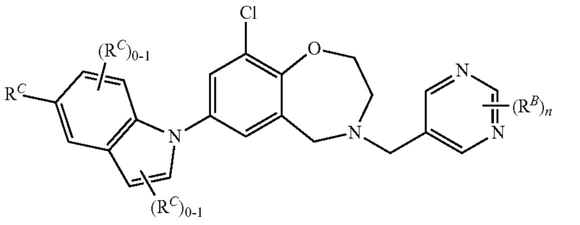

or a pharmaceutically acceptable salt thereof, or a tautomer thereof, wherein:

each $R^B$ is independently selected from the group consisting of halogen, —CN, —$C_{1-4}$ alkyl, —$C_{1-4}$ haloalkyl, —$C_{1-4}$ aminoalkyl, —$C_{1-4}$ hydroxyalkyl, —$C_{1-4}$ methoxyalkyl, —($C_{1-4}$ alkyl)(($C_{1-4}$ alkyl), —C(O)($C_{1-4}$ alkyl), —C(O)OH, —C(O)O($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —NH($C_{3-6}$ cycloalkyl), —NH($C_{3-6}$ heterocycloalkyl), —N($C_{1-4}$ alkyl)$_2$, —NHC(O)$C_{1-4}$ alkyl, —NHC(O)O($C_{1-4}$ alkyl), —NHS(O)$_2C_{1-4}$ alkyl, —OH, —O($C_{1-4}$ alkyl), —O($C_{1-4}$ haloalkyl), —SH, —S($C_{1-4}$ alkyl), —SO($C_{1-4}$ alkyl), —S(O)$_2$($C_{1-4}$ alkyl), —S(O)$_2NH_2$, —S($O_2$)$NHCH_3$, substituted or unsubstituted $C_{3-6}$ cycloalkyl, or substituted or unsubstituted 3- to 6-membered heterocyclyl; and each $R^C$ is independently selected from the group consisting of halogen, —CN, —$C_{1-4}$ alkyl, —$C_{1-4}$ haloalkyl, —($C_{1-4}$ alkyl)O($C_{1-4}$ alkyl), —C(O)OH, —C(O)O ($C_{1-4}$ alkyl), —C(O)$NH_2$, —C(O)NH($C_{1-4}$ alkyl), —C(O)N($C_{1-4}$ alkyl)$_2$, —$NH_2$, —NH($C_{1-4}$ alkyl), —N($C_{1-4}$ alkyl)$_2$, —OH, —O($C_{1-4}$ alkyl), —O($C_{1-4}$ haloalkyl), —S($C_{1-4}$ alkyl), —$SO_2C_{1-4}$ alkyl, —$SO_2NHC_{1-4}$ alkyl, substituted or unsubstituted $C_{3-6}$ cycloalkyl, or substituted or unsubstituted 3- to 6-membered heterocyclyl; or two $R^C$ taken together form a carbonyl.

19. The compound of claim 1, wherein n is 1.

20. The compound of claim 1, wherein n is 2.

21. The compound of claim 1, wherein n is 3.

22. A pharmaceutical composition comprising a compound of claim 1, or a pharmaceutically acceptable salt, or solvate thereof, and at least one pharmaceutically acceptable excipient.

23. A method of modulating the activity of the prostaglandin E2 receptor 2 (EP2) in a mammal comprising administering to the mammal a compound of claim 1, or a pharmaceutically acceptable salt, or solvate thereof.

24. A method of treating a disease or condition that would benefit from the modulation of prostaglandin E2 receptor 2 (EP2) activity comprising administering to the mammal a compound of claim 1, or a pharmaceutically acceptable salt, or solvate thereof.

* * * * *